US010989719B2

(12) United States Patent
Okazawa

(10) Patent No.: US 10,989,719 B2
(45) Date of Patent: Apr. 27, 2021

(54) METHODS FOR TREATING SPINOCEREBELLAR ATAXIA TYPE I USING RPA1

(71) Applicant: National University Corporation Tokyo Medical and Dental University, Tokyo (JP)

(72) Inventor: Hitoshi Okazawa, Tokyo (JP)

(73) Assignee: National University Corporation Tokyo Medical and Dental University, Tokyo (JP)

( * ) Notice: Subject to any disclaimer, the term of this patent is extended or adjusted under 35 U.S.C. 154(b) by 223 days.

(21) Appl. No.: 15/028,571

(22) PCT Filed: Oct. 10, 2014

(86) PCT No.: PCT/JP2014/077258
§ 371 (c)(1),
(2) Date: Apr. 11, 2016

(87) PCT Pub. No.: WO2015/053402
PCT Pub. Date: Apr. 16, 2015

(65) Prior Publication Data

US 2016/0252530 A1 Sep. 1, 2016

(30) Foreign Application Priority Data

Oct. 11, 2013 (JP) ............................ JP2013-214155

(51) Int. Cl.

| | |
|---|---|
| ***A61K 38/00*** | (2006.01) |
| ***A61K 49/00*** | (2006.01) |
| ***C07K 14/00*** | (2006.01) |
| ***C12N 15/63*** | (2006.01) |
| ***C12N 5/10*** | (2006.01) |
| ***C12N 15/00*** | (2006.01) |
| ***C12N 15/11*** | (2006.01) |
| ***G01N 33/68*** | (2006.01) |
| ***C12Q 1/48*** | (2006.01) |

(Continued)

(52) U.S. Cl.
CPC ....... *G01N 33/6896* (2013.01); *A61K 31/465* (2013.01); *A61K 31/4704* (2013.01); *A61K 31/4748* (2013.01); *A61K 31/497* (2013.01); *A61K 31/519* (2013.01); *A61K 31/5377* (2013.01); *A61K 31/553* (2013.01); *A61K 38/00* (2013.01); *A61K 38/04* (2013.01); *A61K 38/16* (2013.01); *A61K 38/1709* (2013.01); *A61K 45/06* (2013.01); *A61K 49/0058* (2013.01); *A61P 25/00* (2018.01); *A61P 25/28* (2018.01); *C12N 7/00* (2013.01); *C12Q 1/485* (2013.01); *C12Q 1/6897* (2013.01); *G01N 33/5058* (2013.01); *A61K 48/00* (2013.01); *C12N 2750/14143* (2013.01); *C12N 2750/14171* (2013.01); *G01N 2800/28* (2013.01); *G01N 2800/2821* (2013.01); *G01N 2800/2835* (2013.01)

(58) Field of Classification Search
CPC .. A61K 31/497; A61K 31/519; A61K 31/553; A61K 31/435; A61K 31/4439; A61K 31/495; A61K 38/00; A61K 38/1709; A61K 38/465; A61K 45/06; A61K 47/48092; A61K 48/00; A61K 48/05; A61K 38/38; C07D 215/233; C07D 231/56; C07D 237/14; C07D 519/00; C12N 15/11; C12N 15/902; C12N 9/22; C12N 15/85; C12N 15/907; C12N 2310/14; C12N 2310/3513; C12N 2750/14171; C12N 2800/80; C12N 9/96; G01N 2800/28; G01N 2800/2821; G01N 2800/2835; G01N 33/5058; G01N 33/6896
See application file for complete search history.

(56) References Cited

U.S. PATENT DOCUMENTS 8,476,294 B2 * 7/2013 Furet .................... C07D 471/04 514/293
8,987,257 B2 * 3/2015 Radetich ............. C07D 487/04 514/232.5

(Continued)

FOREIGN PATENT DOCUMENTS

JP 2008-512344 A 4/2008
JP 2011-254701 A 12/2011

(Continued)

OTHER PUBLICATIONS

Pawson et al. 2003, Science 300:445-452.*

(Continued)

*Primary Examiner* — Chang-Yu Wang
(74) *Attorney, Agent, or Firm* — Sughrue Mion, PLLC

(57) ABSTRACT

To provide a compound which enables treatment or prevention of spinocerebellar ataxia, analyses were carried out based on a screening using a spinocerebellar ataxia type 1 (SCA1) fly model and on the like. As a result, the following proteins ameliorating the pathology of spinocerebellar ataxia were identified: RPA1, PNKP, XRCC3, XRCC4, CCNH, POLE, POLH, and PER1. On the other hand, the following proteins aggravating the pathology were identified: CHK1, LIG3, FEN1, LIG1, ERCC5, XAB2, ERCC2, DMC1, RECQL5, MUS81, EME1, SPO11, and BLM. In addition, it has been revealed that ATXN1, which is a cause of SCA1, binds to RPA1, BRCA1, and BRCA2, and suppresses the activities of these proteins, so that the above-described pathology is caused.

1 Claim, 32 Drawing Sheets
(24 of 32 Drawing Sheet(s) Filed in Color)

Specification includes a Sequence Listing.

(51) Int. Cl.

| | |
|---|---|
| ***G01N 33/50*** | (2006.01) |
| ***A61K 31/5377*** | (2006.01) |
| ***A61K 31/553*** | (2006.01) |
| ***A61K 31/519*** | (2006.01) |
| ***A61K 31/4748*** | (2006.01) |
| ***A61K 31/465*** | (2006.01) |
| ***A61K 31/4704*** | (2006.01) |
| ***A61K 45/06*** | (2006.01) |
| ***A61K 31/497*** | (2006.01) |
| ***A61P 25/28*** | (2006.01) |
| ***A61P 25/00*** | (2006.01) |
| ***A61K 38/04*** | (2006.01) |
| ***A61K 38/16*** | (2006.01) |
| ***A61K 38/17*** | (2006.01) |
| ***C12N 7/00*** | (2006.01) |
| ***C12Q 1/6897*** | (2018.01) |
| *A61K 48/00* | (2006.01) |

(56) References Cited

U.S. PATENT DOCUMENTS

| | | | | |
|---|---|---|---|---|
| 9,458,163 | B2 * | 10/2016 | Radetich | C07D 487/04 |
| 2004/0121407 | A1 * | 6/2004 | Distefano | G01N 33/74<br>435/7.1 |
| 2007/0185031 | A1 * | 8/2007 | Morimoto | A01K 67/0336<br>514/8.6 |
| 2007/0196850 | A1 * | 8/2007 | Kennedy | C12Q 1/6883<br>435/6.1 |
| 2008/0027116 | A1 | 1/2008 | Yoshikawa et al. | |
| 2009/0275619 | A1 * | 11/2009 | Boueres | C07D 231/56<br>514/359 |
| 2009/0280488 | A1 | 11/2009 | Okazawa | |
| 2010/0158923 | A1 * | 6/2010 | Morimoto | A01K 67/0336<br>424/158.1 |
| 2010/0311714 | A1 * | 12/2010 | Furet | C07D 471/14<br>514/210.21 |
| 2010/0317657 | A1 * | 12/2010 | Furet | C07D 471/04<br>514/230.5 |
| 2011/0230444 | A1 * | 9/2011 | Garcia-Echeverria | A61K 31/436<br>514/80 |
| 2012/0220576 | A1 * | 8/2012 | Radetich | C07D 487/04<br>514/230.5 |
| 2014/0005163 | A1 * | 1/2014 | Furet | C07D 471/04<br>514/210.18 |
| 2014/0242088 | A1 * | 8/2014 | Garcia-Echeverria | A61K 31/436<br>424/143.1 |
| 2015/0344479 | A1 * | 12/2015 | Radetich | C07D 487/04<br>514/230.5 |
| 2016/0045532 | A1 * | 2/2016 | Roberts | A61K 31/713<br>514/34 |

FOREIGN PATENT DOCUMENTS

| | | | | |
|---|---|---|---|---|
| WO | WO 2010118390 | A1 * | 10/2010 | A61K 31/437 |
| WO | 2014/151529 | A1 | 9/2014 | |

OTHER PUBLICATIONS

Blight Nat. Neurosci. 2002. 5: 1051-4; p. 316.*
Schmidt et al. Annu. Rev. Biomed. Eng. 2003. 5: 293-347.*
Hoke et al. Nat. Clin. Pract. Neurol. 2006: 448-454.*
Burgess et al. J of Cell Bio. 1990, 111:2129-2138.*
Bowie et al. Science, 1990, 247:1306-1310.*
Caldecott. Cell, 2003; 112:7-10.*
The factsheet of spinocerebellar ataxia retrieved from NIH website: rarediseases.info.nih.gov/diseases/10748/spinocerebellar-ataxia on Jun. 11, 2018.*
Spinocerebellar ataxia phenotype factsheet reterived from OMIM website: omim.org/phenotypicSeries/PS164400 on Jun. 11, 2018.*
Cendelin. Cerebellum & Ataxias; 2014; 1:4; p. 1-21.*
Scott et al. Nat. Genet. 1999; 21:440-443.*
Tse et al. Clin. Cancer Res. 2007; 13: 591-602.*
Takuya Tamura et al., "Effect of DNA damage repair genes on spinocerebellar ataxia 1; in vivo screening ni yoru Kaiseki", The 54th Annual Meeting of the Japanese Society of Neurology Program Shorokushu, May 22, 2013 (received date), pp. 380 P(2)-132, entire text. (total 2 pages).
Lim, J. et al., "Opposing effects of polyglutamine expansion on native protein complexes contribute to SCA1", Nature, Apr. 10, 2008, vol. 452, pp. 713-718, (total 7 pages).
Chen, H.K. et al., "Interaction of Akt-Phosphorylated Ataxin-1 with 14-3-3 Mediates Neurodegeneration in Spinocerebellar Ataxia Type 1", Cell, May 16, 2003, vol. 113, pp. 457-468.
Lai, S. et al., "14-3-3 Binding to Ataxin-1(ATXN1) Regulates Its Dephosphorylation at Ser-776 and Transport to the Nucleus", The Journal of Biological Chemistry, Oct. 7, 2011, vol. 286, No. 40, pp. 34606-34616.
De Chiara, C. et al., "The AXH module: an independently folded domain common to ataxin-1 and HBP1", FEBS Letters, 2003, vol. 551, pp. 107-112.
Serra, H. G. et al., "RORα-Mediated Purkinje Cell Development Determines Disease Severity in Adult SCA1 Mice", Cell, Nov. 17, 2006, vol. 127, pp. 697-708.
Makarov, E. M. et al., "Small Nuclear Ribonucleoprotein Remodeling During Catalytic Activation of the Spliceosome", Science, Dec. 13, 2002, vol. 298, pp. 2205-2208.
Makarova, O. V. et al., "A subset of human 35S U5 proteins, including Prp19, function prior to catalytic step 1 of splicing", The EMBO Journal, 2004, vol. 23, No. 12, pp. 2381-2391.
Okazawa, H. et al., "Interaction between Mutant Ataxin-1 and PQBP-1 Affects Transcription and Cell Death", Neuron, May 30, 2002, vol. 34, pp. 701-713.
Orr, H. T., "Cell biology of spinocerebellar ataxia", The Journal of Cell Biology, Apr. 16, 2012, vol. 197, No. 2, pp. 167-177.
Qi, M. L. et al., "Proteome analysis of soluble nuclear proteins reveals that HMGB1/2 suppress genotoxic stress in polyglutamine diseases", Nature Cell Biology, Apr. 2007, vol. 9, No. 4, pp. 402-414 (total 23 pages).
Chaouki, A.S. et al., "*Drosophila* SPF45: A Bifunctional Protein with Roles in Both Splicing and DNA Repair", PLoS Genetics, Dec. 2006, vol. 2, Issue 12, pp. 1974-1983.
Rass, U. et al., "Defective DNA Repair and Neurodegenerative Disease", Cell, Sep. 21, 2007, vol. 130, pp. 991-1004.
Gueven, N. et al., "A Subgroup of Spinocerebellar Ataxias Defective in DNA Damage Responses", Neuroscience, 2007, vol. 145, pp. 1418-1425.
Fernandez-Funez, P. et al., "Identification of genes that modify ataxin-1-induced neurodegeneration", Nature, Nov. 2, 2000, vol. 408, pp. 101-106.
Date, H. et al., "Early-onset ataxia with ocular motor apraxia and hypoalbuminemia is caused by mutations in a new HIT superfamily gene", Nature Genetics, Oct. 2001, vol. 29, pp. 184-188 (total 6 pages).
Moreira, M. C. et al., "The gene mutated in ataxia-ocular apraxia 1 encodes the new HIT/Zn-finger protein aprataxin", Nature Genetics, Oct. 2001, vol. 29, pp. 189-193 (total 6 pages).
Date, H. et al., "The FHA domain of aprataxin interacts with the C-terminal region of XRCC1", Biochemical and Biophysical Research Communications, 2004, vol. 325, pp. 1279-1285.
Moreira, M. C. et al., "Senataxin, the ortholog of a yeast RNA helicase, is mutant in ataxia-ocular aparaxia 2", Nature Genetics, Mar. 2004, vol. 36, No. 3, pp. 225-227.
Skourti-Stathaki, K. et al., "Human Senataxin Resolves RNA/DNA Hybrids Formed at Transcriptional Pause Sites to Promote Xrn2-Dependent Termination", Molecular Cell, Jun. 24, 2011, vol. 42, pp. 794-805.
Suraweera, A. et al., "Functional role for senataxin, defective in ataxia oculomotor apraxia type 2, in transcriptional regulation", Human Molecular Genetics, Jun. 10, 2009, vol. 18, No. 18, pp. 3384-3396.

(56) References Cited

OTHER PUBLICATIONS

International Search Report dated Dec. 22, 2014, issued by the International Searching Authority in application No. PCT/JP2014/077258.
International Preliminary Report on Patentability and Written Opinion dated Apr. 21, 2016, issued by the International Searching Authority in application No. PCT/JP2014/077258.
Communication, dated Feb. 16, 2017, issued by the European Patent Office in counterpart European Patent Application No. 14852695.7.
Kyota, Fujita et al. "A functional deficiency of TERA/VCP/p97 contributes to impaired DNA repair in multiple polyglutamine diseases," Nature Communications, vol. 4; May 7, 2013 (13 pages total).
Tamura, Takuya et al. "P2-r19 DNA damage repair in Spinocerebellar ataxia 1," Abstracts/Neuroscience Research, vol. 71S, Sep. 1, 2011 (1 page).
Li, Guo-Min et al. "Repair of CAG/CTG repeat loop in human cells," The FASEB Journal, vol. 22, No. 1, Apr. 2008 (2 pages total).
Communication, dated Jun. 22, 2017, issued by the European Patent Office in counterpart European Patent Application No. 14852695.7.

* cited by examiner

METHODS FOR TREATING SPINOCEREBELLAR ATAXIA TYPE I USING RPA1

CROSS REFERENCE TO RELATED APPLICATIONS

This application is a National Stage of International Application No. PCT/JP2014/077258 filed Oct. 10, 2014, claiming priority based on Japanese Patent Application No. 2013-214155 filed Oct. 11, 2013.

TECHNICAL FIELD

The present invention relates to an agent for preventing or treating spinocerebellar ataxia. The present invention also relates to a screening method for a candidate compound for preventing or treating spinocerebellar ataxia.

BACKGROUND ART

Spinocerebellar ataxia (SCA) is a disease whose main symptom is ataxia and in which neurons ranging from the cerebellum and brainstem to the spinal cord are gradually disrupted and lost. Among neurodegenerative diseases, the number of patients with SCA is the third largest, following Alzheimer's disease and Parkinson's disease. However, no effective method for treating SCA has been established yet, and the elucidation of its pathology and the development of a method for treating SCA have been regarded as social issues which have to be urgently addressed.

In addition, it is also revealed that various biological abnormalities occur in the SCA pathology. For example, in spinocerebellar ataxia type 1 (SCA1), which is a type of SCA, it has been revealed that RBM17, which has an RNA recognition motif and is also called splicing factor 45 (SPF45), binds to ataxin 1 (ATXN1), which is a cause of SCA1, in a manner dependent on the length of the polyglutamine chain (polyQ) in the protein (NPL 1). In addition, it has been revealed that 14-3-3 binds to a C-terminal region of ATXN1, when phosphorylated by Akt (NPL 2). Moreover, it is also revealed that the binding of 14-3-3 to ATXN1 causes the dephosphorylation of ATXN1 (NPL 3), and the phosphorylation plays an important role in the above-described binding between RBM17 and ATXN (NPL 1). It is also known that the transcriptional repressor CIC/capicua, Sox2-like high mobility group (HMG) protein, HBP-1, and HMG-box transcription factor interact with the AXH domain of ATXN1 (NPL 4). It is also revealed that retinoic acid receptor-related orphan receptor a is involved in Purkinje cell development, and further that the effect is weakened by mutant ATXN1 (NPL 5). It is also known that polyglutamine-binding protein-1 is a constituent of the spliceosome (NPLs 6 and 7), and that polyglutamine-binding protein-1 binds to the polyglutamine chain of ATXN1, and is co-localized with ATXN1 in specific nucleoli (NPL 8).

In addition, the interactions of ATXN1 with various factors cause dysfunctions in splicing and transcription in which these factors are involved, and cause various abnormalities at downstream, finally leading to the typical SCA1 phenotype (NPL 9).

Here, it is known that transcription and splicing are closely related to DNA damage repair. For example, when DNA damage occurs, the transcription is paused until the damaged genomic DNA is repaired, and an influence is exerted also on the alternative splicing. In addition, DNA double-strand breaks (DSBs) are created during the transcription to relax the coiled double-stranded DNA and allow the transcription mechanism to access the coiled double-stranded DNA.

Moreover, DNA damage repair is suggested to be involved also in the SCA1 pathology. For example, it has been revealed that mutant ATXN1, which is a cause of SCA1, reduces the expression of the DNA architectural proteins HMGB1 and HMGB2, which are known to play important roles in various DNA damage repair mechanisms (NPL 10). It is also known that a *Drosophila* homologous protein of RBM17 mentioned above also binds to ATXN1, and is involved in DNA damage repair (NPL 11).

It is suggested that DNA damage repair is involved also in the onset of other types of SCA than SCA1 (NPLs 12 and 13). For example, ataxia telangiectasia is shown to be caused by dysfunctions of the ATM gene, which is involved in the control of the DNA double-strand break repair (DSBR) (NPL 14). In addition, reportedly, ataxia with oculomotor apraxia type 1 (AOA1) is caused by mutations in aprataxin, which is a member of the HIT gene family mainly involved in the single-strand DNA break repair (SSBR) (NPLs 12 and 15 to 17). In addition, the pathology of AOA2 is shown to be associated with mutations in senataxin (NPL 18). Senataxin is thought to resolve DNA-RNA hybrids formed at sites where transcription is paused (NPL 19). In addition, senataxin is an ortholog of yeast RNA helicase, which may be involved in various types of DNA repair, such as transcription coupled repair (NPL 20).

Thus, elucidation of the molecular SCA pathology through transcription, splicing, and further DNA damage repair is extremely important in developing an agent for treating or preventing this disease, or the like.

However, especially, the DNA damage repair is achieved through complex steps, and includes various types such as DSBR, SSBR, base-excision repair (BER), and nucleotide-excision repair (NER). For this reason, it is extremely difficult to elucidate what type of DNA damage repair or what molecule makes a great contribution to the SCA pathology, and no agent for effectively treating or preventing SCA or the like has been developed yet under the current situation.

CITATION LIST

Non Patent Literature

[NPL 1] Lim, J. et al., Nature, 2008, Vol. 452, pp. 713 to 718

[NPL 2] Chen, H. K. et al., Cell, 2003, Vol. 113, pp. 457 to 468

[NPL 3] Lai, S. et al., J Biol Chem, 2011, Vol. 286, pp. 34606 to 34616

[NPL 4] de Chiara, C. et al., FEBS Lett, 2003, Vol. 551, pp. 107 to 112

[NPL 5] Serra, H. G. et al., Cell, 2006, Vol. 127, pp. 697 to 708

[NPL 6] Makarov, E. M. et al., Science, 2002, Vol. 298, pp. 2205 to 2208

[NPL 7] Makarova, O. V. et al., Embo J, 2004, Vol. 23, pp. 2381 to 2391

[NPL 8] Okazawa, H. et al., Neuron, 2002, Vol. 34, pp. 701 to 713

[NPL 9] Orr, H. T., J Cell Biol, 2012, Vol. 197, pp. 167 to 177

[NPL 10] Qi, M. L. et al., Nat Cell Biol, 2007, Vol. 9, pp. 402 to 414

[NPL 11] Chaouki, A. S. et al., PLoS Genet, 2006, 2, e178.

[NPL 12] Rass, U. et al., Cell, 2007, Vol. 130, pp. 991 to 1004

[NPL 13] Gueven, N. et al., Neuroscience, 2007, Vol. 145, pp. 1418 to 1425

[NPL 14] Fernandez-Funez, P. et al., Nature, 2000, Vol. 408, pp. 101 to 106

[NPL 15] Date, H. et al., Nat Genet, 2001, Vol. 29, pp. 184 to 188

[NPL 16] Moreira, M. C. et al., Nat Genet, 2001, Vol. 29, pp. 189 to 193

[NPL 17] Date, H. et al., Biochem Biophys Res Commun, 2004, Vol. 325, pp. 1279 to 1285

[NPL 18] Moreira, M. C. et al., Nat Genet, 2004, Vol. 36, pp. 225 to 227

[NPL 19] Skourti-Stathaki, K. et al., Mol Cell, 2011, Vol. 42, pp. 794 to 805

[NPL 20] Suraweera, A. et al., Hum Mol Genet, 2009, Vol. 18, pp. 3384 to 3396

SUMMARY OF INVENTION

Technical Problem

The present invention has been made in view of the above-described problems of the conventional technologies, and an object of the present invention is to provide a compound which makes it possible to treat or prevent spinocerebellar ataxia and a screening method for a candidate compound for preventing or treating spinocerebellar ataxia.

Solution to Problem

To achieve the above-described object, the present inventors prepared an SCA1 fly model by expressing mutant human ataxin 1 (mutant ATXN1), which is a cause of spinocerebellar ataxia type 1 (SCA1), in *Drosophila*. Moreover, *Drosophila* homologous genes related to DNA repair were overexpressed in this fly model. Then, an in-vivo screening for DNA repair genes involved in an SCA pathology was conducted by using whether the shortened lifespan, which is one of the symptoms in the SCA1 fly model, was recovered as an index.

As a result, RPA1, PNKP, XRCC3, XRCC4, CCNH, POLE, POLH, and PER1 were identified as genes which relieved the SCA pathology. On the other hand, CHK1, LIG3, FEN1, LIG1, ERCC5, XAB2, ERCC2, DMC1, RECQL5, MUS81, EME1, SPO11, and BLM were identified as genes which further shortened the lifespan of the SCA1 fly model, i.e., as genes which aggravated the SCA pathology. These identified genes were genes whose involvement in the pathology of a polyglutamine disease such as SCA had not been known previously.

Moreover, these genes shown to be involved in the SCA pathology were analyzed based on the systems biology. The results showed the presence of core networks connecting these genes. Especially, it has been revealed that RPA1, which exerts the largest influence on the lifespan elongation of the SCA1 fly model, is located at the center of the connection of DNA repair systems such as homologous recombination (HR). On the other hand, regarding the genes involved in the lifespan shortening, it has been revealed that CHK1 receives various signals from BLM, FEN1, and LIG1 directly or indirectly, and hence CHK1 plays an important role in the further shortening of the lifespan of the SCA1 fly model.

Next, RPA1, which exerted the largest influence on the relief of the SCA pathology, and BRCA1 and BRCA2, which are important partners of RPA1 in a DNA repair system based on homologous recombination, were analyzed for the presence or absence of interactions with ATXN1, which is a cause of SCA1. The results have revealed that each of the proteins, RPA1, BRCA1, and BRCA2, can bind to ATXN1 and a mutant thereof. Moreover, it has also been revealed that the aberrant ATXN1 (mutant ATXN1), but not normal ATXN1 (wild-type ATXN1), impairs the intranuclear dynamics of RPA1, which is necessary for the DNA repair, after DNA damage.

In addition, it has been found that overexpression of RPA1 in the SCA1 fly model relieves an eye degeneration state, which is one of the symptoms of the SCA1 fly model.

Moreover, it has been found that overexpression of RPA1 in the cerebellum in an SCA1 mouse model also relieves motor disorder, which is one of the symptoms of the mouse model.

In addition, abnormal entry into the S phase of Purkinje cells of a mutant ATXN1 knock-in mouse has been revealed. This has suggested that the abnormal entry of the Purkinje cells into the S phase induces DNA damage repair in the cells, and eventually induces homologous recombination-type DNA repair based on RPA1, so that the SCA pathology is relieved.

In addition, to chemically or genetically inhibit the function of CHK1, which plays an important role in further aggravation of the SCA pathologies, a CHK1-specific inhibitor was administered to the SCA1 fly model, or siRNA against CHK1 was expressed in the SCA1 fly model. The results showed that the lifespan of the SCA1 fly model was elongated, and the eye degeneration state was relieved. These findings have led to the completion of the present invention. Specifically, the present invention provides the following:

(1) An agent for preventing or treating spinocerebellar ataxia, comprising, as an active ingredient, at least one of the following (a) to (d):

(a) at least one protein selected from the group consisting of RPA1, BRCA1, BRCA2, PNKP, XRCC3, XRCC4, CCNH, POLE, POLH, and PER1 or a nucleic acid encoding the protein;

(b) a compound which enhances expression or activity of at least one protein selected from the group consisting of RPA1, BRCA1, BRCA2, PNKP, XRCC3, XRCC4, CCNH, POLE, POLH, and PER1;

(c) a compound which inhibits binding between ATXN1 and at least one protein selected from the group consisting of RPA1, BRCA1, and BRCA2; and (d) a compound which suppresses expression or activity of at least one protein selected from the group consisting of CHK1, LIG3, FEN1, LIG1, ERCC5, DMC1, XAB2, ERCC2, RECQL5, MUS81, EME1, SPO11 and BLM.

(2) The agent according to item (1), wherein a compound which suppresses activity of CHK1 protein is contained as the active ingredient, and the compound is at least one compound selected from the group consisting of 4-[((3S)-1-azabicyclo[2.2.2]oct-3-yl)amino]-3-(1H-benzimidazol-2-yl)-6-chloroquinolin-2(1H)-one, (S)-1-(5-bromo-4-methyl-2-(morpholin-2-ylmethoxy)phenyl)-3-(5-methylpyrazin-2-yl)urea, 6-bromo-3-(1-methyl-1H-pyrazol-4-yl)-5-(3R)-3-piperidinylpyrazolo[1,5-a]pyrimidine-7-amine, (R)-α-amino-N-[5,6-dihydro-2-(1-methyl-1H-pyrazol-4-yl)-6-oxo-1H-pyrrolo[4,3,2-ef] [2,3]benzodiazepin-8-yl]-cyclohexaneacetamide, 1-(2-((S)-piperidin-3-ylcarbamoyl)-5-(3-fluorophenyl)thiophen-3-yl)urea, XL844, 7-hydroxystaurosporine, (R)—N-(4-(3-aminopiperidin-1-yl)-5-bromo-1H-pyrrolo[2,3-b]pyridin-3-yl)nicotinamide, (R)—N-(4-(3-aminopiperidin-1-yl)-5-bromo-1H-pyrrolo[2,3-b]pyridin-3-yl)isobutylamide, (R)—N-(5-bromo-4-(3-(methylamino)piperidin-1-yl)-1H-pyrrolo[2,3-b]pyridin-3-yl)nicotinamide, (R)—N-(4-(3-aminopiperidin-1-yl)-5-bromo-1H-pyrrolo[2,3-b]pyridin-3-yl)-5-methylnicotinamide, (R)—N-(4-(3-aminopiperidin-1-yl)-5-bromo-1H-pyrrolo[2,3-b]pyridin-3-yl)cyclopropanecarboxamide, (R)—N-(4-(3-aminopiperidin-1-yl)-5-bromo-1H-pyrrolo[2,3-b]pyridin-3-yl)-3-methyl-butanamide, and (R)—N-(4-(3-aminopiperidin-1-yl)-5-bromo-1H-pyrrolo[2,3-b]pyridin-3-yl)-2-cyclopropylacetamide.

(3) A screening method for a candidate compound for preventing or treating spinocerebellar ataxia, the method comprising the following steps (a) to (c):

(a) bringing ATXN1 and at least one protein selected from the group consisting of RPA1, BRCA1, and BRCA2 into contact with each other in the presence of an analyte compound, (b) detecting binding between the ATXN1 and the at least one protein selected from the group consisting of RPA1, BRCA1, and BRCA2; and (c) selecting the compound, if the compound inhibits the binding.

(4) A screening method for a candidate compound for preventing or treating spinocerebellar ataxia, the method comprising the following steps (a) and (b):

(a) applying an analyte compound to a system in which expression or activity of at least one protein selected from the group consisting of RPA1, BRCA1, BRCA2, PNKP, XRCC3, XRCC4, CCNH, POLE, POLH, and PER1 is detectable; and (b) selecting the compound, if the compound enhances the expression or the activity of the protein.

(5) A screening method for a candidate compound for preventing or treating spinocerebellar ataxia, the method comprising the following steps (a) and (b):

(a) applying an analyte compound to a system in which a function of at least one protein selected from the group consisting of CHK1, LIG3, FEN1, LIG1, ERCC5, DMC1, XAB2, ERCC2, RECQL5, MUS81, EME1, SPO11, and BLM is detectable; and (b) selecting the compound, if the compound suppresses expression or activity of the protein.

Note that, in the present invention, the term "spinocerebellar ataxia," which is also referred to as SCD (spinocerebellar degeneration) or SCA (spinocerebellar atrophy), means a neurodegenerative disease in which neurons ranging from the cerebellum and brainstem to the spinal cord are gradually disrupted and lost. Types of spinocerebellar ataxia can be generally classified into two groups, namely, a hereditary group and a nonhereditary group. Examples of the hereditary types include hereditary olivopontocerebellar atrophy, hereditary cortical cerebellar atrophy, Machado-Joseph disease, Friedreich's ataxia, ataxia with oculomotor apraxia type 1 (AOA1), AOA2, hereditary dentatorubral-pallidoluysian atrophy, ataxia telangiectasia, and the like. Examples of the nonhereditary types include olivopontocerebellar atrophy, Shy-Drager syndrome, striatonigral degeneration, and cortical cerebellar atrophy. Moreover, the hereditary types are classified into 31 types (SCA1 to SCA31) according to their causative genes. In this manner, types of spinocerebellar ataxias can be classified into many diseases according to the symptoms, the causative genes, and the like. The major symptom of the SCAs in both the hereditary types of spinocerebellar ataxias and the nonhereditary types of spinocerebellar ataxias is cerebellar or posterior column ataxia, and the types of SCA have common pathological characteristics.

"RPA1" is a protein which is also referred to as RPA70, HSSB, MST075, REPA1, RF-A, or RP-A, and a representative human-derived example thereof comprises an amino acid sequence of SEQ ID NO: 2. Meanwhile, a representative human-derived example of a nucleic acid encoding RPA1 is a nucleic acid comprising the coding region (CDS) as shown in SEQ ID NO: 1.

"BRCA1" is a protein which is also referred to as IRIS, PSCP, BRCC1, PNCA4, RNF53, BROVCA1, or PPP1R53. A representative human-derived example thereof comprises an amino acid sequence of SEQ ID NO: 4. In addition, a representative human-derived example of a nucleic acid encoding BRCA1 is a nucleic acid comprising the CDS as shown in SEQ ID NO: 3.

"BRCA2" is a protein which is also referred to as BRCC2, BROVCA2, FACD, FAD, FAD1, FANCB, FANCD, FANCD1, GLM3, or PNCA2. A representative human-derived example thereof comprises an amino acid sequence of SEQ ID NO: 6. Meanwhile, a representative human-derived example of a nucleic acid encoding BRCA2 is a nucleic acid comprising the CDS as shown in SEQ ID NO: 5.

"PNKP" is a protein which is also referred to as EIEE10, MCSZ, or PNK. A representative human-derived example thereof comprises an amino acid sequence of SEQ ID NO: 8. Meanwhile, a representative human-derived example of a nucleic acid encoding PNKP is a nucleic acid comprising the CDS as shown in SEQ ID NO: 7.

"XRCC3" is a protein which is also referred to as CMM6. A representative human-derived example comprises an amino acid sequence of SEQ ID NO: 10. Meanwhile, a representative human-derived example of a nucleic acid encoding XRCC3 is a nucleic acid comprising the CDS as shown in SEQ ID NO: 9.

A representative human-derived example of "XRCC4" is the protein comprises an amino acid sequence of SEQ ID NO: 12. Meanwhile, a representative human-derived example of a nucleic acid encoding XRCC4 is a nucleic acid comprising the CDS shown in SEQ ID NO: 11.

"CCNH" is a protein which is also referred to as cyclin H, CAK, p34, or p37, and a representative human-derived example thereof comprises an amino acid sequence of SEQ ID NO: 14. Meanwhile, a representative human-derived example of a nucleic acid encoding CCNH is a nucleic acid comprising the CDS shown in SEQ ID NO: 13.

"POLE" is a protein which is also referred to as DNA polymerase epsilon, CRCS12, FILS, or POLE1. A representative human-derived example thereof comprises an amino acid sequence of SEQ ID NO: 16. Meanwhile, a representative human-derived example of a nucleic acid encoding POLE is a nucleic acid comprising the CDS shown in SEQ ID NO: 15.

"POLH" is a protein which is also referred to as DNA polymerase eta, RAD30, RAD30A, XP-V, or XPV. A representative human-derived example thereof comprises an amino acid sequence of SEQ ID NO: 18. Meanwhile, a representative human-derived example of a nucleic acid encoding POLH is a nucleic acid comprising the CDS shown in SEQ ID NO: 17.

"PER1" is a protein which is also referred to as hPER, PER, or RIGUI. A representative human-derived example thereof comprises an amino acid sequence of SEQ ID NO: 20. Meanwhile, a representative human-derived example of a nucleic acid encoding PER1 is a nucleic acid comprising the CDS shown in SEQ ID NO: 19.

"CHK1" is a protein which is also referred to as CHEK1. A representative human-derived example thereof comprises an amino acid sequence of SEQ ID NO: 22 (the protein encoded by the base sequence shown in SEQ ID NO: 21).

"LIG3" is a protein which is also referred to as DNA ligase 3 or LIG2. A representative human-derived example thereof comprises an amino acid sequence of SEQ ID NO: 24 (the protein encoded by the base sequence shown in SEQ ID NO: 23).

"FEN1" is a protein which is also referred to as FEN-1, MF1, or RAD2. A representative human-derived example thereof comprises an amino acid sequence of SEQ ID NO: 26 (the protein encoded by the base sequence shown in SEQ ID NO: 25).

"LIG1" is a protein which is also referred to as DNA ligase 1. A representative human-derived example thereof comprises an amino acid sequence of SEQ ID NO: 28 (the protein encoded by the base sequence shown in SEQ ID NO: 27).

"ERCC5" is a protein which is also referred to as COFS3, ERCM2, UVDR, XPG, or XPGC. A representative human-derived example thereof comprises an amino acid sequence of SEQ ID NO: 30 (the protein encoded by the base sequence shown in SEQ ID NO: 29).

"XAB2" is a protein which is also referred to as HCNP, HCRN, NTC90, or SYF1. A representative human-derived example thereof comprises an amino acid sequence of SEQ ID NO: 32 (the protein encoded by the base sequence shown in SEQ ID NO: 31).

"ERCC2" is a protein which is also referred to as COFS2, EM9, TTD, or XPD. A representative human-derived example thereof comprises an amino acid sequence of SEQ ID NO: 34 (the protein encoded by the base sequence shown in SEQ ID NO: 33).

"DMC1" is a protein which is also referred to as LIM15, dJ199H16.1, DMC1H, or HsLim15. A representative human-derived example thereof comprises an amino acid sequence of SEQ ID NO: 36 (the protein encoded by the base sequence shown in SEQ ID NO: 35).

"RECQL5" is a protein which is also referred to as RECQ5. A representative human-derived example thereof comprises an amino acid sequence of SEQ ID NO: 38 (the protein encoded by the base sequence shown in SEQ ID NO: 37).

"MUS81" is a protein which is also referred to as SLX3. A representative human-derived example thereof comprises an amino acid sequence of SEQ ID NO: 40 (the protein encoded by the base sequence shown in SEQ ID NO: 39).

"EME1" is a protein which is also referred to as FLJ31364 or MMS4 L. A representative human-derived example thereof comprises an amino acid sequence of SEQ ID NO: 42 (the protein encoded by the base sequence shown in SEQ ID NO: 41).

"SPO11" is a protein which is also referred to as CT35, SPATA43, or TOPVIA. A representative human-derived example thereof comprises an amino acid sequence of SEQ ID NO: 44 (the protein encoded by the base sequence shown in SEQ ID NO: 43).

"BLM" is a protein which is also referred to as BS, RECQ2, RECQL2, or RECQL3. A representative human-derived example thereof comprises an amino acid sequence of SEQ ID NO: 46 (the protein encoded by the base sequence shown in SEQ ID NO: 45).

"ATXN1" is a protein which is also referred to as ataxin 1, ATX1, D6S504E, or SCA1. A representative human-derived example thereof comprises an amino acid sequence of SEQ ID NO: 48 (the protein encoded by the base sequence shown in SEQ ID NO: 47).

Advantageous Effects of Invention

The present invention makes it possible to treat or prevent spinocerebellar ataxia, or to provide a candidate compound for treating or preventing spinocerebellar ataxia.

BRIEF DESCRIPTION OF DRAWINGS

The patent or application file contains at least one drawing executed in color. Copies of this patent or patent application publication with color drawings will be provided by the Office upon request and payment of the necessary fee.

In FIG. 15, the upper left panel shows the Western blot analysis results of the RPA1 expression in samples obtained from the mouse and yet-to be subjected to the immunoprecipitation, while the lower left shows the Western blot analysis results of the ATXN1 expression in the samples. The upper right panel shows the Western blot analysis results of the RPA1 expression in precipitates with mouse IgG, an anti-RPA1 antibody, or an anti-ATXN1 antibody ("IP Mouse Normal IgG", "IP Anti-RpA1 (H7)," or "IP Anti-Atxn1 (11NQ)" in FIG. 15), while the two lower right panels show the Western blot analysis results of the ATXN1 expression in the precipitates.

In FIG. 24, the lower panels show images (SEM images) observed under a scanning electron microscope.

DESCRIPTION OF EMBODIMENTS

Figure 1:
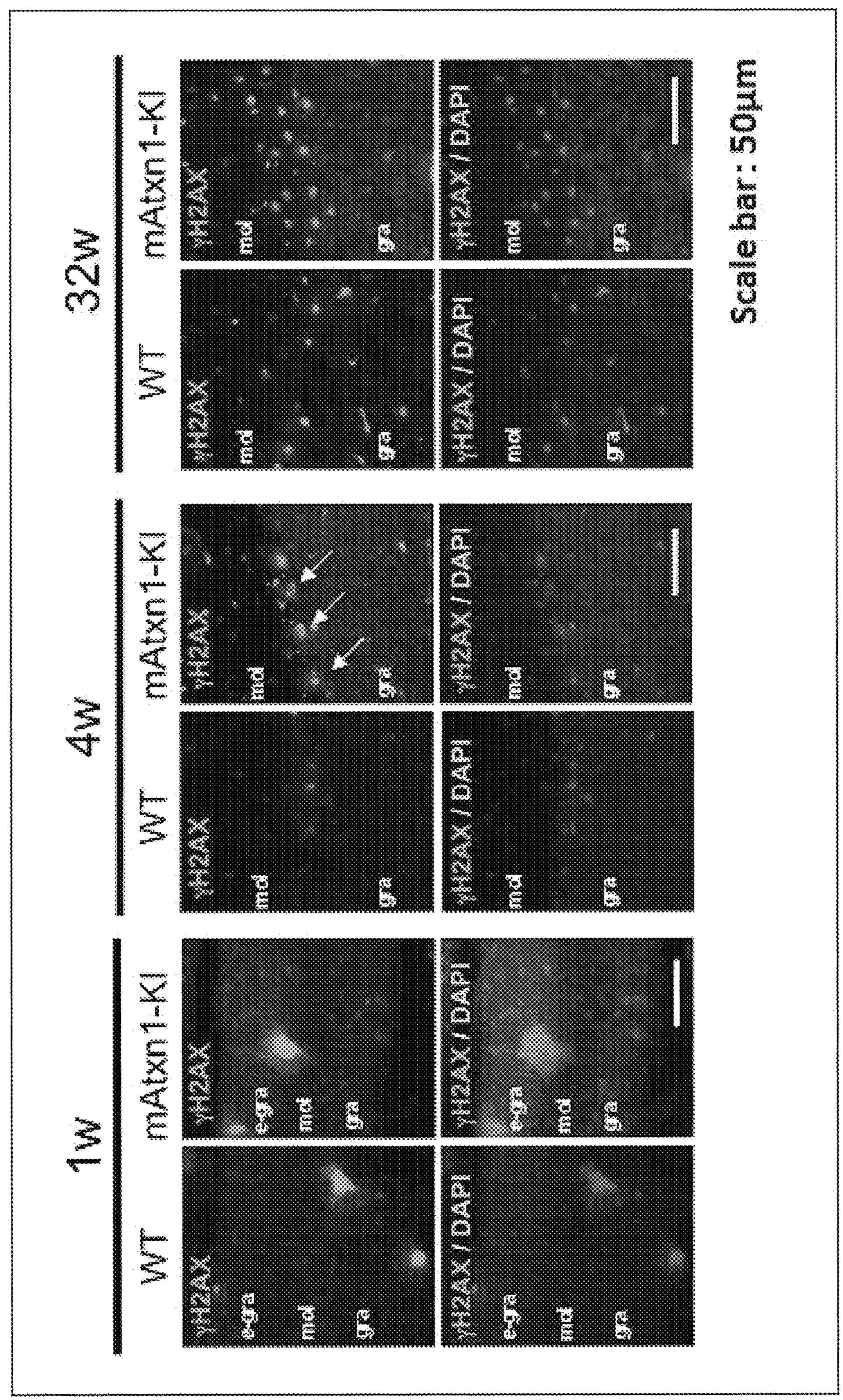
FIG. 1 shows micrographs showing immunohistological analysis results of γH2AX expression in the cerebellum of heterozygous mutant Atxn1-knock-in (mAtxn1-KI) and non-transgenic littermate (WT) mice at 1, 4, and 32 weeks of age. Note that the Atxn1-154Q protein (full-length) was expressed in the mutant Atxn1-knock-in mice. In addition, in the micrographs, "mol" indicates molecular layer, "gra" indicates granular layer, and "e-gra" indicates external granular layer. Arrows indicate activation of γH2AX in Purkinje cells.

<Agent for Preventing or Treating Spinocerebellar Ataxia>

As shown in Examples later, it has been revealed that the overexpression of RPA1, BRCA1, BRCA2, PNKP, XRCC3, XRCC4, CCNH, POLE, POLH, or PER1 in SCA1 fly and SCA1 mouse models relieves their symptoms. Accordingly, the present invention provides an agent for preventing or treating spinocerebellar ataxia, the agent comprising the following (a) as at least one active ingredient:

(a) at least one protein selected from the group consisting of RPA1, BRCA1, BRCA2, PNKP, XRCC3, XRCC4, CCNH, POLE, POLH, and PER1 or a nucleic acid encoding the protein.

Regarding the active ingredient (a) in the agent of the present invention, each of the proteins such as RPA1 does not necessarily have to be the protein (wild-type protein) comprising an amino acid sequence of SEQ ID NO: 2, shown above as its representative example. Instead, the protein may be a mutant protein in which an amino acid is substituted, deleted, or inserted artificially or non-artificially, or may be a modified protein, which undergoes modification, as long as the activity of the protein is retained.

Whether or not the mutant or modified protein retains its activity can be determined by a screening method described later.

The mutant protein may be a protein having an amino acid sequence which is the same as that of the above-described wild-type protein, except that one or multiple amino acids are substituted, deleted, added, and/or inserted. Here, the term "multiple" means generally 50 amino acids or less, preferably 40 amino acids or less, more preferably 30 amino acids or less, further preferably 20 amino acids or less, and particularly preferably 10 amino acids or less (for example, 5 amino acids or less, 3 amino acids or less, 2 amino acids or less, and 1 amino acid). In addition, the substitution of the amino acids is preferably conservative substitution. In the present invention, the term "conservative substitution" means substitution with another amino acid residue having a chemically similar side chain. Groups of amino acid residues having chemically similar amino acid side chains are well known in the technical field to which the present invention pertains.

Alternatively, the mutant protein may be a polypeptide encoded by a nucleic acid which hybridizes with the nucleic acid encoding the above-described wild-type protein under highly stringent conditions. The highly stringent hybridization conditions are, for example, 0.2×SSC and 65° C.

Moreover, the mutant protein may also be a polypeptide having an amino acid sequence with a homology not lower than 80% (for example, not lower than 85%, 90%, 95%, 97%, or 99%) to the amino acid sequence of the above-described wild-type protein. The sequence homology can be determined by using NCBI BLASTP (amino acid level) program (blast.ncbi.nlm.nih.gov/Blast.cgi?PROGRAM=blastp&BLAST_PROGRAMS=blastp&PAGE_TYPE=BlastSearch&SHOW_DEFAULTS=on&LINK_LOC=blasthome) using default parameters of the program.

In addition, a protein added to RPA1 or the like may be an IgG portion of an antibody, a serum albumin portion, or the like. In addition, the protein can be added directly or indirectly to one or each of the N- and C-termini of RPA1 or the like. Moreover, when the protein is indirectly added, a linker having any amino acid sequence can be used.

Examples of the modification include phosphorylation, acetylation, methylation, ADP-ribosylation, ubiquitin bonding, glycosylation, carbonylation, and SUMOylation, as well as covalent bonding with at least one polymer selected from polyethylene glycol, polypropylene glycol, and polyoxyalkylenes.

In addition, the form of the nucleic acid in the present invention may be any, as long as the protein such as RPA1 can be encoded. Specifically, the nucleic acid may be cDNA synthesized from mRNA, genomic DNA, chemically synthesized DNA, or the like. In addition, nucleic acids having any base sequences based on the codon degeneracy are included, as long as the protein such as RPA1 can be encoded.

Moreover, the nucleic acid may be in a vector-inserted form. The vector may be any, as long as the vector is capable of expressing the protein encoded by the nucleic acid in a subject to which the agent of the present invention is administered. Examples of the vector include virus vectors such as lentivirus, retrovirus, adenovirus, adeno-associated (AAV) virus, herpes virus, and Sendai virus vectors; episomal vectors; PiggyBac transposon vectors; and plasmid vectors. Examples of promoters used for these vectors include CAG promoter, SR α promoter, SV40 promoter, LTR promoter, CMV promoter, RSV promoter, and HSV-TK promoter. In addition, the vectors may further contain an enhancer, a poly-A addition signal, and the like, in addition to the promoter.

In addition, those skilled in the art can prepare the nucleic acid by using a gene amplification or genetic recombination technique such as polymerase chain reaction (PCR), restriction enzyme treatment, or site-directed mutagenesis.

Then, the nucleic acid thus prepared is inserted into a suitable vector, and the vector is introduced into a cell-free protein synthesis system (for example, reticulocyte extract or wheat germ extract), followed by incubation. Alternatively, the vector is introduced into suitable cells (for example, *Escherichia coli*, yeast, insect cells, or animal cells), and the obtained transformant is cultured. In these manners, the above-described protein can be prepared. Moreover, the protein can be purified by a known method. Examples of the method include a solvent extraction method, a salting-out and desalination method using ammonium sulfate or the like, a precipitation method using an organic solvent, DEAE-Sepharose, ion-exchange chromatography, hydrophobic chromatography, a gel filtration method, and affinity chromatography.

In addition, the above-described protein and nucleic acid can also be prepared by chemical synthesis using a commercially available synthesizer.

As described earlier, it has been revealed that the overexpression of RPA1 or the like in the SCA1 fly and SCA1 mouse models relieves their symptoms. Accordingly, the present invention provides an agent for preventing or treating spinocerebellar ataxia, the agent comprising the following (b) as at least one active ingredient:

(b) a compound which enhances expression or activity of at least one protein selected from the group consisting of RPA1, BRCA1, BRCA2, PNKP, XRCC4, XRCC4, CCNH, POLE, POLH, and PER1.

As shown in Examples described later, the proteins such as RPA1 are involved in the SCA pathology via DNA repair. Accordingly, the "activity" to be suppressed by a compound described later means an activity related to DNA repair. The activity includes not only functions exerted in a DNA repair mechanism in which RPA1 or the like is involved (DNA synthetic activity, DNA ligase activity, nuclease activity, topoisomerase activity, polynucleotide kinase activity, and the like), but also activities necessary for exhibition of the above-described functions, such as binding capacities to other proteins, modification activities of other proteins (ubiquitin ligase activity, protein kinase activity, and the like), and binding capacities to DNA to be repaired.

The "compound which enhances expression or activity of RPA1 or the like" may be a known compound, or a compound identified by a screening described later.

In addition, a mutation in the base sequence of the nucleic acid encoding the protein to be enhanced by the compound occurs in the natural world (i.e., non-artificially), and, in turn, a mutation occurs also in the amino acid sequence of the protein. Accordingly, each of the proteins is not limited to the protein having the amino acid sequence shown as its representative example above, but a mutant protein which may occur in the natural world may be enhanced by the compound.

As shown in Examples described later, it has been revealed that RPA1, BRCA1, or BRCA2 can bind to ATXN1 or a mutant thereof. Moreover, it has been revealed that mutant ATXN1 contributes to the onset of SCA1 and the progression of symptoms of SCA1 by impairing the intranuclear dynamics of RPA1, which is necessary for DNA repair after DNA is damaged. Accordingly, the present invention provides an agent for preventing or treating spinocerebellar ataxia, the agent comprising the following (c) as at least one active ingredient:

(c) a compound which inhibits binding between ATXN1 and at least one protein selected from the group consisting of RPA1, BRCA1, and BRCA2.

Regarding the active ingredient (c) of the agent of the present invention, each of RPA1, BRCA1, BRCA2, and ATXN1 is not limited to the protein having the amino acid sequence shown as its representative example above, but may be a mutant protein which may occur in the natural world. Especially, ATXN1 is preferably ATXN1 having an abnormally expanded polyglutamine chain, from the viewpoint that it binds more strongly to RPA and BRCA1, and exerts influences on the intracellular dynamics of these proteins, as shown in Examples described later and the like. The "ATXN1 having an abnormally expanded polyglutamine chain" is not particularly limited, as long as the ATXN1 causes SCA1. In general, the ATXN1 is ATXN1 having a polyglutamine chain consisting of 39 or more glutamine residues (preferably, ATXN1 (ATXN1-82Q) having a polyglutamine chain consisting of 82 glutamine residues, ATXN1 (ATXN1-86Q) having a polyglutamine chain consisting of 86 glutamine residues, or ATXN1 (ATXN1-154Q) having a polyglutamine chain consisting of 154 glutamine residues).

The "compound which inhibits binding between ATXN1 and RPA1 or the like" is not particularly limited, and may be a known compound, or a compound identified by a screening described later. Note that, in the present invention, the meaning of the "inhibition" of the binding between ATXN1 and RPA1 or the like includes not only complete inhibition (prohibition) of the binding, but also partial inhibition of the binding.

As shown in Examples described later, it has been revealed that the overexpression of CHK1, LIG3, FEN1, LIG1, ERCC5, XAB2, ERCC2, DMC1, RECQL5, MUS81, EME1, SPO11, or BLM in an SCA1 fly model aggravates the symptoms. Moreover, it has been revealed that the symptoms of the SCA1 fly model are relieved by suppressing the expression and the activity of CHK1 with siRNA against CHK1 and an inhibitor (CHIR-124), respectively. Accordingly, the present invention provides an agent for preventing or treating spinocerebellar ataxia, the agent comprising the following (d) as at least one active ingredient:

(d) a compound which suppresses expression or activity of at least one protein selected from the group consisting of CHK1, LIG3, FEN1, LIG1, ERCC5, XAB2, ERCC2, DMC1, RECQL5, MUS81, EME1, SPO11 and BLM.

As shown in Examples described later, the proteins such as CHK1 are also involved in the SCA pathology via DNA repair, as in the case of RPA1 described above. Accordingly, the "activity" to be suppressed by a compound described later means an activity related to DNA repair, as in the case of the above-described active ingredient (b).

In addition, in the present invention, the meaning of the "suppression" of the expression of a protein includes not only complete suppression (blocking) of the expression, but also partial suppression of the expression.

Regarding the active ingredient (d) of the agent of the present invention, each of CHK1 and the like is not limited to the protein having the amino acid sequence shown as its representative example above, but may be a mutant protein, which may occur in the natural world.

The "compound which suppresses expression or activity of CHK1 or the like" is not particularly limited, and may be a known compound, or a compound identified by a screening described later. Examples of the compound include low-molecular weight compounds capable of binding to CHK1 or the like, RNAs capable of binding to transcription products of genes encoding CHK1 and the like, antibodies to CHK1 and the like, peptides having dominant negative phenotypes to CHK1 and the like.

Examples of the low molecular weight compounds capable of binding to CHK1 include 4-[((3S)-1-azabicyclo[2.2.2]oct-3-yl)amino]-3-(1H-benzimidazol-2-yl)-6-chloroquinolin-2(1H)-one (CAS Registry Number: 405168-58-3, CHIR-124) and (S)-1-(5-bromo-4-methyl-2-(morpholin-2-ylmethoxy)phenyl)-3-(5-methylpyrazin-2-yl)urea (CAS Registry Number: 911222-45-2, IC-83, LY2603618) (see Clin. Cancer Res., 2007, Vol. 13, No. 2, pp. 591 to 602), 6-bromo-3-(1-methyl-1H-pyrazol-4-yl)-5-(3R)-3-piperidinylpyrazolo[1,5-a]pyrimidine-7-amine (CAS Registry Number: 891494-63-6, SCH900776, MK-8776), (R)-α-amino-N-[5,6-dihydro-2-(1-methyl-1H-pyrazol-4-yl)-6-oxo-1H-pyrrolo[4,3,2-ef][2,3]benzodiazepin-8-yl]-cyclohexaneacetamide (CAS Registry Number: 952021-60-2, PF-00477736), 1-(2-((S)-piperidin-3-ylcarbamoyl)-5-(3-fluorophenyl)thiophen-3-yl)urea (CAS Registry Number: 860352-01-8, AZD7762), XL844 (manufactured by Exilixis, see 2008 EORTC, Poster #395 [available on the world wide web at exelixis.com/eortc/posters/EORTC08_395_XL844-002.pdf]) and 7-hydroxystaurosporine (CAS Registry Number: 112953-11-4, UCN-01), as well as (R)—N-(4-(3-aminopiperidin-1-yl)-5-bromo-1H-pyrrolo[2,3-b]pyridin-3-yl)nicotinamide, (R)—N-(4-(3-aminopiperidin-1-yl)-5-bromo-1H-pyrrolo[2,3-b]pyridin-3-yl)isobutylamide, (R)—N-(5-bromo-4-(3-(methylamino)piperidin-1-yl)-1H-pyrrolo[2,3-b]pyridin-3-yl)nicotinamide, (R)—N-(4-(3-aminopiperidin-1-yl)-5-bromo-1H-pyrrolo[2,3-b]pyridin-3-yl)-5-methylnicotinamide, (R)—N-(4-(3-aminopiperidin-1-yl)-5-bromo-1H-pyrrolo[2,3-b]pyridin-3-yl)cyclopropanecarboxamide, (R)—N-(4-(3-aminopiperidin-1-yl)-5-bromo-1H-pyrrolo[2,3-b]pyridin-3-yl)-3-methyl-butanamide, and (R)—N-(4-(3-aminopiperidin-1-yl)-5-bromo-1H-pyrrolo[2,3-b]pyridin-3-yl)-2-cyclopropylacetamide (see International Publication No. WO2010-118390).

The "RNA capable of binding to a transcription product of a gene encoding CHK1 or the like" may be dsRNA (double-stranded RNA), such as siRNA or shRNA (short hairpin RNA), complementary to the transcription product of the gene encoding the protein such as CHK1. The length of the dsRNA is not particularly limited, as long as the dsRNA can suppress the expression of the target gene, and the dsRNA does not have toxicity. The length is, for example, 15 to 49 base pairs, preferably 15 to 35 base pairs, and further preferably 21 to 30 base pairs. The dsRNA does not necessarily have to be completely the same as the base sequence of the target gene, but has a sequence identity of at least 70% or higher, preferably 80% or higher, and further preferably 90% or higher (for example, 95%, 96%, 97%, 98%, and 99% or higher). The sequence identity can be determined using BLAST program.

Another form of the "RNA capable of binding to a transcription product of a gene encoding CHK1 or the like" may be antisense RNA complementary to the transcription product of the gene encoding CHK1 or the like, or RNA (ribozyme) having a ribozyme activity to specifically cleave the transcription product.

Any of the above-described RNAs may be partially or entirely substituted with an artificial nucleic acid such as PNA, LNA, or ENA. In addition, each of these RNAs may be in a form of an expression vector carrying DNA encoding the RNA for the expression of the RNA in a subject to which the agent of the present invention is administered. In addition, those skilled in the art can prepare these RNAs by chemical synthesis using a commercially available synthesizer or the like.

The "antibody to CHK1 or the like" may be a polyclonal antibody or a monoclonal antibody. Moreover, the antibody may be a functional fragment of an antibody. The antibody includes all the classes and subclasses of immunoglobulin. The "functional fragment" of an antibody means a part (partial fragment) of an antibody, which specifically recognizes the protein such as CHK1. Specifically, the "functional fragment" includes Fab, Fab', F(ab') 2, variable region fragment (Fv), disulfide-stabilized Fv, single-chain Fv (scFv), sc(Fv) 2, diabody, polyspecific antibody, polymers thereof, and the like. In addition, the antibody includes chimeric antibodies, humanized antibodies, human antibodies, and functional fragments of these antibodies. Moreover, if necessary, these antibodies may be subjected to alteration of the amino acid sequence, modification, or the like. In addition, those skilled in the art can prepare such an antibody, as appropriate, by a known antibody preparation method.

The "peptide having a dominant negative phenotype to CHK1 or the like" may be a polypeptide which competes with a binding site of the protein such as CHK1 in binding to DNA serving as a substrate or the like in DNA repair, another protein constituting a DNA repair mechanism, or the like (for example, a partial peptide of the protein such as CHK1), or the like.

The agent of the present invention may comprise a pharmacologically acceptable carrier or medium, in addition to the above-described compounds (a) to (d). Examples of the carrier or medium include surfactants, vehicles, coloring agents, flavors, preservatives, stabilizers, buffering agents, suspending agents, tonicity-adjusting agents, binders, disintegrators, lubricants, fluidity-improving agents, corrigents, and the like. However, the carrier or medium is not limited to these examples, but other commonly used carriers or mediums can be used, as appropriate. Specifically, examples of the other commonly used carriers or mediums include light anhydrous silicic acid, lactose, crystalline cellulose, mannitol, starch, carmellose calcium, carmellose sodium, hydroxypropylcellulose, hydroxypropyl methyl cellulose, polyvinylacetal diethylaminoacetate, polyvinylpyrrolidone, gelatin, medium-chain fatty acid triglyceride, polyoxyethylene hardened castor oil 60, white soft sugar, carboxymethyl cellulose, corn starch, inorganic salts, and the like. Moreover, the agent of the present invention may comprise a carrier for introducing the nucleic acid, the protein, or the like into cells. Examples of the carrier include positively charged substances such as cationic liposomes, and lipophilic substances (cholesterol, derivatives thereof, lipids (for example, glycolipids, phospholipids, sphingolipids, and the like), and vitamins such as vitamin E (tocopherols)). In addition, the agent of the present invention may be used in combination with a known pharmaceutical used for treating or preventing SCA.

Targets for which the agent of the present invention can be used include animals including humans. The animals other than humans are not particularly limited, and the non-human targets include domestic animals, poultry, pet animals, experimental animals, and the like. In addition, a preferred target disease of the agent of the present invention is spinocerebellar ataxia type 1 (SCA1). SCA1 means a disease caused by the repetition and expansion of the CAG trinucleotide, which codes glutamine, present in the ataxin 1 (ATXN1) gene. In addition, the number of the CAG trinucleotide repeats is not particularly limited, and is 39 or more, in general.

An administration route of the agent of the present invention is not particularly limited, and examples thereof include intravenous administration, intraarterial administration, intraperitoneal administration, subcutaneous administration, intradermal administration, intratracheal administration, rectal administration, intramuscular administration, administration by infusion, and direct administration to a target site (the cerebellum, brainstem, spinal cord, or the like). The direct administration to a target site is preferable, from the viewpoints of a high therapeutic effect and reduction in amount of the agent administered. The administration to the target site can be carried out with or by, for example, a cannula (a catheter), incision, a drug delivery system, injection, or the like. More specifically, it is possible to employ a method in which a cannula or the like is inserted by a stereotactic surgery method, and the agent of the present invention is administered into the brain through the cannula; a method in which, after craniotomy, a sustained-release drug delivery system (for example, an osmotic pump manufactured by ALZET) containing the agent of the present invention is embedded in the brain; or a method in which the agent of the present invention is introduced into cells in the brain by an electroporation method. In addition, when the agent of the present invention is in a form of a virus vector, it is also possible to directly inject the agent to a target site, as shown in Examples described later.

In addition, when the agent of the present invention is not directly administered into the brain, a method may be employed in which any of the above-described compounds (a) to (d) to which a blood-brain barrier-permeable substance is bound is administered. Note that the blood-brain barrier-permeable substance is, for example, the glycoprotein derived from the rabies virus and consisting of 29 amino acids (see Nature, Jul. 5, 2007, Vol. 448, pp. 39 to 43), but is not limited thereto.

The amount of the agent of the present invention administered and the number of times of the administration can be adjusted, as appropriate, according to the type of the compound serving as the active ingredient, the intended effect, the age and body weight of the patient, and the like. The number of times of the administration can be adjusted, as appropriate, according to the administration amount, the administration route, and the like.

As described above, the present invention also provides a method for treating or preventing spinocerebellar ataxia (SCA) in a subject, the method comprising administering the agent of the present invention to the subject.

A product of the agent of the present invention or a description of the product may be provided with an indication stating that the agent is used for treating or preventing SCA. Here, the "product or description provided with an indication" means that the indication is attached to the main body, container, package, or the like of the product, or the indication is provided in a description, package insert, advertisement, other printed matters, or the like disclosing information of the product.

<Screening Method 1 for Candidate Compound for Preventing or Treating Spinocerebellar Ataxia>

As shown in Examples described later, it has been revealed that ATXN1, which is a cause of SCA1, binds to RPA1, BRCA1, and BRCA2 to adversely affect the functions or intracellular dynamics of RPA1 and the like during DNA repair, and, in turn, contributes to the onset and progression of SCA. Accordingly, based on this finding, the present invention can provide the following screening method.

A screening method for a candidate compound for preventing or treating spinocerebellar ataxia, the method comprising the following steps (a) to (c):

(a) bringing ATXN1 and at least one protein selected from the group consisting of RPA1, BRCA1, and BRCA2 into contact with each other in the presence of an analyte compound;

(b) detecting binding between the ATXN1 and the at least one protein selected from the group consisting of RPA1, BRCA1, and BRCA2; and (c) selecting the compound, if the compound inhibits the binding.

The analyte compound used in the screening method of the present invention is not particularly limited, and examples thereof include expression products of a gene library, a synthetic low-molecular weight compound library, a peptide library, antibodies, substances released from bacteria, extraction liquids and culture supernatants of cells (microorganisms, plant cells, or animal cells), purified or partially purified polypeptides, marine organisms, plant or animal extracts, soil, and a random phage peptide display library.

In addition, RPA1, BRCA1, BRCA2, and ATXN1 used in this screening method are the same as those described for the active ingredient (c) of the agent of the present invention above. A reporter protein (for example, GFP or luciferase), a protein tag for purification (for example, histidine tag, FLAG tag, or GST tag), or the like may be added to these proteins from the viewpoint of ease of the detection of the binding. In addition, these proteins may be partial peptides, unless the binding between ATXN1 and RPA1 or the like is impaired.

In the step (a), ATXN1 and RPA1 or the like, which bind to each other, are brought into contact with each other in the presence of the analyte compound. It is only necessary that the contact be performed under a condition where the binding between ATXN1 and RPA1 or the like is not inhibited, if the analyte compound is absent.

In the step (b), the binding between ATXN1 and RPA1 or the like is detected. A known approach can be employed, as appropriate, for the detection of the binding, without any particular limitation. For example, it is possible to employ immunoprecipitation, yeast two-hybrid system, ELISA, a method using a detector utilizing the surface plasmon resonance phenomenon (for example, BIAcore (manufactured by GE Healthcare)), or a method utilizing FRET (fluorescence resonance energy transfer).

In the step (c), the compound is selected, if the compound inhibits the binding. For example, when immunoprecipitation is employed, evaluation can be made by comparing the amount of RPA1 or the like coprecipitated with ATXN1 precipitated using an antibody specific to ATXN1 in the presence of the analyte compound with the amount (control value) of RPA1 or and the like in the absence of the analyte compound. Specifically, when the amount of RPA1 or the like achieved in the presence of the analyte compound is smaller than that achieved in the absence of the analyte compound (for example, when the amount is 80% or less, 50% or less, or 30% or less of the control value), the analyte compound can be evaluated as a candidate compound for preventing or treating spinocerebellar ataxia. Also when a method other than the immunoprecipitation method is employed for detecting the binding, the evaluation can be made similarly by using the degree of the binding in the absence of the analyte compound as a control value.

<Screening Methods 2 and 3 for Candidate Compound for Preventing or Treating Spinocerebellar Ataxia>

As shown in Examples described later, it has been revealed that the enhancement of the expression of RPA1, BRCA1, BRCA2, PNKP, XRCC3, XRCC4, CCNH, POLE, POLH, or PER1 can relieve the SCA pathology. Accordingly, based on this finding, the present invention can provide the following screening method.

A screening method for a candidate compound for preventing or treating spinocerebellar ataxia, the method comprising the following steps (a) and (b):

(a) applying an analyte compound to a system in which expression or activity of at least one protein selected from the group consisting of RPA1, BRCA1, BRCA2, PNKP, XRCC3, XRCC4, CCNH, POLE, POLH, and PER1 is detectable; and (b) selecting the compound, if the compound enhances the expression or the activity of the protein.

On the other hand, as shown in Examples described later, it has been revealed that the enhancement of the expression of CHK1, LIG3, FEN1, LIG1, ERCC5, XAB2, ERCC2, DMC1, RECQL5, MUS81, EME1, SPO11, or BLM aggravates the SCA pathology. Moreover, it is also revealed that the suppression of the expression or activity of CHK1 reliefs the SCA pathology. Accordingly, based on this finding, the present invention can also provide the following screening method.

A screening method for a candidate compound for preventing or treating spinocerebellar ataxia, the method comprising the following steps (a) and (b):

(a) applying an analyte compound to a system in which a function of at least one protein selected from the group consisting of CHK1, LIG3, FEN1, LIG1, ERCC5, XAB2, ERCC2, DMC1, RECQL5, MUS81, EME1, SPO11, and BLM is detectable; and (b) selecting the compound, if the compound suppresses expression or activity of the protein.

In the two embodiments of the screening method of the present invention, the analyte compound used is not particularly limited, and examples thereof areas described above. In addition, RPA1 and the like and CHK1 and the like used in these screening methods are each the same as that described for the active ingredients (b) and (d) of the agent of the present invention above.

Examples of the "system in which expression of a protein is detectable" used in the step (a) of these screening methods include cells having DNA to which a reporter gene (luciferase gene, CAT gene, GFP gene, or the like) is functionally bound at a downstream of a promoter region of a gene encoding the protein, or an extraction liquid of the cells. Here, the term "functionally bound" means that the promoter region of the gene and the reporter gene are bound in such a manner that the expression of the reporter gene can be induced, when a transcription factor binds to the promoter region of the gene. In addition, the analyte compound is applied to the system, and the activity (light emission by luciferase, acetylation by chloramphenicol, fluorescence of GFP protein, or the like) of the protein encoded by the reporter gene is measured. If the detected activity is higher than that detected in the absence of the analyte compound, the analyte compound is evaluated to have an activity to enhance the expression of the protein. On the other hand, if the detected activity is lower, the analyte compound is evaluated to have an activity to suppress the expression of the protein.

A form of the "system in which the expression of a protein is detectable" other than the above-described reporter system may be a system in which the expression of the protein is directly detected. In the system, an analyte compound is applied to cells expressing the protein, and the expression of the protein in the cells is detected. Then, if the detected expression of the protein is higher than that detected in the absence of the analyte compound, the analyte compound is evaluated to have an activity to enhance the expression of the protein. On the other hand, if the expression is lower, the analyte compound is evaluated to have an activity to suppress the expression of the protein. When the expression of the protein itself is detected for this detection of the expression of the protein, an ELISA method, radioimmunoassay, a Western blotting method, an immunoprecipitation method, or the like can be employed. Meanwhile, when the expression of the protein is detected based on the expression of the gene at the transcription level, a northern blotting method, a RT-PCR method, a dot blotting method, or the like can be employed.

In addition, those skilled in the art can construct the "system in which activity of the protein is detectable" used in the step (a) of these screening methods by obtaining and referring to, as appropriate, information on the activity of the protein used as an index in DNA repair, and on methods for evaluating and measuring the activity from a literature database or the like (for example, PubMed [available on the world wide web at ncbi.nlm.nih.gov/pubmed]). Examples of such evaluation (measurement) are as follows.

When the protein used as the index is RPA1, the activity of the protein can be evaluated (determined) by, for example, detecting the binding of the protein to single-stranded DNA (see Nature, Jan. 9, 1997, Vol. 385, No. 6612, pp. 176 to 181).

When the protein used as the index is BRCA1, the activity of the protein can be evaluated (determined) by detecting, for example, the E3 ubiquitin ligase activity of the protein (see EMBO J., Dec. 16, 2002, Vol. 21, No. 24, pp. 6755 to 6762).

When the protein used as the index is BRCA2, the activity of the protein can be evaluated (determined) by detecting, for example, the binding of the protein to RAD51 or PALB2 (see Nature, Mar. 31, 2005, Vol. 434, No. 7033, pp. 598 to 604, and Mol Cell, Jun. 23, 2006, Vol. 22, No. 6, pp. 719 to 729).

When the protein used as the index is PNKP, the activity of the protein can be evaluated (determined) by detecting, for example, the polynucleotide kinase activity by using oligo (dT) as a substrate (see J Biol Chem., Aug. 20, 1999, Vol. 274, No. 34, pp. 24176 to 24186).

When the protein used as the index is XRCC3, the activity of the protein can be evaluated (determined) by detecting, for example, the binding of the protein to RAD51 (see Mol Cell, May, 1998, Vol. 1, No. 6, pp. 783 to 793).

When the protein used as the index is XRCC4, the activity of the protein can be evaluated (determined) by detecting, for example, the binding of the protein to ligase 4 and the binding of the protein to DNA (see Cell, Dec. 29, 1995, Vol. 83, No. 7, pp. 1079 to 1089).

When the protein used as the index is CCNH, the activity of the protein can be evaluated (determined) by detecting, for example, the binding of the protein to CDK7 (see Nature, Mar. 16, 1995, Vol. 374, No. 6519, pp. 283 to 287).

When the protein used as the index is POLE, the activity of the protein can be evaluated (determined) by detecting, for example, the DNA synthetic activity of the protein (see Proc Natl Acad Sci USA, September, 1990, Vol. 87, No. 17, pp. 6664 to 6668).

When the protein used as the index is POLH, the activity of the protein can be evaluated (determined) by detecting, for example, the DNA synthetic activity of the protein or the binding of the protein to RAD51 (see Mol Cell, Dec. 9, 2005, Vol. 20, No. 5, pp. 783 to 792).

When the protein used as the index is PER1, the activity of the protein can be evaluated (determined) by detecting, for example, the binding of the protein to ATM or CHK2 (see Mol Cell, May 5, 2006, Vol. 22, No. 3, pp. 375 to 382).

When the protein used as the index is CHK1, the activity of the protein can be evaluated (determined) by detecting, for example, phosphorylation of CDC25A achieved by the protein or decomposition of CDC25A induced by the phosphorylation (see Science, May 26, 2000, Vol. 288, No. 5470, pp. 1425 to 1429, and Proc Natl Acad Sci USA, Nov. 12, 2002, Vol. 99, No. 23, pp. 14795 to 14800).

When the protein used as the index is LIG3, the activity of the protein can be evaluated (determined) by detecting, for example, the ligation activity of the protein (see Mol Cell Biol., June, 1995, Vol. 15, No. 6, pp. 3206 to 3216).

When the protein used as the index is FEN1, the activity of the protein can be evaluated (determined) by detecting, for example, the flap structure-removing activity of the protein by using double-stranded DNA having 5'-end overhanging structure as a substrate (see Genomics, Jan. 1, 1995, Vol. 25, No. 1, pp. 220 to 225).

When the protein used as the index is LIG1, the activity of the protein can be evaluated (determined) by detecting, for example, the ligation activity of the protein (see Proc Natl Acad Sci USA, September, 1990, Vol. 87, No. 17, pp. 6679 to 83).

When the protein used as the index is ERCC5, the activity of the protein can be evaluated (determined) by detecting, for example, the endonuclease activity of the protein by using partially double-stranded DNA having a bubble structure as a substrate (see Nature, Sep. 29, 1994, Vol. 371, No. 6496, pp. 432 to 435).

When the protein used as the index is XAB2, the activity of the protein can be evaluated (determined) by detecting for example, the interaction between the protein and XPA, CSA, CSB, or RNA polymerase II (see J Biol Chem., Nov. 10, 2000, Vol. 275, No. 45, pp. 34931 to 34937).

When the protein used as the index is ERCC2, the activity of the protein can be evaluated (determined) by detecting, for example, the binding of the protein to p44 or the 5'→3' helicase activity induced by the binding (see Nat Genet., October, 1998, Vol. 20, No. 2, pp. 184 to 188).

When the protein used as the index is DMC1, the activity of the protein can be evaluated (determined) by detecting, for example, the binding of the protein to single-stranded DNA or a gap structure of double-stranded DNA or the binding of the protein to RAD51 (see EMBO J., Nov. 15, 1999, Vol. 18, No. 22, pp. 6552 to 6560).

When the protein used as the index is RECQL5, the activity of the protein can be evaluated (determined) by detecting, for example, the binding of the protein to RAD51 (see Genes Dev., Dec. 1, 2007, Vol. 21, No. 23, pp. 3073 to 3084).

When the protein used as the index is MUS81 or EME1, the activity of the protein can be evaluated (determined) by detecting, for example, the endonuclease activity of a complex comprising MUS81 and EME1 (see J Biol Chem., Jun. 13, 2003, Vol. 278, No. 24, pp. 21715 to 21720).

When the protein used as the index is SPO11, the activity of the protein can be evaluated (determined) by detecting, for example, the type 2 topoisomerase activity of the protein (see Nature, Aug. 18, 2005, Vol. 436, No. 7053, pp. 1053 to 1057).

When the protein used as the index is BLM, the activity of the protein can be evaluated (determined) by detecting, for example, the binding of the protein to topoisomerase IIIα (see J Biol Chem., Mar. 31, 2000, Vol. 275, No. 13, pp. 9636 to 9644, and Hum Mol Genet., Jun. 1, 2001, Vol. 10, No. 12, pp. 1287 to 1298).

Then, the thus obtained evaluation (measurement) results are compared between the case of detection with the analyte compound applied and the case of detection in the absence of the analyte compound. Based on this comparison, those skilled in the art can determine that the analyte compound is a compound which enhances the activity of the protein or a compound which suppresses the activity of the protein according to the type of the activity of the protein employed as the index.

Note that, for example, when the system is cells, the "application" of the analyte compound to the system can be achieved by contact of the analyte compound with the cells, introduction of the analyte compound into the cells, or the like. Meanwhile, when the system is an extraction liquid from cells, the "application" of the analyte compound to the system can be achieved by adding the analyte compound to the extraction liquid.

In addition, in the screening method of the present invention, candidate compounds for preventing or treating spinocerebellar ataxia selected by any of the above-described screening methods 1, 2, and 3 can be further narrowed down by administering the compounds to SCA model animals and using the relief of the symptoms of the model animals as an index. Examples of the SCA model animals include animals (*Drosophila*, nematode, mouse, marmoset, and the like) into which an SCA causative gene (ATXN1-82Q, ATXN1-86Q, ATXN1-154Q, or the like) is introduced, as shown in Examples described later.

EXAMPLES

Hereinafter, the present invention is described more specifically on the basis of Examples; however, the present invention is not limited to Examples below. In addition, methods of experiments employed in the examples and the like are as follows.

<Immunohistochemical Analysis of *Drosophila*>

The proboscis, wings, legs, and abdomen were removed from adult female *Drosophila*, and the residual head and thorax were fixed by immersion in 4% paraformaldehyde-containing phosphate buffered saline (PBS) for 30 minutes on ice. The fixed flies were stored in 30% sucrose-containing PBS at 4° C. overnight or longer. Next, after the heads were frozen in dry ice/n-hexane, horizontal sections were prepared at intervals of 10 mm with a cryostat microtome, and stained with an anti-histone H2Av pSer137 antibody (manufactured by Acris, Catalog No: AP09307PU-N, derived from rabbit, diluted 1:200 before use) or an anti-ataxin-1 (H21) antibody (manufactured by Santa Cruz, derived from goat, diluted 1:100 before use) and an Alexa Fluor 488-labeled secondary antibody or a Cy5-labeled secondary antibody (manufactured by Jackson, diluted 1:50 before use). Note that all samples were mounted in a mounting medium for Fluorescent DNA labeling (Trade name: VectaShield with DAPI Mounting Medium, manufactured by Vector Laboratories), and analyzed.

<Immunohistochemical Analysis of Mice>

Fresh brains of Atxn1-154Q-KI (knock-in) heterozygous mice (32-week old) were fixed in 4% paraformaldehyde—containing phosphate buffer and embedded in paraffin. Sections (thicknesses: 5 to 10 μm) prepared from the brains were deparaffinized by immersion in xylene, and rehydrated with ethanol stepwise. Subsequently, the sections were immersed in 10 mM citrate buffer (pH 6.0), and boiled in a microwave oven three times. Then, the sections were kept at room temperature for 30 minutes. To block nonspecific binding, the sections were incubated in PBS containing 1% bovine serum albumin and 0.01% (V/V) Triton X-100 for 30 minutes. The samples thus prepared were incubated overnight at 4° C. with a primary antibody, and then incubated for 1 hour at room temperature with a secondary antibody. Next, after a treatment with DAPI for 2 minutes, Fluoromount was placed on the brain samples, which were further covered with coverslips. Then, cells in the samples thus prepared were visualized with a confocal microscope (LSM510 manufactured by Carl Zeiss).

Note that primary antibodies used for the immunohistochemical analyses and the dilution conditions of these antibodies were as follows:

anti-CAG antibody (HD1, derived from rabbit, gift from Dr. Wanker, diluted 1:100 before use), anti-Atxn1 antibody (11NQ, clone N76/8, derived from mouse, manufactured by Millipore, diluted 1:100 before use), anti-RpA1 antibody (H-7, derived from rabbit, manufactured by Santa Cruz Biotechnology, diluted 1:100 before use), anti-RpA1 antibody (mouse monoclonal antibody, manufactured by Calbiochem, diluted 1:100 before use), anti-BRCA1 antibody (C-20, derived from rabbit, manufactured by Santa Cruz Biotechnology, diluted 1:100 before use), anti-BRCA2 antibody (ab123491, derived from rabbit, manufactured by Abcam, diluted 1:100 before use), and anti-H2AX antibody (Ser139, derived from mouse, manufactured by Millipore, diluted 1:500 before use).

Meanwhile, secondary antibodies used for the immunohistochemical analyses and the dilution conditions of the antibodies were as follows.

Alexa Fluor 488-labeled anti-mouse antibody (manufactured by Molecular Probes, diluted 1:1000 before use), Cy3-labeled anti-rabbit antibody (manufactured by Jackson Laboratory, diluted 1:1000 before use).

<Immunoblotting Analysis of *Drosophila*>

Samples for Western blotting were prepared as follows. Specifically, 25 female flies were dissolved in 50 μL of lysis buffer containing 62.5 mM Tris/HCl (pH 6.8), 2% (w/v) SDS, 2.5% (v/v) 2-mercaptoethanol, 5% (v/v) glycerin, and 0.0025% (w/v) bromophenol blue. Then, the obtained samples were each fractionated by SDS-PAGE, and then transferred onto Immobilon-P Transfer Membrane (manufactured by Millipore) by a semi-dry method. Next, the membranes were subjected to a blocking treatment with 5% milk-containing Tween 20 (TBST) (10 mM Tris/Cl, pH 8.0, 150 mM NaCl and 0.05% Tween 20), and incubated with a primary antibody overnight at 4° C. Primary antibodies used in the immunoblotting analysis and the dilution conditions of the antibodies were as follows:

mouse anti-RPA-70 (H-7, manufactured by Santa Cruz, diluted 1:200 before use), mouse anti-actin (C4, manufactured by Chemicon, diluted 1:1000 before use).

Next, the membranes were incubated with horseradish peroxidase (HRP)-labeled anti-mouse IgG (manufactured by GE Healthcare) diluted 1:10000 for 1 hour at room temperature. Finally, target molecules were visualized with an enhanced chemiluminescence WB detection system (ECL, manufactured by GE Healthcare).

<Immunoblotting Analysis of Primary Neurons>

Samples for Western blotting were prepared as follows. Specifically, cerebellar granule neurons cultured for 4 days after introduction of a plasmid DNA described later were collected. The collected neuron samples were washed three times with ice-cold PBS, and dissolved in a lysis buffer containing 62.5 mM Tris/HCl (pH 6.8), 2% (w/v) SDS, 2.5% (v/v) 2-mercaptoethanol, and 5% (v/v) glycerin. The protein concentrations in the thus prepared solutions were quantified by the BCA method using Micro BCA Protein Assay Reagent Kit (manufactured by Pierce Chemical).

Primary and secondary antibodies for the immunoblotting analysis and the dilution conditions of the antibodies were as follows:

mouse antiphospho-histone H2AX (γH2AX) (Ser-139, manufactured by Millipore, diluted 1:750 before use), anti-mouse polyglutamine (IC2) antibody (MAB1574, manufactured by Chemicon, diluted 1:2000 before use), anti-goat Atxn1 antibody (H-21, manufactured by Santa Cruz Biotechnology, diluted 1:1000 before use), mouse anti-glyceraldehyde phosphate dehydrogenase antibody (GAPDH, manufactured by Millipore, diluted 1:10000 before use), horseradish peroxidase (HRP)-labeled anti-mouse IgG antibody (GE Healthcare, manufactured by Amersham), and HRP-labeled anti-goat IgG antibody (manufactured by Dako, diluted 1:3000 before use).

Note that each antibody was diluted with 5% skimmed milk-containing TBST (Tris-buffered saline containing Tween-20).

<Fly Stocks and Rearing Conditions>

All flies were raised on corn-meal medium (9.2% corn-meal, 3.85% yeast, 3.8% sucrose, 1.05% potassium tartrate, 0.09% calcium chloride, 7.6% glucose, 2.416% nipagin, and 1% agar). In addition, all the flies were maintained at 25° C. and humidity of 60%±10% under a 12:12-hour light-dark cycle, unless otherwise noted.

The GS line flies described later were obtained from *Drosophila* Genetic Resource Center in Kyoto, Japan. Note that, for the transgenic flies hAtxn1-82Q (y1w1118UAS: Atxn1-82Q), UAS-mKu70, and OK6-Ga14, and their genetic control strain, Cantonised w1118 strain w (CS10), see NPLs 19 and 44. In addition, the Cantonised w1118 strain w (CS10) was the parental strain of all the transgenic flies. In addition, RNAi lines RpA70 (9633R-3) and grp (17161R-2) were obtained from National Institute of Genetics in Mishima, Japan.

Virgin females for each crossing were collected within 8 hours after eclosion, and maintained in maximum numbers of 20 per vial for 3 to 4 days before being used in the crossing.

In experiments on the lifespan described later, flies of the genotype $y^1w^{1118}$UAS-Atxn1-82Q/+; +/OK6-GAL4; +/+ were used as positive controls, while flies of the genotypes $y^1w^{1118}$UAS-Atxn1-82Q/+;+/+;+/+ and +/+;+/OK6-GAL4;+/+ were used as negative controls. In addition, all the flies used were virgin females.

<Screening Method for Factors Contributing to SCA Pathology Among DNA Damage Repair Genes>

First, *Drosophila* genes which were homologous to human DNA damage repair genes and which were to be subjected to a screening described later were extracted. Specifically, to extract available homologous genes of *Drosophila* related to DNA damage repair, the latest comprehensive list of human DNA repair genes (human DNA repair genes available in the list of human DNA repair genes disclosed by Wood R D of the University of Texas MD Anderson Cancer Center (sciencepark.mdanderson.org/labs/wood/dna_repair_genes.html)) were compared with NCBI HomoloGene.

Next, the homologous genes of *Drosophila* related to DNA damage repair were searched in FlyBase (flybase.org). Then, *Drosophila* overexpressing the genes were prepared by selection from the mutant group prepared based on the gene search (GS) system provided by *Drosophila* Genetic Resource Centre.

Note that the GS system is a method for the efficient detection and rapid molecular identification of genes in *Drosophila*. In the method, a GS vector, which is based on the P element, has UAS, a core promoter, and a marker gene "mini-white," and is to be inserted into the *Drosophila* genome at random. Then, the P element is inserted near a target gene (a DNA repair gene in this screening). By crossing a transgenic fly of the GS line in which the P element is inserted with flies bearing GAL4 driver, flies in which the gene is overexpressed can be obtained (see Toba, G. et al., Genetics, 1999, Vol. 151, pp. 725 to 737).

In this respect, the SCA1 fly model crossed with the GS line was prepared by introducing not only the human Atxn182Q (hAtxn182Q) gene, which is a cause of SCA1, but also an OK6-GAL4 driver.

Then, a screening was performed by using the lifespan-shortening, which is one of the pathologies of SCA1, as an index in *Drosophila* obtained by crossing the thus prepared GS line with the SCA1 fly model.

Specifically, experiments on lifespan were conducted at 25° C. and a humidity of 60±10% under a 12:12-hour light-dark cycle using the same corn-meal medium as that used to create the final generation. In addition, the flies used in the experiments were anesthetized with ether only on the first day of their lives for selection purposes. In addition, 20 flies were maintained per vial and transferred to fresh medium every 2 to 3 days. Then, dead flies were counted and removed every 2 to 3 days. This experiment was conducted two to three separate times. Note that any flies that escaped were excluded from the subjects of the experiment. In addition, based on the data thus obtained, the median and average value of the lifespans were calculated, and the presence or absence of any influence of the DNA damage repair gene on the SCA pathology was evaluated by using the numeric values as indices.

<Systems Biology Analyses>

Systems biology analyses described later were performed by using Ingenuity-IPA software (manufactured by Ingenuity Systems, Inc.) based on human databases. Note that, in a path-explorer analysis (shortest+1), a novel path appears when two genes are connected to the same new molecule.

In addition, genes found in the in-vivo screening and the path-explorer analysis were subjected to core analysis to deduce the signal transduction pathways containing the genes found in the in-vivo screening at a high frequency. Moreover, an enrichment analysis was performed by Fisher's exact test with the B-H multiple test correction to calculate q values. Note that, for the core analysis, eight popular databases (BIND, BIOGRID, Cognia, DIP, INTACT, Interactome studies, MINT, and MIPS) related to protein-protein interactions (PPI) and the Ingenuity original database based on research papers, "Indirect Interactions"

(miRecords, TarBase, TargetScan Human, Clinical Trials.gov, Gene Ontology, GVKBiosciences, KEGG, miRBase, MGD, and Obesity Gene Map Database) were used.

<Plasmid Construction>

For pDsRed-monomer C1, Atxn1-86Q-pDsRed, myc-Atxn1-33Q, and myc-Atxn1-86Q, see Fujita, K. et al., Nat Commun, 2013, 4, 1816.

For construction of EGFP-RpA1, cDNA fragments encoding the full-length of RpA1 were amplified by PCR using B6 wild-type mouse embryonic brain RNA, and subcloned by insertion between the EcoRI and XhoI recognition sites of pLVSIN-CMV-pur (manufactured by Takara). In addition, the cDNA fragments were subcloned by insertion between the EcoRI and BamHI recognition sites of pEGFP-C1 (manufactured by Takara) in the same manner as described above.

<Laser Microirradiation>

Laser microirradiation and signal acquisition from the DNA damaged areas were performed based on the method described in Fujita, K. et al., Nat Commun, 2013, 4, 1816. Specifically, U2OS cells cultured on 25-mm coverslips were transfected with RpA1-EGFP and with pDsRed-monomer C1 or Atxn1-86Q-pDsRed. Twenty four hours after the transfection, the cells were treated with 2 μM Hoechst 33258 (manufactured by Dojindo) for 20 minutes to facilitate the introduction of DNA double-strand breaks (DSBs). By using a microscope (LSM510META, manufactured by Carl Zeiss) equipped with software (AIM4.2, manufactured by Carl Zeiss), rectangular areas located at the cell nuclei were irradiated with UV (maximum power: 30 mW, laser output: 75%, wavelength: 405 nm, iteration: 5, pixel time: 12 μsec, zoom 6). Then, time-lapse images were obtained every 30 seconds. In addition, regions of interest (ROI) matching completely with the bleached areas were determined using Adobe Photoshop CS3. In addition, the average values of signal intensities per pixel of RpA1 in the ROIs were obtained. The signal intensities were normalized by those of the non-irradiated areas. The data are shown in terms of normalized fluorescence units.

<Chemical Therapy on hSCA1 *Drosophila*>

Figure 29:
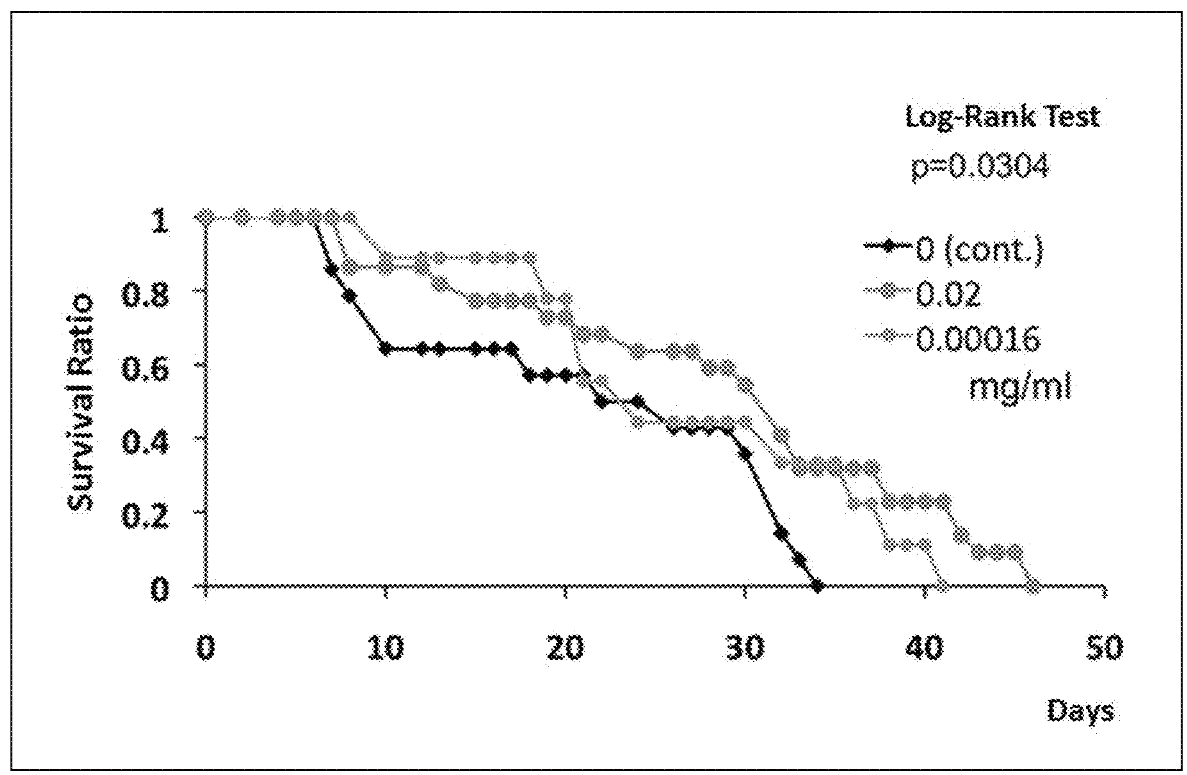
FIG. 29 is a graph showing the results of a lifespan analysis of OK6>SCA1 flies fed on media supplemented with a CHK1 inhibitor (CHIR-124). The statistical analysis of the average values of the lifespan was performed by log-rank test. In addition, the results of this analysis showed that the feeding on a medium supplemented with 0.02 mg/mL of CHIR-124 ameliorated the lifespan-shortening in the SCA1 fly model ($p=0.0304$).

A CHK1-specific inhibitor, CHIR-124 (manufactured by AXON MEDCHEM), was dissolved at 5 mg/mL in 1N hydrogen chloride and diluted to multiple concentrations with 0.05 N solution. Three milliliters of each solution was added to 1 g of *Drosophila* medium to achieve the final concentration shown in FIG. 29. Note that the medium used here was a 1:1 mixture of Instant *Drosophila* medium D7670 (manufactured by Sigma Aldrich) and Formula 4-24 Instant *Drosophila* medium (manufactured by Calolina). As a control, a medium to which an equal amount of 0.05 N hydrogen chloride solution was added was also prepared.

<Immunoprecipitation (IP)>

Hela cells ($2\times10^6$) were plated on 10-cm dishes, and transfected with a plasmid for expressing a protein described later by using Lipofectamine 2000 (manufactured by Invitrogen) according to the manual. Then, the cells were incubated for 36 hours. After washing with PBS twice, cells were collected from each dish, and were homogenized in 2 mL TNE buffer (10 mM Tris-HCl, pH 7.5, 150 mM NaCl, 1 mM ethylenediaminetetraacetic acid (EDTA), Nonidet P-40). Then, the homogenate was incubated at 4° C. with rotation. Thirty minutes after the start of the rotation, the homogenate was centrifuged at $1\times10^4$ g for 20 minutes, and the supernatant was collected. The collected supernatant was incubated with protein G agarose beads (manufactured by GE Healthcare) for 2 hours at 4° C. with rotation. After the beads were removed, the lysate was incubated with 2 to 10 μg of anti-Myc antibody, anti-RPA1 antibody, anti-BRCA1 antibody, or anti-BRCA2 antibody at 4° C. overnight with rotation. After that, the lysate was incubated with protein G agarose beads for further 2 hours. The beads were washed three times with 500 μL of TNE buffer, followed by dissolution into SDS-polyacrylamide gel electrophoresis sample buffer. The solution was fractionated by SDS-PAGE, and then subjected to Western blotting.

In addition, the brains of mice (20-week old) were homogenized in TNE buffer, and centrifuged at 2,000×g for 1 minute at 4° C. Then, the obtained supernatants were immunoprecipitated by the same method as that for the Hela cells.

Note that 400 μg of protein was incubated with anti-RPA1 antibody (H-7, manufactured by Santa Cruz Biotechnology, diluted 1:20 before use) or anti-Atxn1 antibody (11NQ, clone N76/8, manufactured by Millipore, diluted 1:100 before use).

In addition, for the Western blotting, the following primary antibodies were used:

anti-Myc antibody (9E10, manufactured by Santa Cruz Biotechnology, diluted 1:500), anti-RPA1 antibody (H-7, manufactured by Santa Cruz Biotechnology, diluted 1:100), anti-RPA1 antibody (B-10, manufactured by Santa Cruz Biotechnology, diluted 1:1000 before use for mouse samples), anti-BRCA1/2 antibody (manufactured by Abcam, diluted 1:2000), anti-Atxn1 antibody (11NQ, clone N76/8, manufactured by Millipore, diluted 1:2000). In addition, HRP-labeled anti-mouse IgG or HRP-labeled anti-rabbit IgG (manufactured by Amersham) was diluted 1:3000 before use.

<Gene Therapy on SCA1 Mouse Model>

Atxn1-154Q-KI mice were used as an SCA1 mouse model. RPA was overexpressed in the cerebellum of the mice to evaluate the therapeutic effect of RPA.

Specifically, first, an adeno-associated virus (AAV) vector (hereinafter, also referred to as RPA1-AAV) in which an expression cassette containing a human immediate-early promoter (CMV promoter), human growth hormone first intron, cDNA encoding RPA, woodchuck hepatitis virus posttranscriptional regulatory element (WPRE), and an SV40 polyA signal sequence in this order was inserted between the inverted terminal repeats of the AAV3 genome was prepared in a usual manner. Note that transfection and purification of this vector were performed according to the methods described in Li X G. et al., Mol. Ther., 2006, Vol. 1, pp. 160 to 166.

Then, the obtained virus vector thus prepared was injected into the cerebellar surface of the Atxn1-154Q-KI mice by the method described below. Each of the mice at weeks of age was anesthetized by intraperitoneal administration of Nembutal, and fixed onto stereotaxic instruments (manufactured by Narishige). The forehead of the mouse was tilted at 20°, and a hole with a diameter of 1 mm was made using an ELA steel bar (manufactured by Shofu) at −9.2 mm from the bregma, ±0 mm lateral to the midline. Subsequently, a glass syringe was inserted by 3.5 mm from the outer surface of the bone hole along the internal surface of the occipital bone. Then, 8 μL of an RPA1-AAV virus solution (~$1\times10^{12}$ particles) was injected four different positions in total (positions at 60°, 90°, 270°, and 330°, clockwise from the anterior to posterior). At each position, 2 μL of the RPA1-AAV virus solution was injected by using a micropump (manufactured by Narishige) at 0.5 μL/min. This method enables an efficient supply of a virus vector to the cerebellar surface with good reproducibility. In addition, Atxn1-154Q-KI mice in which an AAV vector (hereinafter, also referred to as GFP-AAV) having cDNA encoding GFP inserted therein instead of RPA was injected into the cerebellar surface were prepared as a negative control group in the same manner as described above.

<Mouse Behavioral Test>

Mice were segregated by sex, housed at 2 to 5 per cage, provided with water and rodent feed, and maintained in a 12:12-hour light/dark cycle. All the tests were performed during the light period (10:00 to 19:00) using male mice between 5 to 40 weeks of age.

In a rotarod test, each mouse was placed on a rotarod (rotation speed: 3.5 rpm), and the rotation speed was lineally increased to 35 rpm in 300 seconds, and then kept at a constant speed (35 rpm) up to 600 seconds. This test was performed four times a day for three consecutive days. The average time before the mouse fell off from the rotarod was calculated for every testing day.

Example 1

<Confirmation of DNA Damage in Spinocerebellar Ataxia (SCA)>

The present inventors have revealed that Ku70, which is an important molecule for the DNA double-strand break (DSB)-type DNA repair, restores the shortened lifespan and further improves motor performance of a human Huntington's disease (HD) *Drosophila* model (UAS-Htt103Q/+: OK6-GAL4/+*Drosophila*) (see Tamura, T. et al., PLoS One, 2011, 6, e27408). In addition, the present inventors have also revealed that the function of TERA/VCP/p97, which is another molecule involved in the DSB-type DNA repair, is inhibited in various polyglutamine diseases, and the supplementation of this protein relieves the symptoms of the *Drosophila* model. Moreover, the present inventors have revealed that DSBs are increased in cerebellar neurons of a spinocerebellar ataxia type 1 (SCA1) mouse model (see Fujita, K. et al., Nat Commun, 2013, 4, 1816).

As described above, a relation is suggested between DNA damage and polyglutamine diseases, such as SCA and Huntington's disease, caused by the aberrant expansion of the polyglutamine chain. Moreover, the present inventors have also shown that the symptoms of Huntington's disease and the like are relieved by factors involved in the damage repair. In addition, DSB is known to be DNA damage generally occurring at the final stage in various DNA damage cascades (see Bohgaki, T. et al., Genome Integr, 2010, 1, 15, Mladenov, E. et al., Mutat Res, 2011, Vol. 711, pp. 61 to 72, and Nowosielska, A. et al., DNA Repair (Amst), 2008, Vol. 7, pp. 48 to 56).

To obtain a base for search for molecules effective in treating or preventing SCA in view of such knowledge, the present inventors first expressed mutant ATXN1 in cerebellar neurons of a mammal, and tested whether DSB-type DNA damage occurred.

Figure 2:
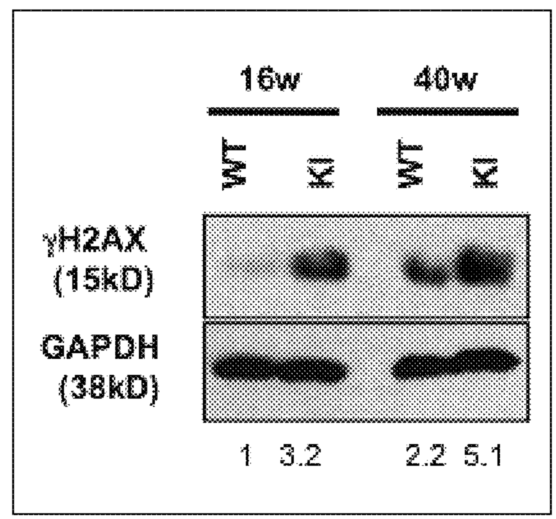
FIG. 2 shows photographs showing Western blot analysis results of γH2AX expression levels in cerebellar protein extracts (7 μg) of wild-type (WT) and mAtxn1-KI (KI) mice at 16 and 40 weeks of age.
Figure 3:
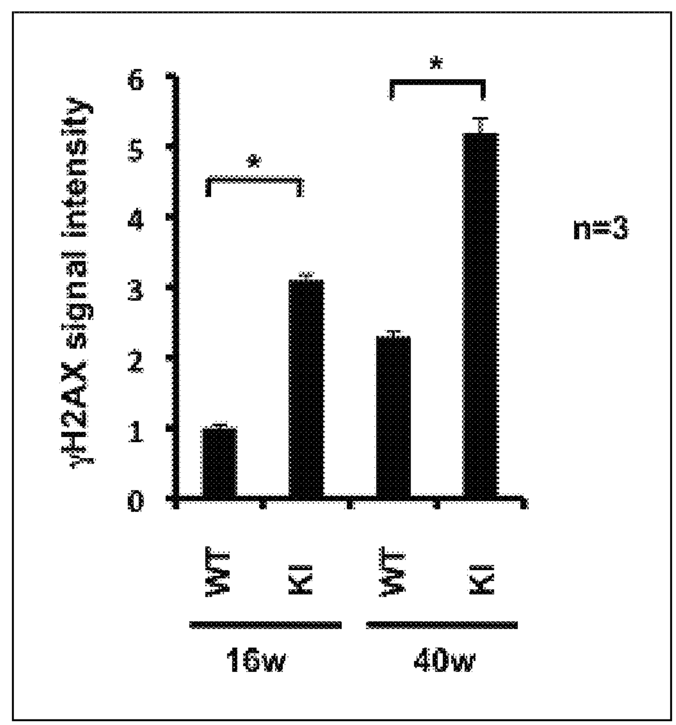
FIG. 3 is a graph showing the results of a quantitative analysis of the signal intensity of γH2A in three wild-type mice (WT) and three mAtxn1-KI mice (KI) at 16 and 40 weeks of age based on Western blotting. In the graph, the error bars represent SEM. Asterisks indicate $P<0.01$ in Student's t-test.

Specifically, the phosphorylation at serine 139 of histone 2A (H2AX), which is a DSB marker, was analyzed in Atxn1-154Q knock-in mice. As a result, many small spot signals were observed in Purkinje cells and granule cells, as shown in FIG. 1. In addition, it was found that the H2AX phosphorylation was increased before the onset of the symptoms of the Atxn1-154Q knock-in mice (see FIGS. 2 and 3).

Example 2

<Screening Using SCA1 *Drosophila* Model>

Next, a screening system was constructed to identify what type of the DNA repair cascades were involved in the onset of SCA. For the construction of the screening system, the present inventors focused on *Drosophila*, which has a short generation time and whose phenotypes can be evaluated quantitatively, to appropriately narrow down candidates among various factors and networks in which these factors are involved. Note that the present inventors have revealed the similarity between pathologies of the *Drosophila* SCA1 model and those of a mammalian SCA1 model on the basis of prior research results.

Figure 4:
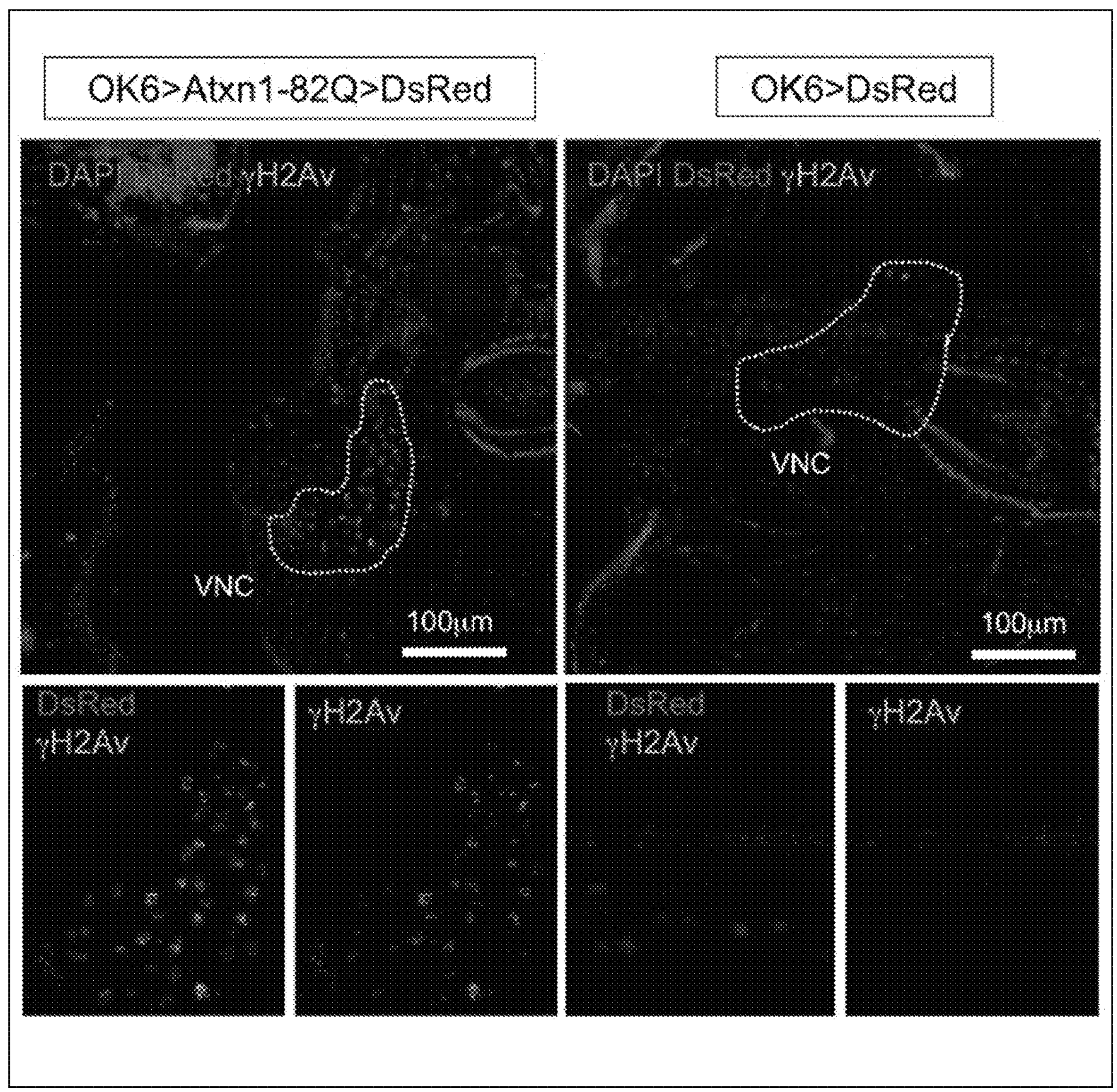
FIG. 4 shows micrographs showing the analysis results of DNA double-strand breaks (DSBs) in the thoracic motor neurons and the ventral nerve cord (VNC) of *Drosophila* in which Atxn1-82Q/DsRed or DsRed alone was expressed in motor neurons by the OK6 driver, the analysis being made based on the expression of a DSB marker γH2Av. Specifically, the left panels are micrographs showing increase in γH2Av signal in the VNC of the flies expressing mutant ATXN1, in comparison with a control fly expressing DsRed alone. Note that the flies were dissected on day 7 to day 10, and subjected to this analysis.
Figure 5:
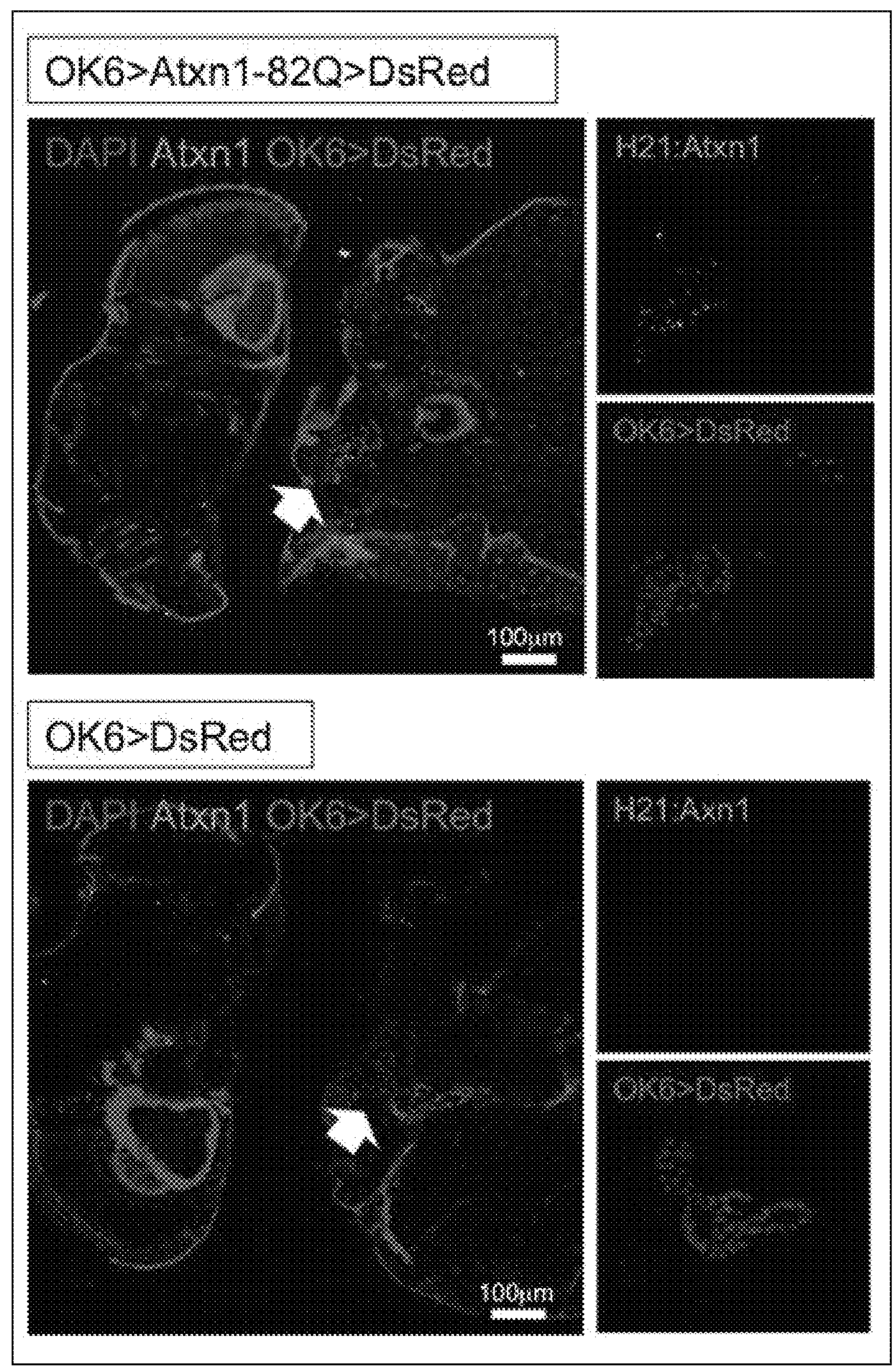
FIG. 5 shows micrographs showing the results of the expression of Atxn1 in motor neurons of OK6-driven Atxn1 transgenic flies detected by immunostaining with an H21 anti-Atxn1 antibody. Specifically, the micrographs show that the ATXN1 expression was observed in the VNC of the transgenic flies in contrast to the control fly expressing DsRed alone. Note that the flies were dissected on day 7 to day 10, and subjected to this analysis.

In this respect, the present inventors first checked that DSB-type DNA damage was also increased in a *Drosophila* SCA1 model, as in the case of the mice. Specifically, analysis results of transgenic flies expressing human Atxn1-82Q in motor neurons by using an OK6-Ga14/UAS system showed increased phosphorylation of H2Av, which is a *Drosophila* H2AX homolog (see FIGS. 4 and 5). Note that strong signals of γH2Av were observed in cells induced by OK6 to express DsRed in the ventral nerve cord (VNC), and it was revealed that DsRed and γH2Av were localized at the same positions (see FIG. 4). In addition, it was also found that cells induced by OK6 to express DsRed actually expressed mutant Atxn1 (see FIG. 5).

As described above, the DSB-type DNA damage is the final stage of other types of DNA damage such as single-stranded DNA break (SSB) and oxidative base damage. Accordingly, in view of this point in combination with the above-described results, the *Drosophila* SCA1 model was considered to be an effective tool for search for DNA damage repair cascades which contributed to the SCA pathology. Thus, an in-vivo screening was performed by using the *Drosophila* model.

Specifically, a screening enabling a short-time and quantitative analysis was performed by overexpressing each of all the available *Drosophila* homologous genes related to DNA repair in the *Drosophila* SCAT model, and using the influence on the lifespan shortening, which is one of the symptoms of the *Drosophila* model, as an index. Table 1 shows the relationships between human DNA repair genes subjected to the screening and their *Drosophila* homologous genes.

In addition, Table 2 shows the lifespan average values of flies (OK6>Atxn1-82Q;GS) co-expressing human Atxn1-82Q and DNA damage repair genes whose expression was induced by a GS line cassette. In addition, Table 2 also shows P values calculated by using the Wilcoxon rank sum test to determine the differences from UAS-Atxn1-82Q/+: OK6-GAL4/+(OK6>Atxn1-82Q), which was a positive control.

In addition, in Tables 1 and 2, "BER" indicates genes related to base-excision repair, "NER" indicates genes related to nucleotide-excision repair, "DSBR" indicates genes related to DNA double-strand break repair, "DSBR+CLR" indicates genes related to DNA double-strand break repair and DNA cross-link repair, and "MMR" indicates genes related to mismatch repair. Note that RPA1, which has multiple functions, is tentatively classified into NER.

In addition, although not shown in drawings, it was found that the positive control UAS-Atxn1-82Q/+:OK6-GAL4/+ (OK6>Atxn1) had a shorter lifespan than the negative control Atxn1/+ or OK6/+ in this in-vivo screening system.

TABLE 1

| | Chromosome | Human DNA repair gene | Drosophila homologous gene |
|---|---|---|---|
| BER | 2R | MBD4 | toutatis |
| | 3R | LIG3 | lig3 |
| | 3R | PNKP | CG9601 |
| | 2R | FEN1 (DNaseIV) | Fen1 |
| NER | 2R | XPC | mus210 |
| | 2R | ERCC1 | Ercc1 |
| | 2R | LIG1 | CG5602 |
| | 3L | GTF2H2 | Ssl1 |
| | 3L | GTF2H4 | Tfb2 |
| | 2L | ERCC5 (XPG) | Chrac-14 |
| | 2R | XAB2 (HCNP) | CG6197 |
| | 2R | ERCC2 | Xpd |
| DSBR | 3R | RPA1 | RpA1/RpA-70 |
| | 2R | RAD50 | rad50 |
| | 3R | XRCC3 | spindle B (spn-B) |
| | 3L | GEN1 | CG10670 (Gen) |
| | 3L | RECQL5 | RecQ5 |
| | 3R | ATM | tefu |
| | 3R | Ku70 | lrbp |
| | X | MUS81 | mus81 |
| | X | XRCC4 | CG12728 |
| | 2R | EME1 (MMS4L) | CG12936 |

TABLE 1-continued

| | Chromosome | Human DNA repair gene | Drosophila homologous gene |
|---|---|---|---|
| DSBR + CLR | 2L | TDP1 | Gkt |
| MMR | 2R | PMS2 | Pms2 |
| | 3L | MSH6 | Msh6 |
| | 2R | PCNA | mus209 |
| Others | 2R | SPO11 | mei-W68 |
| | 2L | CHK1 | Grp |
| | 3L | CCNH | CycH |
| | 3L | POLD1 | DNA pol-delta |
| | 3R | POLE | DNA pol-epsilon |
| | 3L | POLH | DNApol-eta |
| | 3R | RAD18 | CG5524 |
| | 3R | UBE2A (RAD6A) | UbcD6 |
| | X | PER1 | period |
| | 2L | OBFC2B | CG5181 |
| | 3R | BLM | mus309 |

TABLE 2

| | GS line | Average lifespan day (95% CI) | p value (Wilcoxon rank sum test) |
|---|---|---|---|
| BER | Toutatis 206588 | 23.07 (20.65-25.49) | 0.725 |
| | Toutatis 206898 | 25.07 (23.42-26.73) | 0.313 |
| | lig 3 | 14.13 (12.10-16.16) | 0.000 |
| | CG9601 | 28.62 (26.58-30.66) | 0.011 |
| | Fen1 | 13.50 (12.18-14.82) | 0.000 |
| NER | Mus210 | 24.76 (22.81-26.70) | 0.364 |
| | Ercc1 | 19.41 (17.64-21.19) | 0.119 |
| | CG5602 | 14.73 (13.33-16.14) | 0.000 |
| | Ssl1 | 24.24 (22.31-26.17) | 0.575 |
| | Tfb2 | 23.22 (21.07-25.38) | 0.539 |
| | Chrac14 | 4.55 (4.45-4.65) | 0.000 |
| | CG6197 | 15.80 (14.27-17.33) | 0.000 |
| | Xpd | 12.27 (11.58-12.95) | 0.000 |
| DSBR | RpA1/RpA-70 | 33.90 (31.66-36.14) | 0.000 |
| | Rad50 | 22.22 (20.41-24.03) | 0.491 |
| | spn-B | 28.67 (27.05-30.29) | 0.007 |
| | CG10670 (Gen) | 20.09 (18.44-21.74) | 0.087 |
| | Irbp | 23.19 (21.05-25.33) | 0.944 |
| | RecQ5 | 15.38 (13.85-16.91) | 0.001 |
| | tefu | 24.94 (23.28-26.59) | 0.298 |
| | Mus81 | 18.82 (17.98-19.65) | 0.001 |
| | CG12728 | 30.64 (29.25-32.04) | 0.000 |
| | CG12936 | 12.31 (11.41-13.22) | 0.000 |
| DSBR + CLR | Gkt/TDP1 | 21.29 (19.34-23.23) | 0.704 |
| MMR | Pms2 | 22.71 (21.17-24.25) | 0.912 |
| | Msh6 | 25.07 (23.41-26.72) | 0.755 |
| Others | mus 209 | 19.54 (18.10-20.98) | 0.095 |
| | mei-W68 | 13.08 (12.02-14.15) | 0.000 |
| | CycH | 27.57 (25.99-29.15) | 0.031 |
| | Grp | 11.29 (10.22-12.36) | 0.000 |
| | DNA pol-delta | 24.59 (23.09-26.08) | 0.191 |
| | DNA pol-epsilon | 28.97 (27.35-30.58) | 0.001 |
| | DMA pol-eta | 31.80 (30.39-33.21) | 0.000 |
| | CG5524 | 22.63 (21.18-24.09) | 0.948 |
| | UbcD6 | 24.98 (23.58-26.39) | 0.395 |
| | per | 27.42 (25.90-28.95) | 0.046 |
| | CG5181 | 25.65 (23.11-28.19) | 0.247 |
| | mus309 | 19.63 (18.46-20.79) | 0.009 |

As shown in Table 2, the results of the in-vivo screening showed that the overexpression of PNKP, RpA1, Spn-B, XRCC4, DNA polymerase eta, DNA polymerase epsilon, CycH, or Per ameliorated the lifespan shortening of the SCA1 fly model. In addition, although not shown in the drawings, it was revealed that most of these genes improved the survival rate over the period from the young stage to the aged stage of adult flies. For example, on day 21, the survival rate of the positive control flies (UAS-Atxn1-82Q/+:OK6-GAL4/+) was 75%, whereas the Spn-B over-expression line, the XRCC4/CG12728 overexpression line, the DNA polymerase eta overexpression line, and the CycH overexpress ion line showed high survival rates of 85%, 92%, 86%, and 83%, respectively. Moreover, their survival rates remained higher than that of the SCA1 fly model on Day 30 and later. In addition, although not shown in the drawings, it was also revealed that the maximum lifespan value was remarkably elongated by RpA1, Per, Spn-B or XRCC4/CG12728.

On the other hand, unexpectedly, 12 genes were identified which further shortened the lifespan of the SCA1 flymodel. The genes were Lig1, Lig3, Fen1, chrac-14, XAB2, Xpd, CG8841, RecQ5, mus81, EME1, meiW68, mus309/BLM/RecQ2, and grp. Note that, in the example of the CG8841 (DMC1) overexpression, the toxicity was so high that no adult flies were obtained, and the lifespan was extremely short.

In addition, RecQ family proteins are known to be highly conserved from bacteria to human and to have 3'-5' DNA helicase activity. Among five members (mus309/BLM/RecQ2, WRN/RecQ3, RecQ4, and RecQ5) of human RecQ1, two RecQ proteins exerted an adverse influence on the lifespan. Especially, RecQ5 showed DNA-strand annealing activity. Moreover, this activity is shown to be inhibited by RpA1 (see Garcia, P. L., EMBO J, 2004, Vol. 23, pp. 2882 to 2891), which is consistent with the reverse actions of RecQ5 and the above-described RPA1.

In addition, as described above, the present inventors have revealed that Ku70 ameliorates the lifespan shortening of mutant Huntingtin transgenic flies. However, in this in-vivo screening, the Irbp GS line expressing a gene homologous to Ku70 did not significantly ameliorate the lifespan shortening of the UAS-Atxn1-82Q/+: OK6-GAL4/+*Drosophila* model. However, although not shown in the drawings, it has been confirmed that a favorable influence on the survival time is exerted slightly but definitely in transgenic flies co-expressing human Ku70. The discrepant effects of Ku70 on Huntington's disease and SCA suggest that molecules used for DNA damage repair in the two polyglutamine diseases are different from each other in terms of quantity and quality.

Example 3

<Elucidation of DNA Repair Network Involved in SCA Pathology by Systems Biology>

Next, the above-described screening results were analyzed based on systems biology. Specifically, quantitative data on the amelioration by DNA repair genes and protein-protein interaction (PPI) data (BIND, BIOGRID, Cognia, DIP, INTACT, Interactome studies, MINT, and MIPS) were integrated to identify core molecular networks which induced survival time shortening or elongation in the SCA1 fly model. At the same time, a search was conducted for new molecules constituting networks having influences on the lifespan of the *Drosophila* SCA1 model. More specifically, two algorithms were used for the purpose.

In a network 1 created by using a first algorithm, protein pathways were selected from the protein-protein interactome (PPI) database, when two gene products exerted any influence on the lifespan directly (Segment 1) or via another protein (Segment 2). In the map of network 1, proteins linked to a larger number of proteins were arranged closer to the center. Moreover, determinant genes were located in the periphery of the network in this analysis.

In a network 2 created by using a second algorithm, closed triangle pathways were selected from the PPI database, when 1 to 3 proteins having influences on the lifespan were components of the triangle protein pathways. If possible, the rest of the proteins having influences on the lifespan were linked to the deduced network.

Then, using the two networks, functional interactions of lifespan-elongating genes and lifespan-shortening genes were analyzed, among DNA damage repair-related genes isolated by the above-described in-vivo screening.

Figure 6:
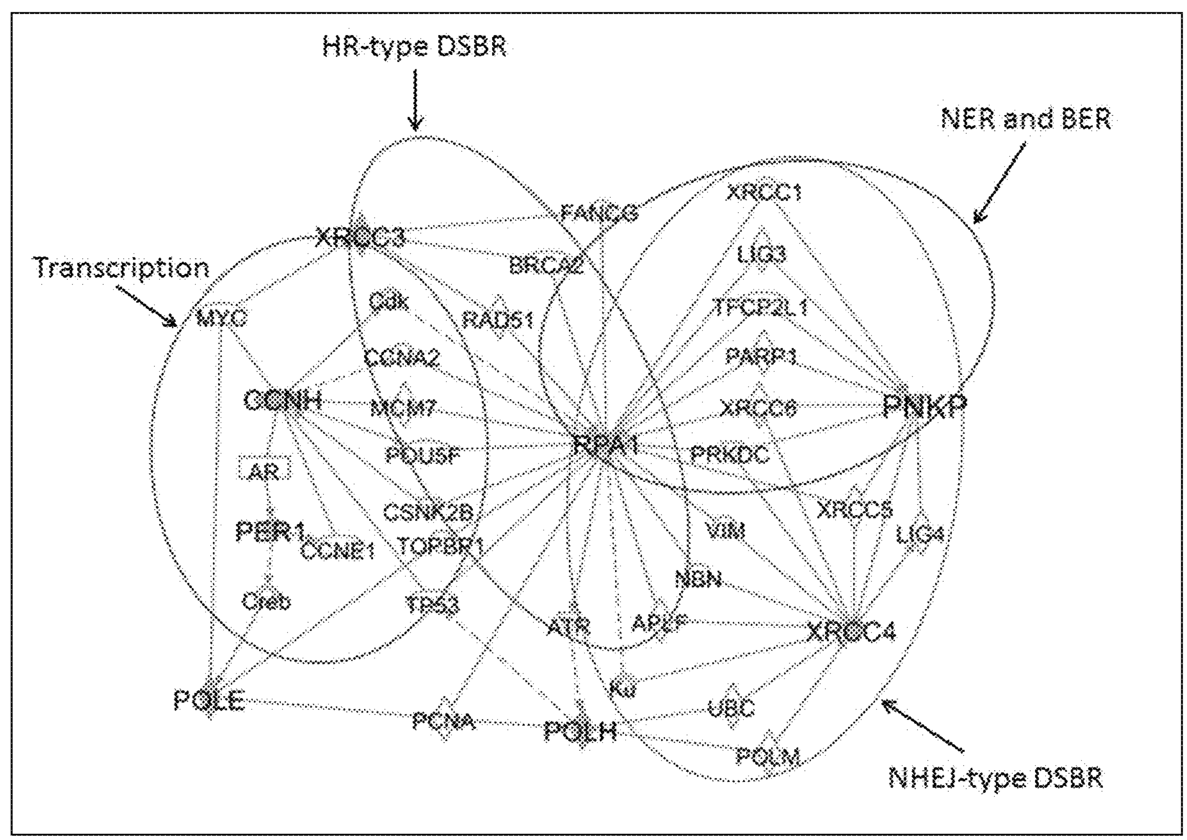
FIG. 6 is a diagram showing a DNA damage repair network-1 which contributes to the lifespan elongation of the SCA1 fly model and is predicted by Ingenuity-IPA software using the human protein-protein interaction database. Note that, in the diagram, the genes in the circle marked with "NHEJ-type DSBR" are related to nonhomologous end joining-type DNA double-strand break repair, the genes in the circle marked with "HR-type DSBR" are related to homologous recombination-type DNA double-strand break repair, the genes in the circle marked with "NER and BER" are related to nucleotide-excision repair or base-excision repair, and the genes in the circle marked with "transcription" are related to transcription. "Ku70" represents XRCC6, and "Ku" marked with a double circle is discriminated from the Ku70/Ku80 complex. In addition, PARP1 is a gene related to the single-strand break repair (SSBR) and the nucleotide-excision repair (NER). XRCC1, LIG3, and PARP1 are genes also involved in another type of DNA double-strand break repair (B-NHEJ).

The results showed that the algorithm for creating the network 1 was useful for accentuating important genes contributing to the lifespan elongation, as shown in FIG. 6. In other words, it was fund that RPA1 was located at the center in the lifespan elongation-related network 1 (2 segments), and linked to various DNA damage repair or transcription-related proteins. In addition, genes linked to RPA1 were classified into the following groups which critically regulate specific types of DNA repair or transcription.

Specifically, a first group is linked to XRCC4, and related to nonhomologous end joining (NHEJ)-type DNA repair. A second group is linked to bifunctional polynucleotide phosphatase/kinases (PNKPs) such as XRCC1, ligase3 (LIG3), and PolyADP ribose polymerase (PARP), and is involved in NHEJ (B-NHEJ) and further in the backup pathway of SSBR, BER, or NER. A third group, which is linked to XRCC3, is related to homologous recombination (HR)-type DNA repair, and involved in repair of DSBs in genome replication. A fourth group is linked to cyclin H (CCNH), and involved mainly in transcription.

In addition, various proteins such as PARP1, RAD51, TOPBP1, CDK, and Ku70 act on RPA1, whereas RPA1 acts on only ATR. This suggests that a functional target of these gene groups is RPA1, and that RPA1 is extremely important as a hub molecule for various systems of DSB and transcription.

The above-described results are consistent with the notion that RPA1 plays a central role in the protection of single-stranded DNA produced during various types of DNA damage repair and transcriptional interruption. In addition, these results account for the reason why RPA1 achieved the most remarkable amelioration of the SCA symptoms in the analysis results of the fly model.

Figure 7:
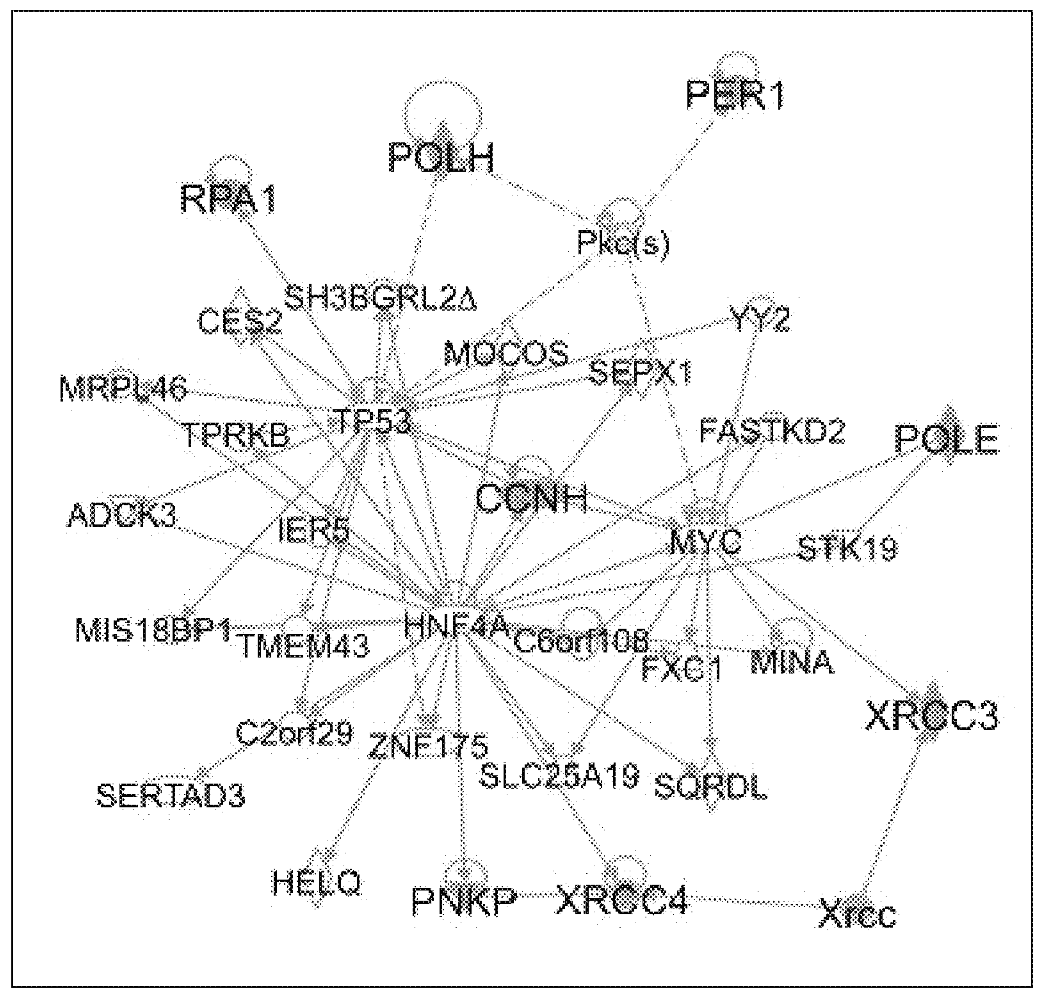
FIG. 7 is a diagram showing a DNA damage repair network-2 which contributes to the lifespan elongation of the SCA1 fly model predicted by Ingenuity-IPA software using the human protein-protein interaction database.

In network 2, dense interactions among genes selected by the screening are extracted (see FIG. 7). This network 2 suggests that the tumor protein TP53, hepatocyte nuclear factor 4α (HNF4A), and Myc are connected to many proteins, and involved in various systems contributing to lifespan elongation. Interestingly, according to the Allen Brain Atlas (http://developingmouse.brain-map.org/data/Hnf4a/100093888/thumnails.html), HNF4A is expressed in the adult cerebellar cortex. HNF4A is a transcription factor which binds to CREB-binding protein (CBP), and regulates the expression of genes such as cytochrome P450 3A4 (CYP3A4), which is important for the metabolism of xenobiotics (see Tirona, R. G. et al., Nat Med, 2003, Vol. 9, pp. 220 to 224). Hence, HNF4A might regulate multiple systems which elongate the lifespan of the SCAT fly model (see FIG. 7). However, HNF4A, itself, was not positive in the above-described screening. In addition, to be a positive gene, a gene has to be involved in multiple paths (see FIG. 7). Hence, HNF4A can be considered to function as an indirect modulator.

Figure 8:
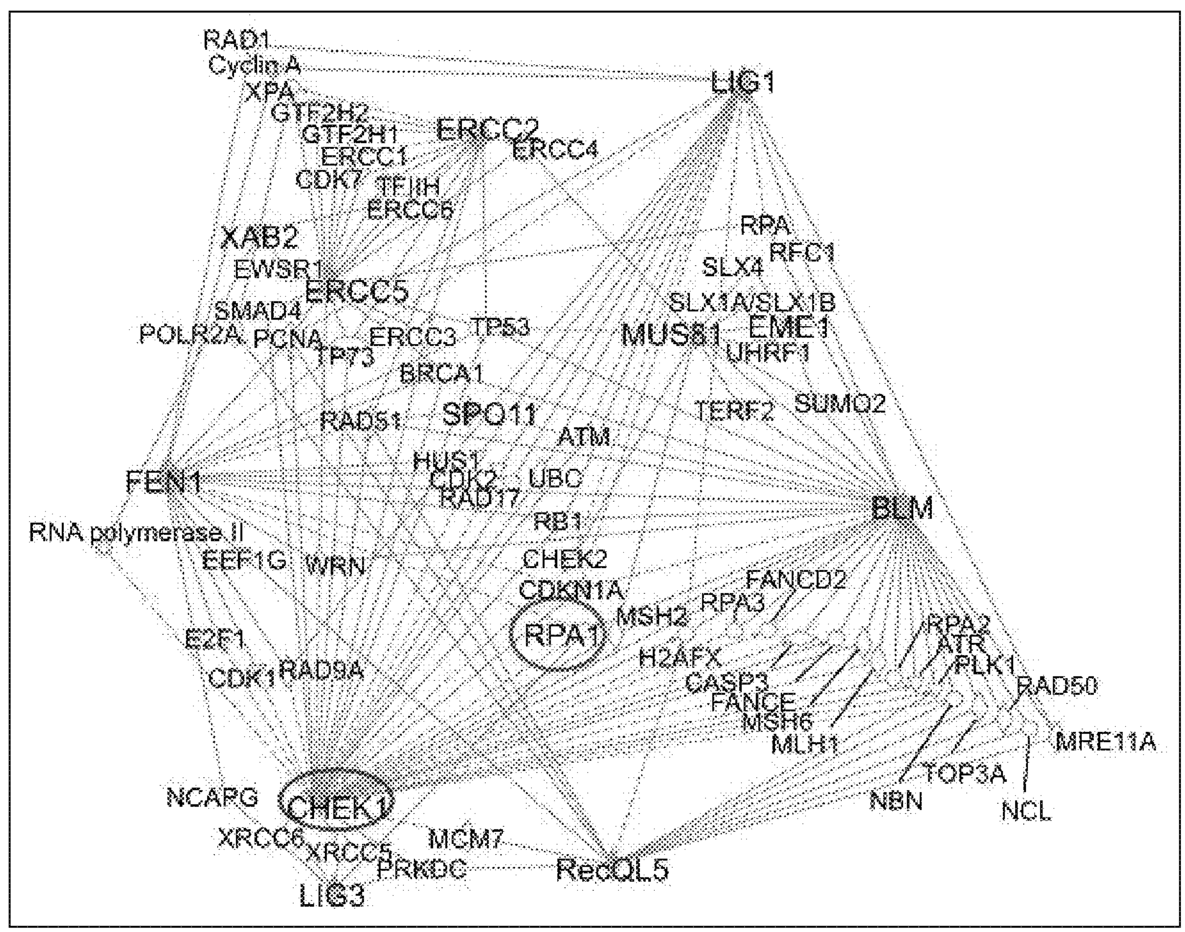
FIG. 8 is a diagram showing a DNA damage repair network-1 which contributes to the lifespan-shortening of the SCA1 fly model and is predicted by Ingenuity-IPA software using the human protein-protein interaction database. The diagram shows that CHK1 receives many signals from hub genes which shorten the lifespan. The diagram also shows that RPA1 is connected to the hub genes, BLM and FEN1, which shorten the lifespan.

In the lifespan shortening-related network 1, FEN1, LIG1, CHK1, and BLM are located at the center of the network, and are linked to many proteins (see FIG. 8). Interestingly, RPA1 is also located at the center, and has relationships with BLM and FEN1. Accordingly, RPA1 might be influenced by these proteins (see FIG. 8). Meanwhile, in the lifespan shortening-related network 2, similar genes are selected as main players (see FIG. 9). In addition, network 2 revealed that RPA (a complex including RPA1 and RPA2) sends suppressive signals to FEN1 and LIG1 directly or indirectly, while RPA1 receives feedback from FEN1. In addition, this network analysis has showed that ATM, ATR, and RNA polymerase II are involved in DSB repair, and are linked to one or multiple proteins of FEN1, LIG1, CHK1, and BLM.

Example 4

<Involvement of HR-DSBR Molecules in SCA Pathology>

As described above, molecular networks of genes involved in lifespan elongation were predicted from the systems biology analyses of DNA damage repair genes which had not attracted attention previously, including many new subgroups (see FIG. 7).

In particular, RPA1 plays an important role in the protection of naked single-stranded DNA produced after various types of DNA damage. In addition, it has been revealed that DNA protected with RPA1 is repaired by homologous recombination with BRCA2 and RAD51.

In this respect, to examine whether or not the RPA1/BRCA2/RAD51 network, which is the most important pathway for HR-dependent DSBR, was involved in the SCA pathology, an analysis was conducted as to whether or not RPA1 and ATXN1 physically interacted with each other in the BRCA2/RAD51 pathway in a mammalian cell line. FIGS. 11 to 15 show the obtained results.

Figure 11:
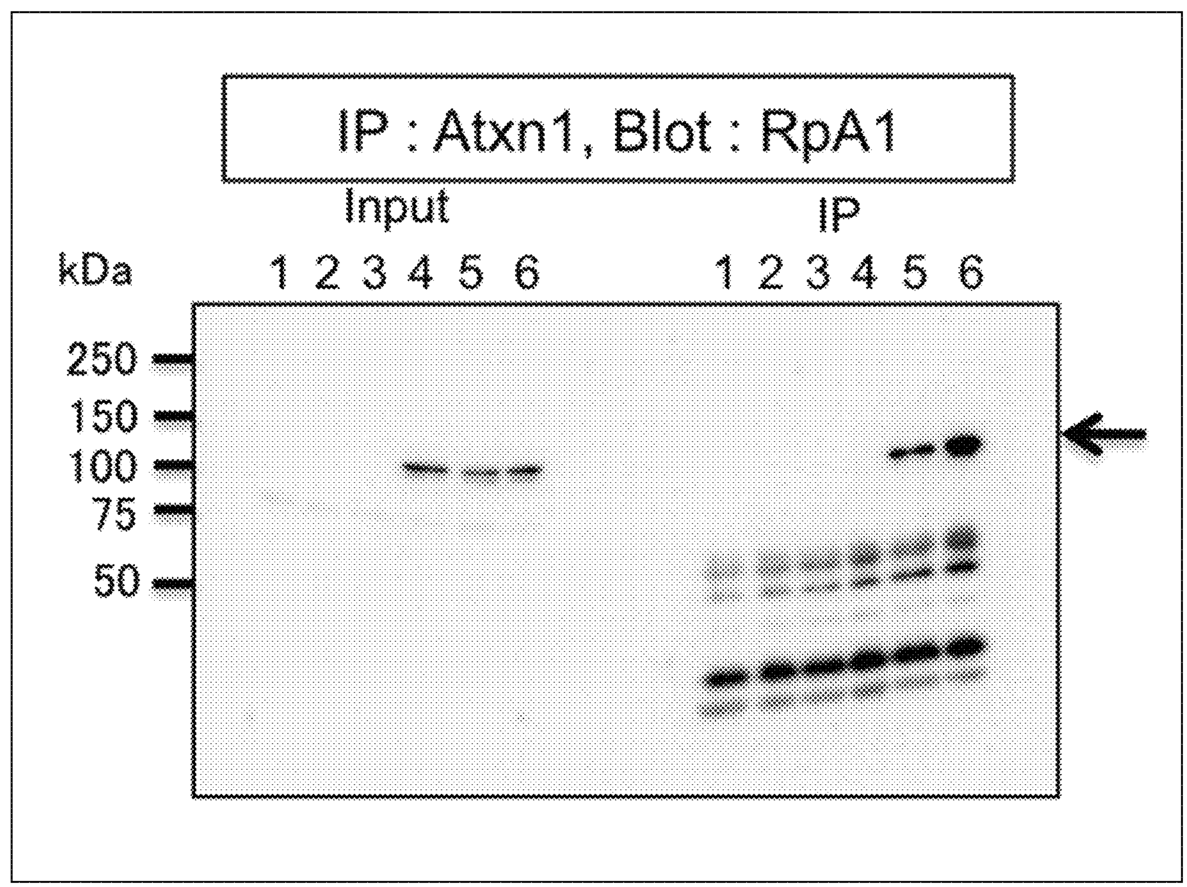
FIG. 11 relates to the interaction between ATXN1 and RPA1 and is a photograph showing the results obtained by performing an immunoprecipitation assay using an anti-ATXN1 antibody, followed by a Western blot analysis using an anti-RPA1 antibody. In this photograph, lane 1 shows a result of Hela cells co-expressing EGFP and Myc; lane 2 shows a result of Hela cells co-expressing EGFP and Atxn1-33Q-Myc; lane 3 shows a result of Hela cells co-expressing EGFP and Atxn1-86Q-Myc; lane 4 shows a result of Hela cells expressing EGFP-RpA1 alone; lane 5 shows a result of Hela cells co-expressing EGFP-RpA1 and Atxn1-33Q-Myc; and lane 6 shows a result of Hela cells co-expressing EGFP-RpA1 and Atxn1-86Q-Myc. In addition, "Input" indicates the results before the immunoprecipitation using the anti-ATXN1 antibody, and "IP" indicates the results of the analysis of precipitates with the anti-ATXN1 antibody.
Figure 12:
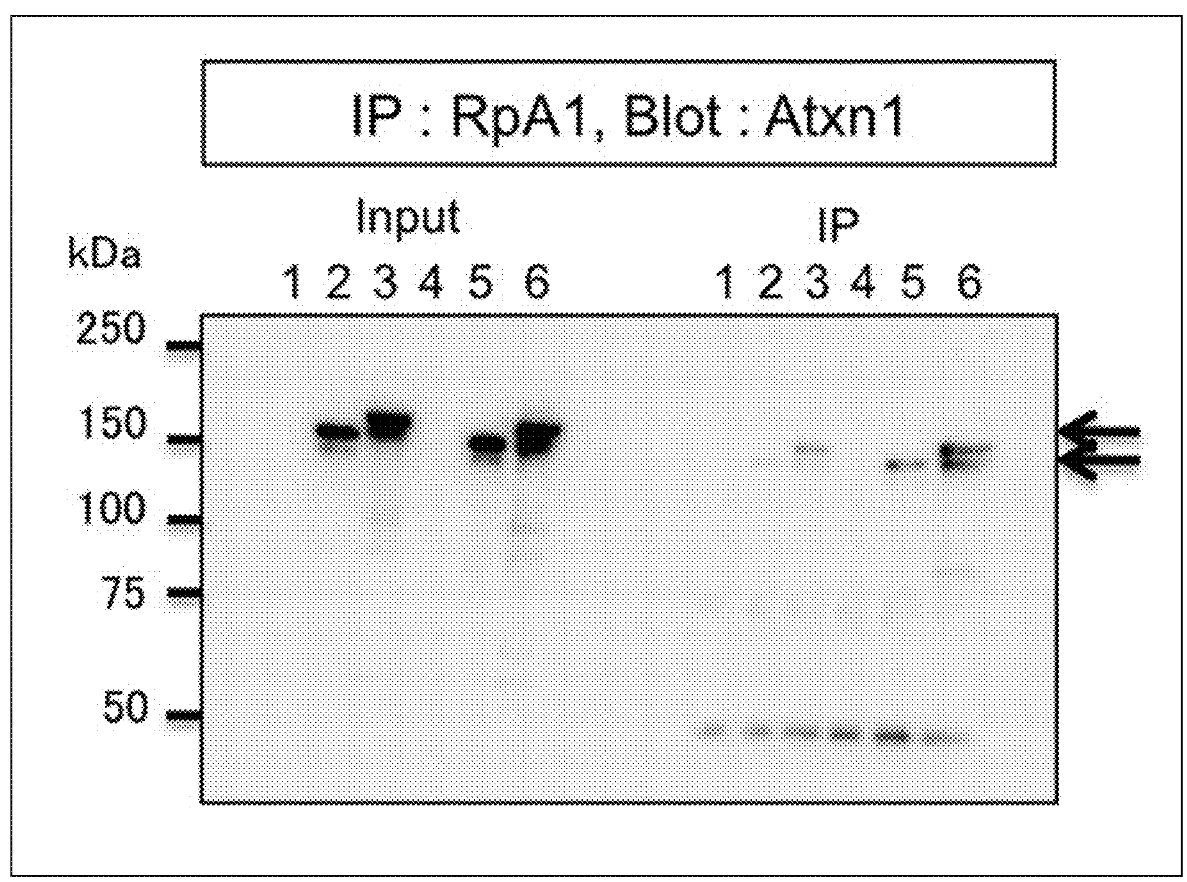
FIG. 12 relates to the interaction between ATXN1 and RPA1 and is a photograph showing the results obtained by performing an immunoprecipitation assay using an anti-RPA1 antibody, followed by a Western blot analysis using an anti-ATXN1 antibody. In this photograph, the notations of the lanes are the same as in FIG. 11. "Input" indicates the results before the immunoprecipitation using the anti-RPA1 antibody, and "IP" indicates the results of the analysis of precipitates with the anti-RPA1 antibody.
Figure 13:
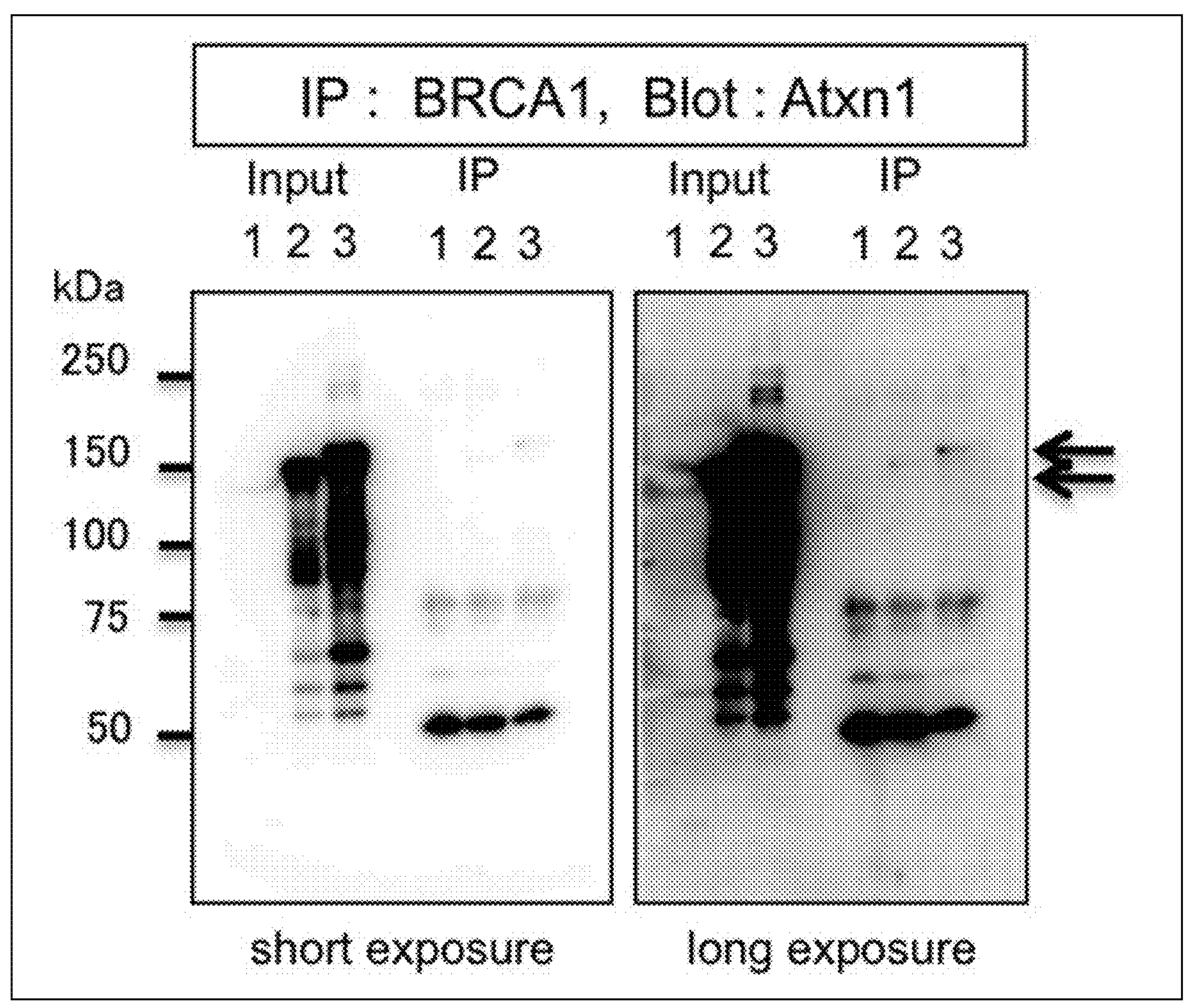
FIG. 13 relates to the interaction between ATXN1 and BRCA1 and is a photograph showing the results obtained by performing an immunoprecipitation assay using an anti-BRCA1 antibody, followed by a Western blot analysis using an anti-ATXN1 antibody. In the photograph; lane 1 shows a result of Hela cells co-expressing EGFP and Myc; lane 2 shows a result of Hela cells co-expressing EGFP and Atxn1-33Q-Myc; and lane 3 shows a result of Hela cells co-expressing EGFP and Atxn1-86Q-Myc. In addition, "Input" indicates the results before the immunoprecipitation using the anti-BRCA1 antibody, and "IP" indicates the results of the analysis of precipitates with the anti-BRCA1 antibody. In addition, the left panel shows the results obtained by detecting the chemiluminescence from the Western blot by short-time exposure, and the right panel shows the results obtained by detecting the chemiluminescence from the Western blot by long-time exposure.
Figure 14:
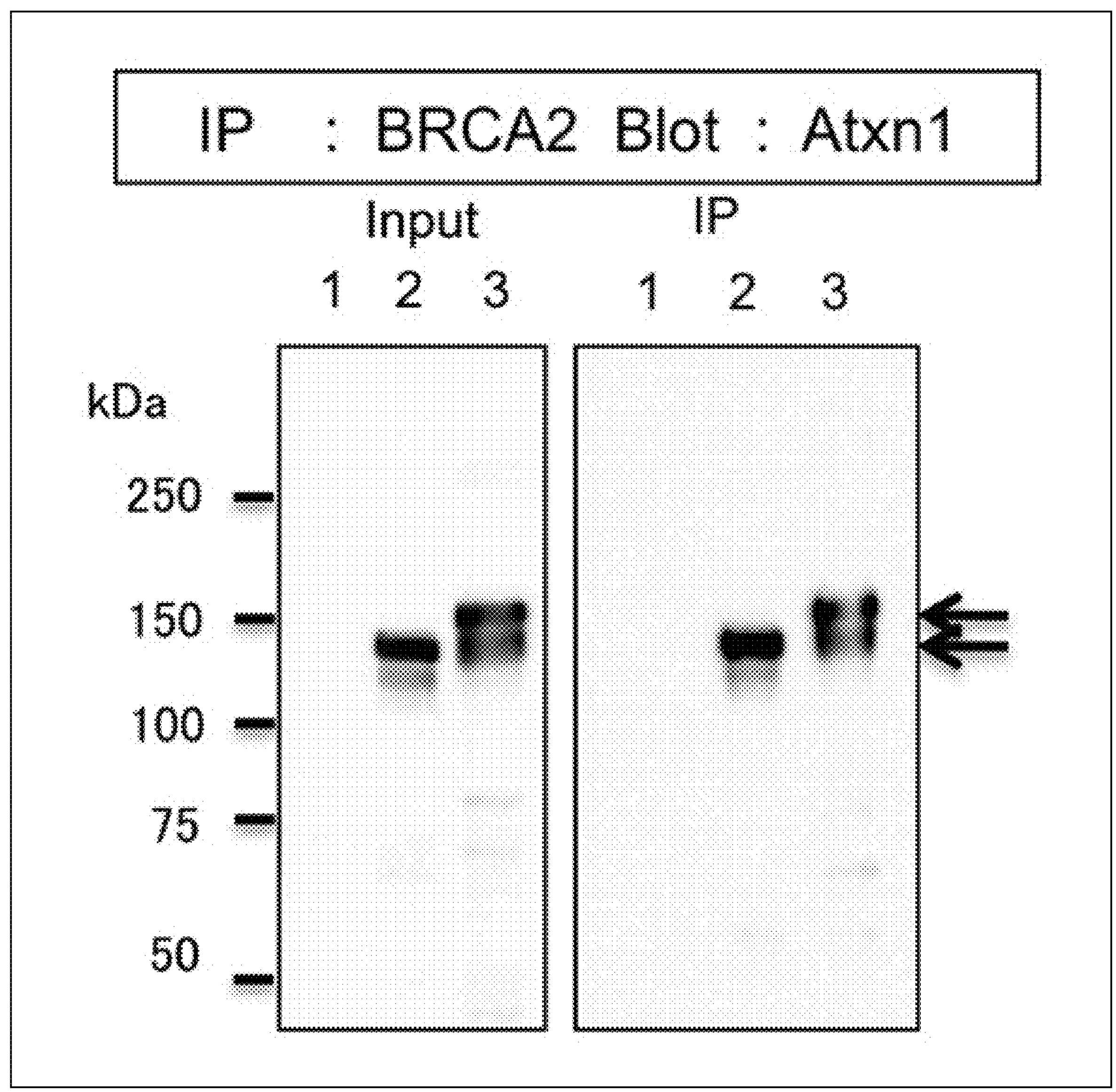
FIG. 14 relates to the interaction between ATXN1 and BRCA2 and is a photograph showing the results obtained by performing an immunoprecipitation assay using an anti-BRCA2 antibody, followed by a Western blot analysis using an anti-ATXN1 antibody. In the photograph, the notations of the lanes are the same as those in FIG. 13. "Input" indicates the results before the immunoprecipitation using the anti-BRCA2 antibody, and "IP" indicates the results of the analysis of precipitates with the anti-BRCA2 antibody.
Figure 15:
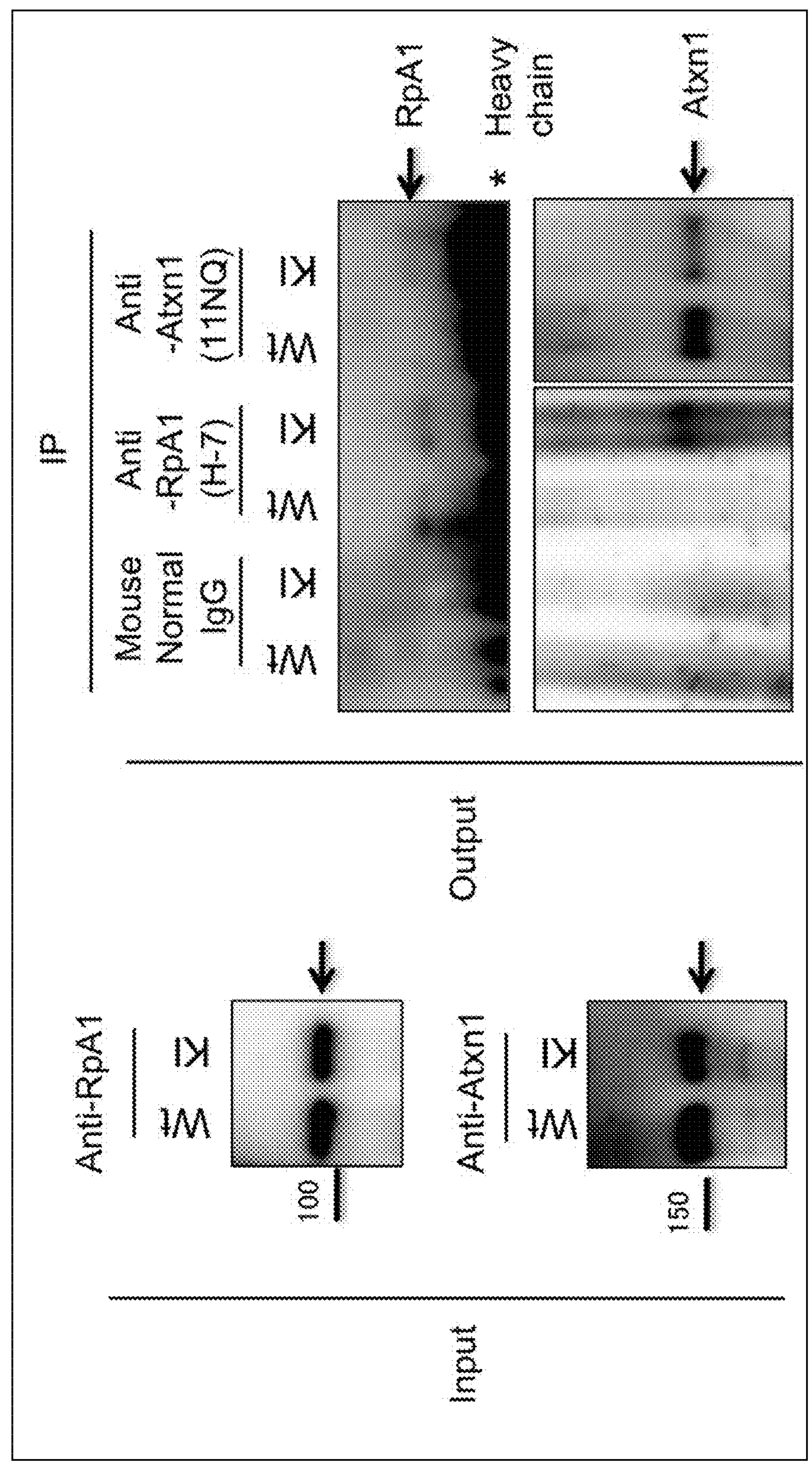
FIG. 15 shows photographs showing the results obtained by analyzing mutant Atxn1-KI (KI) and non-transgenic littermate (WT) mice by immunoprecipitation with an anti-RPA1 antibody or an anti-ATXN1 antibody. Specifically, the photographs show that mutant ATXN1 binds to RPA1 more strongly than wild-type ATXN1.

As a result of the analysis, an immunoprecipitation assay using Hela cells revealed that exogenously expressed ATXN1 interacted with co-expressed RPA1 (see FIGS. 11 and 12). In addition, it was revealed that ATXN1 bound to endogenous BRCA1 weakly (see FIG. 13), and to BRCA2 strongly (see FIG. 14). Moreover, it was confirmed that ATXN1 interacted with RPA1 also in living organisms by using Atxn1-KI mice and their non-transgenic littermate mice (see FIG. 15).

Figure 16:
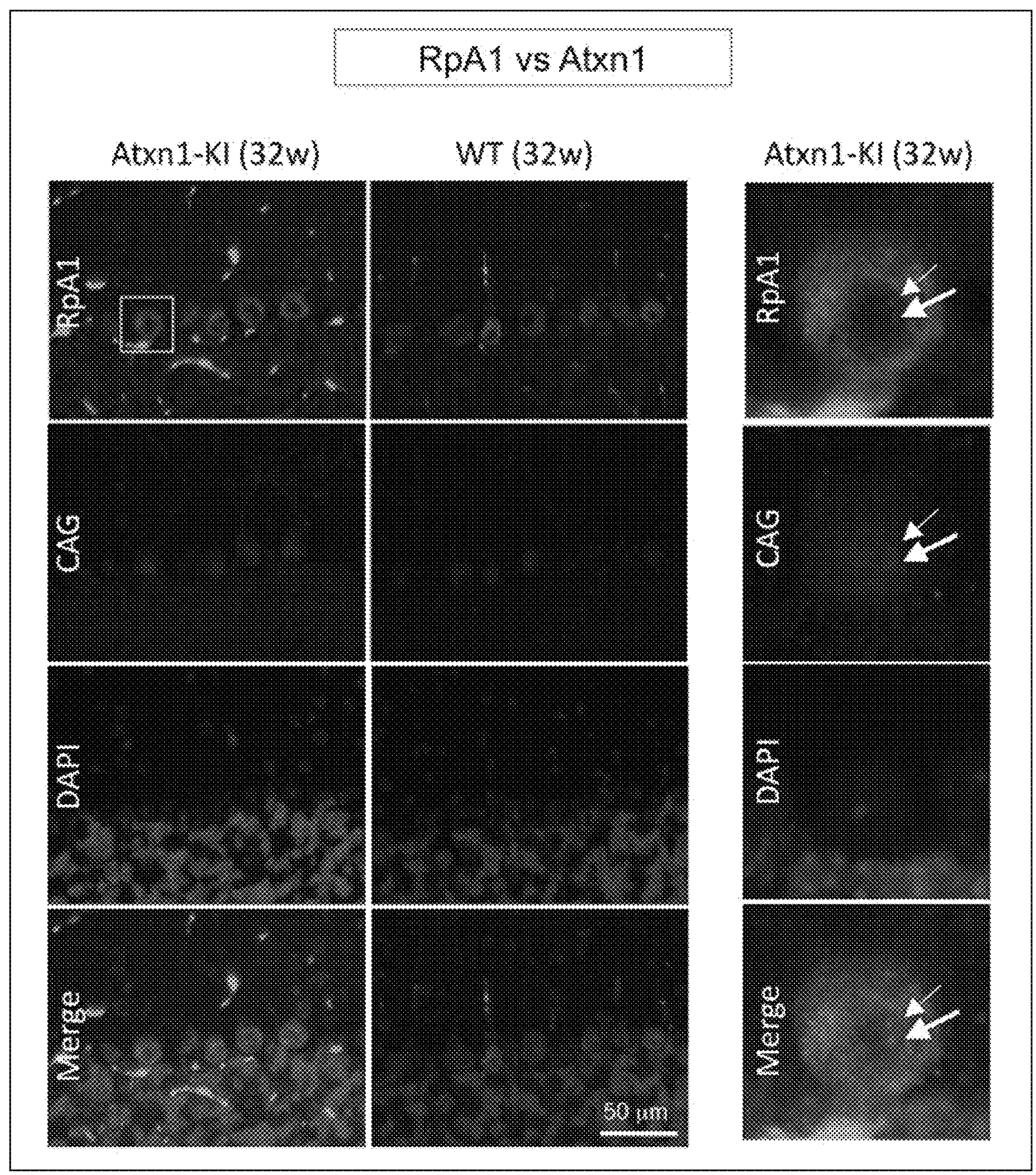
FIG. 16 shows micrographs showing the analysis results of the co-localization of RPA1 and ATXN1 in Purkinje cells. Specifically, the micrographs show the results of observation of mutant Atxn1-KI mouse (154Q) Purkinje cells subjected to double staining for RPA1 and BRCA1 under a confocal microscope, and indicate the co-localization of RPA1 and BRCA1 (see arrows in the drawing). Note that the co-localization was not detected in wild-type mice (WT) by the observation.
Figure 17:
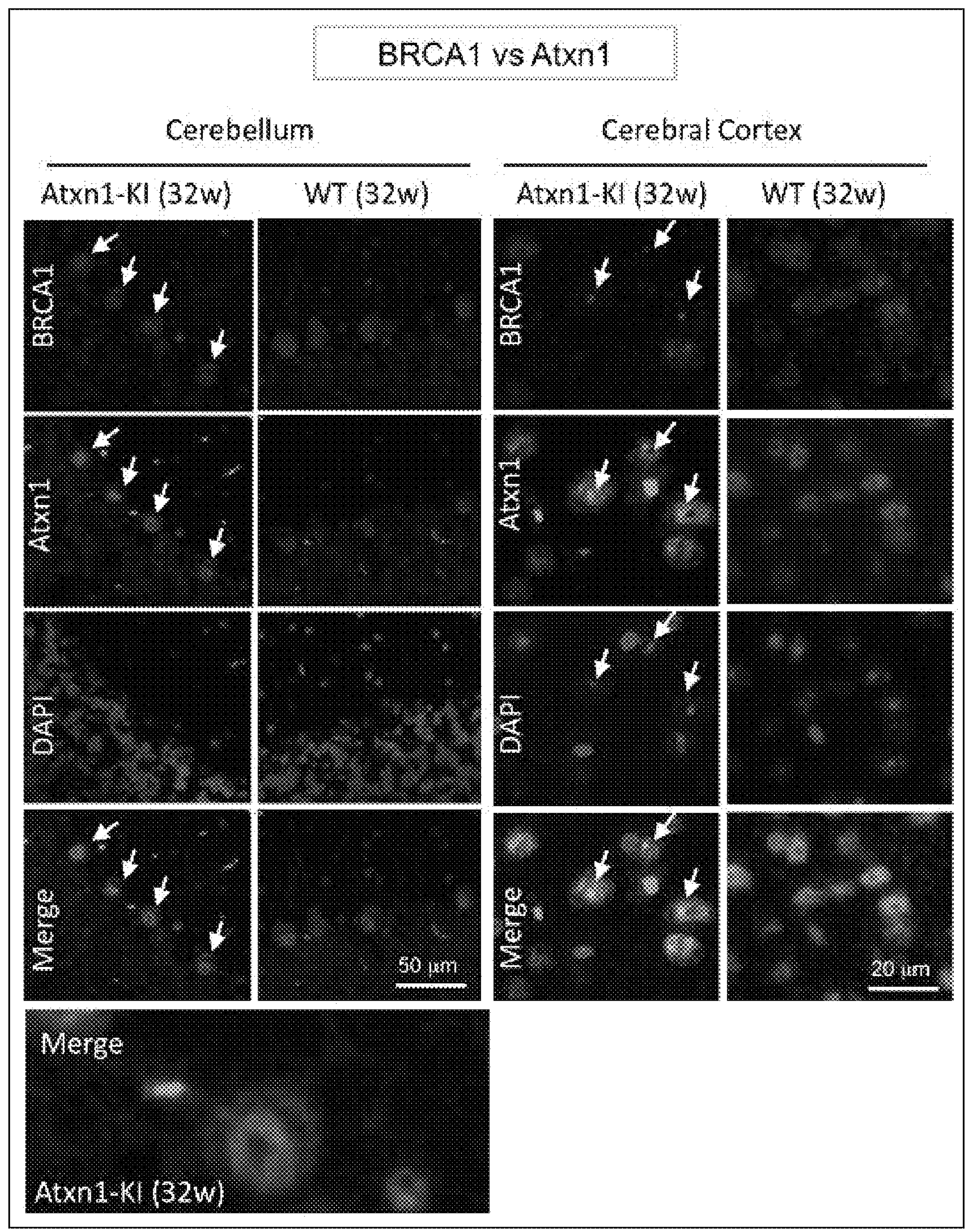
FIG. 17 shows micrographs showing the analysis results of the co-localization of BRCA1 and ATXN1 in cortical neurons. Specifically, the micrographs show the results of double staining of neurons in the cerebral cortex and in the nuclei of Purkinje cells in the cerebellum of wild-type (WT) and mutant Atxn1-KI (154Q) mice, and indicate the co-localization of BRCA1 and ATXN1. Note that some cortical neurons having inclusion bodies to which BRCA1 was sequestered with ATXN1 were observed (see arrows in the micrographs).

In addition, immunohistochemical analysis results of the mutant Atxn1-KI mice brain also revealed that RPA1 and ATXN1 were co-localized in Purkinje cells (see FIG. 16), and further that BRCA1 and ATXN1 were also co-localized in Purkinje cells (see FIG. 17).

Figure 18:
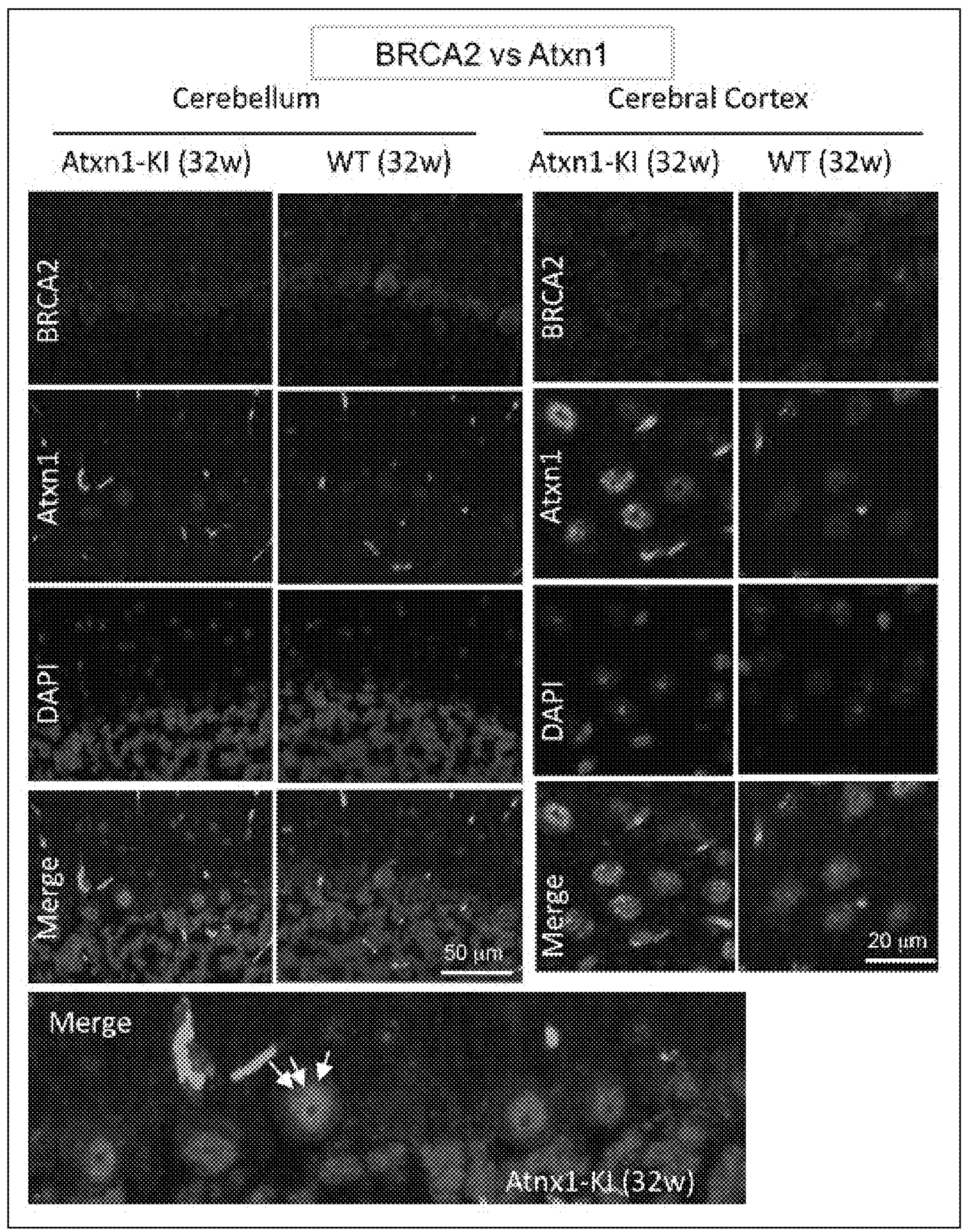
FIG. 18 shows micrographs showing the analysis results of the localization of BRCA2 and ATXN1 in nuclei. Specifically, the micrographs shows that BRCA2 was mainly localized in the cytoplasm of Purkinje cells of the wild-type (WT) and mutant Atxn1-KI (154Q) mice. Note that the localization of ATXN1 stained with an 11NQ antibody partially overlapped with the localization of BRCA2 in the nuclei. In addition, such partial co-localization was similarly observed in cortical neurons.

It has been known that, in Atxn1-KI mice, inclusion bodies are formed in cortical neurons, which are resistant to SCA1, whereas no inclusion bodies are formed in Purkinje cells, which are vulnerable to SCA1 (see Watase, K. et al., Neuron, 2002, Vol. 34, pp. 905 to 919). In this respect, as shown in FIG. 17, BRCA1 was sequestered in inclusion bodies of cortical neurons. On the other hand, it was revealed that BRCA1 and mutant ATXN1 were uniformly dispersed and co-localized in the nuclei of Purkinje cells. In addition, it was revealed that BRCA2 and ATXN1 were partially co-localized in the nuclear foci of Purkinje cells (see FIG. 18). Moreover, interestingly, it was revealed that RPA2, which forms the RPA complex with RPA1, was localized mainly in the cytoplasm of neurons in a normal state, as in the case of RPA1 shown in FIG. 16, although this is not shown in the drawings.

From the above-described results, it is conceivable that mutant ATXN1 inhibits the dynamics of RPA1 and its partners, BRCA1 and BRCA2, and thus impairs their DNA damage repair functions.

Figure 19:
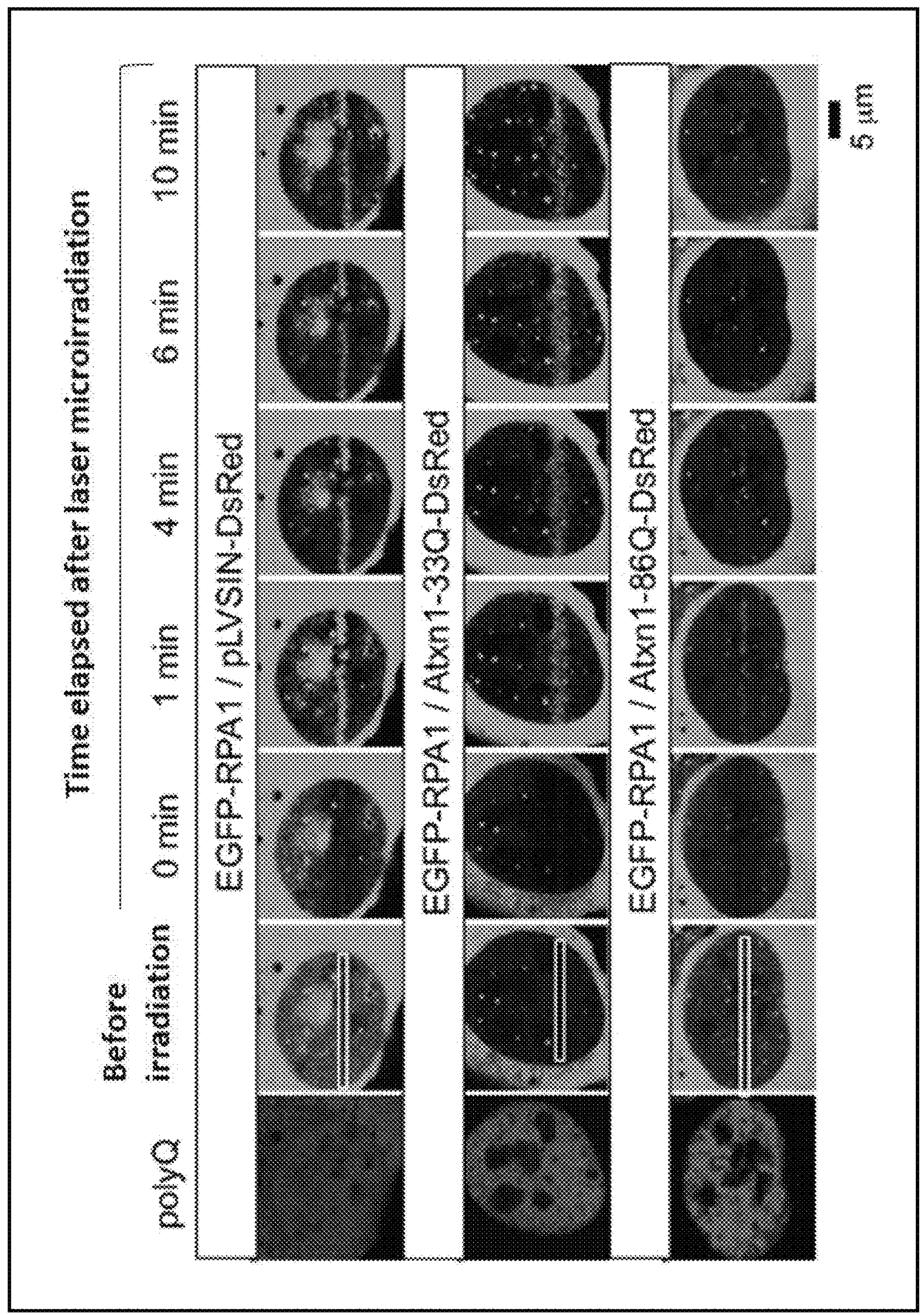
FIG. 19 shows micrographs showing the results obtained by inducing linear DNA DSBs by high-energy UVA in U2OS cells expressing Atxn1-86Q-DsRed, and observing the accumulation of VCP-EGFP in the linear DNA DSB sites. A result of comparison with Atxn1-33Q-DsRed-expressing cells showed that the recruitment of RPA1 to DNA damage foci was inhibited in cells expressing the mutant ATXN1 (Atxn1-86Q).
Figure 20:
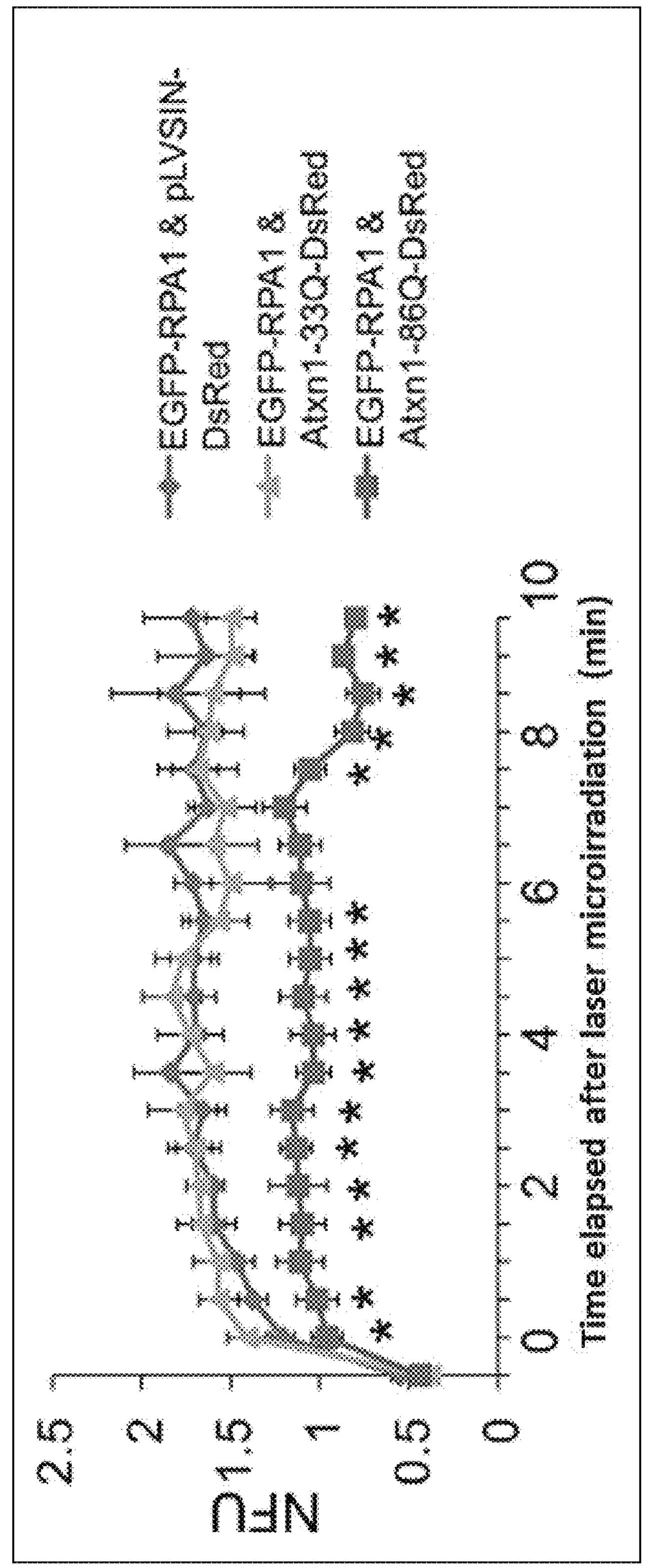
FIG. 20 is a graph which relates to the results shown in FIG. 19 and shows the results of a quantitative analysis of the EGFP signal in the linear DNA DSB sites from 0 to 10 minutes after microirradiation. NFU represents normalized fluorescence unit.

In this respect, the intranuclear dynamics of RPA1 in response to linear DNA DSBs was directly examined in U2OS cells expressing mutant ATXN1. The results showed that the accumulation of RPA1-EGFP at the site of linear DNA damage was slower in Atxn1-86Q-DsRed-expressing cells than in DsRed-expressing cells and in Atxn1-33Q-DsRed-expressing cells, which were controls (see FIGS. 19 and 20).

In addition, the signal intensity of RPA1 decreased 7 minutes after the induction of DNA damage. This suggested that RPA1 was stored in two compartments. Presumably, the movement of RPA1 from the fast compartment was partially inhibited, and release from a late compartment was further inhibited by interaction with mutant ATXN1. This hypothesis is supported by the fact that RPA1 was sequestered in nucleus inclusion bodies in Purkinje cells of mutant ATXN1 mice (see FIG. 16).

Figure 21:
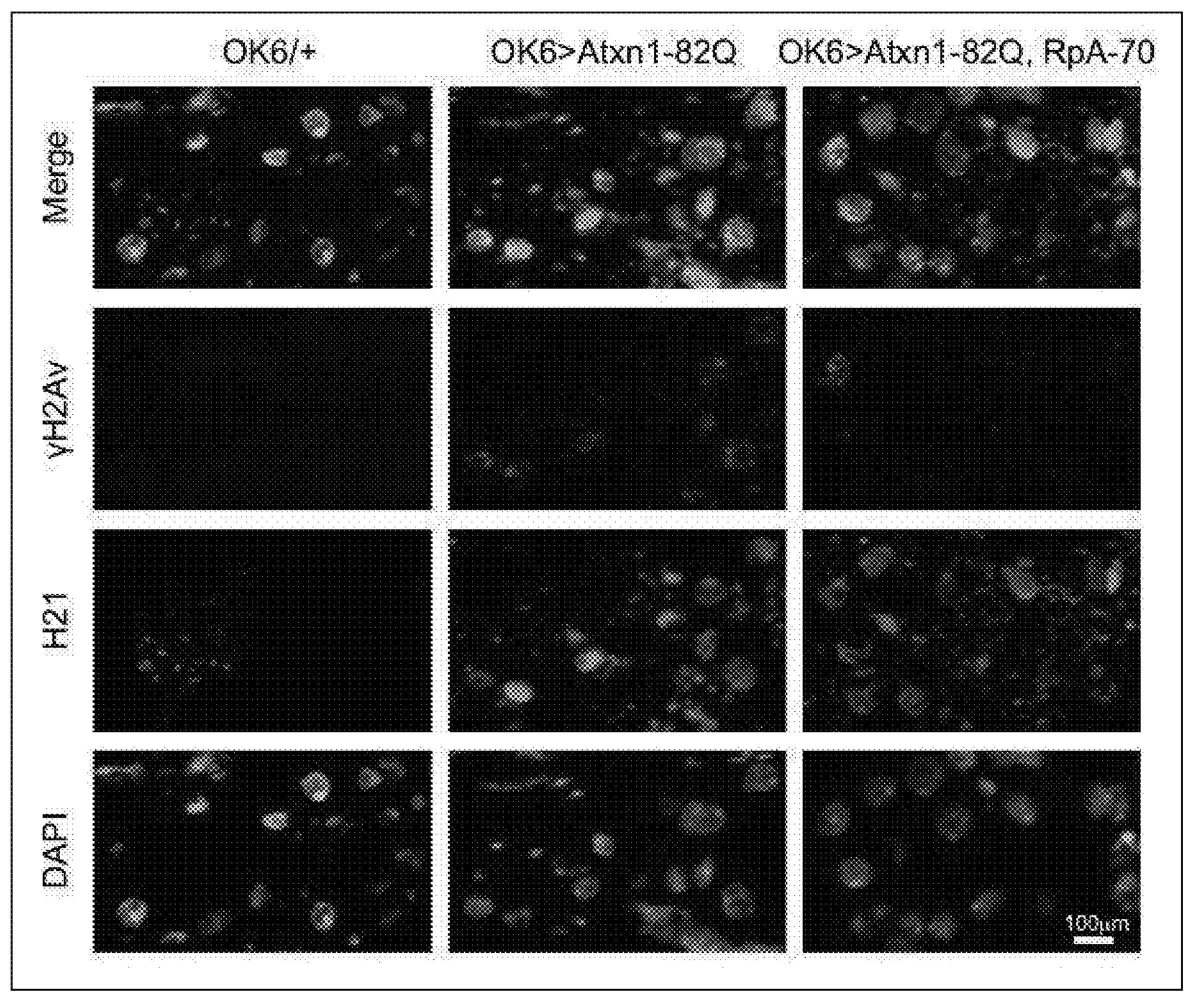
FIG. 21 shows micrographs showing that the increase in DSBs in mutant ATXN1-expressing motor neurons was ameliorated by co-expression of RPA1/RPA70 without being affected by H21-stained ATXN1. Note that DSBs were detected by using the expression of γH2AV as an index.
Figure 22:
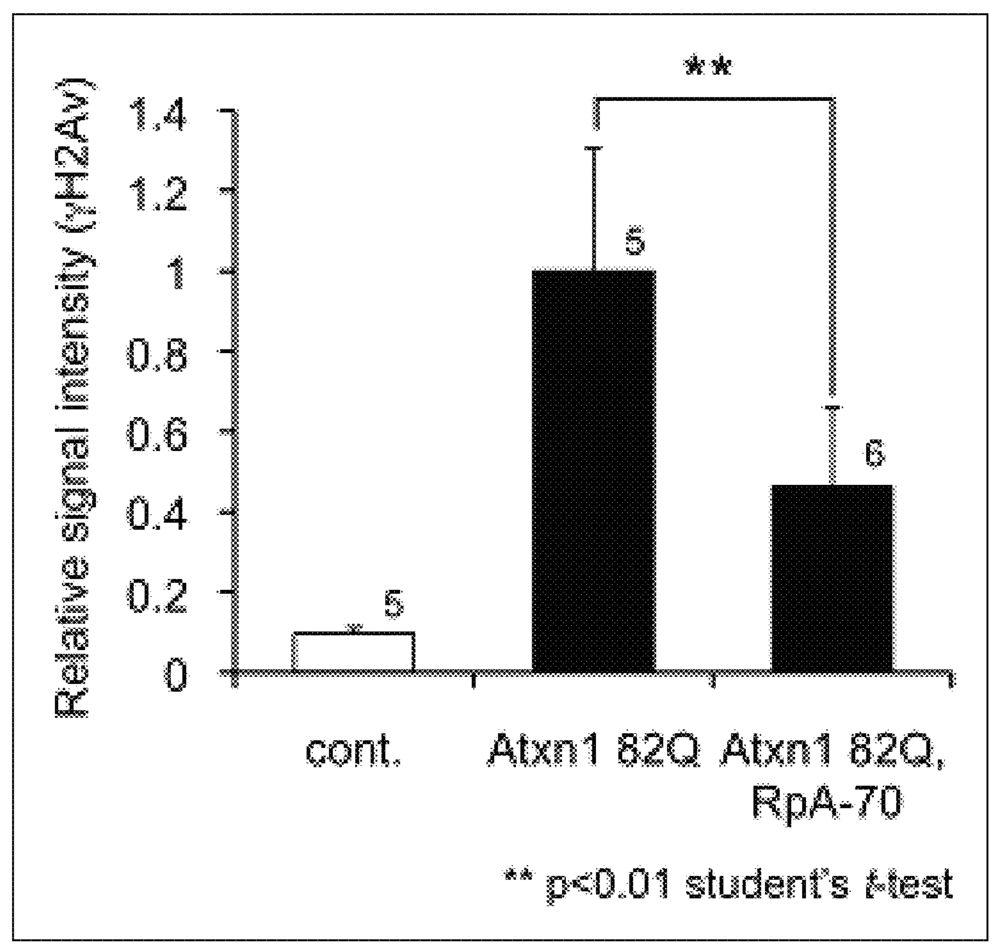
FIG. 22 is a graph which relates to the results shown in FIG. 21 and shows quantification results of the γH2Av signal in the motor neurons. Specifically, this graph shows an ameliorating effect of RPA1/RPA70 on DSBs.

Moreover, it was also revealed that RPA1 mitigated DSBs caused by mutant ATXN1 in *Drosophila* motor neurons, without affecting the aggregation of mutant ATXN1 (see FIGS. 21 and 22).

The above-described results have revealed that mutant ATXN1 is involved in the onset and progression of SCA by impairing the dynamics of RPA1, which is a hub molecule, and exerting influences on many groups of DNA damage repair molecules.

Example 5

<Test 1 of Therapeutic Effect of RPA1 on SCA>

Figure 23:
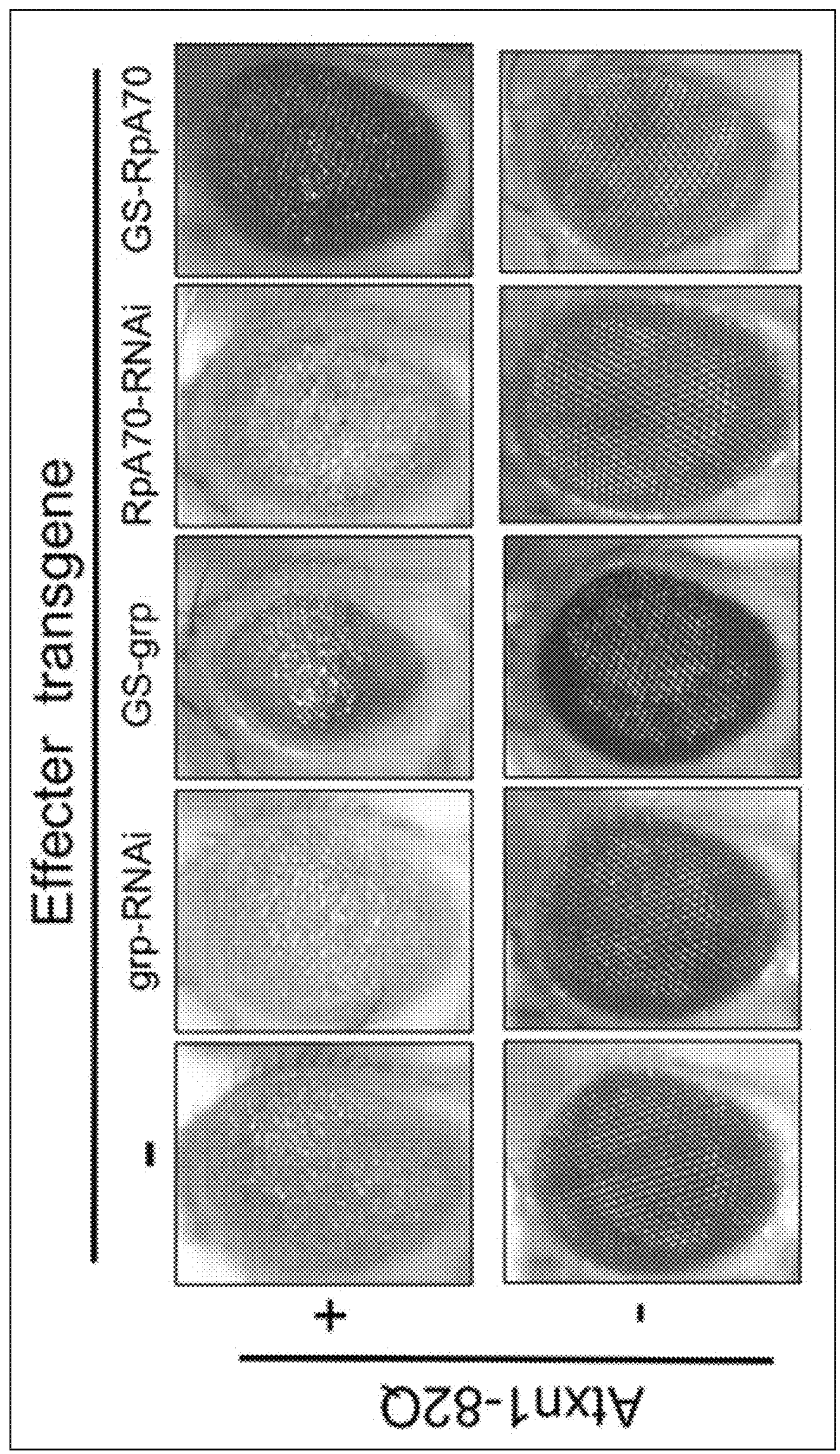
FIG. 23 shows photographs showing the analysis results of the genetic interaction of ATXN1 with CHK1/grp or RPA1/RpA70 by using the rough eye phenotype of the SCA1 fly model as an index. Flies subjected to this analysis were obtained by crossing GS line flies ("GS-grp" or "GS-RpA70" in the drawing) or UAS-RNAi transgenic flies ("grp-RNAi" or "RpA70-RNAi" in the drawing) with GMR>Atxn1-82Q flies ("Atxn1-82Q+" in the drawing). In addition, the analysis results showed that CHK1 knockdown ameliorated the eye degeneration state, whereas CHK1 overexpression aggravated the eye degeneration state. Moreover, the analysis results also showed that RPA1 overexpression ameliorated the eye degeneration state, whereas RPA1 knockdown aggravated the eye degeneration state.
Figure 24:
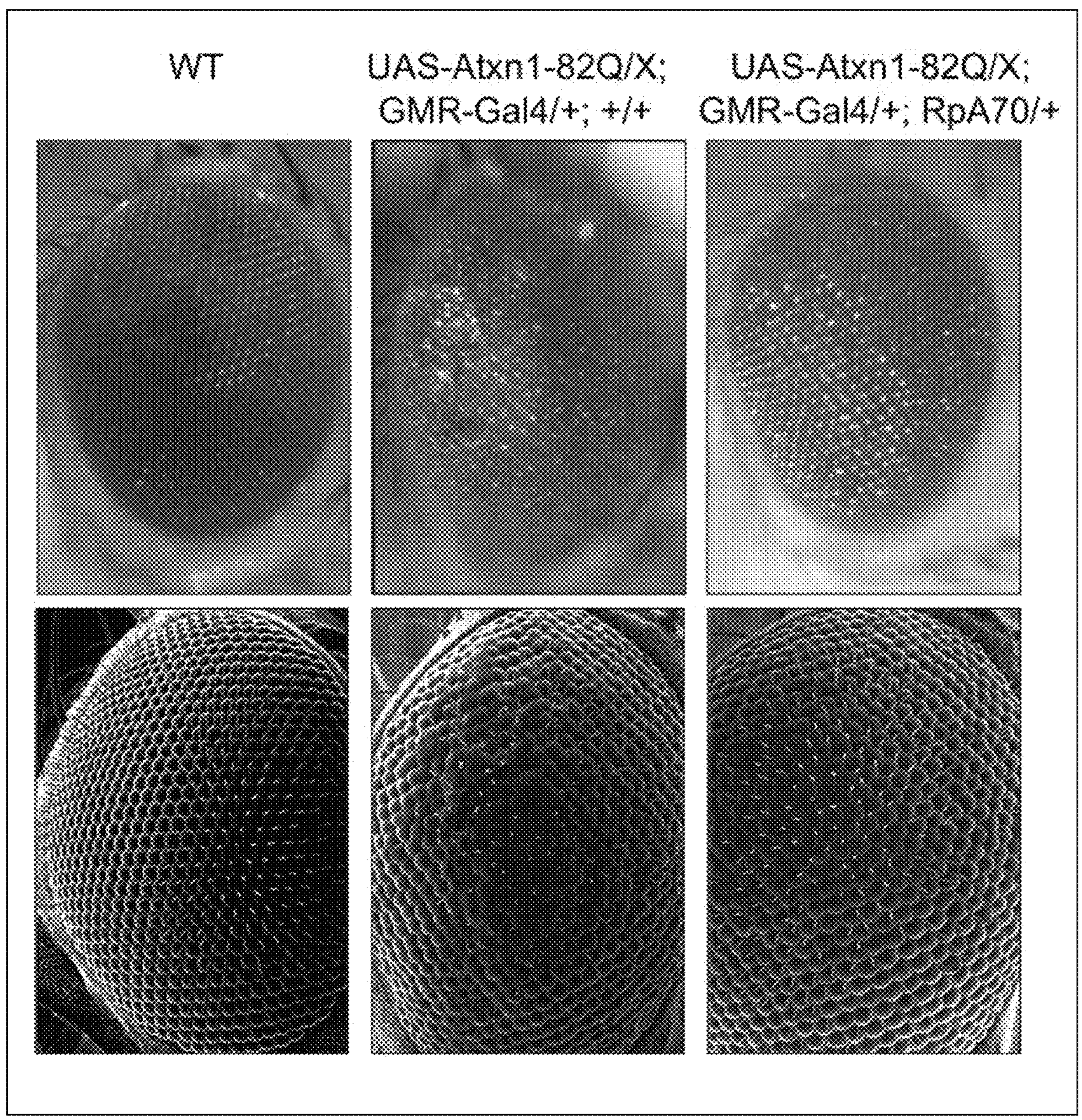
FIG. 24 shows photographs showing improvement in the eye degeneration state in RPA1/RpA70 and mutant ATXN1 double transgenic flies. Specifically, the induction of the expression of mutation ATXN1 (Atxn1-82Q) by GMR in photoreceptor cells causes eye degeneration and the rough eye phenotype. Here, the photographs show that the phenotype is ameliorated by co-expression of RPA1/RpA70.

As described above, the overexpression of RPA1 recovered the shortened lifespan, which was one of the symptoms of the SCA1 fly model. In this respect, a therapeutic effect of RPA1/RpA70 was tested by using eye degeneration, which was another symptom of the SCA1 fly model, as an index. Specifically, RpA70 or siRNA against RpA70 (RpA70-RNAi) was co-expressed with Atxn1-82Q in photoreceptor cells by using the GMR-Gal4 driver. In addition, GS line was used as an example of overexpression. On the other hand, UAS-RpA70-RNAi transgenic flies were used as an example of knockdown. The results showed that the co-expression of RpA70 achieved clear amelioration of the rough eye phenotype. On the other hand, the knockdown of RpA70 aggravated the SCA1 symptom (see FIGS. 23 and 24).

Example 6

<Test 2 of Therapeutic Effect of RPA1 on SCA>

Figure 25:
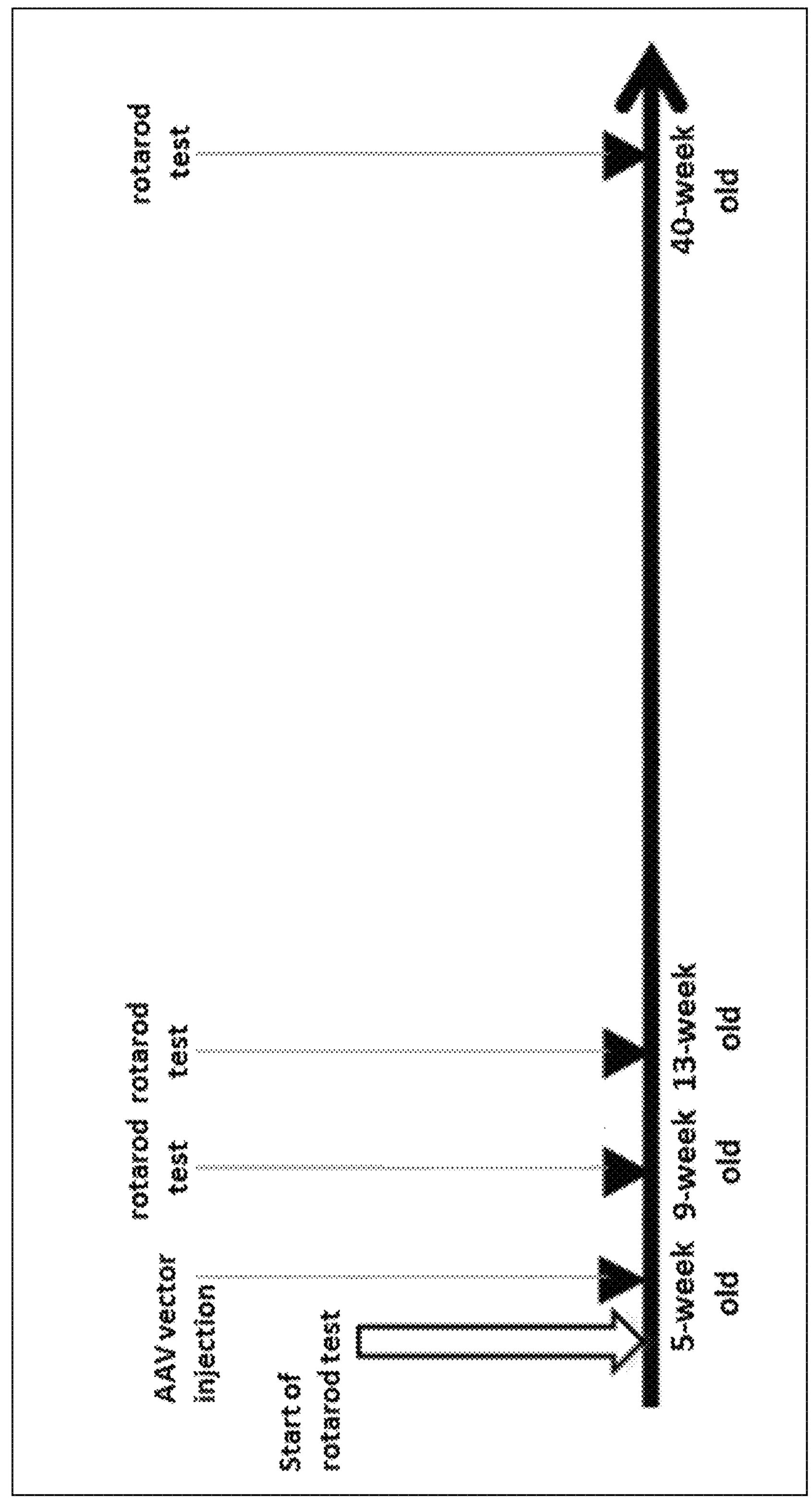
FIG. 25 is a schematic diagram showing the procedure of rotarod tests performed on a SCA1 mouse model in which an AAV vector encoding RPA1 was injected into the cerebellum.
Figure 26:
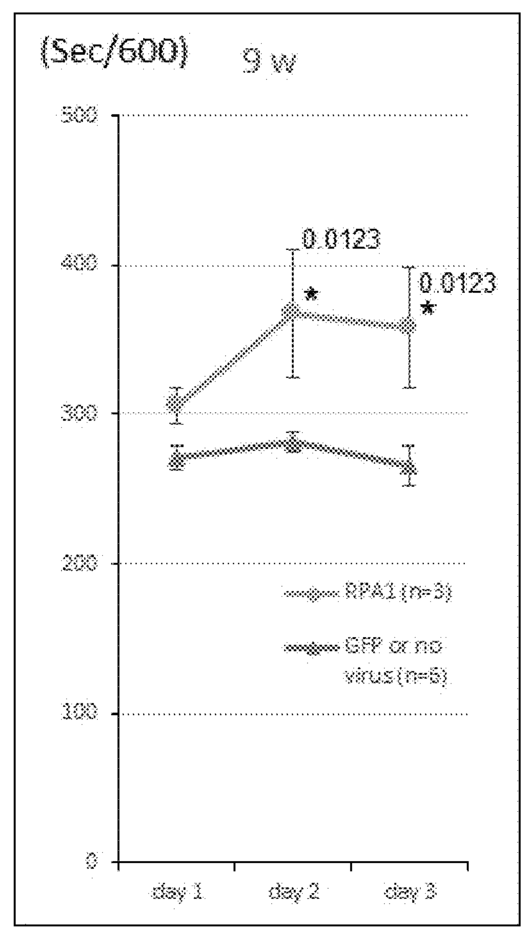
FIG. 26 is a graph showing results (average value ±standard deviation) of rotarod tests performed on the SCA1 mouse model (9-week old) in which the AAV vector encoding RPA1 was injected into the cerebellum. In the graph, the horizontal axis represents the testing day of the rotarod test conducted for three consecutive days. The vertical axis represents the time for which the mouse did not fall dawn but was stayed on a rod rotated for 600 seconds (an average time of four tests on each day). "RPA1" indicates the results of the SCA1 mouse model to which the AAV vector encoding RPA1 was injected into the cerebellum, and "GFP or no virus" indicates the results of an SCA1 mouse model in which the AAV vector was not injected into the cerebellum, and an SCA1 mouse model in which an AAV vector encoding GFP was injected into the cerebellum (results of negative control groups). In addition, the numbers in parentheses attached to "RPA1" and "GFP or no virus" represent the numbers of mice subjected to the test. The asterisks indicate $P<0.05$ in Student's t-test (one-tailed test).
Figure 27:
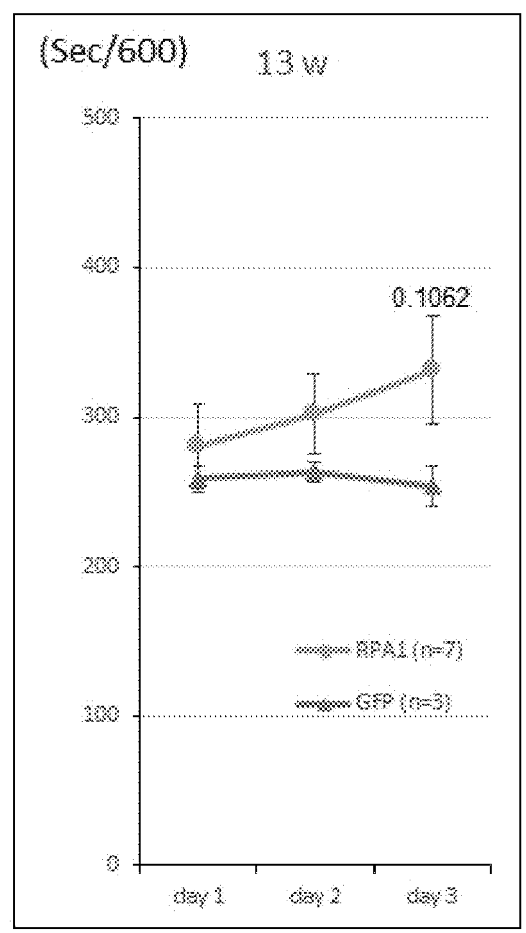
FIG. 27 is a graph showing the results of a rotarod test conducted on the SCA1 mouse model (13-week old) in which the AAV vector encoding RPA1 was injected into the cerebellum. The notations in the graph are the same as those in FIG. 26.
Figure 28:
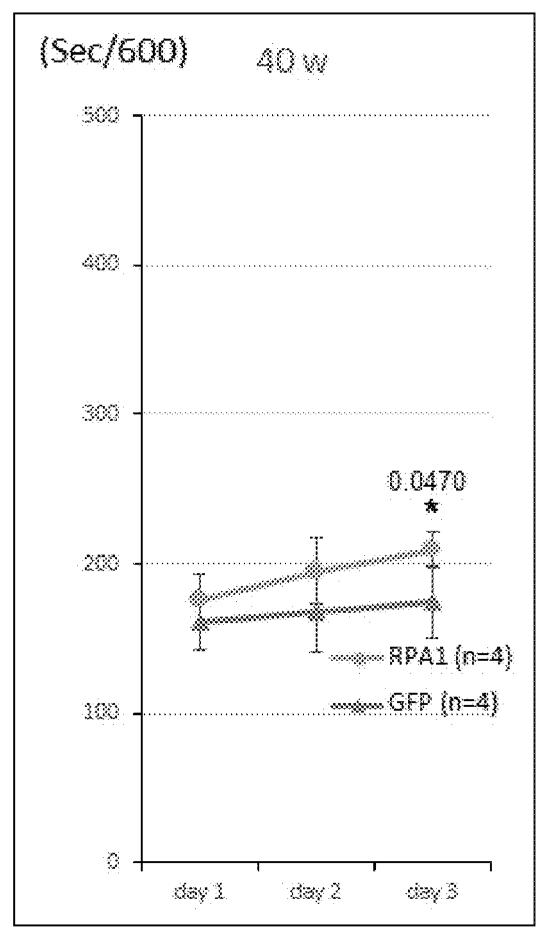
FIG. 28 is a graph showing the results of a rotarod test conducted on the SCA1 mouse model (40-week old) in which the AAV vector encoding RPA1 was injected into the cerebellum. The notations in the graph are the same as those in FIG. 26.

The therapeutic effect of the RPA1 overexpression confirmed in the SCA1 fly model as described above was tested also in the SCA1 mouse model. Specifically, as shown in the experimental schedule in FIG. 25, an RPA1 expression virus vector was injected into the cerebellum of the SCA1 mouse model (5-week old), and a rotarod tests were performed 4 months (9-week old), 8 months (13-week old), and 35 months (40-week old) after the injection to evaluate the recovery from motor disorder in the SCA1 mouse model. FIGS. 26, 27, and 28 show the obtained results. Note that the deterioration in motor activity of the SCA1 mouse model at 5 weeks of age was confirmed in advance by the rotarod test.

As is apparent from the results shown in FIGS. 26, 27, and 28, the time before the mouse fell down from the rotating rod of the SCA1 mouse model to which RPA1-AAV was injected ("RPA1" in the drawing) was significantly longer than that of negative control groups ("no virus" and "GFP" in the drawing; an SCA1 mouse model to which GFP-AAV was injected).

Accordingly, the relief of the symptom (motor disorder) by the RPA1 overexpression, i.e., a therapeutic effect of the RPA1 overexpression was observed also in the SCA1 mouse model.

Example 7

<Test of Therapeutic Effect of CHK1 Function Inhibition on SCA>

Figure 9:
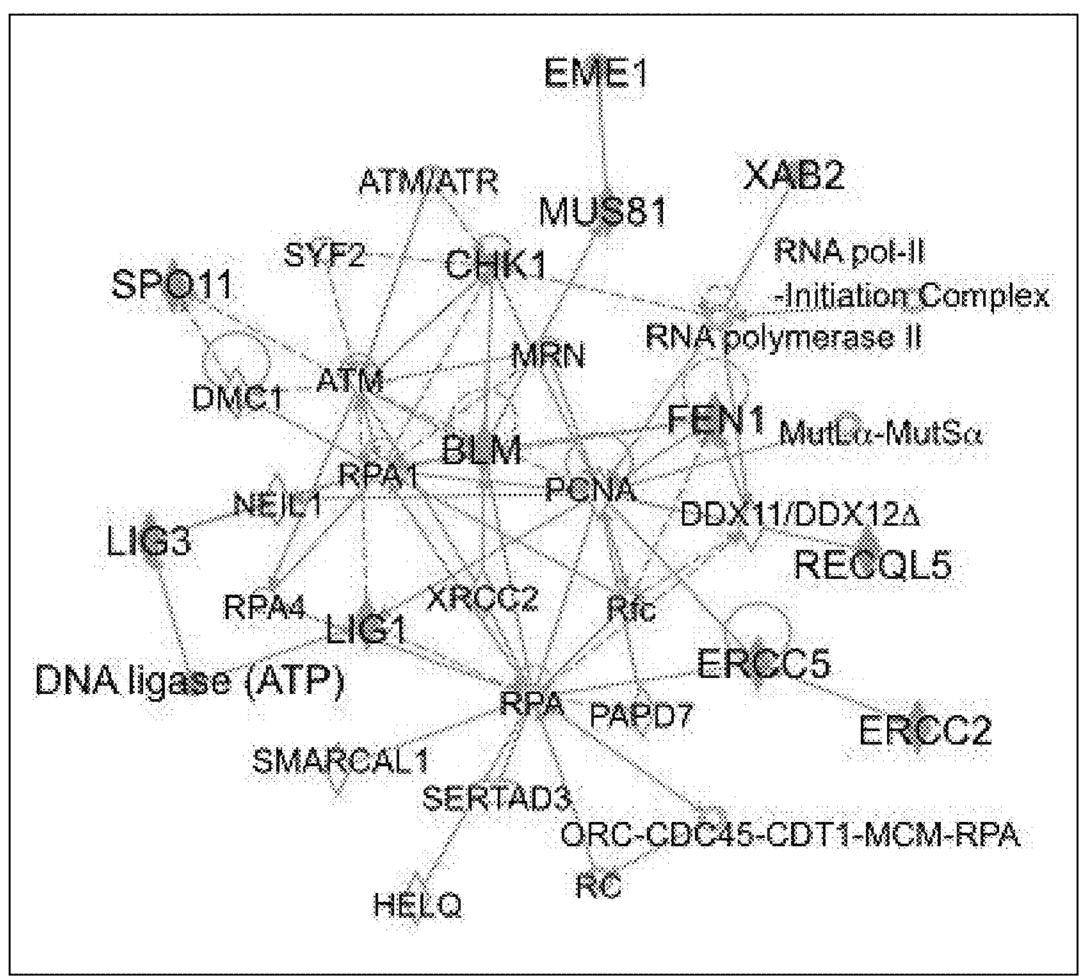
FIG. 9 is a diagram showing a DNA damage repair network-2 which contributes to the lifespan-shortening of the SCA1 fly model and is predicted by Ingenuity-IPA software using the human protein-protein interaction database.
Figure 10:
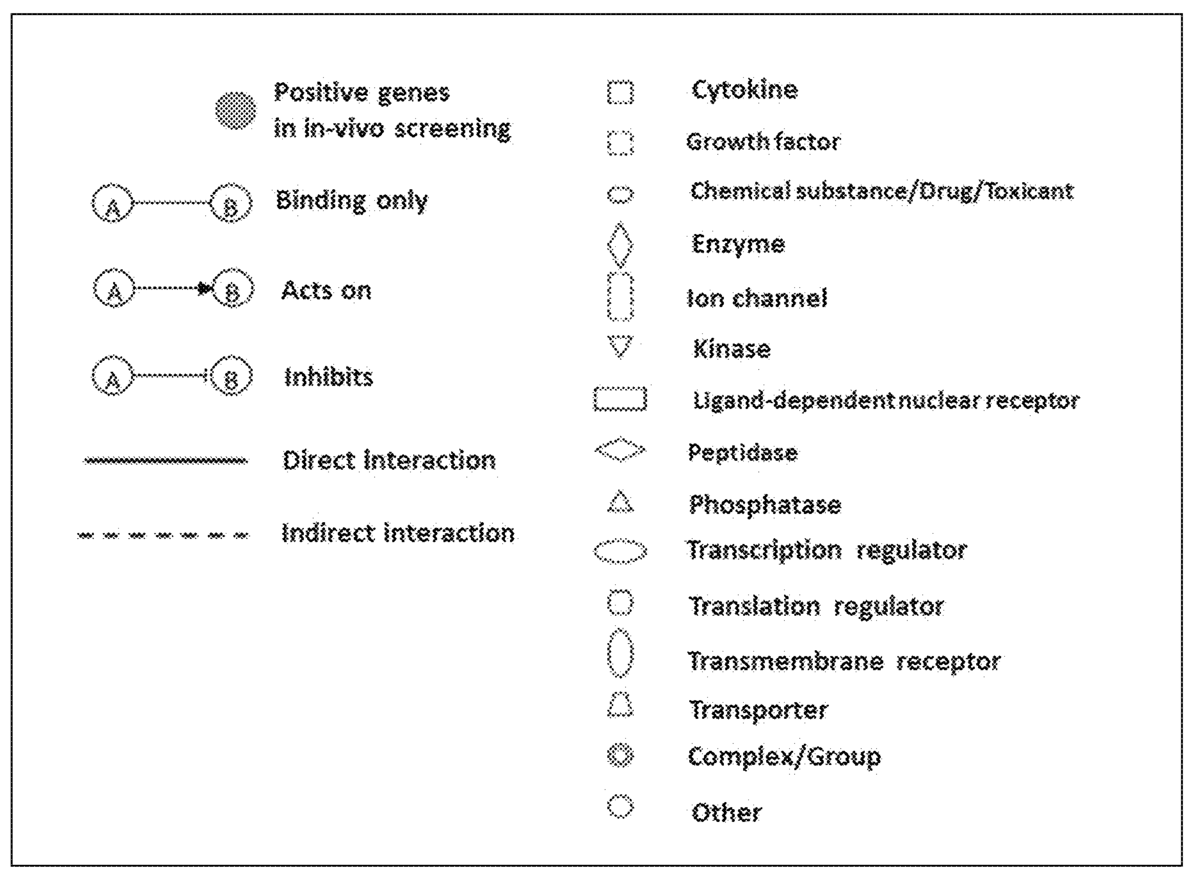
FIG. 10 shows explanations of the notation in FIGS. 6 to 9.

From the results of the construction and analyses of the network of lifespan shortening-related genes, it was revealed that CHK1 received various signals from BLM, FEN1, and LIG1 either directly or indirectly, and prompted the lifespan shortening in the SCA1 fly model (see FIGS. 8 and 9). Moreover, the above-described results of the screening and informatics analysis suggest that CHK1, which is one of the most important transducers of DNA damage signaling, plays an important role in SCA pathology.

In this respect, whether or not the inhibition of a signal mediated by CHK1 mitigates the lifespan shortening in the SCA1 fly model was examined. Specifically, a CHK1-specific inhibitor (CHIR-124) was used. This inhibitor was added to feed (corn-meal medium) at multiple concentrations, and adult flies were fed on the feed. As a result, the lifespan of OK6>SCA1 was improved at 0.00016 mg/mL and 0.02 mg/mL (see FIG. 29). In addition, the improvement effect was more remarkable in an example where the inhibitor was given at a higher concentration. The lifespan of the flies treated with CHIR-124 at 0.02 mg/mL was elongated by 35% (see FIG. 29).

Moreover, the genetic interaction between CHK1/grp and ATXN1 was also investigated. Specifically, Atxn1-82Q was co-expressed with grp or grp-RNAi in photoreceptor cells by using the GMR-Ga14 driver. In addition, GS line was used as an example of overexpression. On the other hand, UAS-grp-RNAi transgenic flies were used as an example of knockdown. As a result, the expression of siRNA against grp slightly relieved the symptom (eye degeneration state) in SCA1. On the other hand, the overexpression of grp remarkably accelerated the eye degeneration (see FIG. 23).

Accordingly, it has been revealed that the inhibition of CHK1 function can reduce the lifespan shortening in the adult SCA1 flies.

Example 8

<Test of Cell Cycle in Purkinje Cells>

Next, how RPA1 was involved in the SCA pathology was investigated. As shown in FIG. 6, RPA1 is linked to various DNA damage repair paths such as those of nonhomologous end joining (NHEJ)-type DSBR, HR-type DSBR, nucleotide-excision repair (NER), and base-excision repair (BER). In addition, RPA1 is known to basically protect naked single-stranded DNA and be involved in HR, NER, and BER, which occurs mainly in proliferating cells. For this reason, the following mechanisms are conceivable through which the above-described therapeutic effect of the RPA1 may be achieved.

1) RPA1 is involved in non-cell-autonomous pathology via glial cell, including Bergmann glia or astrocytes. Note that the non-cell-autonomous pathology means that abnormality in cells other than neurons causes dysfunction or cell death of neurons, and is mainly caused by glial cells. In other words, the non-cell-autonomous pathology is one caused by aberration of glia, which has a protective effect on neurons, such as Bergmann glia.

2) RPA1 is involved in stem cell pathology via embryonic or adult stem cells.

3) RPA1 is involved in DNA damage repair in Purkinje cells at an abnormal cell cycle stage.

The first possibility is based on the analogy to the non-cell-autonomous pathology of amyotrophic lateral sclerosis (see Yamanaka, K. et al., Nat Neurosci, 2008, Vol. 11, pp. 251 to 253, Yamanaka, K. et al., Proc Natl Acad Sci USA, 2008, 105, pp. 7594 to 7599, Nagai, M. et al., Nat Neurosci, 2007, Vol. 10, pp. 615 to 622, and Di Giorgio et al., Nat Neurosci, 2007, Vol. 10, pp. 608 to 614) or the result indicating the involvement of Bergmann glia in SCA1 pathology (see Shiwaku, H. et al., Embo J, 2010, Vol. 29, pp. 2446 to 2460). The second possibility is based on the previous observation result that RORα exerts an influence on Purkinje cells during progression of SCA pathology (see Serra, H. G. et al., Cell, 2006, Vol. 127, pp. 697 to 708). The third possibility is based on an abnormal cell cycle in neurodegenerative diseases, i.e., the fact that the entry of neurons into the S phase is impaired in neurodegenerative diseases (see Herrup, K. et al., Nat Rev Neurosci, 2007, Vol. 8, pp. 368 to 378).

Figure 30:
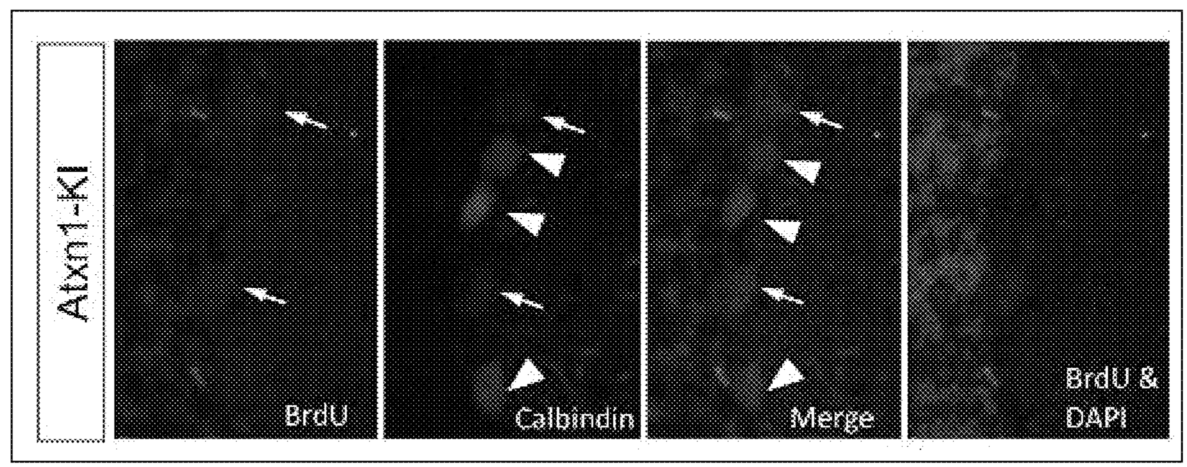
FIG. 30 shows micrographs showing that weak signals of BrdU taken up into degraded Purkinje cells were detected by double staining ("Merge" in FIG. 30) with an anti-BrdU antibody ("BrdU" in FIG. 30) and an anti-calbindin antibody ("Calbindin" in FIG. 30) (see arrows in FIG. 30). Note that no signals of BrdU were detected in normal Purkinje cells in which strong signals of calbindin were detected.
Figure 31:
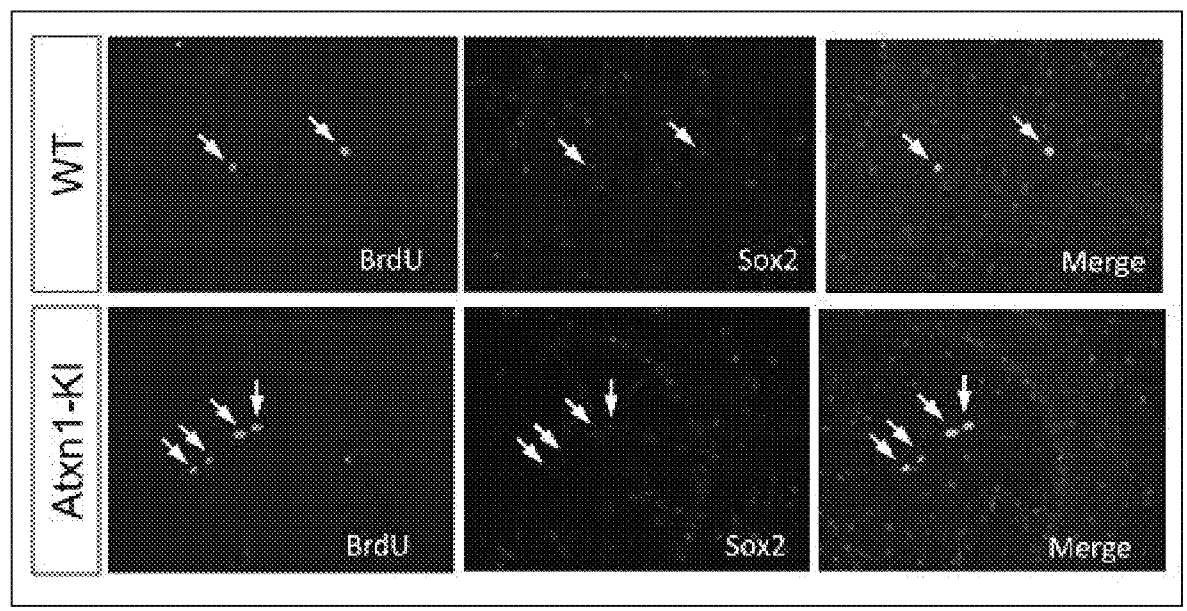
FIG. 31 shows micrographs of double staining ("Merge" in FIG. 31) with an anti-BrdU antibody ("BrdU" in FIG. 31) and an anti-Sox2 antibody ("Sox2" in FIG. 31) showing that Sox2-positive Bergmann glia present in the Purkinje cell layer did not take up RrdU (see arrows in FIG. 31). In addition, BrdU/Sox2 double-positive cells present in the white matter were observed in the double staining with the anti-BrdU antibody and the anti-Sox2 antibody (see arrows FIG. 31)).
Figure 32:
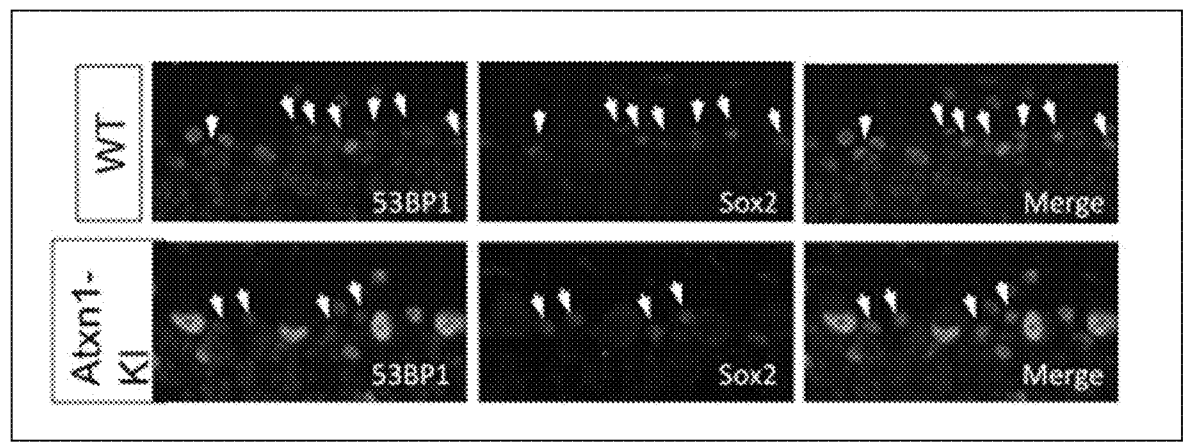
FIG. 32 shows micrographs showing that the signal intensity of 53BP1 in Atxn1-KI mice was similar in Bergmann glia but was increased in Purkinje cells in comparison with those of wild-type mice (WT) (see arrows).

Regarding the above-described three possibilities, proliferation-type cells or S-phase cells in the cerebellum were examined. Specifically, BrdU was injected into adult mice at 32 weeks of age, and the uptake in various types of cells was analyzed. As a result, deteriorated Purkinje cells which were stained with anti-calbindin antibody and took up BrdU were observed (see FIGS. 30 to 32). Accordingly, the third possibility that RPA1 is involved in DNA damage repair in Purkinje cells at an abnormal cell cycle stage is supported.

Figure 33:
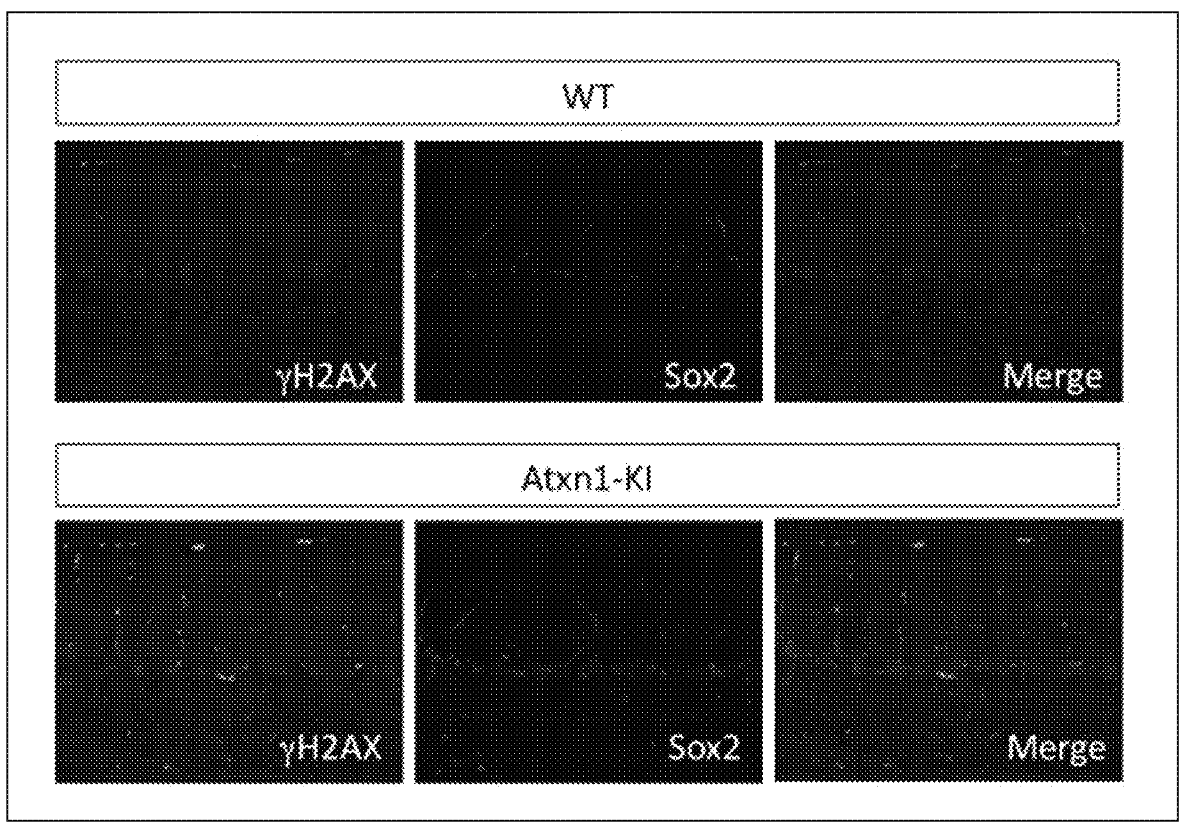
FIG. 33 shows micrographs showing that no signals of BrdU were detected in Bergmann glia of the Atxn1-KI mice by double staining ("Merge" in FIG. 33) with an anti-γH2A antibody ("γH2A" in FIG. 33) and an anti-Sox2 antibody ("Sox2" in the drawing).

Regarding the first and second possibilities, double staining of BrdU and Sox2 was performed in the cerebellum. Note that Sox2 is a stem cell marker, and used for the staining to identify adult stem cells in the cerebellum. As a result, two or three double-stained cells were observed in the white matter and molecular layer of the cerebellar cortex (see FIGS. 30 to 32). In addition, no BrdU uptake by Bergmann glia was observed. Moreover, γH2AX signals were not increased in Sox2-positive Bergmann cells (see FIG. 33). Therefore, the first and second possibilities seem to be less likely.

In sum, it is suggested that abnormal entry of Purkinje cells into the S phase induces DNA damage repair in the cells, and in turn homologous recombination by RPA1, so that the SCA pathology is relieved.

INDUSTRIAL APPLICABILITY

As described above, the present invention makes it possible to relieve the SCA pathology by enhancement of the expression of RPA1, BRCA1, BRCA2, PNKP, XRCC3, XRCC4, CCNH, POLE, POLH, or PER1, or the like. In addition, it is also possible to relieve the SCA pathology by inhibiting the binding of ATXN1, which is a cause of SCA1, to RPA1, BRCA1, or BRCA2. Moreover, it is also possible to relieve the SCA pathology by suppression of the expression of CHK1, LIG3, FEN1, LIG1, ERCC5, XAB2, ERCC2, DMC1, RECQL5, MUS81, EME1, SPO11 or BLM, or the like.

Accordingly, the agent and the screening method for a candidate compound for such an agent of the present invention are useful for treating and preventing SCA, and for developing a method for treating and preventing SCA.

The invention claimed is:

1. A method for treating a spinocerebellar ataxia, comprising administering to a subject in need thereof, an effective amount of an agent comprising as an active ingredient, a Replication protein AI (RPA1) or a nucleic acid encoding the protein; wherein said spinocerebellar ataxia is spinocerebellar ataxia type 1, and a dysfunction of DNA damage repair is involved in the onset of said spinocerebellar ataxia type I, and wherein said RPA1 comprises the amino acid sequence of SEQ ID NO: 2; or comprises an amino acid sequence having at least 95% identity to the entirety of the amino acid sequence of SEQ ID NO: 2.

* * * * *

SEQUENCE LISTING

```
<160> NUMBER OF SEQ ID NOS: 48

<210> SEQ ID NO 1
<211> LENGTH: 4345
<212> TYPE: DNA
<213> ORGANISM: Homo sapiens
<220> FEATURE:
<221> NAME/KEY: CDS
<222> LOCATION: (116)..(1966)
<223> OTHER INFORMATION: RPA1

<400> SEQUENCE: 1

gggggcggga gcggtgcgcg caacttctcg ggccaataac tgcgcagcgc gcgggacccg      60

ggtggggaag ctggagctgt tgcggggtcc gcggggaagt cttggcggtg gagcc atg      118
                                                             Met
                                                             1

gtc ggc caa ctg agc gag ggg gcc att gcg gcc atc atg cag aag ggg      166
Val Gly Gln Leu Ser Glu Gly Ala Ile Ala Ala Ile Met Gln Lys Gly
            5                   10                  15

gat aca aac ata aag ccc atc ctc caa gtc atc aac atc cgt ccc att      214
Asp Thr Asn Ile Lys Pro Ile Leu Gln Val Ile Asn Ile Arg Pro Ile
        20                  25                  30

act acg ggg aat agt ccg ccg cgt tat cga ctg ctc atg agt gat gga      262
Thr Thr Gly Asn Ser Pro Pro Arg Tyr Arg Leu Leu Met Ser Asp Gly
    35                  40                  45

ttg aac act cta tcc tct ttc atg ttg gcg aca cag ttg aac cct ctc      310
Leu Asn Thr Leu Ser Ser Phe Met Leu Ala Thr Gln Leu Asn Pro Leu
50                  55                  60                  65

gtg gag gaa gaa caa ttg tcc agc aac tgt gta tgc cag att cac aga      358
Val Glu Glu Glu Gln Leu Ser Ser Asn Cys Val Cys Gln Ile His Arg
                70                  75                  80

ttt att gtg aac act ctg aaa gac gga agg aga gta gtt atc ttg atg      406
Phe Ile Val Asn Thr Leu Lys Asp Gly Arg Arg Val Val Ile Leu Met
            85                  90                  95

gaa tta gaa gtt ttg aag tca gct gaa gca gtt gga gtg aag att ggc      454
Glu Leu Glu Val Leu Lys Ser Ala Glu Ala Val Gly Val Lys Ile Gly
        100                 105                 110

aat cca gtg ccc tat aat gaa gga ctc ggg cag ccg caa gta gct cct      502
Asn Pro Val Pro Tyr Asn Glu Gly Leu Gly Gln Pro Gln Val Ala Pro
    115                 120                 125

cca gcg cca gca gcc agc cca gca gca agc agc agg ccc cag ccg cag      550
Pro Ala Pro Ala Ala Ser Pro Ala Ala Ser Ser Arg Pro Gln Pro Gln
130                 135                 140                 145

aat gga agc tcg gga atg ggt tct act gtt tct aag gct tat ggt gct      598
Asn Gly Ser Ser Gly Met Gly Ser Thr Val Ser Lys Ala Tyr Gly Ala
                150                 155                 160

tca aag aca ttt gga aaa gct gca ggt ccc agc ctg tca cac act tct      646
Ser Lys Thr Phe Gly Lys Ala Ala Gly Pro Ser Leu Ser His Thr Ser
            165                 170                 175

ggg gga aca cag tcc aaa gtg gtg ccc att gcc agc ctc act cct tac      694
Gly Gly Thr Gln Ser Lys Val Val Pro Ile Ala Ser Leu Thr Pro Tyr
        180                 185                 190

cag tcc aag tgg acc att tgt gct cgt gtt acc aac aaa agt cag atc      742
Gln Ser Lys Trp Thr Ile Cys Ala Arg Val Thr Asn Lys Ser Gln Ile
    195                 200                 205
```

```
cgt acc tgg agc aac tcc cga ggg gaa ggg aag ctt ttc tcc cta gaa      790
Arg Thr Trp Ser Asn Ser Arg Gly Glu Gly Lys Leu Phe Ser Leu Glu
210                 215                 220                 225

ctg gtt gac gaa agt ggt gaa atc cga gct aca gct ttc aat gag caa      838
Leu Val Asp Glu Ser Gly Glu Ile Arg Ala Thr Ala Phe Asn Glu Gln
                230                 235                 240

gtg gac aag ttc ttt cct ctt att gaa gtg aac aag gtg tat tat ttc      886
Val Asp Lys Phe Phe Pro Leu Ile Glu Val Asn Lys Val Tyr Tyr Phe
            245                 250                 255

tcg aaa ggc acc ctg aag att gct aac aag cag ttc aca gct gtt aaa      934
Ser Lys Gly Thr Leu Lys Ile Ala Asn Lys Gln Phe Thr Ala Val Lys
        260                 265                 270

aat gac tac gag atg acc ttc aat aac gag act tcc gtc atg ccc tgt      982
Asn Asp Tyr Glu Met Thr Phe Asn Asn Glu Thr Ser Val Met Pro Cys
    275                 280                 285

gag gac gac cat cat tta cct acg gtt cag ttt gat ttc acg ggg att     1030
Glu Asp Asp His His Leu Pro Thr Val Gln Phe Asp Phe Thr Gly Ile
290                 295                 300                 305

gat gac ctc gag aac aag tcg aaa gac tca ctt gta gac atc atc ggg     1078
Asp Asp Leu Glu Asn Lys Ser Lys Asp Ser Leu Val Asp Ile Ile Gly
                310                 315                 320

atc tgc aag agc tat gaa gac gcc act aaa atc aca gtg agg tct aac     1126
Ile Cys Lys Ser Tyr Glu Asp Ala Thr Lys Ile Thr Val Arg Ser Asn
            325                 330                 335

aac aga gaa gtt gcc aag agg aat atc tac ttg atg gac aca tcc ggg     1174
Asn Arg Glu Val Ala Lys Arg Asn Ile Tyr Leu Met Asp Thr Ser Gly
        340                 345                 350

aag gtg gtg act gct aca ctg tgg ggg gaa gat gct gat aaa ttt gat     1222
Lys Val Val Thr Ala Thr Leu Trp Gly Glu Asp Ala Asp Lys Phe Asp
    355                 360                 365

ggt tct aga cag ccc gtg ttg gct atc aaa gga gcc cga gtc tct gat     1270
Gly Ser Arg Gln Pro Val Leu Ala Ile Lys Gly Ala Arg Val Ser Asp
370                 375                 380                 385

ttc ggt gga cgg agc ctc tcc gtg ctg tct tca agc act atc att gcg     1318
Phe Gly Gly Arg Ser Leu Ser Val Leu Ser Ser Ser Thr Ile Ile Ala
                390                 395                 400

aat cct gac atc cca gag gcc tat aag ctt cgt gga tgg ttt gac gca     1366
Asn Pro Asp Ile Pro Glu Ala Tyr Lys Leu Arg Gly Trp Phe Asp Ala
            405                 410                 415

gaa gga caa gcc tta gat ggt gtt tcc atc tct gat cta aag agc ggc     1414
Glu Gly Gln Ala Leu Asp Gly Val Ser Ile Ser Asp Leu Lys Ser Gly
        420                 425                 430

gga gtc gga ggg agt aac acc aac tgg aaa acc ttg tat gag gtc aaa     1462
Gly Val Gly Gly Ser Asn Thr Asn Trp Lys Thr Leu Tyr Glu Val Lys
    435                 440                 445

tcc gag aac ctg ggc caa ggc gac aag ccg gac tac ttt agt tct gtg     1510
Ser Glu Asn Leu Gly Gln Gly Asp Lys Pro Asp Tyr Phe Ser Ser Val
450                 455                 460                 465

gcc aca gtg gtg tat ctt cgc aaa gag aac tgc atg tac caa gcc tgc     1558
Ala Thr Val Val Tyr Leu Arg Lys Glu Asn Cys Met Tyr Gln Ala Cys
                470                 475                 480

ccg act cag gac tgc aat aag aaa gtg att gat caa cag aat gga ttg     1606
Pro Thr Gln Asp Cys Asn Lys Lys Val Ile Asp Gln Gln Asn Gly Leu
            485                 490                 495

tac cgc tgt gag aag tgc gac acc gaa ttt ccc aat ttc aag tac cgc     1654
Tyr Arg Cys Glu Lys Cys Asp Thr Glu Phe Pro Asn Phe Lys Tyr Arg
        500                 505                 510

atg atc ctg tca gta aat att gca gat ttt caa gag aat cag tgg gtg     1702
Met Ile Leu Ser Val Asn Ile Ala Asp Phe Gln Glu Asn Gln Trp Val
    515                 520                 525
```

```
act tgt ttc cag gag tct gct gaa gct atc ctt gga caa aat gct gct     1750
Thr Cys Phe Gln Glu Ser Ala Glu Ala Ile Leu Gly Gln Asn Ala Ala
530                 535                 540                 545

tat ctt ggg gaa tta aaa gac aag aat gaa cag gca ttt gaa gaa gtt     1798
Tyr Leu Gly Glu Leu Lys Asp Lys Asn Glu Gln Ala Phe Glu Glu Val
                550                 555                 560

ttc cag aat gcc aac ttc cga tct ttc ata ttc aga gtc agg gtc aaa     1846
Phe Gln Asn Ala Asn Phe Arg Ser Phe Ile Phe Arg Val Arg Val Lys
            565                 570                 575

gtg gag acc tac aac gac gag tct cga att aag gcc act gtg atg gac     1894
Val Glu Thr Tyr Asn Asp Glu Ser Arg Ile Lys Ala Thr Val Met Asp
        580                 585                 590

gtg aag ccc gtg gac tac aga gag tat ggc cga agg ctg gtc atg agc     1942
Val Lys Pro Val Asp Tyr Arg Glu Tyr Gly Arg Arg Leu Val Met Ser
    595                 600                 605

atc agg aga agt gca ttg atg tga gaggagcagt gccaatcggg cagaagtttg    1996
Ile Arg Arg Ser Ala Leu Met
610                 615

caaataggca gaatggaatc gatttcctcc cacctccgtg tgacgatccc atgttagcta   2056

cacagtgcag aggctcttga tggtggacta agcaatttcc cccctcgtgc gcatctcaga   2116

acccatcggt aggcaaagga aaatacgctc aggtggttgt ggtgtagact gtgtcaggcc   2176

tacggagtca gccagtggct agcgcaagac cagtcactcc ctctgccttc aggcttctgt   2236

caatttcatt atcatcaagc aggaattatg tcgtaagtca ctgaccctaa ctgcagacca   2296

tgaagtaaat tatgtaacta ggtttttgct tctccagtgg tgaccacccc cccccatccc   2356

cgctcacaac ttgggttctt ctcagcgggg cgagctgaga agcggtcatg agcacctggg   2416

gattttagta agtgtgtctt cctagaattc gaaggctctc tctttctaga ggtgctacat   2476

agttggtaat gcttggaatg gcaatagggt agaatgatta atcaaaggca tatcttctat   2536

atctgaagag tatccttcct tcagggttta atagactgag tcagatgggt ctgatattaa   2596

tcaaaattgt ctcttctgag gaccgctgat aagcattgac ttgccgtccc ctaaggaaat   2656

ccgagcggct acaaagcgtt tctttacttc tcacttcaat taatgctgcg cttcgcttgg   2716

tgagtgcgta ctttttctac ctgtacacat tcctgcattc atgtattttg ttttttttga   2776

ctaaagctat gttacatgga aaggatttg  aagccttttg tttcccttgc tttgttttaa   2836

taaacagtat attctttggt tgtgaatcct actttctttg aatgcaaaga gttcctataa   2896

ctggaaagca attaattagc cttcataata aatgttcact tggggggggat gttaactcat  2956

tataaacccg aagattagtc caaggcatgg agatccttct tcctagtgtt tgcagccctg   3016

aaatgcatct ttcaaagcat gaaaacacta aaaacaaaaa gccattttgc ctgaggatgc   3076

tgatgatctg gcacttggga ttttattgat gtttacgcag cagtctaaca ccaaccacgc   3136

tttgaaatgt gtacagacag tgagctggta agaaaacagt aattatgcta gtgggccttt   3196

cagtcagcaa aagcatgctc gctctgtgtg ttcctaatca tattaattat ctatccggtg   3256

gctgcaacac accgcctgcc attggccgca catctcgccg tcgtaccccg gcagtgcggc   3316

ggtcactctg cagccagagg acctgctgtt catcactgca catgccgcct gcggaggctt   3376

ttggatatgg ggagtgatgg tgtcctgtct gtctcccccc tcggtgtctg ccgttgacat   3436

aggggccagc cagccctaga cgggatgact tccgttcctg aggacagaca cagagggact   3496

cctgctcagc ctcactaatt gtttagacac attccttcct acccttctct agtctcagga   3556

gatggtaact gggtcgcatt tcagtctctg actgaggcct cagccatttt tacggaagtt   3616
```

ctttctgtc tgaccttgct tataaagcat cgacgagaaa attacagtct tcaaccctct 3676 tctggattga caaattgtgg ctgggaagtg gcgatctagc tttcagccca gtaaccagtc 3736 tttcatgcct actactccca gcattccctc ctctccccac gtgtctgtcc acacagtgaa 3796 gaggcctgac cagccgtggt accaggacag gacgtgtcca gggaacgctg acacctgtcc 3856 tcgcgccttc tcagtggcca gcgtgatgaa accagcacgt ctccgtggat gtgattggga 3916 acccaggggc agtgccaggg ggagggctcc ctcgaggagg ctgtttctaa cagatttccc 3976 cactcaaaga tcagatcacc agcagaggag catcagaaac tggctccact gttgggcttt 4036 tcagagattt tggtccctgc gggttgccta aatagattct ggcccacagt ttacctcgaa 4096 aggctgttga tgttgttctg tttctcctct ttcacttaga gatcaatgtt gattttgcgt 4156 acaccatgac atcagcgtta ggcaattagg agaaaaaaat ctaatcattt cgcctttatt 4216 tcaagtggtt cttgaattcc ctccagtctc attgtgaaag gggcagggaa aaaaataaaa 4276 gggtaataat ctgatttctg tccatatttc cagtgtttta tgctttccat taaaaccttg 4336 ctaatctct 4345

<210> SEQ ID NO 2
<211> LENGTH: 616
<212> TYPE: PRT
<213> ORGANISM: Homo sapiens

<400> SEQUENCE: 2

Met Val Gly Gln Leu Ser Glu Gly Ala Ile Ala Ala Ile Met Gln Lys
1 5 10 15

Gly Asp Thr Asn Ile Lys Pro Ile Leu Gln Val Ile Asn Ile Arg Pro
20 25 30

Ile Thr Thr Gly Asn Ser Pro Pro Arg Tyr Arg Leu Leu Met Ser Asp
35 40 45

Gly Leu Asn Thr Leu Ser Ser Phe Met Leu Ala Thr Gln Leu Asn Pro
50 55 60

Leu Val Glu Glu Glu Gln Leu Ser Ser Asn Cys Val Cys Gln Ile His
65 70 75 80

Arg Phe Ile Val Asn Thr Leu Lys Asp Gly Arg Arg Val Val Ile Leu
85 90 95

Met Glu Leu Glu Val Leu Lys Ser Ala Glu Ala Val Gly Val Lys Ile
100 105 110

Gly Asn Pro Val Pro Tyr Asn Glu Gly Leu Gly Gln Pro Gln Val Ala
115 120 125

Pro Pro Ala Pro Ala Ala Ser Pro Ala Ala Ser Ser Arg Pro Gln Pro
130 135 140

Gln Asn Gly Ser Ser Gly Met Gly Ser Thr Val Ser Lys Ala Tyr Gly
145 150 155 160

Ala Ser Lys Thr Phe Gly Lys Ala Ala Gly Pro Ser Leu Ser His Thr
165 170 175

Ser Gly Gly Thr Gln Ser Lys Val Val Pro Ile Ala Ser Leu Thr Pro
180 185 190

Tyr Gln Ser Lys Trp Thr Ile Cys Ala Arg Val Thr Asn Lys Ser Gln
195 200 205

Ile Arg Thr Trp Ser Asn Ser Arg Gly Glu Gly Lys Leu Phe Ser Leu
210 215 220

Glu Leu Val Asp Glu Ser Gly Glu Ile Arg Ala Thr Ala Phe Asn Glu
225 230 235 240

```
Gln Val Asp Lys Phe Phe Pro Leu Ile Glu Val Asn Lys Val Tyr Tyr
                245                 250                 255

Phe Ser Lys Gly Thr Leu Lys Ile Ala Asn Lys Gln Phe Thr Ala Val
            260                 265                 270

Lys Asn Asp Tyr Glu Met Thr Phe Asn Asn Glu Thr Ser Val Met Pro
        275                 280                 285

Cys Glu Asp Asp His His Leu Pro Thr Val Gln Phe Asp Phe Thr Gly
    290                 295                 300

Ile Asp Asp Leu Glu Asn Lys Ser Lys Asp Ser Leu Val Asp Ile Ile
305                 310                 315                 320

Gly Ile Cys Lys Ser Tyr Glu Asp Ala Thr Lys Ile Thr Val Arg Ser
                325                 330                 335

Asn Asn Arg Glu Val Ala Lys Arg Asn Ile Tyr Leu Met Asp Thr Ser
            340                 345                 350

Gly Lys Val Val Thr Ala Thr Leu Trp Gly Glu Asp Ala Asp Lys Phe
        355                 360                 365

Asp Gly Ser Arg Gln Pro Val Leu Ala Ile Lys Gly Ala Arg Val Ser
    370                 375                 380

Asp Phe Gly Gly Arg Ser Leu Ser Val Leu Ser Ser Ser Thr Ile Ile
385                 390                 395                 400

Ala Asn Pro Asp Ile Pro Glu Ala Tyr Lys Leu Arg Gly Trp Phe Asp
                405                 410                 415

Ala Glu Gly Gln Ala Leu Asp Gly Val Ser Ile Ser Asp Leu Lys Ser
            420                 425                 430

Gly Gly Val Gly Gly Ser Asn Thr Asn Trp Lys Thr Leu Tyr Glu Val
        435                 440                 445

Lys Ser Glu Asn Leu Gly Gln Gly Asp Lys Pro Asp Tyr Phe Ser Ser
    450                 455                 460

Val Ala Thr Val Val Tyr Leu Arg Lys Glu Asn Cys Met Tyr Gln Ala
465                 470                 475                 480

Cys Pro Thr Gln Asp Cys Asn Lys Lys Val Ile Asp Gln Gln Asn Gly
                485                 490                 495

Leu Tyr Arg Cys Glu Lys Cys Asp Thr Glu Phe Pro Asn Phe Lys Tyr
            500                 505                 510

Arg Met Ile Leu Ser Val Asn Ile Ala Asp Phe Gln Glu Asn Gln Trp
        515                 520                 525

Val Thr Cys Phe Gln Glu Ser Ala Glu Ala Ile Leu Gly Gln Asn Ala
    530                 535                 540

Ala Tyr Leu Gly Glu Leu Lys Asp Lys Asn Glu Gln Ala Phe Glu Glu
545                 550                 555                 560

Val Phe Gln Asn Ala Asn Phe Arg Ser Phe Ile Phe Arg Val Arg Val
                565                 570                 575

Lys Val Glu Thr Tyr Asn Asp Glu Ser Arg Ile Lys Ala Thr Val Met
            580                 585                 590

Asp Val Lys Pro Val Asp Tyr Arg Glu Tyr Gly Arg Arg Leu Val Met
        595                 600                 605

Ser Ile Arg Arg Ser Ala Leu Met
    610                 615
```

<210> SEQ ID NO 3
<211> LENGTH: 7224
<212> TYPE: DNA
<213> ORGANISM: Homo sapiens
<220> FEATURE:
<221> NAME/KEY: CDS

```
<222> LOCATION: (233)..(5824)
<223> OTHER INFORMATION: BRCA1

<400> SEQUENCE: 3

gtaccttgat ttcgtattct gagaggctgc tgcttagcgg tagccccttg gtttccgtgg      60

caacggaaaa gcgcgggaat tacagataaa ttaaaactgc gactgcgcgg cgtgagctcg     120

ctgagacttc ctggacgggg gacaggctgt ggggtttctc agataactgg gcccctgcgc     180

tcaggaggcc ttcaccctct gctctgggta aagttcattg gaacagaaag aa atg gat     238
                                                           Met Asp
                                                           1

tta tct gct ctt cgc gtt gaa gaa gta caa aat gtc att aat gct atg      286
Leu Ser Ala Leu Arg Val Glu Glu Val Gln Asn Val Ile Asn Ala Met
        5                   10                  15

cag aaa atc tta gag tgt ccc atc tgt ctg gag ttg atc aag gaa cct      334
Gln Lys Ile Leu Glu Cys Pro Ile Cys Leu Glu Leu Ile Lys Glu Pro
    20                  25                  30

gtc tcc aca aag tgt gac cac ata ttt tgc aaa ttt tgc atg ctg aaa      382
Val Ser Thr Lys Cys Asp His Ile Phe Cys Lys Phe Cys Met Leu Lys
35                  40                  45                  50

ctt ctc aac cag aag aaa ggg cct tca cag tgt cct tta tgt aag aat      430
Leu Leu Asn Gln Lys Lys Gly Pro Ser Gln Cys Pro Leu Cys Lys Asn
                55                  60                  65

gat ata acc aaa agg agc cta caa gaa agt acg aga ttt agt caa ctt      478
Asp Ile Thr Lys Arg Ser Leu Gln Glu Ser Thr Arg Phe Ser Gln Leu
            70                  75                  80

gtt gaa gag cta ttg aaa atc att tgt gct ttt cag ctt gac aca ggt      526
Val Glu Glu Leu Leu Lys Ile Ile Cys Ala Phe Gln Leu Asp Thr Gly
        85                  90                  95

ttg gag tat gca aac agc tat aat ttt gca aaa aag gaa aat aac tct      574
Leu Glu Tyr Ala Asn Ser Tyr Asn Phe Ala Lys Lys Glu Asn Asn Ser
    100                 105                 110

cct gaa cat cta aaa gat gaa gtt tct atc atc caa agt atg ggc tac      622
Pro Glu His Leu Lys Asp Glu Val Ser Ile Ile Gln Ser Met Gly Tyr
115                 120                 125                 130

aga aac cgt gcc aaa aga ctt cta cag agt gaa ccc gaa aat cct tcc      670
Arg Asn Arg Ala Lys Arg Leu Leu Gln Ser Glu Pro Glu Asn Pro Ser
                135                 140                 145

ttg cag gaa acc agt ctc agt gtc caa ctc tct aac ctt gga act gtg      718
Leu Gln Glu Thr Ser Leu Ser Val Gln Leu Ser Asn Leu Gly Thr Val
            150                 155                 160

aga act ctg agg aca aag cag cgg ata caa cct caa aag acg tct gtc      766
Arg Thr Leu Arg Thr Lys Gln Arg Ile Gln Pro Gln Lys Thr Ser Val
        165                 170                 175

tac att gaa ttg gga tct gat tct tct gaa gat acc gtt aat aag gca      814
Tyr Ile Glu Leu Gly Ser Asp Ser Ser Glu Asp Thr Val Asn Lys Ala
    180                 185                 190

act tat tgc agt gtg gga gat caa gaa ttg tta caa atc acc cct caa      862
Thr Tyr Cys Ser Val Gly Asp Gln Glu Leu Leu Gln Ile Thr Pro Gln
195                 200                 205                 210

gga acc agg gat gaa atc agt ttg gat tct gca aaa aag gct gct tgt      910
Gly Thr Arg Asp Glu Ile Ser Leu Asp Ser Ala Lys Lys Ala Ala Cys
                215                 220                 225

gaa ttt tct gag acg gat gta aca aat act gaa cat cat caa ccc agt      958
Glu Phe Ser Glu Thr Asp Val Thr Asn Thr Glu His His Gln Pro Ser
            230                 235                 240

aat aat gat ttg aac acc act gag aag cgt gca gct gag agg cat cca     1006
Asn Asn Asp Leu Asn Thr Thr Glu Lys Arg Ala Ala Glu Arg His Pro
        245                 250                 255
```

```
gaa aag tat cag ggt agt tct gtt tca aac ttg cat gtg gag cca tgt      1054
Glu Lys Tyr Gln Gly Ser Ser Val Ser Asn Leu His Val Glu Pro Cys
    260                 265                 270

ggc aca aat act cat gcc agc tca tta cag cat gag aac agc agt tta      1102
Gly Thr Asn Thr His Ala Ser Ser Leu Gln His Glu Asn Ser Ser Leu
275                 280                 285                 290

tta ctc act aaa gac aga atg aat gta gaa aag gct gaa ttc tgt aat      1150
Leu Leu Thr Lys Asp Arg Met Asn Val Glu Lys Ala Glu Phe Cys Asn
                295                 300                 305

aaa agc aaa cag cct ggc tta gca agg agc caa cat aac aga tgg gct      1198
Lys Ser Lys Gln Pro Gly Leu Ala Arg Ser Gln His Asn Arg Trp Ala
            310                 315                 320

gga agt aag gaa aca tgt aat gat agg cgg act ccc agc aca gaa aaa      1246
Gly Ser Lys Glu Thr Cys Asn Asp Arg Arg Thr Pro Ser Thr Glu Lys
        325                 330                 335

aag gta gat ctg aat gct gat ccc ctg tgt gag aga aaa gaa tgg aat      1294
Lys Val Asp Leu Asn Ala Asp Pro Leu Cys Glu Arg Lys Glu Trp Asn
    340                 345                 350

aag cag aaa ctg cca tgc tca gag aat cct aga gat act gaa gat gtt      1342
Lys Gln Lys Leu Pro Cys Ser Glu Asn Pro Arg Asp Thr Glu Asp Val
355                 360                 365                 370

cct tgg ata aca cta aat agc agc att cag aaa gtt aat gag tgg ttt      1390
Pro Trp Ile Thr Leu Asn Ser Ser Ile Gln Lys Val Asn Glu Trp Phe
                375                 380                 385

tcc aga agt gat gaa ctg tta ggt tct gat gac tca cat gat ggg gag      1438
Ser Arg Ser Asp Glu Leu Leu Gly Ser Asp Asp Ser His Asp Gly Glu
            390                 395                 400

tct gaa tca aat gcc aaa gta gct gat gta ttg gac gtt cta aat gag      1486
Ser Glu Ser Asn Ala Lys Val Ala Asp Val Leu Asp Val Leu Asn Glu
        405                 410                 415

gta gat gaa tat tct ggt tct tca gag aaa ata gac tta ctg gcc agt      1534
Val Asp Glu Tyr Ser Gly Ser Ser Glu Lys Ile Asp Leu Leu Ala Ser
    420                 425                 430

gat cct cat gag gct tta ata tgt aaa agt gaa aga gtt cac tcc aaa      1582
Asp Pro His Glu Ala Leu Ile Cys Lys Ser Glu Arg Val His Ser Lys
435                 440                 445                 450

tca gta gag agt aat att gaa gac aaa ata ttt ggg aaa acc tat cgg      1630
Ser Val Glu Ser Asn Ile Glu Asp Lys Ile Phe Gly Lys Thr Tyr Arg
                455                 460                 465

aag aag gca agc ctc ccc aac tta agc cat gta act gaa aat cta att      1678
Lys Lys Ala Ser Leu Pro Asn Leu Ser His Val Thr Glu Asn Leu Ile
            470                 475                 480

ata gga gca ttt gtt act gag cca cag ata ata caa gag cgt ccc ctc      1726
Ile Gly Ala Phe Val Thr Glu Pro Gln Ile Ile Gln Glu Arg Pro Leu
        485                 490                 495

aca aat aaa tta aag cgt aaa agg aga cct aca tca ggc ctt cat cct      1774
Thr Asn Lys Leu Lys Arg Lys Arg Arg Pro Thr Ser Gly Leu His Pro
    500                 505                 510

gag gat ttt atc aag aaa gca gat ttg gca gtt caa aag act cct gaa      1822
Glu Asp Phe Ile Lys Lys Ala Asp Leu Ala Val Gln Lys Thr Pro Glu
515                 520                 525                 530

atg ata aat cag gga act aac caa acg gag cag aat ggt caa gtg atg      1870
Met Ile Asn Gln Gly Thr Asn Gln Thr Glu Gln Asn Gly Gln Val Met
                535                 540                 545

aat att act aat agt ggt cat gag aat aaa aca aaa ggt gat tct att      1918
Asn Ile Thr Asn Ser Gly His Glu Asn Lys Thr Lys Gly Asp Ser Ile
            550                 555                 560

cag aat gag aaa aat cct aac cca ata gaa tca ctc gaa aaa gaa tct      1966
Gln Asn Glu Lys Asn Pro Asn Pro Ile Glu Ser Leu Glu Lys Glu Ser
        565                 570                 575
```

```
gct ttc aaa acg aaa gct gaa cct ata agc agc agt ata agc aat atg     2014
Ala Phe Lys Thr Lys Ala Glu Pro Ile Ser Ser Ser Ile Ser Asn Met
    580                 585                 590

gaa ctc gaa tta aat atc cac aat tca aaa gca cct aaa aag aat agg     2062
Glu Leu Glu Leu Asn Ile His Asn Ser Lys Ala Pro Lys Lys Asn Arg
595                 600                 605                 610

ctg agg agg aag tct tct acc agg cat att cat gcg ctt gaa cta gta     2110
Leu Arg Arg Lys Ser Ser Thr Arg His Ile His Ala Leu Glu Leu Val
                615                 620                 625

gtc agt aga aat cta agc cca cct aat tgt act gaa ttg caa att gat     2158
Val Ser Arg Asn Leu Ser Pro Pro Asn Cys Thr Glu Leu Gln Ile Asp
            630                 635                 640

agt tgt tct agc agt gaa gag ata aag aaa aaa aag tac aac caa atg     2206
Ser Cys Ser Ser Ser Glu Glu Ile Lys Lys Lys Lys Tyr Asn Gln Met
        645                 650                 655

cca gtc agg cac agc aga aac cta caa ctc atg gaa ggt aaa gaa cct     2254
Pro Val Arg His Ser Arg Asn Leu Gln Leu Met Glu Gly Lys Glu Pro
    660                 665                 670

gca act gga gcc aag aag agt aac aag cca aat gaa cag aca agt aaa     2302
Ala Thr Gly Ala Lys Lys Ser Asn Lys Pro Asn Glu Gln Thr Ser Lys
675                 680                 685                 690

aga cat gac agc gat act ttc cca gag ctg aag tta aca aat gca cct     2350
Arg His Asp Ser Asp Thr Phe Pro Glu Leu Lys Leu Thr Asn Ala Pro
                695                 700                 705

ggt tct ttt act aag tgt tca aat acc agt gaa ctt aaa gaa ttt gtc     2398
Gly Ser Phe Thr Lys Cys Ser Asn Thr Ser Glu Leu Lys Glu Phe Val
            710                 715                 720

aat cct agc ctt cca aga gaa gaa aaa gaa gag aaa cta gaa aca gtt     2446
Asn Pro Ser Leu Pro Arg Glu Glu Lys Glu Glu Lys Leu Glu Thr Val
        725                 730                 735

aaa gtg tct aat aat gct gaa gac ccc aaa gat ctc atg tta agt gga     2494
Lys Val Ser Asn Asn Ala Glu Asp Pro Lys Asp Leu Met Leu Ser Gly
    740                 745                 750

gaa agg gtt ttg caa act gaa aga tct gta gag agt agc agt att tca     2542
Glu Arg Val Leu Gln Thr Glu Arg Ser Val Glu Ser Ser Ser Ile Ser
755                 760                 765                 770

ttg gta cct ggt act gat tat ggc act cag gaa agt atc tcg tta ctg     2590
Leu Val Pro Gly Thr Asp Tyr Gly Thr Gln Glu Ser Ile Ser Leu Leu
                775                 780                 785

gaa gtt agc act cta ggg aag gca aaa aca gaa cca aat aaa tgt gtg     2638
Glu Val Ser Thr Leu Gly Lys Ala Lys Thr Glu Pro Asn Lys Cys Val
            790                 795                 800

agt cag tgt gca gca ttt gaa aac ccc aag gga cta att cat ggt tgt     2686
Ser Gln Cys Ala Ala Phe Glu Asn Pro Lys Gly Leu Ile His Gly Cys
        805                 810                 815

tcc aaa gat aat aga aat gac aca gaa ggc ttt aag tat cca ttg gga     2734
Ser Lys Asp Asn Arg Asn Asp Thr Glu Gly Phe Lys Tyr Pro Leu Gly
    820                 825                 830

cat gaa gtt aac cac agt cgg gaa aca agc ata gaa atg gaa gaa agt     2782
His Glu Val Asn His Ser Arg Glu Thr Ser Ile Glu Met Glu Glu Ser
835                 840                 845                 850

gaa ctt gat gct cag tat ttg cag aat aca ttc aag gtt tca aag cgc     2830
Glu Leu Asp Ala Gln Tyr Leu Gln Asn Thr Phe Lys Val Ser Lys Arg
                855                 860                 865

cag tca ttt gct ccg ttt tca aat cca gga aat gca gaa gag gaa tgt     2878
Gln Ser Phe Ala Pro Phe Ser Asn Pro Gly Asn Ala Glu Glu Glu Cys
            870                 875                 880

gca aca ttc tct gcc cac tct ggg tcc tta aag aaa caa agt cca aaa     2926
Ala Thr Phe Ser Ala His Ser Gly Ser Leu Lys Lys Gln Ser Pro Lys
```

```
        885                 890                 895

gtc act ttt gaa tgt gaa caa aag gaa gaa aat caa gga aag aat gag     2974
Val Thr Phe Glu Cys Glu Gln Lys Glu Glu Asn Gln Gly Lys Asn Glu
    900                 905                 910

tct aat atc aag cct gta cag aca gtt aat atc act gca ggc ttt cct     3022
Ser Asn Ile Lys Pro Val Gln Thr Val Asn Ile Thr Ala Gly Phe Pro
915                 920                 925                 930

gtg gtt ggt cag aaa gat aag cca gtt gat aat gcc aaa tgt agt atc     3070
Val Val Gly Gln Lys Asp Lys Pro Val Asp Asn Ala Lys Cys Ser Ile
                935                 940                 945

aaa gga ggc tct agg ttt tgt cta tca tct cag ttc aga ggc aac gaa     3118
Lys Gly Gly Ser Arg Phe Cys Leu Ser Ser Gln Phe Arg Gly Asn Glu
            950                 955                 960

act gga ctc att act cca aat aaa cat gga ctt tta caa aac cca tat     3166
Thr Gly Leu Ile Thr Pro Asn Lys His Gly Leu Leu Gln Asn Pro Tyr
        965                 970                 975

cgt ata cca cca ctt ttt ccc atc aag tca ttt gtt aaa act aaa tgt     3214
Arg Ile Pro Pro Leu Phe Pro Ile Lys Ser Phe Val Lys Thr Lys Cys
    980                 985                 990

aag aaa aat ctg cta gag  gaa aac ttt gag gaa  cat tca atg tca      3259
Lys Lys Asn Leu Leu Glu  Glu Asn Phe Glu Glu  His Ser Met Ser
995                 1000                1005

cct  gaa aga gaa atg gga  aat gag aac att cca  agt aca gtg agc     3304
Pro  Glu Arg Glu Met Gly  Asn Glu Asn Ile Pro  Ser Thr Val Ser
1010                 1015                 1020

aca  att agc cgt aat aac  att aga gaa aat gtt  ttt aaa gaa gcc     3349
Thr  Ile Ser Arg Asn Asn  Ile Arg Glu Asn Val  Phe Lys Glu Ala
1025                 1030                 1035

agc  tca agc aat att aat  gaa gta ggt tcc agt  act aat gaa gtg     3394
Ser  Ser Ser Asn Ile Asn  Glu Val Gly Ser Ser  Thr Asn Glu Val
1040                 1045                 1050

ggc  tcc agt att aat gaa  ata ggt tcc agt gat  gaa aac att caa     3439
Gly  Ser Ser Ile Asn Glu  Ile Gly Ser Ser Asp  Glu Asn Ile Gln
1055                 1060                 1065

gca  gaa cta ggt aga aac  aga ggg cca aaa ttg  aat gct atg ctt     3484
Ala  Glu Leu Gly Arg Asn  Arg Gly Pro Lys Leu  Asn Ala Met Leu
1070                 1075                 1080

aga  tta ggg gtt ttg caa  cct gag gtc tat aaa  caa agt ctt cct     3529
Arg  Leu Gly Val Leu Gln  Pro Glu Val Tyr Lys  Gln Ser Leu Pro
1085                 1090                 1095

gga  agt aat tgt aag cat  cct gaa ata aaa aag  caa gaa tat gaa     3574
Gly  Ser Asn Cys Lys His  Pro Glu Ile Lys Lys  Gln Glu Tyr Glu
1100                 1105                 1110

gaa  gta gtt cag act gtt  aat aca gat ttc tct  cca tat ctg att     3619
Glu  Val Val Gln Thr Val  Asn Thr Asp Phe Ser  Pro Tyr Leu Ile
1115                 1120                 1125

tca  gat aac tta gaa cag  cct atg gga agt agt  cat gca tct cag     3664
Ser  Asp Asn Leu Glu Gln  Pro Met Gly Ser Ser  His Ala Ser Gln
1130                 1135                 1140

gtt  tgt tct gag aca cct  gat gac ctg tta gat  gat ggt gaa ata     3709
Val  Cys Ser Glu Thr Pro  Asp Asp Leu Leu Asp  Asp Gly Glu Ile
1145                 1150                 1155

aag  gaa gat act agt ttt  gct gaa aat gac att  aag gaa agt tct     3754
Lys  Glu Asp Thr Ser Phe  Ala Glu Asn Asp Ile  Lys Glu Ser Ser
1160                 1165                 1170

gct  gtt ttt agc aaa agc  gtc cag aaa gga gag  ctt agc agg agt     3799
Ala  Val Phe Ser Lys Ser  Val Gln Lys Gly Glu  Leu Ser Arg Ser
1175                 1180                 1185

cct  agc cct ttc acc cat  aca cat ttg gct cag  ggt tac cga aga     3844
```

```
Pro  Ser Pro Phe Thr His  Thr His Leu Ala Gln  Gly Tyr Arg Arg
1190                 1195                 1200

ggg  gcc aag aaa tta gag  tcc tca gaa gag aac  tta tct agt gag      3889
Gly  Ala Lys Lys Leu Glu  Ser Ser Glu Glu Asn  Leu Ser Ser Glu
1205                 1210                 1215

gat  gaa gag ctt ccc tgc  ttc caa cac ttg tta  ttt ggt aaa gta      3934
Asp  Glu Glu Leu Pro Cys  Phe Gln His Leu Leu  Phe Gly Lys Val
1220                 1225                 1230

aac  aat ata cct tct cag  tct act agg cat agc  acc gtt gct acc      3979
Asn  Asn Ile Pro Ser Gln  Ser Thr Arg His Ser  Thr Val Ala Thr
1235                 1240                 1245

gag  tgt ctg tct aag aac  aca gag gag aat tta  tta tca ttg aag      4024
Glu  Cys Leu Ser Lys Asn  Thr Glu Glu Asn Leu  Leu Ser Leu Lys
1250                 1255                 1260

aat  agc tta aat gac tgc  agt aac cag gta ata  ttg gca aag gca      4069
Asn  Ser Leu Asn Asp Cys  Ser Asn Gln Val Ile  Leu Ala Lys Ala
1265                 1270                 1275

tct  cag gaa cat cac ctt  agt gag gaa aca aaa  tgt tct gct agc      4114
Ser  Gln Glu His His Leu  Ser Glu Glu Thr Lys  Cys Ser Ala Ser
1280                 1285                 1290

ttg  ttt tct tca cag tgc  agt gaa ttg gaa gac  ttg act gca aat      4159
Leu  Phe Ser Ser Gln Cys  Ser Glu Leu Glu Asp  Leu Thr Ala Asn
1295                 1300                 1305

aca  aac acc cag gat cct  ttc ttg att ggt tct  tcc aaa caa atg      4204
Thr  Asn Thr Gln Asp Pro  Phe Leu Ile Gly Ser  Ser Lys Gln Met
1310                 1315                 1320

agg  cat cag tct gaa agc  cag gga gtt ggt ctg  agt gac aag gaa      4249
Arg  His Gln Ser Glu Ser  Gln Gly Val Gly Leu  Ser Asp Lys Glu
1325                 1330                 1335

ttg  gtt tca gat gat gaa  gaa aga gga acg ggc  ttg gaa gaa aat      4294
Leu  Val Ser Asp Asp Glu  Glu Arg Gly Thr Gly  Leu Glu Glu Asn
1340                 1345                 1350

aat  caa gaa gag caa agc  atg gat tca aac tta  ggt gaa gca gca      4339
Asn  Gln Glu Glu Gln Ser  Met Asp Ser Asn Leu  Gly Glu Ala Ala
1355                 1360                 1365

tct  ggg tgt gag agt gaa  aca agc gtc tct gaa  gac tgc tca ggg      4384
Ser  Gly Cys Glu Ser Glu  Thr Ser Val Ser Glu  Asp Cys Ser Gly
1370                 1375                 1380

cta  tcc tct cag agt gac  att tta acc act cag  cag agg gat acc      4429
Leu  Ser Ser Gln Ser Asp  Ile Leu Thr Thr Gln  Gln Arg Asp Thr
1385                 1390                 1395

atg  caa cat aac ctg ata  aag ctc cag cag gaa  atg gct gaa cta      4474
Met  Gln His Asn Leu Ile  Lys Leu Gln Gln Glu  Met Ala Glu Leu
1400                 1405                 1410

gaa  gct gtg tta gaa cag  cat ggg agc cag cct  tct aac agc tac      4519
Glu  Ala Val Leu Glu Gln  His Gly Ser Gln Pro  Ser Asn Ser Tyr
1415                 1420                 1425

cct  tcc atc ata agt gac  tct tct gcc ctt gag  gac ctg cga aat      4564
Pro  Ser Ile Ile Ser Asp  Ser Ser Ala Leu Glu  Asp Leu Arg Asn
1430                 1435                 1440

cca  gaa caa agc aca tca  gaa aaa gca gta tta  act tca cag aaa      4609
Pro  Glu Gln Ser Thr Ser  Glu Lys Ala Val Leu  Thr Ser Gln Lys
1445                 1450                 1455

agt  agt gaa tac cct ata  agc cag aat cca gaa  ggc ctt tct gct      4654
Ser  Ser Glu Tyr Pro Ile  Ser Gln Asn Pro Glu  Gly Leu Ser Ala
1460                 1465                 1470

gac  aag ttt gag gtg tct  gca gat agt tct acc  agt aaa aat aaa      4699
Asp  Lys Phe Glu Val Ser  Ala Asp Ser Ser Thr  Ser Lys Asn Lys
1475                 1480                 1485
```

```
gaa  cca gga gtg gaa agg  tca tcc cct tct aaa  tgc cca tca tta      4744
Glu  Pro Gly Val Glu Arg  Ser Ser Pro Ser Lys  Cys Pro Ser Leu
1490                1495                 1500

gat  gat agg tgg tac atg  cac agt tgc tct ggg  agt ctt cag aat      4789
Asp  Asp Arg Trp Tyr Met  His Ser Cys Ser Gly  Ser Leu Gln Asn
1505                1510                 1515

aga  aac tac cca tct caa  gag gag ctc att aag  gtt gtt gat gtg      4834
Arg  Asn Tyr Pro Ser Gln  Glu Glu Leu Ile Lys  Val Val Asp Val
1520                1525                 1530

gag  gag caa cag ctg gaa  gag tct ggg cca cac  gat ttg acg gaa      4879
Glu  Glu Gln Gln Leu Glu  Glu Ser Gly Pro His  Asp Leu Thr Glu
1535                1540                 1545

aca  tct tac ttg cca agg  caa gat cta gag gga  acc cct tac ctg      4924
Thr  Ser Tyr Leu Pro Arg  Gln Asp Leu Glu Gly  Thr Pro Tyr Leu
1550                1555                 1560

gaa  tct gga atc agc ctc  ttc tct gat gac cct  gaa tct gat cct      4969
Glu  Ser Gly Ile Ser Leu  Phe Ser Asp Asp Pro  Glu Ser Asp Pro
1565                1570                 1575

tct  gaa gac aga gcc cca  gag tca gct cgt gtt  ggc aac ata cca      5014
Ser  Glu Asp Arg Ala Pro  Glu Ser Ala Arg Val  Gly Asn Ile Pro
1580                1585                 1590

tct  tca acc tct gca ttg  aaa gtt ccc caa ttg  aaa gtt gca gaa      5059
Ser  Ser Thr Ser Ala Leu  Lys Val Pro Gln Leu  Lys Val Ala Glu
1595                1600                 1605

tct  gcc cag agt cca gct  gct gct cat act act  gat act gct ggg      5104
Ser  Ala Gln Ser Pro Ala  Ala Ala His Thr Thr  Asp Thr Ala Gly
1610                1615                 1620

tat  aat gca atg gaa gaa  agt gtg agc agg gag  aag cca gaa ttg      5149
Tyr  Asn Ala Met Glu Glu  Ser Val Ser Arg Glu  Lys Pro Glu Leu
1625                1630                 1635

aca  gct tca aca gaa agg  gtc aac aaa aga atg  tcc atg gtg gtg      5194
Thr  Ala Ser Thr Glu Arg  Val Asn Lys Arg Met  Ser Met Val Val
1640                1645                 1650

tct  ggc ctg acc cca gaa  gaa ttt atg ctc gtg  tac aag ttt gcc      5239
Ser  Gly Leu Thr Pro Glu  Glu Phe Met Leu Val  Tyr Lys Phe Ala
1655                1660                 1665

aga  aaa cac cac atc act  tta act aat cta att  act gaa gag act      5284
Arg  Lys His His Ile Thr  Leu Thr Asn Leu Ile  Thr Glu Glu Thr
1670                1675                 1680

act  cat gtt gtt atg aaa  aca gat gct gag ttt  gtg tgt gaa cgg      5329
Thr  His Val Val Met Lys  Thr Asp Ala Glu Phe  Val Cys Glu Arg
1685                1690                 1695

aca  ctg aaa tat ttt cta  gga att gcg gga gga  aaa tgg gta gtt      5374
Thr  Leu Lys Tyr Phe Leu  Gly Ile Ala Gly Gly  Lys Trp Val Val
1700                1705                 1710

agc  tat ttc tgg gtg acc  cag tct att aaa gaa  aga aaa atg ctg      5419
Ser  Tyr Phe Trp Val Thr  Gln Ser Ile Lys Glu  Arg Lys Met Leu
1715                1720                 1725

aat  gag cat gat ttt gaa  gtc aga gga gat gtg  gtc aat gga aga      5464
Asn  Glu His Asp Phe Glu  Val Arg Gly Asp Val  Val Asn Gly Arg
1730                1735                 1740

aac  cac caa ggt cca aag  cga gca aga gaa tcc  cag gac aga aag      5509
Asn  His Gln Gly Pro Lys  Arg Ala Arg Glu Ser  Gln Asp Arg Lys
1745                1750                 1755

atc  ttc agg ggg cta gaa  atc tgt tgc tat ggg  ccc ttc acc aac      5554
Ile  Phe Arg Gly Leu Glu  Ile Cys Cys Tyr Gly  Pro Phe Thr Asn
1760                1765                 1770

atg  ccc aca gat caa ctg  gaa tgg atg gta cag  ctg tgt ggt gct      5599
Met  Pro Thr Asp Gln Leu  Glu Trp Met Val Gln  Leu Cys Gly Ala
1775                1780                 1785
```

```
tct  gtg gtg aag gag ctt  tca tca ttc acc ctt  ggc aca ggt gtc      5644
Ser  Val Val Lys Glu Leu  Ser Ser Phe Thr Leu  Gly Thr Gly Val
1790                 1795                 1800

cac  cca att gtg gtt gtg  cag cca gat gcc tgg  aca gag gac aat      5689
His  Pro Ile Val Val Val  Gln Pro Asp Ala Trp  Thr Glu Asp Asn
1805                 1810                 1815

ggc  ttc cat gca att ggg  cag atg tgt gag gca  cct gtg gtg acc      5734
Gly  Phe His Ala Ile Gly  Gln Met Cys Glu Ala  Pro Val Val Thr
1820                 1825                 1830

cga  gag tgg gtg ttg gac  agt gta gca ctc tac  cag tgc cag gag      5779
Arg  Glu Trp Val Leu Asp  Ser Val Ala Leu Tyr  Gln Cys Gln Glu
1835                 1840                 1845

ctg  gac acc tac ctg ata  ccc cag atc ccc cac  agc cac tac tga      5824
Leu  Asp Thr Tyr Leu Ile  Pro Gln Ile Pro His  Ser His Tyr
1850                 1855                 1860

ctgcagccag ccacaggtac agagccacag gaccccaaga atgagcttac aaagtggcct   5884

ttccaggccc tgggagctcc tctcactctt cagtccttct actgtcctgg ctactaaata   5944

ttttatgtac atcagcctga aaaggacttc tggctatgca agggtccctt aaagattttc   6004

tgcttgaagt ctcccttgga aatctgccat gagcacaaaa ttatggtaat tttcacctg    6064

agaagatttt aaaaccattt aaacgccacc aattgagcaa gatgctgatt cattatttat   6124

cagccctatt ctttctattc aggctgttgt tggcttaggg ctggaagcac agagtggctt   6184

ggcctcaaga gaatagctgg tttccctaag tttacttctc taaaaccctg tgttcacaaa   6244

ggcagagagt cagacccttc aatggaagga gagtgcttgg gatcgattat gtgacttaaa   6304

gtcagaatag tccttgggca gttctcaaat gttggagtgg aacattgggg aggaaattct   6364

gaggcaggta ttagaaatga aaaggaaact tgaaacctgg gcatggtggc tcacgcctgt   6424

aatcccagca ctttgggagg ccaaggtggg cagatcactg gaggtcagga gttcgaaacc   6484

agcctggcca acatggtgaa accccatctc tactaaaaat acagaaatta gccggtcatg   6544

gtggtggaca cctgtaatcc cagctactca ggtggctaag gcaggagaat cacttcagcc   6604

cgggaggtgg aggttgcagt gagccaagat cataccacgg cactccagcc tgggtgacag   6664

tgagactgtg gctcaaaaaa aaaaaaaaaa aaaggaaaat gaaactagaa gagatttcta   6724

aaagtctgag atatatttgc tagatttcta aagaatgtgt tctaaaacag cagaagattt   6784

tcaagaaccg gtttccaaag acagtcttct aattcctcat tagtaataag taaaatgttt   6844

attgttgtag ctctggtata taatccattc ctcttaaaat ataagacctc tggcatgaat   6904

atttcatatc tataaaatga cagatcccac caggaaggaa gctgttgctt tctttgaggt   6964

gatttttttc ctttgctccc tgttgctgaa accatacagc ttcataaata attttgcttg   7024

ctgaaggaag aaaaagtgtt tttcataaac ccattatcca ggactgttta tagctgttgg   7084

aaggactagg tcttccctag ccccccagt gtgcaagggc agtgaagact tgattgtaca    7144

aaatacgttt tgtaaatgtt gtgctgttaa cactgcaaat aaacttggta gcaaacactt   7204

ccaaaaaaaa aaaaaaaaaa                                               7224


<210> SEQ ID NO 4
<211> LENGTH: 1863
<212> TYPE: PRT
<213> ORGANISM: Homo sapiens

<400> SEQUENCE: 4

Met Asp Leu Ser Ala Leu Arg Val Glu Glu Val Gln Asn Val Ile Asn
1               5                   10                  15
```

```
Ala Met Gln Lys Ile Leu Glu Cys Pro Ile Cys Leu Glu Leu Ile Lys
            20                  25                  30

Glu Pro Val Ser Thr Lys Cys Asp His Ile Phe Cys Lys Phe Cys Met
        35                  40                  45

Leu Lys Leu Leu Asn Gln Lys Lys Gly Pro Ser Gln Cys Pro Leu Cys
    50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
        115                 120                 125

Gly Tyr Arg Asn Arg Ala Lys Arg Leu Leu Gln Ser Glu Pro Glu Asn
    130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                165                 170                 175

Ser Val Tyr Ile Glu Leu Gly Ser Asp Ser Ser Glu Asp Thr Val Asn
            180                 185                 190

Lys Ala Thr Tyr Cys Ser Val Gly Asp Gln Glu Leu Leu Gln Ile Thr
        195                 200                 205

Pro Gln Gly Thr Arg Asp Glu Ile Ser Leu Asp Ser Ala Lys Lys Ala
    210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
                245                 250                 255

His Pro Glu Lys Tyr Gln Gly Ser Ser Val Ser Asn Leu His Val Glu
            260                 265                 270

Pro Cys Gly Thr Asn Thr His Ala Ser Ser Leu Gln His Glu Asn Ser
        275                 280                 285

Ser Leu Leu Leu Thr Lys Asp Arg Met Asn Val Glu Lys Ala Glu Phe
    290                 295                 300

Cys Asn Lys Ser Lys Gln Pro Gly Leu Ala Arg Ser Gln His Asn Arg
305                 310                 315                 320

Trp Ala Gly Ser Lys Glu Thr Cys Asn Asp Arg Arg Thr Pro Ser Thr
                325                 330                 335

Glu Lys Lys Val Asp Leu Asn Ala Asp Pro Leu Cys Glu Arg Lys Glu
            340                 345                 350

Trp Asn Lys Gln Lys Leu Pro Cys Ser Glu Asn Pro Arg Asp Thr Glu
        355                 360                 365

Asp Val Pro Trp Ile Thr Leu Asn Ser Ser Ile Gln Lys Val Asn Glu
    370                 375                 380

Trp Phe Ser Arg Ser Asp Glu Leu Leu Gly Ser Asp Asp Ser His Asp
385                 390                 395                 400

Gly Glu Ser Glu Ser Asn Ala Lys Val Ala Asp Val Leu Asp Val Leu
                405                 410                 415

Asn Glu Val Asp Glu Tyr Ser Gly Ser Ser Glu Lys Ile Asp Leu Leu
            420                 425                 430
```

```
Ala Ser Asp Pro His Glu Ala Leu Ile Cys Lys Ser Glu Arg Val His
        435                 440                 445

Ser Lys Ser Val Glu Ser Asn Ile Glu Asp Lys Ile Phe Gly Lys Thr
    450                 455                 460

Tyr Arg Lys Lys Ala Ser Leu Pro Asn Leu Ser His Val Thr Glu Asn
465                 470                 475                 480

Leu Ile Ile Gly Ala Phe Val Thr Glu Pro Gln Ile Ile Gln Glu Arg
                485                 490                 495

Pro Leu Thr Asn Lys Leu Lys Arg Lys Arg Arg Pro Thr Ser Gly Leu
            500                 505                 510

His Pro Glu Asp Phe Ile Lys Lys Ala Asp Leu Ala Val Gln Lys Thr
        515                 520                 525

Pro Glu Met Ile Asn Gln Gly Thr Asn Gln Thr Glu Gln Asn Gly Gln
    530                 535                 540

Val Met Asn Ile Thr Asn Ser Gly His Glu Asn Lys Thr Lys Gly Asp
545                 550                 555                 560

Ser Ile Gln Asn Glu Lys Asn Pro Asn Pro Ile Glu Ser Leu Glu Lys
                565                 570                 575

Glu Ser Ala Phe Lys Thr Lys Ala Glu Pro Ile Ser Ser Ser Ile Ser
            580                 585                 590

Asn Met Glu Leu Glu Leu Asn Ile His Asn Ser Lys Ala Pro Lys Lys
        595                 600                 605

Asn Arg Leu Arg Arg Lys Ser Ser Thr Arg His Ile His Ala Leu Glu
    610                 615                 620

Leu Val Val Ser Arg Asn Leu Ser Pro Pro Asn Cys Thr Glu Leu Gln
625                 630                 635                 640

Ile Asp Ser Cys Ser Ser Ser Glu Glu Ile Lys Lys Lys Lys Tyr Asn
                645                 650                 655

Gln Met Pro Val Arg His Ser Arg Asn Leu Gln Leu Met Glu Gly Lys
            660                 665                 670

Glu Pro Ala Thr Gly Ala Lys Lys Ser Asn Lys Pro Asn Glu Gln Thr
        675                 680                 685

Ser Lys Arg His Asp Ser Asp Thr Phe Pro Glu Leu Lys Leu Thr Asn
    690                 695                 700

Ala Pro Gly Ser Phe Thr Lys Cys Ser Asn Thr Ser Glu Leu Lys Glu
705                 710                 715                 720

Phe Val Asn Pro Ser Leu Pro Arg Glu Glu Lys Glu Glu Lys Leu Glu
                725                 730                 735

Thr Val Lys Val Ser Asn Asn Ala Glu Asp Pro Lys Asp Leu Met Leu
            740                 745                 750

Ser Gly Glu Arg Val Leu Gln Thr Glu Arg Ser Val Glu Ser Ser Ser
        755                 760                 765

Ile Ser Leu Val Pro Gly Thr Asp Tyr Gly Thr Gln Glu Ser Ile Ser
    770                 775                 780

Leu Leu Glu Val Ser Thr Leu Gly Lys Ala Lys Thr Glu Pro Asn Lys
785                 790                 795                 800

Cys Val Ser Gln Cys Ala Ala Phe Glu Asn Pro Lys Gly Leu Ile His
                805                 810                 815

Gly Cys Ser Lys Asp Asn Arg Asn Asp Thr Glu Gly Phe Lys Tyr Pro
            820                 825                 830

Leu Gly His Glu Val Asn His Ser Arg Glu Thr Ser Ile Glu Met Glu
        835                 840                 845

Glu Ser Glu Leu Asp Ala Gln Tyr Leu Gln Asn Thr Phe Lys Val Ser
```

```
    850                 855                 860

Lys Arg Gln Ser Phe Ala Pro Phe Ser Asn Pro Gly Asn Ala Glu Glu
865                 870                 875                 880

Glu Cys Ala Thr Phe Ser Ala His Ser Gly Ser Leu Lys Lys Gln Ser
                885                 890                 895

Pro Lys Val Thr Phe Glu Cys Glu Gln Lys Glu Glu Asn Gln Gly Lys
            900                 905                 910

Asn Glu Ser Asn Ile Lys Pro Val Gln Thr Val Asn Ile Thr Ala Gly
        915                 920                 925

Phe Pro Val Val Gly Gln Lys Asp Lys Pro Val Asp Asn Ala Lys Cys
    930                 935                 940

Ser Ile Lys Gly Gly Ser Arg Phe Cys Leu Ser Ser Gln Phe Arg Gly
945                 950                 955                 960

Asn Glu Thr Gly Leu Ile Thr Pro Asn Lys His Gly Leu Leu Gln Asn
                965                 970                 975

Pro Tyr Arg Ile Pro Pro Leu Phe Pro Ile Lys Ser Phe Val Lys Thr
            980                 985                 990

Lys Cys Lys Lys Asn Leu Leu Glu  Glu Asn Phe Glu Glu  His Ser Met
        995                 1000                 1005

Ser Pro  Glu Arg Glu Met Gly  Asn Glu Asn Ile Pro  Ser Thr Val
    1010                 1015                 1020

Ser Thr  Ile Ser Arg Asn Asn  Ile Arg Glu Asn Val  Phe Lys Glu
    1025                 1030                 1035

Ala Ser  Ser Ser Asn Ile Asn  Glu Val Gly Ser Ser  Thr Asn Glu
    1040                 1045                 1050

Val Gly  Ser Ser Ile Asn Glu  Ile Gly Ser Ser Asp  Glu Asn Ile
    1055                 1060                 1065

Gln Ala  Glu Leu Gly Arg Asn  Arg Gly Pro Lys Leu  Asn Ala Met
    1070                 1075                 1080

Leu Arg  Leu Gly Val Leu Gln  Pro Glu Val Tyr Lys  Gln Ser Leu
    1085                 1090                 1095

Pro Gly  Ser Asn Cys Lys His  Pro Glu Ile Lys Lys  Gln Glu Tyr
    1100                 1105                 1110

Glu Glu  Val Val Gln Thr Val  Asn Thr Asp Phe Ser  Pro Tyr Leu
    1115                 1120                 1125

Ile Ser  Asp Asn Leu Glu Gln  Pro Met Gly Ser Ser  His Ala Ser
    1130                 1135                 1140

Gln Val  Cys Ser Glu Thr Pro  Asp Asp Leu Leu Asp  Asp Gly Glu
    1145                 1150                 1155

Ile Lys  Glu Asp Thr Ser Phe  Ala Glu Asn Asp Ile  Lys Glu Ser
    1160                 1165                 1170

Ser Ala  Val Phe Ser Lys Ser  Val Gln Lys Gly Glu  Leu Ser Arg
    1175                 1180                 1185

Ser Pro  Ser Pro Phe Thr His  Thr His Leu Ala Gln  Gly Tyr Arg
    1190                 1195                 1200

Arg Gly  Ala Lys Lys Leu Glu  Ser Ser Glu Glu Asn  Leu Ser Ser
    1205                 1210                 1215

Glu Asp  Glu Glu Leu Pro Cys  Phe Gln His Leu Leu  Phe Gly Lys
    1220                 1225                 1230

Val Asn  Asn Ile Pro Ser Gln  Ser Thr Arg His Ser  Thr Val Ala
    1235                 1240                 1245

Thr Glu  Cys Leu Ser Lys Asn  Thr Glu Glu Asn Leu  Leu Ser Leu
    1250                 1255                 1260
```

```
Lys Asn Ser Leu Asn Asp Cys Ser Asn Gln Val Ile Leu Ala Lys
    1265                1270                1275

Ala Ser Gln Glu His His Leu Ser Glu Glu Thr Lys Cys Ser Ala
    1280                1285                1290

Ser Leu Phe Ser Ser Gln Cys Ser Glu Leu Glu Asp Leu Thr Ala
    1295                1300                1305

Asn Thr Asn Thr Gln Asp Pro Phe Leu Ile Gly Ser Ser Lys Gln
    1310                1315                1320

Met Arg His Gln Ser Glu Ser Gln Gly Val Gly Leu Ser Asp Lys
    1325                1330                1335

Glu Leu Val Ser Asp Asp Glu Glu Arg Gly Thr Gly Leu Glu Glu
    1340                1345                1350

Asn Asn Gln Glu Glu Gln Ser Met Asp Ser Asn Leu Gly Glu Ala
    1355                1360                1365

Ala Ser Gly Cys Glu Ser Glu Thr Ser Val Ser Glu Asp Cys Ser
    1370                1375                1380

Gly Leu Ser Ser Gln Ser Asp Ile Leu Thr Thr Gln Gln Arg Asp
    1385                1390                1395

Thr Met Gln His Asn Leu Ile Lys Leu Gln Gln Glu Met Ala Glu
    1400                1405                1410

Leu Glu Ala Val Leu Glu Gln His Gly Ser Gln Pro Ser Asn Ser
    1415                1420                1425

Tyr Pro Ser Ile Ile Ser Asp Ser Ser Ala Leu Glu Asp Leu Arg
    1430                1435                1440

Asn Pro Glu Gln Ser Thr Ser Glu Lys Ala Val Leu Thr Ser Gln
    1445                1450                1455

Lys Ser Ser Glu Tyr Pro Ile Ser Gln Asn Pro Glu Gly Leu Ser
    1460                1465                1470

Ala Asp Lys Phe Glu Val Ser Ala Asp Ser Ser Thr Ser Lys Asn
    1475                1480                1485

Lys Glu Pro Gly Val Glu Arg Ser Ser Pro Ser Lys Cys Pro Ser
    1490                1495                1500

Leu Asp Asp Arg Trp Tyr Met His Ser Cys Ser Gly Ser Leu Gln
    1505                1510                1515

Asn Arg Asn Tyr Pro Ser Gln Glu Glu Leu Ile Lys Val Val Asp
    1520                1525                1530

Val Glu Glu Gln Gln Leu Glu Glu Ser Gly Pro His Asp Leu Thr
    1535                1540                1545

Glu Thr Ser Tyr Leu Pro Arg Gln Asp Leu Glu Gly Thr Pro Tyr
    1550                1555                1560

Leu Glu Ser Gly Ile Ser Leu Phe Ser Asp Asp Pro Glu Ser Asp
    1565                1570                1575

Pro Ser Glu Asp Arg Ala Pro Glu Ser Ala Arg Val Gly Asn Ile
    1580                1585                1590

Pro Ser Ser Thr Ser Ala Leu Lys Val Pro Gln Leu Lys Val Ala
    1595                1600                1605

Glu Ser Ala Gln Ser Pro Ala Ala Ala His Thr Thr Asp Thr Ala
    1610                1615                1620

Gly Tyr Asn Ala Met Glu Glu Ser Val Ser Arg Glu Lys Pro Glu
    1625                1630                1635

Leu Thr Ala Ser Thr Glu Arg Val Asn Lys Arg Met Ser Met Val
    1640                1645                1650
```

```
Val Ser  Gly Leu Thr Pro Glu  Glu Phe Met Leu Val  Tyr Lys Phe
    1655                 1660                 1665

Ala Arg  Lys His His Ile Thr  Leu Thr Asn Leu Ile  Thr Glu Glu
    1670                 1675                 1680

Thr Thr  His Val Val Met Lys  Thr Asp Ala Glu Phe  Val Cys Glu
    1685                 1690                 1695

Arg Thr  Leu Lys Tyr Phe Leu  Gly Ile Ala Gly Gly  Lys Trp Val
    1700                 1705                 1710

Val Ser  Tyr Phe Trp Val Thr  Gln Ser Ile Lys Glu  Arg Lys Met
    1715                 1720                 1725

Leu Asn  Glu His Asp Phe Glu  Val Arg Gly Asp Val  Val Asn Gly
    1730                 1735                 1740

Arg Asn  His Gln Gly Pro Lys  Arg Ala Arg Glu Ser  Gln Asp Arg
    1745                 1750                 1755

Lys Ile  Phe Arg Gly Leu Glu  Ile Cys Cys Tyr Gly  Pro Phe Thr
    1760                 1765                 1770

Asn Met  Pro Thr Asp Gln Leu  Glu Trp Met Val Gln  Leu Cys Gly
    1775                 1780                 1785

Ala Ser  Val Val Lys Glu Leu  Ser Ser Phe Thr Leu  Gly Thr Gly
    1790                 1795                 1800

Val His  Pro Ile Val Val Val  Gln Pro Asp Ala Trp  Thr Glu Asp
    1805                 1810                 1815

Asn Gly  Phe His Ala Ile Gly  Gln Met Cys Glu Ala  Pro Val Val
    1820                 1825                 1830

Thr Arg  Glu Trp Val Leu Asp  Ser Val Ala Leu Tyr  Gln Cys Gln
    1835                 1840                 1845

Glu Leu  Asp Thr Tyr Leu Ile  Pro Gln Ile Pro His  Ser His Tyr
    1850                 1855                 1860
```

<210> SEQ ID NO 5
<211> LENGTH: 11386
<212> TYPE: DNA
<213> ORGANISM: Homo sapiens
<220> FEATURE:
<221> NAME/KEY: CDS
<222> LOCATION: (228)..(10484)
<223> OTHER INFORMATION: BRCA2

<400> SEQUENCE: 5

```
gtggcgcgag cttctgaaac taggcggcag aggcggagcc gctgtggcac tgctgcgcct     60

ctgctgcgcc tcgggtgtct tttgcggcgg tgggtcgccg ccgggagaag cgtgagggga    120

cagatttgtg accggcgcgg tttttgtcag cttactccgg ccaaaaaaga actgcacctc    180

tggagcggac ttatttacca agcattggag gaatatcgta ggtaaaa atg cct att      236
                                                    Met Pro Ile
                                                    1

gga tcc aaa gag agg cca aca ttt ttt gaa att ttt aag aca cgc tgc      284
Gly Ser Lys Glu Arg Pro Thr Phe Phe Glu Ile Phe Lys Thr Arg Cys
    5                   10                  15

aac aaa gca gat tta gga cca ata agt ctt aat tgg ttt gaa gaa ctt      332
Asn Lys Ala Asp Leu Gly Pro Ile Ser Leu Asn Trp Phe Glu Glu Leu
20                  25                  30                  35

tct tca gaa gct cca ccc tat aat tct gaa cct gca gaa gaa tct gaa      380
Ser Ser Glu Ala Pro Pro Tyr Asn Ser Glu Pro Ala Glu Glu Ser Glu
                40                  45                  50

cat aaa aac aac aat tac gaa cca aac cta ttt aaa act cca caa agg      428
His Lys Asn Asn Asn Tyr Glu Pro Asn Leu Phe Lys Thr Pro Gln Arg
            55                  60                  65
```

```
aaa cca tct tat aat cag ctg gct tca act cca ata ata ttc aaa gag      476
Lys Pro Ser Tyr Asn Gln Leu Ala Ser Thr Pro Ile Ile Phe Lys Glu
        70                  75                  80

caa ggg ctg act ctg ccg ctg tac caa tct cct gta aaa gaa tta gat      524
Gln Gly Leu Thr Leu Pro Leu Tyr Gln Ser Pro Val Lys Glu Leu Asp
    85                  90                  95

aaa ttc aaa tta gac tta gga agg aat gtt ccc aat agt aga cat aaa      572
Lys Phe Lys Leu Asp Leu Gly Arg Asn Val Pro Asn Ser Arg His Lys
100                 105                 110                 115

agt ctt cgc aca gtg aaa act aaa atg gat caa gca gat gat gtt tcc      620
Ser Leu Arg Thr Val Lys Thr Lys Met Asp Gln Ala Asp Asp Val Ser
                120                 125                 130

tgt cca ctt cta aat tct tgt ctt agt gaa agt cct gtt gtt cta caa      668
Cys Pro Leu Leu Asn Ser Cys Leu Ser Glu Ser Pro Val Val Leu Gln
            135                 140                 145

tgt aca cat gta aca cca caa aga gat aag tca gtg gta tgt ggg agt      716
Cys Thr His Val Thr Pro Gln Arg Asp Lys Ser Val Val Cys Gly Ser
        150                 155                 160

ttg ttt cat aca cca aag ttt gtg aag ggt cgt cag aca cca aaa cat      764
Leu Phe His Thr Pro Lys Phe Val Lys Gly Arg Gln Thr Pro Lys His
    165                 170                 175

att tct gaa agt cta gga gct gag gtg gat cct gat atg tct tgg tca      812
Ile Ser Glu Ser Leu Gly Ala Glu Val Asp Pro Asp Met Ser Trp Ser
180                 185                 190                 195

agt tct tta gct aca cca ccc acc ctt agt tct act gtg ctc ata gtc      860
Ser Ser Leu Ala Thr Pro Pro Thr Leu Ser Ser Thr Val Leu Ile Val
                200                 205                 210

aga aat gaa gaa gca tct gaa act gta ttt cct cat gat act act gct      908
Arg Asn Glu Glu Ala Ser Glu Thr Val Phe Pro His Asp Thr Thr Ala
            215                 220                 225

aat gtg aaa agc tat ttt tcc aat cat gat gaa agt ctg aag aaa aat      956
Asn Val Lys Ser Tyr Phe Ser Asn His Asp Glu Ser Leu Lys Lys Asn
        230                 235                 240

gat aga ttt atc gct tct gtg aca gac agt gaa aac aca aat caa aga     1004
Asp Arg Phe Ile Ala Ser Val Thr Asp Ser Glu Asn Thr Asn Gln Arg
    245                 250                 255

gaa gct gca agt cat gga ttt gga aaa aca tca ggg aat tca ttt aaa     1052
Glu Ala Ala Ser His Gly Phe Gly Lys Thr Ser Gly Asn Ser Phe Lys
260                 265                 270                 275

gta aat agc tgc aaa gac cac att gga aag tca atg cca aat gtc cta     1100
Val Asn Ser Cys Lys Asp His Ile Gly Lys Ser Met Pro Asn Val Leu
                280                 285                 290

gaa gat gaa gta tat gaa aca gtt gta gat acc tct gaa gaa gat agt     1148
Glu Asp Glu Val Tyr Glu Thr Val Val Asp Thr Ser Glu Glu Asp Ser
            295                 300                 305

ttt tca tta tgt ttt tct aaa tgt aga aca aaa aat cta caa aaa gta     1196
Phe Ser Leu Cys Phe Ser Lys Cys Arg Thr Lys Asn Leu Gln Lys Val
        310                 315                 320

aga act agc aag act agg aaa aaa att ttc cat gaa gca aac gct gat     1244
Arg Thr Ser Lys Thr Arg Lys Lys Ile Phe His Glu Ala Asn Ala Asp
    325                 330                 335

gaa tgt gaa aaa tct aaa aac caa gtg aaa gaa aaa tac tca ttt gta     1292
Glu Cys Glu Lys Ser Lys Asn Gln Val Lys Glu Lys Tyr Ser Phe Val
340                 345                 350                 355

tct gaa gtg gaa cca aat gat act gat cca tta gat tca aat gta gca     1340
Ser Glu Val Glu Pro Asn Asp Thr Asp Pro Leu Asp Ser Asn Val Ala
                360                 365                 370

aat cag aag ccc ttt gag agt gga agt gac aaa atc tcc aag gaa gtt     1388
Asn Gln Lys Pro Phe Glu Ser Gly Ser Asp Lys Ile Ser Lys Glu Val
```

```
        375                 380                 385

gta ccg tct ttg gcc tgt gaa tgg tct caa cta acc ctt tca ggt cta      1436
Val Pro Ser Leu Ala Cys Glu Trp Ser Gln Leu Thr Leu Ser Gly Leu
            390                 395                 400

aat gga gcc cag atg gag aaa ata ccc cta ttg cat att tct tca tgt      1484
Asn Gly Ala Gln Met Glu Lys Ile Pro Leu Leu His Ile Ser Ser Cys
    405                 410                 415

gac caa aat att tca gaa aaa gac cta tta gac aca gag aac aaa aga      1532
Asp Gln Asn Ile Ser Glu Lys Asp Leu Leu Asp Thr Glu Asn Lys Arg
420                 425                 430                 435

aag aaa gat ttt ctt act tca gag aat tct ttg cca cgt att tct agc      1580
Lys Lys Asp Phe Leu Thr Ser Glu Asn Ser Leu Pro Arg Ile Ser Ser
                440                 445                 450

cta cca aaa tca gag aag cca tta aat gag gaa aca gtg gta aat aag      1628
Leu Pro Lys Ser Glu Lys Pro Leu Asn Glu Glu Thr Val Val Asn Lys
            455                 460                 465

aga gat gaa gag cag cat ctt gaa tct cat aca gac tgc att ctt gca      1676
Arg Asp Glu Glu Gln His Leu Glu Ser His Thr Asp Cys Ile Leu Ala
        470                 475                 480

gta aag cag gca ata tct gga act tct cca gtg gct tct tca ttt cag      1724
Val Lys Gln Ala Ile Ser Gly Thr Ser Pro Val Ala Ser Ser Phe Gln
    485                 490                 495

ggt atc aaa aag tct ata ttc aga ata aga gaa tca cct aaa gag act      1772
Gly Ile Lys Lys Ser Ile Phe Arg Ile Arg Glu Ser Pro Lys Glu Thr
500                 505                 510                 515

ttc aat gca agt ttt tca ggt cat atg act gat cca aac ttt aaa aaa      1820
Phe Asn Ala Ser Phe Ser Gly His Met Thr Asp Pro Asn Phe Lys Lys
                520                 525                 530

gaa act gaa gcc tct gaa agt gga ctg gaa ata cat act gtt tgc tca      1868
Glu Thr Glu Ala Ser Glu Ser Gly Leu Glu Ile His Thr Val Cys Ser
            535                 540                 545

cag aag gag gac tcc tta tgt cca aat tta att gat aat gga agc tgg      1916
Gln Lys Glu Asp Ser Leu Cys Pro Asn Leu Ile Asp Asn Gly Ser Trp
        550                 555                 560

cca gcc acc acc aca cag aat tct gta gct ttg aag aat gca ggt tta      1964
Pro Ala Thr Thr Thr Gln Asn Ser Val Ala Leu Lys Asn Ala Gly Leu
    565                 570                 575

ata tcc act ttg aaa aag aaa aca aat aag ttt att tat gct ata cat      2012
Ile Ser Thr Leu Lys Lys Lys Thr Asn Lys Phe Ile Tyr Ala Ile His
580                 585                 590                 595

gat gaa aca tct tat aaa gga aaa aaa ata ccg aaa gac caa aaa tca      2060
Asp Glu Thr Ser Tyr Lys Gly Lys Lys Ile Pro Lys Asp Gln Lys Ser
                600                 605                 610

gaa cta att aac tgt tca gcc cag ttt gaa gca aat gct ttt gaa gca      2108
Glu Leu Ile Asn Cys Ser Ala Gln Phe Glu Ala Asn Ala Phe Glu Ala
            615                 620                 625

cca ctt aca ttt gca aat gct gat tca ggt tta ttg cat tct tct gtg      2156
Pro Leu Thr Phe Ala Asn Ala Asp Ser Gly Leu Leu His Ser Ser Val
        630                 635                 640

aaa aga agc tgt tca cag aat gat tct gaa gaa cca act ttg tcc tta      2204
Lys Arg Ser Cys Ser Gln Asn Asp Ser Glu Glu Pro Thr Leu Ser Leu
    645                 650                 655

act agc tct ttt ggg aca att ctg agg aaa tgt tct aga aat gaa aca      2252
Thr Ser Ser Phe Gly Thr Ile Leu Arg Lys Cys Ser Arg Asn Glu Thr
660                 665                 670                 675

tgt tct aat aat aca gta atc tct cag gat ctt gat tat aaa gaa gca      2300
Cys Ser Asn Asn Thr Val Ile Ser Gln Asp Leu Asp Tyr Lys Glu Ala
                680                 685                 690

aaa tgt aat aag gaa aaa cta cag tta ttt att acc cca gaa gct gat      2348
```

```
Lys Cys Asn Lys Glu Lys Leu Gln Leu Phe Ile Thr Pro Glu Ala Asp
            695                 700                 705

tct ctg tca tgc ctg cag gaa gga cag tgt gaa aat gat cca aaa agc      2396
Ser Leu Ser Cys Leu Gln Glu Gly Gln Cys Glu Asn Asp Pro Lys Ser
        710                 715                 720

aaa aaa gtt tca gat ata aaa gaa gag gtc ttg gct gca gca tgt cac      2444
Lys Lys Val Ser Asp Ile Lys Glu Glu Val Leu Ala Ala Ala Cys His
    725                 730                 735

cca gta caa cat tca aaa gtg gaa tac agt gat act gac ttt caa tcc      2492
Pro Val Gln His Ser Lys Val Glu Tyr Ser Asp Thr Asp Phe Gln Ser
740                 745                 750                 755

cag aaa agt ctt tta tat gat cat gaa aat gcc agc act ctt att tta      2540
Gln Lys Ser Leu Leu Tyr Asp His Glu Asn Ala Ser Thr Leu Ile Leu
                760                 765                 770

act cct act tcc aag gat gtt ctg tca aac cta gtc atg att tct aga      2588
Thr Pro Thr Ser Lys Asp Val Leu Ser Asn Leu Val Met Ile Ser Arg
            775                 780                 785

ggc aaa gaa tca tac aaa atg tca gac aag ctc aaa ggt aac aat tat      2636
Gly Lys Glu Ser Tyr Lys Met Ser Asp Lys Leu Lys Gly Asn Asn Tyr
        790                 795                 800

gaa tct gat gtt gaa tta acc aaa aat att ccc atg gaa aag aat caa      2684
Glu Ser Asp Val Glu Leu Thr Lys Asn Ile Pro Met Glu Lys Asn Gln
    805                 810                 815

gat gta tgt gct tta aat gaa aat tat aaa aac gtt gag ctg ttg cca      2732
Asp Val Cys Ala Leu Asn Glu Asn Tyr Lys Asn Val Glu Leu Leu Pro
820                 825                 830                 835

cct gaa aaa tac atg aga gta gca tca cct tca aga aag gta caa ttc      2780
Pro Glu Lys Tyr Met Arg Val Ala Ser Pro Ser Arg Lys Val Gln Phe
                840                 845                 850

aac caa aac aca aat cta aga gta atc caa aaa aat caa gaa gaa act      2828
Asn Gln Asn Thr Asn Leu Arg Val Ile Gln Lys Asn Gln Glu Glu Thr
            855                 860                 865

act tca att tca aaa ata act gtc aat cca gac tct gaa gaa ctt ttc      2876
Thr Ser Ile Ser Lys Ile Thr Val Asn Pro Asp Ser Glu Glu Leu Phe
        870                 875                 880

tca gac aat gag aat aat ttt gtc ttc caa gta gct aat gaa agg aat      2924
Ser Asp Asn Glu Asn Asn Phe Val Phe Gln Val Ala Asn Glu Arg Asn
    885                 890                 895

aat ctt gct tta gga aat act aag gaa ctt cat gaa aca gac ttg act      2972
Asn Leu Ala Leu Gly Asn Thr Lys Glu Leu His Glu Thr Asp Leu Thr
900                 905                 910                 915

tgt gta aac gaa ccc att ttc aag aac tct acc atg gtt tta tat gga      3020
Cys Val Asn Glu Pro Ile Phe Lys Asn Ser Thr Met Val Leu Tyr Gly
                920                 925                 930

gac aca ggt gat aaa caa gca acc caa gtg tca att aaa aaa gat ttg      3068
Asp Thr Gly Asp Lys Gln Ala Thr Gln Val Ser Ile Lys Lys Asp Leu
            935                 940                 945

gtt tat gtt ctt gca gag gag aac aaa aat agt gta aag cag cat ata      3116
Val Tyr Val Leu Ala Glu Glu Asn Lys Asn Ser Val Lys Gln His Ile
        950                 955                 960

aaa atg act cta ggt caa gat tta aaa tcg gac atc tcc ttg aat ata      3164
Lys Met Thr Leu Gly Gln Asp Leu Lys Ser Asp Ile Ser Leu Asn Ile
    965                 970                 975

gat aaa ata cca gaa aaa aat aat gat tac atg aac aaa tgg gca gga      3212
Asp Lys Ile Pro Glu Lys Asn Asn Asp Tyr Met Asn Lys Trp Ala Gly
980                 985                 990                 995

ctc tta ggt cca att  tca aat cac agt ttt  gga ggt agc ttc aga        3257
Leu Leu Gly Pro Ile  Ser Asn His Ser Phe  Gly Gly Ser Phe Arg
                1000                 1005                 1010
```

```
aca gct tca aat aag  gaa atc aag ctc tct  gaa cat aac att aag       3302
Thr Ala Ser Asn Lys  Glu Ile Lys Leu Ser  Glu His Asn Ile Lys
                1015                 1020                 1025

aag agc aaa atg ttc  ttc aaa gat att gaa  gaa caa tat cct act       3347
Lys Ser Lys Met Phe  Phe Lys Asp Ile Glu  Glu Gln Tyr Pro Thr
                1030                 1035                 1040

agt tta gct tgt gtt  gaa att gta aat acc  ttg gca tta gat aat       3392
Ser Leu Ala Cys Val  Glu Ile Val Asn Thr  Leu Ala Leu Asp Asn
                1045                 1050                 1055

caa aag aaa ctg agc  aag cct cag tca att  aat act gta tct gca       3437
Gln Lys Lys Leu Ser  Lys Pro Gln Ser Ile  Asn Thr Val Ser Ala
                1060                 1065                 1070

cat tta cag agt agt  gta gtt gtt tct gat  tgt aaa aat agt cat       3482
His Leu Gln Ser Ser  Val Val Val Ser Asp  Cys Lys Asn Ser His
                1075                 1080                 1085

ata acc cct cag atg  tta ttt tcc aag cag  gat ttt aat tca aac       3527
Ile Thr Pro Gln Met  Leu Phe Ser Lys Gln  Asp Phe Asn Ser Asn
                1090                 1095                 1100

cat aat tta aca cct  agc caa aag gca gaa  att aca gaa ctt tct       3572
His Asn Leu Thr Pro  Ser Gln Lys Ala Glu  Ile Thr Glu Leu Ser
                1105                 1110                 1115

act ata tta gaa gaa  tca gga agt cag ttt  gaa ttt act cag ttt       3617
Thr Ile Leu Glu Glu  Ser Gly Ser Gln Phe  Glu Phe Thr Gln Phe
                1120                 1125                 1130

aga aaa cca agc tac  ata ttg cag aag agt  aca ttt gaa gtg cct       3662
Arg Lys Pro Ser Tyr  Ile Leu Gln Lys Ser  Thr Phe Glu Val Pro
                1135                 1140                 1145

gaa aac cag atg act  atc tta aag acc act  tct gag gaa tgc aga       3707
Glu Asn Gln Met Thr  Ile Leu Lys Thr Thr  Ser Glu Glu Cys Arg
                1150                 1155                 1160

gat gct gat ctt cat  gtc ata atg aat gcc  cca tcg att ggt cag       3752
Asp Ala Asp Leu His  Val Ile Met Asn Ala  Pro Ser Ile Gly Gln
                1165                 1170                 1175

gta gac agc agc aag  caa ttt gaa ggt aca  gtt gaa att aaa cgg       3797
Val Asp Ser Ser Lys  Gln Phe Glu Gly Thr  Val Glu Ile Lys Arg
                1180                 1185                 1190

aag ttt gct ggc ctg  ttg aaa aat gac tgt  aac aaa agt gct tct       3842
Lys Phe Ala Gly Leu  Leu Lys Asn Asp Cys  Asn Lys Ser Ala Ser
                1195                 1200                 1205

ggt tat tta aca gat  gaa aat gaa gtg ggg  ttt agg ggc ttt tat       3887
Gly Tyr Leu Thr Asp  Glu Asn Glu Val Gly  Phe Arg Gly Phe Tyr
                1210                 1215                 1220

tct gct cat ggc aca  aaa ctg aat gtt tct  act gaa gct ctg caa       3932
Ser Ala His Gly Thr  Lys Leu Asn Val Ser  Thr Glu Ala Leu Gln
                1225                 1230                 1235

aaa gct gtg aaa ctg  ttt agt gat att gag  aat att agt gag gaa       3977
Lys Ala Val Lys Leu  Phe Ser Asp Ile Glu  Asn Ile Ser Glu Glu
                1240                 1245                 1250

act tct gca gag gta  cat cca ata agt tta  tct tca agt aaa tgt       4022
Thr Ser Ala Glu Val  His Pro Ile Ser Leu  Ser Ser Ser Lys Cys
                1255                 1260                 1265

cat gat tct gtt gtt  tca atg ttt aag ata  gaa aat cat aat gat       4067
His Asp Ser Val Val  Ser Met Phe Lys Ile  Glu Asn His Asn Asp
                1270                 1275                 1280

aaa act gta agt gaa  aaa aat aat aaa tgc  caa ctg ata tta caa       4112
Lys Thr Val Ser Glu  Lys Asn Asn Lys Cys  Gln Leu Ile Leu Gln
                1285                 1290                 1295

aat aat att gaa atg  act act ggc act ttt  gtt gaa gaa att act       4157
Asn Asn Ile Glu Met  Thr Thr Gly Thr Phe  Val Glu Glu Ile Thr
                1300                 1305                 1310
```

```
gaa aat tac aag aga  aat act gaa aat gaa  gat aac aaa tat act       4202
Glu Asn Tyr Lys Arg  Asn Thr Glu Asn Glu  Asp Asn Lys Tyr Thr
                1315                 1320                 1325

gct gcc agt aga aat  tct cat aac tta gaa  ttt gat ggc agt gat       4247
Ala Ala Ser Arg Asn  Ser His Asn Leu Glu  Phe Asp Gly Ser Asp
                1330                 1335                 1340

tca agt aaa aat gat  act gtt tgt att cat  aaa gat gaa acg gac       4292
Ser Ser Lys Asn Asp  Thr Val Cys Ile His  Lys Asp Glu Thr Asp
                1345                 1350                 1355

ttg cta ttt act gat  cag cac aac ata tgt  ctt aaa tta tct ggc       4337
Leu Leu Phe Thr Asp  Gln His Asn Ile Cys  Leu Lys Leu Ser Gly
                1360                 1365                 1370

cag ttt atg aag gag  gga aac act cag att  aaa gaa gat ttg tca       4382
Gln Phe Met Lys Glu  Gly Asn Thr Gln Ile  Lys Glu Asp Leu Ser
                1375                 1380                 1385

gat tta act ttt ttg  gaa gtt gcg aaa gct  caa gaa gca tgt cat       4427
Asp Leu Thr Phe Leu  Glu Val Ala Lys Ala  Gln Glu Ala Cys His
                1390                 1395                 1400

ggt aat act tca aat  aaa gaa cag tta act  gct act aaa acg gag       4472
Gly Asn Thr Ser Asn  Lys Glu Gln Leu Thr  Ala Thr Lys Thr Glu
                1405                 1410                 1415

caa aat ata aaa gat  ttt gag act tct gat  aca ttt ttt cag act       4517
Gln Asn Ile Lys Asp  Phe Glu Thr Ser Asp  Thr Phe Phe Gln Thr
                1420                 1425                 1430

gca agt ggg aaa aat  att agt gtc gcc aaa  gag tca ttt aat aaa       4562
Ala Ser Gly Lys Asn  Ile Ser Val Ala Lys  Glu Ser Phe Asn Lys
                1435                 1440                 1445

att gta aat ttc ttt  gat cag aaa cca gaa  gaa ttg cat aac ttt       4607
Ile Val Asn Phe Phe  Asp Gln Lys Pro Glu  Glu Leu His Asn Phe
                1450                 1455                 1460

tcc tta aat tct gaa  tta cat tct gac ata  aga aag aac aaa atg       4652
Ser Leu Asn Ser Glu  Leu His Ser Asp Ile  Arg Lys Asn Lys Met
                1465                 1470                 1475

gac att cta agt tat  gag gaa aca gac ata  gtt aaa cac aaa ata       4697
Asp Ile Leu Ser Tyr  Glu Glu Thr Asp Ile  Val Lys His Lys Ile
                1480                 1485                 1490

ctg aaa gaa agt gtc  cca gtt ggt act gga  aat caa cta gtg acc       4742
Leu Lys Glu Ser Val  Pro Val Gly Thr Gly  Asn Gln Leu Val Thr
                1495                 1500                 1505

ttc cag gga caa ccc  gaa cgt gat gaa aag  atc aaa gaa cct act       4787
Phe Gln Gly Gln Pro  Glu Arg Asp Glu Lys  Ile Lys Glu Pro Thr
                1510                 1515                 1520

cta ttg ggt ttt cat  aca gct agc ggg aaa  aaa gtt aaa att gca       4832
Leu Leu Gly Phe His  Thr Ala Ser Gly Lys  Lys Val Lys Ile Ala
                1525                 1530                 1535

aag gaa tct ttg gac  aaa gtg aaa aac ctt  ttt gat gaa aaa gag       4877
Lys Glu Ser Leu Asp  Lys Val Lys Asn Leu  Phe Asp Glu Lys Glu
                1540                 1545                 1550

caa ggt act agt gaa  atc acc agt ttt agc  cat caa tgg gca aag       4922
Gln Gly Thr Ser Glu  Ile Thr Ser Phe Ser  His Gln Trp Ala Lys
                1555                 1560                 1565

acc cta aag tac aga  gag gcc tgt aaa gac  ctt gaa tta gca tgt       4967
Thr Leu Lys Tyr Arg  Glu Ala Cys Lys Asp  Leu Glu Leu Ala Cys
                1570                 1575                 1580

gag acc att gag atc  aca gct gcc cca aag  tgt aaa gaa atg cag       5012
Glu Thr Ile Glu Ile  Thr Ala Ala Pro Lys  Cys Lys Glu Met Gln
                1585                 1590                 1595

aat tct ctc aat aat  gat aaa aac ctt gtt  tct att gag act gtg       5057
Asn Ser Leu Asn Asn  Asp Lys Asn Leu Val  Ser Ile Glu Thr Val
```

```
                1600                1605                1610

gtg cca cct aag ctc  tta agt gat aat tta  tgt aga caa act gaa       5102
Val Pro Pro Lys Leu  Leu Ser Asp Asn Leu  Cys Arg Gln Thr Glu
                1615                1620                1625

aat ctc aaa aca tca  aaa agt atc ttt ttg  aaa gtt aaa gta cat       5147
Asn Leu Lys Thr Ser  Lys Ser Ile Phe Leu  Lys Val Lys Val His
                1630                1635                1640

gaa aat gta gaa aaa  gaa aca gca aaa agt  cct gca act tgt tac       5192
Glu Asn Val Glu Lys  Glu Thr Ala Lys Ser  Pro Ala Thr Cys Tyr
                1645                1650                1655

aca aat cag tcc cct  tat tca gtc att gaa  aat tca gcc tta gct       5237
Thr Asn Gln Ser Pro  Tyr Ser Val Ile Glu  Asn Ser Ala Leu Ala
                1660                1665                1670

ttt tac aca agt tgt  agt aga aaa act tct  gtg agt cag act tca       5282
Phe Tyr Thr Ser Cys  Ser Arg Lys Thr Ser  Val Ser Gln Thr Ser
                1675                1680                1685

tta ctt gaa gca aaa  aaa tgg ctt aga gaa  gga ata ttt gat ggt       5327
Leu Leu Glu Ala Lys  Lys Trp Leu Arg Glu  Gly Ile Phe Asp Gly
                1690                1695                1700

caa cca gaa aga ata  aat act gca gat tat  gta gga aat tat ttg       5372
Gln Pro Glu Arg Ile  Asn Thr Ala Asp Tyr  Val Gly Asn Tyr Leu
                1705                1710                1715

tat gaa aat aat tca  aac agt act ata gct  gaa aat gac aaa aat       5417
Tyr Glu Asn Asn Ser  Asn Ser Thr Ile Ala  Glu Asn Asp Lys Asn
                1720                1725                1730

cat ctc tcc gaa aaa  caa gat act tat tta  agt aac agt agc atg       5462
His Leu Ser Glu Lys  Gln Asp Thr Tyr Leu  Ser Asn Ser Ser Met
                1735                1740                1745

tct aac agc tat tcc  tac cat tct gat gag  gta tat aat gat tca       5507
Ser Asn Ser Tyr Ser  Tyr His Ser Asp Glu  Val Tyr Asn Asp Ser
                1750                1755                1760

gga tat ctc tca aaa  aat aaa ctt gat tct  ggt att gag cca gta       5552
Gly Tyr Leu Ser Lys  Asn Lys Leu Asp Ser  Gly Ile Glu Pro Val
                1765                1770                1775

ttg aag aat gtt gaa  gat caa aaa aac act  agt ttt tcc aaa gta       5597
Leu Lys Asn Val Glu  Asp Gln Lys Asn Thr  Ser Phe Ser Lys Val
                1780                1785                1790

ata tcc aat gta aaa  gat gca aat gca tac  cca caa act gta aat       5642
Ile Ser Asn Val Lys  Asp Ala Asn Ala Tyr  Pro Gln Thr Val Asn
                1795                1800                1805

gaa gat att tgc gtt  gag gaa ctt gtg act  agc tct tca ccc tgc       5687
Glu Asp Ile Cys Val  Glu Glu Leu Val Thr  Ser Ser Ser Pro Cys
                1810                1815                1820

aaa aat aaa aat gca  gcc att aaa ttg tcc  ata tct aat agt aat       5732
Lys Asn Lys Asn Ala  Ala Ile Lys Leu Ser  Ile Ser Asn Ser Asn
                1825                1830                1835

aat ttt gag gta ggg  cca cct gca ttt agg  ata gcc agt ggt aaa       5777
Asn Phe Glu Val Gly  Pro Pro Ala Phe Arg  Ile Ala Ser Gly Lys
                1840                1845                1850

atc gtt tgt gtt tca  cat gaa aca att aaa  aaa gtg aaa gac ata       5822
Ile Val Cys Val Ser  His Glu Thr Ile Lys  Lys Val Lys Asp Ile
                1855                1860                1865

ttt aca gac agt ttc  agt aaa gta att aag  gaa aac aac gag aat       5867
Phe Thr Asp Ser Phe  Ser Lys Val Ile Lys  Glu Asn Asn Glu Asn
                1870                1875                1880

aaa tca aaa att tgc  caa acg aaa att atg  gca ggt tgt tac gag       5912
Lys Ser Lys Ile Cys  Gln Thr Lys Ile Met  Ala Gly Cys Tyr Glu
                1885                1890                1895

gca ttg gat gat tca  gag gat att ctt cat  aac tct cta gat aat       5957
```

```
Ala Leu Asp Asp Ser  Glu Asp Ile Leu His  Asn Ser Leu Asp Asn
                1900                 1905                 1910

gat gaa tgt agc acg  cat tca cat aag gtt  ttt gct gac att cag      6002
Asp Glu Cys Ser Thr  His Ser His Lys Val  Phe Ala Asp Ile Gln
                1915                 1920                 1925

agt gaa gaa att tta  caa cat aac caa aat  atg tct gga ttg gag      6047
Ser Glu Glu Ile Leu  Gln His Asn Gln Asn  Met Ser Gly Leu Glu
                1930                 1935                 1940

aaa gtt tct aaa ata  tca cct tgt gat gtt  agt ttg gaa act tca      6092
Lys Val Ser Lys Ile  Ser Pro Cys Asp Val  Ser Leu Glu Thr Ser
                1945                 1950                 1955

gat ata tgt aaa tgt  agt ata ggg aag ctt  cat aag tca gtc tca      6137
Asp Ile Cys Lys Cys  Ser Ile Gly Lys Leu  His Lys Ser Val Ser
                1960                 1965                 1970

tct gca aat act tgt  ggg att ttt agc aca  gca agt gga aaa tct      6182
Ser Ala Asn Thr Cys  Gly Ile Phe Ser Thr  Ala Ser Gly Lys Ser
                1975                 1980                 1985

gtc cag gta tca gat  gct tca tta caa aac  gca aga caa gtg ttt      6227
Val Gln Val Ser Asp  Ala Ser Leu Gln Asn  Ala Arg Gln Val Phe
                1990                 1995                 2000

tct gaa ata gaa gat  agt acc aag caa gtc  ttt tcc aaa gta ttg      6272
Ser Glu Ile Glu Asp  Ser Thr Lys Gln Val  Phe Ser Lys Val Leu
                2005                 2010                 2015

ttt aaa agt aac gaa  cat tca gac cag ctc  aca aga gaa gaa aat      6317
Phe Lys Ser Asn Glu  His Ser Asp Gln Leu  Thr Arg Glu Glu Asn
                2020                 2025                 2030

act gct ata cgt act  cca gaa cat tta ata  tcc caa aaa ggc ttt      6362
Thr Ala Ile Arg Thr  Pro Glu His Leu Ile  Ser Gln Lys Gly Phe
                2035                 2040                 2045

tca tat aat gtg gta  aat tca tct gct ttc  tct gga ttt agt aca      6407
Ser Tyr Asn Val Val  Asn Ser Ser Ala Phe  Ser Gly Phe Ser Thr
                2050                 2055                 2060

gca agt gga aag caa  gtt tcc att tta gaa  agt tcc tta cac aaa      6452
Ala Ser Gly Lys Gln  Val Ser Ile Leu Glu  Ser Ser Leu His Lys
                2065                 2070                 2075

gtt aag gga gtg tta  gag gaa ttt gat tta  atc aga act gag cat      6497
Val Lys Gly Val Leu  Glu Glu Phe Asp Leu  Ile Arg Thr Glu His
                2080                 2085                 2090

agt ctt cac tat tca  cct acg tct aga caa  aat gta tca aaa ata      6542
Ser Leu His Tyr Ser  Pro Thr Ser Arg Gln  Asn Val Ser Lys Ile
                2095                 2100                 2105

ctt cct cgt gtt gat  aag aga aac cca gag  cac tgt gta aac tca      6587
Leu Pro Arg Val Asp  Lys Arg Asn Pro Glu  His Cys Val Asn Ser
                2110                 2115                 2120

gaa atg gaa aaa acc  tgc agt aaa gaa ttt  aaa tta tca aat aac      6632
Glu Met Glu Lys Thr  Cys Ser Lys Glu Phe  Lys Leu Ser Asn Asn
                2125                 2130                 2135

tta aat gtt gaa ggt  ggt tct tca gaa aat  aat cac tct att aaa      6677
Leu Asn Val Glu Gly  Gly Ser Ser Glu Asn  Asn His Ser Ile Lys
                2140                 2145                 2150

gtt tct cca tat ctc  tct caa ttt caa caa  gac aaa caa cag ttg      6722
Val Ser Pro Tyr Leu  Ser Gln Phe Gln Gln  Asp Lys Gln Gln Leu
                2155                 2160                 2165

gta tta gga acc aaa  gtg tca ctt gtt gag  aac att cat gtt ttg      6767
Val Leu Gly Thr Lys  Val Ser Leu Val Glu  Asn Ile His Val Leu
                2170                 2175                 2180

gga aaa gaa cag gct  tca cct aaa aac gta  aaa atg gaa att ggt      6812
Gly Lys Glu Gln Ala  Ser Pro Lys Asn Val  Lys Met Glu Ile Gly
                2185                 2190                 2195
```

```
aaa act gaa act ttt  tct gat gtt cct gtg  aaa aca aat ata gaa       6857
Lys Thr Glu Thr Phe  Ser Asp Val Pro Val  Lys Thr Asn Ile Glu
                2200                 2205                 2210

gtt tgt tct act tac  tcc aaa gat tca gaa  aac tac ttt gaa aca       6902
Val Cys Ser Thr Tyr  Ser Lys Asp Ser Glu  Asn Tyr Phe Glu Thr
                2215                 2220                 2225

gaa gca gta gaa att  gct aaa gct ttt atg  gaa gat gat gaa ctg       6947
Glu Ala Val Glu Ile  Ala Lys Ala Phe Met  Glu Asp Asp Glu Leu
                2230                 2235                 2240

aca gat tct aaa ctg  cca agt cat gcc aca  cat tct ctt ttt aca       6992
Thr Asp Ser Lys Leu  Pro Ser His Ala Thr  His Ser Leu Phe Thr
                2245                 2250                 2255

tgt ccc gaa aat gag  gaa atg gtt ttg tca  aat tca aga att gga       7037
Cys Pro Glu Asn Glu  Glu Met Val Leu Ser  Asn Ser Arg Ile Gly
                2260                 2265                 2270

aaa aga aga gga gag  ccc ctt atc tta gtg  gga gaa ccc tca atc       7082
Lys Arg Arg Gly Glu  Pro Leu Ile Leu Val  Gly Glu Pro Ser Ile
                2275                 2280                 2285

aaa aga aac tta tta  aat gaa ttt gac agg  ata ata gaa aat caa       7127
Lys Arg Asn Leu Leu  Asn Glu Phe Asp Arg  Ile Ile Glu Asn Gln
                2290                 2295                 2300

gaa aaa tcc tta aag  gct tca aaa agc act  cca gat ggc aca ata       7172
Glu Lys Ser Leu Lys  Ala Ser Lys Ser Thr  Pro Asp Gly Thr Ile
                2305                 2310                 2315

aaa gat cga aga ttg  ttt atg cat cat gtt  tct tta gag ccg att       7217
Lys Asp Arg Arg Leu  Phe Met His His Val  Ser Leu Glu Pro Ile
                2320                 2325                 2330

acc tgt gta ccc ttt  cgc aca act aag gaa  cgt caa gag ata cag       7262
Thr Cys Val Pro Phe  Arg Thr Thr Lys Glu  Arg Gln Glu Ile Gln
                2335                 2340                 2345

aat cca aat ttt acc  gca cct ggt caa gaa  ttt ctg tct aaa tct       7307
Asn Pro Asn Phe Thr  Ala Pro Gly Gln Glu  Phe Leu Ser Lys Ser
                2350                 2355                 2360

cat ttg tat gaa cat  ctg act ttg gaa aaa  tct tca agc aat tta       7352
His Leu Tyr Glu His  Leu Thr Leu Glu Lys  Ser Ser Ser Asn Leu
                2365                 2370                 2375

gca gtt tca gga cat  cca ttt tat caa gtt  tct gct aca aga aat       7397
Ala Val Ser Gly His  Pro Phe Tyr Gln Val  Ser Ala Thr Arg Asn
                2380                 2385                 2390

gaa aaa atg aga cac  ttg att act aca ggc  aga cca acc aaa gtc       7442
Glu Lys Met Arg His  Leu Ile Thr Thr Gly  Arg Pro Thr Lys Val
                2395                 2400                 2405

ttt gtt cca cct ttt  aaa act aaa tca cat  ttt cac aga gtt gaa       7487
Phe Val Pro Pro Phe  Lys Thr Lys Ser His  Phe His Arg Val Glu
                2410                 2415                 2420

cag tgt gtt agg aat  att aac ttg gag gaa  aac aga caa aag caa       7532
Gln Cys Val Arg Asn  Ile Asn Leu Glu Glu  Asn Arg Gln Lys Gln
                2425                 2430                 2435

aac att gat gga cat  ggc tct gat gat agt  aaa aat aag att aat       7577
Asn Ile Asp Gly His  Gly Ser Asp Asp Ser  Lys Asn Lys Ile Asn
                2440                 2445                 2450

gac aat gag att cat  cag ttt aac aaa aac  aac tcc aat caa gca       7622
Asp Asn Glu Ile His  Gln Phe Asn Lys Asn  Asn Ser Asn Gln Ala
                2455                 2460                 2465

gca gct gta act ttc  aca aag tgt gaa gaa  gaa cct tta gat tta       7667
Ala Ala Val Thr Phe  Thr Lys Cys Glu Glu  Glu Pro Leu Asp Leu
                2470                 2475                 2480

att aca agt ctt cag  aat gcc aga gat ata  cag gat atg cga att       7712
Ile Thr Ser Leu Gln  Asn Ala Arg Asp Ile  Gln Asp Met Arg Ile
                2485                 2490                 2495
```

```
aag aag aaa caa agg  caa cgc gtc ttt cca  cag cca ggc agt ctg       7757
Lys Lys Lys Gln Arg  Gln Arg Val Phe Pro  Gln Pro Gly Ser Leu
                2500                 2505                 2510

tat ctt gca aaa aca  tcc act ctg cct cga  atc tct ctg aaa gca       7802
Tyr Leu Ala Lys Thr  Ser Thr Leu Pro Arg  Ile Ser Leu Lys Ala
                2515                 2520                 2525

gca gta gga ggc caa  gtt ccc tct gcg tgt  tct cat aaa cag ctg       7847
Ala Val Gly Gly Gln  Val Pro Ser Ala Cys  Ser His Lys Gln Leu
                2530                 2535                 2540

tat acg tat ggc gtt  tct aaa cat tgc ata  aaa att aac agc aaa       7892
Tyr Thr Tyr Gly Val  Ser Lys His Cys Ile  Lys Ile Asn Ser Lys
                2545                 2550                 2555

aat gca gag tct ttt  cag ttt cac act gaa  gat tat ttt ggt aag       7937
Asn Ala Glu Ser Phe  Gln Phe His Thr Glu  Asp Tyr Phe Gly Lys
                2560                 2565                 2570

gaa agt tta tgg act  gga aaa gga ata cag  ttg gct gat ggt gga       7982
Glu Ser Leu Trp Thr  Gly Lys Gly Ile Gln  Leu Ala Asp Gly Gly
                2575                 2580                 2585

tgg ctc ata ccc tcc  aat gat gga aag gct  gga aaa gaa gaa ttt       8027
Trp Leu Ile Pro Ser  Asn Asp Gly Lys Ala  Gly Lys Glu Glu Phe
                2590                 2595                 2600

tat agg gct ctg tgt  gac act cca ggt gtg  gat cca aag ctt att       8072
Tyr Arg Ala Leu Cys  Asp Thr Pro Gly Val  Asp Pro Lys Leu Ile
                2605                 2610                 2615

tct aga att tgg gtt  tat aat cac tat aga  tgg atc ata tgg aaa       8117
Ser Arg Ile Trp Val  Tyr Asn His Tyr Arg  Trp Ile Ile Trp Lys
                2620                 2625                 2630

ctg gca gct atg gaa  tgt gcc ttt cct aag  gaa ttt gct aat aga       8162
Leu Ala Ala Met Glu  Cys Ala Phe Pro Lys  Glu Phe Ala Asn Arg
                2635                 2640                 2645

tgc cta agc cca gaa  agg gtg ctt ctt caa  cta aaa tac aga tat       8207
Cys Leu Ser Pro Glu  Arg Val Leu Leu Gln  Leu Lys Tyr Arg Tyr
                2650                 2655                 2660

gat acg gaa att gat  aga agc aga aga tcg  gct ata aaa aag ata       8252
Asp Thr Glu Ile Asp  Arg Ser Arg Arg Ser  Ala Ile Lys Lys Ile
                2665                 2670                 2675

atg gaa agg gat gac  aca gct gca aaa aca  ctt gtt ctc tgt gtt       8297
Met Glu Arg Asp Asp  Thr Ala Ala Lys Thr  Leu Val Leu Cys Val
                2680                 2685                 2690

tct gac ata att tca  ttg agc gca aat ata  tct gaa act tct agc       8342
Ser Asp Ile Ile Ser  Leu Ser Ala Asn Ile  Ser Glu Thr Ser Ser
                2695                 2700                 2705

aat aaa act agt agt  gca gat acc caa aaa  gtg gcc att att gaa       8387
Asn Lys Thr Ser Ser  Ala Asp Thr Gln Lys  Val Ala Ile Ile Glu
                2710                 2715                 2720

ctt aca gat ggg tgg  tat gct gtt aag gcc  cag tta gat cct ccc       8432
Leu Thr Asp Gly Trp  Tyr Ala Val Lys Ala  Gln Leu Asp Pro Pro
                2725                 2730                 2735

ctc tta gct gtc tta  aag aat ggc aga ctg  aca gtt ggt cag aag       8477
Leu Leu Ala Val Leu  Lys Asn Gly Arg Leu  Thr Val Gly Gln Lys
                2740                 2745                 2750

att att ctt cat gga  gca gaa ctg gtg ggc  tct cct gat gcc tgt       8522
Ile Ile Leu His Gly  Ala Glu Leu Val Gly  Ser Pro Asp Ala Cys
                2755                 2760                 2765

aca cct ctt gaa gcc  cca gaa tct ctt atg  tta aag att tct gct       8567
Thr Pro Leu Glu Ala  Pro Glu Ser Leu Met  Leu Lys Ile Ser Ala
                2770                 2775                 2780

aac agt act cgg cct  gct cgc tgg tat acc  aaa ctt gga ttc ttt       8612
Asn Ser Thr Arg Pro  Ala Arg Trp Tyr Thr  Lys Leu Gly Phe Phe
```

```
                2785                2790                2795

cct gac cct aga cct  ttt cct ctg ccc tta  tca tcg ctt ttc agt       8657
Pro Asp Pro Arg Pro  Phe Pro Leu Pro Leu  Ser Ser Leu Phe Ser
                2800                2805                2810

gat gga gga aat gtt  ggt tgt gtt gat gta  att att caa aga gca       8702
Asp Gly Gly Asn Val  Gly Cys Val Asp Val  Ile Ile Gln Arg Ala
                2815                2820                2825

tac cct ata cag tgg  atg gag aag aca tca  tct gga tta tac ata       8747
Tyr Pro Ile Gln Trp  Met Glu Lys Thr Ser  Ser Gly Leu Tyr Ile
                2830                2835                2840

ttt cgc aat gaa aga  gag gaa gaa aag gaa  gca gca aaa tat gtg       8792
Phe Arg Asn Glu Arg  Glu Glu Glu Lys Glu  Ala Ala Lys Tyr Val
                2845                2850                2855

gag gcc caa caa aag  aga cta gaa gcc tta  ttc act aaa att cag       8837
Glu Ala Gln Gln Lys  Arg Leu Glu Ala Leu  Phe Thr Lys Ile Gln
                2860                2865                2870

gag gaa ttt gaa gaa  cat gaa gaa aac aca  aca aaa cca tat tta       8882
Glu Glu Phe Glu Glu  His Glu Glu Asn Thr  Thr Lys Pro Tyr Leu
                2875                2880                2885

cca tca cgt gca cta  aca aga cag caa gtt  cgt gct ttg caa gat       8927
Pro Ser Arg Ala Leu  Thr Arg Gln Gln Val  Arg Ala Leu Gln Asp
                2890                2895                2900

ggt gca gag ctt tat  gaa gca gtg aag aat  gca gca gac cca gct       8972
Gly Ala Glu Leu Tyr  Glu Ala Val Lys Asn  Ala Ala Asp Pro Ala
                2905                2910                2915

tac ctt gag ggt tat  ttc agt gaa gag cag  tta aga gcc ttg aat       9017
Tyr Leu Glu Gly Tyr  Phe Ser Glu Glu Gln  Leu Arg Ala Leu Asn
                2920                2925                2930

aat cac agg caa atg  ttg aat gat aag aaa  caa gct cag atc cag       9062
Asn His Arg Gln Met  Leu Asn Asp Lys Lys  Gln Ala Gln Ile Gln
                2935                2940                2945

ttg gaa att agg aag  gcc atg gaa tct gct  gaa caa aag gaa caa       9107
Leu Glu Ile Arg Lys  Ala Met Glu Ser Ala  Glu Gln Lys Glu Gln
                2950                2955                2960

ggt tta tca agg gat  gtc aca acc gtg tgg  aag ttg cgt att gta       9152
Gly Leu Ser Arg Asp  Val Thr Thr Val Trp  Lys Leu Arg Ile Val
                2965                2970                2975

agc tat tca aaa aaa  gaa aaa gat tca gtt  ata ctg agt att tgg       9197
Ser Tyr Ser Lys Lys  Glu Lys Asp Ser Val  Ile Leu Ser Ile Trp
                2980                2985                2990

cgt cca tca tca gat  tta tat tct ctg tta  aca gaa gga aag aga       9242
Arg Pro Ser Ser Asp  Leu Tyr Ser Leu Leu  Thr Glu Gly Lys Arg
                2995                3000                3005

tac aga att tat cat  ctt gca act tca aaa  tct aaa agt aaa tct       9287
Tyr Arg Ile Tyr His  Leu Ala Thr Ser Lys  Ser Lys Ser Lys Ser
                3010                3015                3020

gaa aga gct aac ata  cag tta gca gcg aca  aaa aaa act cag tat       9332
Glu Arg Ala Asn Ile  Gln Leu Ala Ala Thr  Lys Lys Thr Gln Tyr
                3025                3030                3035

caa caa cta ccg gtt  tca gat gaa att tta  ttt cag att tac cag       9377
Gln Gln Leu Pro Val  Ser Asp Glu Ile Leu  Phe Gln Ile Tyr Gln
                3040                3045                3050

cca cgg gag ccc ctt  cac ttc agc aaa ttt  tta gat cca gac ttt       9422
Pro Arg Glu Pro Leu  His Phe Ser Lys Phe  Leu Asp Pro Asp Phe
                3055                3060                3065

cag cca tct tgt tct  gag gtg gac cta ata  gga ttt gtc gtt tct       9467
Gln Pro Ser Cys Ser  Glu Val Asp Leu Ile  Gly Phe Val Val Ser
                3070                3075                3080

gtt gtg aaa aaa aca  gga ctt gcc cct ttc  gtc tat ttg tca gac       9512
```

```
Val Val Lys Lys Thr  Gly Leu Ala Pro Phe  Val Tyr Leu Ser Asp
                3085                 3090                 3095

gaa tgt tac aat tta  ctg gca ata aag ttt  tgg ata gac ctt aat      9557
Glu Cys Tyr Asn Leu  Leu Ala Ile Lys Phe  Trp Ile Asp Leu Asn
                3100                 3105                 3110

gag gac att att aag  cct cat atg tta att  gct gca agc aac ctc      9602
Glu Asp Ile Ile Lys  Pro His Met Leu Ile  Ala Ala Ser Asn Leu
                3115                 3120                 3125

cag tgg cga cca gaa  tcc aaa tca ggc ctt  ctt act tta ttt gct      9647
Gln Trp Arg Pro Glu  Ser Lys Ser Gly Leu  Leu Thr Leu Phe Ala
                3130                 3135                 3140

gga gat ttt tct gtg  ttt tct gct agt cca  aaa gag ggc cac ttt      9692
Gly Asp Phe Ser Val  Phe Ser Ala Ser Pro  Lys Glu Gly His Phe
                3145                 3150                 3155

caa gag aca ttc aac  aaa atg aaa aat act  gtt gag aat att gac      9737
Gln Glu Thr Phe Asn  Lys Met Lys Asn Thr  Val Glu Asn Ile Asp
                3160                 3165                 3170

ata ctt tgc aat gaa  gca gaa aac aag ctt  atg cat ata ctg cat      9782
Ile Leu Cys Asn Glu  Ala Glu Asn Lys Leu  Met His Ile Leu His
                3175                 3180                 3185

gca aat gat ccc aag  tgg tcc acc cca act  aaa gac tgt act tca      9827
Ala Asn Asp Pro Lys  Trp Ser Thr Pro Thr  Lys Asp Cys Thr Ser
                3190                 3195                 3200

ggg ccg tac act gct  caa atc att cct ggt  aca gga aac aag ctt      9872
Gly Pro Tyr Thr Ala  Gln Ile Ile Pro Gly  Thr Gly Asn Lys Leu
                3205                 3210                 3215

ctg atg tct tct cct  aat tgt gag ata tat  tat caa agt cct tta      9917
Leu Met Ser Ser Pro  Asn Cys Glu Ile Tyr  Tyr Gln Ser Pro Leu
                3220                 3225                 3230

tca ctt tgt atg gcc  aaa agg aag tct gtt  tcc aca cct gtc tca      9962
Ser Leu Cys Met Ala  Lys Arg Lys Ser Val  Ser Thr Pro Val Ser
                3235                 3240                 3245

gcc cag atg act tca  aag tct tgt aaa ggg  gag aaa gag att gat     10007
Ala Gln Met Thr Ser  Lys Ser Cys Lys Gly  Glu Lys Glu Ile Asp
                3250                 3255                 3260

gac caa aag aac tgc  aaa aag aga aga gcc  ttg gat ttc ttg agt     10052
Asp Gln Lys Asn Cys  Lys Lys Arg Arg Ala  Leu Asp Phe Leu Ser
                3265                 3270                 3275

aga ctg cct tta cct  cca cct gtt agt ccc  att tgt aca ttt gtt     10097
Arg Leu Pro Leu Pro  Pro Pro Val Ser Pro  Ile Cys Thr Phe Val
                3280                 3285                 3290

tct ccg gct gca cag  aag gca ttt cag cca  cca agg agt tgt ggc     10142
Ser Pro Ala Ala Gln  Lys Ala Phe Gln Pro  Pro Arg Ser Cys Gly
                3295                 3300                 3305

acc aaa tac gaa aca  ccc ata aag aaa aaa  gaa ctg aat tct cct     10187
Thr Lys Tyr Glu Thr  Pro Ile Lys Lys Lys  Glu Leu Asn Ser Pro
                3310                 3315                 3320

cag atg act cca ttt  aaa aaa ttc aat gaa  att tct ctt ttg gaa     10232
Gln Met Thr Pro Phe  Lys Lys Phe Asn Glu  Ile Ser Leu Leu Glu
                3325                 3330                 3335

agt aat tca ata gct  gac gaa gaa ctt gca  ttg ata aat acc caa     10277
Ser Asn Ser Ile Ala  Asp Glu Glu Leu Ala  Leu Ile Asn Thr Gln
                3340                 3345                 3350

gct ctt ttg tct ggt  tca aca gga gaa aaa  caa ttt ata tct gtc     10322
Ala Leu Leu Ser Gly  Ser Thr Gly Glu Lys  Gln Phe Ile Ser Val
                3355                 3360                 3365

agt gaa tcc act agg  act gct ccc acc agt  tca gaa gat tat ctc     10367
Ser Glu Ser Thr Arg  Thr Ala Pro Thr Ser  Ser Glu Asp Tyr Leu
                3370                 3375                 3380
```

```
aga ctg aaa cga cgt  tgt act aca tct ctg  atc aaa gaa cag gag      10412
Arg Leu Lys Arg Arg  Cys Thr Thr Ser Leu  Ile Lys Glu Gln Glu
                3385                 3390                 3395

agt tcc cag gcc agt  acg gaa gaa tgt gag  aaa aat aag cag gac      10457
Ser Ser Gln Ala Ser  Thr Glu Glu Cys Glu  Lys Asn Lys Gln Asp
                3400                 3405                 3410

aca att aca act aaa  aaa tat atc taa gcatttgcaa aggcgacaat         10504
Thr Ile Thr Thr Lys  Lys Tyr Ile
                3415

aaattattga cgcttaacct ttccagttta taagactgga atataatttc aaaccacaca  10564

ttagtactta tgttgcacaa tgagaaaaga aattagtttc aaatttacct cagcgtttgt  10624

gtatcgggca aaaatcgttt tgcccgattc cgtattggta tacttttgct tcagttgcat  10684

atcttaaaac taaatgtaat ttattaacta atcaagaaaa acatctttgg ctgagctcgg  10744

tggctcatgc ctgtaatccc aacactttga gaagctgagg tgggaggagt gcttgaggcc  10804

aggagttcaa gaccagcctg ggcaacatag ggagaccccc atctttacaa agaaaaaaaa  10864

aaggggaaaa gaaaatcttt taaatctttg gatttgatca ctacaagtat tattttacaa  10924

gtgaaataaa cataccattt tcttttagat tgtgtcatta aatggaatga ggtctcttag  10984

tacagttatt ttgatgcaga taattccttt tagtttagct actattttag ggatttttt   11044

ttagaggtaa ctcactatga aatagttctc cttaatgcaa atatgttggt tctgctatag  11104

ttccatcctg ttcaaaagtc aggatgaata tgaagagtgg tgtttccttt tgagcaattc  11164

ttcatcctta agtcagcatg attataagaa aaatagaacc ctcagtgtaa ctctaattcc  11224

tttttactat tccagtgtga tctctgaaat taaattactt caactaaaaa ttcaaatact  11284

ttaaatcaga agatttcata gttaatttat tttttttttc aacaaaatgg tcatccaaac  11344

tcaaacttga gaaaatatct tgctttcaaa ttggcactga tt                     11386


<210> SEQ ID NO 6
<211> LENGTH: 3418
<212> TYPE: PRT
<213> ORGANISM: Homo sapiens

<400> SEQUENCE: 6

Met Pro Ile Gly Ser Lys Glu Arg Pro Thr Phe Phe Glu Ile Phe Lys
1               5                   10                  15

Thr Arg Cys Asn Lys Ala Asp Leu Gly Pro Ile Ser Leu Asn Trp Phe
            20                  25                  30

Glu Glu Leu Ser Ser Glu Ala Pro Pro Tyr Asn Ser Glu Pro Ala Glu
        35                  40                  45

Glu Ser Glu His Lys Asn Asn Asn Tyr Glu Pro Asn Leu Phe Lys Thr
    50                  55                  60

Pro Gln Arg Lys Pro Ser Tyr Asn Gln Leu Ala Ser Thr Pro Ile Ile
65                  70                  75                  80

Phe Lys Glu Gln Gly Leu Thr Leu Pro Leu Tyr Gln Ser Pro Val Lys
                85                  90                  95

Glu Leu Asp Lys Phe Lys Leu Asp Leu Gly Arg Asn Val Pro Asn Ser
            100                 105                 110

Arg His Lys Ser Leu Arg Thr Val Lys Thr Lys Met Asp Gln Ala Asp
        115                 120                 125

Asp Val Ser Cys Pro Leu Leu Asn Ser Cys Leu Ser Glu Ser Pro Val
    130                 135                 140

Val Leu Gln Cys Thr His Val Thr Pro Gln Arg Asp Lys Ser Val Val
145                 150                 155                 160
```

```
Cys Gly Ser Leu Phe His Thr Pro Lys Phe Val Lys Gly Arg Gln Thr
                165                 170                 175

Pro Lys His Ile Ser Glu Ser Leu Gly Ala Glu Val Asp Pro Asp Met
            180                 185                 190

Ser Trp Ser Ser Ser Leu Ala Thr Pro Pro Thr Leu Ser Ser Thr Val
        195                 200                 205

Leu Ile Val Arg Asn Glu Glu Ala Ser Glu Thr Val Phe Pro His Asp
    210                 215                 220

Thr Thr Ala Asn Val Lys Ser Tyr Phe Ser Asn His Asp Glu Ser Leu
225                 230                 235                 240

Lys Lys Asn Asp Arg Phe Ile Ala Ser Val Thr Asp Ser Glu Asn Thr
                245                 250                 255

Asn Gln Arg Glu Ala Ala Ser His Gly Phe Gly Lys Thr Ser Gly Asn
            260                 265                 270

Ser Phe Lys Val Asn Ser Cys Lys Asp His Ile Gly Lys Ser Met Pro
        275                 280                 285

Asn Val Leu Glu Asp Glu Val Tyr Glu Thr Val Val Asp Thr Ser Glu
    290                 295                 300

Glu Asp Ser Phe Ser Leu Cys Phe Ser Lys Cys Arg Thr Lys Asn Leu
305                 310                 315                 320

Gln Lys Val Arg Thr Ser Lys Thr Arg Lys Lys Ile Phe His Glu Ala
                325                 330                 335

Asn Ala Asp Glu Cys Glu Lys Ser Lys Asn Gln Val Lys Glu Lys Tyr
            340                 345                 350

Ser Phe Val Ser Glu Val Glu Pro Asn Asp Thr Asp Pro Leu Asp Ser
        355                 360                 365

Asn Val Ala Asn Gln Lys Pro Phe Glu Ser Gly Ser Asp Lys Ile Ser
    370                 375                 380

Lys Glu Val Val Pro Ser Leu Ala Cys Glu Trp Ser Gln Leu Thr Leu
385                 390                 395                 400

Ser Gly Leu Asn Gly Ala Gln Met Glu Lys Ile Pro Leu Leu His Ile
                405                 410                 415

Ser Ser Cys Asp Gln Asn Ile Ser Glu Lys Asp Leu Leu Asp Thr Glu
            420                 425                 430

Asn Lys Arg Lys Lys Asp Phe Leu Thr Ser Glu Asn Ser Leu Pro Arg
        435                 440                 445

Ile Ser Ser Leu Pro Lys Ser Glu Lys Pro Leu Asn Glu Glu Thr Val
    450                 455                 460

Val Asn Lys Arg Asp Glu Glu Gln His Leu Glu Ser His Thr Asp Cys
465                 470                 475                 480

Ile Leu Ala Val Lys Gln Ala Ile Ser Gly Thr Ser Pro Val Ala Ser
                485                 490                 495

Ser Phe Gln Gly Ile Lys Lys Ser Ile Phe Arg Ile Arg Glu Ser Pro
            500                 505                 510

Lys Glu Thr Phe Asn Ala Ser Phe Ser Gly His Met Thr Asp Pro Asn
        515                 520                 525

Phe Lys Lys Glu Thr Glu Ala Ser Glu Ser Gly Leu Glu Ile His Thr
    530                 535                 540

Val Cys Ser Gln Lys Glu Asp Ser Leu Cys Pro Asn Leu Ile Asp Asn
545                 550                 555                 560

Gly Ser Trp Pro Ala Thr Thr Thr Gln Asn Ser Val Ala Leu Lys Asn
                565                 570                 575
```

```
Ala Gly Leu Ile Ser Thr Leu Lys Lys Lys Thr Asn Lys Phe Ile Tyr
            580                 585                 590

Ala Ile His Asp Glu Thr Ser Tyr Lys Gly Lys Lys Ile Pro Lys Asp
        595                 600                 605

Gln Lys Ser Glu Leu Ile Asn Cys Ser Ala Gln Phe Glu Ala Asn Ala
    610                 615                 620

Phe Glu Ala Pro Leu Thr Phe Ala Asn Ala Asp Ser Gly Leu Leu His
625                 630                 635                 640

Ser Ser Val Lys Arg Ser Cys Ser Gln Asn Asp Ser Glu Glu Pro Thr
                645                 650                 655

Leu Ser Leu Thr Ser Ser Phe Gly Thr Ile Leu Arg Lys Cys Ser Arg
            660                 665                 670

Asn Glu Thr Cys Ser Asn Asn Thr Val Ile Ser Gln Asp Leu Asp Tyr
        675                 680                 685

Lys Glu Ala Lys Cys Asn Lys Glu Lys Leu Gln Leu Phe Ile Thr Pro
    690                 695                 700

Glu Ala Asp Ser Leu Ser Cys Leu Gln Glu Gly Gln Cys Glu Asn Asp
705                 710                 715                 720

Pro Lys Ser Lys Lys Val Ser Asp Ile Lys Glu Glu Val Leu Ala Ala
                725                 730                 735

Ala Cys His Pro Val Gln His Ser Lys Val Glu Tyr Ser Asp Thr Asp
            740                 745                 750

Phe Gln Ser Gln Lys Ser Leu Leu Tyr Asp His Glu Asn Ala Ser Thr
        755                 760                 765

Leu Ile Leu Thr Pro Thr Ser Lys Asp Val Leu Ser Asn Leu Val Met
    770                 775                 780

Ile Ser Arg Gly Lys Glu Ser Tyr Lys Met Ser Asp Lys Leu Lys Gly
785                 790                 795                 800

Asn Asn Tyr Glu Ser Asp Val Glu Leu Thr Lys Asn Ile Pro Met Glu
                805                 810                 815

Lys Asn Gln Asp Val Cys Ala Leu Asn Glu Asn Tyr Lys Asn Val Glu
            820                 825                 830

Leu Leu Pro Pro Glu Lys Tyr Met Arg Val Ala Ser Pro Ser Arg Lys
        835                 840                 845

Val Gln Phe Asn Gln Asn Thr Asn Leu Arg Val Ile Gln Lys Asn Gln
    850                 855                 860

Glu Glu Thr Thr Ser Ile Ser Lys Ile Thr Val Asn Pro Asp Ser Glu
865                 870                 875                 880

Glu Leu Phe Ser Asp Asn Glu Asn Asn Phe Val Phe Gln Val Ala Asn
                885                 890                 895

Glu Arg Asn Asn Leu Ala Leu Gly Asn Thr Lys Glu Leu His Glu Thr
            900                 905                 910

Asp Leu Thr Cys Val Asn Glu Pro Ile Phe Lys Asn Ser Thr Met Val
        915                 920                 925

Leu Tyr Gly Asp Thr Gly Asp Lys Gln Ala Thr Gln Val Ser Ile Lys
    930                 935                 940

Lys Asp Leu Val Tyr Val Leu Ala Glu Glu Asn Lys Asn Ser Val Lys
945                 950                 955                 960

Gln His Ile Lys Met Thr Leu Gly Gln Asp Leu Lys Ser Asp Ile Ser
                965                 970                 975

Leu Asn Ile Asp Lys Ile Pro Glu Lys Asn Asn Asp Tyr Met Asn Lys
            980                 985                 990

Trp Ala Gly Leu Leu Gly Pro Ile  Ser Asn His Ser Phe  Gly Gly Ser
```

```
        995                 1000                1005

Phe Arg  Thr Ala Ser Asn Lys  Glu Ile Lys Leu Ser  Glu His Asn
    1010                 1015                 1020

Ile Lys  Lys Ser Lys Met Phe  Phe Lys Asp Ile Glu  Glu Gln Tyr
    1025                 1030                 1035

Pro Thr  Ser Leu Ala Cys Val  Glu Ile Val Asn Thr  Leu Ala Leu
    1040                 1045                 1050

Asp Asn  Gln Lys Lys Leu Ser  Lys Pro Gln Ser Ile  Asn Thr Val
    1055                 1060                 1065

Ser Ala  His Leu Gln Ser Ser  Val Val Val Ser Asp  Cys Lys Asn
    1070                 1075                 1080

Ser His  Ile Thr Pro Gln Met  Leu Phe Ser Lys Gln  Asp Phe Asn
    1085                 1090                 1095

Ser Asn  His Asn Leu Thr Pro  Ser Gln Lys Ala Glu  Ile Thr Glu
    1100                 1105                 1110

Leu Ser  Thr Ile Leu Glu Glu  Ser Gly Ser Gln Phe  Glu Phe Thr
    1115                 1120                 1125

Gln Phe  Arg Lys Pro Ser Tyr  Ile Leu Gln Lys Ser  Thr Phe Glu
    1130                 1135                 1140

Val Pro  Glu Asn Gln Met Thr  Ile Leu Lys Thr Thr  Ser Glu Glu
    1145                 1150                 1155

Cys Arg  Asp Ala Asp Leu His  Val Ile Met Asn Ala  Pro Ser Ile
    1160                 1165                 1170

Gly Gln  Val Asp Ser Ser Lys  Gln Phe Glu Gly Thr  Val Glu Ile
    1175                 1180                 1185

Lys Arg  Lys Phe Ala Gly Leu  Leu Lys Asn Asp Cys  Asn Lys Ser
    1190                 1195                 1200

Ala Ser  Gly Tyr Leu Thr Asp  Glu Asn Glu Val Gly  Phe Arg Gly
    1205                 1210                 1215

Phe Tyr  Ser Ala His Gly Thr  Lys Leu Asn Val Ser  Thr Glu Ala
    1220                 1225                 1230

Leu Gln  Lys Ala Val Lys Leu  Phe Ser Asp Ile Glu  Asn Ile Ser
    1235                 1240                 1245

Glu Glu  Thr Ser Ala Glu Val  His Pro Ile Ser Leu  Ser Ser Ser
    1250                 1255                 1260

Lys Cys  His Asp Ser Val Val  Ser Met Phe Lys Ile  Glu Asn His
    1265                 1270                 1275

Asn Asp  Lys Thr Val Ser Glu  Lys Asn Asn Lys Cys  Gln Leu Ile
    1280                 1285                 1290

Leu Gln  Asn Asn Ile Glu Met  Thr Thr Gly Thr Phe  Val Glu Glu
    1295                 1300                 1305

Ile Thr  Glu Asn Tyr Lys Arg  Asn Thr Glu Asn Glu  Asp Asn Lys
    1310                 1315                 1320

Tyr Thr  Ala Ala Ser Arg Asn  Ser His Asn Leu Glu  Phe Asp Gly
    1325                 1330                 1335

Ser Asp  Ser Ser Lys Asn Asp  Thr Val Cys Ile His  Lys Asp Glu
    1340                 1345                 1350

Thr Asp  Leu Leu Phe Thr Asp  Gln His Asn Ile Cys  Leu Lys Leu
    1355                 1360                 1365

Ser Gly  Gln Phe Met Lys Glu  Gly Asn Thr Gln Ile  Lys Glu Asp
    1370                 1375                 1380

Leu Ser  Asp Leu Thr Phe Leu  Glu Val Ala Lys Ala  Gln Glu Ala
    1385                 1390                 1395
```

```
Cys His Gly Asn Thr Ser Asn Lys Glu Gln Leu Thr Ala Thr Lys
    1400                1405                1410

Thr Glu Gln Asn Ile Lys Asp Phe Glu Thr Ser Asp Thr Phe Phe
    1415                1420                1425

Gln Thr Ala Ser Gly Lys Asn Ile Ser Val Ala Lys Glu Ser Phe
    1430                1435                1440

Asn Lys Ile Val Asn Phe Phe Asp Gln Lys Pro Glu Glu Leu His
    1445                1450                1455

Asn Phe Ser Leu Asn Ser Glu Leu His Ser Asp Ile Arg Lys Asn
    1460                1465                1470

Lys Met Asp Ile Leu Ser Tyr Glu Glu Thr Asp Ile Val Lys His
    1475                1480                1485

Lys Ile Leu Lys Glu Ser Val Pro Val Gly Thr Gly Asn Gln Leu
    1490                1495                1500

Val Thr Phe Gln Gly Gln Pro Glu Arg Asp Glu Lys Ile Lys Glu
    1505                1510                1515

Pro Thr Leu Leu Gly Phe His Thr Ala Ser Gly Lys Lys Val Lys
    1520                1525                1530

Ile Ala Lys Glu Ser Leu Asp Lys Val Lys Asn Leu Phe Asp Glu
    1535                1540                1545

Lys Glu Gln Gly Thr Ser Glu Ile Thr Ser Phe Ser His Gln Trp
    1550                1555                1560

Ala Lys Thr Leu Lys Tyr Arg Glu Ala Cys Lys Asp Leu Glu Leu
    1565                1570                1575

Ala Cys Glu Thr Ile Glu Ile Thr Ala Ala Pro Lys Cys Lys Glu
    1580                1585                1590

Met Gln Asn Ser Leu Asn Asn Asp Lys Asn Leu Val Ser Ile Glu
    1595                1600                1605

Thr Val Val Pro Pro Lys Leu Leu Ser Asp Asn Leu Cys Arg Gln
    1610                1615                1620

Thr Glu Asn Leu Lys Thr Ser Lys Ser Ile Phe Leu Lys Val Lys
    1625                1630                1635

Val His Glu Asn Val Glu Lys Glu Thr Ala Lys Ser Pro Ala Thr
    1640                1645                1650

Cys Tyr Thr Asn Gln Ser Pro Tyr Ser Val Ile Glu Asn Ser Ala
    1655                1660                1665

Leu Ala Phe Tyr Thr Ser Cys Ser Arg Lys Thr Ser Val Ser Gln
    1670                1675                1680

Thr Ser Leu Leu Glu Ala Lys Lys Trp Leu Arg Glu Gly Ile Phe
    1685                1690                1695

Asp Gly Gln Pro Glu Arg Ile Asn Thr Ala Asp Tyr Val Gly Asn
    1700                1705                1710

Tyr Leu Tyr Glu Asn Asn Ser Asn Ser Thr Ile Ala Glu Asn Asp
    1715                1720                1725

Lys Asn His Leu Ser Glu Lys Gln Asp Thr Tyr Leu Ser Asn Ser
    1730                1735                1740

Ser Met Ser Asn Ser Tyr Ser Tyr His Ser Asp Glu Val Tyr Asn
    1745                1750                1755

Asp Ser Gly Tyr Leu Ser Lys Asn Lys Leu Asp Ser Gly Ile Glu
    1760                1765                1770

Pro Val Leu Lys Asn Val Glu Asp Gln Lys Asn Thr Ser Phe Ser
    1775                1780                1785
```

```
Lys Val  Ile Ser Asn Val Lys  Asp Ala Asn Ala Tyr  Pro Gln Thr
    1790                 1795                 1800

Val Asn  Glu Asp Ile Cys Val  Glu Glu Leu Val Thr  Ser Ser Ser
    1805                 1810                 1815

Pro Cys  Lys Asn Lys Asn Ala  Ala Ile Lys Leu Ser  Ile Ser Asn
    1820                 1825                 1830

Ser Asn  Asn Phe Glu Val Gly  Pro Pro Ala Phe Arg  Ile Ala Ser
    1835                 1840                 1845

Gly Lys  Ile Val Cys Val Ser  His Glu Thr Ile Lys  Lys Val Lys
    1850                 1855                 1860

Asp Ile  Phe Thr Asp Ser Phe  Ser Lys Val Ile Lys  Glu Asn Asn
    1865                 1870                 1875

Glu Asn  Lys Ser Lys Ile Cys  Gln Thr Lys Ile Met  Ala Gly Cys
    1880                 1885                 1890

Tyr Glu  Ala Leu Asp Asp Ser  Glu Asp Ile Leu His  Asn Ser Leu
    1895                 1900                 1905

Asp Asn  Asp Glu Cys Ser Thr  His Ser His Lys Val  Phe Ala Asp
    1910                 1915                 1920

Ile Gln  Ser Glu Glu Ile Leu  Gln His Asn Gln Asn  Met Ser Gly
    1925                 1930                 1935

Leu Glu  Lys Val Ser Lys Ile  Ser Pro Cys Asp Val  Ser Leu Glu
    1940                 1945                 1950

Thr Ser  Asp Ile Cys Lys Cys  Ser Ile Gly Lys Leu  His Lys Ser
    1955                 1960                 1965

Val Ser  Ser Ala Asn Thr Cys  Gly Ile Phe Ser Thr  Ala Ser Gly
    1970                 1975                 1980

Lys Ser  Val Gln Val Ser Asp  Ala Ser Leu Gln Asn  Ala Arg Gln
    1985                 1990                 1995

Val Phe  Ser Glu Ile Glu Asp  Ser Thr Lys Gln Val  Phe Ser Lys
    2000                 2005                 2010

Val Leu  Phe Lys Ser Asn Glu  His Ser Asp Gln Leu  Thr Arg Glu
    2015                 2020                 2025

Glu Asn  Thr Ala Ile Arg Thr  Pro Glu His Leu Ile  Ser Gln Lys
    2030                 2035                 2040

Gly Phe  Ser Tyr Asn Val Val  Asn Ser Ser Ala Phe  Ser Gly Phe
    2045                 2050                 2055

Ser Thr  Ala Ser Gly Lys Gln  Val Ser Ile Leu Glu  Ser Ser Leu
    2060                 2065                 2070

His Lys  Val Lys Gly Val Leu  Glu Glu Phe Asp Leu  Ile Arg Thr
    2075                 2080                 2085

Glu His  Ser Leu His Tyr Ser  Pro Thr Ser Arg Gln  Asn Val Ser
    2090                 2095                 2100

Lys Ile  Leu Pro Arg Val Asp  Lys Arg Asn Pro Glu  His Cys Val
    2105                 2110                 2115

Asn Ser  Glu Met Glu Lys Thr  Cys Ser Lys Glu Phe  Lys Leu Ser
    2120                 2125                 2130

Asn Asn  Leu Asn Val Glu Gly  Gly Ser Ser Glu Asn  Asn His Ser
    2135                 2140                 2145

Ile Lys  Val Ser Pro Tyr Leu  Ser Gln Phe Gln Gln  Asp Lys Gln
    2150                 2155                 2160

Gln Leu  Val Leu Gly Thr Lys  Val Ser Leu Val Glu  Asn Ile His
    2165                 2170                 2175

Val Leu  Gly Lys Glu Gln Ala  Ser Pro Lys Asn Val  Lys Met Glu
```

```
    2180                2185                2190

Ile Gly  Lys Thr Glu Thr Phe  Ser Asp Val Pro Val  Lys Thr Asn
    2195                2200                2205

Ile Glu  Val Cys Ser Thr Tyr  Ser Lys Asp Ser Glu  Asn Tyr Phe
    2210                2215                2220

Glu Thr  Glu Ala Val Glu Ile  Ala Lys Ala Phe Met  Glu Asp Asp
    2225                2230                2235

Glu Leu  Thr Asp Ser Lys Leu  Pro Ser His Ala Thr  His Ser Leu
    2240                2245                2250

Phe Thr  Cys Pro Glu Asn Glu  Glu Met Val Leu Ser  Asn Ser Arg
    2255                2260                2265

Ile Gly  Lys Arg Arg Gly Glu  Pro Leu Ile Leu Val  Gly Glu Pro
    2270                2275                2280

Ser Ile  Lys Arg Asn Leu Leu  Asn Glu Phe Asp Arg  Ile Ile Glu
    2285                2290                2295

Asn Gln  Glu Lys Ser Leu Lys  Ala Ser Lys Ser Thr  Pro Asp Gly
    2300                2305                2310

Thr Ile  Lys Asp Arg Arg Leu  Phe Met His His Val  Ser Leu Glu
    2315                2320                2325

Pro Ile  Thr Cys Val Pro Phe  Arg Thr Thr Lys Glu  Arg Gln Glu
    2330                2335                2340

Ile Gln  Asn Pro Asn Phe Thr  Ala Pro Gly Gln Glu  Phe Leu Ser
    2345                2350                2355

Lys Ser  His Leu Tyr Glu His  Leu Thr Leu Glu Lys  Ser Ser Ser
    2360                2365                2370

Asn Leu  Ala Val Ser Gly His  Pro Phe Tyr Gln Val  Ser Ala Thr
    2375                2380                2385

Arg Asn  Glu Lys Met Arg His  Leu Ile Thr Thr Gly  Arg Pro Thr
    2390                2395                2400

Lys Val  Phe Val Pro Pro Phe  Lys Thr Lys Ser His  Phe His Arg
    2405                2410                2415

Val Glu  Gln Cys Val Arg Asn  Ile Asn Leu Glu Glu  Asn Arg Gln
    2420                2425                2430

Lys Gln  Asn Ile Asp Gly His  Gly Ser Asp Asp Ser  Lys Asn Lys
    2435                2440                2445

Ile Asn  Asp Asn Glu Ile His  Gln Phe Asn Lys Asn  Asn Ser Asn
    2450                2455                2460

Gln Ala  Ala Ala Val Thr Phe  Thr Lys Cys Glu Glu  Glu Pro Leu
    2465                2470                2475

Asp Leu  Ile Thr Ser Leu Gln  Asn Ala Arg Asp Ile  Gln Asp Met
    2480                2485                2490

Arg Ile  Lys Lys Lys Gln Arg  Gln Arg Val Phe Pro  Gln Pro Gly
    2495                2500                2505

Ser Leu  Tyr Leu Ala Lys Thr  Ser Thr Leu Pro Arg  Ile Ser Leu
    2510                2515                2520

Lys Ala  Ala Val Gly Gly Gln  Val Pro Ser Ala Cys  Ser His Lys
    2525                2530                2535

Gln Leu  Tyr Thr Tyr Gly Val  Ser Lys His Cys Ile  Lys Ile Asn
    2540                2545                2550

Ser Lys  Asn Ala Glu Ser Phe  Gln Phe His Thr Glu  Asp Tyr Phe
    2555                2560                2565

Gly Lys  Glu Ser Leu Trp Thr  Gly Lys Gly Ile Gln  Leu Ala Asp
    2570                2575                2580
```

```
Gly Gly Trp Leu Ile Pro Ser Asn Asp Gly Lys Ala Gly Lys Glu
    2585                2590                2595

Glu Phe Tyr Arg Ala Leu Cys Asp Thr Pro Gly Val Asp Pro Lys
    2600                2605                2610

Leu Ile Ser Arg Ile Trp Val Tyr Asn His Tyr Arg Trp Ile Ile
    2615                2620                2625

Trp Lys Leu Ala Ala Met Glu Cys Ala Phe Pro Lys Glu Phe Ala
    2630                2635                2640

Asn Arg Cys Leu Ser Pro Glu Arg Val Leu Leu Gln Leu Lys Tyr
    2645                2650                2655

Arg Tyr Asp Thr Glu Ile Asp Arg Ser Arg Arg Ser Ala Ile Lys
    2660                2665                2670

Lys Ile Met Glu Arg Asp Asp Thr Ala Ala Lys Thr Leu Val Leu
    2675                2680                2685

Cys Val Ser Asp Ile Ile Ser Leu Ser Ala Asn Ile Ser Glu Thr
    2690                2695                2700

Ser Ser Asn Lys Thr Ser Ser Ala Asp Thr Gln Lys Val Ala Ile
    2705                2710                2715

Ile Glu Leu Thr Asp Gly Trp Tyr Ala Val Lys Ala Gln Leu Asp
    2720                2725                2730

Pro Pro Leu Leu Ala Val Leu Lys Asn Gly Arg Leu Thr Val Gly
    2735                2740                2745

Gln Lys Ile Ile Leu His Gly Ala Glu Leu Val Gly Ser Pro Asp
    2750                2755                2760

Ala Cys Thr Pro Leu Glu Ala Pro Glu Ser Leu Met Leu Lys Ile
    2765                2770                2775

Ser Ala Asn Ser Thr Arg Pro Ala Arg Trp Tyr Thr Lys Leu Gly
    2780                2785                2790

Phe Phe Pro Asp Pro Arg Pro Phe Pro Leu Pro Leu Ser Ser Leu
    2795                2800                2805

Phe Ser Asp Gly Gly Asn Val Gly Cys Val Asp Val Ile Ile Gln
    2810                2815                2820

Arg Ala Tyr Pro Ile Gln Trp Met Glu Lys Thr Ser Ser Gly Leu
    2825                2830                2835

Tyr Ile Phe Arg Asn Glu Arg Glu Glu Glu Lys Glu Ala Ala Lys
    2840                2845                2850

Tyr Val Glu Ala Gln Gln Lys Arg Leu Glu Ala Leu Phe Thr Lys
    2855                2860                2865

Ile Gln Glu Glu Phe Glu Glu His Glu Glu Asn Thr Thr Lys Pro
    2870                2875                2880

Tyr Leu Pro Ser Arg Ala Leu Thr Arg Gln Gln Val Arg Ala Leu
    2885                2890                2895

Gln Asp Gly Ala Glu Leu Tyr Glu Ala Val Lys Asn Ala Ala Asp
    2900                2905                2910

Pro Ala Tyr Leu Glu Gly Tyr Phe Ser Glu Glu Gln Leu Arg Ala
    2915                2920                2925

Leu Asn Asn His Arg Gln Met Leu Asn Asp Lys Lys Gln Ala Gln
    2930                2935                2940

Ile Gln Leu Glu Ile Arg Lys Ala Met Glu Ser Ala Glu Gln Lys
    2945                2950                2955

Glu Gln Gly Leu Ser Arg Asp Val Thr Thr Val Trp Lys Leu Arg
    2960                2965                2970
```

```
Ile Val  Ser Tyr Ser Lys Lys  Glu Lys Asp Ser Val  Ile Leu Ser
    2975                 2980                 2985

Ile Trp  Arg Pro Ser Ser Asp  Leu Tyr Ser Leu Leu  Thr Glu Gly
    2990                 2995                 3000

Lys Arg  Tyr Arg Ile Tyr His  Leu Ala Thr Ser Lys  Ser Lys Ser
    3005                 3010                 3015

Lys Ser  Glu Arg Ala Asn Ile  Gln Leu Ala Ala Thr  Lys Lys Thr
    3020                 3025                 3030

Gln Tyr  Gln Gln Leu Pro Val  Ser Asp Glu Ile Leu  Phe Gln Ile
    3035                 3040                 3045

Tyr Gln  Pro Arg Glu Pro Leu  His Phe Ser Lys Phe  Leu Asp Pro
    3050                 3055                 3060

Asp Phe  Gln Pro Ser Cys Ser  Glu Val Asp Leu Ile  Gly Phe Val
    3065                 3070                 3075

Val Ser  Val Val Lys Lys Thr  Gly Leu Ala Pro Phe  Val Tyr Leu
    3080                 3085                 3090

Ser Asp  Glu Cys Tyr Asn Leu  Leu Ala Ile Lys Phe  Trp Ile Asp
    3095                 3100                 3105

Leu Asn  Glu Asp Ile Ile Lys  Pro His Met Leu Ile  Ala Ala Ser
    3110                 3115                 3120

Asn Leu  Gln Trp Arg Pro Glu  Ser Lys Ser Gly Leu  Leu Thr Leu
    3125                 3130                 3135

Phe Ala  Gly Asp Phe Ser Val  Phe Ser Ala Ser Pro  Lys Glu Gly
    3140                 3145                 3150

His Phe  Gln Glu Thr Phe Asn  Lys Met Lys Asn Thr  Val Glu Asn
    3155                 3160                 3165

Ile Asp  Ile Leu Cys Asn Glu  Ala Glu Asn Lys Leu  Met His Ile
    3170                 3175                 3180

Leu His  Ala Asn Asp Pro Lys  Trp Ser Thr Pro Thr  Lys Asp Cys
    3185                 3190                 3195

Thr Ser  Gly Pro Tyr Thr Ala  Gln Ile Ile Pro Gly  Thr Gly Asn
    3200                 3205                 3210

Lys Leu  Leu Met Ser Ser Pro  Asn Cys Glu Ile Tyr  Tyr Gln Ser
    3215                 3220                 3225

Pro Leu  Ser Leu Cys Met Ala  Lys Arg Lys Ser Val  Ser Thr Pro
    3230                 3235                 3240

Val Ser  Ala Gln Met Thr Ser  Lys Ser Cys Lys Gly  Glu Lys Glu
    3245                 3250                 3255

Ile Asp  Asp Gln Lys Asn Cys  Lys Lys Arg Arg Ala  Leu Asp Phe
    3260                 3265                 3270

Leu Ser  Arg Leu Pro Leu Pro  Pro Pro Val Ser Pro  Ile Cys Thr
    3275                 3280                 3285

Phe Val  Ser Pro Ala Ala Gln  Lys Ala Phe Gln Pro  Pro Arg Ser
    3290                 3295                 3300

Cys Gly  Thr Lys Tyr Glu Thr  Pro Ile Lys Lys Lys  Glu Leu Asn
    3305                 3310                 3315

Ser Pro  Gln Met Thr Pro Phe  Lys Lys Phe Asn Glu  Ile Ser Leu
    3320                 3325                 3330

Leu Glu  Ser Asn Ser Ile Ala  Asp Glu Glu Leu Ala  Leu Ile Asn
    3335                 3340                 3345

Thr Gln  Ala Leu Leu Ser Gly  Ser Thr Gly Glu Lys  Gln Phe Ile
    3350                 3355                 3360

Ser Val  Ser Glu Ser Thr Arg  Thr Ala Pro Thr Ser  Ser Glu Asp
```

```
    3365                3370                3375

Tyr Leu  Arg Leu Lys Arg Arg  Cys Thr Thr Ser Leu  Ile Lys Glu
    3380                3385                3390

Gln Glu  Ser Ser Gln Ala Ser  Thr Glu Glu Cys Glu  Lys Asn Lys
    3395                3400                3405

Gln Asp  Thr Ile Thr Thr Lys  Lys Tyr Ile
    3410                3415


<210> SEQ ID NO 7
<211> LENGTH: 1721
<212> TYPE: DNA
<213> ORGANISM: Homo sapiens
<220> FEATURE:
<221> NAME/KEY: CDS
<222> LOCATION: (111)..(1676)
<223> OTHER INFORMATION: PNKP

<400> SEQUENCE: 7

ccgaggaacc gaccgccgcc ggccgggttg caggcggggc acctcgggca ggacctccct      60

ggtcggaagt ggccgtgagc ccaagccgcg gtcccgggcc ggcacccagg atg ggc       116
                                                       Met Gly
                                                       1

gag gtg gag gcc ccg ggc cgc ttg tgg ctc gag agc ccc cct ggg gga      164
Glu Val Glu Ala Pro Gly Arg Leu Trp Leu Glu Ser Pro Pro Gly Gly
        5                   10                  15

gcg ccc ccc atc ttc ctg ccc tcg gac ggg caa gcc ctg gtc ctg ggc      212
Ala Pro Pro Ile Phe Leu Pro Ser Asp Gly Gln Ala Leu Val Leu Gly
    20                  25                  30

agg gga ccc ctg acc cag gtt acg gac cgg aag tgc tcc aga act caa      260
Arg Gly Pro Leu Thr Gln Val Thr Asp Arg Lys Cys Ser Arg Thr Gln
35                  40                  45                  50

gtg gag ctg gtc gca gat cct gag acc cgg aca gtg gca gtg aaa cag      308
Val Glu Leu Val Ala Asp Pro Glu Thr Arg Thr Val Ala Val Lys Gln
                55                  60                  65

ctg gga gtt aac ccc tca act acc ggg acc cag gag ttg aag ccg ggg      356
Leu Gly Val Asn Pro Ser Thr Thr Gly Thr Gln Glu Leu Lys Pro Gly
            70                  75                  80

ttg gag ggc tct ctg ggg gtg ggg gac aca ctg tat ttg gtc aat ggc      404
Leu Glu Gly Ser Leu Gly Val Gly Asp Thr Leu Tyr Leu Val Asn Gly
        85                  90                  95

ctc cac cca ctg acc ctg cgc tgg gaa gag acc cgc aca cca gaa tcc      452
Leu His Pro Leu Thr Leu Arg Trp Glu Glu Thr Arg Thr Pro Glu Ser
    100                 105                 110

cag cca gat act ccg cct ggc acc cct ctg gtg tcc caa gat gag aag      500
Gln Pro Asp Thr Pro Pro Gly Thr Pro Leu Val Ser Gln Asp Glu Lys
115                 120                 125                 130

aga gat gct gag ctg ccg aag aag cgt atg cgg aag tca aac ccc ggc      548
Arg Asp Ala Glu Leu Pro Lys Lys Arg Met Arg Lys Ser Asn Pro Gly
                135                 140                 145

tgg gag aac ttg gag aag ttg cta gtg ttc acc gca gct ggg gtg aaa      596
Trp Glu Asn Leu Glu Lys Leu Leu Val Phe Thr Ala Ala Gly Val Lys
            150                 155                 160

ccc cag ggc aag gtg gct ggc ttt gat ctg gac ggg acg ctc atc acc      644
Pro Gln Gly Lys Val Ala Gly Phe Asp Leu Asp Gly Thr Leu Ile Thr
        165                 170                 175

aca cgc tct ggg aag gtc ttt ccc act ggc ccc agt gac tgg agg atc      692
Thr Arg Ser Gly Lys Val Phe Pro Thr Gly Pro Ser Asp Trp Arg Ile
    180                 185                 190

ttg tac cca gag att ccc cgt aag ctc cga gag ctg gaa gcc gag ggc      740
Leu Tyr Pro Glu Ile Pro Arg Lys Leu Arg Glu Leu Glu Ala Glu Gly
```

-continued

```
195                 200                 205                 210

tac aag ctg gtg atc ttc acc aac cag atg agc atc ggg cgc ggg aag      788
Tyr Lys Leu Val Ile Phe Thr Asn Gln Met Ser Ile Gly Arg Gly Lys
                215                 220                 225

ctg cca gcc gag gag ttc aag gcc aag gtg gag gct gtg gtg gag aag      836
Leu Pro Ala Glu Glu Phe Lys Ala Lys Val Glu Ala Val Val Glu Lys
            230                 235                 240

ctg ggg gtc ccc ttc cag gtg ctg gtg gcc acg cac gca ggc ttg tac      884
Leu Gly Val Pro Phe Gln Val Leu Val Ala Thr His Ala Gly Leu Tyr
        245                 250                 255

cgg aag ccg gtg acg ggc atg tgg gac cat ctg cag gag cag gcc aac      932
Arg Lys Pro Val Thr Gly Met Trp Asp His Leu Gln Glu Gln Ala Asn
    260                 265                 270

gac ggc acg ccc ata tcc atc ggg gac agc atc ttt gtg gga gac gca      980
Asp Gly Thr Pro Ile Ser Ile Gly Asp Ser Ile Phe Val Gly Asp Ala
275                 280                 285                 290

gcc gga cgc ccg gcc aac tgg gcc ccg ggg cgg aag aag aaa gac ttc     1028
Ala Gly Arg Pro Ala Asn Trp Ala Pro Gly Arg Lys Lys Lys Asp Phe
                295                 300                 305

tcc tgc gcc gat cgc ctg ttt gcc ctc aac ctt ggc ctg ccc ttc gcc     1076
Ser Cys Ala Asp Arg Leu Phe Ala Leu Asn Leu Gly Leu Pro Phe Ala
            310                 315                 320

acg cct gag gag ttc ttt ctc aag tgg cca gca gcc ggc ttc gag ctc     1124
Thr Pro Glu Glu Phe Phe Leu Lys Trp Pro Ala Ala Gly Phe Glu Leu
        325                 330                 335

cca gcc ttt gat ccg agg act gtc tcc cgc tca ggg cct ctc tgc ctc     1172
Pro Ala Phe Asp Pro Arg Thr Val Ser Arg Ser Gly Pro Leu Cys Leu
    340                 345                 350

ccc gag tcc agg gcc ctc ctg agc gcc agc ccg gag gtg gtt gtc gca     1220
Pro Glu Ser Arg Ala Leu Leu Ser Ala Ser Pro Glu Val Val Val Ala
355                 360                 365                 370

gtg gga ttc cct ggg gcc ggg aag tcc acc ttt ctc aag aag cac ctc     1268
Val Gly Phe Pro Gly Ala Gly Lys Ser Thr Phe Leu Lys Lys His Leu
                375                 380                 385

gtg tcg gcc gga tat gtc cac gtg aac agg gac acg cta ggc tcc tgg     1316
Val Ser Ala Gly Tyr Val His Val Asn Arg Asp Thr Leu Gly Ser Trp
            390                 395                 400

cag cgc tgt gtg acc acg tgt gag aca gcc ctg aag caa ggg aaa cgg     1364
Gln Arg Cys Val Thr Thr Cys Glu Thr Ala Leu Lys Gln Gly Lys Arg
        405                 410                 415

gtc gcc atc gac aac aca aac cca gac gcc gcg agc cgc gcc agg tac     1412
Val Ala Ile Asp Asn Thr Asn Pro Asp Ala Ala Ser Arg Ala Arg Tyr
    420                 425                 430

gtc cag tgt gcc cga gcc gcg ggc gtc ccc tgc cgc tgc ttc ctc ttc     1460
Val Gln Cys Ala Arg Ala Ala Gly Val Pro Cys Arg Cys Phe Leu Phe
435                 440                 445                 450

acc gcc act ctg gag cag gcg cgc cac aac aac cgg ttt cga gag atg     1508
Thr Ala Thr Leu Glu Gln Ala Arg His Asn Asn Arg Phe Arg Glu Met
                455                 460                 465

acg gac tcc tct cat atc ccc gtg tca gac atg gtc atg tat ggc tac     1556
Thr Asp Ser Ser His Ile Pro Val Ser Asp Met Val Met Tyr Gly Tyr
            470                 475                 480

agg aag cag ttc gag gcc cca acg ctg gct gaa ggc ttc tct gcc atc     1604
Arg Lys Gln Phe Glu Ala Pro Thr Leu Ala Glu Gly Phe Ser Ala Ile
        485                 490                 495

ctg gag atc ccg ttc cgg cta tgg gtg gag ccg agg ctg ggg cgg ctg     1652
Leu Glu Ile Pro Phe Arg Leu Trp Val Glu Pro Arg Leu Gly Arg Leu
    500                 505                 510

tac tgc cag ttc tcc gag ggc tga gccccgccca gctcccctcc acaataaacg    1706
```

```
Tyr Cys Gln Phe Ser Glu Gly
515                 520

ctgtttctcc ttgag                                                      1721


<210> SEQ ID NO 8
<211> LENGTH: 521
<212> TYPE: PRT
<213> ORGANISM: Homo sapiens

<400> SEQUENCE: 8

Met Gly Glu Val Glu Ala Pro Gly Arg Leu Trp Leu Glu Ser Pro Pro
1               5                   10                  15

Gly Gly Ala Pro Pro Ile Phe Leu Pro Ser Asp Gly Gln Ala Leu Val
            20                  25                  30

Leu Gly Arg Gly Pro Leu Thr Gln Val Thr Asp Arg Lys Cys Ser Arg
        35                  40                  45

Thr Gln Val Glu Leu Val Ala Asp Pro Glu Thr Arg Thr Val Ala Val
    50                  55                  60

Lys Gln Leu Gly Val Asn Pro Ser Thr Thr Gly Thr Gln Glu Leu Lys
65                  70                  75                  80

Pro Gly Leu Glu Gly Ser Leu Gly Val Gly Asp Thr Leu Tyr Leu Val
                85                  90                  95

Asn Gly Leu His Pro Leu Thr Leu Arg Trp Glu Glu Thr Arg Thr Pro
            100                 105                 110

Glu Ser Gln Pro Asp Thr Pro Pro Gly Thr Pro Leu Val Ser Gln Asp
        115                 120                 125

Glu Lys Arg Asp Ala Glu Leu Pro Lys Lys Arg Met Arg Lys Ser Asn
    130                 135                 140

Pro Gly Trp Glu Asn Leu Glu Lys Leu Leu Val Phe Thr Ala Ala Gly
145                 150                 155                 160

Val Lys Pro Gln Gly Lys Val Ala Gly Phe Asp Leu Asp Gly Thr Leu
                165                 170                 175

Ile Thr Thr Arg Ser Gly Lys Val Phe Pro Thr Gly Pro Ser Asp Trp
            180                 185                 190

Arg Ile Leu Tyr Pro Glu Ile Pro Arg Lys Leu Arg Glu Leu Glu Ala
        195                 200                 205

Glu Gly Tyr Lys Leu Val Ile Phe Thr Asn Gln Met Ser Ile Gly Arg
    210                 215                 220

Gly Lys Leu Pro Ala Glu Glu Phe Lys Ala Lys Val Glu Ala Val Val
225                 230                 235                 240

Glu Lys Leu Gly Val Pro Phe Gln Val Leu Val Ala Thr His Ala Gly
                245                 250                 255

Leu Tyr Arg Lys Pro Val Thr Gly Met Trp Asp His Leu Gln Glu Gln
            260                 265                 270

Ala Asn Asp Gly Thr Pro Ile Ser Ile Gly Asp Ser Ile Phe Val Gly
        275                 280                 285

Asp Ala Ala Gly Arg Pro Ala Asn Trp Ala Pro Gly Arg Lys Lys Lys
    290                 295                 300

Asp Phe Ser Cys Ala Asp Arg Leu Phe Ala Leu Asn Leu Gly Leu Pro
305                 310                 315                 320

Phe Ala Thr Pro Glu Glu Phe Phe Leu Lys Trp Pro Ala Ala Gly Phe
                325                 330                 335

Glu Leu Pro Ala Phe Asp Pro Arg Thr Val Ser Arg Ser Gly Pro Leu
            340                 345                 350
```

```
Cys Leu Pro Glu Ser Arg Ala Leu Leu Ser Ala Ser Pro Glu Val Val
        355                 360                 365

Val Ala Val Gly Phe Pro Gly Ala Gly Lys Ser Thr Phe Leu Lys Lys
    370                 375                 380

His Leu Val Ser Ala Gly Tyr Val His Val Asn Arg Asp Thr Leu Gly
385                 390                 395                 400

Ser Trp Gln Arg Cys Val Thr Thr Cys Glu Thr Ala Leu Lys Gln Gly
                405                 410                 415

Lys Arg Val Ala Ile Asp Asn Thr Asn Pro Asp Ala Ala Ser Arg Ala
            420                 425                 430

Arg Tyr Val Gln Cys Ala Arg Ala Ala Gly Val Pro Cys Arg Cys Phe
        435                 440                 445

Leu Phe Thr Ala Thr Leu Glu Gln Ala Arg His Asn Asn Arg Phe Arg
    450                 455                 460

Glu Met Thr Asp Ser Ser His Ile Pro Val Ser Asp Met Val Met Tyr
465                 470                 475                 480

Gly Tyr Arg Lys Gln Phe Glu Ala Pro Thr Leu Ala Glu Gly Phe Ser
                485                 490                 495

Ala Ile Leu Glu Ile Pro Phe Arg Leu Trp Val Glu Pro Arg Leu Gly
            500                 505                 510

Arg Leu Tyr Cys Gln Phe Ser Glu Gly
        515                 520


<210> SEQ ID NO 9
<211> LENGTH: 2563
<212> TYPE: DNA
<213> ORGANISM: Homo sapiens
<220> FEATURE:
<221> NAME/KEY: CDS
<222> LOCATION: (324)..(1364)
<223> OTHER INFORMATION: XRCC3

<400> SEQUENCE: 9

ctattggagg agaaggccga gaggagcagg acggcgggaa gaggagtgcg gaacccgcgg      60

gagagtcccc agggagacac ttaagggaaa ttaaactgca gagtgcaaga gatgcctcag     120

tcaagtcagc caaaaacacg cgggtcatcc ccaagcccca gagagtgaca gagccccgat     180

gacacggaca cctcggctgc tgtcacttcc ctggttcggg cctcccacag gctttgaatt     240

gaaggcgagt gcctcagaat ttgcatccat tgttctgtct ttcctgggaa gttattcatc     300

ctggtggcca gcccaccgac aaa atg gat ttg gat cta ctg gac ctg aat ccc     353
                          Met Asp Leu Asp Leu Leu Asp Leu Asn Pro
                          1               5                   10

aga att att gct gca att aag aaa gcc aaa ctg aaa tcg gta aag gag       401
Arg Ile Ile Ala Ala Ile Lys Lys Ala Lys Leu Lys Ser Val Lys Glu
                15                  20                  25

gtt tta cac ttt tct gga cca gac ttg aag aga ctg acc aac ctc tcc       449
Val Leu His Phe Ser Gly Pro Asp Leu Lys Arg Leu Thr Asn Leu Ser
            30                  35                  40

agc ccc gag gtc tgg cac ttg ctg aga acg gcc tcc tta cac ttg cgg       497
Ser Pro Glu Val Trp His Leu Leu Arg Thr Ala Ser Leu His Leu Arg
        45                  50                  55

gga agc agc atc ctt aca gca ctg cag ctg cac cag cag aag gag cgg       545
Gly Ser Ser Ile Leu Thr Ala Leu Gln Leu His Gln Gln Lys Glu Arg
    60                  65                  70

ttc ccc acg cag cac cag cgc ctg agc ctg ggc tgc ccg gtg ctg gac       593
Phe Pro Thr Gln His Gln Arg Leu Ser Leu Gly Cys Pro Val Leu Asp
75                  80                  85                  90
```

```
gcg ctg ctc cgc ggt ggc ctg ccc ctg gac ggc atc act gag ctg gcc      641
Ala Leu Leu Arg Gly Gly Leu Pro Leu Asp Gly Ile Thr Glu Leu Ala
                95                  100                 105

gga cgc agc tcg gca ggg aag acc cag ctg gcg ctg cag ctc tgc ctg      689
Gly Arg Ser Ser Ala Gly Lys Thr Gln Leu Ala Leu Gln Leu Cys Leu
            110                 115                 120

gct gtg cag ttc ccg cgg cag cac gga ggc ctg gag gct gga gcc gtc      737
Ala Val Gln Phe Pro Arg Gln His Gly Gly Leu Glu Ala Gly Ala Val
        125                 130                 135

tac atc tgc acg gaa gac gcc ttc ccg cac aag cgc ctg cag cag ctc      785
Tyr Ile Cys Thr Glu Asp Ala Phe Pro His Lys Arg Leu Gln Gln Leu
    140                 145                 150

atg gcc cag cag ccg cgg ctg cgc act gac gtt cca gga gag ctg ctt      833
Met Ala Gln Gln Pro Arg Leu Arg Thr Asp Val Pro Gly Glu Leu Leu
155                 160                 165                 170

cag aag ctc cga ttt ggc agc cag atc ttc atc gag cac gtg gcc gat      881
Gln Lys Leu Arg Phe Gly Ser Gln Ile Phe Ile Glu His Val Ala Asp
                175                 180                 185

gtg gac acc ttg ttg gag tgt gtg aat aag aag gtc ccc gta ctg ctg      929
Val Asp Thr Leu Leu Glu Cys Val Asn Lys Lys Val Pro Val Leu Leu
            190                 195                 200

tct cgg ggc atg gct cgc ctg gtg gtc atc gac tcg gtg gca gcc cca      977
Ser Arg Gly Met Ala Arg Leu Val Val Ile Asp Ser Val Ala Ala Pro
        205                 210                 215

ttc cgc tgt gaa ttt gac agc cag gcc tcc gcc ccc agg gcc agg cat     1025
Phe Arg Cys Glu Phe Asp Ser Gln Ala Ser Ala Pro Arg Ala Arg His
    220                 225                 230

ctg cag tcc ctg ggg gcc acg ctg cgt gag ctg agc agt gcc ttc cag     1073
Leu Gln Ser Leu Gly Ala Thr Leu Arg Glu Leu Ser Ser Ala Phe Gln
235                 240                 245                 250

agc cct gtg ctg tgc atc aac cag gtg aca gag gcc atg gag gag cag     1121
Ser Pro Val Leu Cys Ile Asn Gln Val Thr Glu Ala Met Glu Glu Gln
                255                 260                 265

ggc gca gca cac ggg ccg ctg ggg ttc tgg gac gaa cgt gtt tcc cca     1169
Gly Ala Ala His Gly Pro Leu Gly Phe Trp Asp Glu Arg Val Ser Pro
            270                 275                 280

gcc ctt ggc ata acc tgg gct aac cag ctc ctg gtg aga ctg ctg gct     1217
Ala Leu Gly Ile Thr Trp Ala Asn Gln Leu Leu Val Arg Leu Leu Ala
        285                 290                 295

gac cgg ctc cgc gag gaa gag gct gcc ctc ggc tgc cca gcc cgg acc     1265
Asp Arg Leu Arg Glu Glu Glu Ala Ala Leu Gly Cys Pro Ala Arg Thr
    300                 305                 310

ctg cgg gtg ctc tct gcc ccc cac ctg ccc ccc tcc tcc tgt tcc tac     1313
Leu Arg Val Leu Ser Ala Pro His Leu Pro Pro Ser Ser Cys Ser Tyr
315                 320                 325                 330

acg atc agt gcc gaa ggg gtg cga ggg aca cct ggg acc cag tcc cac     1361
Thr Ile Ser Ala Glu Gly Val Arg Gly Thr Pro Gly Thr Gln Ser His
                335                 340                 345

tga cacggtggcg gctgcacaac agccctgcct gagaagcccc gacacacggg          1414

gctcgggcct ttaaaacgcg tctgcctggg ccgtggcaca gctgggagcc tggttcagac   1474

acagctcttc cagggcagcg gctccacttt ctcatccgaa gatggtggcc acagactgac   1534

ccccatctga gctgggggga tgttctgcct ctccctgggt ctggggacag gcccgcttgc   1594

tgggtacctg gtccccactg ctgagctggc ccttggggag aggtgattct cagggctgga   1654

gcctggggtg tcctacagtg actccctggg agccgcctgc ttcttctctc cacatggaag   1714

cccaactggg gttgcgtctg aggcctgccc cctgggctgg ggcctcagac cccctcagcc   1774

ttgggaccgt gcccacgagg gtctcccctc ctgcacacag ggcagtcctt actcccccac   1834
```

```
cactcaggcc acagtggggc tgcaggcagg cggctcctcc tcacccacct ctgggtcctt   1894

ggctcccggg ggccccacct cggcacacac tgtgccccac aaaacttcag tgtggtacaa   1954

ggtggagaaa gcatatccca ccaacctcca gtgtcagggt ccaggagagc ctgggggtgg   2014

ggggactgcc ttgtctctag tagtgtggcc tgtgccagca ccacagccgg tcagaggagc   2074

gcaggcagcg cagggctggc acgtgacagg ctcgtcagcc acctgggaac acagttctgg   2134

gcaaagagga tccgaggttg agaggaagga gggtcccggt gtatcctggc cctgggggtc   2194

tgggcgtcca gctcagccct ggcctggctg ggtggtattc tggtagggat atggcaggac   2254

tcctggcagg gccacctgca ggaccctgtc ctgcagtccc acactgtgca gacccagtcc   2314

cacactgtgg ccaggcctta catctggctg gaaagcagag cctcctggga acacatctgg   2374

ctgcacaggc tgaaatatcc acccagcagg cagagtggcg tggcctcccc atgggcacag   2434

tggtgacccc cttgattccc accgtacaac cccctccacc ccccactcag tgcctccaca   2494

tgctgcctgg cacagaccag gcctttgaca aataaatgtt caatggatgc aaaaaaaaaa   2554

aaaaaaaaa                                                           2563
```

<210> SEQ ID NO 10
<211> LENGTH: 346
<212> TYPE: PRT
<213> ORGANISM: Homo sapiens

<400> SEQUENCE: 10

```
Met Asp Leu Asp Leu Leu Asp Leu Asn Pro Arg Ile Ile Ala Ala Ile
1               5                   10                  15

Lys Lys Ala Lys Leu Lys Ser Val Lys Glu Val Leu His Phe Ser Gly
            20                  25                  30

Pro Asp Leu Lys Arg Leu Thr Asn Leu Ser Ser Pro Glu Val Trp His
        35                  40                  45

Leu Leu Arg Thr Ala Ser Leu His Leu Arg Gly Ser Ser Ile Leu Thr
    50                  55                  60

Ala Leu Gln Leu His Gln Gln Lys Glu Arg Phe Pro Thr Gln His Gln
65                  70                  75                  80

Arg Leu Ser Leu Gly Cys Pro Val Leu Asp Ala Leu Leu Arg Gly Gly
                85                  90                  95

Leu Pro Leu Asp Gly Ile Thr Glu Leu Ala Gly Arg Ser Ser Ala Gly
            100                 105                 110

Lys Thr Gln Leu Ala Leu Gln Leu Cys Leu Ala Val Gln Phe Pro Arg
        115                 120                 125

Gln His Gly Gly Leu Glu Ala Gly Ala Val Tyr Ile Cys Thr Glu Asp
    130                 135                 140

Ala Phe Pro His Lys Arg Leu Gln Gln Leu Met Ala Gln Gln Pro Arg
145                 150                 155                 160

Leu Arg Thr Asp Val Pro Gly Glu Leu Leu Gln Lys Leu Arg Phe Gly
                165                 170                 175

Ser Gln Ile Phe Ile Glu His Val Ala Asp Val Asp Thr Leu Leu Glu
            180                 185                 190

Cys Val Asn Lys Lys Val Pro Val Leu Leu Ser Arg Gly Met Ala Arg
        195                 200                 205

Leu Val Val Ile Asp Ser Val Ala Ala Pro Phe Arg Cys Glu Phe Asp
    210                 215                 220

Ser Gln Ala Ser Ala Pro Arg Ala Arg His Leu Gln Ser Leu Gly Ala
225                 230                 235                 240
```

Thr Leu Arg Glu Leu Ser Ser Ala Phe Gln Ser Pro Val Leu Cys Ile
245 250 255

Asn Gln Val Thr Glu Ala Met Glu Glu Gln Gly Ala Ala His Gly Pro
260 265 270

Leu Gly Phe Trp Asp Glu Arg Val Ser Pro Ala Leu Gly Ile Thr Trp
275 280 285

Ala Asn Gln Leu Leu Val Arg Leu Leu Ala Asp Arg Leu Arg Glu Glu
290 295 300

Glu Ala Ala Leu Gly Cys Pro Ala Arg Thr Leu Arg Val Leu Ser Ala
305 310 315 320

Pro His Leu Pro Pro Ser Ser Cys Ser Tyr Thr Ile Ser Ala Glu Gly
325 330 335

Val Arg Gly Thr Pro Gly Thr Gln Ser His
340 345

<210> SEQ ID NO 11
<211> LENGTH: 1777
<212> TYPE: DNA
<213> ORGANISM: Homo sapiens
<220> FEATURE:
<221> NAME/KEY: CDS
<222> LOCATION: (218)..(1222)
<223> OTHER INFORMATION: XRCC4

<400> SEQUENCE: 11
ctccagccgt ccggttgggc ttgtcacggc accgcctacc aagacgggcg gttaagacac 60
taggataggc tcctctccac cggaaaaggc gggatttaga tcacgtcccg caggccggcg 120
gaagtagctg atactctcat tggttgcaaa accttgatct gtgaaagcgg gcgttttgga 180
agataccgga agtagagtca cggagaggta ttaagaa atg gag aga aaa ata agc 235
Met Glu Arg Lys Ile Ser
1 5 aga atc cac ctt gtt tct gaa ccc agt ata act cat ttt cta caa gta 283
Arg Ile His Leu Val Ser Glu Pro Ser Ile Thr His Phe Leu Gln Val
10 15 20 tct tgg gag aaa aca ctg gaa tct ggt ttt gtt att aca ctt act gat 331
Ser Trp Glu Lys Thr Leu Glu Ser Gly Phe Val Ile Thr Leu Thr Asp
25 30 35 ggt cat tca gca tgg act ggg aca gtt tct gaa tca gag att tcc caa 379
Gly His Ser Ala Trp Thr Gly Thr Val Ser Glu Ser Glu Ile Ser Gln
40 45 50 gaa gct gat gac atg gca atg gaa aaa ggg aaa tat gtt ggt gaa ctg 427
Glu Ala Asp Asp Met Ala Met Glu Lys Gly Lys Tyr Val Gly Glu Leu
55 60 65 70 aga aaa gca ttg ttg tca gga gca gga cca gct gat gta tac acg ttt 475
Arg Lys Ala Leu Leu Ser Gly Ala Gly Pro Ala Asp Val Tyr Thr Phe
75 80 85 aat ttt tct aaa gag tct tgt tat ttc ttc ttt gag aaa aac ctg aaa 523
Asn Phe Ser Lys Glu Ser Cys Tyr Phe Phe Phe Glu Lys Asn Leu Lys
90 95 100 gat gtc tca ttc aga ctt ggt tcc ttc aac cta gag aaa gtt gaa aac 571
Asp Val Ser Phe Arg Leu Gly Ser Phe Asn Leu Glu Lys Val Glu Asn
105 110 115 cca gct gaa gtc att aga gaa ctt att tgt tat tgc ttg gac acc att 619
Pro Ala Glu Val Ile Arg Glu Leu Ile Cys Tyr Cys Leu Asp Thr Ile
120 125 130 gca gaa aat caa gcc aaa aat gag cac ctg cag aaa gaa aat gaa agg 667
Ala Glu Asn Gln Ala Lys Asn Glu His Leu Gln Lys Glu Asn Glu Arg
135 140 145 150

```
ctt ctg aga gat tgg aat gat gtt caa gga cga ttt gaa aaa tgt gtg      715
Leu Leu Arg Asp Trp Asn Asp Val Gln Gly Arg Phe Glu Lys Cys Val
                155                 160                 165

agt gct aag gaa gct ttg gag act gat ctt tat aag cgg ttt att ctg      763
Ser Ala Lys Glu Ala Leu Glu Thr Asp Leu Tyr Lys Arg Phe Ile Leu
            170                 175                 180

gtg ttg aat gag aag aaa aca aaa atc aga agt ttg cat aat aaa tta      811
Val Leu Asn Glu Lys Lys Thr Lys Ile Arg Ser Leu His Asn Lys Leu
        185                 190                 195

tta aat gca gct caa gaa cga gaa aag gac atc aaa caa gaa ggg gaa      859
Leu Asn Ala Ala Gln Glu Arg Glu Lys Asp Ile Lys Gln Glu Gly Glu
    200                 205                 210

act gca atc tgt tct gaa atg act gct gac cga gat cca gtc tat gat      907
Thr Ala Ile Cys Ser Glu Met Thr Ala Asp Arg Asp Pro Val Tyr Asp
215                 220                 225                 230

gag agt act gat gag gaa agt gaa aac caa act gat ctc tct ggg ttg      955
Glu Ser Thr Asp Glu Glu Ser Glu Asn Gln Thr Asp Leu Ser Gly Leu
                235                 240                 245

gct tca gct gct gta agt aaa gat gat tcc att att tca agt ctt gat     1003
Ala Ser Ala Ala Val Ser Lys Asp Asp Ser Ile Ile Ser Ser Leu Asp
            250                 255                 260

gtc act gat att gca cca agt aga aaa agg aga cag cga atg caa aga     1051
Val Thr Asp Ile Ala Pro Ser Arg Lys Arg Arg Gln Arg Met Gln Arg
        265                 270                 275

aat ctt ggg aca gaa cct aaa atg gct cct cag gag aat cag ctt caa     1099
Asn Leu Gly Thr Glu Pro Lys Met Ala Pro Gln Glu Asn Gln Leu Gln
    280                 285                 290

gaa aag gaa aag cct gat tct tca cta cct gag acg tct aaa aag gag     1147
Glu Lys Glu Lys Pro Asp Ser Ser Leu Pro Glu Thr Ser Lys Lys Glu
295                 300                 305                 310

cac atc tca gct gaa aac atg tct tta gaa act ctg aga aac agc agc     1195
His Ile Ser Ala Glu Asn Met Ser Leu Glu Thr Leu Arg Asn Ser Ser
                315                 320                 325

cca gaa gac ctc ttt gat gag att taa cagtctcaaa aaatactttg           1242
Pro Glu Asp Leu Phe Asp Glu Ile
            330

atgttcacta gactatgttt tctattcatt tctttaaaat gaaaaaggag aatttcaagt   1302

cagcagccgc tattaccgta tcttacaatt taattacata cacagtgaat tgaaaccatt   1362

gtgcaaaatg gattacacat gtatacaaag atacgatttg atgatgacac tggcacatta   1422

ttctaaacta ttcattcagc atgcctataa ttacataaat tgtatgagac tttttgttgc   1482

aaaggacaca tttatcatat tcattcacac atattatatg tgatagctgt ccaacatcct   1542

gtctgggaag attttgaaaa caggacaaag aaaacatcat tttaaaatgt cttcagcttt   1602

ttttgaatag acgtattcaa acatattctg aacattgatg tttgaacatt ttaatttgtg   1662

tgatgatgta gaaaatataa ttttagtttg tacataaaca ttgtgaaaat ctgataataa   1722

aatttttgat acattgaaaa aaaaaaaaaa aaaaaaaaaa aaaaaaaaaa aaaaa        1777
```

<210> SEQ ID NO 12
<211> LENGTH: 334
<212> TYPE: PRT
<213> ORGANISM: Homo sapiens

<400> SEQUENCE: 12

```
Met Glu Arg Lys Ile Ser Arg Ile His Leu Val Ser Glu Pro Ser Ile
1               5                   10                  15

Thr His Phe Leu Gln Val Ser Trp Glu Lys Thr Leu Glu Ser Gly Phe
```

```
            20                  25                  30

Val Ile Thr Leu Thr Asp Gly His Ser Ala Trp Thr Gly Thr Val Ser
        35                  40                  45

Glu Ser Glu Ile Ser Gln Glu Ala Asp Asp Met Ala Met Glu Lys Gly
    50                  55                  60

Lys Tyr Val Gly Glu Leu Arg Lys Ala Leu Leu Ser Gly Ala Gly Pro
65                  70                  75                  80

Ala Asp Val Tyr Thr Phe Asn Phe Ser Lys Glu Ser Cys Tyr Phe Phe
                85                  90                  95

Phe Glu Lys Asn Leu Lys Asp Val Ser Phe Arg Leu Gly Ser Phe Asn
            100                 105                 110

Leu Glu Lys Val Glu Asn Pro Ala Glu Val Ile Arg Glu Leu Ile Cys
        115                 120                 125

Tyr Cys Leu Asp Thr Ile Ala Glu Asn Gln Ala Lys Asn Glu His Leu
    130                 135                 140

Gln Lys Glu Asn Glu Arg Leu Leu Arg Asp Trp Asn Asp Val Gln Gly
145                 150                 155                 160

Arg Phe Glu Lys Cys Val Ser Ala Lys Glu Ala Leu Glu Thr Asp Leu
                165                 170                 175

Tyr Lys Arg Phe Ile Leu Val Leu Asn Glu Lys Lys Thr Lys Ile Arg
            180                 185                 190

Ser Leu His Asn Lys Leu Leu Asn Ala Ala Gln Glu Arg Glu Lys Asp
        195                 200                 205

Ile Lys Gln Glu Gly Glu Thr Ala Ile Cys Ser Glu Met Thr Ala Asp
    210                 215                 220

Arg Asp Pro Val Tyr Asp Glu Ser Thr Asp Glu Glu Ser Glu Asn Gln
225                 230                 235                 240

Thr Asp Leu Ser Gly Leu Ala Ser Ala Ala Val Ser Lys Asp Asp Ser
                245                 250                 255

Ile Ile Ser Ser Leu Asp Val Thr Asp Ile Ala Pro Ser Arg Lys Arg
            260                 265                 270

Arg Gln Arg Met Gln Arg Asn Leu Gly Thr Glu Pro Lys Met Ala Pro
        275                 280                 285

Gln Glu Asn Gln Leu Gln Glu Lys Glu Lys Pro Asp Ser Ser Leu Pro
    290                 295                 300

Glu Thr Ser Lys Lys Glu His Ile Ser Ala Glu Asn Met Ser Leu Glu
305                 310                 315                 320

Thr Leu Arg Asn Ser Ser Pro Glu Asp Leu Phe Asp Glu Ile
                325                 330


<210> SEQ ID NO 13
<211> LENGTH: 1403
<212> TYPE: DNA
<213> ORGANISM: Homo sapiens
<220> FEATURE:
<221> NAME/KEY: CDS
<222> LOCATION: (240)..(1211)
<223> OTHER INFORMATION: CCNH

<400> SEQUENCE: 13

acttacgtct cagtgggcgc cctaacgaac ccgggatacg gtctgttcct agtccgctcc      60

ggaaatgcaa ctgcgtacgg gctggccgcg taatcgtgac gacagcgcgc cagcgccggc     120

tagccggacg ccctaggctt ccgcgagatc ttcggtgggg gtacgggtgt tttacgccag     180

gacgctgatg cgtttgggtt ctcgtctgca gaccctctgg acctggtcac gattccata      239
```

-continued

```
atg tac cac aac agt agt cag aag cgg cac tgg acc ttc tcc agc gag      287
Met Tyr His Asn Ser Ser Gln Lys Arg His Trp Thr Phe Ser Ser Glu
1               5                   10                  15

gag cag ctg gca aga ctg cgg gct gac gcc aac cgc aaa ttc aga tgc      335
Glu Gln Leu Ala Arg Leu Arg Ala Asp Ala Asn Arg Lys Phe Arg Cys
            20                  25                  30

aaa gcc gtg gcc aac ggg aag gtt ctt ccg aat gat cca gtc ttt ctt      383
Lys Ala Val Ala Asn Gly Lys Val Leu Pro Asn Asp Pro Val Phe Leu
        35                  40                  45

gag cct cat gaa gaa atg aca ctc tgc aaa tac tat gag aaa agg tta      431
Glu Pro His Glu Glu Met Thr Leu Cys Lys Tyr Tyr Glu Lys Arg Leu
    50                  55                  60

ttg gaa ttc tgt tcg gtg ttt aag cca gca atg cca aga tct gtt gtg      479
Leu Glu Phe Cys Ser Val Phe Lys Pro Ala Met Pro Arg Ser Val Val
65                  70                  75                  80

ggt acg gct tgt atg tat ttc aaa cgt ttt tat ctt aat aac tca gta      527
Gly Thr Ala Cys Met Tyr Phe Lys Arg Phe Tyr Leu Asn Asn Ser Val
                85                  90                  95

atg gaa tat cac ccc agg ata ata atg ctc act tgt gca ttt ttg gcc      575
Met Glu Tyr His Pro Arg Ile Ile Met Leu Thr Cys Ala Phe Leu Ala
            100                 105                 110

tgc aaa gta gat gaa ttc aat gta tct agt cct cag ttt gtt gga aac      623
Cys Lys Val Asp Glu Phe Asn Val Ser Ser Pro Gln Phe Val Gly Asn
        115                 120                 125

ctc cgg gag agt cct ctt gga cag gag aag gca ctt gaa cag ata ctg      671
Leu Arg Glu Ser Pro Leu Gly Gln Glu Lys Ala Leu Glu Gln Ile Leu
    130                 135                 140

gaa tat gaa cta ctt ctt ata cag caa ctt aat ttc cac ctt att gtc      719
Glu Tyr Glu Leu Leu Leu Ile Gln Gln Leu Asn Phe His Leu Ile Val
145                 150                 155                 160

cac aat cct tac aga cca ttt gag ggc ttc ctc atc gac tta aag acc      767
His Asn Pro Tyr Arg Pro Phe Glu Gly Phe Leu Ile Asp Leu Lys Thr
                165                 170                 175

cgc tat ccc ata ttg gag aat cca gag att ttg agg aaa aca gct gat      815
Arg Tyr Pro Ile Leu Glu Asn Pro Glu Ile Leu Arg Lys Thr Ala Asp
            180                 185                 190

gac ttt ctt aat aga att gca ttg acg gat gct tac ctt tta tac aca      863
Asp Phe Leu Asn Arg Ile Ala Leu Thr Asp Ala Tyr Leu Leu Tyr Thr
        195                 200                 205

cct tcc caa att gcc ctg act gcc att tta tct agt gcc tcc agg gct      911
Pro Ser Gln Ile Ala Leu Thr Ala Ile Leu Ser Ser Ala Ser Arg Ala
    210                 215                 220

gga att act atg gaa agt tat tta tca gag agt ctg atg ctg aaa gag      959
Gly Ile Thr Met Glu Ser Tyr Leu Ser Glu Ser Leu Met Leu Lys Glu
225                 230                 235                 240

aac aga act tgc ctg tca cag tta cta gat ata atg aaa agc atg aga     1007
Asn Arg Thr Cys Leu Ser Gln Leu Leu Asp Ile Met Lys Ser Met Arg
                245                 250                 255

aac tta gta aag aag tat gaa cca ccc aga tct gaa gaa gtt gct gtt     1055
Asn Leu Val Lys Lys Tyr Glu Pro Pro Arg Ser Glu Glu Val Ala Val
            260                 265                 270

ctg aaa cag aag ttg gag cga tgt cat tct gct gag ctt gca ctt aac     1103
Leu Lys Gln Lys Leu Glu Arg Cys His Ser Ala Glu Leu Ala Leu Asn
        275                 280                 285

gta atc acg aag aag agg aaa ggc tat gaa gat gat gat tac gtc tca     1151
Val Ile Thr Lys Lys Arg Lys Gly Tyr Glu Asp Asp Asp Tyr Val Ser
    290                 295                 300

aag aaa tcc aaa cat gag gag gaa gaa tgg act gat gac gac ctg gta     1199
Lys Lys Ser Lys His Glu Glu Glu Glu Trp Thr Asp Asp Asp Leu Val
305                 310                 315                 320
```

```
gaa tct ctc taa ccatttgaag ttgatttctc aatgctaact aatcaagaga        1251
Glu Ser Leu

agtaggaagc atatcaaacg tttaacttta tttaaaaagt ataatgtgaa aacataaaat   1311

atattaaaac ttttctattg ttttctttcc ctttcacagt aactttatgt aaaataaacc   1371

atcttcaaaa gagctagaat agcaaaaaaa aa                                 1403


<210> SEQ ID NO 14
<211> LENGTH: 323
<212> TYPE: PRT
<213> ORGANISM: Homo sapiens

<400> SEQUENCE: 14

Met Tyr His Asn Ser Ser Gln Lys Arg His Trp Thr Phe Ser Ser Glu
1               5                   10                  15

Glu Gln Leu Ala Arg Leu Arg Ala Asp Ala Asn Arg Lys Phe Arg Cys
            20                  25                  30

Lys Ala Val Ala Asn Gly Lys Val Leu Pro Asn Asp Pro Val Phe Leu
        35                  40                  45

Glu Pro His Glu Glu Met Thr Leu Cys Lys Tyr Tyr Glu Lys Arg Leu
    50                  55                  60

Leu Glu Phe Cys Ser Val Phe Lys Pro Ala Met Pro Arg Ser Val Val
65                  70                  75                  80

Gly Thr Ala Cys Met Tyr Phe Lys Arg Phe Tyr Leu Asn Asn Ser Val
                85                  90                  95

Met Glu Tyr His Pro Arg Ile Ile Met Leu Thr Cys Ala Phe Leu Ala
            100                 105                 110

Cys Lys Val Asp Glu Phe Asn Val Ser Ser Pro Gln Phe Val Gly Asn
        115                 120                 125

Leu Arg Glu Ser Pro Leu Gly Gln Glu Lys Ala Leu Glu Gln Ile Leu
    130                 135                 140

Glu Tyr Glu Leu Leu Leu Ile Gln Gln Leu Asn Phe His Leu Ile Val
145                 150                 155                 160

His Asn Pro Tyr Arg Pro Phe Glu Gly Phe Leu Ile Asp Leu Lys Thr
                165                 170                 175

Arg Tyr Pro Ile Leu Glu Asn Pro Glu Ile Leu Arg Lys Thr Ala Asp
            180                 185                 190

Asp Phe Leu Asn Arg Ile Ala Leu Thr Asp Ala Tyr Leu Leu Tyr Thr
        195                 200                 205

Pro Ser Gln Ile Ala Leu Thr Ala Ile Leu Ser Ser Ala Ser Arg Ala
    210                 215                 220

Gly Ile Thr Met Glu Ser Tyr Leu Ser Glu Ser Leu Met Leu Lys Glu
225                 230                 235                 240

Asn Arg Thr Cys Leu Ser Gln Leu Leu Asp Ile Met Lys Ser Met Arg
                245                 250                 255

Asn Leu Val Lys Lys Tyr Glu Pro Pro Arg Ser Glu Glu Val Ala Val
            260                 265                 270

Leu Lys Gln Lys Leu Glu Arg Cys His Ser Ala Glu Leu Ala Leu Asn
        275                 280                 285

Val Ile Thr Lys Lys Arg Lys Gly Tyr Glu Asp Asp Asp Tyr Val Ser
    290                 295                 300

Lys Lys Ser Lys His Glu Glu Glu Glu Trp Thr Asp Asp Asp Leu Val
305                 310                 315                 320

Glu Ser Leu
```

```
<210> SEQ ID NO 15
<211> LENGTH: 8024
<212> TYPE: DNA
<213> ORGANISM: Homo sapiens
<220> FEATURE:
<221> NAME/KEY: CDS
<222> LOCATION: (210)..(7070)
<223> OTHER INFORMATION: POLE

<400> SEQUENCE: 15

ggtgcgccgc gcgcgcctac cacacacttt tccccggtcc ctgccggcca cctcccccgc      60

cgggcgccgg cgccaattgg agcgcctcgg ggggcggggg aggggcggag cgcgcctctt     120

gatggacggc ggcatttccg gctctcgcga gtctgggtgg gagcgcgcca aatttctccc     180

ctgaagcaga ggtggtagcc aacggctcc atg tct ctg agg agc ggc ggg cgg      233
                                Met Ser Leu Arg Ser Gly Gly Arg
                                1               5

cgg cgc gcg gac cca ggc gcg gat ggc gag gcc agc agg gat gat ggc      281
Arg Arg Ala Asp Pro Gly Ala Asp Gly Glu Ala Ser Arg Asp Asp Gly
    10                  15                  20

gcc act tcc tca gtt tcg gca ctc aag cgc ctg gaa cgg agt cag tgg      329
Ala Thr Ser Ser Val Ser Ala Leu Lys Arg Leu Glu Arg Ser Gln Trp
25                  30                  35                  40

acg gat aag atg gat ttg cgg ttt ggt ttt gag cgg ctg aag gag cct      377
Thr Asp Lys Met Asp Leu Arg Phe Gly Phe Glu Arg Leu Lys Glu Pro
                45                  50                  55

ggt gag aag aca ggc tgg ctc att aac atg cat cct acc gag att tta      425
Gly Glu Lys Thr Gly Trp Leu Ile Asn Met His Pro Thr Glu Ile Leu
            60                  65                  70

gat gaa gat aag cgc tta ggc agt gca gtg gat tac tac ttt att caa      473
Asp Glu Asp Lys Arg Leu Gly Ser Ala Val Asp Tyr Tyr Phe Ile Gln
        75                  80                  85

gat gac gga agc aga ttt aag gtg gct ttg ccc tat aaa ccg tat ttc      521
Asp Asp Gly Ser Arg Phe Lys Val Ala Leu Pro Tyr Lys Pro Tyr Phe
    90                  95                  100

tac att gcg acc aga aag ggt tgt gag cga gaa gtt tca tct ttt ctc      569
Tyr Ile Ala Thr Arg Lys Gly Cys Glu Arg Glu Val Ser Ser Phe Leu
105                 110                 115                 120

tcc aag aag ttt cag ggc aaa att gca aaa gtg gag act gtc ccc aaa      617
Ser Lys Lys Phe Gln Gly Lys Ile Ala Lys Val Glu Thr Val Pro Lys
                125                 130                 135

gag gat ctg gac ttg cca aat cac ttg gtg ggt ttg aag cga aat tac      665
Glu Asp Leu Asp Leu Pro Asn His Leu Val Gly Leu Lys Arg Asn Tyr
            140                 145                 150

atc agg ctg tcc ttc cac act gtg gag gat ctt gtc aaa gtg agg aag      713
Ile Arg Leu Ser Phe His Thr Val Glu Asp Leu Val Lys Val Arg Lys
        155                 160                 165

gag atc tcc cct gcc gtg aag aag aac agg gag cag gat cac gcc agc      761
Glu Ile Ser Pro Ala Val Lys Lys Asn Arg Glu Gln Asp His Ala Ser
    170                 175                 180

gac gcg tac aca gct ctg ctt tcc agt gtt ctg cag agg ggc ggt gtc      809
Asp Ala Tyr Thr Ala Leu Leu Ser Ser Val Leu Gln Arg Gly Gly Val
185                 190                 195                 200

att act gat gaa gag gaa acc tct aag aag ata gct gac cag ttg gac      857
Ile Thr Asp Glu Glu Glu Thr Ser Lys Lys Ile Ala Asp Gln Leu Asp
                205                 210                 215

aac att gtg gac atg cgc gag tac gat gtt ccc tac cac atc cgc ctc      905
Asn Ile Val Asp Met Arg Glu Tyr Asp Val Pro Tyr His Ile Arg Leu
            220                 225                 230
```

```
tcc att gac ctg aag atc cac gtg gct cat tgg tac aat gtc aga tac      953
Ser Ile Asp Leu Lys Ile His Val Ala His Trp Tyr Asn Val Arg Tyr
        235                 240                 245

cga gga aat gct ttt ccg gta gaa atc acc cgc cga gat gac ctt gtt     1001
Arg Gly Asn Ala Phe Pro Val Glu Ile Thr Arg Arg Asp Asp Leu Val
    250                 255                 260

gaa cga cct gac cct gtg gtt ttg gca ttt gac att gag acg acc aaa     1049
Glu Arg Pro Asp Pro Val Val Leu Ala Phe Asp Ile Glu Thr Thr Lys
265                 270                 275                 280

ctg ccc ctc aag ttt cct gat gct gag aca gac cag att atg atg att     1097
Leu Pro Leu Lys Phe Pro Asp Ala Glu Thr Asp Gln Ile Met Met Ile
                285                 290                 295

tcc tac atg atc gat ggc cag ggc tac ctc atc acc aac agg gag att     1145
Ser Tyr Met Ile Asp Gly Gln Gly Tyr Leu Ile Thr Asn Arg Glu Ile
            300                 305                 310

gtt tca gaa gat att gaa gat ttt gag ttc acc ccc aag cca gaa tat     1193
Val Ser Glu Asp Ile Glu Asp Phe Glu Phe Thr Pro Lys Pro Glu Tyr
        315                 320                 325

gaa ggc ccc ttt tgt gtc ttc aat gaa ccc gat gag gct cat ctg atc     1241
Glu Gly Pro Phe Cys Val Phe Asn Glu Pro Asp Glu Ala His Leu Ile
    330                 335                 340

caa agg tgg ttt gaa cac gtc cag gag acc aaa ccc acc atc atg gtc     1289
Gln Arg Trp Phe Glu His Val Gln Glu Thr Lys Pro Thr Ile Met Val
345                 350                 355                 360

acc tac aac ggg gac ttt ttt gac tgg cca ttt gtg gag gcc cgg gca     1337
Thr Tyr Asn Gly Asp Phe Phe Asp Trp Pro Phe Val Glu Ala Arg Ala
                365                 370                 375

gca gtc cac ggt ctg agc atg cag cag gag ata ggc ttc cag aag gac     1385
Ala Val His Gly Leu Ser Met Gln Gln Glu Ile Gly Phe Gln Lys Asp
            380                 385                 390

agc cag ggg gag tac aag gcg ccc cag tgc atc cac atg gac tgc ctc     1433
Ser Gln Gly Glu Tyr Lys Ala Pro Gln Cys Ile His Met Asp Cys Leu
        395                 400                 405

agg tgg gtg aag agg gac agt tac ctt cct gtg ggc agt cat aat ctc     1481
Arg Trp Val Lys Arg Asp Ser Tyr Leu Pro Val Gly Ser His Asn Leu
    410                 415                 420

aag gcg gcc gcc aag gcc aag cta ggc tat gat ccc gtg gag cta gac     1529
Lys Ala Ala Ala Lys Ala Lys Leu Gly Tyr Asp Pro Val Glu Leu Asp
425                 430                 435                 440

ccg gag gac atg tgc cgg atg gcc acg gag cag ccc cag act ctg gcc     1577
Pro Glu Asp Met Cys Arg Met Ala Thr Glu Gln Pro Gln Thr Leu Ala
                445                 450                 455

acg tat tct gtg tca gat gct gtc gcc act tac tac ctg tac atg aag     1625
Thr Tyr Ser Val Ser Asp Ala Val Ala Thr Tyr Tyr Leu Tyr Met Lys
            460                 465                 470

tac gtc cac cca ttc atc ttt gct ctg tgc acc att att ccc atg gag     1673
Tyr Val His Pro Phe Ile Phe Ala Leu Cys Thr Ile Ile Pro Met Glu
        475                 480                 485

ccc gac gag gtg ctg cgg aag ggc tct ggc act ctg tgt gag gcc ttg     1721
Pro Asp Glu Val Leu Arg Lys Gly Ser Gly Thr Leu Cys Glu Ala Leu
    490                 495                 500

ctg atg gtg cag gcc ttc cac gcc aac atc atc ttc ccc aac aag caa     1769
Leu Met Val Gln Ala Phe His Ala Asn Ile Ile Phe Pro Asn Lys Gln
505                 510                 515                 520

gag cag gag ttc aat aag ctg acg gac gac gga cac gtg ctg gac tct     1817
Glu Gln Glu Phe Asn Lys Leu Thr Asp Asp Gly His Val Leu Asp Ser
                525                 530                 535

gag acc tac gtc ggg ggc cac gtg gag gcc ctc gag tct ggg gtt ttc     1865
Glu Thr Tyr Val Gly Gly His Val Glu Ala Leu Glu Ser Gly Val Phe
            540                 545                 550
```

```
cgc agc gat atc cct tgc cgg ttt agg atg aat cct gcc gcc ttt gac      1913
Arg Ser Asp Ile Pro Cys Arg Phe Arg Met Asn Pro Ala Ala Phe Asp
        555                 560                 565

ttc ctg ctg cag cgg gtt gag aag acc ttg cgc cac gcc ctt gag gaa      1961
Phe Leu Leu Gln Arg Val Glu Lys Thr Leu Arg His Ala Leu Glu Glu
    570                 575                 580

gag gag aaa gtg cct gtg gag caa gtc acc aac ttt gaa gag gtg tgt      2009
Glu Glu Lys Val Pro Val Glu Gln Val Thr Asn Phe Glu Glu Val Cys
585                 590                 595                 600

gat gag att aag agc aag ctt gcc tcc ctg aag gac gtt ccc agc cgc      2057
Asp Glu Ile Lys Ser Lys Leu Ala Ser Leu Lys Asp Val Pro Ser Arg
                605                 610                 615

atc gag tgt cca ctc atc tac cac ctg gac gtg ggg gcc atg tac ccc      2105
Ile Glu Cys Pro Leu Ile Tyr His Leu Asp Val Gly Ala Met Tyr Pro
            620                 625                 630

aac atc atc ctg acc aac cgc ctg cag ccc tct gcc atg gtg gac gaa      2153
Asn Ile Ile Leu Thr Asn Arg Leu Gln Pro Ser Ala Met Val Asp Glu
        635                 640                 645

gcc acc tgt gct gcc tgt gac ttc aat aag cct gga gca aac tgc cag      2201
Ala Thr Cys Ala Ala Cys Asp Phe Asn Lys Pro Gly Ala Asn Cys Gln
    650                 655                 660

cgg aag atg gcc tgg cag tgg agg ggc gag ttc atg cca gcc agt cgc      2249
Arg Lys Met Ala Trp Gln Trp Arg Gly Glu Phe Met Pro Ala Ser Arg
665                 670                 675                 680

agc gaa tac cat cgg atc cag cac cag ctg gag tca gag aag ttc ccc      2297
Ser Glu Tyr His Arg Ile Gln His Gln Leu Glu Ser Glu Lys Phe Pro
                685                 690                 695

ccc ttg ttc cca gag ggg cca gct cgg gcc ttt cat gaa ctg tcc cgc      2345
Pro Leu Phe Pro Glu Gly Pro Ala Arg Ala Phe His Glu Leu Ser Arg
            700                 705                 710

gag gaa cag gcg aaa tac gag aag aga agg ctg gcg gat tac tgc cgg      2393
Glu Glu Gln Ala Lys Tyr Glu Lys Arg Arg Leu Ala Asp Tyr Cys Arg
        715                 720                 725

aaa gcc tac aag aag atc cac atc acc aag gtg gaa gag cgt ctc acc      2441
Lys Ala Tyr Lys Lys Ile His Ile Thr Lys Val Glu Glu Arg Leu Thr
    730                 735                 740

acc atc tgc cag cgg gaa aac tcc ttc tac gtg gac acc gtg cgt gcc      2489
Thr Ile Cys Gln Arg Glu Asn Ser Phe Tyr Val Asp Thr Val Arg Ala
745                 750                 755                 760

ttc cgg gac agg cgt tac gag ttc aaa ggg ctc cac aag gtg tgg aaa      2537
Phe Arg Asp Arg Arg Tyr Glu Phe Lys Gly Leu His Lys Val Trp Lys
                765                 770                 775

aag aag ctc tcg gcg gcc gtg gag gtg ggc gac gcg gct gag gtg aag      2585
Lys Lys Leu Ser Ala Ala Val Glu Val Gly Asp Ala Ala Glu Val Lys
            780                 785                 790

cgc tgc aag aac atg gag gtg ctg tat gac tcg ctg cag ctg gcc cac      2633
Arg Cys Lys Asn Met Glu Val Leu Tyr Asp Ser Leu Gln Leu Ala His
        795                 800                 805

aag tgc atc ctg aac tcc ttc tat ggc tat gtc atg cgc aag ggg gct      2681
Lys Cys Ile Leu Asn Ser Phe Tyr Gly Tyr Val Met Arg Lys Gly Ala
    810                 815                 820

cgc tgg tac tcc atg gag atg gct ggc atc gtc tgc ttc aca ggg gcc      2729
Arg Trp Tyr Ser Met Glu Met Ala Gly Ile Val Cys Phe Thr Gly Ala
825                 830                 835                 840

aac atc atc acc cag gca cgg gag ctg atc gag cag att ggg agg ccc      2777
Asn Ile Ile Thr Gln Ala Arg Glu Leu Ile Glu Gln Ile Gly Arg Pro
                845                 850                 855

tta gag ctg gac aca gat ggt ata tgg tgc gtc ctg ccc aac agc ttc      2825
Leu Glu Leu Asp Thr Asp Gly Ile Trp Cys Val Leu Pro Asn Ser Phe
```

```
            860                 865                 870

cca gaa aat ttt gtc ttc aag acg acc aat gtg aag aag ccc aaa gtg     2873
Pro Glu Asn Phe Val Phe Lys Thr Thr Asn Val Lys Lys Pro Lys Val
        875                 880                 885

acc atc tcc tac cca ggc gcc atg ttg aac atc atg gtc aag gaa ggc     2921
Thr Ile Ser Tyr Pro Gly Ala Met Leu Asn Ile Met Val Lys Glu Gly
    890                 895                 900

ttc acc aat gac cag tac cag gag ctg gct gag ccg tcc tca ctc acc     2969
Phe Thr Asn Asp Gln Tyr Gln Glu Leu Ala Glu Pro Ser Ser Leu Thr
905                 910                 915                 920

tac gtc acc cgc tca gag aac agc atc ttt ttt gag gtt gat ggg ccc     3017
Tyr Val Thr Arg Ser Glu Asn Ser Ile Phe Phe Glu Val Asp Gly Pro
                925                 930                 935

tac ctt gcc atg att ctt cca gcc tcc aag gaa gaa ggc aag aaa ttg     3065
Tyr Leu Ala Met Ile Leu Pro Ala Ser Lys Glu Glu Gly Lys Lys Leu
            940                 945                 950

aag aag agg tat gct gtg ttc aat gaa gac ggt tct ctg gct gag ctc     3113
Lys Lys Arg Tyr Ala Val Phe Asn Glu Asp Gly Ser Leu Ala Glu Leu
        955                 960                 965

aag ggc ttt gag gtc aaa cgc cgc ggg gaa ctg cag ctg att aag atc     3161
Lys Gly Phe Glu Val Lys Arg Arg Gly Glu Leu Gln Leu Ile Lys Ile
    970                 975                 980

ttc caa tcc tcg gtg ttt gag gcc ttc ctc aag ggc agc acg ctg gaa     3209
Phe Gln Ser Ser Val Phe Glu Ala Phe Leu Lys Gly Ser Thr Leu Glu
985                 990                 995                 1000

gag gtg tat ggc tct  gta gcc aag gtg gct  gac tac tgg ctg gac      3254
Glu Val Tyr Gly Ser  Val Ala Lys Val Ala  Asp Tyr Trp Leu Asp
                1005                 1010                 1015

gtg ctg tac agc aag  gca gcc aac atg cct  gac tct gag cta ttc      3299
Val Leu Tyr Ser Lys  Ala Ala Asn Met Pro  Asp Ser Glu Leu Phe
                1020                 1025                 1030

gag ctc atc tct gag  aac cgt tcc atg tct  cgg aag ctg gaa gat      3344
Glu Leu Ile Ser Glu  Asn Arg Ser Met Ser  Arg Lys Leu Glu Asp
                1035                 1040                 1045

tac ggg gag cag aag  tct acg tcc atc agc  aca gca aag cgc ctg      3389
Tyr Gly Glu Gln Lys  Ser Thr Ser Ile Ser  Thr Ala Lys Arg Leu
                1050                 1055                 1060

gcc gag ttc ctg gga  gac cag atg gtc aag  gat gca ggg ctg agt      3434
Ala Glu Phe Leu Gly  Asp Gln Met Val Lys  Asp Ala Gly Leu Ser
                1065                 1070                 1075

tgc cgc tac atc atc  tcc cgc aag ccc gag  ggc tcc cct gtc acg      3479
Cys Arg Tyr Ile Ile  Ser Arg Lys Pro Glu  Gly Ser Pro Val Thr
                1080                 1085                 1090

gag agg gcc atc cca  ctt gcc att ttc caa  gca gag ccc acg gtg      3524
Glu Arg Ala Ile Pro  Leu Ala Ile Phe Gln  Ala Glu Pro Thr Val
                1095                 1100                 1105

agg aag cac ttt ctc  cgg aaa tgg ctc aag  agc tct tcc ctt caa      3569
Arg Lys His Phe Leu  Arg Lys Trp Leu Lys  Ser Ser Ser Leu Gln
                1110                 1115                 1120

gac ttt gat att cga  gca att ctg gat tgg  gac tac tac att gag      3614
Asp Phe Asp Ile Arg  Ala Ile Leu Asp Trp  Asp Tyr Tyr Ile Glu
                1125                 1130                 1135

cgg ctg gga agc gcc  atc cag aag atc atc  acc atc cct gcg gcc      3659
Arg Leu Gly Ser Ala  Ile Gln Lys Ile Ile  Thr Ile Pro Ala Ala
                1140                 1145                 1150

ctg cag cag gta aag  aac cca gtg cca cgt  gtc aaa cac ccc gac      3704
Leu Gln Gln Val Lys  Asn Pro Val Pro Arg  Val Lys His Pro Asp
                1155                 1160                 1165

tgg ctg cac aaa aaa  ctg ctg gag aag aat  gat gtc tac aag cag      3749
```

-continued

```
Trp Leu His Lys Lys  Leu Leu Glu Lys Asn  Asp Val Tyr Lys Gln
                1170                 1175                 1180

aag aag atc agt gag  ctc ttc acc ctg gag  ggc agg aga cag gtc       3794
Lys Lys Ile Ser Glu  Leu Phe Thr Leu Glu  Gly Arg Arg Gln Val
                1185                 1190                 1195

acg atg gcc gag gcc  tca gaa gac agt ccg  agg cca agt gct cct       3839
Thr Met Ala Glu Ala  Ser Glu Asp Ser Pro  Arg Pro Ser Ala Pro
                1200                 1205                 1210

gac atg gag gac ttc  ggc ctc gta aag ctg  cct cac cca gca gcc       3884
Asp Met Glu Asp Phe  Gly Leu Val Lys Leu  Pro His Pro Ala Ala
                1215                 1220                 1225

cct gtc act gtg aag  agg aag cga gtt ctt  tgg gag agc cag gag       3929
Pro Val Thr Val Lys  Arg Lys Arg Val Leu  Trp Glu Ser Gln Glu
                1230                 1235                 1240

gag tcc cag gac ctc  acg ccg act gtg ccc  tgg cag gaa atc ttg       3974
Glu Ser Gln Asp Leu  Thr Pro Thr Val Pro  Trp Gln Glu Ile Leu
                1245                 1250                 1255

ggg cag cct ccc gcc  ctg gga acc agc cag  gag gaa tgg ctt gtc       4019
Gly Gln Pro Pro Ala  Leu Gly Thr Ser Gln  Glu Glu Trp Leu Val
                1260                 1265                 1270

tgg ctc cgg ttc cac  aag aag aag tgg cag  ctg cag gcc cgg cag       4064
Trp Leu Arg Phe His  Lys Lys Lys Trp Gln  Leu Gln Ala Arg Gln
                1275                 1280                 1285

cgc ctc gcc cgc agg  aag agg cag cgt ctg  gag tcg gca gag ggt       4109
Arg Leu Ala Arg Arg  Lys Arg Gln Arg Leu  Glu Ser Ala Glu Gly
                1290                 1295                 1300

gtg ctc agg ccc ggg  gcc atc cgg gat ggt  cct gcc acg ggg ctg       4154
Val Leu Arg Pro Gly  Ala Ile Arg Asp Gly  Pro Ala Thr Gly Leu
                1305                 1310                 1315

ggg agc ttc ttg cga  aga act gcc cgc agc  atc ctg gac ctt ccg       4199
Gly Ser Phe Leu Arg  Arg Thr Ala Arg Ser  Ile Leu Asp Leu Pro
                1320                 1325                 1330

tgg cag att gtg cag  atc agc gag acc agc  cag gcc ggc ctg ttc       4244
Trp Gln Ile Val Gln  Ile Ser Glu Thr Ser  Gln Ala Gly Leu Phe
                1335                 1340                 1345

agg ctg tgg gcg ctc  gtt ggc agt gac ttg  cac tgc atc agg ctg       4289
Arg Leu Trp Ala Leu  Val Gly Ser Asp Leu  His Cys Ile Arg Leu
                1350                 1355                 1360

agc atc ccc cgt gtg  ttc tac gtg aac cag  cga gtc gct aaa gcg       4334
Ser Ile Pro Arg Val  Phe Tyr Val Asn Gln  Arg Val Ala Lys Ala
                1365                 1370                 1375

gag gag ggt gct tcg  tat cgc aag gta aat  cgg gtc ctt cct cgc       4379
Glu Glu Gly Ala Ser  Tyr Arg Lys Val Asn  Arg Val Leu Pro Arg
                1380                 1385                 1390

tcc aac atg gtc tac  aat ctc tat gag tat  tca gtg cca gag gac       4424
Ser Asn Met Val Tyr  Asn Leu Tyr Glu Tyr  Ser Val Pro Glu Asp
                1395                 1400                 1405

atg tac cag gaa cac  atc aac gag atc aac  gct gag ctg tca gcg       4469
Met Tyr Gln Glu His  Ile Asn Glu Ile Asn  Ala Glu Leu Ser Ala
                1410                 1415                 1420

cca gac atc gag ggc  gta tat gag act cag  gtt ccg tta ctg ttc       4514
Pro Asp Ile Glu Gly  Val Tyr Glu Thr Gln  Val Pro Leu Leu Phe
                1425                 1430                 1435

cgg gcc ctg gtg cac  ctg ggc tgt gtg tgt  gtg gtc aat aaa cag       4559
Arg Ala Leu Val His  Leu Gly Cys Val Cys  Val Val Asn Lys Gln
                1440                 1445                 1450

ctg gtg agg cac ctt  tca ggc tgg gaa gca  gag acc ttt gct ctt       4604
Leu Val Arg His Leu  Ser Gly Trp Glu Ala  Glu Thr Phe Ala Leu
                1455                 1460                 1465
```

```
gag cac ctg gag atg  cgc tct ctg gcc cag  ttc agc tac ctg gaa       4649
Glu His Leu Glu Met  Arg Ser Leu Ala Gln  Phe Ser Tyr Leu Glu
                1470                 1475                 1480

cca ggg agt atc cgc  cat atc tac ctg tac  cac cac gca cag gcc       4694
Pro Gly Ser Ile Arg  His Ile Tyr Leu Tyr  His His Ala Gln Ala
                1485                 1490                 1495

cac aaa gcg ctc ttc  ggg atc ttc atc ccc  tca cag cgc agg gca       4739
His Lys Ala Leu Phe  Gly Ile Phe Ile Pro  Ser Gln Arg Arg Ala
                1500                 1505                 1510

tcc gtc ttt gtg ctg  gac act gtg cgc agc  aac cag atg ccc agc       4784
Ser Val Phe Val Leu  Asp Thr Val Arg Ser  Asn Gln Met Pro Ser
                1515                 1520                 1525

ctt ggc gcc ctg tac  tca gca gag cac ggc  ctc ctc ctg gag aag       4829
Leu Gly Ala Leu Tyr  Ser Ala Glu His Gly  Leu Leu Leu Glu Lys
                1530                 1535                 1540

gtg ggc cct gag ctc  ctg cca ccc ccc aaa  cac acc ttc gaa gtt       4874
Val Gly Pro Glu Leu  Leu Pro Pro Pro Lys  His Thr Phe Glu Val
                1545                 1550                 1555

cgg gca gaa act gac  ctg aag acc atc tgc  aga gcc atc cag cga       4919
Arg Ala Glu Thr Asp  Leu Lys Thr Ile Cys  Arg Ala Ile Gln Arg
                1560                 1565                 1570

ttc ctg ctc gcc tac  aag gag gag cgc cgg  ggg ccc aca ctc atc       4964
Phe Leu Leu Ala Tyr  Lys Glu Glu Arg Arg  Gly Pro Thr Leu Ile
                1575                 1580                 1585

gct gtt cag tcc agc  tgg gag ctg aag agg  ctg gcc agt gaa att       5009
Ala Val Gln Ser Ser  Trp Glu Leu Lys Arg  Leu Ala Ser Glu Ile
                1590                 1595                 1600

cct gtc ttg gag gaa  ttc cca ctg gtg cct  atc tgt gtg gct gac       5054
Pro Val Leu Glu Glu  Phe Pro Leu Val Pro  Ile Cys Val Ala Asp
                1605                 1610                 1615

aag atc aac tat ggg  gtc ctg gac tgg cag  cgc cat gga gcc cgg       5099
Lys Ile Asn Tyr Gly  Val Leu Asp Trp Gln  Arg His Gly Ala Arg
                1620                 1625                 1630

cgc atg atc cgt cac  tac ctc aac ctg gac  acc tgc ctg tcg cag       5144
Arg Met Ile Arg His  Tyr Leu Asn Leu Asp  Thr Cys Leu Ser Gln
                1635                 1640                 1645

gcc ttc gag atg agc  agg tac ttt cac att  ccc att ggg aac cta       5189
Ala Phe Glu Met Ser  Arg Tyr Phe His Ile  Pro Ile Gly Asn Leu
                1650                 1655                 1660

cca gag gac atc tcc  aca ttc ggc tcc gac  ctc ttc ttt gcc cgc       5234
Pro Glu Asp Ile Ser  Thr Phe Gly Ser Asp  Leu Phe Phe Ala Arg
                1665                 1670                 1675

cac ctc cag cgc cac  aac cac ctg ctc tgg  ctg tcc cct aca gcc       5279
His Leu Gln Arg His  Asn His Leu Leu Trp  Leu Ser Pro Thr Ala
                1680                 1685                 1690

cgc cct gac ctg ggt  gga aag gag gct gat  gac aac tgt ctt gtc       5324
Arg Pro Asp Leu Gly  Gly Lys Glu Ala Asp  Asp Asn Cys Leu Val
                1695                 1700                 1705

atg gag ttc gat gac  caa gcc act gtt gag  atc aac agt tca ggc       5369
Met Glu Phe Asp Asp  Gln Ala Thr Val Glu  Ile Asn Ser Ser Gly
                1710                 1715                 1720

tgt tac tcc aca gtg  tgt gtg gag ctg gac  ctt cag aac ctg gcc       5414
Cys Tyr Ser Thr Val  Cys Val Glu Leu Asp  Leu Gln Asn Leu Ala
                1725                 1730                 1735

gtc aac acc att ctc  cag tct cac cat gtc  aac gac atg gag ggg       5459
Val Asn Thr Ile Leu  Gln Ser His His Val  Asn Asp Met Glu Gly
                1740                 1745                 1750

gcc gac agc atg ggg  atc agc ttc gac gtg  atc cag cag gcc tcc       5504
Ala Asp Ser Met Gly  Ile Ser Phe Asp Val  Ile Gln Gln Ala Ser
                1755                 1760                 1765
```

```
ctg gag gac atg atc  acg ggt ggt cag gct  gcc agt gcc ccg gcc       5549
Leu Glu Asp Met Ile  Thr Gly Gly Gln Ala  Ala Ser Ala Pro Ala
                1770                 1775                 1780

agc tac gat gag aca  gcc ctg tgc tct aac  acc ttc agg atc ctg       5594
Ser Tyr Asp Glu Thr  Ala Leu Cys Ser Asn  Thr Phe Arg Ile Leu
                1785                 1790                 1795

aag agc atg gtc gtg  ggc tgg gtg aag gag  atc acc cag tac cac       5639
Lys Ser Met Val Val  Gly Trp Val Lys Glu  Ile Thr Gln Tyr His
                1800                 1805                 1810

aac atc tat gca gac  aac cag gtg atg cac  ttc tac cgc tgg ctt       5684
Asn Ile Tyr Ala Asp  Asn Gln Val Met His  Phe Tyr Arg Trp Leu
                1815                 1820                 1825

cgg tcg cca tcc tct  ctg ctt cat gac cct  gcc ctg cac cgc aca       5729
Arg Ser Pro Ser Ser  Leu Leu His Asp Pro  Ala Leu His Arg Thr
                1830                 1835                 1840

ctc cac aac atg atg  aag aag ctc ttc ctg  cag ctc atc gct gag       5774
Leu His Asn Met Met  Lys Lys Leu Phe Leu  Gln Leu Ile Ala Glu
                1845                 1850                 1855

ttc aag cgc ctg ggg  tca tca gtc atc tac  gcc aac ttc aac cgc       5819
Phe Lys Arg Leu Gly  Ser Ser Val Ile Tyr  Ala Asn Phe Asn Arg
                1860                 1865                 1870

atc atc ctc tgt aca  aag aag cgc cgt gtg  gaa gat gcc atc gct       5864
Ile Ile Leu Cys Thr  Lys Lys Arg Arg Val  Glu Asp Ala Ile Ala
                1875                 1880                 1885

tac gtg gag tac atc  acc agc agc atc cat  tca aag gag acc ttc       5909
Tyr Val Glu Tyr Ile  Thr Ser Ser Ile His  Ser Lys Glu Thr Phe
                1890                 1895                 1900

cat tct ctg aca att  tct ttc tct cga tgc  tgg gaa ttt ctt ctc       5954
His Ser Leu Thr Ile  Ser Phe Ser Arg Cys  Trp Glu Phe Leu Leu
                1905                 1910                 1915

tgg atg gat cca tct  aac tat ggc gga atc  aaa gga aaa gtt tca       5999
Trp Met Asp Pro Ser  Asn Tyr Gly Gly Ile  Lys Gly Lys Val Ser
                1920                 1925                 1930

tct cgt att cac tgt  gga ctg caa gac tcc  cag aaa gca ggg gga       6044
Ser Arg Ile His Cys  Gly Leu Gln Asp Ser  Gln Lys Ala Gly Gly
                1935                 1940                 1945

gca gag gat gag cag  gaa aat gag gac gat  gag gag gaa aga gat       6089
Ala Glu Asp Glu Gln  Glu Asn Glu Asp Asp  Glu Glu Glu Arg Asp
                1950                 1955                 1960

ggg gag gag gag gaa  gag gcg gag gaa tcc  aac gtg gag gat tta       6134
Gly Glu Glu Glu Glu  Glu Ala Glu Glu Ser  Asn Val Glu Asp Leu
                1965                 1970                 1975

ctg gaa aac aac tgg  aac att ttg cag ttt  ttg cca cag gca gcc       6179
Leu Glu Asn Asn Trp  Asn Ile Leu Gln Phe  Leu Pro Gln Ala Ala
                1980                 1985                 1990

tcc tgc cag aac tac  ttc ctc atg att gtt  tca gcg tac atc gtg       6224
Ser Cys Gln Asn Tyr  Phe Leu Met Ile Val  Ser Ala Tyr Ile Val
                1995                 2000                 2005

gcc gtg tac cac tgc  atg aag gac ggg ctg  agg cgc agt gct cca       6269
Ala Val Tyr His Cys  Met Lys Asp Gly Leu  Arg Arg Ser Ala Pro
                2010                 2015                 2020

ggg agc acc ccc gtg  agg agg agg ggg gcc  agc cag ctc tcc cag       6314
Gly Ser Thr Pro Val  Arg Arg Arg Gly Ala  Ser Gln Leu Ser Gln
                2025                 2030                 2035

gag gcc gag ggg gcg  gtc gga gcc ctt ccc  gga atg atc acc ttc       6359
Glu Ala Glu Gly Ala  Val Gly Ala Leu Pro  Gly Met Ile Thr Phe
                2040                 2045                 2050

tct cag gat tat gtc  gca aat gag ctc act  cag agc ttc ttc acc       6404
Ser Gln Asp Tyr Val  Ala Asn Glu Leu Thr  Gln Ser Phe Phe Thr
```

```
                2055                2060                2065

atc act cag aag att  cag aag aaa gtc aca  ggc tct cgg aac tcc       6449
Ile Thr Gln Lys Ile  Gln Lys Lys Val Thr  Gly Ser Arg Asn Ser
                2070                2075                2080

act gag ctc tca gag  atg ttt cct gtc ctc  ccc ggt tcc cac ttg       6494
Thr Glu Leu Ser Glu  Met Phe Pro Val Leu  Pro Gly Ser His Leu
                2085                2090                2095

ctg ctc aat aac cct  gcc ctg gag ttc atc  aaa tac gtg tgc aag       6539
Leu Leu Asn Asn Pro  Ala Leu Glu Phe Ile  Lys Tyr Val Cys Lys
                2100                2105                2110

gtg ctg tcc ctg gac  acc aac atc aca aac  cag gtg aat aag ctg       6584
Val Leu Ser Leu Asp  Thr Asn Ile Thr Asn  Gln Val Asn Lys Leu
                2115                2120                2125

aac cga gac ctg ctt  cgc ctg gtg gat gtc  ggc gag ttc tcc gag       6629
Asn Arg Asp Leu Leu  Arg Leu Val Asp Val  Gly Glu Phe Ser Glu
                2130                2135                2140

gag gcc cag ttc cga  gac ccc tgc cgc tcc  tac gtg ctt cct gag       6674
Glu Ala Gln Phe Arg  Asp Pro Cys Arg Ser  Tyr Val Leu Pro Glu
                2145                2150                2155

gtc atc tgc cgc agc  tgt aac ttc tgc cgc  gac ctg gac ctg tgt       6719
Val Ile Cys Arg Ser  Cys Asn Phe Cys Arg  Asp Leu Asp Leu Cys
                2160                2165                2170

aaa gac tct tcc ttc  tca gag gat ggg gcg  gtc ctg cct cag tgg       6764
Lys Asp Ser Ser Phe  Ser Glu Asp Gly Ala  Val Leu Pro Gln Trp
                2175                2180                2185

ctc tgc tcc aac tgt  cag gcg ccc tac gac  tcc tct gcc atc gag       6809
Leu Cys Ser Asn Cys  Gln Ala Pro Tyr Asp  Ser Ser Ala Ile Glu
                2190                2195                2200

atg acg ctg gtg gaa  gtt cta cag aag aag  ctg atg gcc ttc acc       6854
Met Thr Leu Val Glu  Val Leu Gln Lys Lys  Leu Met Ala Phe Thr
                2205                2210                2215

ctg cag gac ctg gtc  tgc ctg aag tgc cgc  ggg gtg aag gag acc       6899
Leu Gln Asp Leu Val  Cys Leu Lys Cys Arg  Gly Val Lys Glu Thr
                2220                2225                2230

agc atg cct gtg tac  tgc agc tgc gcg gga  gac ttc gcc ctc acc       6944
Ser Met Pro Val Tyr  Cys Ser Cys Ala Gly  Asp Phe Ala Leu Thr
                2235                2240                2245

atc cac acc cag gtc  ttc atg gaa cag atc  gga ata ttc cgg aac       6989
Ile His Thr Gln Val  Phe Met Glu Gln Ile  Gly Ile Phe Arg Asn
                2250                2255                2260

att gcc cag cac tac  ggc atg tcg tac ctc  ctg gag acc ctg gag       7034
Ile Ala Gln His Tyr  Gly Met Ser Tyr Leu  Leu Glu Thr Leu Glu
                2265                2270                2275

tgg ctg ctg cag aag  aac cca cag ctg ggc  cat tag ccagccccgg        7080
Trp Leu Leu Gln Lys  Asn Pro Gln Leu Gly  His
                2280                2285

gccccgggtg cctctgcgtc cgtgccaggc ctcctgatgc caaggccaca tccccgtgct   7140

tccagtgacc agaccactga ccaccctgac tgtccaaacc tgtgacccca ggccagggaa   7200

cggggaggaa accaaagaaa accattttca gggagctcag acgtcacagg agggagcggg   7260

agcaggatgt ggccctggcc tcgccagagc acctgaagaa gcaggccgtg agcgaggctg   7320

cgagtgccct gggcgccgtt tctcacgcag tgaatgcttt tccaggcctc tgttgcttcc   7380

tgcaccacac ctggtggggt gggagcgtcc tctaggtgcc cctagttctt tgtcctgcct   7440

cccagaggga ggaaaagccc ctgggggctt ctggctccct gagattgggc tctgagacga   7500

gacgggttcc caaggccctg gtggggctgg agtctcacct gtttgcatgg agaaatgggc   7560

tggccccaca gcctcacagg agcagtttgt gggctggttt ccccaggaat ccagacccta   7620
```

```
acccgtgaga atctggattt tggcttgtga gccctgctta tttggagccg ggtctagagg   7680

gaaccctcta tcagcctcag gaaaacaaga cctctgtgca cctcactttt ggctcactgc   7740

agcccttgtc cttcacctcc acacaggacc agctggaagc agaaagaaga aaggccaatt   7800

tcacagggca ccaaacaagt atgaaatgta aatcagaaat gcagacaccc cagacgagag   7860

cctcacagga gggagggggc cccacaggct ccccaggagg ctcgtgtctt tggcccagag   7920

ccagccttag tttgtccctg ccatctactg tctgaggcca tcgctgctac actttgtttt   7980

tatttgtatt tcatactgaa gtttcaaaaa aaaaaaaaaa aaaa                    8024


<210> SEQ ID NO 16
<211> LENGTH: 2286
<212> TYPE: PRT
<213> ORGANISM: Homo sapiens

<400> SEQUENCE: 16

Met Ser Leu Arg Ser Gly Gly Arg Arg Arg Ala Asp Pro Gly Ala Asp
1               5                   10                  15

Gly Glu Ala Ser Arg Asp Asp Gly Ala Thr Ser Ser Val Ser Ala Leu
            20                  25                  30

Lys Arg Leu Glu Arg Ser Gln Trp Thr Asp Lys Met Asp Leu Arg Phe
        35                  40                  45

Gly Phe Glu Arg Leu Lys Glu Pro Gly Glu Lys Thr Gly Trp Leu Ile
    50                  55                  60

Asn Met His Pro Thr Glu Ile Leu Asp Glu Asp Lys Arg Leu Gly Ser
65                  70                  75                  80

Ala Val Asp Tyr Tyr Phe Ile Gln Asp Asp Gly Ser Arg Phe Lys Val
                85                  90                  95

Ala Leu Pro Tyr Lys Pro Tyr Phe Tyr Ile Ala Thr Arg Lys Gly Cys
            100                 105                 110

Glu Arg Glu Val Ser Ser Phe Leu Ser Lys Lys Phe Gln Gly Lys Ile
        115                 120                 125

Ala Lys Val Glu Thr Val Pro Lys Glu Asp Leu Asp Leu Pro Asn His
    130                 135                 140

Leu Val Gly Leu Lys Arg Asn Tyr Ile Arg Leu Ser Phe His Thr Val
145                 150                 155                 160

Glu Asp Leu Val Lys Val Arg Lys Glu Ile Ser Pro Ala Val Lys Lys
                165                 170                 175

Asn Arg Glu Gln Asp His Ala Ser Asp Ala Tyr Thr Ala Leu Leu Ser
            180                 185                 190

Ser Val Leu Gln Arg Gly Gly Val Ile Thr Asp Glu Glu Glu Thr Ser
        195                 200                 205

Lys Lys Ile Ala Asp Gln Leu Asp Asn Ile Val Asp Met Arg Glu Tyr
    210                 215                 220

Asp Val Pro Tyr His Ile Arg Leu Ser Ile Asp Leu Lys Ile His Val
225                 230                 235                 240

Ala His Trp Tyr Asn Val Arg Tyr Arg Gly Asn Ala Phe Pro Val Glu
                245                 250                 255

Ile Thr Arg Arg Asp Asp Leu Val Glu Arg Pro Asp Pro Val Val Leu
            260                 265                 270

Ala Phe Asp Ile Glu Thr Thr Lys Leu Pro Leu Lys Phe Pro Asp Ala
        275                 280                 285

Glu Thr Asp Gln Ile Met Met Ile Ser Tyr Met Ile Asp Gly Gln Gly
    290                 295                 300
```

```
Tyr Leu Ile Thr Asn Arg Glu Ile Val Ser Glu Asp Ile Glu Asp Phe
305                 310                 315                 320

Glu Phe Thr Pro Lys Pro Glu Tyr Glu Gly Pro Phe Cys Val Phe Asn
                325                 330                 335

Glu Pro Asp Glu Ala His Leu Ile Gln Arg Trp Phe Glu His Val Gln
            340                 345                 350

Glu Thr Lys Pro Thr Ile Met Val Thr Tyr Asn Gly Asp Phe Phe Asp
        355                 360                 365

Trp Pro Phe Val Glu Ala Arg Ala Ala Val His Gly Leu Ser Met Gln
    370                 375                 380

Gln Glu Ile Gly Phe Gln Lys Asp Ser Gln Gly Glu Tyr Lys Ala Pro
385                 390                 395                 400

Gln Cys Ile His Met Asp Cys Leu Arg Trp Val Lys Arg Asp Ser Tyr
                405                 410                 415

Leu Pro Val Gly Ser His Asn Leu Lys Ala Ala Ala Lys Ala Lys Leu
            420                 425                 430

Gly Tyr Asp Pro Val Glu Leu Asp Pro Glu Asp Met Cys Arg Met Ala
        435                 440                 445

Thr Glu Gln Pro Gln Thr Leu Ala Thr Tyr Ser Val Ser Asp Ala Val
    450                 455                 460

Ala Thr Tyr Tyr Leu Tyr Met Lys Tyr Val His Pro Phe Ile Phe Ala
465                 470                 475                 480

Leu Cys Thr Ile Ile Pro Met Glu Pro Asp Glu Val Leu Arg Lys Gly
                485                 490                 495

Ser Gly Thr Leu Cys Glu Ala Leu Leu Met Val Gln Ala Phe His Ala
            500                 505                 510

Asn Ile Ile Phe Pro Asn Lys Gln Glu Gln Glu Phe Asn Lys Leu Thr
        515                 520                 525

Asp Asp Gly His Val Leu Asp Ser Glu Thr Tyr Val Gly Gly His Val
    530                 535                 540

Glu Ala Leu Glu Ser Gly Val Phe Arg Ser Asp Ile Pro Cys Arg Phe
545                 550                 555                 560

Arg Met Asn Pro Ala Ala Phe Asp Phe Leu Leu Gln Arg Val Glu Lys
                565                 570                 575

Thr Leu Arg His Ala Leu Glu Glu Glu Glu Lys Val Pro Val Glu Gln
            580                 585                 590

Val Thr Asn Phe Glu Glu Val Cys Asp Glu Ile Lys Ser Lys Leu Ala
        595                 600                 605

Ser Leu Lys Asp Val Pro Ser Arg Ile Glu Cys Pro Leu Ile Tyr His
    610                 615                 620

Leu Asp Val Gly Ala Met Tyr Pro Asn Ile Ile Leu Thr Asn Arg Leu
625                 630                 635                 640

Gln Pro Ser Ala Met Val Asp Glu Ala Thr Cys Ala Ala Cys Asp Phe
                645                 650                 655

Asn Lys Pro Gly Ala Asn Cys Gln Arg Lys Met Ala Trp Gln Trp Arg
            660                 665                 670

Gly Glu Phe Met Pro Ala Ser Arg Ser Glu Tyr His Arg Ile Gln His
        675                 680                 685

Gln Leu Glu Ser Glu Lys Phe Pro Pro Leu Phe Pro Glu Gly Pro Ala
    690                 695                 700

Arg Ala Phe His Glu Leu Ser Arg Glu Glu Gln Ala Lys Tyr Glu Lys
705                 710                 715                 720
```

```
Arg Arg Leu Ala Asp Tyr Cys Arg Lys Ala Tyr Lys Lys Ile His Ile
                725                 730                 735

Thr Lys Val Glu Glu Arg Leu Thr Thr Ile Cys Gln Arg Glu Asn Ser
            740                 745                 750

Phe Tyr Val Asp Thr Val Arg Ala Phe Arg Asp Arg Arg Tyr Glu Phe
        755                 760                 765

Lys Gly Leu His Lys Val Trp Lys Lys Lys Leu Ser Ala Ala Val Glu
    770                 775                 780

Val Gly Asp Ala Ala Glu Val Lys Arg Cys Lys Asn Met Glu Val Leu
785                 790                 795                 800

Tyr Asp Ser Leu Gln Leu Ala His Lys Cys Ile Leu Asn Ser Phe Tyr
                805                 810                 815

Gly Tyr Val Met Arg Lys Gly Ala Arg Trp Tyr Ser Met Glu Met Ala
            820                 825                 830

Gly Ile Val Cys Phe Thr Gly Ala Asn Ile Ile Thr Gln Ala Arg Glu
        835                 840                 845

Leu Ile Glu Gln Ile Gly Arg Pro Leu Glu Leu Asp Thr Asp Gly Ile
    850                 855                 860

Trp Cys Val Leu Pro Asn Ser Phe Pro Glu Asn Phe Val Phe Lys Thr
865                 870                 875                 880

Thr Asn Val Lys Lys Pro Lys Val Thr Ile Ser Tyr Pro Gly Ala Met
                885                 890                 895

Leu Asn Ile Met Val Lys Glu Gly Phe Thr Asn Asp Gln Tyr Gln Glu
            900                 905                 910

Leu Ala Glu Pro Ser Ser Leu Thr Tyr Val Thr Arg Ser Glu Asn Ser
        915                 920                 925

Ile Phe Phe Glu Val Asp Gly Pro Tyr Leu Ala Met Ile Leu Pro Ala
    930                 935                 940

Ser Lys Glu Glu Gly Lys Lys Leu Lys Lys Arg Tyr Ala Val Phe Asn
945                 950                 955                 960

Glu Asp Gly Ser Leu Ala Glu Leu Lys Gly Phe Glu Val Lys Arg Arg
                965                 970                 975

Gly Glu Leu Gln Leu Ile Lys Ile Phe Gln Ser Ser Val Phe Glu Ala
            980                 985                 990

Phe Leu Lys Gly Ser Thr Leu Glu  Glu Val Tyr Gly Ser  Val Ala Lys
        995                 1000                 1005

Val Ala  Asp Tyr Trp Leu Asp  Val Leu Tyr Ser Lys  Ala Ala Asn
    1010                 1015                 1020

Met Pro  Asp Ser Glu Leu Phe  Glu Leu Ile Ser Glu  Asn Arg Ser
    1025                 1030                 1035

Met Ser  Arg Lys Leu Glu Asp  Tyr Gly Glu Gln Lys  Ser Thr Ser
    1040                 1045                 1050

Ile Ser  Thr Ala Lys Arg Leu  Ala Glu Phe Leu Gly  Asp Gln Met
    1055                 1060                 1065

Val Lys  Asp Ala Gly Leu Ser  Cys Arg Tyr Ile Ile  Ser Arg Lys
    1070                 1075                 1080

Pro Glu  Gly Ser Pro Val Thr  Glu Arg Ala Ile Pro  Leu Ala Ile
    1085                 1090                 1095

Phe Gln  Ala Glu Pro Thr Val  Arg Lys His Phe Leu  Arg Lys Trp
    1100                 1105                 1110

Leu Lys  Ser Ser Ser Leu Gln  Asp Phe Asp Ile Arg  Ala Ile Leu
    1115                 1120                 1125

Asp Trp  Asp Tyr Tyr Ile Glu  Arg Leu Gly Ser Ala  Ile Gln Lys
```

```
    1130                1135                1140

Ile Ile  Thr Ile Pro Ala Ala  Leu Gln Gln Val Lys  Asn Pro Val
    1145                1150                1155

Pro Arg  Val Lys His Pro Asp  Trp Leu His Lys Lys  Leu Leu Glu
    1160                1165                1170

Lys Asn  Asp Val Tyr Lys Gln  Lys Lys Ile Ser Glu  Leu Phe Thr
    1175                1180                1185

Leu Glu  Gly Arg Arg Gln Val  Thr Met Ala Glu Ala  Ser Glu Asp
    1190                1195                1200

Ser Pro  Arg Pro Ser Ala Pro  Asp Met Glu Asp Phe  Gly Leu Val
    1205                1210                1215

Lys Leu  Pro His Pro Ala Ala  Pro Val Thr Val Lys  Arg Lys Arg
    1220                1225                1230

Val Leu  Trp Glu Ser Gln Glu  Glu Ser Gln Asp Leu  Thr Pro Thr
    1235                1240                1245

Val Pro  Trp Gln Glu Ile Leu  Gly Gln Pro Pro Ala  Leu Gly Thr
    1250                1255                1260

Ser Gln  Glu Glu Trp Leu Val  Trp Leu Arg Phe His  Lys Lys Lys
    1265                1270                1275

Trp Gln  Leu Gln Ala Arg Gln  Arg Leu Ala Arg Arg  Lys Arg Gln
    1280                1285                1290

Arg Leu  Glu Ser Ala Glu Gly  Val Leu Arg Pro Gly  Ala Ile Arg
    1295                1300                1305

Asp Gly  Pro Ala Thr Gly Leu  Gly Ser Phe Leu Arg  Arg Thr Ala
    1310                1315                1320

Arg Ser  Ile Leu Asp Leu Pro  Trp Gln Ile Val Gln  Ile Ser Glu
    1325                1330                1335

Thr Ser  Gln Ala Gly Leu Phe  Arg Leu Trp Ala Leu  Val Gly Ser
    1340                1345                1350

Asp Leu  His Cys Ile Arg Leu  Ser Ile Pro Arg Val  Phe Tyr Val
    1355                1360                1365

Asn Gln  Arg Val Ala Lys Ala  Glu Glu Gly Ala Ser  Tyr Arg Lys
    1370                1375                1380

Val Asn  Arg Val Leu Pro Arg  Ser Asn Met Val Tyr  Asn Leu Tyr
    1385                1390                1395

Glu Tyr  Ser Val Pro Glu Asp  Met Tyr Gln Glu His  Ile Asn Glu
    1400                1405                1410

Ile Asn  Ala Glu Leu Ser Ala  Pro Asp Ile Glu Gly  Val Tyr Glu
    1415                1420                1425

Thr Gln  Val Pro Leu Leu Phe  Arg Ala Leu Val His  Leu Gly Cys
    1430                1435                1440

Val Cys  Val Val Asn Lys Gln  Leu Val Arg His Leu  Ser Gly Trp
    1445                1450                1455

Glu Ala  Glu Thr Phe Ala Leu  Glu His Leu Glu Met  Arg Ser Leu
    1460                1465                1470

Ala Gln  Phe Ser Tyr Leu Glu  Pro Gly Ser Ile Arg  His Ile Tyr
    1475                1480                1485

Leu Tyr  His His Ala Gln Ala  His Lys Ala Leu Phe  Gly Ile Phe
    1490                1495                1500

Ile Pro  Ser Gln Arg Arg Ala  Ser Val Phe Val Leu  Asp Thr Val
    1505                1510                1515

Arg Ser  Asn Gln Met Pro Ser  Leu Gly Ala Leu Tyr  Ser Ala Glu
    1520                1525                1530
```

```
His Gly Leu Leu Leu Glu Lys Val Gly Pro Glu Leu Leu Pro Pro
    1535                1540                1545

Pro Lys His Thr Phe Glu Val Arg Ala Glu Thr Asp Leu Lys Thr
    1550                1555                1560

Ile Cys Arg Ala Ile Gln Arg Phe Leu Leu Ala Tyr Lys Glu Glu
    1565                1570                1575

Arg Arg Gly Pro Thr Leu Ile Ala Val Gln Ser Ser Trp Glu Leu
    1580                1585                1590

Lys Arg Leu Ala Ser Glu Ile Pro Val Leu Glu Glu Phe Pro Leu
    1595                1600                1605

Val Pro Ile Cys Val Ala Asp Lys Ile Asn Tyr Gly Val Leu Asp
    1610                1615                1620

Trp Gln Arg His Gly Ala Arg Arg Met Ile Arg His Tyr Leu Asn
    1625                1630                1635

Leu Asp Thr Cys Leu Ser Gln Ala Phe Glu Met Ser Arg Tyr Phe
    1640                1645                1650

His Ile Pro Ile Gly Asn Leu Pro Glu Asp Ile Ser Thr Phe Gly
    1655                1660                1665

Ser Asp Leu Phe Phe Ala Arg His Leu Gln Arg His Asn His Leu
    1670                1675                1680

Leu Trp Leu Ser Pro Thr Ala Arg Pro Asp Leu Gly Gly Lys Glu
    1685                1690                1695

Ala Asp Asp Asn Cys Leu Val Met Glu Phe Asp Asp Gln Ala Thr
    1700                1705                1710

Val Glu Ile Asn Ser Ser Gly Cys Tyr Ser Thr Val Cys Val Glu
    1715                1720                1725

Leu Asp Leu Gln Asn Leu Ala Val Asn Thr Ile Leu Gln Ser His
    1730                1735                1740

His Val Asn Asp Met Glu Gly Ala Asp Ser Met Gly Ile Ser Phe
    1745                1750                1755

Asp Val Ile Gln Gln Ala Ser Leu Glu Asp Met Ile Thr Gly Gly
    1760                1765                1770

Gln Ala Ala Ser Ala Pro Ala Ser Tyr Asp Glu Thr Ala Leu Cys
    1775                1780                1785

Ser Asn Thr Phe Arg Ile Leu Lys Ser Met Val Val Gly Trp Val
    1790                1795                1800

Lys Glu Ile Thr Gln Tyr His Asn Ile Tyr Ala Asp Asn Gln Val
    1805                1810                1815

Met His Phe Tyr Arg Trp Leu Arg Ser Pro Ser Ser Leu Leu His
    1820                1825                1830

Asp Pro Ala Leu His Arg Thr Leu His Asn Met Met Lys Lys Leu
    1835                1840                1845

Phe Leu Gln Leu Ile Ala Glu Phe Lys Arg Leu Gly Ser Ser Val
    1850                1855                1860

Ile Tyr Ala Asn Phe Asn Arg Ile Ile Leu Cys Thr Lys Lys Arg
    1865                1870                1875

Arg Val Glu Asp Ala Ile Ala Tyr Val Glu Tyr Ile Thr Ser Ser
    1880                1885                1890

Ile His Ser Lys Glu Thr Phe His Ser Leu Thr Ile Ser Phe Ser
    1895                1900                1905

Arg Cys Trp Glu Phe Leu Leu Trp Met Asp Pro Ser Asn Tyr Gly
    1910                1915                1920
```

```
Gly Ile  Lys Gly Lys Val Ser  Ser Arg Ile His Cys  Gly Leu Gln
    1925                 1930                 1935

Asp Ser  Gln Lys Ala Gly Gly  Ala Glu Asp Glu Gln  Glu Asn Glu
    1940                 1945                 1950

Asp Asp  Glu Glu Glu Arg Asp  Gly Glu Glu Glu Glu  Glu Ala Glu
    1955                 1960                 1965

Glu Ser  Asn Val Glu Asp Leu  Leu Glu Asn Asn Trp  Asn Ile Leu
    1970                 1975                 1980

Gln Phe  Leu Pro Gln Ala Ala  Ser Cys Gln Asn Tyr  Phe Leu Met
    1985                 1990                 1995

Ile Val  Ser Ala Tyr Ile Val  Ala Val Tyr His Cys  Met Lys Asp
    2000                 2005                 2010

Gly Leu  Arg Arg Ser Ala Pro  Gly Ser Thr Pro Val  Arg Arg Arg
    2015                 2020                 2025

Gly Ala  Ser Gln Leu Ser Gln  Glu Ala Glu Gly Ala  Val Gly Ala
    2030                 2035                 2040

Leu Pro  Gly Met Ile Thr Phe  Ser Gln Asp Tyr Val  Ala Asn Glu
    2045                 2050                 2055

Leu Thr  Gln Ser Phe Phe Thr  Ile Thr Gln Lys Ile  Gln Lys Lys
    2060                 2065                 2070

Val Thr  Gly Ser Arg Asn Ser  Thr Glu Leu Ser Glu  Met Phe Pro
    2075                 2080                 2085

Val Leu  Pro Gly Ser His Leu  Leu Leu Asn Asn Pro  Ala Leu Glu
    2090                 2095                 2100

Phe Ile  Lys Tyr Val Cys Lys  Val Leu Ser Leu Asp  Thr Asn Ile
    2105                 2110                 2115

Thr Asn  Gln Val Asn Lys Leu  Asn Arg Asp Leu Leu  Arg Leu Val
    2120                 2125                 2130

Asp Val  Gly Glu Phe Ser Glu  Glu Ala Gln Phe Arg  Asp Pro Cys
    2135                 2140                 2145

Arg Ser  Tyr Val Leu Pro Glu  Val Ile Cys Arg Ser  Cys Asn Phe
    2150                 2155                 2160

Cys Arg  Asp Leu Asp Leu Cys  Lys Asp Ser Ser Phe  Ser Glu Asp
    2165                 2170                 2175

Gly Ala  Val Leu Pro Gln Trp  Leu Cys Ser Asn Cys  Gln Ala Pro
    2180                 2185                 2190

Tyr Asp  Ser Ser Ala Ile Glu  Met Thr Leu Val Glu  Val Leu Gln
    2195                 2200                 2205

Lys Lys  Leu Met Ala Phe Thr  Leu Gln Asp Leu Val  Cys Leu Lys
    2210                 2215                 2220

Cys Arg  Gly Val Lys Glu Thr  Ser Met Pro Val Tyr  Cys Ser Cys
    2225                 2230                 2235

Ala Gly  Asp Phe Ala Leu Thr  Ile His Thr Gln Val  Phe Met Glu
    2240                 2245                 2250

Gln Ile  Gly Ile Phe Arg Asn  Ile Ala Gln His Tyr  Gly Met Ser
    2255                 2260                 2265

Tyr Leu  Leu Glu Thr Leu Glu  Trp Leu Leu Gln Lys  Asn Pro Gln
    2270                 2275                 2280

Leu Gly  His
    2285
```

<210> SEQ ID NO 17
<211> LENGTH: 8412
<212> TYPE: DNA

```
<213> ORGANISM: Homo sapiens
<220> FEATURE:
<221> NAME/KEY: CDS
<222> LOCATION: (305)..(2446)
<223> OTHER INFORMATION: POLH

<400> SEQUENCE: 17

agccgcgtca acggcccttc gcagcgggcg cgctgtcaga cctcagtctg gcggctgcat      60

tgctgggcgc gccgctctcg tctgatccct gctggggacg gttgcccggg caggatcctt     120

tacgatccct tctcggtttc tccgtcgtca cagggaataa atctcgctcg aaactcactg     180

gaccgctcct agaaaggcga aaagatattc aggagccctt ccattttcct tccagtaggc     240

accgaaccca gcattttcgg caaccgctgc tggcagtttt gccaggtgtt tgttaccttg     300

aaaa atg gct act gga cag gat cga gtg gtt gct ctc gtg gac atg gac      349
     Met Ala Thr Gly Gln Asp Arg Val Val Ala Leu Val Asp Met Asp
     1               5                   10                  15

tgt ttt ttt gtt caa gtg gag cag cgg caa aat cct cat ttg agg aat       397
Cys Phe Phe Val Gln Val Glu Gln Arg Gln Asn Pro His Leu Arg Asn
                20                  25                  30

aaa cct tgt gca gtt gta cag tac aaa tca tgg aag ggt ggt gga ata       445
Lys Pro Cys Ala Val Val Gln Tyr Lys Ser Trp Lys Gly Gly Gly Ile
            35                  40                  45

att gca gtg agt tat gaa gct cgt gca ttt gga gtc act aga agt atg       493
Ile Ala Val Ser Tyr Glu Ala Arg Ala Phe Gly Val Thr Arg Ser Met
        50                  55                  60

tgg gca gat gat gct aag aag tta tgt cca gat ctt cta ctg gca caa       541
Trp Ala Asp Asp Ala Lys Lys Leu Cys Pro Asp Leu Leu Leu Ala Gln
    65                  70                  75

gtt cgt gag tcc cgt ggg aaa gct aac ctc acc aag tac cgg gaa gcc       589
Val Arg Glu Ser Arg Gly Lys Ala Asn Leu Thr Lys Tyr Arg Glu Ala
80                  85                  90                  95

agt gtt gaa gtg atg gag ata atg tct cgt ttt gct gtg att gaa cgt       637
Ser Val Glu Val Met Glu Ile Met Ser Arg Phe Ala Val Ile Glu Arg
                100                 105                 110

gcc agc att gat gag gct tac gta gat ctg acc agt gct gta caa gag       685
Ala Ser Ile Asp Glu Ala Tyr Val Asp Leu Thr Ser Ala Val Gln Glu
            115                 120                 125

aga cta caa aag cta caa ggt cag cct atc tcg gca gac ttg ttg cca       733
Arg Leu Gln Lys Leu Gln Gly Gln Pro Ile Ser Ala Asp Leu Leu Pro
        130                 135                 140

agc act tac att gaa ggg ttg ccc caa ggc cct aca acg gca gaa gag       781
Ser Thr Tyr Ile Glu Gly Leu Pro Gln Gly Pro Thr Thr Ala Glu Glu
    145                 150                 155

act gtt cag aaa gag ggg atg cga aaa caa ggc tta ttt caa tgg ctc       829
Thr Val Gln Lys Glu Gly Met Arg Lys Gln Gly Leu Phe Gln Trp Leu
160                 165                 170                 175

gat tct ctt cag att gat aac ctc acc tct cca gac ctg cag ctc acc       877
Asp Ser Leu Gln Ile Asp Asn Leu Thr Ser Pro Asp Leu Gln Leu Thr
                180                 185                 190

gtg gga gca gtg att gtg gag gaa atg aga gca gcc ata gag agg gag       925
Val Gly Ala Val Ile Val Glu Glu Met Arg Ala Ala Ile Glu Arg Glu
            195                 200                 205

act ggt ttt cag tgt tca gct gga att tca cac aat aag gtc ctg gca       973
Thr Gly Phe Gln Cys Ser Ala Gly Ile Ser His Asn Lys Val Leu Ala
        210                 215                 220

aaa ctg gcc tgt gga cta aac aag ccc aac cgc caa acc ctg gtt tca      1021
Lys Leu Ala Cys Gly Leu Asn Lys Pro Asn Arg Gln Thr Leu Val Ser
    225                 230                 235

cat ggg tca gtc cca cag ctc ttc agc caa atg ccc att cgc aaa atc      1069
```

```
His Gly Ser Val Pro Gln Leu Phe Ser Gln Met Pro Ile Arg Lys Ile
240                 245                 250                 255

cgt agt ctt gga gga aag cta ggg gcc tct gtc att gag atc cta ggg     1117
Arg Ser Leu Gly Gly Lys Leu Gly Ala Ser Val Ile Glu Ile Leu Gly
                260                 265                 270

ata gaa tac atg ggt gaa ctg acc cag ttc act gaa tcc cag ctc cag     1165
Ile Glu Tyr Met Gly Glu Leu Thr Gln Phe Thr Glu Ser Gln Leu Gln
            275                 280                 285

agt cat ttt ggg gag aag aat ggg tct tgg cta tat gcc atg tgc cga     1213
Ser His Phe Gly Glu Lys Asn Gly Ser Trp Leu Tyr Ala Met Cys Arg
        290                 295                 300

ggg att gaa cat gat cca gtt aaa ccc agg caa cta ccc aaa acc att     1261
Gly Ile Glu His Asp Pro Val Lys Pro Arg Gln Leu Pro Lys Thr Ile
    305                 310                 315

ggc tgt agt aag aac ttc cca gga aaa aca gct ctt gct act cgg gaa     1309
Gly Cys Ser Lys Asn Phe Pro Gly Lys Thr Ala Leu Ala Thr Arg Glu
320                 325                 330                 335

cag gta caa tgg tgg ctg ttg caa tta gcc cag gaa cta gag gag aga     1357
Gln Val Gln Trp Trp Leu Leu Gln Leu Ala Gln Glu Leu Glu Glu Arg
                340                 345                 350

ctg act aaa gac cga aat gat aat gac agg gta gcc acc cag ctg gtt     1405
Leu Thr Lys Asp Arg Asn Asp Asn Asp Arg Val Ala Thr Gln Leu Val
            355                 360                 365

gtg agc att cgt gta caa gga gac aaa cgc ctc agc agc ctg cgc cgc     1453
Val Ser Ile Arg Val Gln Gly Asp Lys Arg Leu Ser Ser Leu Arg Arg
        370                 375                 380

tgc tgt gcc ctt acc cgc tat gat gct cac aag atg agc cat gat gca     1501
Cys Cys Ala Leu Thr Arg Tyr Asp Ala His Lys Met Ser His Asp Ala
    385                 390                 395

ttt act gtc atc aag aac tgt aat act tct gga atc cag aca gaa tgg     1549
Phe Thr Val Ile Lys Asn Cys Asn Thr Ser Gly Ile Gln Thr Glu Trp
400                 405                 410                 415

tct cct cct ctc aca atg ctt ttc ctc tgt gct aca aaa ttt tct gcc     1597
Ser Pro Pro Leu Thr Met Leu Phe Leu Cys Ala Thr Lys Phe Ser Ala
                420                 425                 430

tct gcc cct tca tct tct aca gac atc acc agc ttc ttg agc agt gac     1645
Ser Ala Pro Ser Ser Ser Thr Asp Ile Thr Ser Phe Leu Ser Ser Asp
            435                 440                 445

cca agt tct ctg cca aag gtg cca gtt acc agc tca gaa gct aag acc     1693
Pro Ser Ser Leu Pro Lys Val Pro Val Thr Ser Ser Glu Ala Lys Thr
        450                 455                 460

cag gga agt ggc cca gcg gtg aca gcc act aag aaa gca acc acg tct     1741
Gln Gly Ser Gly Pro Ala Val Thr Ala Thr Lys Lys Ala Thr Thr Ser
    465                 470                 475

ctg gaa tca ttc ttc caa aaa gct gca gaa agg cag aaa gtt aaa gaa     1789
Leu Glu Ser Phe Phe Gln Lys Ala Ala Glu Arg Gln Lys Val Lys Glu
480                 485                 490                 495

gct tcg ctt tca tct ctt act gct ccc act cag gct ccc atg agc aat     1837
Ala Ser Leu Ser Ser Leu Thr Ala Pro Thr Gln Ala Pro Met Ser Asn
                500                 505                 510

tca cca tcc aag ccc tca tta cct ttt caa acc agt caa agt aca gga     1885
Ser Pro Ser Lys Pro Ser Leu Pro Phe Gln Thr Ser Gln Ser Thr Gly
            515                 520                 525

act gag ccc ttc ttt aag cag aaa agt ctg ctt cta aag cag aaa cag     1933
Thr Glu Pro Phe Phe Lys Gln Lys Ser Leu Leu Leu Lys Gln Lys Gln
        530                 535                 540

ctt aat aat tct tca gtt tct tcc ccc caa caa aac cca tgg tcc aac     1981
Leu Asn Asn Ser Ser Val Ser Ser Pro Gln Gln Asn Pro Trp Ser Asn
    545                 550                 555
```

```
tgt aaa gca tta cca aac tct tta cca aca gag tat cca ggg tgt gtc     2029
Cys Lys Ala Leu Pro Asn Ser Leu Pro Thr Glu Tyr Pro Gly Cys Val
560                 565                 570                 575

cct gtt tgt gaa ggg gtg tcg aag cta gaa gaa tcc tct aaa gca act     2077
Pro Val Cys Glu Gly Val Ser Lys Leu Glu Glu Ser Ser Lys Ala Thr
                580                 585                 590

cct gca gag atg gat ttg gcc cac aac agc caa agc atg cac gcc tct     2125
Pro Ala Glu Met Asp Leu Ala His Asn Ser Gln Ser Met His Ala Ser
            595                 600                 605

tca gct tcc aaa tct gtg ctg gag gtg act cag aaa gca acc cca aat     2173
Ser Ala Ser Lys Ser Val Leu Glu Val Thr Gln Lys Ala Thr Pro Asn
        610                 615                 620

cca agt ctt cta gct gct gag gac caa gtg ccc tgt gag aag tgt ggc     2221
Pro Ser Leu Leu Ala Ala Glu Asp Gln Val Pro Cys Glu Lys Cys Gly
    625                 630                 635

tcc ctg gta ccg gta tgg gat atg cca gaa cac atg gac tat cat ttt     2269
Ser Leu Val Pro Val Trp Asp Met Pro Glu His Met Asp Tyr His Phe
640                 645                 650                 655

gca ttg gag ttg cag aaa tcc ttt ttg cag ccc cac tct tca aac ccc     2317
Ala Leu Glu Leu Gln Lys Ser Phe Leu Gln Pro His Ser Ser Asn Pro
                660                 665                 670

cag gtt gtt tct gcc gta tct cat caa ggc aaa aga aat ccc aag agc     2365
Gln Val Val Ser Ala Val Ser His Gln Gly Lys Arg Asn Pro Lys Ser
            675                 680                 685

cct ttg gcc tgc act aat aaa cgc ccc agg cct gag ggc atg caa aca     2413
Pro Leu Ala Cys Thr Asn Lys Arg Pro Arg Pro Glu Gly Met Gln Thr
        690                 695                 700

ttg gaa tca ttt ttt aag cca tta aca cat tag tgctgccctc aggcttgcct   2466
Leu Glu Ser Phe Phe Lys Pro Leu Thr His
    705                 710

gtaggattta atatttttta tctttacaga tctttatctt taatatttta tctttacaga   2526

tttccctgag aaagggaatt atgaaatttt taatacaaaa aataatccat ttaggtgctg   2586

agttacggtc ccatctcttc acaggcatgg attctaatcc cactgctgac agagatgtaa   2646

aaattcatcc taccagagtt tttaatcttt agcatttagg gaggcagtgt cataaagtaa   2706

aaagtgtgtg ggccttggag tctaagagac gtggttgcaa acttagctct ggttattgca   2766

atgagggcct tgaacaagtc attttcttca cattctcatc tgtaaaatgg agataatacc   2826

ttacagatta ttgcagatta ataacaatgt attcaaatta tgtaactcgg ccgggtacaa   2886

tggctcacgc ctgtaatcct aacactttgg gaggccgagg cagacagatc acctgaggtc   2946

aggagtttga gaccagcctg gccaacatgg caaaaccatc tctactaaaa atagaaaaat   3006

tagccaggca cgttccaggc acctgtgatc ccagctactt agaggctgag gcagaagaat   3066

tgctttaacc ttggaggcgg aggttgcatt gagctgagat catgctagtg cgctccagcc   3126

tgggcaacag agcgagactt catctcagaa aataaaaaat aggggccagg cacagtggct   3186

catacctgta atgccagcac tttgggaggc caaggcgggc agatcacgag gtcaggagtt   3246

tcagaccaat atggtgaaac cccatctcta ctaaaattac aaaaaaaatt atccaggcgt   3306

ggtggtgcac gcctgtaatc ccagctactc aggaggctaa ggcaggagaa tcacttgaac   3366

ccaggaggca gaggttggag tgagctgaga tcgcgccacc gcactccagc ctgggcaaca   3426

gagcgagact ccatctcaaa caaaaacaag aacaaaaaca aacataaagt tggcacagaa   3486

aagggaccaa gtttaaaaaa gggttttaaa tgtaatgaga cttgcatagt taaaaaaaaa   3546

aaagggatta tttttatttt tattttttat ttttgagacg gagtctccct ctgtcgtcag   3606

gctagaatgc agtggtgcgt tctcagctca ccgcaacctc cgtctcctgg gttcaagcaa   3666
```

```
ttctcctgcc tcagcctccc aagtagctgg gactacaggc acgtgctacc acactcagct   3726
aatttttgta tttttaatag agatgaggtt tcaccatgtt ggccaggatg gtctcgattg   3786
cttgacctca tgatccgcct gcctcgacct cccaaagttg ctgggattac agatgttagc   3846
caccgatcct ggccccccca aaaaaaggat tttaagaaaa acttctcttg gccgggcgca   3906
gtggctcacg cctgcaatcc cagcactttg ggaggccgag gcgggcggat cacaaggtca   3966
ggagatcgag accacggtga aaccccgtct ctactaaaaa atacaaaaaa aaattagccg   4026
ggtgcggtgg caggcgcctg tagtcccagc tactcgggag gctgaggcag gagaatggtg   4086
tgaacccggg aggcggagct tgcagtgagc cgagagcgcg ccactgcact ccagcctggg   4146
tgacagagcg agactccgtc tcaaaaaaaa aaaaaaaaga aaaacttctc tttaggctgg   4206
gtgcggttcc tcatgcctat aatcccagca tttagggagg ctgaggtgag tggattgcag   4266
gagctcagga gttcgagacc agcctgggca aggtggcaaa accccgtctc tactaaaaaa   4326
aattagctgg gcttggtggc aggcgcctgt aatcccaggt actcgggaga ctgaggcagg   4386
agaattgctt gaacctggaa ggtggaggtt gcagtgagtt gagatcacac caatgcactc   4446
cagccagggt gagagtgaga gactgtctca aaaaaaaaaa aaacaaaaga aaaacttctc   4506
tctagctctg tgacgggcag ttcagataat accttcacca gatttacctg ttttcagctg   4566
aagaatgtga gatgaagcct tgaaacccta aaagtgatat ggtaactagg gcaggtcttt   4626
ctgtacataa aagtgactta ataaacagtg aatttcatac aggtaaaccc tattataccc   4686
tcagttctaa ccattggcct atctcttgcg ttttgttcta atgtagaatt agattgctac   4746
ttgactagtt caggaactct gtttagatct gataagtcat aatcaaatct tgccaggcgt   4806
ggtggtttat gcctgttatc ccagcacttt gggaggccaa ggcaggtgga ccacgtgaag   4866
tcaggagttc aagacaagca tggccaacat ggcgaaaccc tgtatctact aaaaatacaa   4926
aaattagccg ggcatggtgg tgggtgcgtg taatcccagc tagttgggag gctgaggcag   4986
gagaatcact tgaacctggg aggcagaggt tgcagtgagc cgagatttcc actgcattcc   5046
agcctgggcg atagagtaac tctgtctcaa aaaaacccac tagatcatct ctagaacatt   5106
gctactccca agtatgattt gaggaacagc agcctcagta tcaccaggga acttattaga   5166
aatagtctca gcctcaccac tattcccact taattgtaat ctgatattaa caagatttcc   5226
caatgtgggt caggtgtggt ggctcatgcc tgtaatccca cactttggga ggccaaggtg   5286
ggcggatcac ttgaggctgg gagtttgaga ccaggctggc caacatgggg aaaacccatc   5346
tctacaaaaa ataacaaaaa ttaggtgtgt gtggtgacgc atgcgtgtaa tcccagctac   5406
ttaggaggct gaggcaggag aatcacttga atctgggagg cagaggttgt agtgagctga   5466
gattgtgcca ctgcactcca gtctgggcaa cagagtgaca ctgtttaaaa aaaaaaaaat   5526
tcccaatgtg ggccgggtgc agtggctcat gcctgtaatc ccagcacttt gggaggctga   5586
ggtgggtgta tcacgaggtc aagagatcaa ggccatcctg gccaacatgg tgaaaccccg   5646
tctctactga aaatacaact gggcgtggtg gtgcacgcct gtagtcccag ctacttggga   5706
ggctgaggca gaagaattgc ttgacctggg aggcggagct tgcagtgagc ccagatcgtg   5766
ccactgcact gcaccctggc gacacagcaa gactgtctca aaaaaaaaaa aattcccaat   5826
gtgtatctta aagtttgaga aatgctgatc taaaagatac taatgaccag gtgtgtagag   5886
gacattttct taagccctta agtacaaatt taagaggtaa gtgcttcagc cattagggtt   5946
actggcttgt tcatctttcc cactgagtgt aaatatttag cttagggttt aaaatttgtt   6006
```

```
atgtagcttt ttgcacttgt ccatgtttat actactgtat tattattatt tttttttgag   6066
atggagtctc gctgtgtagc caggctggag tgcagtggtg caatcttggc tcactgcaac   6126
ctccgtctct cgggttcaag caattctcct gcctcagctt cccgaatagc tgagactaca   6186
agcgtgcacc accatgccca gctaattttt gtatttttag tagagacagg ttttcaccat   6246
gttggccagg ctggtctcta tctagacctc gtgatccatc cgcctcggcc tcccaaagtg   6306
ctgggattat aggcatgagc caccacgccc agcctatagt actgtattct tattctccac   6366
tcttgtgtgt gaaaagtcag ctcttttggc ttttctgtta tggggaaact tgaattacac   6426
agggaaccca actgaagaaa atgaactgaa gtaggtggcg ctgggtgaag tgggcccaga   6486
gaatggtgta cacatccctc ccatacatat acccaaactt ctattttttt atgtgacgga   6546
gtttctctca tcgccccggc tggaatgcaa tggcacgatc tcggctcact gcaacctccg   6606
cctcccgggt tcaagcgatt ctcctgcatc agcctcctga gtagctggga ttataggcat   6666
gcaccatcac gcctggctaa tttttgtatt tttagtagag atggggtttc gccacgttgg   6726
ccaggctggt cttgaactct tgatctcaag tgatccaccc gccctggcct cccaaagtgc   6786
tgggattaca ggcctgagcc accaggccag ccccaacttc tactttttat tttatttata   6846
aattgggggg ggggttctat atttagtttg aagaggtggg gaagatttga aaaccactag   6906
atttaccagg aaattttttt cttcaaaaat attttctgct tttatgatac ttgaatatct   6966
aataaaagac aatatttagc cagtcacggt ggctgatgct tgtaatccta acactttggg   7026
aggctgaggt gggtggacta ctggagccct ggagttcaaa accggcctaa gccacatggc   7086
aaaacagtct ttacaaaaaa tacaaagatg gtggcttatg cctgtagtcg tacctactca   7146
ggaggctgag gttgggagga tcacctgaat ctgggagttt ggggctgcaa taagccatga   7206
ttgtgccgct gcactccagc ctgggtgaca gtctgagacc ctgtctcaaa aaaaaaaaaa   7266
aaaaaaaaaa aaaaaaagac tacattcact gtatacgtgg ccttttcccc ctaactagct   7326
atgtagcttc ttaaaggcaa agattcttca tagtgctttg cacatgatag gtgctgatac   7386
tcattggatg aatgtatata gtgaagaatt ttagatctga ttaccacaat tgggatcata   7446
aacatgtata aactccttgg gagtctgcct tatatacttt ttatccccct aaatgttcca   7506
ttaatgttgc agagaggctc actagttcct ggagatgtct tattaagtac tgaaatgtga   7566
ttttccaaaa ttttctttac aatacaggca aaagataagt aaattgtgga caaagctttc   7626
atctctatca gcagctatag agaggaagta aacagcttag cccctaatac aggaggaagt   7686
tgttcaacta caggcttgtt agtagcaagt taaaccagtt acattttata aaacagcctg   7746
agtggtaggg aagctatcac tttaatactc tagaggcaga atgccacata ggactttggg   7806
tcacatattt cttttccagg gtctcctcaa aatgcagttt ctatttacag ttgactttgg   7866
cccctattta cccataaaat gtcaaaatca agtagtatga acatggaaac aggagcaggg   7926
actaaggttt ggtcaagtgg ccctcattgt tccaagagta atttaggcta tgtaaacttg   7986
aaaaatatgg gaccagatta ccttttgtct ctaaattcta ctcttcttta agtagctggc   8046
actgtatctc tgccagggca cagaagtggg ctccttacta ttctgaccac tagcaagtgg   8106
ccaactcttc aaatacaggg tagctaccta tttcacgtga aaggcctcag tattctgctc   8166
acttgaacta cggaaaatag gccacaatac ttggttacaa tactggaact ctgaacctat   8226
gtggaggaga gaaaaacaat ggtgaacgag ataccagctg ggctctttcc acattcaggg   8286
ctcagcagtg ttggggtttc acttgtctct aatcctgaag aggtatctag ccctggaagg   8346
aagctgagcc tgtagctaac gcataagcac agtgtattca ataaaacatt tttattctgt   8406
```

acaata 8412

<210> SEQ ID NO 18
<211> LENGTH: 713
<212> TYPE: PRT
<213> ORGANISM: Homo sapiens

<400> SEQUENCE: 18

```
Met Ala Thr Gly Gln Asp Arg Val Val Ala Leu Val Asp Met Asp Cys
1               5                   10                  15

Phe Phe Val Gln Val Glu Gln Arg Gln Asn Pro His Leu Arg Asn Lys
            20                  25                  30

Pro Cys Ala Val Val Gln Tyr Lys Ser Trp Lys Gly Gly Gly Ile Ile
        35                  40                  45

Ala Val Ser Tyr Glu Ala Arg Ala Phe Gly Val Thr Arg Ser Met Trp
    50                  55                  60

Ala Asp Asp Ala Lys Lys Leu Cys Pro Asp Leu Leu Leu Ala Gln Val
65                  70                  75                  80

Arg Glu Ser Arg Gly Lys Ala Asn Leu Thr Lys Tyr Arg Glu Ala Ser
                85                  90                  95

Val Glu Val Met Glu Ile Met Ser Arg Phe Ala Val Ile Glu Arg Ala
            100                 105                 110

Ser Ile Asp Glu Ala Tyr Val Asp Leu Thr Ser Ala Val Gln Glu Arg
        115                 120                 125

Leu Gln Lys Leu Gln Gly Gln Pro Ile Ser Ala Asp Leu Leu Pro Ser
    130                 135                 140

Thr Tyr Ile Glu Gly Leu Pro Gln Gly Pro Thr Thr Ala Glu Glu Thr
145                 150                 155                 160

Val Gln Lys Glu Gly Met Arg Lys Gln Gly Leu Phe Gln Trp Leu Asp
                165                 170                 175

Ser Leu Gln Ile Asp Asn Leu Thr Ser Pro Asp Leu Gln Leu Thr Val
            180                 185                 190

Gly Ala Val Ile Val Glu Glu Met Arg Ala Ala Ile Glu Arg Glu Thr
        195                 200                 205

Gly Phe Gln Cys Ser Ala Gly Ile Ser His Asn Lys Val Leu Ala Lys
    210                 215                 220

Leu Ala Cys Gly Leu Asn Lys Pro Asn Arg Gln Thr Leu Val Ser His
225                 230                 235                 240

Gly Ser Val Pro Gln Leu Phe Ser Gln Met Pro Ile Arg Lys Ile Arg
                245                 250                 255

Ser Leu Gly Gly Lys Leu Gly Ala Ser Val Ile Glu Ile Leu Gly Ile
            260                 265                 270

Glu Tyr Met Gly Glu Leu Thr Gln Phe Thr Glu Ser Gln Leu Gln Ser
        275                 280                 285

His Phe Gly Glu Lys Asn Gly Ser Trp Leu Tyr Ala Met Cys Arg Gly
    290                 295                 300

Ile Glu His Asp Pro Val Lys Pro Arg Gln Leu Pro Lys Thr Ile Gly
305                 310                 315                 320

Cys Ser Lys Asn Phe Pro Gly Lys Thr Ala Leu Ala Thr Arg Glu Gln
                325                 330                 335

Val Gln Trp Trp Leu Leu Gln Leu Ala Gln Glu Leu Glu Glu Arg Leu
            340                 345                 350

Thr Lys Asp Arg Asn Asp Asn Asp Arg Val Ala Thr Gln Leu Val Val
        355                 360                 365
```

```
Ser Ile Arg Val Gln Gly Asp Lys Arg Leu Ser Ser Leu Arg Arg Cys
    370                 375                 380

Cys Ala Leu Thr Arg Tyr Asp Ala His Lys Met Ser His Asp Ala Phe
385                 390                 395                 400

Thr Val Ile Lys Asn Cys Asn Thr Ser Gly Ile Gln Thr Glu Trp Ser
                405                 410                 415

Pro Pro Leu Thr Met Leu Phe Leu Cys Ala Thr Lys Phe Ser Ala Ser
            420                 425                 430

Ala Pro Ser Ser Ser Thr Asp Ile Thr Ser Phe Leu Ser Ser Asp Pro
        435                 440                 445

Ser Ser Leu Pro Lys Val Pro Val Thr Ser Ser Glu Ala Lys Thr Gln
    450                 455                 460

Gly Ser Gly Pro Ala Val Thr Ala Thr Lys Lys Ala Thr Thr Ser Leu
465                 470                 475                 480

Glu Ser Phe Phe Gln Lys Ala Ala Glu Arg Gln Lys Val Lys Glu Ala
                485                 490                 495

Ser Leu Ser Ser Leu Thr Ala Pro Thr Gln Ala Pro Met Ser Asn Ser
            500                 505                 510

Pro Ser Lys Pro Ser Leu Pro Phe Gln Thr Ser Gln Ser Thr Gly Thr
        515                 520                 525

Glu Pro Phe Phe Lys Gln Lys Ser Leu Leu Leu Lys Gln Lys Gln Leu
    530                 535                 540

Asn Asn Ser Ser Val Ser Ser Pro Gln Gln Asn Pro Trp Ser Asn Cys
545                 550                 555                 560

Lys Ala Leu Pro Asn Ser Leu Pro Thr Glu Tyr Pro Gly Cys Val Pro
                565                 570                 575

Val Cys Glu Gly Val Ser Lys Leu Glu Glu Ser Ser Lys Ala Thr Pro
            580                 585                 590

Ala Glu Met Asp Leu Ala His Asn Ser Gln Ser Met His Ala Ser Ser
        595                 600                 605

Ala Ser Lys Ser Val Leu Glu Val Thr Gln Lys Ala Thr Pro Asn Pro
    610                 615                 620

Ser Leu Leu Ala Ala Glu Asp Gln Val Pro Cys Glu Lys Cys Gly Ser
625                 630                 635                 640

Leu Val Pro Val Trp Asp Met Pro Glu His Met Asp Tyr His Phe Ala
                645                 650                 655

Leu Glu Leu Gln Lys Ser Phe Leu Gln Pro His Ser Ser Asn Pro Gln
            660                 665                 670

Val Val Ser Ala Val Ser His Gln Gly Lys Arg Asn Pro Lys Ser Pro
        675                 680                 685

Leu Ala Cys Thr Asn Lys Arg Pro Arg Pro Glu Gly Met Gln Thr Leu
    690                 695                 700

Glu Ser Phe Phe Lys Pro Leu Thr His
705                 710
```

<210> SEQ ID NO 19
<211> LENGTH: 4717
<212> TYPE: DNA
<213> ORGANISM: Homo sapiens
<220> FEATURE:
<221> NAME/KEY: CDS
<222> LOCATION: (239)..(4111)
<223> OTHER INFORMATION: PER1

<400> SEQUENCE: 19

```
attatgcaac ccgcctcccc gcccgcccgg tggagcttcc actcggctgc gggctggagc      60

ggcggcgggc aggcgtgcgg aggacactcc tgcgaccagg tactggctgt gatcgaactt     120

ctcaaccctc agagacttag atcttccacc tcactccctc agccaagcct ccaggccccc     180

tcgtgcatcc gtggtggcct ctctgccttc tctgttctgt tctccccatg gcccagac       238

atg agt ggc ccc cta gaa ggg gct gat ggg gga ggg gac ccc agg cct      286

Met Ser Gly Pro Leu Glu Gly Ala Asp Gly Gly Gly Asp Pro Arg Pro
1               5                   10                  15

ggg gaa tca ttt tgt cct ggg ggc gtc cca tcc cct ggg ccc cca cag      334
Gly Glu Ser Phe Cys Pro Gly Gly Val Pro Ser Pro Gly Pro Pro Gln
            20                  25                  30

cac cgg cct tgc cca ggc ccc agc ctg gcc gat gac acc gat gcc aac      382
His Arg Pro Cys Pro Gly Pro Ser Leu Ala Asp Asp Thr Asp Ala Asn
        35                  40                  45

agc aat ggt tca agt ggc aat gag tcc aac ggg cat gag tct aga ggc      430
Ser Asn Gly Ser Ser Gly Asn Glu Ser Asn Gly His Glu Ser Arg Gly
    50                  55                  60

gca tct cag cgg agc tca cac agc tcc tcc tca ggc aac ggc aag gac      478
Ala Ser Gln Arg Ser Ser His Ser Ser Ser Ser Gly Asn Gly Lys Asp
65                  70                  75                  80

tca gcc ctg ctg gag acc act gag agc agc aag agc aca aac tct cag      526
Ser Ala Leu Leu Glu Thr Thr Glu Ser Ser Lys Ser Thr Asn Ser Gln
                85                  90                  95

agc cca tcc cca ccc agc agt tcc att gcc tac agc ctc ctg agt gcc      574
Ser Pro Ser Pro Pro Ser Ser Ser Ile Ala Tyr Ser Leu Leu Ser Ala
            100                 105                 110

agc tca gag cag gac aac ccg tcc acc agt ggc tgc agc agt gaa cag      622
Ser Ser Glu Gln Asp Asn Pro Ser Thr Ser Gly Cys Ser Ser Glu Gln
        115                 120                 125

tca gcc cgg gca agg act cag aag gaa ctc atg aca gca ctt cga gag      670
Ser Ala Arg Ala Arg Thr Gln Lys Glu Leu Met Thr Ala Leu Arg Glu
    130                 135                 140

ctc aag ctt cga ctg ccg cca gag cgc cgg ggc aag ggc cgc tct ggg      718
Leu Lys Leu Arg Leu Pro Pro Glu Arg Arg Gly Lys Gly Arg Ser Gly
145                 150                 155                 160

acc ctg gcc acg ctg cag tac gca ctg gcc tgt gtc aag cag gtg cag      766
Thr Leu Ala Thr Leu Gln Tyr Ala Leu Ala Cys Val Lys Gln Val Gln
                165                 170                 175

gcc aac cag gaa tac tac cag cag tgg agc ctg gag gag ggc gag cct      814
Ala Asn Gln Glu Tyr Tyr Gln Gln Trp Ser Leu Glu Glu Gly Glu Pro
            180                 185                 190

tgc tcc atg gac atg tcc acc tat acc ctg gag gag ctg gag cac atc      862
Cys Ser Met Asp Met Ser Thr Tyr Thr Leu Glu Glu Leu Glu His Ile
        195                 200                 205

acg tct gag tac aca ctt cag aac cag gat acc ttc tca gtg gct gtc      910
Thr Ser Glu Tyr Thr Leu Gln Asn Gln Asp Thr Phe Ser Val Ala Val
    210                 215                 220

tcc ttc ctg acg ggc cga atc gtc tac att tcg gag cag gca gcc gtc      958
Ser Phe Leu Thr Gly Arg Ile Val Tyr Ile Ser Glu Gln Ala Ala Val
225                 230                 235                 240

ctg ctg cgt tgc aag cgg gac gtg ttc cgg ggt acc cgc ttc tct gag     1006
Leu Leu Arg Cys Lys Arg Asp Val Phe Arg Gly Thr Arg Phe Ser Glu
                245                 250                 255

ctc ctg gct ccc cag gat gtg gga gtc ttc tat ggt tcc act gct cca     1054
Leu Leu Ala Pro Gln Asp Val Gly Val Phe Tyr Gly Ser Thr Ala Pro
            260                 265                 270

tct cgc ctg ccc acc tgg ggc aca ggg gcc tca gca ggt tca ggc ctc     1102
Ser Arg Leu Pro Thr Trp Gly Thr Gly Ala Ser Ala Gly Ser Gly Leu
```

```
        275                 280                 285

agg gac ttt acc cag gag aag tcc gtc ttc tgc cgt atc aga gga ggt      1150
Arg Asp Phe Thr Gln Glu Lys Ser Val Phe Cys Arg Ile Arg Gly Gly
    290                 295                 300

cct gac cgg gat cca ggg cct cgg tac cag cca ttc cgc cta acc ccg      1198
Pro Asp Arg Asp Pro Gly Pro Arg Tyr Gln Pro Phe Arg Leu Thr Pro
305                 310                 315                 320

tat gtg acc aag atc cgg gtc tca gat ggg gcc cct gca cag ccg tgc      1246
Tyr Val Thr Lys Ile Arg Val Ser Asp Gly Ala Pro Ala Gln Pro Cys
                325                 330                 335

tgc ctg ctg att gca gag cgc atc cat tcg ggt tac gaa gct ccc cgg      1294
Cys Leu Leu Ile Ala Glu Arg Ile His Ser Gly Tyr Glu Ala Pro Arg
            340                 345                 350

ata ccc cct gac aag agg att ttc act acg cgg cac aca ccc agc tgc      1342
Ile Pro Pro Asp Lys Arg Ile Phe Thr Thr Arg His Thr Pro Ser Cys
        355                 360                 365

ctc ttc cag gat gtg gat gaa agg gct gcc ccc ctg ctg ggc tac ctg      1390
Leu Phe Gln Asp Val Asp Glu Arg Ala Ala Pro Leu Leu Gly Tyr Leu
    370                 375                 380

ccc cag gac ctc ctg ggg gcc cca gtg ctc ctg ttc ctg cat cct gag      1438
Pro Gln Asp Leu Leu Gly Ala Pro Val Leu Leu Phe Leu His Pro Glu
385                 390                 395                 400

gac cga ccc ctc atg ctg gct atc cac aag aag att ctg cag ttg gcg      1486
Asp Arg Pro Leu Met Leu Ala Ile His Lys Lys Ile Leu Gln Leu Ala
                405                 410                 415

ggc cag ccc ttt gac cac tcc cct atc cgc ttc tgt gcc cgc aac ggg      1534
Gly Gln Pro Phe Asp His Ser Pro Ile Arg Phe Cys Ala Arg Asn Gly
            420                 425                 430

gag tat gtc acc atg gac acc agc tgg gct ggc ttt gtg cac ccc tgg      1582
Glu Tyr Val Thr Met Asp Thr Ser Trp Ala Gly Phe Val His Pro Trp
        435                 440                 445

agc cgc aag gta gcc ttc gtg ttg ggc cgc cac aaa gta cgc acg gcc      1630
Ser Arg Lys Val Ala Phe Val Leu Gly Arg His Lys Val Arg Thr Ala
    450                 455                 460

ccc ctg aat gag gac gtg ttc act ccc ccg gcc ccc agc cca gct ccc      1678
Pro Leu Asn Glu Asp Val Phe Thr Pro Pro Ala Pro Ser Pro Ala Pro
465                 470                 475                 480

tcc ctg gac act gat atc cag gag ctg tca gag cag atc cac cgg ctg      1726
Ser Leu Asp Thr Asp Ile Gln Glu Leu Ser Glu Gln Ile His Arg Leu
                485                 490                 495

ctg ctg cag ccc gtc cac agc ccc agc ccc acg gga ctc tgt gga gtc      1774
Leu Leu Gln Pro Val His Ser Pro Ser Pro Thr Gly Leu Cys Gly Val
            500                 505                 510

ggc gcc gtg aca tcc cca ggc cct ctc cac agc cct ggg tcc tcc agt      1822
Gly Ala Val Thr Ser Pro Gly Pro Leu His Ser Pro Gly Ser Ser Ser
        515                 520                 525

gat agc aac ggg ggt gat gca gag ggg cct ggg cct cct gcg cca gtg      1870
Asp Ser Asn Gly Gly Asp Ala Glu Gly Pro Gly Pro Pro Ala Pro Val
    530                 535                 540

act ttc cag cag atc tgt aag gat gtg cat ctg gtg aag cac cag ggc      1918
Thr Phe Gln Gln Ile Cys Lys Asp Val His Leu Val Lys His Gln Gly
545                 550                 555                 560

cag cag ctt ttt att gag tct cgg gcc cgg cct cag tcc cgg ccc cgc      1966
Gln Gln Leu Phe Ile Glu Ser Arg Ala Arg Pro Gln Ser Arg Pro Arg
                565                 570                 575

ctc cct gct aca ggc acg ttc aag gcc aag gcc ctt ccc tgc caa tcc      2014
Leu Pro Ala Thr Gly Thr Phe Lys Ala Lys Ala Leu Pro Cys Gln Ser
            580                 585                 590

cca gac cca gag ctg gag gcg ggt tct gct ccc gtc cag gcc cca cta      2062
```

```
Pro Asp Pro Glu Leu Glu Ala Gly Ser Ala Pro Val Gln Ala Pro Leu
        595                 600                 605

gcc ttg gtc cct gag gag gcc gag agg aaa gaa gcc tcc agc tgc tcc      2110
Ala Leu Val Pro Glu Glu Ala Glu Arg Lys Glu Ala Ser Ser Cys Ser
    610                 615                 620

tac cag cag atc aac tgc ctg gac agc atc ctc agg tac ctg gag agc      2158
Tyr Gln Gln Ile Asn Cys Leu Asp Ser Ile Leu Arg Tyr Leu Glu Ser
625                 630                 635                 640

tgc aac ctc ccc agc acc act aag cgt aaa tgt gcc tcc tcc tcc tcc      2206
Cys Asn Leu Pro Ser Thr Thr Lys Arg Lys Cys Ala Ser Ser Ser Ser
                645                 650                 655

tat acc acc tcc tca gcc tct gac gac gac agg cag agg aca ggt cca      2254
Tyr Thr Thr Ser Ser Ala Ser Asp Asp Asp Arg Gln Arg Thr Gly Pro
            660                 665                 670

gtc tct gtg ggg acc aag aaa gat ccg ccg tca gca gcg ctg tct ggg      2302
Val Ser Val Gly Thr Lys Lys Asp Pro Pro Ser Ala Ala Leu Ser Gly
        675                 680                 685

gag ggg gcc acc cca cgg aag gag cca gtg gtg gga ggc acc ctg agc      2350
Glu Gly Ala Thr Pro Arg Lys Glu Pro Val Val Gly Gly Thr Leu Ser
    690                 695                 700

ccg ctc gcc ctg gcc aat aag gcg gag agt gtg gtg tcc gtc acc agt      2398
Pro Leu Ala Leu Ala Asn Lys Ala Glu Ser Val Val Ser Val Thr Ser
705                 710                 715                 720

cag tgt agc ttc agc tcc acc atc gtc cat gtg gga gac aag aag ccc      2446
Gln Cys Ser Phe Ser Ser Thr Ile Val His Val Gly Asp Lys Lys Pro
                725                 730                 735

ccg gag tcg gac atc atc atg atg gag gac ctg cct ggc cta gcc cca      2494
Pro Glu Ser Asp Ile Ile Met Met Glu Asp Leu Pro Gly Leu Ala Pro
            740                 745                 750

ggc cca gcc ccc agc cca gcc ccc agc ccc aca gta gcc cct gac cca      2542
Gly Pro Ala Pro Ser Pro Ala Pro Ser Pro Thr Val Ala Pro Asp Pro
        755                 760                 765

gcc cca gac gcc tac cgt cca gtg ggg ctg acc aag gcc gtg ctg tcc      2590
Ala Pro Asp Ala Tyr Arg Pro Val Gly Leu Thr Lys Ala Val Leu Ser
    770                 775                 780

ctg cac aca cag aag gaa gag caa gcc ttc ctc agc cgc ttc cga gac      2638
Leu His Thr Gln Lys Glu Glu Gln Ala Phe Leu Ser Arg Phe Arg Asp
785                 790                 795                 800

ctg ggc agg ctg cgt gga ctc gac agc tct tcc aca gct ccc tca gcc      2686
Leu Gly Arg Leu Arg Gly Leu Asp Ser Ser Ser Thr Ala Pro Ser Ala
                805                 810                 815

ctt ggc gag cga ggc tgc cac cac ggc ccc gca ccc cca agc cgc cga      2734
Leu Gly Glu Arg Gly Cys His His Gly Pro Ala Pro Pro Ser Arg Arg
            820                 825                 830

cac cac tgc cga tcc aaa gcc aag cgc tca cgc cac cac cag aac cct      2782
His His Cys Arg Ser Lys Ala Lys Arg Ser Arg His His Gln Asn Pro
        835                 840                 845

cgg gct gaa gcg ccc tgc tat gtc tca cac ccc tca ccc gtg cca ccc      2830
Arg Ala Glu Ala Pro Cys Tyr Val Ser His Pro Ser Pro Val Pro Pro
    850                 855                 860

tcc acc ccc tgg ccc acc cca cca gcc act acc ccc ttc cca gcg gtt      2878
Ser Thr Pro Trp Pro Thr Pro Pro Ala Thr Thr Pro Phe Pro Ala Val
865                 870                 875                 880

gtc cag ccc tac cct ctc cca gtg ttc tct cct cga gga ggc ccc cag      2926
Val Gln Pro Tyr Pro Leu Pro Val Phe Ser Pro Arg Gly Gly Pro Gln
                885                 890                 895

cct ctt ccc cct gct ccc aca tct gtg ccc cca gct gct ttc ccc gcc      2974
Pro Leu Pro Pro Ala Pro Thr Ser Val Pro Pro Ala Ala Phe Pro Ala
            900                 905                 910
```

-continued

```
cct ttg gtg acc cca atg gtg gcc ttg gtg ctc cct aac tat ctg ttc     3022
Pro Leu Val Thr Pro Met Val Ala Leu Val Leu Pro Asn Tyr Leu Phe
        915                 920                 925

cca acc cca tcc agc tat cct tat ggg gca ctc cag acc cct gct gaa     3070
Pro Thr Pro Ser Ser Tyr Pro Tyr Gly Ala Leu Gln Thr Pro Ala Glu
    930                 935                 940

ggg cct ccc act cct gcc tcg cac tcc cct tct cca tcc ttg ccc gcc     3118
Gly Pro Pro Thr Pro Ala Ser His Ser Pro Ser Pro Ser Leu Pro Ala
945                 950                 955                 960

ctc gcc ccg agt cct cct cac cgc ccg gac tct cca ctg ttc aac tcg     3166
Leu Ala Pro Ser Pro Pro His Arg Pro Asp Ser Pro Leu Phe Asn Ser
            965                 970                 975

aga tgc agc tct cca ctc cag ctc aat ctg ctg cag ctg gag gag ctc     3214
Arg Cys Ser Ser Pro Leu Gln Leu Asn Leu Leu Gln Leu Glu Glu Leu
            980                 985                 990

ccc cgt gct gag ggg gct gct gtt  gca gga ggc cct ggg  agc agt gcc   3262
Pro Arg Ala Glu Gly Ala Ala Val  Ala Gly Gly Pro Gly  Ser Ser Ala
        995                 1000                1005

ggg ccc  cca cct ccc agt gcg  gag gct gct gag cca  gag gcc aga      3307
Gly Pro  Pro Pro Pro Ser Ala  Glu Ala Ala Glu Pro  Glu Ala Arg
    1010                 1015                 1020

ctg gcg  gag gtc act gag tcc  tcc aat cag gac gca  ctt tcc ggc      3352
Leu Ala  Glu Val Thr Glu Ser  Ser Asn Gln Asp Ala  Leu Ser Gly
    1025                 1030                 1035

tcc agt  gac ctg ctc gaa ctt  ctg ctg caa gag gac  tcg cgc tcc      3397
Ser Ser  Asp Leu Leu Glu Leu  Leu Leu Gln Glu Asp  Ser Arg Ser
    1040                 1045                 1050

ggc aca  ggc tcc gca gcc tcg  ggc tcc ttg ggc tct  ggc ttg ggc      3442
Gly Thr  Gly Ser Ala Ala Ser  Gly Ser Leu Gly Ser  Gly Leu Gly
    1055                 1060                 1065

tct ggg  tct ggt tca ggc tcc  cat gaa ggg ggc agc  acc tca gcc      3487
Ser Gly  Ser Gly Ser Gly Ser  His Glu Gly Gly Ser  Thr Ser Ala
    1070                 1075                 1080

agc atc  act cgc agc agc cag  agc agc cac aca agc  aaa tac ttt      3532
Ser Ile  Thr Arg Ser Ser Gln  Ser Ser His Thr Ser  Lys Tyr Phe
    1085                 1090                 1095

ggc agc  atc gac tct tcc gag  gct gag gct ggg gct  gct cgg ggc      3577
Gly Ser  Ile Asp Ser Ser Glu  Ala Glu Ala Gly Ala  Ala Arg Gly
    1100                 1105                 1110

ggg gct  gag cct ggg gac cag  gtg att aag tac gtg  ctc cag gat      3622
Gly Ala  Glu Pro Gly Asp Gln  Val Ile Lys Tyr Val  Leu Gln Asp
    1115                 1120                 1125

ccc att  tgg ctg ctc atg gcc  aat gct gac cag cgc  gtc atg atg      3667
Pro Ile  Trp Leu Leu Met Ala  Asn Ala Asp Gln Arg  Val Met Met
    1130                 1135                 1140

acc tac  cag gtg ccc tcc agg  gac atg acc tct gtg  ctg aag cag      3712
Thr Tyr  Gln Val Pro Ser Arg  Asp Met Thr Ser Val  Leu Lys Gln
    1145                 1150                 1155

gat cgg  gag cgg ctc cga gcc  atg cag aag cag cag  cct cgg ttt      3757
Asp Arg  Glu Arg Leu Arg Ala  Met Gln Lys Gln Gln  Pro Arg Phe
    1160                 1165                 1170

tct gag  gac cag cgg cgg gaa  ctg ggt gct gtg cac  tcc tgg gtc      3802
Ser Glu  Asp Gln Arg Arg Glu  Leu Gly Ala Val His  Ser Trp Val
    1175                 1180                 1185

cgg aag  ggc caa ctg cct cgg  gct ctt gat gtg atg  gcc tgt gtg      3847
Arg Lys  Gly Gln Leu Pro Arg  Ala Leu Asp Val Met  Ala Cys Val
    1190                 1195                 1200

gac tgt  ggg agc agc acc caa  gat cct ggt cac cct  gat gac cca      3892
Asp Cys  Gly Ser Ser Thr Gln  Asp Pro Gly His Pro  Asp Asp Pro
    1205                 1210                 1215
```

```
ctc ttc  tca gag ctg gat gga  ctg ggg ctg gag ccc  atg gaa gag      3937
Leu Phe  Ser Glu Leu Asp Gly  Leu Gly Leu Glu Pro  Met Glu Glu
    1220                 1225                 1230

ggt gga  ggc gag cag ggc agc  agc ggt ggc ggc agt  ggt gag gga      3982
Gly Gly  Gly Glu Gln Gly Ser  Ser Gly Gly Gly Ser  Gly Glu Gly
    1235                 1240                 1245

gag ggc  tgc gag gag gcc caa  ggc ggg gcc aag gct  tca agc tct      4027
Glu Gly  Cys Glu Glu Ala Gln  Gly Gly Ala Lys Ala  Ser Ser Ser
    1250                 1255                 1260

cag gac  ttg gct atg gag gag  gag gaa gaa ggc agg  agc tca tcc      4072
Gln Asp  Leu Ala Met Glu Glu  Glu Glu Glu Gly Arg  Ser Ser Ser
    1265                 1270                 1275

agt cca  gcc tta cct aca gca  gga aac tgc acc agc  tag actccattct   4121
Ser Pro  Ala Leu Pro Thr Ala  Gly Asn Cys Thr Ser
    1280                 1285                 1290

gggaccatct ccaggagtcc atgagaggct ttcttctcct atgtcccaat tctcagaact   4181

cagatgtggc tagaccaacc agtgggaaac tgccccagct tctcccacca tagggggccg   4241

gacccccatc accagcctag gatccagggg ctgcctctgg cctcttaggg agcagagagc   4301

agaactccgc agcccagccc agaggagtgt cacctcccac ctttggagag gaatccttcc   4361

ctcccctgga caaagttgct gacaagctgc tgaagtggcc tctccatatt ccagctgagc   4421

ctgaatctga ctcttgaggg ttggggctgc acttatttat tgcggggaga cagctctctc   4481

tcccacctcc tccccagatg ggaggagagc ctgaggccca agcaggaccc gggggttcca   4541

gcccctagct gctctggagt gggggaggtt ggtggaccat ggagtccctg gtgctgcccc   4601

tcaggtggga cccaggcgtt ctcagctgta ccctctgccg atggcatttg tgtttttgat   4661

atttgtgtct gttactactt ttttaataca aaaagataaa aacgcccaaa aaaaaa       4717


<210> SEQ ID NO 20
<211> LENGTH: 1290
<212> TYPE: PRT
<213> ORGANISM: Homo sapiens

<400> SEQUENCE: 20

Met Ser Gly Pro Leu Glu Gly Ala Asp Gly Gly Gly Asp Pro Arg Pro
1               5                   10                  15

Gly Glu Ser Phe Cys Pro Gly Gly Val Pro Ser Pro Gly Pro Pro Gln
            20                  25                  30

His Arg Pro Cys Pro Gly Pro Ser Leu Ala Asp Asp Thr Asp Ala Asn
        35                  40                  45

Ser Asn Gly Ser Ser Gly Asn Glu Ser Asn Gly His Glu Ser Arg Gly
    50                  55                  60

Ala Ser Gln Arg Ser Ser His Ser Ser Ser Ser Gly Asn Gly Lys Asp
65                  70                  75                  80

Ser Ala Leu Leu Glu Thr Thr Glu Ser Ser Lys Ser Thr Asn Ser Gln
                85                  90                  95

Ser Pro Ser Pro Pro Ser Ser Ser Ile Ala Tyr Ser Leu Leu Ser Ala
            100                 105                 110

Ser Ser Glu Gln Asp Asn Pro Ser Thr Ser Gly Cys Ser Ser Glu Gln
        115                 120                 125

Ser Ala Arg Ala Arg Thr Gln Lys Glu Leu Met Thr Ala Leu Arg Glu
    130                 135                 140

Leu Lys Leu Arg Leu Pro Pro Glu Arg Arg Gly Lys Gly Arg Ser Gly
145                 150                 155                 160
```

```
Thr Leu Ala Thr Leu Gln Tyr Ala Leu Ala Cys Val Lys Gln Val Gln
                165                 170                 175

Ala Asn Gln Glu Tyr Tyr Gln Gln Trp Ser Leu Glu Glu Gly Glu Pro
            180                 185                 190

Cys Ser Met Asp Met Ser Thr Tyr Thr Leu Glu Glu Leu Glu His Ile
        195                 200                 205

Thr Ser Glu Tyr Thr Leu Gln Asn Gln Asp Thr Phe Ser Val Ala Val
    210                 215                 220

Ser Phe Leu Thr Gly Arg Ile Val Tyr Ile Ser Glu Gln Ala Ala Val
225                 230                 235                 240

Leu Leu Arg Cys Lys Arg Asp Val Phe Arg Gly Thr Arg Phe Ser Glu
                245                 250                 255

Leu Leu Ala Pro Gln Asp Val Gly Val Phe Tyr Gly Ser Thr Ala Pro
            260                 265                 270

Ser Arg Leu Pro Thr Trp Gly Thr Gly Ala Ser Ala Gly Ser Gly Leu
        275                 280                 285

Arg Asp Phe Thr Gln Glu Lys Ser Val Phe Cys Arg Ile Arg Gly Gly
    290                 295                 300

Pro Asp Arg Asp Pro Gly Pro Arg Tyr Gln Pro Phe Arg Leu Thr Pro
305                 310                 315                 320

Tyr Val Thr Lys Ile Arg Val Ser Asp Gly Ala Pro Ala Gln Pro Cys
                325                 330                 335

Cys Leu Leu Ile Ala Glu Arg Ile His Ser Gly Tyr Glu Ala Pro Arg
            340                 345                 350

Ile Pro Pro Asp Lys Arg Ile Phe Thr Thr Arg His Thr Pro Ser Cys
        355                 360                 365

Leu Phe Gln Asp Val Asp Glu Arg Ala Ala Pro Leu Leu Gly Tyr Leu
    370                 375                 380

Pro Gln Asp Leu Leu Gly Ala Pro Val Leu Leu Phe Leu His Pro Glu
385                 390                 395                 400

Asp Arg Pro Leu Met Leu Ala Ile His Lys Lys Ile Leu Gln Leu Ala
                405                 410                 415

Gly Gln Pro Phe Asp His Ser Pro Ile Arg Phe Cys Ala Arg Asn Gly
            420                 425                 430

Glu Tyr Val Thr Met Asp Thr Ser Trp Ala Gly Phe Val His Pro Trp
        435                 440                 445

Ser Arg Lys Val Ala Phe Val Leu Gly Arg His Lys Val Arg Thr Ala
    450                 455                 460

Pro Leu Asn Glu Asp Val Phe Thr Pro Pro Ala Pro Ser Pro Ala Pro
465                 470                 475                 480

Ser Leu Asp Thr Asp Ile Gln Glu Leu Ser Glu Gln Ile His Arg Leu
                485                 490                 495

Leu Leu Gln Pro Val His Ser Pro Ser Pro Thr Gly Leu Cys Gly Val
            500                 505                 510

Gly Ala Val Thr Ser Pro Gly Pro Leu His Ser Pro Gly Ser Ser Ser
        515                 520                 525

Asp Ser Asn Gly Gly Asp Ala Glu Gly Pro Gly Pro Pro Ala Pro Val
    530                 535                 540

Thr Phe Gln Gln Ile Cys Lys Asp Val His Leu Val Lys His Gln Gly
545                 550                 555                 560

Gln Gln Leu Phe Ile Glu Ser Arg Ala Arg Pro Gln Ser Arg Pro Arg
                565                 570                 575

Leu Pro Ala Thr Gly Thr Phe Lys Ala Lys Ala Leu Pro Cys Gln Ser
```

```
        580                 585                 590

Pro Asp Pro Glu Leu Glu Ala Gly Ser Ala Pro Val Gln Ala Pro Leu
    595                 600                 605

Ala Leu Val Pro Glu Glu Ala Glu Arg Lys Glu Ala Ser Ser Cys Ser
    610                 615                 620

Tyr Gln Gln Ile Asn Cys Leu Asp Ser Ile Leu Arg Tyr Leu Glu Ser
625                 630                 635                 640

Cys Asn Leu Pro Ser Thr Thr Lys Arg Lys Cys Ala Ser Ser Ser Ser
                645                 650                 655

Tyr Thr Thr Ser Ser Ala Ser Asp Asp Asp Arg Gln Arg Thr Gly Pro
            660                 665                 670

Val Ser Val Gly Thr Lys Lys Asp Pro Pro Ser Ala Ala Leu Ser Gly
        675                 680                 685

Glu Gly Ala Thr Pro Arg Lys Glu Pro Val Val Gly Gly Thr Leu Ser
    690                 695                 700

Pro Leu Ala Leu Ala Asn Lys Ala Glu Ser Val Val Ser Val Thr Ser
705                 710                 715                 720

Gln Cys Ser Phe Ser Ser Thr Ile Val His Val Gly Asp Lys Lys Pro
                725                 730                 735

Pro Glu Ser Asp Ile Ile Met Met Glu Asp Leu Pro Gly Leu Ala Pro
            740                 745                 750

Gly Pro Ala Pro Ser Pro Ala Pro Ser Pro Thr Val Ala Pro Asp Pro
        755                 760                 765

Ala Pro Asp Ala Tyr Arg Pro Val Gly Leu Thr Lys Ala Val Leu Ser
    770                 775                 780

Leu His Thr Gln Lys Glu Glu Gln Ala Phe Leu Ser Arg Phe Arg Asp
785                 790                 795                 800

Leu Gly Arg Leu Arg Gly Leu Asp Ser Ser Ser Thr Ala Pro Ser Ala
                805                 810                 815

Leu Gly Glu Arg Gly Cys His His Gly Pro Ala Pro Pro Ser Arg Arg
            820                 825                 830

His His Cys Arg Ser Lys Ala Lys Arg Ser Arg His His Gln Asn Pro
        835                 840                 845

Arg Ala Glu Ala Pro Cys Tyr Val Ser His Pro Ser Pro Val Pro Pro
    850                 855                 860

Ser Thr Pro Trp Pro Thr Pro Pro Ala Thr Thr Pro Phe Pro Ala Val
865                 870                 875                 880

Val Gln Pro Tyr Pro Leu Pro Val Phe Ser Pro Arg Gly Gly Pro Gln
                885                 890                 895

Pro Leu Pro Pro Ala Pro Thr Ser Val Pro Pro Ala Ala Phe Pro Ala
            900                 905                 910

Pro Leu Val Thr Pro Met Val Ala Leu Val Leu Pro Asn Tyr Leu Phe
        915                 920                 925

Pro Thr Pro Ser Ser Tyr Pro Tyr Gly Ala Leu Gln Thr Pro Ala Glu
    930                 935                 940

Gly Pro Pro Thr Pro Ala Ser His Ser Pro Ser Pro Ser Leu Pro Ala
945                 950                 955                 960

Leu Ala Pro Ser Pro Pro His Arg Pro Asp Ser Pro Leu Phe Asn Ser
                965                 970                 975

Arg Cys Ser Ser Pro Leu Gln Leu Asn Leu Leu Gln Leu Glu Glu Leu
            980                 985                 990

Pro Arg Ala Glu Gly Ala Ala Val  Ala Gly Gly Pro Gly  Ser Ser Ala
        995                 1000                1005
```

```
Gly Pro  Pro Pro Pro Ser Ala  Glu Ala Ala Glu Pro  Glu Ala Arg
    1010                 1015                 1020

Leu Ala  Glu Val Thr Glu Ser  Ser Asn Gln Asp Ala  Leu Ser Gly
    1025                 1030                 1035

Ser Ser  Asp Leu Leu Glu Leu  Leu Leu Gln Glu Asp  Ser Arg Ser
    1040                 1045                 1050

Gly Thr  Gly Ser Ala Ala Ser  Gly Ser Leu Gly Ser  Gly Leu Gly
    1055                 1060                 1065

Ser Gly  Ser Gly Ser Gly Ser  His Glu Gly Gly Ser  Thr Ser Ala
    1070                 1075                 1080

Ser Ile  Thr Arg Ser Ser Gln  Ser Ser His Thr Ser  Lys Tyr Phe
    1085                 1090                 1095

Gly Ser  Ile Asp Ser Ser Glu  Ala Glu Ala Gly Ala  Ala Arg Gly
    1100                 1105                 1110

Gly Ala  Glu Pro Gly Asp Gln  Val Ile Lys Tyr Val  Leu Gln Asp
    1115                 1120                 1125

Pro Ile  Trp Leu Leu Met Ala  Asn Ala Asp Gln Arg  Val Met Met
    1130                 1135                 1140

Thr Tyr  Gln Val Pro Ser Arg  Asp Met Thr Ser Val  Leu Lys Gln
    1145                 1150                 1155

Asp Arg  Glu Arg Leu Arg Ala  Met Gln Lys Gln Gln  Pro Arg Phe
    1160                 1165                 1170

Ser Glu  Asp Gln Arg Arg Glu  Leu Gly Ala Val His  Ser Trp Val
    1175                 1180                 1185

Arg Lys  Gly Gln Leu Pro Arg  Ala Leu Asp Val Met  Ala Cys Val
    1190                 1195                 1200

Asp Cys  Gly Ser Ser Thr Gln  Asp Pro Gly His Pro  Asp Asp Pro
    1205                 1210                 1215

Leu Phe  Ser Glu Leu Asp Gly  Leu Gly Leu Glu Pro  Met Glu Glu
    1220                 1225                 1230

Gly Gly  Gly Glu Gln Gly Ser  Ser Gly Gly Gly Ser  Gly Glu Gly
    1235                 1240                 1245

Glu Gly  Cys Glu Glu Ala Gln  Gly Gly Ala Lys Ala  Ser Ser Ser
    1250                 1255                 1260

Gln Asp  Leu Ala Met Glu Glu  Glu Glu Glu Gly Arg  Ser Ser Ser
    1265                 1270                 1275

Ser Pro  Ala Leu Pro Thr Ala  Gly Asn Cys Thr Ser
    1280                 1285                 1290
```

<210> SEQ ID NO 21
<211> LENGTH: 2699
<212> TYPE: DNA
<213> ORGANISM: Homo sapiens
<220> FEATURE:
<221> NAME/KEY: CDS
<222> LOCATION: (898)..(2328)
<223> OTHER INFORMATION: CHK1

<400> SEQUENCE: 21

```
cttttaaatt tgcgttgtaa gatttatttt ggctctcccc gcctgttctt tgcacattaa     60

aaatgaaaaa gtttgtagaa ctaagctaag cagatggtct tcctgcaaaa agaccgggct    120

gaagtaaagc attgttttgg agctggttca cagaaaaaag gcaaaactgg ttatcctgac    180

ttcaagctcc aacataaact gctcgctttc tccgggaaac ttgccccgcc acacacactt    240

gactgcgtgg ccagttcttt cgaagcctct cgctcccaac acggagttcc tcccatttct    300
```

```
tcacagtcgg ctctcagcag ctgctgctgg tttctcggct ccagcaccac gagtaccgca    360

ctctgaggtt tacaaagcac tctgcttcac cgactgtgat cctcacagtc ctgtccggtg    420

gcctcacgca ggtggcggtg cagcctttca ggcccagagc ggccaggagc gaagcccgca    480

gccccgcctg gaagcgcagc gcggtcggtc gcgcgcccct gaggcttgga ggcctgggct    540

tcccccagca gcgctcgagc accgcccagt cgagcctcac accggatgcc acttcatatt    600

tgggcccaga gctcaattcg cgccgatgcg gtccgccgtc cttaaatctc ttcagccagg    660

atctctcccc gactgcaaag cagccctggg cgggagcggc aacatctcca cgtcaccctt    720

ttggagccgc cgacattcag aggggcagga cacgggaacg cgcgctgtct tgctttacgg    780

cgcgggtgcg cgagtttgcg gcagcgtgac gccctcaagt tttggcggga aaagcgctgc    840

atttggattc ctgcagtggt gggcaaagga cagtccgccg aggtgctcgg tggagtc      897

atg gca gtg ccc ttt gtg gaa gac tgg gac ttg gtg caa acc ctg gga      945
Met Ala Val Pro Phe Val Glu Asp Trp Asp Leu Val Gln Thr Leu Gly
1               5                   10                  15

gaa ggt gcc tat gga gaa gtt caa ctt gct gtg aat aga gta act gaa      993
Glu Gly Ala Tyr Gly Glu Val Gln Leu Ala Val Asn Arg Val Thr Glu
            20                  25                  30

gaa gca gtc gca gtg aag att gta gat atg aag cgt gcc gta gac tgt     1041
Glu Ala Val Ala Val Lys Ile Val Asp Met Lys Arg Ala Val Asp Cys
        35                  40                  45

cca gaa aat att aag aaa gag atc tgt atc aat aaa atg cta aat cat     1089
Pro Glu Asn Ile Lys Lys Glu Ile Cys Ile Asn Lys Met Leu Asn His
    50                  55                  60

gaa aat gta gta aaa ttc tat ggt cac agg aga gaa ggc aat atc caa     1137
Glu Asn Val Val Lys Phe Tyr Gly His Arg Arg Glu Gly Asn Ile Gln
65                  70                  75                  80

tat tta ttt ctg gag tac tgt agt gga gga gag ctt ttt gac aga ata     1185
Tyr Leu Phe Leu Glu Tyr Cys Ser Gly Gly Glu Leu Phe Asp Arg Ile
                85                  90                  95

gag cca gac ata ggc atg cct gaa cca gat gct cag aga ttc ttc cat     1233
Glu Pro Asp Ile Gly Met Pro Glu Pro Asp Ala Gln Arg Phe Phe His
            100                 105                 110

caa ctc atg gca ggg gtg gtt tat ctg cat ggt att gga ata act cac     1281
Gln Leu Met Ala Gly Val Val Tyr Leu His Gly Ile Gly Ile Thr His
        115                 120                 125

agg gat att aaa cca gaa aat ctt ctg ttg gat gaa agg gat aac ctc     1329
Arg Asp Ile Lys Pro Glu Asn Leu Leu Leu Asp Glu Arg Asp Asn Leu
    130                 135                 140

aaa atc tca gac ttt ggc ttg gca aca gta ttt cgg tat aat aat cgt     1377
Lys Ile Ser Asp Phe Gly Leu Ala Thr Val Phe Arg Tyr Asn Asn Arg
145                 150                 155                 160

gag cgt ttg ttg aac aag atg tgt ggt act tta cca tat gtt gct cca     1425
Glu Arg Leu Leu Asn Lys Met Cys Gly Thr Leu Pro Tyr Val Ala Pro
                165                 170                 175

gaa ctt ctg aag aga aga gaa ttt cat gca gaa cca gtt gat gtt tgg     1473
Glu Leu Leu Lys Arg Arg Glu Phe His Ala Glu Pro Val Asp Val Trp
            180                 185                 190

tcc tgt gga ata gta ctt act gca atg ctc gct gga gaa ttg cca tgg     1521
Ser Cys Gly Ile Val Leu Thr Ala Met Leu Ala Gly Glu Leu Pro Trp
        195                 200                 205

gac caa ccc agt gac agc tgt cag gag tat tct gac tgg aaa gaa aaa     1569
Asp Gln Pro Ser Asp Ser Cys Gln Glu Tyr Ser Asp Trp Lys Glu Lys
    210                 215                 220

aaa aca tac ctc aac cct tgg aaa aaa atc gat tct gct cct cta gct     1617
Lys Thr Tyr Leu Asn Pro Trp Lys Lys Ile Asp Ser Ala Pro Leu Ala
```

```
225                 230                 235                 240

ctg ctg cat aaa atc tta gtt gag aat cca tca gca aga att acc att      1665
Leu Leu His Lys Ile Leu Val Glu Asn Pro Ser Ala Arg Ile Thr Ile
                245                 250                 255

cca gac atc aaa aaa gat aga tgg tac aac aaa ccc ctc aag aaa ggg      1713
Pro Asp Ile Lys Lys Asp Arg Trp Tyr Asn Lys Pro Leu Lys Lys Gly
            260                 265                 270

gca aaa agg ccc cga gtc act tca ggt ggt gtg tca gag tct ccc agt      1761
Ala Lys Arg Pro Arg Val Thr Ser Gly Gly Val Ser Glu Ser Pro Ser
        275                 280                 285

gga ttt tct aag cac att caa tcc aat ttg gac ttc tct cca gta aac      1809
Gly Phe Ser Lys His Ile Gln Ser Asn Leu Asp Phe Ser Pro Val Asn
    290                 295                 300

agt gct tct agt gaa gaa aat gtg aag tac tcc agt tct cag cca gaa      1857
Ser Ala Ser Ser Glu Glu Asn Val Lys Tyr Ser Ser Ser Gln Pro Glu
305                 310                 315                 320

ccc cgc aca ggt ctt tcc tta tgg gat acc agc ccc tca tac att gat      1905
Pro Arg Thr Gly Leu Ser Leu Trp Asp Thr Ser Pro Ser Tyr Ile Asp
                325                 330                 335

aaa ttg gta caa ggg atc agc ttt tcc cag ccc aca tgt cct gat cat      1953
Lys Leu Val Gln Gly Ile Ser Phe Ser Gln Pro Thr Cys Pro Asp His
            340                 345                 350

atg ctt ttg aat agt cag tta ctt ggc acc cca gga tcc tca cag aac      2001
Met Leu Leu Asn Ser Gln Leu Leu Gly Thr Pro Gly Ser Ser Gln Asn
        355                 360                 365

ccc tgg cag cgg ttg gtc aaa aga atg aca cga ttc ttt acc aaa ttg      2049
Pro Trp Gln Arg Leu Val Lys Arg Met Thr Arg Phe Phe Thr Lys Leu
    370                 375                 380

gat gca gac aaa tct tat caa tgc ctg aaa gag act tgt gag aag ttg      2097
Asp Ala Asp Lys Ser Tyr Gln Cys Leu Lys Glu Thr Cys Glu Lys Leu
385                 390                 395                 400

ggc tat caa tgg aag aaa agt tgt atg aat cag gtt act ata tca aca      2145
Gly Tyr Gln Trp Lys Lys Ser Cys Met Asn Gln Val Thr Ile Ser Thr
                405                 410                 415

act gat agg aga aac aat aaa ctc att ttc aaa gtg aat ttg tta gaa      2193
Thr Asp Arg Arg Asn Asn Lys Leu Ile Phe Lys Val Asn Leu Leu Glu
            420                 425                 430

atg gat gat aaa ata ttg gtt gac ttc cgg ctt tct aag ggt gat gga      2241
Met Asp Asp Lys Ile Leu Val Asp Phe Arg Leu Ser Lys Gly Asp Gly
        435                 440                 445

ttg gag ttc aag aga cac ttc ctg aag att aaa ggg aag ctg att gat      2289
Leu Glu Phe Lys Arg His Phe Leu Lys Ile Lys Gly Lys Leu Ile Asp
    450                 455                 460

att gtg agc agc cag aag att tgg ctt cct gcc aca tga tcggaccatc      2338
Ile Val Ser Ser Gln Lys Ile Trp Leu Pro Ala Thr
465                 470                 475

ggctctgggg aatcctgatg gagtttcact cttgtctccc aggctggagt acaatggcat   2398

gatctcagct tactgcaacc tccgtctcct gggttcaagc gattctcctg cctcagcctt   2458

ccaagtagct gggattacag gtgcccacca ccacacctgg ctaggttttg tatttttagt   2518

agagatgggg ttttttcatg ttggccaggc tgatctggaa ctcctgacct caagtgatcc   2578

acctgccttg gcctcccaaa gtgctgggat tttaggtgtg agccacctcg cctggcaagg   2638

gattctgttc ttagtccttg aaaaaataaa gttctgaatc ttcaaaaaaa aaaaaaaaaa   2698

a                                                                   2699


<210> SEQ ID NO 22
<211> LENGTH: 476
```

```
<212> TYPE: PRT
<213> ORGANISM: Homo sapiens

<400> SEQUENCE: 22

Met Ala Val Pro Phe Val Glu Asp Trp Asp Leu Val Gln Thr Leu Gly
1               5                   10                  15

Glu Gly Ala Tyr Gly Glu Val Gln Leu Ala Val Asn Arg Val Thr Glu
            20                  25                  30

Glu Ala Val Ala Val Lys Ile Val Asp Met Lys Arg Ala Val Asp Cys
        35                  40                  45

Pro Glu Asn Ile Lys Lys Glu Ile Cys Ile Asn Lys Met Leu Asn His
    50                  55                  60

Glu Asn Val Val Lys Phe Tyr Gly His Arg Arg Glu Gly Asn Ile Gln
65                  70                  75                  80

Tyr Leu Phe Leu Glu Tyr Cys Ser Gly Gly Glu Leu Phe Asp Arg Ile
                85                  90                  95

Glu Pro Asp Ile Gly Met Pro Glu Pro Asp Ala Gln Arg Phe Phe His
            100                 105                 110

Gln Leu Met Ala Gly Val Val Tyr Leu His Gly Ile Gly Ile Thr His
        115                 120                 125

Arg Asp Ile Lys Pro Glu Asn Leu Leu Leu Asp Glu Arg Asp Asn Leu
    130                 135                 140

Lys Ile Ser Asp Phe Gly Leu Ala Thr Val Phe Arg Tyr Asn Asn Arg
145                 150                 155                 160

Glu Arg Leu Leu Asn Lys Met Cys Gly Thr Leu Pro Tyr Val Ala Pro
                165                 170                 175

Glu Leu Leu Lys Arg Arg Glu Phe His Ala Glu Pro Val Asp Val Trp
            180                 185                 190

Ser Cys Gly Ile Val Leu Thr Ala Met Leu Ala Gly Glu Leu Pro Trp
        195                 200                 205

Asp Gln Pro Ser Asp Ser Cys Gln Glu Tyr Ser Asp Trp Lys Glu Lys
    210                 215                 220

Lys Thr Tyr Leu Asn Pro Trp Lys Lys Ile Asp Ser Ala Pro Leu Ala
225                 230                 235                 240

Leu Leu His Lys Ile Leu Val Glu Asn Pro Ser Ala Arg Ile Thr Ile
                245                 250                 255

Pro Asp Ile Lys Lys Asp Arg Trp Tyr Asn Lys Pro Leu Lys Lys Gly
            260                 265                 270

Ala Lys Arg Pro Arg Val Thr Ser Gly Gly Val Ser Glu Ser Pro Ser
        275                 280                 285

Gly Phe Ser Lys His Ile Gln Ser Asn Leu Asp Phe Ser Pro Val Asn
    290                 295                 300

Ser Ala Ser Ser Glu Glu Asn Val Lys Tyr Ser Ser Ser Gln Pro Glu
305                 310                 315                 320

Pro Arg Thr Gly Leu Ser Leu Trp Asp Thr Ser Pro Ser Tyr Ile Asp
                325                 330                 335

Lys Leu Val Gln Gly Ile Ser Phe Ser Gln Pro Thr Cys Pro Asp His
            340                 345                 350

Met Leu Leu Asn Ser Gln Leu Leu Gly Thr Pro Gly Ser Ser Gln Asn
        355                 360                 365

Pro Trp Gln Arg Leu Val Lys Arg Met Thr Arg Phe Phe Thr Lys Leu
    370                 375                 380

Asp Ala Asp Lys Ser Tyr Gln Cys Leu Lys Glu Thr Cys Glu Lys Leu
385                 390                 395                 400
```

```
Gly Tyr Gln Trp Lys Lys Ser Cys Met Asn Gln Val Thr Ile Ser Thr
                405                 410                 415

Thr Asp Arg Arg Asn Asn Lys Leu Ile Phe Lys Val Asn Leu Leu Glu
            420                 425                 430

Met Asp Asp Lys Ile Leu Val Asp Phe Arg Leu Ser Lys Gly Asp Gly
        435                 440                 445

Leu Glu Phe Lys Arg His Phe Leu Lys Ile Lys Gly Lys Leu Ile Asp
    450                 455                 460

Ile Val Ser Ser Gln Lys Ile Trp Leu Pro Ala Thr
465                 470                 475


<210> SEQ ID NO 23
<211> LENGTH: 3722
<212> TYPE: DNA
<213> ORGANISM: Homo sapiens
<220> FEATURE:
<221> NAME/KEY: CDS
<222> LOCATION: (130)..(3159)
<223> OTHER INFORMATION: LIG3

<400> SEQUENCE: 23

gcgcgctgcc tcccgctcta ggacccggat ttaaagagac aggcgctcca accgtcgtgg      60

gctgcccgcg gcctgtaatg agcaagttcc gaggcctacg gtgagcgccg gagccggaga     120

ggcagctat atg tct ttg gct ttc aag atc ttc ttt cca caa acc ctc cgt     171
          Met Ser Leu Ala Phe Lys Ile Phe Phe Pro Gln Thr Leu Arg
          1               5                   10

gca ctc agc cga aaa gaa ctg tgc cta ttc cga aaa cat cac tgg cgt       219
Ala Leu Ser Arg Lys Glu Leu Cys Leu Phe Arg Lys His His Trp Arg
15                  20                  25                  30

gat gta aga caa ttc agc cag tgg tca gaa aca gat ctg ctt cat gga       267
Asp Val Arg Gln Phe Ser Gln Trp Ser Glu Thr Asp Leu Leu His Gly
                35                  40                  45

cat ccc ctc ttc ctg aga aga aag cct gtt cta tca ttc cag gga agc       315
His Pro Leu Phe Leu Arg Arg Lys Pro Val Leu Ser Phe Gln Gly Ser
            50                  55                  60

cat cta aga tca cgt gcc acc tac ctt gtt ttc ttg cca ggg ttg cat       363
His Leu Arg Ser Arg Ala Thr Tyr Leu Val Phe Leu Pro Gly Leu His
        65                  70                  75

gtg gga ctc tgc agt ggc ccc tgt gag atg gct gag caa cgg ttc tgt       411
Val Gly Leu Cys Ser Gly Pro Cys Glu Met Ala Glu Gln Arg Phe Cys
    80                  85                  90

gtg gac tat gcc aag cgt ggc aca gct ggc tgc aaa aaa tgc aag gaa       459
Val Asp Tyr Ala Lys Arg Gly Thr Ala Gly Cys Lys Lys Cys Lys Glu
95                  100                 105                 110

aag att gtg aag ggc gta tgc cga att ggc aaa gtg gtg ccc aat ccc       507
Lys Ile Val Lys Gly Val Cys Arg Ile Gly Lys Val Val Pro Asn Pro
                115                 120                 125

ttc tca gag tct ggg ggt gat atg aaa gag tgg tac cac att aaa tgc       555
Phe Ser Glu Ser Gly Gly Asp Met Lys Glu Trp Tyr His Ile Lys Cys
            130                 135                 140

atg ttt gag aaa cta gag cgg gcc cgg gcc acc aca aaa aaa atc gag       603
Met Phe Glu Lys Leu Glu Arg Ala Arg Ala Thr Thr Lys Lys Ile Glu
        145                 150                 155

gac ctc aca gag ctg gaa ggc tgg gaa gag ctg gaa gat aat gag aag       651
Asp Leu Thr Glu Leu Glu Gly Trp Glu Glu Leu Glu Asp Asn Glu Lys
    160                 165                 170

gaa cag ata acc cag cac att gca gat ctg tct tct aag gca gca ggt       699
Glu Gln Ile Thr Gln His Ile Ala Asp Leu Ser Ser Lys Ala Ala Gly
175                 180                 185                 190
```

-continued

```
aca cca aag aag aaa gct gtt gtc cag gct aag ttg aca acc act ggc      747
Thr Pro Lys Lys Lys Ala Val Val Gln Ala Lys Leu Thr Thr Thr Gly
                195                 200                 205

cag gtg act tct cca gtg aaa ggc gcc tca ttt gtc acc agt acc aat      795
Gln Val Thr Ser Pro Val Lys Gly Ala Ser Phe Val Thr Ser Thr Asn
            210                 215                 220

ccc cgg aaa ttt tct ggc ttt tca gcc aag ccc aac aac tct ggg gaa      843
Pro Arg Lys Phe Ser Gly Phe Ser Ala Lys Pro Asn Asn Ser Gly Glu
        225                 230                 235

gcc ccc tcg agc ccc acc cct aag aga agt ctg tct tca agc aaa tgt      891
Ala Pro Ser Ser Pro Thr Pro Lys Arg Ser Leu Ser Ser Ser Lys Cys
    240                 245                 250

gac ccc agg cat aag gac tgt ctg cta cgg gag ttt cga aag tta tgc      939
Asp Pro Arg His Lys Asp Cys Leu Leu Arg Glu Phe Arg Lys Leu Cys
255                 260                 265                 270

gcc atg gtg gcc gat aat cct agc tac aac acg aag acc cag atc atc      987
Ala Met Val Ala Asp Asn Pro Ser Tyr Asn Thr Lys Thr Gln Ile Ile
                275                 280                 285

cag gac ttc ctt cgg aaa ggc tca gca gga gat ggt ttc cac ggt gat     1035
Gln Asp Phe Leu Arg Lys Gly Ser Ala Gly Asp Gly Phe His Gly Asp
            290                 295                 300

gtg tac cta aca gtg aag ctg ctg ctg cca gga gtc att aag act gtt     1083
Val Tyr Leu Thr Val Lys Leu Leu Leu Pro Gly Val Ile Lys Thr Val
        305                 310                 315

tac aac ttg aac gat aag cag att gtg aag ctt ttc agt cgc att ttt     1131
Tyr Asn Leu Asn Asp Lys Gln Ile Val Lys Leu Phe Ser Arg Ile Phe
    320                 325                 330

aac tgc aac cca gat gat atg gca cgg gac cta gag cag ggt gac gtg     1179
Asn Cys Asn Pro Asp Asp Met Ala Arg Asp Leu Glu Gln Gly Asp Val
335                 340                 345                 350

tca gag aca atc aga gtc ttc ttt gag cag agc aag tct ttc ccc cca     1227
Ser Glu Thr Ile Arg Val Phe Phe Glu Gln Ser Lys Ser Phe Pro Pro
                355                 360                 365

gct gcc aag agc ctc ctt acc atc cag gaa gtg gat gag ttc ctt ctg     1275
Ala Ala Lys Ser Leu Leu Thr Ile Gln Glu Val Asp Glu Phe Leu Leu
            370                 375                 380

cgg ctg tcc aag ctc acc aag gag gat gag cag caa cag gcc cta cag     1323
Arg Leu Ser Lys Leu Thr Lys Glu Asp Glu Gln Gln Gln Ala Leu Gln
        385                 390                 395

gac att gcc tcc agg tgt aca gcc aat gac ctt aaa tgc atc atc agg     1371
Asp Ile Ala Ser Arg Cys Thr Ala Asn Asp Leu Lys Cys Ile Ile Arg
    400                 405                 410

ttg atc aaa cat gat ctg aag atg aac tca ggt gca aaa cat gtg tta     1419
Leu Ile Lys His Asp Leu Lys Met Asn Ser Gly Ala Lys His Val Leu
415                 420                 425                 430

gac gcc ctt gac ccc aat gcc tat gaa gcc ttc aaa gcc tcg cgc aac     1467
Asp Ala Leu Asp Pro Asn Ala Tyr Glu Ala Phe Lys Ala Ser Arg Asn
                435                 440                 445

ctg cag gat gtg gtg gag cgg gtc ctt cac aac gcg cag gag gtg gag     1515
Leu Gln Asp Val Val Glu Arg Val Leu His Asn Ala Gln Glu Val Glu
            450                 455                 460

aag gag ccg ggc cag aga cga gct ctg agc gtc cag gcc tcg ctg atg     1563
Lys Glu Pro Gly Gln Arg Arg Ala Leu Ser Val Gln Ala Ser Leu Met
        465                 470                 475

aca cct gtg cag ccc atg ttg gcg gag gcc tgc aag tcc gtt gag tat     1611
Thr Pro Val Gln Pro Met Leu Ala Glu Ala Cys Lys Ser Val Glu Tyr
    480                 485                 490

gca atg aag aaa tgt ccc aat ggc atg ttc tct gag atc aag tac gat     1659
Ala Met Lys Lys Cys Pro Asn Gly Met Phe Ser Glu Ile Lys Tyr Asp
```

```
495                 500                 505                 510

gga gag cga gtc cag gtg cat aag aat gga gac cac ttc agc tac ttc      1707
Gly Glu Arg Val Gln Val His Lys Asn Gly Asp His Phe Ser Tyr Phe
                515                 520                 525

agc cgc agt ctc aag ccc gtc ctt cct cac aag gtg gcc cac ttt aag      1755
Ser Arg Ser Leu Lys Pro Val Leu Pro His Lys Val Ala His Phe Lys
            530                 535                 540

gac tac att ccc cag gct ttt cct ggg ggc cac agc atg atc ttg gat      1803
Asp Tyr Ile Pro Gln Ala Phe Pro Gly Gly His Ser Met Ile Leu Asp
        545                 550                 555

tct gaa gtg ctt ctg att gac aac aag aca ggc aaa cca ctg ccc ttt      1851
Ser Glu Val Leu Leu Ile Asp Asn Lys Thr Gly Lys Pro Leu Pro Phe
    560                 565                 570

ggg act ctg gga gta cac aag aaa gca gcc ttc cag gat gct aat gtc      1899
Gly Thr Leu Gly Val His Lys Lys Ala Ala Phe Gln Asp Ala Asn Val
575                 580                 585                 590

tgc ctg ttt gtt ttt gat tgt atc tac ttt aat gat gtc agc ttg atg      1947
Cys Leu Phe Val Phe Asp Cys Ile Tyr Phe Asn Asp Val Ser Leu Met
                595                 600                 605

gac aga cct ctg tgt gag cgg cgg aag ttt ctt cat gac aac atg gtt      1995
Asp Arg Pro Leu Cys Glu Arg Arg Lys Phe Leu His Asp Asn Met Val
            610                 615                 620

gaa att cca aac cgg atc atg ttc tca gaa atg aag cga gtc aca aaa      2043
Glu Ile Pro Asn Arg Ile Met Phe Ser Glu Met Lys Arg Val Thr Lys
        625                 630                 635

gct ttg gac ttg gct gac atg ata acc cgg gtg atc cag gag gga ttg      2091
Ala Leu Asp Leu Ala Asp Met Ile Thr Arg Val Ile Gln Glu Gly Leu
    640                 645                 650

gag ggg ctg gtg ctg aag gat gtg aag ggt aca tat gag cct ggg aag      2139
Glu Gly Leu Val Leu Lys Asp Val Lys Gly Thr Tyr Glu Pro Gly Lys
655                 660                 665                 670

cgg cac tgg ctg aaa gtg aag aaa gac tat ttg aac gag ggg gcc atg      2187
Arg His Trp Leu Lys Val Lys Lys Asp Tyr Leu Asn Glu Gly Ala Met
                675                 680                 685

gcc gac aca gct gac ctg gtg gtc ctt gga gcc ttc tat ggg caa ggg      2235
Ala Asp Thr Ala Asp Leu Val Val Leu Gly Ala Phe Tyr Gly Gln Gly
            690                 695                 700

agc aaa ggc ggc atg atg tca atc ttc ctc atg ggc tgc tac gac cct      2283
Ser Lys Gly Gly Met Met Ser Ile Phe Leu Met Gly Cys Tyr Asp Pro
        705                 710                 715

ggc agc cag aag tgg tgc aca gtc acc aag tgt gca gga ggc cat gat      2331
Gly Ser Gln Lys Trp Cys Thr Val Thr Lys Cys Ala Gly Gly His Asp
    720                 725                 730

gat gcc acg ctt gcc cgc ctg cag aat gaa cta gac atg gtg aag atc      2379
Asp Ala Thr Leu Ala Arg Leu Gln Asn Glu Leu Asp Met Val Lys Ile
735                 740                 745                 750

agc aag gac ccc agc aaa ata ccc agc tgg ttg aag gtc aac aag atc      2427
Ser Lys Asp Pro Ser Lys Ile Pro Ser Trp Leu Lys Val Asn Lys Ile
                755                 760                 765

tac tat cct gac ttc atc gtc cca gac cca aag aaa gct gcc gtg tgg      2475
Tyr Tyr Pro Asp Phe Ile Val Pro Asp Pro Lys Lys Ala Ala Val Trp
            770                 775                 780

gag atc aca ggg gct gaa ttc tcc aaa tcg gag gct cat aca gct gac      2523
Glu Ile Thr Gly Ala Glu Phe Ser Lys Ser Glu Ala His Thr Ala Asp
        785                 790                 795

ggg atc tcc atc cga ttc cct cgc tgc acc cga atc cga gat gat aag      2571
Gly Ile Ser Ile Arg Phe Pro Arg Cys Thr Arg Ile Arg Asp Asp Lys
    800                 805                 810

gac tgg aaa tct gcc act aac ctt ccc caa ctc aag gaa ctg tac cag      2619
```

```
Asp Trp Lys Ser Ala Thr Asn Leu Pro Gln Leu Lys Glu Leu Tyr Gln
815                 820                 825                 830

ttg tcc aag gag aag gca gac ttc act gta gtg gct gga gat gag ggg     2667
Leu Ser Lys Glu Lys Ala Asp Phe Thr Val Val Ala Gly Asp Glu Gly
                835                 840                 845

agc tcc act aca ggg ggt agc agt gaa gag aat aag ggt ccc tca ggg     2715
Ser Ser Thr Thr Gly Gly Ser Ser Glu Glu Asn Lys Gly Pro Ser Gly
            850                 855                 860

tct gct gtg tcc cgc aag gcc ccc agc aag ccc tca gcc agt acc aag     2763
Ser Ala Val Ser Arg Lys Ala Pro Ser Lys Pro Ser Ala Ser Thr Lys
        865                 870                 875

aaa gca gaa ggg aag ctg agt aac tcc aac agc aaa gat ggc aac atg     2811
Lys Ala Glu Gly Lys Leu Ser Asn Ser Asn Ser Lys Asp Gly Asn Met
    880                 885                 890

cag act gca aag cct tcc gct atg aag gtg ggg gag aag ctg gcc aca     2859
Gln Thr Ala Lys Pro Ser Ala Met Lys Val Gly Glu Lys Leu Ala Thr
895                 900                 905                 910

aag tct tct cca gtg aaa gta ggg gag aag cgg aaa gct gct gat gag     2907
Lys Ser Ser Pro Val Lys Val Gly Glu Lys Arg Lys Ala Ala Asp Glu
                915                 920                 925

acg ctg tgc caa aca aag gta ttg ctg gac atc ttc act ggg gtg cgg     2955
Thr Leu Cys Gln Thr Lys Val Leu Leu Asp Ile Phe Thr Gly Val Arg
            930                 935                 940

ctt tac ttg cca ccc tcc aca cca gac ttc agc cgt ctc aga cgc tac     3003
Leu Tyr Leu Pro Pro Ser Thr Pro Asp Phe Ser Arg Leu Arg Arg Tyr
        945                 950                 955

ttt gtg gca ttc gac ggg gac ctg gta cag gaa ttt gat atg act tca     3051
Phe Val Ala Phe Asp Gly Asp Leu Val Gln Glu Phe Asp Met Thr Ser
    960                 965                 970

gcc acg cac gtg ctg ggt agc agg gac aag aac cct gcg gcc cag cag     3099
Ala Thr His Val Leu Gly Ser Arg Asp Lys Asn Pro Ala Ala Gln Gln
975                 980                 985                 990

gtc tcc cca gag tgg att tgg gca tgt atc  cgg aaa cgg aga ctg  gta   3147
Val Ser Pro Glu Trp Ile Trp Ala Cys Ile  Arg Lys Arg Arg Leu  Val
                995                 1000                1005

gct ccc tgc tag gtttgctgtc ttccctctcc ctcaggccat actctccttt         3199
Ala Pro Cys

accatactac tggactggac tcaggctgga ggcagataga cacagtatag ggggaatggg   3259

cttgcttctc ccaaacccac cagttctcca ctgtctcttc tggaccagga attagttgct   3319

gtgggtgcca cagctgaagt cagtttgtct tgctggttta aatagatctt tcagagctgg   3379

gtgctgggtt tgccatcttt ttgttttctt tgaaaagcag cttagttacc ctttttataa   3439

ataaaatatc ttgcagttat ctttgtcctt tccccaccta cacccccaat aatttcccta   3499

gagattaagg agtaaaggct gggctatggc agctctgtcc acaaagcctt ctctcccatc   3559

cttgcctgtt cctttgtact tccaggctca ttttaaagtt gtatttaaag gactgccctc   3619

ggaaatgctt ctgtttagcg gaacttgtat tcagcctgac acgctttgcc aggaacaaac   3679

ctcatgtgaa agaaaacaaa atgaattttt ttactttctt ctc                     3722


<210> SEQ ID NO 24
<211> LENGTH: 1009
<212> TYPE: PRT
<213> ORGANISM: Homo sapiens

<400> SEQUENCE: 24

Met Ser Leu Ala Phe Lys Ile Phe Phe Pro Gln Thr Leu Arg Ala Leu
1               5                   10                  15
```

```
Ser Arg Lys Glu Leu Cys Leu Phe Arg Lys His His Trp Arg Asp Val
            20                  25                  30

Arg Gln Phe Ser Gln Trp Ser Glu Thr Asp Leu Leu His Gly His Pro
        35                  40                  45

Leu Phe Leu Arg Arg Lys Pro Val Leu Ser Phe Gln Gly Ser His Leu
    50                  55                  60

Arg Ser Arg Ala Thr Tyr Leu Val Phe Leu Pro Gly Leu His Val Gly
65                  70                  75                  80

Leu Cys Ser Gly Pro Cys Glu Met Ala Glu Gln Arg Phe Cys Val Asp
                85                  90                  95

Tyr Ala Lys Arg Gly Thr Ala Gly Cys Lys Lys Cys Lys Glu Lys Ile
            100                 105                 110

Val Lys Gly Val Cys Arg Ile Gly Lys Val Val Pro Asn Pro Phe Ser
        115                 120                 125

Glu Ser Gly Gly Asp Met Lys Glu Trp Tyr His Ile Lys Cys Met Phe
    130                 135                 140

Glu Lys Leu Glu Arg Ala Arg Ala Thr Thr Lys Lys Ile Glu Asp Leu
145                 150                 155                 160

Thr Glu Leu Glu Gly Trp Glu Glu Leu Glu Asp Asn Glu Lys Glu Gln
                165                 170                 175

Ile Thr Gln His Ile Ala Asp Leu Ser Ser Lys Ala Ala Gly Thr Pro
            180                 185                 190

Lys Lys Lys Ala Val Val Gln Ala Lys Leu Thr Thr Thr Gly Gln Val
        195                 200                 205

Thr Ser Pro Val Lys Gly Ala Ser Phe Val Thr Ser Thr Asn Pro Arg
    210                 215                 220

Lys Phe Ser Gly Phe Ser Ala Lys Pro Asn Asn Ser Gly Glu Ala Pro
225                 230                 235                 240

Ser Ser Pro Thr Pro Lys Arg Ser Leu Ser Ser Ser Lys Cys Asp Pro
                245                 250                 255

Arg His Lys Asp Cys Leu Leu Arg Glu Phe Arg Lys Leu Cys Ala Met
            260                 265                 270

Val Ala Asp Asn Pro Ser Tyr Asn Thr Lys Thr Gln Ile Ile Gln Asp
        275                 280                 285

Phe Leu Arg Lys Gly Ser Ala Gly Asp Gly Phe His Gly Asp Val Tyr
    290                 295                 300

Leu Thr Val Lys Leu Leu Leu Pro Gly Val Ile Lys Thr Val Tyr Asn
305                 310                 315                 320

Leu Asn Asp Lys Gln Ile Val Lys Leu Phe Ser Arg Ile Phe Asn Cys
                325                 330                 335

Asn Pro Asp Asp Met Ala Arg Asp Leu Glu Gln Gly Asp Val Ser Glu
            340                 345                 350

Thr Ile Arg Val Phe Phe Glu Gln Ser Lys Ser Phe Pro Pro Ala Ala
        355                 360                 365

Lys Ser Leu Leu Thr Ile Gln Glu Val Asp Glu Phe Leu Leu Arg Leu
    370                 375                 380

Ser Lys Leu Thr Lys Glu Asp Glu Gln Gln Gln Ala Leu Gln Asp Ile
385                 390                 395                 400

Ala Ser Arg Cys Thr Ala Asn Asp Leu Lys Cys Ile Ile Arg Leu Ile
                405                 410                 415

Lys His Asp Leu Lys Met Asn Ser Gly Ala Lys His Val Leu Asp Ala
            420                 425                 430

Leu Asp Pro Asn Ala Tyr Glu Ala Phe Lys Ala Ser Arg Asn Leu Gln
```

```
        435                 440                 445

Asp Val Val Glu Arg Val Leu His Asn Ala Gln Glu Val Glu Lys Glu
    450                 455                 460

Pro Gly Gln Arg Arg Ala Leu Ser Val Gln Ala Ser Leu Met Thr Pro
465                 470                 475                 480

Val Gln Pro Met Leu Ala Glu Ala Cys Lys Ser Val Glu Tyr Ala Met
                485                 490                 495

Lys Lys Cys Pro Asn Gly Met Phe Ser Glu Ile Lys Tyr Asp Gly Glu
            500                 505                 510

Arg Val Gln Val His Lys Asn Gly Asp His Phe Ser Tyr Phe Ser Arg
        515                 520                 525

Ser Leu Lys Pro Val Leu Pro His Lys Val Ala His Phe Lys Asp Tyr
    530                 535                 540

Ile Pro Gln Ala Phe Pro Gly Gly His Ser Met Ile Leu Asp Ser Glu
545                 550                 555                 560

Val Leu Leu Ile Asp Asn Lys Thr Gly Lys Pro Leu Pro Phe Gly Thr
                565                 570                 575

Leu Gly Val His Lys Lys Ala Ala Phe Gln Asp Ala Asn Val Cys Leu
            580                 585                 590

Phe Val Phe Asp Cys Ile Tyr Phe Asn Asp Val Ser Leu Met Asp Arg
        595                 600                 605

Pro Leu Cys Glu Arg Arg Lys Phe Leu His Asp Asn Met Val Glu Ile
    610                 615                 620

Pro Asn Arg Ile Met Phe Ser Glu Met Lys Arg Val Thr Lys Ala Leu
625                 630                 635                 640

Asp Leu Ala Asp Met Ile Thr Arg Val Ile Gln Glu Gly Leu Glu Gly
                645                 650                 655

Leu Val Leu Lys Asp Val Lys Gly Thr Tyr Glu Pro Gly Lys Arg His
            660                 665                 670

Trp Leu Lys Val Lys Lys Asp Tyr Leu Asn Glu Gly Ala Met Ala Asp
        675                 680                 685

Thr Ala Asp Leu Val Val Leu Gly Ala Phe Tyr Gly Gln Gly Ser Lys
    690                 695                 700

Gly Gly Met Met Ser Ile Phe Leu Met Gly Cys Tyr Asp Pro Gly Ser
705                 710                 715                 720

Gln Lys Trp Cys Thr Val Thr Lys Cys Ala Gly Gly His Asp Asp Ala
                725                 730                 735

Thr Leu Ala Arg Leu Gln Asn Glu Leu Asp Met Val Lys Ile Ser Lys
            740                 745                 750

Asp Pro Ser Lys Ile Pro Ser Trp Leu Lys Val Asn Lys Ile Tyr Tyr
        755                 760                 765

Pro Asp Phe Ile Val Pro Asp Pro Lys Lys Ala Ala Val Trp Glu Ile
    770                 775                 780

Thr Gly Ala Glu Phe Ser Lys Ser Glu Ala His Thr Ala Asp Gly Ile
785                 790                 795                 800

Ser Ile Arg Phe Pro Arg Cys Thr Arg Ile Arg Asp Asp Lys Asp Trp
                805                 810                 815

Lys Ser Ala Thr Asn Leu Pro Gln Leu Lys Glu Leu Tyr Gln Leu Ser
            820                 825                 830

Lys Glu Lys Ala Asp Phe Thr Val Val Ala Gly Asp Glu Gly Ser Ser
        835                 840                 845

Thr Thr Gly Gly Ser Ser Glu Glu Asn Lys Gly Pro Ser Gly Ser Ala
    850                 855                 860
```

```
Val Ser Arg Lys Ala Pro Ser Lys Pro Ser Ala Ser Thr Lys Lys Ala
865                 870                 875                 880

Glu Gly Lys Leu Ser Asn Ser Asn Ser Lys Asp Gly Asn Met Gln Thr
                885                 890                 895

Ala Lys Pro Ser Ala Met Lys Val Gly Glu Lys Leu Ala Thr Lys Ser
            900                 905                 910

Ser Pro Val Lys Val Gly Glu Lys Arg Lys Ala Ala Asp Glu Thr Leu
        915                 920                 925

Cys Gln Thr Lys Val Leu Leu Asp Ile Phe Thr Gly Val Arg Leu Tyr
    930                 935                 940

Leu Pro Pro Ser Thr Pro Asp Phe Ser Arg Leu Arg Arg Tyr Phe Val
945                 950                 955                 960

Ala Phe Asp Gly Asp Leu Val Gln Glu Phe Asp Met Thr Ser Ala Thr
                965                 970                 975

His Val Leu Gly Ser Arg Asp Lys Asn Pro Ala Ala Gln Gln Val Ser
            980                 985                 990

Pro Glu Trp Ile Trp Ala Cys Ile  Arg Lys Arg Arg Leu  Val Ala Pro
        995                 1000                1005

Cys


<210> SEQ ID NO 25
<211> LENGTH: 2308
<212> TYPE: DNA
<213> ORGANISM: Homo sapiens
<220> FEATURE:
<221> NAME/KEY: CDS
<222> LOCATION: (414)..(1556)
<223> OTHER INFORMATION: FEN1

<400> SEQUENCE: 25

aaaggaagtg cctccggcgc aagtggcatt gagggacttg tagtcctgcg atttcgggtg      60

tagagggagc aggggcctgc ggggacctgg tgtgggtgga gtggggacaa gcggtggaga     120

agggtacgcc agggtcgctg agagactctg ttctccctgg agggactggt tgccatgaga     180

gcagccgtct gaggggacgc agcctgcact acgcgcccca agaggctgtg cgtggcgagc     240

aggtcacgtg acgggagcgc gggctttgga aggcggctga acgtcaggcc acccgccgct     300

aagctgagaa gggagagcga gcttaggacc gcctgcccgg ggcaaccccg aaccaagctt     360

tagccgccga ggccgcgtgt cccaaaggcc agtcatccct cctctgtgtt gcc atg        416
                                                           Met
                                                           1

gga att caa ggc ctg gcc aaa cta att gct gat gtg gcc ccc agt gcc       464
Gly Ile Gln Gly Leu Ala Lys Leu Ile Ala Asp Val Ala Pro Ser Ala
            5                   10                  15

atc cgg gag aat gac atc aag agc tac ttt ggc cgt aag gtg gcc att       512
Ile Arg Glu Asn Asp Ile Lys Ser Tyr Phe Gly Arg Lys Val Ala Ile
        20                  25                  30

gat gcc tct atg agc att tat cag ttc ctg att gct gtt cgc cag ggt       560
Asp Ala Ser Met Ser Ile Tyr Gln Phe Leu Ile Ala Val Arg Gln Gly
    35                  40                  45

ggg gat gtg ctg cag aat gag gag ggt gag acc acc agc cac ctg atg       608
Gly Asp Val Leu Gln Asn Glu Glu Gly Glu Thr Thr Ser His Leu Met
50                  55                  60                  65

ggc atg ttc tac cgc acc att cgc atg atg gag aac ggc atc aag ccc       656
Gly Met Phe Tyr Arg Thr Ile Arg Met Met Glu Asn Gly Ile Lys Pro
                70                  75                  80

gtg tat gtc ttt gat ggc aag ccg cca cag ctc aag tca ggc gag ctg       704
```

```
Val Tyr Val Phe Asp Gly Lys Pro Pro Gln Leu Lys Ser Gly Glu Leu
            85                  90                  95

gcc aaa cgc agt gag cgg cgg gct gag gca gag aag cag ctg cag cag      752
Ala Lys Arg Ser Glu Arg Arg Ala Glu Ala Glu Lys Gln Leu Gln Gln
        100                 105                 110

gct cag gct gct ggg gcc gag cag gag gtg gaa aaa ttc act aag cgg      800
Ala Gln Ala Ala Gly Ala Glu Gln Glu Val Glu Lys Phe Thr Lys Arg
    115                 120                 125

ctg gtg aag gtc act aag cag cac aat gat gag tgc aaa cat ctg ctg      848
Leu Val Lys Val Thr Lys Gln His Asn Asp Glu Cys Lys His Leu Leu
130                 135                 140                 145

agc ctc atg ggc atc cct tat ctt gat gca ccc agt gag gca gag gcc      896
Ser Leu Met Gly Ile Pro Tyr Leu Asp Ala Pro Ser Glu Ala Glu Ala
                150                 155                 160

agc tgt gct gcc ctg gtg aag gct ggc aaa gtc tat gct gcg gct acc      944
Ser Cys Ala Ala Leu Val Lys Ala Gly Lys Val Tyr Ala Ala Ala Thr
            165                 170                 175

gag gac atg gac tgc ctc acc ttc ggc agc cct gtg cta atg cga cac      992
Glu Asp Met Asp Cys Leu Thr Phe Gly Ser Pro Val Leu Met Arg His
        180                 185                 190

ctg act gcc agt gaa gcc aaa aag ctg cca atc cag gaa ttc cac ctg     1040
Leu Thr Ala Ser Glu Ala Lys Lys Leu Pro Ile Gln Glu Phe His Leu
    195                 200                 205

agc cgg att ctg cag gag ctg ggc ctg aac cag gaa cag ttt gtg gat     1088
Ser Arg Ile Leu Gln Glu Leu Gly Leu Asn Gln Glu Gln Phe Val Asp
210                 215                 220                 225

ctg tgc atc ctg cta ggc agt gac tac tgt gag agt atc cgg ggt att     1136
Leu Cys Ile Leu Leu Gly Ser Asp Tyr Cys Glu Ser Ile Arg Gly Ile
                230                 235                 240

ggg ccc aag cgg gct gtg gac ctc atc cag aag cac aag agc atc gag     1184
Gly Pro Lys Arg Ala Val Asp Leu Ile Gln Lys His Lys Ser Ile Glu
            245                 250                 255

gag atc gtg cgg cga ctt gac ccc aac aag tac cct gtg cca gaa aat     1232
Glu Ile Val Arg Arg Leu Asp Pro Asn Lys Tyr Pro Val Pro Glu Asn
        260                 265                 270

tgg ctc cac aag gag gct cac cag ctc ttc ttg gaa cct gag gtg ctg     1280
Trp Leu His Lys Glu Ala His Gln Leu Phe Leu Glu Pro Glu Val Leu
    275                 280                 285

gac cca gag tct gtg gag ctg aag tgg agc gag cca aat gaa gaa gag     1328
Asp Pro Glu Ser Val Glu Leu Lys Trp Ser Glu Pro Asn Glu Glu Glu
290                 295                 300                 305

ctg atc aag ttc atg tgt ggt gaa aag cag ttc tct gag gag cga atc     1376
Leu Ile Lys Phe Met Cys Gly Glu Lys Gln Phe Ser Glu Glu Arg Ile
                310                 315                 320

cgc agt ggg gtc aag agg ctg agt aag agc cgc caa ggc agc acc cag     1424
Arg Ser Gly Val Lys Arg Leu Ser Lys Ser Arg Gln Gly Ser Thr Gln
            325                 330                 335

ggc cgc ctg gat gat ttc ttc aag gtg acc ggc tca ctc tct tca gct     1472
Gly Arg Leu Asp Asp Phe Phe Lys Val Thr Gly Ser Leu Ser Ser Ala
        340                 345                 350

aag cgc aag gag cca gaa ccc aag gga tcc act aag aag aag gca aag     1520
Lys Arg Lys Glu Pro Glu Pro Lys Gly Ser Thr Lys Lys Lys Ala Lys
    355                 360                 365

act ggg gca gca ggg aag ttt aaa agg gga aaa taa atgtgtttcc          1566
Thr Gly Ala Ala Gly Lys Phe Lys Arg Gly Lys
370                 375                 380

ccattatacc tccttcaccc cagaatattt gccgtcttgt acccttaaga gctacagcta   1626

gagaaacctt cacggggtgg agagaggatt ctaaggcttt tctagcgtga cccttttcag   1686
```

```
tagtgctagt cccttttta cttgatctta atggcaagaa ggccacagag gtacttttcc   1746

tttttagct caggaaaata tgtcaggctc aaaccacttc tcaggcagtt taatggacac   1806

taagtccatt gttacatgaa agtgatagat agcaacaagt tttggagaag agagagggag   1866

ataaaagggg gagacaaaag atgtacagaa atgatttcct ggctggccaa ctggtggcca   1926

gtgggaggtg atggtggacc tagactgtgc ttttctgtct tgttcagcct tgacccacct   1986

tgagagagag ccaccaggaa ggcgcatctt agcagatggg aggaactgct gagagaagat   2046

gggcagaaag ctggagcccc tggagttggc tgtgtctgtg tttgtgactg attactggct   2106

gtgtcttggg tgggcagaaa ctcgaacttg ctatgtaatt tgtgtctagt tattcagagg   2166

agtaagatgg tgatgttcac ctggcaatca gctgagttga gactttggaa taagacactg   2226

gttttcatgc gctgttttg ttttaaagtt atgaagaaaa aagtcaataa aattctaaaa   2286

gtaaccaaaa aaaaaaaaaa aa                                            2308


<210> SEQ ID NO 26
<211> LENGTH: 380
<212> TYPE: PRT
<213> ORGANISM: Homo sapiens

<400> SEQUENCE: 26

Met Gly Ile Gln Gly Leu Ala Lys Leu Ile Ala Asp Val Ala Pro Ser
1               5                   10                  15

Ala Ile Arg Glu Asn Asp Ile Lys Ser Tyr Phe Gly Arg Lys Val Ala
            20                  25                  30

Ile Asp Ala Ser Met Ser Ile Tyr Gln Phe Leu Ile Ala Val Arg Gln
        35                  40                  45

Gly Gly Asp Val Leu Gln Asn Glu Glu Gly Glu Thr Thr Ser His Leu
    50                  55                  60

Met Gly Met Phe Tyr Arg Thr Ile Arg Met Met Glu Asn Gly Ile Lys
65                  70                  75                  80

Pro Val Tyr Val Phe Asp Gly Lys Pro Pro Gln Leu Lys Ser Gly Glu
                85                  90                  95

Leu Ala Lys Arg Ser Glu Arg Arg Ala Glu Ala Glu Lys Gln Leu Gln
            100                 105                 110

Gln Ala Gln Ala Ala Gly Ala Glu Gln Glu Val Glu Lys Phe Thr Lys
        115                 120                 125

Arg Leu Val Lys Val Thr Lys Gln His Asn Asp Glu Cys Lys His Leu
    130                 135                 140

Leu Ser Leu Met Gly Ile Pro Tyr Leu Asp Ala Pro Ser Glu Ala Glu
145                 150                 155                 160

Ala Ser Cys Ala Ala Leu Val Lys Ala Gly Lys Val Tyr Ala Ala Ala
                165                 170                 175

Thr Glu Asp Met Asp Cys Leu Thr Phe Gly Ser Pro Val Leu Met Arg
            180                 185                 190

His Leu Thr Ala Ser Glu Ala Lys Lys Leu Pro Ile Gln Glu Phe His
        195                 200                 205

Leu Ser Arg Ile Leu Gln Glu Leu Gly Leu Asn Gln Glu Gln Phe Val
    210                 215                 220

Asp Leu Cys Ile Leu Leu Gly Ser Asp Tyr Cys Glu Ser Ile Arg Gly
225                 230                 235                 240

Ile Gly Pro Lys Arg Ala Val Asp Leu Ile Gln Lys His Lys Ser Ile
                245                 250                 255

Glu Glu Ile Val Arg Arg Leu Asp Pro Asn Lys Tyr Pro Val Pro Glu
```

```
            260                 265                 270

Asn Trp Leu His Lys Glu Ala His Gln Leu Phe Leu Glu Pro Glu Val
        275                 280                 285

Leu Asp Pro Glu Ser Val Glu Leu Lys Trp Ser Glu Pro Asn Glu Glu
    290                 295                 300

Glu Leu Ile Lys Phe Met Cys Gly Glu Lys Gln Phe Ser Glu Glu Arg
305                 310                 315                 320

Ile Arg Ser Gly Val Lys Arg Leu Ser Lys Ser Arg Gln Gly Ser Thr
                325                 330                 335

Gln Gly Arg Leu Asp Asp Phe Phe Lys Val Thr Gly Ser Leu Ser Ser
            340                 345                 350

Ala Lys Arg Lys Glu Pro Glu Pro Lys Gly Ser Thr Lys Lys Lys Ala
        355                 360                 365

Lys Thr Gly Ala Ala Gly Lys Phe Lys Arg Gly Lys
    370                 375                 380


<210> SEQ ID NO 27
<211> LENGTH: 3410
<212> TYPE: DNA
<213> ORGANISM: Homo sapiens
<220> FEATURE:
<221> NAME/KEY: CDS
<222> LOCATION: (421)..(3180)
<223> OTHER INFORMATION: LIG1

<400> SEQUENCE: 27

ctcgcggggg cgcttccacc gattcctcct ctttccctgc cagtcactcc tcagaccctc      60

agccacaccc gctcatccag ggcgagggaa agcgcgggca ttttcccagt gtgctctgcg     120

ggagggctcg ccccacttca ccccttttcc cgccctcctc ccattcggga gactacgact     180

cccagtgtcc tccgcgcgac ggcggcggtg cggacggtgc ccaggtcccg cccctaggct     240

ctgccccgcc cccgcccgca gacgtctgcg cgcgaatgcc gtggcgcgaa cttgggactg     300

cagaggcgcg cctggcggat ctgagtgtgt tgcccgggca gcggcgcgcg ggaccaacgc     360

aaggagcagc tgacagacga agaaaagtgc tggacaggaa gggagaattc tgacgccaac     420

atg cag cga agt atc atg tca ttt ttc cac ccc aag aaa gag ggt aaa       468

Met Gln Arg Ser Ile Met Ser Phe Phe His Pro Lys Lys Glu Gly Lys
1               5                   10                  15

gca aag aag cct gag aag gag gca tcc aat agc agc aga gag acg gag       516
Ala Lys Lys Pro Glu Lys Glu Ala Ser Asn Ser Ser Arg Glu Thr Glu
            20                  25                  30

ccc cct cca aag gcg gca ctg aag gag tgg aat gga gtg gtg tcc gag       564
Pro Pro Pro Lys Ala Ala Leu Lys Glu Trp Asn Gly Val Val Ser Glu
        35                  40                  45

agt gac tct ccg gtg aag agg cca ggg agg aag gcg gcc cgg gtc ctg       612
Ser Asp Ser Pro Val Lys Arg Pro Gly Arg Lys Ala Ala Arg Val Leu
    50                  55                  60

ggc agc gaa ggg gaa gag gag gat gaa gcc ctt agc cct gct aaa ggc       660
Gly Ser Glu Gly Glu Glu Glu Asp Glu Ala Leu Ser Pro Ala Lys Gly
65                  70                  75                  80

cag aag cct gcc ctg gac tgc tca cag gtc tcc ccg ccc cgt cct gcc       708
Gln Lys Pro Ala Leu Asp Cys Ser Gln Val Ser Pro Pro Arg Pro Ala
                85                  90                  95

aca tct cct gag aac aat gct tcc ctc tct gac acc tct ccc atg gac       756
Thr Ser Pro Glu Asn Asn Ala Ser Leu Ser Asp Thr Ser Pro Met Asp
            100                 105                 110

agt tcc cca tca ggg att ccg aag cgt cgc aca gct cgg aag cag ctc       804
```

```
Ser Ser Pro Ser Gly Ile Pro Lys Arg Arg Thr Ala Arg Lys Gln Leu
        115                 120                 125

ccg aaa cgg acc att cag gaa gtc ctg gaa gag cag agt gag gac gag      852
Pro Lys Arg Thr Ile Gln Glu Val Leu Glu Glu Gln Ser Glu Asp Glu
    130                 135                 140

gac aga gaa gcc aag agg aag aag gag gag gaa gaa gag gag acc ccg      900
Asp Arg Glu Ala Lys Arg Lys Lys Glu Glu Glu Glu Glu Glu Thr Pro
145                 150                 155                 160

aaa gaa agc ctc aca gag gct gaa gtg gcc aca gag aag gaa gga gaa      948
Lys Glu Ser Leu Thr Glu Ala Glu Val Ala Thr Glu Lys Glu Gly Glu
                165                 170                 175

gac ggg gac cag ccc acc acg cct ccc aag ccc cta aag acc tcc aaa      996
Asp Gly Asp Gln Pro Thr Thr Pro Pro Lys Pro Leu Lys Thr Ser Lys
            180                 185                 190

gca gag acc ccg acg gaa agc gtt tca gag cct gag gtg gcc acg aag     1044
Ala Glu Thr Pro Thr Glu Ser Val Ser Glu Pro Glu Val Ala Thr Lys
        195                 200                 205

cag gaa ctg cag gag gag gaa gag cag acc aag cct ccc cgc aga gct     1092
Gln Glu Leu Gln Glu Glu Glu Glu Gln Thr Lys Pro Pro Arg Arg Ala
    210                 215                 220

ccc aag acg ctc agc agc ttc ttc acc ccc cgg aag cca gca gtc aaa     1140
Pro Lys Thr Leu Ser Ser Phe Phe Thr Pro Arg Lys Pro Ala Val Lys
225                 230                 235                 240

aaa gaa gtg aag gaa gag gag cca ggg gct cca gga aag gag gga gct     1188
Lys Glu Val Lys Glu Glu Glu Pro Gly Ala Pro Gly Lys Glu Gly Ala
                245                 250                 255

gct gag gga ccc ctg gat cca tct ggt tac aat cct gcc aag aac aac     1236
Ala Glu Gly Pro Leu Asp Pro Ser Gly Tyr Asn Pro Ala Lys Asn Asn
            260                 265                 270

tat cat ccc gtg gaa gat gcc tgc tgg aaa ccg ggc cag aag gtt cct     1284
Tyr His Pro Val Glu Asp Ala Cys Trp Lys Pro Gly Gln Lys Val Pro
        275                 280                 285

tac ctg gct gtg gcc cgg acg ttt gag aag atc gag gag gtg tct gct     1332
Tyr Leu Ala Val Ala Arg Thr Phe Glu Lys Ile Glu Glu Val Ser Ala
    290                 295                 300

cgg ctc cgg atg gtg gag acg ctg agc aac ttg ctg cgc tcc gtg gtg     1380
Arg Leu Arg Met Val Glu Thr Leu Ser Asn Leu Leu Arg Ser Val Val
305                 310                 315                 320

gcc ctg tcg cct cca gac ctc ctc cct gtc ctc tac ctc agc ctc aac     1428
Ala Leu Ser Pro Pro Asp Leu Leu Pro Val Leu Tyr Leu Ser Leu Asn
                325                 330                 335

cac ctt ggg cca ccc cag cag ggc ctg gag ctt ggc gtg ggt gat ggt     1476
His Leu Gly Pro Pro Gln Gln Gly Leu Glu Leu Gly Val Gly Asp Gly
            340                 345                 350

gtc ctt ctc aag gca gtg gcc cag gcc aca ggt cgg cag ctg gag tcc     1524
Val Leu Leu Lys Ala Val Ala Gln Ala Thr Gly Arg Gln Leu Glu Ser
        355                 360                 365

gtc cgg gct gag gca gcc gag aaa ggc gac gtg ggg ctg gtg gcc gag     1572
Val Arg Ala Glu Ala Ala Glu Lys Gly Asp Val Gly Leu Val Ala Glu
    370                 375                 380

aac agc cgc agc acc cag agg ctc atg ctg cca cca cct ccg ctc act     1620
Asn Ser Arg Ser Thr Gln Arg Leu Met Leu Pro Pro Pro Pro Leu Thr
385                 390                 395                 400

gcc tcc ggg gtc ttc agc aag ttc cgc gac atc gcc agg ctc act ggc     1668
Ala Ser Gly Val Phe Ser Lys Phe Arg Asp Ile Ala Arg Leu Thr Gly
                405                 410                 415

agt gct tcc aca gcc aag aag ata gac atc atc aaa ggc ctc ttt gtg     1716
Ser Ala Ser Thr Ala Lys Lys Ile Asp Ile Ile Lys Gly Leu Phe Val
            420                 425                 430
```

```
gcc tgc cgc cac tca gaa gcc cgg ttc atc gct agg tcc ctg agc gga      1764
Ala Cys Arg His Ser Glu Ala Arg Phe Ile Ala Arg Ser Leu Ser Gly
        435                 440                 445

cgg ctg cgc ctt ggg ctg gca gag cag tcg gtg ctg gct gcc ctc tcc      1812
Arg Leu Arg Leu Gly Leu Ala Glu Gln Ser Val Leu Ala Ala Leu Ser
    450                 455                 460

cag gca gtg agc ctc acg ccc ccg ggc caa gaa ttc cca cca gcc atg      1860
Gln Ala Val Ser Leu Thr Pro Pro Gly Gln Glu Phe Pro Pro Ala Met
465                 470                 475                 480

gtg gat gct ggg aag ggc aag aca gca gag gcc aga aag acg tgg ctg      1908
Val Asp Ala Gly Lys Gly Lys Thr Ala Glu Ala Arg Lys Thr Trp Leu
                485                 490                 495

gag gag caa ggc atg atc ctg aag cag acg ttc tgc gag gtt ccc gac      1956
Glu Glu Gln Gly Met Ile Leu Lys Gln Thr Phe Cys Glu Val Pro Asp
            500                 505                 510

ctg gac cga att atc ccc gtg ctg ctg gag cac ggc ctg gaa cgt ctc      2004
Leu Asp Arg Ile Ile Pro Val Leu Leu Glu His Gly Leu Glu Arg Leu
        515                 520                 525

ccg gag cac tgc aag ctg agc cca ggg att ccc ctg aaa cca atg ttg      2052
Pro Glu His Cys Lys Leu Ser Pro Gly Ile Pro Leu Lys Pro Met Leu
    530                 535                 540

gcc cat ccc acc cgg ggc atc agc gag gtc ctg aaa cgc ttt gag gag      2100
Ala His Pro Thr Arg Gly Ile Ser Glu Val Leu Lys Arg Phe Glu Glu
545                 550                 555                 560

gca gct ttc acc tgc gaa tac aaa tat gac ggg cag agg gca cag atc      2148
Ala Ala Phe Thr Cys Glu Tyr Lys Tyr Asp Gly Gln Arg Ala Gln Ile
                565                 570                 575

cac gcc ctg gaa ggc ggg gag gtg aag atc ttc agc agg aat cag gaa      2196
His Ala Leu Glu Gly Gly Glu Val Lys Ile Phe Ser Arg Asn Gln Glu
            580                 585                 590

gac aac act ggg aag tac ccg gac atc atc agc cgc atc ccc aag att      2244
Asp Asn Thr Gly Lys Tyr Pro Asp Ile Ile Ser Arg Ile Pro Lys Ile
        595                 600                 605

aaa ctc cca tcg gtc aca tcc ttc atc ctg gac acc gaa gcc gtg gct      2292
Lys Leu Pro Ser Val Thr Ser Phe Ile Leu Asp Thr Glu Ala Val Ala
    610                 615                 620

tgg gac cgg gaa aag aag cag atc cag cca ttc caa gtg ctc acc acc      2340
Trp Asp Arg Glu Lys Lys Gln Ile Gln Pro Phe Gln Val Leu Thr Thr
625                 630                 635                 640

cgc aaa cgc aag gag gtg gat gcg tct gag atc cag gtg cag gtg tgt      2388
Arg Lys Arg Lys Glu Val Asp Ala Ser Glu Ile Gln Val Gln Val Cys
                645                 650                 655

ttg tac gcc ttc gac ctc atc tac ctc aat gga gag tcc ctg gta cgt      2436
Leu Tyr Ala Phe Asp Leu Ile Tyr Leu Asn Gly Glu Ser Leu Val Arg
            660                 665                 670

gag ccc ctt tcc cgg cgc cgg cag ctg ctc cgg gag aac ttt gtg gag      2484
Glu Pro Leu Ser Arg Arg Arg Gln Leu Leu Arg Glu Asn Phe Val Glu
        675                 680                 685

aca gag ggc gag ttt gtc ttc gcc acc tcc ctg gac acc aag gac atc      2532
Thr Glu Gly Glu Phe Val Phe Ala Thr Ser Leu Asp Thr Lys Asp Ile
    690                 695                 700

gag cag atc gcc gag ttc ctg gag cag tca gtg aaa gac tcc tgc gag      2580
Glu Gln Ile Ala Glu Phe Leu Glu Gln Ser Val Lys Asp Ser Cys Glu
705                 710                 715                 720

ggg ctg atg gtg aag acc ctg gat gtt gat gcc acc tac gag atc gcc      2628
Gly Leu Met Val Lys Thr Leu Asp Val Asp Ala Thr Tyr Glu Ile Ala
                725                 730                 735

aag aga tcg cac aac tgg ctc aag ctg aag aag gac tac ctt gat ggc      2676
Lys Arg Ser His Asn Trp Leu Lys Leu Lys Lys Asp Tyr Leu Asp Gly
            740                 745                 750
```

```
gtg ggt gac acc ctg gac ctg gtg gtg atc ggc gcc tac ctg ggc cgg     2724
Val Gly Asp Thr Leu Asp Leu Val Val Ile Gly Ala Tyr Leu Gly Arg
        755                 760                 765

ggg aag cgg gcc ggc cgg tac ggg ggc ttc ctg ctg gcc tcc tac gac     2772
Gly Lys Arg Ala Gly Arg Tyr Gly Gly Phe Leu Leu Ala Ser Tyr Asp
    770                 775                 780

gag gac agt gag gag ctg cag gcc ata tgc aag ctt gga act ggc ttc     2820
Glu Asp Ser Glu Glu Leu Gln Ala Ile Cys Lys Leu Gly Thr Gly Phe
785                 790                 795                 800

agt gat gag gag ctg gag gag cat cac cag agc ctc aag gcg ctg gtg     2868
Ser Asp Glu Glu Leu Glu Glu His His Gln Ser Leu Lys Ala Leu Val
                805                 810                 815

ctg ccc agc cca cgc cct tac gtg cgg ata gat ggc gct gtg att ccc     2916
Leu Pro Ser Pro Arg Pro Tyr Val Arg Ile Asp Gly Ala Val Ile Pro
            820                 825                 830

gac cac tgg ctg gac ccc agc gct gtg tgg gag gtg aag tgc gct gac     2964
Asp His Trp Leu Asp Pro Ser Ala Val Trp Glu Val Lys Cys Ala Asp
        835                 840                 845

ctc tcc ctc tct ccc atc tac cct gct gcg cgg ggc ctg gtg gat agt     3012
Leu Ser Leu Ser Pro Ile Tyr Pro Ala Ala Arg Gly Leu Val Asp Ser
    850                 855                 860

gac aag ggc atc tcc ctt cgc ttc cct cgg ttt att cga gtc cgt gaa     3060
Asp Lys Gly Ile Ser Leu Arg Phe Pro Arg Phe Ile Arg Val Arg Glu
865                 870                 875                 880

gac aag cag ccg gag cag gcc acc acc agt gct cag gtg gcc tgt ttg     3108
Asp Lys Gln Pro Glu Gln Ala Thr Thr Ser Ala Gln Val Ala Cys Leu
                885                 890                 895

tac cgg aag caa agt cag att cag aac caa caa ggc gag gac tca ggc     3156
Tyr Arg Lys Gln Ser Gln Ile Gln Asn Gln Gln Gly Glu Asp Ser Gly
            900                 905                 910

tct gac cct gaa gat acc tac taa gccctcgccc tcctagggcc tgggtacagg    3210
Ser Asp Pro Glu Asp Thr Tyr
        915

gcatgagttg gacggacccc agggttatta ttgcctttgc tttttagcaa atctgctgtg   3270

gcaggctgtg gattttgaga gtcaggggag gggtgtgtgt gtgagggggt ggcttactcc   3330

ggagtctggg attcatcccg tcatttcttt caataaataa ttattggata gctaaaaaaa   3390

aaaaaaaaaa aaaaaaaaaa                                               3410


<210> SEQ ID NO 28
<211> LENGTH: 919
<212> TYPE: PRT
<213> ORGANISM: Homo sapiens

<400> SEQUENCE: 28

Met Gln Arg Ser Ile Met Ser Phe Phe His Pro Lys Lys Glu Gly Lys
1               5                   10                  15

Ala Lys Lys Pro Glu Lys Glu Ala Ser Asn Ser Ser Arg Glu Thr Glu
            20                  25                  30

Pro Pro Pro Lys Ala Ala Leu Lys Glu Trp Asn Gly Val Val Ser Glu
        35                  40                  45

Ser Asp Ser Pro Val Lys Arg Pro Gly Arg Lys Ala Ala Arg Val Leu
    50                  55                  60

Gly Ser Glu Gly Glu Glu Glu Asp Glu Ala Leu Ser Pro Ala Lys Gly
65                  70                  75                  80

Gln Lys Pro Ala Leu Asp Cys Ser Gln Val Ser Pro Pro Arg Pro Ala
                85                  90                  95
```

```
Thr Ser Pro Glu Asn Asn Ala Ser Leu Ser Asp Thr Ser Pro Met Asp
            100                 105                 110

Ser Ser Pro Ser Gly Ile Pro Lys Arg Arg Thr Ala Arg Lys Gln Leu
        115                 120                 125

Pro Lys Arg Thr Ile Gln Glu Val Leu Glu Glu Gln Ser Glu Asp Glu
    130                 135                 140

Asp Arg Glu Ala Lys Arg Lys Lys Glu Glu Glu Glu Glu Glu Thr Pro
145                 150                 155                 160

Lys Glu Ser Leu Thr Glu Ala Glu Val Ala Thr Glu Lys Glu Gly Glu
                165                 170                 175

Asp Gly Asp Gln Pro Thr Thr Pro Pro Lys Pro Leu Lys Thr Ser Lys
            180                 185                 190

Ala Glu Thr Pro Thr Glu Ser Val Ser Glu Pro Glu Val Ala Thr Lys
        195                 200                 205

Gln Glu Leu Gln Glu Glu Glu Glu Gln Thr Lys Pro Pro Arg Arg Ala
    210                 215                 220

Pro Lys Thr Leu Ser Ser Phe Phe Thr Pro Arg Lys Pro Ala Val Lys
225                 230                 235                 240

Lys Glu Val Lys Glu Glu Glu Pro Gly Ala Pro Gly Lys Glu Gly Ala
                245                 250                 255

Ala Glu Gly Pro Leu Asp Pro Ser Gly Tyr Asn Pro Ala Lys Asn Asn
            260                 265                 270

Tyr His Pro Val Glu Asp Ala Cys Trp Lys Pro Gly Gln Lys Val Pro
        275                 280                 285

Tyr Leu Ala Val Ala Arg Thr Phe Glu Lys Ile Glu Glu Val Ser Ala
    290                 295                 300

Arg Leu Arg Met Val Glu Thr Leu Ser Asn Leu Leu Arg Ser Val Val
305                 310                 315                 320

Ala Leu Ser Pro Pro Asp Leu Leu Pro Val Leu Tyr Leu Ser Leu Asn
                325                 330                 335

His Leu Gly Pro Pro Gln Gln Gly Leu Glu Leu Gly Val Gly Asp Gly
            340                 345                 350

Val Leu Leu Lys Ala Val Ala Gln Ala Thr Gly Arg Gln Leu Glu Ser
        355                 360                 365

Val Arg Ala Glu Ala Ala Glu Lys Gly Asp Val Gly Leu Val Ala Glu
    370                 375                 380

Asn Ser Arg Ser Thr Gln Arg Leu Met Leu Pro Pro Pro Pro Leu Thr
385                 390                 395                 400

Ala Ser Gly Val Phe Ser Lys Phe Arg Asp Ile Ala Arg Leu Thr Gly
                405                 410                 415

Ser Ala Ser Thr Ala Lys Lys Ile Asp Ile Ile Lys Gly Leu Phe Val
            420                 425                 430

Ala Cys Arg His Ser Glu Ala Arg Phe Ile Ala Arg Ser Leu Ser Gly
        435                 440                 445

Arg Leu Arg Leu Gly Leu Ala Glu Gln Ser Val Leu Ala Ala Leu Ser
    450                 455                 460

Gln Ala Val Ser Leu Thr Pro Pro Gly Gln Glu Phe Pro Pro Ala Met
465                 470                 475                 480

Val Asp Ala Gly Lys Gly Lys Thr Ala Glu Ala Arg Lys Thr Trp Leu
                485                 490                 495

Glu Glu Gln Gly Met Ile Leu Lys Gln Thr Phe Cys Glu Val Pro Asp
            500                 505                 510

Leu Asp Arg Ile Ile Pro Val Leu Leu Glu His Gly Leu Glu Arg Leu
```

```
        515                 520                 525

Pro Glu His Cys Lys Leu Ser Pro Gly Ile Pro Leu Lys Pro Met Leu
    530                 535                 540

Ala His Pro Thr Arg Gly Ile Ser Glu Val Leu Lys Arg Phe Glu Glu
545                 550                 555                 560

Ala Ala Phe Thr Cys Glu Tyr Lys Tyr Asp Gly Gln Arg Ala Gln Ile
                565                 570                 575

His Ala Leu Glu Gly Gly Glu Val Lys Ile Phe Ser Arg Asn Gln Glu
            580                 585                 590

Asp Asn Thr Gly Lys Tyr Pro Asp Ile Ile Ser Arg Ile Pro Lys Ile
        595                 600                 605

Lys Leu Pro Ser Val Thr Ser Phe Ile Leu Asp Thr Glu Ala Val Ala
    610                 615                 620

Trp Asp Arg Glu Lys Lys Gln Ile Gln Pro Phe Gln Val Leu Thr Thr
625                 630                 635                 640

Arg Lys Arg Lys Glu Val Asp Ala Ser Glu Ile Gln Val Gln Val Cys
                645                 650                 655

Leu Tyr Ala Phe Asp Leu Ile Tyr Leu Asn Gly Glu Ser Leu Val Arg
            660                 665                 670

Glu Pro Leu Ser Arg Arg Arg Gln Leu Leu Arg Glu Asn Phe Val Glu
        675                 680                 685

Thr Glu Gly Glu Phe Val Phe Ala Thr Ser Leu Asp Thr Lys Asp Ile
    690                 695                 700

Glu Gln Ile Ala Glu Phe Leu Glu Gln Ser Val Lys Asp Ser Cys Glu
705                 710                 715                 720

Gly Leu Met Val Lys Thr Leu Asp Val Asp Ala Thr Tyr Glu Ile Ala
                725                 730                 735

Lys Arg Ser His Asn Trp Leu Lys Leu Lys Lys Asp Tyr Leu Asp Gly
            740                 745                 750

Val Gly Asp Thr Leu Asp Leu Val Val Ile Gly Ala Tyr Leu Gly Arg
        755                 760                 765

Gly Lys Arg Ala Gly Arg Tyr Gly Gly Phe Leu Leu Ala Ser Tyr Asp
    770                 775                 780

Glu Asp Ser Glu Glu Leu Gln Ala Ile Cys Lys Leu Gly Thr Gly Phe
785                 790                 795                 800

Ser Asp Glu Glu Leu Glu Glu His His Gln Ser Leu Lys Ala Leu Val
                805                 810                 815

Leu Pro Ser Pro Arg Pro Tyr Val Arg Ile Asp Gly Ala Val Ile Pro
            820                 825                 830

Asp His Trp Leu Asp Pro Ser Ala Val Trp Glu Val Lys Cys Ala Asp
        835                 840                 845

Leu Ser Leu Ser Pro Ile Tyr Pro Ala Ala Arg Gly Leu Val Asp Ser
    850                 855                 860

Asp Lys Gly Ile Ser Leu Arg Phe Pro Arg Phe Ile Arg Val Arg Glu
865                 870                 875                 880

Asp Lys Gln Pro Glu Gln Ala Thr Thr Ser Ala Gln Val Ala Cys Leu
                885                 890                 895

Tyr Arg Lys Gln Ser Gln Ile Gln Asn Gln Gln Gly Glu Asp Ser Gly
            900                 905                 910

Ser Asp Pro Glu Asp Thr Tyr
        915
```

<210> SEQ ID NO 29

```
<211> LENGTH: 4091
<212> TYPE: DNA
<213> ORGANISM: Homo sapiens
<220> FEATURE:
<221> NAME/KEY: CDS
<222> LOCATION: (427)..(3987)
<223> OTHER INFORMATION: ERCC5

<400> SEQUENCE: 29

attttcatg ggtttgcgga cccaccagcg aaggcgggag gtgtcgcagg gacatcttct      60

ggctgtttcc gtcgcctgcg tggcccttgc accccggtct tccattagcg gcgcagacgt    120

ttgggcctaa gcgctgggcg aggcgaggcc ctgcccctcc ccgccaacgg ccattctctg    180

gacctgtctt tcttccggga ggcggtgaca gctgctgaga cgtgttgcag ccagagtctc    240

tccgctttaa tgcgctccca ttagtgccgt cccccactgg aaaaccgtgg cttctgtatt    300

atttgccatc tttgttgtgt aggagcaggg agggcttcct cccggggtcc taggcggcgg    360

tgcagtccgt cgtagaagaa ttagagtaga agttgtcggg gtccgctctt aggacgcagc    420

cgcctc atg ggg gtc cag ggg ctc tgg aag ctg ctg gag tgc tcc ggg      468
       Met Gly Val Gln Gly Leu Trp Lys Leu Leu Glu Cys Ser Gly
       1               5                   10

cgg cag gtc agc ccc gaa gcg ctg gaa ggg aag atc ctg gct gtt gat      516
Arg Gln Val Ser Pro Glu Ala Leu Glu Gly Lys Ile Leu Ala Val Asp
15                  20                  25                  30

att agc att tgg tta aac caa gca ctt aaa gga gtc cgg gat cgc cat      564
Ile Ser Ile Trp Leu Asn Gln Ala Leu Lys Gly Val Arg Asp Arg His
                35                  40                  45

ggg aac tca ata gaa aat cct cat ctt ctc act ttg ttt cat cgg ctc      612
Gly Asn Ser Ile Glu Asn Pro His Leu Leu Thr Leu Phe His Arg Leu
            50                  55                  60

tgc aaa ctc tta ttt ttt cga att cgt cct att ttt gtg ttt gat ggg      660
Cys Lys Leu Leu Phe Phe Arg Ile Arg Pro Ile Phe Val Phe Asp Gly
        65                  70                  75

gat gct cca cta ttg aag aaa cag act ttg gtg aag aga agg cag aga      708
Asp Ala Pro Leu Leu Lys Lys Gln Thr Leu Val Lys Arg Arg Gln Arg
    80                  85                  90

aag gac tta gcg tcc agt gac tcc agg aaa acg aca gag aag ctt ctg      756
Lys Asp Leu Ala Ser Ser Asp Ser Arg Lys Thr Thr Glu Lys Leu Leu
95                  100                 105                 110

aaa aca ttt ttg aaa aga caa gcc atc aaa act gcc ttc aga agc aaa      804
Lys Thr Phe Leu Lys Arg Gln Ala Ile Lys Thr Ala Phe Arg Ser Lys
                115                 120                 125

aga gat gaa gca cta ccc agt ctt acc caa gtt cga aga gaa aac gac      852
Arg Asp Glu Ala Leu Pro Ser Leu Thr Gln Val Arg Arg Glu Asn Asp
            130                 135                 140

ctc tat gtt ttg cct cct tta caa gag gaa gaa aaa cac agt tca gaa      900
Leu Tyr Val Leu Pro Pro Leu Gln Glu Glu Glu Lys His Ser Ser Glu
        145                 150                 155

gag gaa gat gaa aaa gaa tgg caa gaa aga atg aat caa aaa caa gca      948
Glu Glu Asp Glu Lys Glu Trp Gln Glu Arg Met Asn Gln Lys Gln Ala
    160                 165                 170

tta cag gaa gag ttc ttt cat aat cct caa gcg ata gat att gag tct      996
Leu Gln Glu Glu Phe Phe His Asn Pro Gln Ala Ile Asp Ile Glu Ser
175                 180                 185                 190

gag gac ttc agc agc ctg ccc cct gaa gta aag cat gaa atc ttg act     1044
Glu Asp Phe Ser Ser Leu Pro Pro Glu Val Lys His Glu Ile Leu Thr
                195                 200                 205

gat atg aaa gag ttc acc aag cgc aga aga aca tta ttt gaa gca atg     1092
Asp Met Lys Glu Phe Thr Lys Arg Arg Arg Thr Leu Phe Glu Ala Met
            210                 215                 220
```

```
cca gag gag tct gat gac ttt tca cag tac caa ctc aaa ggc ttg ctt      1140
Pro Glu Glu Ser Asp Asp Phe Ser Gln Tyr Gln Leu Lys Gly Leu Leu
        225                 230                 235

aaa aag aac tat ctg aac cag cat ata gaa cat gtc caa aag gaa atg      1188
Lys Lys Asn Tyr Leu Asn Gln His Ile Glu His Val Gln Lys Glu Met
    240                 245                 250

aat cag caa cat tca gga cac atc cga agg cag tat gaa gat gaa ggg      1236
Asn Gln Gln His Ser Gly His Ile Arg Arg Gln Tyr Glu Asp Glu Gly
255                 260                 265                 270

ggc ttt ctg aag gag gta gag tca agg aga gtg gtc tct gaa gac act      1284
Gly Phe Leu Lys Glu Val Glu Ser Arg Arg Val Val Ser Glu Asp Thr
                275                 280                 285

tca cat tac atc ttg ata aaa ggt att caa gct aag aca gtt gca gaa      1332
Ser His Tyr Ile Leu Ile Lys Gly Ile Gln Ala Lys Thr Val Ala Glu
            290                 295                 300

gtg gat tca gag tct ctt cct tct tcc agc aaa atg cac ggc atg tct      1380
Val Asp Ser Glu Ser Leu Pro Ser Ser Ser Lys Met His Gly Met Ser
        305                 310                 315

ttt gac gtg aag tca tct cca tgt gaa aaa ctg aag aca gag aaa gag      1428
Phe Asp Val Lys Ser Ser Pro Cys Glu Lys Leu Lys Thr Glu Lys Glu
    320                 325                 330

cct gat gct acc cct cct tct cca aga act tta cta gct atg caa gct      1476
Pro Asp Ala Thr Pro Pro Ser Pro Arg Thr Leu Leu Ala Met Gln Ala
335                 340                 345                 350

gcc ctg ctg gga agt agc tca gaa gag gag ctg gag agt gaa aat cga      1524
Ala Leu Leu Gly Ser Ser Ser Glu Glu Glu Leu Glu Ser Glu Asn Arg
                355                 360                 365

agg cag gcc cgt ggg agg aac gca cct gct gct gta gac gaa ggc tcc      1572
Arg Gln Ala Arg Gly Arg Asn Ala Pro Ala Ala Val Asp Glu Gly Ser
            370                 375                 380

ata tca ccc cgg act ctt tca gcc att aag aga gct ctt gac gat gac      1620
Ile Ser Pro Arg Thr Leu Ser Ala Ile Lys Arg Ala Leu Asp Asp Asp
        385                 390                 395

gaa gat gta aaa gtg tgt gct ggg gat gat gtg cag acg gga ggg cca      1668
Glu Asp Val Lys Val Cys Ala Gly Asp Asp Val Gln Thr Gly Gly Pro
    400                 405                 410

gga gca gaa gaa atg cgt ata aac agc tcc acc gag aac agt gat gaa      1716
Gly Ala Glu Glu Met Arg Ile Asn Ser Ser Thr Glu Asn Ser Asp Glu
415                 420                 425                 430

gga ctt aaa gtg aga gat gga aaa gga ata ccg ttt act gca aca ctt      1764
Gly Leu Lys Val Arg Asp Gly Lys Gly Ile Pro Phe Thr Ala Thr Leu
                435                 440                 445

gcg tca tct agt gtg aac tct gca gag gag cac gta gcc agc act aat      1812
Ala Ser Ser Ser Val Asn Ser Ala Glu Glu His Val Ala Ser Thr Asn
            450                 455                 460

gag ggg aga gag ccc aca gac tca gtt cca aaa gaa caa atg tca ctt      1860
Glu Gly Arg Glu Pro Thr Asp Ser Val Pro Lys Glu Gln Met Ser Leu
        465                 470                 475

gtt cac gtg ggg act gaa gcc ttt ccg ata agt gat gag tct atg att      1908
Val His Val Gly Thr Glu Ala Phe Pro Ile Ser Asp Glu Ser Met Ile
    480                 485                 490

aag gac aga aaa gat cgg ctg cct ctg gag agt gca gtg gtt aga cat      1956
Lys Asp Arg Lys Asp Arg Leu Pro Leu Glu Ser Ala Val Val Arg His
495                 500                 505                 510

agt gac gca cct ggg ctc ccg aat gga agg gaa ctg aca ccg gca tct      2004
Ser Asp Ala Pro Gly Leu Pro Asn Gly Arg Glu Leu Thr Pro Ala Ser
                515                 520                 525

cca act tgt aca aat tct gtg tca aag aat gaa aca cat gct gaa gtg      2052
Pro Thr Cys Thr Asn Ser Val Ser Lys Asn Glu Thr His Ala Glu Val
```

```
            530                 535                 540

ctt gag cag cag aac gaa ctt tgc cca tat gag agt aaa ttc gat tct     2100
Leu Glu Gln Gln Asn Glu Leu Cys Pro Tyr Glu Ser Lys Phe Asp Ser
        545                 550                 555

tct ctt ctt tca agt gat gat gaa aca aaa tgt aaa ccg aat tct gct     2148
Ser Leu Leu Ser Ser Asp Asp Glu Thr Lys Cys Lys Pro Asn Ser Ala
    560                 565                 570

tct gaa gtc att ggc cct gtc agt ttg caa gaa aca agt agc ata gta     2196
Ser Glu Val Ile Gly Pro Val Ser Leu Gln Glu Thr Ser Ser Ile Val
575                 580                 585                 590

agt gtc cct tca gag gca gta gat aat gtg gaa aat gtg gtg tca ttt     2244
Ser Val Pro Ser Glu Ala Val Asp Asn Val Glu Asn Val Val Ser Phe
                595                 600                 605

aat gct aaa gag cat gag aat ttt ctg gaa acc atc caa gaa cag cag     2292
Asn Ala Lys Glu His Glu Asn Phe Leu Glu Thr Ile Gln Glu Gln Gln
            610                 615                 620

acc act gaa tct gca ggc cag gat tta att tcc att cca aag gcc gtg     2340
Thr Thr Glu Ser Ala Gly Gln Asp Leu Ile Ser Ile Pro Lys Ala Val
        625                 630                 635

gaa cca atg gaa att gac tcg gaa gaa agt gaa tct gat gga agt ttc     2388
Glu Pro Met Glu Ile Asp Ser Glu Glu Ser Glu Ser Asp Gly Ser Phe
    640                 645                 650

att gaa gtg caa agt gtg att agt gat gag gaa ctt caa gca gaa ttc     2436
Ile Glu Val Gln Ser Val Ile Ser Asp Glu Glu Leu Gln Ala Glu Phe
655                 660                 665                 670

cct gaa act tcc aaa cct ccc tca gaa caa ggc gaa gag gaa ctg gta     2484
Pro Glu Thr Ser Lys Pro Pro Ser Glu Gln Gly Glu Glu Glu Leu Val
                675                 680                 685

gga act agg gag gga gaa gcc cct gct gag tcc gag agc ctc ctg agg     2532
Gly Thr Arg Glu Gly Glu Ala Pro Ala Glu Ser Glu Ser Leu Leu Arg
            690                 695                 700

gac aac tct gag agg gac gac gtg gat ggt gag cca cag gaa gct gag     2580
Asp Asn Ser Glu Arg Asp Asp Val Asp Gly Glu Pro Gln Glu Ala Glu
        705                 710                 715

aaa gat gcg gaa gat tcg ctc cat gaa tgg caa gat att aat ttg gag     2628
Lys Asp Ala Glu Asp Ser Leu His Glu Trp Gln Asp Ile Asn Leu Glu
    720                 725                 730

gag ttg gaa act ctg gag agc aac ctc tta gca cag cag aat tca ctg     2676
Glu Leu Glu Thr Leu Glu Ser Asn Leu Leu Ala Gln Gln Asn Ser Leu
735                 740                 745                 750

aaa gct caa aaa cag cag caa gaa cgg atc gct gct act gtc acc gga     2724
Lys Ala Gln Lys Gln Gln Gln Glu Arg Ile Ala Ala Thr Val Thr Gly
                755                 760                 765

cag atg ttc ctg gaa agc cag gaa ctc ctg cgc ctg ttc ggc att ccc     2772
Gln Met Phe Leu Glu Ser Gln Glu Leu Leu Arg Leu Phe Gly Ile Pro
            770                 775                 780

tac atc cag gct ccc atg gaa gca gag gcg cag tgc gcc atc ctg gac     2820
Tyr Ile Gln Ala Pro Met Glu Ala Glu Ala Gln Cys Ala Ile Leu Asp
        785                 790                 795

ctg act gat cag act tcc gga acc atc act gat gac agt gat atc tgg     2868
Leu Thr Asp Gln Thr Ser Gly Thr Ile Thr Asp Asp Ser Asp Ile Trp
    800                 805                 810

ctg ttt gga gcg cgg cat gtc tat aga aac ttt ttt aat aaa aac aag     2916
Leu Phe Gly Ala Arg His Val Tyr Arg Asn Phe Phe Asn Lys Asn Lys
815                 820                 825                 830

ttt gta gaa tat tat caa tat gtg gac ttt cac aat caa ttg gga ttg     2964
Phe Val Glu Tyr Tyr Gln Tyr Val Asp Phe His Asn Gln Leu Gly Leu
                835                 840                 845

gac cgg aat aag tta ata aat ttg gct tat ttg ctt gga agt gat tat     3012
```

```
Asp Arg Asn Lys Leu Ile Asn Leu Ala Tyr Leu Leu Gly Ser Asp Tyr
            850                 855                 860

acc gaa gga ata cca act gtg ggt tgt gta acc gcc atg gaa att ctc      3060
Thr Glu Gly Ile Pro Thr Val Gly Cys Val Thr Ala Met Glu Ile Leu
        865                 870                 875

aat gaa ttc cct ggg cat ggc ctg gaa cct ctc cta aaa ttc tca gaa      3108
Asn Glu Phe Pro Gly His Gly Leu Glu Pro Leu Leu Lys Phe Ser Glu
    880                 885                 890

tgg tgg cat gaa gct caa aaa aat cca aag ata aga cct aat cct cat      3156
Trp Trp His Glu Ala Gln Lys Asn Pro Lys Ile Arg Pro Asn Pro His
895                 900                 905                 910

gac acc aaa gtg aaa aaa aaa tta cgg aca ttg caa ctc acc cct ggc      3204
Asp Thr Lys Val Lys Lys Lys Leu Arg Thr Leu Gln Leu Thr Pro Gly
            915                 920                 925

ttt cct aac cca gct gtt gcc gag gcc tac ctc aaa ccc gtg gtg gat      3252
Phe Pro Asn Pro Ala Val Ala Glu Ala Tyr Leu Lys Pro Val Val Asp
            930                 935                 940

gac tcg aag gga tcc ttt ctg tgg ggg aaa cct gat ctc gac aaa att      3300
Asp Ser Lys Gly Ser Phe Leu Trp Gly Lys Pro Asp Leu Asp Lys Ile
        945                 950                 955

aga gaa ttt tgt cag cgg tat ttc ggc tgg aac aga acg aag aca gat      3348
Arg Glu Phe Cys Gln Arg Tyr Phe Gly Trp Asn Arg Thr Lys Thr Asp
    960                 965                 970

gaa tct ctg ttt cct gta tta aag caa ctc gat gcc cag cag aca cag      3396
Glu Ser Leu Phe Pro Val Leu Lys Gln Leu Asp Ala Gln Gln Thr Gln
975                 980                 985                 990

ctc cga att gat tcc ttc ttt aga tta gca  caa cag gag aaa gaa  gat    3444
Leu Arg Ile Asp Ser Phe Phe Arg Leu Ala  Gln Gln Glu Lys Glu  Asp
            995                 1000                1005

gct aaa cgt att  aag agc cag aga cta  aac aga gct gtg aca  tgt       3489
Ala Lys Arg Ile  Lys Ser Gln Arg Leu  Asn Arg Ala Val Thr  Cys
            1010                1015                1020

atg cta agg aaa  gag aaa gaa gca gca  gcc agc gaa ata gaa  gca       3534
Met Leu Arg Lys  Glu Lys Glu Ala Ala  Ala Ser Glu Ile Glu  Ala
            1025                1030                1035

gtt tct gtt gcc  atg gag aaa gaa ttt  gag cta ctt gat aag  gca       3579
Val Ser Val Ala  Met Glu Lys Glu Phe  Glu Leu Leu Asp Lys  Ala
            1040                1045                1050

aaa cga aaa acc  cag aag aga ggc ata  aca aat acc tta gaa  gag       3624
Lys Arg Lys Thr  Gln Lys Arg Gly Ile  Thr Asn Thr Leu Glu  Glu
            1055                1060                1065

tca tca agc ctg  aaa aga aag agg ctt  tca gat tct aaa cga  aag       3669
Ser Ser Ser Leu  Lys Arg Lys Arg Leu  Ser Asp Ser Lys Arg  Lys
            1070                1075                1080

aat aca tgc ggt  gga ttt ttg ggg gag  acc tgc ctc tca gaa  tca       3714
Asn Thr Cys Gly  Gly Phe Leu Gly Glu  Thr Cys Leu Ser Glu  Ser
            1085                1090                1095

tct gat gga tct  tca agt gaa gat gct  gaa agt tca tct tta  atg       3759
Ser Asp Gly Ser  Ser Ser Glu Asp Ala  Glu Ser Ser Ser Leu  Met
            1100                1105                1110

aat gta caa agg  aga aca gct gcg aaa  gag cca aaa acc agt  gct       3804
Asn Val Gln Arg  Arg Thr Ala Ala Lys  Glu Pro Lys Thr Ser  Ala
            1115                1120                1125

tca gat tcg cag  aac tca gtg aag gaa  gct ccc gtg aag aat  gga       3849
Ser Asp Ser Gln  Asn Ser Val Lys Glu  Ala Pro Val Lys Asn  Gly
            1130                1135                1140

ggt gcg acc acc  agc agc tct agt gat  agt gat gac gat gga  ggg       3894
Gly Ala Thr Thr  Ser Ser Ser Ser Asp  Ser Asp Asp Asp Gly  Gly
            1145                1150                1155
```

```
aaa gag aag atg  gtc ctc gtg acc gcc  aga tct gtg ttt ggg  aag      3939
Lys Glu Lys Met  Val Leu Val Thr Ala  Arg Ser Val Phe Gly  Lys
            1160                 1165                 1170

aaa aga agg aaa  cta aga cgt gcg agg  gga aga aaa agg aaa  acc      3984
Lys Arg Arg Lys  Leu Arg Arg Ala Arg  Gly Arg Lys Arg Lys  Thr
            1175                 1180                 1185

taa ttaaaaaata tgtatcctct ataattagtt atgacagcca tttgtaatga         4037

atttgtcgca aagacgtaat aaaattaact ggtggcacgg tctttgtaaa aaaa        4091


<210> SEQ ID NO 30
<211> LENGTH: 1186
<212> TYPE: PRT
<213> ORGANISM: Homo sapiens

<400> SEQUENCE: 30

Met Gly Val Gln Gly Leu Trp Lys Leu Leu Glu Cys Ser Gly Arg Gln
1               5                   10                  15

Val Ser Pro Glu Ala Leu Glu Gly Lys Ile Leu Ala Val Asp Ile Ser
            20                  25                  30

Ile Trp Leu Asn Gln Ala Leu Lys Gly Val Arg Asp Arg His Gly Asn
        35                  40                  45

Ser Ile Glu Asn Pro His Leu Leu Thr Leu Phe His Arg Leu Cys Lys
    50                  55                  60

Leu Leu Phe Phe Arg Ile Arg Pro Ile Phe Val Phe Asp Gly Asp Ala
65                  70                  75                  80

Pro Leu Leu Lys Lys Gln Thr Leu Val Lys Arg Arg Gln Arg Lys Asp
                85                  90                  95

Leu Ala Ser Ser Asp Ser Arg Lys Thr Thr Glu Lys Leu Leu Lys Thr
            100                 105                 110

Phe Leu Lys Arg Gln Ala Ile Lys Thr Ala Phe Arg Ser Lys Arg Asp
        115                 120                 125

Glu Ala Leu Pro Ser Leu Thr Gln Val Arg Arg Glu Asn Asp Leu Tyr
    130                 135                 140

Val Leu Pro Pro Leu Gln Glu Glu Glu Lys His Ser Ser Glu Glu Glu
145                 150                 155                 160

Asp Glu Lys Glu Trp Gln Glu Arg Met Asn Gln Lys Gln Ala Leu Gln
                165                 170                 175

Glu Glu Phe Phe His Asn Pro Gln Ala Ile Asp Ile Glu Ser Glu Asp
            180                 185                 190

Phe Ser Ser Leu Pro Pro Glu Val Lys His Glu Ile Leu Thr Asp Met
        195                 200                 205

Lys Glu Phe Thr Lys Arg Arg Arg Thr Leu Phe Glu Ala Met Pro Glu
    210                 215                 220

Glu Ser Asp Asp Phe Ser Gln Tyr Gln Leu Lys Gly Leu Leu Lys Lys
225                 230                 235                 240

Asn Tyr Leu Asn Gln His Ile Glu His Val Gln Lys Glu Met Asn Gln
                245                 250                 255

Gln His Ser Gly His Ile Arg Arg Gln Tyr Glu Asp Glu Gly Gly Phe
            260                 265                 270

Leu Lys Glu Val Glu Ser Arg Arg Val Val Ser Glu Asp Thr Ser His
        275                 280                 285

Tyr Ile Leu Ile Lys Gly Ile Gln Ala Lys Thr Val Ala Glu Val Asp
    290                 295                 300

Ser Glu Ser Leu Pro Ser Ser Ser Lys Met His Gly Met Ser Phe Asp
305                 310                 315                 320
```

```
Val Lys Ser Ser Pro Cys Glu Lys Leu Lys Thr Glu Lys Glu Pro Asp
                325                 330                 335

Ala Thr Pro Pro Ser Pro Arg Thr Leu Leu Ala Met Gln Ala Ala Leu
            340                 345                 350

Leu Gly Ser Ser Ser Glu Glu Glu Leu Glu Ser Glu Asn Arg Arg Gln
        355                 360                 365

Ala Arg Gly Arg Asn Ala Pro Ala Ala Val Asp Glu Gly Ser Ile Ser
    370                 375                 380

Pro Arg Thr Leu Ser Ala Ile Lys Arg Ala Leu Asp Asp Asp Glu Asp
385                 390                 395                 400

Val Lys Val Cys Ala Gly Asp Asp Val Gln Thr Gly Gly Pro Gly Ala
                405                 410                 415

Glu Glu Met Arg Ile Asn Ser Ser Thr Glu Asn Ser Asp Glu Gly Leu
            420                 425                 430

Lys Val Arg Asp Gly Lys Gly Ile Pro Phe Thr Ala Thr Leu Ala Ser
        435                 440                 445

Ser Ser Val Asn Ser Ala Glu Glu His Val Ala Ser Thr Asn Glu Gly
    450                 455                 460

Arg Glu Pro Thr Asp Ser Val Pro Lys Glu Gln Met Ser Leu Val His
465                 470                 475                 480

Val Gly Thr Glu Ala Phe Pro Ile Ser Asp Glu Ser Met Ile Lys Asp
                485                 490                 495

Arg Lys Asp Arg Leu Pro Leu Glu Ser Ala Val Val Arg His Ser Asp
            500                 505                 510

Ala Pro Gly Leu Pro Asn Gly Arg Glu Leu Thr Pro Ala Ser Pro Thr
        515                 520                 525

Cys Thr Asn Ser Val Ser Lys Asn Glu Thr His Ala Glu Val Leu Glu
    530                 535                 540

Gln Gln Asn Glu Leu Cys Pro Tyr Glu Ser Lys Phe Asp Ser Ser Leu
545                 550                 555                 560

Leu Ser Ser Asp Asp Glu Thr Lys Cys Lys Pro Asn Ser Ala Ser Glu
                565                 570                 575

Val Ile Gly Pro Val Ser Leu Gln Glu Thr Ser Ser Ile Val Ser Val
            580                 585                 590

Pro Ser Glu Ala Val Asp Asn Val Glu Asn Val Val Ser Phe Asn Ala
        595                 600                 605

Lys Glu His Glu Asn Phe Leu Glu Thr Ile Gln Glu Gln Gln Thr Thr
    610                 615                 620

Glu Ser Ala Gly Gln Asp Leu Ile Ser Ile Pro Lys Ala Val Glu Pro
625                 630                 635                 640

Met Glu Ile Asp Ser Glu Glu Ser Glu Ser Asp Gly Ser Phe Ile Glu
                645                 650                 655

Val Gln Ser Val Ile Ser Asp Glu Glu Leu Gln Ala Glu Phe Pro Glu
            660                 665                 670

Thr Ser Lys Pro Pro Ser Glu Gln Gly Glu Glu Glu Leu Val Gly Thr
        675                 680                 685

Arg Glu Gly Glu Ala Pro Ala Glu Ser Glu Ser Leu Leu Arg Asp Asn
    690                 695                 700

Ser Glu Arg Asp Asp Val Asp Gly Glu Pro Gln Glu Ala Glu Lys Asp
705                 710                 715                 720

Ala Glu Asp Ser Leu His Glu Trp Gln Asp Ile Asn Leu Glu Glu Leu
                725                 730                 735
```

```
Glu Thr Leu Glu Ser Asn Leu Leu Ala Gln Gln Asn Ser Leu Lys Ala
            740                 745                 750

Gln Lys Gln Gln Gln Glu Arg Ile Ala Ala Thr Val Thr Gly Gln Met
        755                 760                 765

Phe Leu Glu Ser Gln Glu Leu Leu Arg Leu Phe Gly Ile Pro Tyr Ile
    770                 775                 780

Gln Ala Pro Met Glu Ala Glu Ala Gln Cys Ala Ile Leu Asp Leu Thr
785                 790                 795                 800

Asp Gln Thr Ser Gly Thr Ile Thr Asp Asp Ser Asp Ile Trp Leu Phe
                805                 810                 815

Gly Ala Arg His Val Tyr Arg Asn Phe Phe Asn Lys Asn Lys Phe Val
            820                 825                 830

Glu Tyr Tyr Gln Tyr Val Asp Phe His Asn Gln Leu Gly Leu Asp Arg
        835                 840                 845

Asn Lys Leu Ile Asn Leu Ala Tyr Leu Leu Gly Ser Asp Tyr Thr Glu
    850                 855                 860

Gly Ile Pro Thr Val Gly Cys Val Thr Ala Met Glu Ile Leu Asn Glu
865                 870                 875                 880

Phe Pro Gly His Gly Leu Glu Pro Leu Leu Lys Phe Ser Glu Trp Trp
                885                 890                 895

His Glu Ala Gln Lys Asn Pro Lys Ile Arg Pro Asn Pro His Asp Thr
            900                 905                 910

Lys Val Lys Lys Lys Leu Arg Thr Leu Gln Leu Thr Pro Gly Phe Pro
        915                 920                 925

Asn Pro Ala Val Ala Glu Ala Tyr Leu Lys Pro Val Val Asp Asp Ser
    930                 935                 940

Lys Gly Ser Phe Leu Trp Gly Lys Pro Asp Leu Asp Lys Ile Arg Glu
945                 950                 955                 960

Phe Cys Gln Arg Tyr Phe Gly Trp Asn Arg Thr Lys Thr Asp Glu Ser
                965                 970                 975

Leu Phe Pro Val Leu Lys Gln Leu Asp Ala Gln Gln Thr Gln Leu Arg
            980                 985                 990

Ile Asp Ser Phe Phe Arg Leu Ala  Gln Gln Glu Lys Glu  Asp Ala Lys
        995                 1000                 1005

Arg Ile  Lys Ser Gln Arg Leu  Asn Arg Ala Val Thr  Cys Met Leu
    1010                 1015                 1020

Arg Lys  Glu Lys Glu Ala Ala  Ala Ser Glu Ile Glu  Ala Val Ser
    1025                 1030                 1035

Val Ala  Met Glu Lys Glu Phe  Glu Leu Leu Asp Lys  Ala Lys Arg
    1040                 1045                 1050

Lys Thr  Gln Lys Arg Gly Ile  Thr Asn Thr Leu Glu  Glu Ser Ser
    1055                 1060                 1065

Ser Leu  Lys Arg Lys Arg Leu  Ser Asp Ser Lys Arg  Lys Asn Thr
    1070                 1075                 1080

Cys Gly  Gly Phe Leu Gly Glu  Thr Cys Leu Ser Glu  Ser Ser Asp
    1085                 1090                 1095

Gly Ser  Ser Ser Glu Asp Ala  Glu Ser Ser Ser Leu  Met Asn Val
    1100                 1105                 1110

Gln Arg  Arg Thr Ala Ala Lys  Glu Pro Lys Thr Ser  Ala Ser Asp
    1115                 1120                 1125

Ser Gln  Asn Ser Val Lys Glu  Ala Pro Val Lys Asn  Gly Gly Ala
    1130                 1135                 1140

Thr Thr  Ser Ser Ser Ser Asp  Ser Asp Asp Asp Gly  Gly Lys Glu
```

```
    1145                1150                1155

Lys Met  Val Leu Val Thr Ala  Arg Ser Val Phe Gly  Lys Lys Arg
    1160                1165                1170

Arg Lys  Leu Arg Arg Ala Arg  Gly Arg Lys Arg Lys  Thr
    1175                1180                1185


<210> SEQ ID NO 31
<211> LENGTH: 2682
<212> TYPE: DNA
<213> ORGANISM: Homo sapiens
<220> FEATURE:
<221> NAME/KEY: CDS
<222> LOCATION: (27)..(2594)
<223> OTHER INFORMATION: XAB2

<400> SEQUENCE: 31

tctcctgtac ctgggcatcc agaaaa atg gtg gtg atg gcg cga ctc tcg cgg      53
                             Met Val Val Met Ala Arg Leu Ser Arg
                             1               5

ccc gag cgg ccg gac ctt gtc ttc gag gaa gag gac ctc ccc tat gag      101
Pro Glu Arg Pro Asp Leu Val Phe Glu Glu Glu Asp Leu Pro Tyr Glu
10                  15                  20                  25

gag gaa atc atg cgg aac caa ttc tct gtc aaa tgc tgg ctt cgc tac      149
Glu Glu Ile Met Arg Asn Gln Phe Ser Val Lys Cys Trp Leu Arg Tyr
                30                  35                  40

atc gag ttc aaa cag ggc gcc ccg aag ccc agg ctc aat cag cta tac      197
Ile Glu Phe Lys Gln Gly Ala Pro Lys Pro Arg Leu Asn Gln Leu Tyr
            45                  50                  55

gag cgg gca ctc aag ctg ctg ccc tgc agc tac aaa ctc tgg tac cga      245
Glu Arg Ala Leu Lys Leu Leu Pro Cys Ser Tyr Lys Leu Trp Tyr Arg
        60                  65                  70

tac ctg aag gcg cgt cgg gca cag gtg aag cat cgc tgt gtg acc gac      293
Tyr Leu Lys Ala Arg Arg Ala Gln Val Lys His Arg Cys Val Thr Asp
    75                  80                  85

cct gcc tat gaa gat gtc aac aac tgt cat gag agg gcc ttt gtg ttc      341
Pro Ala Tyr Glu Asp Val Asn Asn Cys His Glu Arg Ala Phe Val Phe
90                  95                  100                 105

atg cac aag atg cct cgt ctg tgg cta gat tac tgc cag ttc ctc atg      389
Met His Lys Met Pro Arg Leu Trp Leu Asp Tyr Cys Gln Phe Leu Met
                110                 115                 120

gac cag ggg cgc gtc aca cac acc cgc cgc acc ttc gac cgt gcc ctc      437
Asp Gln Gly Arg Val Thr His Thr Arg Arg Thr Phe Asp Arg Ala Leu
            125                 130                 135

cgg gca ctg ccc atc acg cag cac tct cga att tgg ccc ctg tat ctg      485
Arg Ala Leu Pro Ile Thr Gln His Ser Arg Ile Trp Pro Leu Tyr Leu
        140                 145                 150

cgc ttc ctg cgc tca cac cca ctg cct gag aca gct gtg cga ggc tat      533
Arg Phe Leu Arg Ser His Pro Leu Pro Glu Thr Ala Val Arg Gly Tyr
    155                 160                 165

cgg cgc ttc ctc aag ctg agt cct gag agt gca gag gag tac att gag      581
Arg Arg Phe Leu Lys Leu Ser Pro Glu Ser Ala Glu Glu Tyr Ile Glu
170                 175                 180                 185

tac ctc aag tca agt gac cgg ctg gat gag gcc gcc cag cgc ctg gcc      629
Tyr Leu Lys Ser Ser Asp Arg Leu Asp Glu Ala Ala Gln Arg Leu Ala
                190                 195                 200

acc gtg gtg aac gac gag cgt ttc gtg tct aag gcc ggc aag tcc aac      677
Thr Val Val Asn Asp Glu Arg Phe Val Ser Lys Ala Gly Lys Ser Asn
            205                 210                 215

tac cag ctg tgg cac gag ctg tgc gac ctc atc tcc cag aat ccg gac      725
Tyr Gln Leu Trp His Glu Leu Cys Asp Leu Ile Ser Gln Asn Pro Asp
        220                 225                 230
```

```
aag gta cag tcc ctc aat gtg gac gcc atc atc cgc ggg ggc ctc acc      773
Lys Val Gln Ser Leu Asn Val Asp Ala Ile Ile Arg Gly Gly Leu Thr
    235                 240                 245

cgc ttc acc gac cag ctg ggc aag ctc tgg tgt tct ctc gcc gac tac      821
Arg Phe Thr Asp Gln Leu Gly Lys Leu Trp Cys Ser Leu Ala Asp Tyr
250                 255                 260                 265

tac atc cgc agc ggc cat ttc gag aag gct cgg gac gtg tac gag gag      869
Tyr Ile Arg Ser Gly His Phe Glu Lys Ala Arg Asp Val Tyr Glu Glu
                270                 275                 280

gcc atc cgg aca gtg atg acc gtg cgg gac ttc aca cag gtg ttt gac      917
Ala Ile Arg Thr Val Met Thr Val Arg Asp Phe Thr Gln Val Phe Asp
            285                 290                 295

agc tac gcc cag ttc gag gag agc atg atc gct gca aag atg gag acc      965
Ser Tyr Ala Gln Phe Glu Glu Ser Met Ile Ala Ala Lys Met Glu Thr
        300                 305                 310

gcc tcg gag ctg ggg cgc gag gag gag gat gat gtg gac ctg gag ctg     1013
Ala Ser Glu Leu Gly Arg Glu Glu Glu Asp Asp Val Asp Leu Glu Leu
    315                 320                 325

cgc ctg gcc cgc ttc gag cag ctc atc agc cgg cgg ccc ctg ctc ctc     1061
Arg Leu Ala Arg Phe Glu Gln Leu Ile Ser Arg Arg Pro Leu Leu Leu
330                 335                 340                 345

aac agc gtc ttg ctg cgc caa aac cca cac cac gtg cac gag tgg cac     1109
Asn Ser Val Leu Leu Arg Gln Asn Pro His His Val His Glu Trp His
                350                 355                 360

aag cgt gtc gcc ctg cac cag ggc cgc ccc cgg gag atc atc aac acc     1157
Lys Arg Val Ala Leu His Gln Gly Arg Pro Arg Glu Ile Ile Asn Thr
            365                 370                 375

tac aca gag gct gtg cag acg gtg gac ccc ttc aag gcc aca ggc aag     1205
Tyr Thr Glu Ala Val Gln Thr Val Asp Pro Phe Lys Ala Thr Gly Lys
        380                 385                 390

ccc cac act ctg tgg gtg gcg ttt gcc aag ttt tat gag gac aac gga     1253
Pro His Thr Leu Trp Val Ala Phe Ala Lys Phe Tyr Glu Asp Asn Gly
    395                 400                 405

cag ctg gac gat gcc cgt gtc atc ctg gag aag gcc acc aag gtg aac     1301
Gln Leu Asp Asp Ala Arg Val Ile Leu Glu Lys Ala Thr Lys Val Asn
410                 415                 420                 425

ttc aag cag gtg gat gac ctg gca agc gtg tgg tgt cag tgc gga gag     1349
Phe Lys Gln Val Asp Asp Leu Ala Ser Val Trp Cys Gln Cys Gly Glu
                430                 435                 440

ctg gag ctc cga cac gag aac tac gat gag gcc ttg cgg ctg ctg cga     1397
Leu Glu Leu Arg His Glu Asn Tyr Asp Glu Ala Leu Arg Leu Leu Arg
            445                 450                 455

aag gcc acg gcg ctg cct gcc cgc cgg gcc gag tac ttt gat ggt tca     1445
Lys Ala Thr Ala Leu Pro Ala Arg Arg Ala Glu Tyr Phe Asp Gly Ser
        460                 465                 470

gag ccc gtg cag aac cgc gtg tac aag tca ctg aag gtc tgg tcc atg     1493
Glu Pro Val Gln Asn Arg Val Tyr Lys Ser Leu Lys Val Trp Ser Met
    475                 480                 485

ctc gcc gac ctg gag gag agc ctc ggc acc ttc cag tcc acc aag gcc     1541
Leu Ala Asp Leu Glu Glu Ser Leu Gly Thr Phe Gln Ser Thr Lys Ala
490                 495                 500                 505

gtg tac gac cgc atc ctg gac ctg cgt atc gca aca ccc cag atc gtc     1589
Val Tyr Asp Arg Ile Leu Asp Leu Arg Ile Ala Thr Pro Gln Ile Val
                510                 515                 520

atc aac tat gcc atg ttc ctg gag gag cac aag tac ttc gag gag agc     1637
Ile Asn Tyr Ala Met Phe Leu Glu Glu His Lys Tyr Phe Glu Glu Ser
            525                 530                 535

ttc aag gcg tac gag cgc ggc atc tcg ctg ttc aag tgg ccc aac gtg     1685
Phe Lys Ala Tyr Glu Arg Gly Ile Ser Leu Phe Lys Trp Pro Asn Val
```

```
        540                 545                 550

tcc gac atc tgg agc acc tac ctg acc aaa ttc att gcc cgc tat ggg      1733
Ser Asp Ile Trp Ser Thr Tyr Leu Thr Lys Phe Ile Ala Arg Tyr Gly
    555                 560                 565

ggc cgc aag ctg gag cgg gca cgg gac ctg ttt gaa cag gct ctg gac      1781
Gly Arg Lys Leu Glu Arg Ala Arg Asp Leu Phe Glu Gln Ala Leu Asp
570                 575                 580                 585

ggc tgc ccc cca aaa tat gcc aag acc ttg tac ctg ctg tac gca cag      1829
Gly Cys Pro Pro Lys Tyr Ala Lys Thr Leu Tyr Leu Leu Tyr Ala Gln
                590                 595                 600

ctg gag gag gag tgg ggc ctg gcc cgg cat gcc atg gcc gtg tac gag      1877
Leu Glu Glu Glu Trp Gly Leu Ala Arg His Ala Met Ala Val Tyr Glu
            605                 610                 615

cgt gcc acc agg gcc gtg gag ccc gcc cag cag tat gac atg ttc aac      1925
Arg Ala Thr Arg Ala Val Glu Pro Ala Gln Gln Tyr Asp Met Phe Asn
        620                 625                 630

atc tac atc aag cgg gcg gcc gag atc tat ggg gtc acc cac acc cgc      1973
Ile Tyr Ile Lys Arg Ala Ala Glu Ile Tyr Gly Val Thr His Thr Arg
    635                 640                 645

ggc atc tac cag aag gcc att gag gtg ctg tcg gac gag cac gcg cgt      2021
Gly Ile Tyr Gln Lys Ala Ile Glu Val Leu Ser Asp Glu His Ala Arg
650                 655                 660                 665

gag atg tgc ctg cgg ttt gca gac atg gag tgc aag ctc ggg gag att      2069
Glu Met Cys Leu Arg Phe Ala Asp Met Glu Cys Lys Leu Gly Glu Ile
                670                 675                 680

gac cgc gcc cgg gcc atc tac agc ttc tgc tcc cag atc tgt gac ccc      2117
Asp Arg Ala Arg Ala Ile Tyr Ser Phe Cys Ser Gln Ile Cys Asp Pro
            685                 690                 695

cgg acg acc ggc gcg ttc tgg cag acg tgg aag gac ttt gag gtc cgg      2165
Arg Thr Thr Gly Ala Phe Trp Gln Thr Trp Lys Asp Phe Glu Val Arg
        700                 705                 710

cat ggc aat gag gac acc atc aag gaa atg ctg cgt atc cgg cgc agc      2213
His Gly Asn Glu Asp Thr Ile Lys Glu Met Leu Arg Ile Arg Arg Ser
    715                 720                 725

gtg cag gcc acg tac aac acg cag gtc aac ttc atg gcc tcg cag atg      2261
Val Gln Ala Thr Tyr Asn Thr Gln Val Asn Phe Met Ala Ser Gln Met
730                 735                 740                 745

ctc aag gtc tcg ggc agt gcc acg ggc acc gtg tct gac ctg gcc cct      2309
Leu Lys Val Ser Gly Ser Ala Thr Gly Thr Val Ser Asp Leu Ala Pro
                750                 755                 760

ggg cag agt ggc atg gac gac atg aag ctg ctg gaa cag cgg gca gag      2357
Gly Gln Ser Gly Met Asp Asp Met Lys Leu Leu Glu Gln Arg Ala Glu
            765                 770                 775

cag ctg gcg gct gag gcg gag cgt gac cag ccc ttg cgc gcc cag agc      2405
Gln Leu Ala Ala Glu Ala Glu Arg Asp Gln Pro Leu Arg Ala Gln Ser
        780                 785                 790

aag atc ctg ttc gtg agg agt gac gcc tcc cgg gag gag ctg gca gag      2453
Lys Ile Leu Phe Val Arg Ser Asp Ala Ser Arg Glu Glu Leu Ala Glu
    795                 800                 805

ctg gca cag cag gtc aac ccc gag gag atc cag ctg ggc gag gac gag      2501
Leu Ala Gln Gln Val Asn Pro Glu Glu Ile Gln Leu Gly Glu Asp Glu
810                 815                 820                 825

gac gag gac gag atg gac ctg gag ccc aac gag gtt cgg ctg gag cag      2549
Asp Glu Asp Glu Met Asp Leu Glu Pro Asn Glu Val Arg Leu Glu Gln
                830                 835                 840

cag agc gtg cca gcc gca gtg ttt ggg agc ctg aag gaa gac tga          2594
Gln Ser Val Pro Ala Ala Val Phe Gly Ser Leu Lys Glu Asp
            845                 850                 855

cccgtccctc ccccatcccc cctcccccacc ccctccccaa tacagctacg tttgtacatc   2654
```

```
aaaaaaaaaa aaaaaaaaaa aaaaaaaa                                  2682


<210> SEQ ID NO 32
<211> LENGTH: 855
<212> TYPE: PRT
<213> ORGANISM: Homo sapiens

<400> SEQUENCE: 32

Met Val Val Met Ala Arg Leu Ser Arg Pro Glu Arg Pro Asp Leu Val
1               5                   10                  15

Phe Glu Glu Glu Asp Leu Pro Tyr Glu Glu Glu Ile Met Arg Asn Gln
            20                  25                  30

Phe Ser Val Lys Cys Trp Leu Arg Tyr Ile Glu Phe Lys Gln Gly Ala
        35                  40                  45

Pro Lys Pro Arg Leu Asn Gln Leu Tyr Glu Arg Ala Leu Lys Leu Leu
    50                  55                  60

Pro Cys Ser Tyr Lys Leu Trp Tyr Arg Tyr Leu Lys Ala Arg Arg Ala
65                  70                  75                  80

Gln Val Lys His Arg Cys Val Thr Asp Pro Ala Tyr Glu Asp Val Asn
                85                  90                  95

Asn Cys His Glu Arg Ala Phe Val Phe Met His Lys Met Pro Arg Leu
            100                 105                 110

Trp Leu Asp Tyr Cys Gln Phe Leu Met Asp Gln Gly Arg Val Thr His
        115                 120                 125

Thr Arg Arg Thr Phe Asp Arg Ala Leu Arg Ala Leu Pro Ile Thr Gln
    130                 135                 140

His Ser Arg Ile Trp Pro Leu Tyr Leu Arg Phe Leu Arg Ser His Pro
145                 150                 155                 160

Leu Pro Glu Thr Ala Val Arg Gly Tyr Arg Arg Phe Leu Lys Leu Ser
                165                 170                 175

Pro Glu Ser Ala Glu Glu Tyr Ile Glu Tyr Leu Lys Ser Ser Asp Arg
            180                 185                 190

Leu Asp Glu Ala Ala Gln Arg Leu Ala Thr Val Val Asn Asp Glu Arg
        195                 200                 205

Phe Val Ser Lys Ala Gly Lys Ser Asn Tyr Gln Leu Trp His Glu Leu
    210                 215                 220

Cys Asp Leu Ile Ser Gln Asn Pro Asp Lys Val Gln Ser Leu Asn Val
225                 230                 235                 240

Asp Ala Ile Ile Arg Gly Gly Leu Thr Arg Phe Thr Asp Gln Leu Gly
                245                 250                 255

Lys Leu Trp Cys Ser Leu Ala Asp Tyr Tyr Ile Arg Ser Gly His Phe
            260                 265                 270

Glu Lys Ala Arg Asp Val Tyr Glu Glu Ala Ile Arg Thr Val Met Thr
        275                 280                 285

Val Arg Asp Phe Thr Gln Val Phe Asp Ser Tyr Ala Gln Phe Glu Glu
    290                 295                 300

Ser Met Ile Ala Ala Lys Met Glu Thr Ala Ser Glu Leu Gly Arg Glu
305                 310                 315                 320

Glu Glu Asp Asp Val Asp Leu Glu Leu Arg Leu Ala Arg Phe Glu Gln
                325                 330                 335

Leu Ile Ser Arg Arg Pro Leu Leu Leu Asn Ser Val Leu Leu Arg Gln
            340                 345                 350

Asn Pro His His Val His Glu Trp His Lys Arg Val Ala Leu His Gln
        355                 360                 365
```

```
Gly Arg Pro Arg Glu Ile Ile Asn Thr Tyr Thr Glu Ala Val Gln Thr
    370                 375                 380

Val Asp Pro Phe Lys Ala Thr Gly Lys Pro His Thr Leu Trp Val Ala
385                 390                 395                 400

Phe Ala Lys Phe Tyr Glu Asp Asn Gly Gln Leu Asp Asp Ala Arg Val
                405                 410                 415

Ile Leu Glu Lys Ala Thr Lys Val Asn Phe Lys Gln Val Asp Asp Leu
            420                 425                 430

Ala Ser Val Trp Cys Gln Cys Gly Glu Leu Glu Leu Arg His Glu Asn
        435                 440                 445

Tyr Asp Glu Ala Leu Arg Leu Leu Arg Lys Ala Thr Ala Leu Pro Ala
    450                 455                 460

Arg Arg Ala Glu Tyr Phe Asp Gly Ser Glu Pro Val Gln Asn Arg Val
465                 470                 475                 480

Tyr Lys Ser Leu Lys Val Trp Ser Met Leu Ala Asp Leu Glu Glu Ser
                485                 490                 495

Leu Gly Thr Phe Gln Ser Thr Lys Ala Val Tyr Asp Arg Ile Leu Asp
            500                 505                 510

Leu Arg Ile Ala Thr Pro Gln Ile Val Ile Asn Tyr Ala Met Phe Leu
        515                 520                 525

Glu Glu His Lys Tyr Phe Glu Glu Ser Phe Lys Ala Tyr Glu Arg Gly
    530                 535                 540

Ile Ser Leu Phe Lys Trp Pro Asn Val Ser Asp Ile Trp Ser Thr Tyr
545                 550                 555                 560

Leu Thr Lys Phe Ile Ala Arg Tyr Gly Gly Arg Lys Leu Glu Arg Ala
                565                 570                 575

Arg Asp Leu Phe Glu Gln Ala Leu Asp Gly Cys Pro Pro Lys Tyr Ala
            580                 585                 590

Lys Thr Leu Tyr Leu Leu Tyr Ala Gln Leu Glu Glu Glu Trp Gly Leu
        595                 600                 605

Ala Arg His Ala Met Ala Val Tyr Glu Arg Ala Thr Arg Ala Val Glu
    610                 615                 620

Pro Ala Gln Gln Tyr Asp Met Phe Asn Ile Tyr Ile Lys Arg Ala Ala
625                 630                 635                 640

Glu Ile Tyr Gly Val Thr His Thr Arg Gly Ile Tyr Gln Lys Ala Ile
                645                 650                 655

Glu Val Leu Ser Asp Glu His Ala Arg Glu Met Cys Leu Arg Phe Ala
            660                 665                 670

Asp Met Glu Cys Lys Leu Gly Glu Ile Asp Arg Ala Arg Ala Ile Tyr
        675                 680                 685

Ser Phe Cys Ser Gln Ile Cys Asp Pro Arg Thr Thr Gly Ala Phe Trp
    690                 695                 700

Gln Thr Trp Lys Asp Phe Glu Val Arg His Gly Asn Glu Asp Thr Ile
705                 710                 715                 720

Lys Glu Met Leu Arg Ile Arg Arg Ser Val Gln Ala Thr Tyr Asn Thr
                725                 730                 735

Gln Val Asn Phe Met Ala Ser Gln Met Leu Lys Val Ser Gly Ser Ala
            740                 745                 750

Thr Gly Thr Val Ser Asp Leu Ala Pro Gly Gln Ser Gly Met Asp Asp
        755                 760                 765

Met Lys Leu Leu Glu Gln Arg Ala Glu Gln Leu Ala Ala Glu Ala Glu
    770                 775                 780
```

Arg Asp Gln Pro Leu Arg Ala Gln Ser Lys Ile Leu Phe Val Arg Ser
785 790 795 800

Asp Ala Ser Arg Glu Glu Leu Ala Glu Leu Ala Gln Gln Val Asn Pro
805 810 815

Glu Glu Ile Gln Leu Gly Glu Asp Glu Asp Glu Asp Glu Met Asp Leu
820 825 830

Glu Pro Asn Glu Val Arg Leu Glu Gln Gln Ser Val Pro Ala Ala Val
835 840 845

Phe Gly Ser Leu Lys Glu Asp
850 855

<210> SEQ ID NO 33
<211> LENGTH: 2568
<212> TYPE: DNA
<213> ORGANISM: Homo sapiens
<220> FEATURE:
<221> NAME/KEY: CDS
<222> LOCATION: (48)..(2330)
<223> OTHER INFORMATION: ERCC2

<400> SEQUENCE: 33
ttcatgaggg aggcgggtcg accccgctgc acagtccggc cggcgcc atg aag ctc 56
Met Lys Leu
1 aac gtg gac ggg ctc ctg gtc tac ttc ccg tac gac tac atc tac ccc 104
Asn Val Asp Gly Leu Leu Val Tyr Phe Pro Tyr Asp Tyr Ile Tyr Pro
5 10 15 gag cag ttc tcc tac atg cgg gag ctc aaa cgc acg ctg gac gcc aag 152
Glu Gln Phe Ser Tyr Met Arg Glu Leu Lys Arg Thr Leu Asp Ala Lys
20 25 30 35 ggt cat gga gtc ctg gag atg ccc tca ggc acc ggg aag aca gta tcc 200
Gly His Gly Val Leu Glu Met Pro Ser Gly Thr Gly Lys Thr Val Ser
40 45 50 ctg ttg gcc ctg atc atg gca tac cag aga gca tat ccg ctg gag gtg 248
Leu Leu Ala Leu Ile Met Ala Tyr Gln Arg Ala Tyr Pro Leu Glu Val
55 60 65 acc aaa ctc atc tac tgc tca aga act gtg cca gag att gag aag gtg 296
Thr Lys Leu Ile Tyr Cys Ser Arg Thr Val Pro Glu Ile Glu Lys Val
70 75 80 att gaa gag ctt cga aag ttg ctc aac ttc tat gag aag cag gag ggc 344
Ile Glu Glu Leu Arg Lys Leu Leu Asn Phe Tyr Glu Lys Gln Glu Gly
85 90 95 gag aag ctg ccg ttt ctg gga ctg gct ctg agc tcc cgc aaa aac ttg 392
Glu Lys Leu Pro Phe Leu Gly Leu Ala Leu Ser Ser Arg Lys Asn Leu
100 105 110 115 tgt att cac cct gag gtg aca ccc ctg cgc ttt ggg aag gac gtc gat 440
Cys Ile His Pro Glu Val Thr Pro Leu Arg Phe Gly Lys Asp Val Asp
120 125 130 ggg aaa tgc cac agc ctc aca gcc tcc tat gtg cgg gcg cag tac cag 488
Gly Lys Cys His Ser Leu Thr Ala Ser Tyr Val Arg Ala Gln Tyr Gln
135 140 145 cat gac acc agc ctg ccc cac tgc cga ttc tat gag gaa ttt gat gcc 536
His Asp Thr Ser Leu Pro His Cys Arg Phe Tyr Glu Glu Phe Asp Ala
150 155 160 cat ggg cgt gag gtg ccc ctc ccc gct ggc atc tac aac ctg gat gac 584
His Gly Arg Glu Val Pro Leu Pro Ala Gly Ile Tyr Asn Leu Asp Asp
165 170 175 ctg aag gcc ctg ggg cgg cgc cag ggc tgg tgc cca tac ttc ctt gct 632
Leu Lys Ala Leu Gly Arg Arg Gln Gly Trp Cys Pro Tyr Phe Leu Ala
180 185 190 195

-continued

```
cga tac tca atc ctg cat gcc aat gtg gtg gtt tat agc tac cac tac      680
Arg Tyr Ser Ile Leu His Ala Asn Val Val Val Tyr Ser Tyr His Tyr
                200                 205                 210

ctc ctg gac ccc aag att gca gac ctg gtg tcc aag gaa ctg gcc cgc      728
Leu Leu Asp Pro Lys Ile Ala Asp Leu Val Ser Lys Glu Leu Ala Arg
            215                 220                 225

aag gcc gtc gtg gtc ttc gac gag gcc cac aac att gac aac gtc tgc      776
Lys Ala Val Val Val Phe Asp Glu Ala His Asn Ile Asp Asn Val Cys
        230                 235                 240

atc gac tcc atg agc gtc aac ctc acc cgc cgg acc ctt gac cgg tgc      824
Ile Asp Ser Met Ser Val Asn Leu Thr Arg Arg Thr Leu Asp Arg Cys
    245                 250                 255

cag ggc aac ctg gag acc ctg cag aag acg gtg ctc agg atc aaa gag      872
Gln Gly Asn Leu Glu Thr Leu Gln Lys Thr Val Leu Arg Ile Lys Glu
260                 265                 270                 275

aca gac gag cag cgc ctg cgg gac gag tac cgg cgt ctg gtg gag ggg      920
Thr Asp Glu Gln Arg Leu Arg Asp Glu Tyr Arg Arg Leu Val Glu Gly
                280                 285                 290

ctg cgg gag gcc agc gcc gcc cgg gag acg gac gcc cac ctg gcc aac      968
Leu Arg Glu Ala Ser Ala Ala Arg Glu Thr Asp Ala His Leu Ala Asn
            295                 300                 305

ccc gtg ctg ccc gac gaa gtg ctg cag gag gca gtg cct ggc tcc atc     1016
Pro Val Leu Pro Asp Glu Val Leu Gln Glu Ala Val Pro Gly Ser Ile
        310                 315                 320

cgc acg gcc gag cat ttc ctg ggc ttc ctg agg cgg ctg ctg gag tac     1064
Arg Thr Ala Glu His Phe Leu Gly Phe Leu Arg Arg Leu Leu Glu Tyr
    325                 330                 335

gtg aag tgg cgg ctg cgt gtg cag cat gtg gtg cag gag agc ccg ccc     1112
Val Lys Trp Arg Leu Arg Val Gln His Val Val Gln Glu Ser Pro Pro
340                 345                 350                 355

gcc ttc ctg agc ggc ctg gcc cag cgc gtg tgc atc cag cgc aag ccc     1160
Ala Phe Leu Ser Gly Leu Ala Gln Arg Val Cys Ile Gln Arg Lys Pro
                360                 365                 370

ctc aga ttc tgt gct gaa cgc ctc cgg tcc ctg ctg cat act ctg gag     1208
Leu Arg Phe Cys Ala Glu Arg Leu Arg Ser Leu Leu His Thr Leu Glu
            375                 380                 385

atc acc gac ctt gct gac ttc tcc ccg ctc acc ctc ctt gct aac ttt     1256
Ile Thr Asp Leu Ala Asp Phe Ser Pro Leu Thr Leu Leu Ala Asn Phe
        390                 395                 400

gcc acc ctt gtc agc acc tac gcc aaa ggc ttc acc atc atc atc gag     1304
Ala Thr Leu Val Ser Thr Tyr Ala Lys Gly Phe Thr Ile Ile Ile Glu
    405                 410                 415

ccc ttt gac gac aga acc ccg acc att gcc aac ccc atc ctg cac ttc     1352
Pro Phe Asp Asp Arg Thr Pro Thr Ile Ala Asn Pro Ile Leu His Phe
420                 425                 430                 435

agc tgc atg gac gcc tcg ctg gcc atc aaa ccc gta ttt gag cgt ttc     1400
Ser Cys Met Asp Ala Ser Leu Ala Ile Lys Pro Val Phe Glu Arg Phe
                440                 445                 450

cag tct gtc atc atc aca tct ggg aca ctg tcc ccg ctg gac atc tac     1448
Gln Ser Val Ile Ile Thr Ser Gly Thr Leu Ser Pro Leu Asp Ile Tyr
            455                 460                 465

ccc aag atc ctg gac ttc cac ccc gtc acc atg gca acc ttc acc atg     1496
Pro Lys Ile Leu Asp Phe His Pro Val Thr Met Ala Thr Phe Thr Met
        470                 475                 480

acg ctg gca cgg gtc tgc ctc tgc cct atg atc atc ggc cgt ggc aat     1544
Thr Leu Ala Arg Val Cys Leu Cys Pro Met Ile Ile Gly Arg Gly Asn
    485                 490                 495

gac cag gtg gcc atc agc tcc aaa ttt gag acc cgg gag gat att gct     1592
Asp Gln Val Ala Ile Ser Ser Lys Phe Glu Thr Arg Glu Asp Ile Ala
500                 505                 510                 515
```

```
gtg atc cgg aac tat ggg aac ctc ctg ctg gag atg tcc gct gtg gtc     1640
Val Ile Arg Asn Tyr Gly Asn Leu Leu Leu Glu Met Ser Ala Val Val
                520                 525                 530

cct gat ggc atc gtg gcc ttc ttc acc agc tac cag tac atg gag agc     1688
Pro Asp Gly Ile Val Ala Phe Phe Thr Ser Tyr Gln Tyr Met Glu Ser
            535                 540                 545

acc gtg gcc tcc tgg tat gag cag ggg atc ctt gag aac atc cag agg     1736
Thr Val Ala Ser Trp Tyr Glu Gln Gly Ile Leu Glu Asn Ile Gln Arg
        550                 555                 560

aac aag ctg ctc ttt att gag acc cag gat ggt gcc gaa acc agt gtc     1784
Asn Lys Leu Leu Phe Ile Glu Thr Gln Asp Gly Ala Glu Thr Ser Val
    565                 570                 575

gcc ctg gag aag tac cag gag gcc tgc gag aat ggc cgc ggg gcc atc     1832
Ala Leu Glu Lys Tyr Gln Glu Ala Cys Glu Asn Gly Arg Gly Ala Ile
580                 585                 590                 595

ctg ctg tca gtg gcc cgg ggc aaa gtg tcc gag gga atc gac ttt gtg     1880
Leu Leu Ser Val Ala Arg Gly Lys Val Ser Glu Gly Ile Asp Phe Val
                600                 605                 610

cac cac tac ggg cgg gcc gtc atc atg ttt ggc gtc ccc tac gtc tac     1928
His His Tyr Gly Arg Ala Val Ile Met Phe Gly Val Pro Tyr Val Tyr
            615                 620                 625

aca cag agc cgc att ctc aag gcg cgg ctg gaa tac ctg cgg gac cag     1976
Thr Gln Ser Arg Ile Leu Lys Ala Arg Leu Glu Tyr Leu Arg Asp Gln
        630                 635                 640

ttc cag att cgt gag aat gac ttt ctt acc ttc gat gcc atg cgc cac     2024
Phe Gln Ile Arg Glu Asn Asp Phe Leu Thr Phe Asp Ala Met Arg His
    645                 650                 655

gcg gcc cag tgt gtg ggt cgg gcc atc agg ggc aag acg gac tac ggc     2072
Ala Ala Gln Cys Val Gly Arg Ala Ile Arg Gly Lys Thr Asp Tyr Gly
660                 665                 670                 675

ctc atg gtc ttt gcc gac aag cgg ttt gcc cgt ggg gac aag cgg ggg     2120
Leu Met Val Phe Ala Asp Lys Arg Phe Ala Arg Gly Asp Lys Arg Gly
                680                 685                 690

aag ctg ccc cgc tgg atc cag gag cac ctc aca gat gcc aac ctc aac     2168
Lys Leu Pro Arg Trp Ile Gln Glu His Leu Thr Asp Ala Asn Leu Asn
            695                 700                 705

ctg acc gtg gac gag ggt gtc cag gtg gcc aag tac ttc ctg cgg cag     2216
Leu Thr Val Asp Glu Gly Val Gln Val Ala Lys Tyr Phe Leu Arg Gln
        710                 715                 720

atg gca cag ccc ttc cac cgg gag gat cag ctg ggc ctg tcc ctg ctc     2264
Met Ala Gln Pro Phe His Arg Glu Asp Gln Leu Gly Leu Ser Leu Leu
    725                 730                 735

agc ctg gag cag cta gaa tca gag gag acg ctg aag agg ata gag cag     2312
Ser Leu Glu Gln Leu Glu Ser Glu Glu Thr Leu Lys Arg Ile Glu Gln
740                 745                 750                 755

att gct cag cag ctc tga gtggggcggg tggggccata aacggttcct            2360
Ile Ala Gln Gln Leu
                760

ggtgactcct gagtcttgcc tggccctggt tcccagcggc ggtggtgcta gaaggtctta   2420

tgaagtcagg tgacatttct cactgtcacg tccacagcct ttaatcgcag gagaaggcag   2480

ctatccacca ggtacccaga ggcaaggggg ggccaggaga tgatagaccc cctctcaccc   2540

caccagccca tccctcctgc actgttcc                                      2568
```

<210> SEQ ID NO 34
<211> LENGTH: 760
<212> TYPE: PRT
<213> ORGANISM: Homo sapiens

<400> SEQUENCE: 34

```
Met Lys Leu Asn Val Asp Gly Leu Leu Val Tyr Phe Pro Tyr Asp Tyr
1               5                   10                  15

Ile Tyr Pro Glu Gln Phe Ser Tyr Met Arg Glu Leu Lys Arg Thr Leu
            20                  25                  30

Asp Ala Lys Gly His Gly Val Leu Glu Met Pro Ser Gly Thr Gly Lys
        35                  40                  45

Thr Val Ser Leu Leu Ala Leu Ile Met Ala Tyr Gln Arg Ala Tyr Pro
    50                  55                  60

Leu Glu Val Thr Lys Leu Ile Tyr Cys Ser Arg Thr Val Pro Glu Ile
65                  70                  75                  80

Glu Lys Val Ile Glu Glu Leu Arg Lys Leu Leu Asn Phe Tyr Glu Lys
                85                  90                  95

Gln Glu Gly Glu Lys Leu Pro Phe Leu Gly Leu Ala Leu Ser Ser Arg
            100                 105                 110

Lys Asn Leu Cys Ile His Pro Glu Val Thr Pro Leu Arg Phe Gly Lys
        115                 120                 125

Asp Val Asp Gly Lys Cys His Ser Leu Thr Ala Ser Tyr Val Arg Ala
    130                 135                 140

Gln Tyr Gln His Asp Thr Ser Leu Pro His Cys Arg Phe Tyr Glu Glu
145                 150                 155                 160

Phe Asp Ala His Gly Arg Glu Val Pro Leu Pro Ala Gly Ile Tyr Asn
                165                 170                 175

Leu Asp Asp Leu Lys Ala Leu Gly Arg Arg Gln Gly Trp Cys Pro Tyr
            180                 185                 190

Phe Leu Ala Arg Tyr Ser Ile Leu His Ala Asn Val Val Val Tyr Ser
        195                 200                 205

Tyr His Tyr Leu Leu Asp Pro Lys Ile Ala Asp Leu Val Ser Lys Glu
    210                 215                 220

Leu Ala Arg Lys Ala Val Val Val Phe Asp Glu Ala His Asn Ile Asp
225                 230                 235                 240

Asn Val Cys Ile Asp Ser Met Ser Val Asn Leu Thr Arg Arg Thr Leu
                245                 250                 255

Asp Arg Cys Gln Gly Asn Leu Glu Thr Leu Gln Lys Thr Val Leu Arg
            260                 265                 270

Ile Lys Glu Thr Asp Glu Gln Arg Leu Arg Asp Glu Tyr Arg Arg Leu
        275                 280                 285

Val Glu Gly Leu Arg Glu Ala Ser Ala Ala Arg Glu Thr Asp Ala His
    290                 295                 300

Leu Ala Asn Pro Val Leu Pro Asp Glu Val Leu Gln Glu Ala Val Pro
305                 310                 315                 320

Gly Ser Ile Arg Thr Ala Glu His Phe Leu Gly Phe Leu Arg Arg Leu
                325                 330                 335

Leu Glu Tyr Val Lys Trp Arg Leu Arg Val Gln His Val Val Gln Glu
            340                 345                 350

Ser Pro Pro Ala Phe Leu Ser Gly Leu Ala Gln Arg Val Cys Ile Gln
        355                 360                 365

Arg Lys Pro Leu Arg Phe Cys Ala Glu Arg Leu Arg Ser Leu Leu His
    370                 375                 380

Thr Leu Glu Ile Thr Asp Leu Ala Asp Phe Ser Pro Leu Thr Leu Leu
385                 390                 395                 400

Ala Asn Phe Ala Thr Leu Val Ser Thr Tyr Ala Lys Gly Phe Thr Ile
                405                 410                 415
```

```
Ile Ile Glu Pro Phe Asp Asp Arg Thr Pro Thr Ile Ala Asn Pro Ile
            420                 425                 430

Leu His Phe Ser Cys Met Asp Ala Ser Leu Ala Ile Lys Pro Val Phe
        435                 440                 445

Glu Arg Phe Gln Ser Val Ile Ile Thr Ser Gly Thr Leu Ser Pro Leu
    450                 455                 460

Asp Ile Tyr Pro Lys Ile Leu Asp Phe His Pro Val Thr Met Ala Thr
465                 470                 475                 480

Phe Thr Met Thr Leu Ala Arg Val Cys Leu Cys Pro Met Ile Ile Gly
                485                 490                 495

Arg Gly Asn Asp Gln Val Ala Ile Ser Ser Lys Phe Glu Thr Arg Glu
            500                 505                 510

Asp Ile Ala Val Ile Arg Asn Tyr Gly Asn Leu Leu Leu Glu Met Ser
        515                 520                 525

Ala Val Val Pro Asp Gly Ile Val Ala Phe Phe Thr Ser Tyr Gln Tyr
    530                 535                 540

Met Glu Ser Thr Val Ala Ser Trp Tyr Glu Gln Gly Ile Leu Glu Asn
545                 550                 555                 560

Ile Gln Arg Asn Lys Leu Leu Phe Ile Glu Thr Gln Asp Gly Ala Glu
                565                 570                 575

Thr Ser Val Ala Leu Glu Lys Tyr Gln Glu Ala Cys Glu Asn Gly Arg
            580                 585                 590

Gly Ala Ile Leu Leu Ser Val Ala Arg Gly Lys Val Ser Glu Gly Ile
        595                 600                 605

Asp Phe Val His His Tyr Gly Arg Ala Val Ile Met Phe Gly Val Pro
    610                 615                 620

Tyr Val Tyr Thr Gln Ser Arg Ile Leu Lys Ala Arg Leu Glu Tyr Leu
625                 630                 635                 640

Arg Asp Gln Phe Gln Ile Arg Glu Asn Asp Phe Leu Thr Phe Asp Ala
                645                 650                 655

Met Arg His Ala Ala Gln Cys Val Gly Arg Ala Ile Arg Gly Lys Thr
            660                 665                 670

Asp Tyr Gly Leu Met Val Phe Ala Asp Lys Arg Phe Ala Arg Gly Asp
        675                 680                 685

Lys Arg Gly Lys Leu Pro Arg Trp Ile Gln Glu His Leu Thr Asp Ala
    690                 695                 700

Asn Leu Asn Leu Thr Val Asp Glu Gly Val Gln Val Ala Lys Tyr Phe
705                 710                 715                 720

Leu Arg Gln Met Ala Gln Pro Phe His Arg Glu Asp Gln Leu Gly Leu
                725                 730                 735

Ser Leu Leu Ser Leu Glu Gln Leu Glu Ser Glu Glu Thr Leu Lys Arg
            740                 745                 750

Ile Glu Gln Ile Ala Gln Gln Leu
        755                 760


<210> SEQ ID NO 35
<211> LENGTH: 2281
<212> TYPE: DNA
<213> ORGANISM: Homo sapiens
<220> FEATURE:
<221> NAME/KEY: CDS
<222> LOCATION: (188)..(1210)
<223> OTHER INFORMATION: DMC1

<400> SEQUENCE: 35
```

```
ctcctcgttt ggcgccaaac cctgtggtca acggcgcgcg ggtctccagg ctccgtgttc      60

taggcccgag ttagaatcct gtcagctgag gaggtcgggc ggggcagagg ggcttcacct     120

tgaaaatctc ggggagactg tgggtacgag ggggaagtga ttatttttct gttgcccact     180

tttcaat atg aag gag gat caa gtt gtg gcg gaa gaa cca gga ttc caa       229
        Met Lys Glu Asp Gln Val Val Ala Glu Glu Pro Gly Phe Gln
        1               5                   10

gat gaa gag gaa tct ttg ttt caa gat att gac ctg tta cag aaa cat       277
Asp Glu Glu Glu Ser Leu Phe Gln Asp Ile Asp Leu Leu Gln Lys His
15                  20                  25                  30

gga att aac gtg gct gac att aag aaa ctg aaa tca gta gga atc tgt       325
Gly Ile Asn Val Ala Asp Ile Lys Lys Leu Lys Ser Val Gly Ile Cys
                35                  40                  45

acc atc aaa ggt ata cag atg aca aca aga aga gct cta tgc aat gtc       373
Thr Ile Lys Gly Ile Gln Met Thr Thr Arg Arg Ala Leu Cys Asn Val
            50                  55                  60

aaa gga ctc tca gaa gcc aaa gta gac aag att aaa gag gca gcg aac       421
Lys Gly Leu Ser Glu Ala Lys Val Asp Lys Ile Lys Glu Ala Ala Asn
        65                  70                  75

aaa cta att gaa cca gga ttc ttg act gca ttt gag tat agt gaa aag       469
Lys Leu Ile Glu Pro Gly Phe Leu Thr Ala Phe Glu Tyr Ser Glu Lys
    80                  85                  90

agg aaa atg gtt ttc cat atc acc acc ggg agc cag gaa ttt gat aag       517
Arg Lys Met Val Phe His Ile Thr Thr Gly Ser Gln Glu Phe Asp Lys
95                  100                 105                 110

tta cta gga ggt gga att gaa agt atg gca att aca gaa gct ttt gga       565
Leu Leu Gly Gly Gly Ile Glu Ser Met Ala Ile Thr Glu Ala Phe Gly
                115                 120                 125

gaa ttt cgt act gga aaa acc cag ctt tct cat acc ctc tgt gtg aca       613
Glu Phe Arg Thr Gly Lys Thr Gln Leu Ser His Thr Leu Cys Val Thr
            130                 135                 140

gct caa ctt cca gga gct ggt ggc tac cca gga gga aag att atc ttc       661
Ala Gln Leu Pro Gly Ala Gly Gly Tyr Pro Gly Gly Lys Ile Ile Phe
        145                 150                 155

att gat aca gaa aat act ttc cgt cca gat cgc ctt agg gac att gct       709
Ile Asp Thr Glu Asn Thr Phe Arg Pro Asp Arg Leu Arg Asp Ile Ala
    160                 165                 170

gat cgc ttt aat gta gac cat gat gca gta ctg gac aac gta ctt tat       757
Asp Arg Phe Asn Val Asp His Asp Ala Val Leu Asp Asn Val Leu Tyr
175                 180                 185                 190

gca cgt gca tat act agt gaa cat cag atg gag cta ctt gat tat gta       805
Ala Arg Ala Tyr Thr Ser Glu His Gln Met Glu Leu Leu Asp Tyr Val
                195                 200                 205

gca gca aag ttc cat gaa gaa gct ggc atc ttc aag cta ttg att atc       853
Ala Ala Lys Phe His Glu Glu Ala Gly Ile Phe Lys Leu Leu Ile Ile
            210                 215                 220

gat tca ata atg gca ctt ttt cga gtg gat ttc agt ggc cgt ggg gag       901
Asp Ser Ile Met Ala Leu Phe Arg Val Asp Phe Ser Gly Arg Gly Glu
        225                 230                 235

ttg gcc gaa cgg cag caa aaa ttg gcc cag atg ttg tca cga ctc caa       949
Leu Ala Glu Arg Gln Gln Lys Leu Ala Gln Met Leu Ser Arg Leu Gln
    240                 245                 250

aaa atc tca gaa gaa tat aac gtg gct gtt ttt gtg acc aat caa atg       997
Lys Ile Ser Glu Glu Tyr Asn Val Ala Val Phe Val Thr Asn Gln Met
255                 260                 265                 270

act gcc gat cca gga gca act atg acc ttt cag gca gat ccc aaa aaa      1045
Thr Ala Asp Pro Gly Ala Thr Met Thr Phe Gln Ala Asp Pro Lys Lys
                275                 280                 285

ccc att ggg gga cac att ctg gct cat gct tca aca aca aga ata agc      1093
```

```
Pro Ile Gly Gly His Ile Leu Ala His Ala Ser Thr Thr Arg Ile Ser
            290                 295                 300

ttg cga aag gga aga gga gag ctc aga att gcc aag att tat gac agt     1141
Leu Arg Lys Gly Arg Gly Glu Leu Arg Ile Ala Lys Ile Tyr Asp Ser
        305                 310                 315

cct gag atg cct gaa aat gaa gcc acc ttc gca ata act gct gga gga     1189
Pro Glu Met Pro Glu Asn Glu Ala Thr Phe Ala Ile Thr Ala Gly Gly
    320                 325                 330

att ggg gat gcc aag gag tag gtggtgaatt gatgcaaatt gcttcttagt       1240
Ile Gly Asp Ala Lys Glu
335                 340

gcttattagg agctgaagaa atggaaaagc agtctccaat ttcacatctt gaaatagagg   1300

tttttcccca catgttacta aagaaaagtc agcaaagaga tttaaatctt atatttatct   1360

taaaagtccc tgatttatga taactataca ttgtatgtaa attcagggat atgtatatgt   1420

atgtttgtgt gtgtgtgtgt ttgtgtgtgt atacctgaca tatatagtag atatatatac   1480

ctattgaaat tctctcactc tgtgtatgta tatataccta tggaaaacta gttgttggga   1540

aaggagtacg tgattccctc cctttcactt ttcaaagtga gccactaaac agaaagtcta   1600

agagttcaga aatgtcccat tctcctaagg actttccctt caccattttt ctagggtata   1660

gtgccactga cttacatagc tagatgtttt tccacaagag gatttaaggg aggaatgttt   1720

ataggacaca cacacaaaag ctctttctat ttataatatc aaactgcata ttcaccttta   1780

tagcaacaga aaacagacat taaattaagc caaattttaa atcatttgac tttgacaagc   1840

agaaattact tttaaaaaat gtatttatgg ctgggcgtgg tggctcacac ctgtaatccc   1900

agcactttgg gaggccgagg caggtggatc acttgaggtc aggagttcaa gaccagcctg   1960

gccaacatgg agaaacccca tctctactaa aaatacaaaa attagccaag tgcagtggca   2020

tgtgcttgta atcccagcta ctctggaggc tgaggcagga gaattgcttg aacccaggag   2080

gcagagattg cggtgagcca agatggcacc actgcactcc agcctaggtg acagagtgag   2140

actccgtctc aaaaaaaaaa aaaaaacttt tttaaaatgt taaaattaat ttaaatgtaa   2200

aatttctgaa tactaatctt agaaatgtgt aaaagatatt attttgattg ttaaacaaat   2260

aaaatcctgt tttcaaaatg c                                             2281


<210> SEQ ID NO 36
<211> LENGTH: 340
<212> TYPE: PRT
<213> ORGANISM: Homo sapiens

<400> SEQUENCE: 36

Met Lys Glu Asp Gln Val Val Ala Glu Glu Pro Gly Phe Gln Asp Glu
1               5                   10                  15

Glu Glu Ser Leu Phe Gln Asp Ile Asp Leu Leu Gln Lys His Gly Ile
            20                  25                  30

Asn Val Ala Asp Ile Lys Lys Leu Lys Ser Val Gly Ile Cys Thr Ile
        35                  40                  45

Lys Gly Ile Gln Met Thr Thr Arg Arg Ala Leu Cys Asn Val Lys Gly
    50                  55                  60

Leu Ser Glu Ala Lys Val Asp Lys Ile Lys Glu Ala Ala Asn Lys Leu
65                  70                  75                  80

Ile Glu Pro Gly Phe Leu Thr Ala Phe Glu Tyr Ser Glu Lys Arg Lys
                85                  90                  95

Met Val Phe His Ile Thr Thr Gly Ser Gln Glu Phe Asp Lys Leu Leu
            100                 105                 110
```

```
Gly Gly Gly Ile Glu Ser Met Ala Ile Thr Glu Ala Phe Gly Glu Phe
        115                 120                 125

Arg Thr Gly Lys Thr Gln Leu Ser His Thr Leu Cys Val Thr Ala Gln
    130                 135                 140

Leu Pro Gly Ala Gly Gly Tyr Pro Gly Gly Lys Ile Ile Phe Ile Asp
145                 150                 155                 160

Thr Glu Asn Thr Phe Arg Pro Asp Arg Leu Arg Asp Ile Ala Asp Arg
                165                 170                 175

Phe Asn Val Asp His Asp Ala Val Leu Asp Asn Val Leu Tyr Ala Arg
            180                 185                 190

Ala Tyr Thr Ser Glu His Gln Met Glu Leu Leu Asp Tyr Val Ala Ala
        195                 200                 205

Lys Phe His Glu Glu Ala Gly Ile Phe Lys Leu Leu Ile Ile Asp Ser
    210                 215                 220

Ile Met Ala Leu Phe Arg Val Asp Phe Ser Gly Arg Gly Glu Leu Ala
225                 230                 235                 240

Glu Arg Gln Gln Lys Leu Ala Gln Met Leu Ser Arg Leu Gln Lys Ile
                245                 250                 255

Ser Glu Glu Tyr Asn Val Ala Val Phe Val Thr Asn Gln Met Thr Ala
            260                 265                 270

Asp Pro Gly Ala Thr Met Thr Phe Gln Ala Asp Pro Lys Lys Pro Ile
        275                 280                 285

Gly Gly His Ile Leu Ala His Ala Ser Thr Thr Arg Ile Ser Leu Arg
    290                 295                 300

Lys Gly Arg Gly Glu Leu Arg Ile Ala Lys Ile Tyr Asp Ser Pro Glu
305                 310                 315                 320

Met Pro Glu Asn Glu Ala Thr Phe Ala Ile Thr Ala Gly Gly Ile Gly
                325                 330                 335

Asp Ala Lys Glu
            340


<210> SEQ ID NO 37
<211> LENGTH: 2444
<212> TYPE: DNA
<213> ORGANISM: Homo sapiens
<220> FEATURE:
<221> NAME/KEY: CDS
<222> LOCATION: (161)..(1468)
<223> OTHER INFORMATION: RECQL5

<400> SEQUENCE: 37

acggatataa gattgcgtgg gttctgccta aagctgaatt cccagcgctt tggcttctct      60

gagttggggt tgtgtatagg ggtcttcgaa cagttccgga accagccagc agcctttaat     120

tcttgggcgg accacggccg gttctgtgtt cttggctaag atg agc agc cac cat       175
                                            Met Ser Ser His His
                                            1               5

acc acc ttt cct ttt gac cct gag cgg cga gtc cgg agt acg ctg aag       223
Thr Thr Phe Pro Phe Asp Pro Glu Arg Arg Val Arg Ser Thr Leu Lys
                10                  15                  20

aag gtc ttt ggg ttt gac tct ttt aag acg cct tta cag gag agt gcg       271
Lys Val Phe Gly Phe Asp Ser Phe Lys Thr Pro Leu Gln Glu Ser Ala
            25                  30                  35

acc atg gct gta gta aaa ggt aac aag gac gtc ttt gtg tgc atg ccc       319
Thr Met Ala Val Val Lys Gly Asn Lys Asp Val Phe Val Cys Met Pro
        40                  45                  50

aca ggg gca gga aaa tcc cta tgc tat cag ctc cct gct ctg ttg gcc       367
```

```
Thr Gly Ala Gly Lys Ser Leu Cys Tyr Gln Leu Pro Ala Leu Leu Ala
    55                  60                  65

aaa ggc atc acc att gta gtc tct cct ctc att gct ttg att cag gac      415
Lys Gly Ile Thr Ile Val Val Ser Pro Leu Ile Ala Leu Ile Gln Asp
70                  75                  80                  85

caa gtg gac cac ttg cta acc cta aag gta cga gta agt tcc ctg aac      463
Gln Val Asp His Leu Leu Thr Leu Lys Val Arg Val Ser Ser Leu Asn
                90                  95                  100

tcg aag ctc tct gca cag gaa agg aag gag ctg ctt gct gac ctg gag      511
Ser Lys Leu Ser Ala Gln Glu Arg Lys Glu Leu Leu Ala Asp Leu Glu
            105                 110                 115

cga gaa aag ccc cag acc aag att ctg tac atc acc cca gag atg gca      559
Arg Glu Lys Pro Gln Thr Lys Ile Leu Tyr Ile Thr Pro Glu Met Ala
        120                 125                 130

gct tca tcc tcc ttc cag ccc acc ctg aac tcc ctg gtg tcc cgc cac      607
Ala Ser Ser Ser Phe Gln Pro Thr Leu Asn Ser Leu Val Ser Arg His
    135                 140                 145

ctg ctg tct tac ttg gtg gtg gat gaa gct cat tgt gtt tcc caa tgg      655
Leu Leu Ser Tyr Leu Val Val Asp Glu Ala His Cys Val Ser Gln Trp
150                 155                 160                 165

ggg cat gac ttt cgt cct gac tac ttg cgt ctg ggt gcc ctg cgc tcc      703
Gly His Asp Phe Arg Pro Asp Tyr Leu Arg Leu Gly Ala Leu Arg Ser
                170                 175                 180

cgc ctg gga cat gcc cct tgt gtg gct ctg acc gcc aca gcc acc cca      751
Arg Leu Gly His Ala Pro Cys Val Ala Leu Thr Ala Thr Ala Thr Pro
            185                 190                 195

cag gtc caa gag gac gtg ttt gct gcc ctg cac ctg aag aaa cca gtt      799
Gln Val Gln Glu Asp Val Phe Ala Ala Leu His Leu Lys Lys Pro Val
        200                 205                 210

gcc atc ttc aag act ccc tgc ttc cgg gcc aac ctc ttc tat gat gtg      847
Ala Ile Phe Lys Thr Pro Cys Phe Arg Ala Asn Leu Phe Tyr Asp Val
    215                 220                 225

caa ttc aag gaa ctg att tct gat ccc tat ggg aac ctg aag gac ttc      895
Gln Phe Lys Glu Leu Ile Ser Asp Pro Tyr Gly Asn Leu Lys Asp Phe
230                 235                 240                 245

tgc ctt aag gct ctt gga cag gag gct gat aaa ggg tta tct ggc tgc      943
Cys Leu Lys Ala Leu Gly Gln Glu Ala Asp Lys Gly Leu Ser Gly Cys
                250                 255                 260

ggc att gtg tac tgc agg act aga gag gct tgt gaa cag ctg gcc ata      991
Gly Ile Val Tyr Cys Arg Thr Arg Glu Ala Cys Glu Gln Leu Ala Ile
            265                 270                 275

gag ctc agc tgc agg ggt gtg aac gcc aag gct tac cat gca ggg ctg     1039
Glu Leu Ser Cys Arg Gly Val Asn Ala Lys Ala Tyr His Ala Gly Leu
        280                 285                 290

aag gcc tct gaa aga acg ctg gtg cag aac gac tgg atg gag gag aag     1087
Lys Ala Ser Glu Arg Thr Leu Val Gln Asn Asp Trp Met Glu Glu Lys
    295                 300                 305

gtc cct gta att gtt gca acc att agt ttt ggg atg gga gtg gat aaa     1135
Val Pro Val Ile Val Ala Thr Ile Ser Phe Gly Met Gly Val Asp Lys
310                 315                 320                 325

gcc aat gtc agg ttt gtc gcc cat tgg aat att gcc aag tct atg gct     1183
Ala Asn Val Arg Phe Val Ala His Trp Asn Ile Ala Lys Ser Met Ala
                330                 335                 340

ggg tac tac cag gag tct ggc cgg gct ggc agg gat ggg aag cct tcc     1231
Gly Tyr Tyr Gln Glu Ser Gly Arg Ala Gly Arg Asp Gly Lys Pro Ser
            345                 350                 355

tgg tgc cgt ctc tat tac tcc agg aat gac cgg gac caa gtc agc ttc     1279
Trp Cys Arg Leu Tyr Tyr Ser Arg Asn Asp Arg Asp Gln Val Ser Phe
        360                 365                 370
```

```
ctg atc agg aag gaa gta gca aaa ctc cag gaa aag aga gga aac aaa     1327
Leu Ile Arg Lys Glu Val Ala Lys Leu Gln Glu Lys Arg Gly Asn Lys
    375                 380                 385

gca tct gat aaa gcc act atc atg gcc ttt gat gcc ctg gtg acc ttc     1375
Ala Ser Asp Lys Ala Thr Ile Met Ala Phe Asp Ala Leu Val Thr Phe
390                 395                 400                 405

tgt gaa gaa ctg ggg cga tgg ggc agg ggc cac gga aag agt ctg agg     1423
Cys Glu Glu Leu Gly Arg Trp Gly Arg Gly His Gly Lys Ser Leu Arg
                410                 415                 420

gct gct tgg tgt agt cag gtt gtg tcc agg cat gcg gag ctg tga         1468
Ala Ala Trp Cys Ser Gln Val Val Ser Arg His Ala Glu Leu
            425                 430                 435

gtgcctgcag gagagacacc caggaggagt ttttacattt tggtctaaaa agctcttgga   1528

ttcatctcat ctcatggaat gatcctgtcg gatgacgctg acgtgattgc ttcagactta   1588

gaggtgaata aattgaggtc cagagaggtc acagtcacga agctcatggt agactgaggc   1648

cactaaacac ccgtctcctg attttcagtg gcgtcctcat ttgcatacac ctgggccatc   1708

ttggtttttg caagaaaaaa gcgaggaaat cagagaaact ctttgggctg tgtgttttta   1768

tttccacctc ctcctgttga ccagtgagtc ggtggcttct ggactgaagc tattttcttc   1828

tccaaactgc tgtctctaat ttggcctctg tggcaagacc acgcccagca aaagtggtcg   1888

gctgcagtgc caggaccacc cttgcctgca gcctttgcga ccagagccct tttcaagcac   1948

aattaatatg ggagttgcta aatttggcct tcttaggctt cttgagcaga gctcttattt   2008

ctggtgagga atgaaagggc caagtgttcc tgttcattgt gagtcctgtt tgctgaaaaa   2068

agctctgggg ctgtctgagg ctctggaatg ctctctggag ggttaactct gcctgtcccc   2128

agggtctgct ccgcctgcca ggcaagggaa caggtcctcc caagggcctc tgccttcatt   2188

tctcctgtca ccttccgggg agctgggact tcttagtgca tcagtggcct ggttgccagg   2248

ggctggggtc caggcatctg tggactcaag gagtccaggt gacggtgttg cgctgcctct   2308

tgagcagcct cgtgcctgtc tcctttgcta catgtgatga ttctgaaatc caggcagcag   2368

gctggaataa acgctgctgg tatgtcaaaa aaaaaaaaaa aaaaaaaaaa aaaaaaaaaa   2428

aaaaaaaaaa aaaaaa                                                   2444


<210> SEQ ID NO 38
<211> LENGTH: 435
<212> TYPE: PRT
<213> ORGANISM: Homo sapiens

<400> SEQUENCE: 38

Met Ser Ser His His Thr Thr Phe Pro Phe Asp Pro Glu Arg Arg Val
1               5                   10                  15

Arg Ser Thr Leu Lys Lys Val Phe Gly Phe Asp Ser Phe Lys Thr Pro
            20                  25                  30

Leu Gln Glu Ser Ala Thr Met Ala Val Val Lys Gly Asn Lys Asp Val
        35                  40                  45

Phe Val Cys Met Pro Thr Gly Ala Gly Lys Ser Leu Cys Tyr Gln Leu
    50                  55                  60

Pro Ala Leu Leu Ala Lys Gly Ile Thr Ile Val Val Ser Pro Leu Ile
65                  70                  75                  80

Ala Leu Ile Gln Asp Gln Val Asp His Leu Leu Thr Leu Lys Val Arg
                85                  90                  95

Val Ser Ser Leu Asn Ser Lys Leu Ser Ala Gln Glu Arg Lys Glu Leu
            100                 105                 110
```

```
Leu Ala Asp Leu Glu Arg Glu Lys Pro Gln Thr Lys Ile Leu Tyr Ile
        115                 120                 125

Thr Pro Glu Met Ala Ala Ser Ser Ser Phe Gln Pro Thr Leu Asn Ser
    130                 135                 140

Leu Val Ser Arg His Leu Leu Ser Tyr Leu Val Val Asp Glu Ala His
145                 150                 155                 160

Cys Val Ser Gln Trp Gly His Asp Phe Arg Pro Asp Tyr Leu Arg Leu
                165                 170                 175

Gly Ala Leu Arg Ser Arg Leu Gly His Ala Pro Cys Val Ala Leu Thr
            180                 185                 190

Ala Thr Ala Thr Pro Gln Val Gln Glu Asp Val Phe Ala Ala Leu His
        195                 200                 205

Leu Lys Lys Pro Val Ala Ile Phe Lys Thr Pro Cys Phe Arg Ala Asn
    210                 215                 220

Leu Phe Tyr Asp Val Gln Phe Lys Glu Leu Ile Ser Asp Pro Tyr Gly
225                 230                 235                 240

Asn Leu Lys Asp Phe Cys Leu Lys Ala Leu Gly Gln Glu Ala Asp Lys
                245                 250                 255

Gly Leu Ser Gly Cys Gly Ile Val Tyr Cys Arg Thr Arg Glu Ala Cys
            260                 265                 270

Glu Gln Leu Ala Ile Glu Leu Ser Cys Arg Gly Val Asn Ala Lys Ala
        275                 280                 285

Tyr His Ala Gly Leu Lys Ala Ser Glu Arg Thr Leu Val Gln Asn Asp
    290                 295                 300

Trp Met Glu Glu Lys Val Pro Val Ile Val Ala Thr Ile Ser Phe Gly
305                 310                 315                 320

Met Gly Val Asp Lys Ala Asn Val Arg Phe Val Ala His Trp Asn Ile
                325                 330                 335

Ala Lys Ser Met Ala Gly Tyr Tyr Gln Glu Ser Gly Arg Ala Gly Arg
            340                 345                 350

Asp Gly Lys Pro Ser Trp Cys Arg Leu Tyr Tyr Ser Arg Asn Asp Arg
        355                 360                 365

Asp Gln Val Ser Phe Leu Ile Arg Lys Glu Val Ala Lys Leu Gln Glu
    370                 375                 380

Lys Arg Gly Asn Lys Ala Ser Asp Lys Ala Thr Ile Met Ala Phe Asp
385                 390                 395                 400

Ala Leu Val Thr Phe Cys Glu Glu Leu Gly Arg Trp Gly Arg Gly His
                405                 410                 415

Gly Lys Ser Leu Arg Ala Ala Trp Cys Ser Gln Val Val Ser Arg His
            420                 425                 430

Ala Glu Leu
        435
```

<210> SEQ ID NO 39
<211> LENGTH: 2406
<212> TYPE: DNA
<213> ORGANISM: Homo sapiens
<220> FEATURE:
<221> NAME/KEY: CDS
<222> LOCATION: (354)..(2009)
<223> OTHER INFORMATION: MUS81

<400> SEQUENCE: 39

```
ctacacaaag accccgctct cgaatctggg gtgacaggaa ggagccggtc caggctccgg      60

gggctgggaa agggcgcgtc tcaaaggctg gctggagtgg agccaaggga aaagatcgtt     120
```

```
agagacagcg cccctgacca accacttaga gcagcgcagg ggtgggaggg cggccgcagg    180

ctctcctctc gttagtgccc cctgtgtttg gggccccgtg atctcaacgg tcctgccctc    240

ggtctccctc ttcccccgcc ccgccctggg ccaggtgttc gaatcccgac tccagaactg    300

gcggcgtccc agtcccgcgg gcgtggagcg ccggaggacc cgccctcggg ctc atg       356
                                                           Met
                                                           1

gcg gcc ccg gtc cgc ctg ggc cgg aag cgc ccg ctg cct gcc tgt ccc      404
Ala Ala Pro Val Arg Leu Gly Arg Lys Arg Pro Leu Pro Ala Cys Pro
            5                   10                  15

aac ccg ctc ttc gtt cgc tgg ctg acc gag tgg cgg gac gag gcg acc      452
Asn Pro Leu Phe Val Arg Trp Leu Thr Glu Trp Arg Asp Glu Ala Thr
        20                  25                  30

cgc agc agg cgc cgc acg cgc ttc gta ttt cag aag gcg ctg cgt tcc      500
Arg Ser Arg Arg Arg Thr Arg Phe Val Phe Gln Lys Ala Leu Arg Ser
    35                  40                  45

ctc cga cgg tac cca ctg ccg ctg cgc agc ggg aag gaa gct aag atc      548
Leu Arg Arg Tyr Pro Leu Pro Leu Arg Ser Gly Lys Glu Ala Lys Ile
50                  55                  60                  65

cta cag cac ttc gga gac ggg ctc tgc cgg atg ctg gac gag cgg ctg      596
Leu Gln His Phe Gly Asp Gly Leu Cys Arg Met Leu Asp Glu Arg Leu
                70                  75                  80

cag cgg cac cga aca tcg ggc ggt gac cat gcc ccg gac tca cca tct      644
Gln Arg His Arg Thr Ser Gly Gly Asp His Ala Pro Asp Ser Pro Ser
            85                  90                  95

gga gag aac agt cca gcc ccg cag ggg cga ctt gcg gaa gtc cag gac      692
Gly Glu Asn Ser Pro Ala Pro Gln Gly Arg Leu Ala Glu Val Gln Asp
        100                 105                 110

tct tcc atg cca gtt cct gcc cag ccc aaa gcg gga ggc tct ggc agc      740
Ser Ser Met Pro Val Pro Ala Gln Pro Lys Ala Gly Gly Ser Gly Ser
    115                 120                 125

tac tgg cca gct cgg cac tca gga gcc cga gtg ata ctg ctg gtg ctc      788
Tyr Trp Pro Ala Arg His Ser Gly Ala Arg Val Ile Leu Leu Val Leu
130                 135                 140                 145

tac cgg gag cac ctg aat cct aat ggt cac cac ttc tta acc aag gag      836
Tyr Arg Glu His Leu Asn Pro Asn Gly His His Phe Leu Thr Lys Glu
                150                 155                 160

gag ctg ctg cag agg tgt gct cag aag tcc ccc agg gta gcc cct ggg      884
Glu Leu Leu Gln Arg Cys Ala Gln Lys Ser Pro Arg Val Ala Pro Gly
            165                 170                 175

agt gct cga ccc tgg cca gcc ctc cgc tcc ctc ctt cac agg aac ctg      932
Ser Ala Arg Pro Trp Pro Ala Leu Arg Ser Leu Leu His Arg Asn Leu
        180                 185                 190

gtc ctc agg aca cac cag cca gcc agg tac tca ttg acc cca gag ggc      980
Val Leu Arg Thr His Gln Pro Ala Arg Tyr Ser Leu Thr Pro Glu Gly
    195                 200                 205

ctg gag ctg gcc cag aag ttg gcc gag tca gaa ggc ctg agc ttg ctg     1028
Leu Glu Leu Ala Gln Lys Leu Ala Glu Ser Glu Gly Leu Ser Leu Leu
210                 215                 220                 225

aat gtg ggc atc ggg ccc aag gag ccc cct ggg gag gag aca gca gtg     1076
Asn Val Gly Ile Gly Pro Lys Glu Pro Pro Gly Glu Glu Thr Ala Val
                230                 235                 240

cca gga gca gct tca gca gag ctt gcc agt gaa gca ggg gtc cag cag     1124
Pro Gly Ala Ala Ser Ala Glu Leu Ala Ser Glu Ala Gly Val Gln Gln
            245                 250                 255

cag cca ctg gag ctg agg cct gga gag tac agg gtg ctg ttg tgt gtg     1172
Gln Pro Leu Glu Leu Arg Pro Gly Glu Tyr Arg Val Leu Leu Cys Val
        260                 265                 270

gac att ggc gag acc cgg ggg ggc ggg cac agg ccg gag ctg ctc cga     1220
```

```
Asp Ile Gly Glu Thr Arg Gly Gly Gly His Arg Pro Glu Leu Leu Arg
    275                 280                 285

gag cta cag cgg ctg cac gtg acc cac acg gtg cgc aag ctg cac gtt      1268
Glu Leu Gln Arg Leu His Val Thr His Thr Val Arg Lys Leu His Val
290                 295                 300                 305

gga gat ttt gtg tgg gtg gcc cag gag acc aat cct aga gac cca gca      1316
Gly Asp Phe Val Trp Val Ala Gln Glu Thr Asn Pro Arg Asp Pro Ala
                310                 315                 320

aac cct ggg gag ttg gta ctg gat cac att gtg gag cgc aag cga ctg      1364
Asn Pro Gly Glu Leu Val Leu Asp His Ile Val Glu Arg Lys Arg Leu
            325                 330                 335

gat gac ctt tgc agc agc atc atc gac ggc cgc ttc cgg gag cag aag      1412
Asp Asp Leu Cys Ser Ser Ile Ile Asp Gly Arg Phe Arg Glu Gln Lys
        340                 345                 350

ttc cgg ctg aag cgc tgt ggt ctg gag cgc cgg gta tac ctg gtg gaa      1460
Phe Arg Leu Lys Arg Cys Gly Leu Glu Arg Arg Val Tyr Leu Val Glu
    355                 360                 365

gag cat ggt tcc gtc cac aac ctc agc ctt cct gag agc aca ctg ctg      1508
Glu His Gly Ser Val His Asn Leu Ser Leu Pro Glu Ser Thr Leu Leu
370                 375                 380                 385

cag gct gtc acc aac act cag gtc att gat ggc ttt ttt gtg aag cgc      1556
Gln Ala Val Thr Asn Thr Gln Val Ile Asp Gly Phe Phe Val Lys Arg
                390                 395                 400

aca gca gac att aag gag tca gcc gcc tac ctg gcc ctc ttg acg cgg      1604
Thr Ala Asp Ile Lys Glu Ser Ala Ala Tyr Leu Ala Leu Leu Thr Arg
            405                 410                 415

ggc ctg cag aga ctc tac cag ggc cac acc cta cgc agc cgc ccc tgg      1652
Gly Leu Gln Arg Leu Tyr Gln Gly His Thr Leu Arg Ser Arg Pro Trp
        420                 425                 430

gga acc cct ggg aac cct gaa tca ggg gcc atg acc tct cca aac cct      1700
Gly Thr Pro Gly Asn Pro Glu Ser Gly Ala Met Thr Ser Pro Asn Pro
    435                 440                 445

ctc tgc tca ctc ctc acc ttc agt gac ttc aac gca gga gcc atc aag      1748
Leu Cys Ser Leu Leu Thr Phe Ser Asp Phe Asn Ala Gly Ala Ile Lys
450                 455                 460                 465

aat aag gcc cag tcg gtg cga gaa gtg ttt gcc cgg cag ctg atg cag      1796
Asn Lys Ala Gln Ser Val Arg Glu Val Phe Ala Arg Gln Leu Met Gln
                470                 475                 480

gtg cgc gga gtg agt ggg gag aag gca gca gcc ctg gtg gat cga tac      1844
Val Arg Gly Val Ser Gly Glu Lys Ala Ala Ala Leu Val Asp Arg Tyr
            485                 490                 495

agc acc cct gcc agc ctc ctg gcc gcc tat gat gcc tgt gcc acc ccc      1892
Ser Thr Pro Ala Ser Leu Leu Ala Ala Tyr Asp Ala Cys Ala Thr Pro
        500                 505                 510

aag gaa caa gag aca ctg ctg agc acc att aag tgt ggg cgt cta cag      1940
Lys Glu Gln Glu Thr Leu Leu Ser Thr Ile Lys Cys Gly Arg Leu Gln
    515                 520                 525

agg aat ctg ggg cct gct ctg agc agg acc tta tcc cag ctc tac tgc      1988
Arg Asn Leu Gly Pro Ala Leu Ser Arg Thr Leu Ser Gln Leu Tyr Cys
530                 535                 540                 545

agc tac ggc ccc ttg acc tga gcttatgccg tgaaacagcc cccagccccc         2039
Ser Tyr Gly Pro Leu Thr
                550

gtctgtcccc caacccaggc tagccagcct tttaacaaca tcttttgggg tacaattaga    2099

atctaagtgt ttgcagccat atgtgtcatg tagaagatgc ctagccctgg ggaccttgtg    2159

aaatacgcag gaaccaggga taccatctgg tccagtggtt tttaaacaaa gctgcttagc    2219

acctggaatt ccctggtcag ggagatggag tcagtggggc attgcagctt ggaatctatt    2279
```

```
ttatgtcacc agttggtcct catcaaataa aatttcctta ggagtgcaga gggctcattg   2339

ggaaaataaa aataataaaa ataaataaaa cttcctaaaa gaaaagattg aaaaccacta   2399

aaaaaaa                                                             2406


<210> SEQ ID NO 40
<211> LENGTH: 551
<212> TYPE: PRT
<213> ORGANISM: Homo sapiens

<400> SEQUENCE: 40

Met Ala Ala Pro Val Arg Leu Gly Arg Lys Arg Pro Leu Pro Ala Cys
1               5                   10                  15

Pro Asn Pro Leu Phe Val Arg Trp Leu Thr Glu Trp Arg Asp Glu Ala
            20                  25                  30

Thr Arg Ser Arg Arg Arg Thr Arg Phe Val Phe Gln Lys Ala Leu Arg
        35                  40                  45

Ser Leu Arg Arg Tyr Pro Leu Pro Leu Arg Ser Gly Lys Glu Ala Lys
    50                  55                  60

Ile Leu Gln His Phe Gly Asp Gly Leu Cys Arg Met Leu Asp Glu Arg
65                  70                  75                  80

Leu Gln Arg His Arg Thr Ser Gly Gly Asp His Ala Pro Asp Ser Pro
                85                  90                  95

Ser Gly Glu Asn Ser Pro Ala Pro Gln Gly Arg Leu Ala Glu Val Gln
            100                 105                 110

Asp Ser Ser Met Pro Val Pro Ala Gln Pro Lys Ala Gly Gly Ser Gly
        115                 120                 125

Ser Tyr Trp Pro Ala Arg His Ser Gly Ala Arg Val Ile Leu Leu Val
    130                 135                 140

Leu Tyr Arg Glu His Leu Asn Pro Asn Gly His His Phe Leu Thr Lys
145                 150                 155                 160

Glu Glu Leu Leu Gln Arg Cys Ala Gln Lys Ser Pro Arg Val Ala Pro
                165                 170                 175

Gly Ser Ala Arg Pro Trp Pro Ala Leu Arg Ser Leu Leu His Arg Asn
            180                 185                 190

Leu Val Leu Arg Thr His Gln Pro Ala Arg Tyr Ser Leu Thr Pro Glu
        195                 200                 205

Gly Leu Glu Leu Ala Gln Lys Leu Ala Glu Ser Glu Gly Leu Ser Leu
    210                 215                 220

Leu Asn Val Gly Ile Gly Pro Lys Glu Pro Pro Gly Glu Glu Thr Ala
225                 230                 235                 240

Val Pro Gly Ala Ala Ser Ala Glu Leu Ala Ser Glu Ala Gly Val Gln
                245                 250                 255

Gln Gln Pro Leu Glu Leu Arg Pro Gly Glu Tyr Arg Val Leu Leu Cys
            260                 265                 270

Val Asp Ile Gly Glu Thr Arg Gly Gly Gly His Arg Pro Glu Leu Leu
        275                 280                 285

Arg Glu Leu Gln Arg Leu His Val Thr His Thr Val Arg Lys Leu His
    290                 295                 300

Val Gly Asp Phe Val Trp Val Ala Gln Glu Thr Asn Pro Arg Asp Pro
305                 310                 315                 320

Ala Asn Pro Gly Glu Leu Val Leu Asp His Ile Val Glu Arg Lys Arg
                325                 330                 335

Leu Asp Asp Leu Cys Ser Ser Ile Ile Asp Gly Arg Phe Arg Glu Gln
            340                 345                 350
```

```
Lys Phe Arg Leu Lys Arg Cys Gly Leu Glu Arg Arg Val Tyr Leu Val
        355                 360                 365

Glu Glu His Gly Ser Val His Asn Leu Ser Leu Pro Glu Ser Thr Leu
    370                 375                 380

Leu Gln Ala Val Thr Asn Thr Gln Val Ile Asp Gly Phe Phe Val Lys
385                 390                 395                 400

Arg Thr Ala Asp Ile Lys Glu Ser Ala Ala Tyr Leu Ala Leu Leu Thr
                405                 410                 415

Arg Gly Leu Gln Arg Leu Tyr Gln Gly His Thr Leu Arg Ser Arg Pro
            420                 425                 430

Trp Gly Thr Pro Gly Asn Pro Glu Ser Gly Ala Met Thr Ser Pro Asn
        435                 440                 445

Pro Leu Cys Ser Leu Leu Thr Phe Ser Asp Phe Asn Ala Gly Ala Ile
    450                 455                 460

Lys Asn Lys Ala Gln Ser Val Arg Glu Val Phe Ala Arg Gln Leu Met
465                 470                 475                 480

Gln Val Arg Gly Val Ser Gly Glu Lys Ala Ala Ala Leu Val Asp Arg
                485                 490                 495

Tyr Ser Thr Pro Ala Ser Leu Leu Ala Ala Tyr Asp Ala Cys Ala Thr
            500                 505                 510

Pro Lys Glu Gln Glu Thr Leu Leu Ser Thr Ile Lys Cys Gly Arg Leu
        515                 520                 525

Gln Arg Asn Leu Gly Pro Ala Leu Ser Arg Thr Leu Ser Gln Leu Tyr
    530                 535                 540

Cys Ser Tyr Gly Pro Leu Thr
545                 550


<210> SEQ ID NO 41
<211> LENGTH: 2332
<212> TYPE: DNA
<213> ORGANISM: Homo sapiens
<220> FEATURE:
<221> NAME/KEY: CDS
<222> LOCATION: (83)..(1795)
<223> OTHER INFORMATION: EME1

<400> SEQUENCE: 41

aggagatcta cttccgggcc ctgcgtggca gttgaaagag tggcgggaga agttgcaggg      60

aattatttga tagcacatac tg atg gct cta aag aag tca tca ccc tca ctg     112
                         Met Ala Leu Lys Lys Ser Ser Pro Ser Leu
                         1               5                   10

gat tct ggt gat agt gac tct gag gag ttg cca aca ttt gcc ttt ctg      160
Asp Ser Gly Asp Ser Asp Ser Glu Glu Leu Pro Thr Phe Ala Phe Leu
                15                  20                  25

aag aag gaa cca tct tca aca aag agg aga cag cct gaa agg gaa gag      208
Lys Lys Glu Pro Ser Ser Thr Lys Arg Arg Gln Pro Glu Arg Glu Glu
            30                  35                  40

aag att gta gtg gtt gac atc tca gat tgt gaa gcc tcc tgt cct cca      256
Lys Ile Val Val Val Asp Ile Ser Asp Cys Glu Ala Ser Cys Pro Pro
        45                  50                  55

gca cca gag tta ttt tca cca cct gtc cca gaa ata gct gaa act gtc      304
Ala Pro Glu Leu Phe Ser Pro Pro Val Pro Glu Ile Ala Glu Thr Val
    60                  65                  70

aca caa aca cag cca gtc agg ttg cta agc agt gaa agt gaa gat gaa      352
Thr Gln Thr Gln Pro Val Arg Leu Leu Ser Ser Glu Ser Glu Asp Glu
75                  80                  85                  90

gaa gaa ttt att cct ctg gct caa agg ctt aca tgt aag ttt ctg acc      400
```

```
Glu Glu Phe Ile Pro Leu Ala Gln Arg Leu Thr Cys Lys Phe Leu Thr
                95                  100                 105

cac aag caa ctg agc cct gag gac tct agc tcc cca gtt aaa agt gtt      448
His Lys Gln Leu Ser Pro Glu Asp Ser Ser Ser Pro Val Lys Ser Val
            110                 115                 120

ttg gat cat caa aat aat gaa ggt gca tca tgt gac tgg aaa aag ccc      496
Leu Asp His Gln Asn Asn Glu Gly Ala Ser Cys Asp Trp Lys Lys Pro
        125                 130                 135

ttt cca aag atc cct gaa gtt ccc ctc cat gat acc cca gag agg agt      544
Phe Pro Lys Ile Pro Glu Val Pro Leu His Asp Thr Pro Glu Arg Ser
    140                 145                 150

gca gca gat aac aag gac ctg atc tta gat cca tgc tgt cag ctt cca      592
Ala Ala Asp Asn Lys Asp Leu Ile Leu Asp Pro Cys Cys Gln Leu Pro
155                 160                 165                 170

gcc tac ctg tct acc tgc cct ggc cag agc agc agc ttg gca gta acc      640
Ala Tyr Leu Ser Thr Cys Pro Gly Gln Ser Ser Ser Leu Ala Val Thr
                175                 180                 185

aaa aca aat tct gac atc ctt cca ccc cag aag aaa acc aag ccg agt      688
Lys Thr Asn Ser Asp Ile Leu Pro Pro Gln Lys Lys Thr Lys Pro Ser
            190                 195                 200

cag aag gtc cag gga aga ggc tca cac gga tgc cgg cag cag aga caa      736
Gln Lys Val Gln Gly Arg Gly Ser His Gly Cys Arg Gln Gln Arg Gln
        205                 210                 215

gca agg cag aag gaa agc acc ctg aga aga cag gaa aga aag aat gca      784
Ala Arg Gln Lys Glu Ser Thr Leu Arg Arg Gln Glu Arg Lys Asn Ala
    220                 225                 230

gca ctg gtt acc agg atg aaa gcc cag agg cca gag gaa tgc tta aaa      832
Ala Leu Val Thr Arg Met Lys Ala Gln Arg Pro Glu Glu Cys Leu Lys
235                 240                 245                 250

cac atc att gta gtg ctg gat cca gtg ctc tta cag atg gaa ggt ggg      880
His Ile Ile Val Val Leu Asp Pro Val Leu Leu Gln Met Glu Gly Gly
                255                 260                 265

ggc cag ctc cta gga gca ctg cag acc atg gag tgc cgc tgt gtg att      928
Gly Gln Leu Leu Gly Ala Leu Gln Thr Met Glu Cys Arg Cys Val Ile
            270                 275                 280

gag gcg cag gct gtg cct tgc agt gtc act tgg agg aga agg gct ggg      976
Glu Ala Gln Ala Val Pro Cys Ser Val Thr Trp Arg Arg Arg Ala Gly
        285                 290                 295

ccg tct gag gac aga gag gac tgg gtg gag gag cca aca gta ctg gtg     1024
Pro Ser Glu Asp Arg Glu Asp Trp Val Glu Glu Pro Thr Val Leu Val
    300                 305                 310

ttg ctc cgg gca gag gca ttt gtg tcc atg atc gac aat gga aag cag     1072
Leu Leu Arg Ala Glu Ala Phe Val Ser Met Ile Asp Asn Gly Lys Gln
315                 320                 325                 330

gga agc ctg gac agc act atg aaa ggg aag gaa acg ctt cag ggc ttt     1120
Gly Ser Leu Asp Ser Thr Met Lys Gly Lys Glu Thr Leu Gln Gly Phe
                335                 340                 345

gta act gac atc aca gca aag aca gca ggg aaa gct ctg tca ctg gtg     1168
Val Thr Asp Ile Thr Ala Lys Thr Ala Gly Lys Ala Leu Ser Leu Val
            350                 355                 360

att gtg gat cag gag aaa tgc ttc agt gct cag aat cct cca aga aga     1216
Ile Val Asp Gln Glu Lys Cys Phe Ser Ala Gln Asn Pro Pro Arg Arg
        365                 370                 375

ggg aaa cag gga gca aat aaa cag acc aag aag cag cag cag aga caa     1264
Gly Lys Gln Gly Ala Asn Lys Gln Thr Lys Lys Gln Gln Gln Arg Gln
    380                 385                 390

cca gag gcc agc ata ggg tcc atg gta tcc agg gta gac gct gaa gag     1312
Pro Glu Ala Ser Ile Gly Ser Met Val Ser Arg Val Asp Ala Glu Glu
395                 400                 405                 410
```

```
gca ttg gtg gat ctg cag cta cac aca gaa gcc cag gct caa att gtg     1360
Ala Leu Val Asp Leu Gln Leu His Thr Glu Ala Gln Ala Gln Ile Val
                415                 420                 425

cag agc tgg aaa gag ctg gcc gac ttc aca tgc gca ttc aca aag gct     1408
Gln Ser Trp Lys Glu Leu Ala Asp Phe Thr Cys Ala Phe Thr Lys Ala
            430                 435                 440

gtg gct gag gcg ccc ttc aag aag ctc cga gat gaa act acc ttc tcc     1456
Val Ala Glu Ala Pro Phe Lys Lys Leu Arg Asp Glu Thr Thr Phe Ser
        445                 450                 455

ttc tgt ctg gag agt gac tgg gct gga ggg gtg aag gtg gac ctt gct     1504
Phe Cys Leu Glu Ser Asp Trp Ala Gly Gly Val Lys Val Asp Leu Ala
    460                 465                 470

ggc agg gga ctc gca cta gtc tgg agg aga cag att cag cag ctg aac     1552
Gly Arg Gly Leu Ala Leu Val Trp Arg Arg Gln Ile Gln Gln Leu Asn
475                 480                 485                 490

cga gtc agc ctg gaa atg gcc agt gca gtt gtg aat gcc tat ccc tcc     1600
Arg Val Ser Leu Glu Met Ala Ser Ala Val Val Asn Ala Tyr Pro Ser
                495                 500                 505

cca cag ctc ctg gta cag gct tat cag cag tgt ttt tcg gat aaa gaa     1648
Pro Gln Leu Leu Val Gln Ala Tyr Gln Gln Cys Phe Ser Asp Lys Glu
            510                 515                 520

cgc cag aat ttg ctc gca gac ata cag gtg cgc cgt ggg gaa ggt gtg     1696
Arg Gln Asn Leu Leu Ala Asp Ile Gln Val Arg Arg Gly Glu Gly Val
        525                 530                 535

aca tcc act tct cgc cgc att gga cca gaa cta tcc agg cgt atc tac     1744
Thr Ser Thr Ser Arg Arg Ile Gly Pro Glu Leu Ser Arg Arg Ile Tyr
    540                 545                 550

ctt cag atg acc act tta cag cca cat ctc tct tta gat agt gct gac     1792
Leu Gln Met Thr Thr Leu Gln Pro His Leu Ser Leu Asp Ser Ala Asp
555                 560                 565                 570

tga ttctagccct cagggatgag gatgaaaagc tggaaacttc cacttcccca          1845

acctcagagc ctgactgtaa tgaagagact ggcagcacct cctggaacac aagcctaggt   1905

gaggcccagt ctttcttggg tcttattatt tgtgaaggtc tctctgcctg tcggctgggg   1965

cagagactga aatactgcca cctacctttg gcatttaatg ttcctctcct ggcaaaaatt   2025

cactgccaca gacaaaccac ccccactcct acccagccag ccctcaaaac acaaaggaac   2085

aaagacagtc cactcagaca cttatttaat aactgtagaa atccaaaaga attagcatca   2145

aatcttgaag tcgtgagtga agctgcgggt tggcttgact gggctcagcc actgagctgc   2205

ctcaaccggc caaggaacgg gattatgatg actatgcgga cttctatatt gtcttcatct   2265

cattgtgtgt attatgtatt tagtttcaat aaagcatttg taccaatggc aaaaaaaaaa   2325

aaaaaaa                                                             2332


<210> SEQ ID NO 42
<211> LENGTH: 570
<212> TYPE: PRT
<213> ORGANISM: Homo sapiens

<400> SEQUENCE: 42

Met Ala Leu Lys Lys Ser Ser Pro Ser Leu Asp Ser Gly Asp Ser Asp
1               5                   10                  15

Ser Glu Glu Leu Pro Thr Phe Ala Phe Leu Lys Lys Glu Pro Ser Ser
            20                  25                  30

Thr Lys Arg Arg Gln Pro Glu Arg Glu Glu Lys Ile Val Val Val Asp
        35                  40                  45

Ile Ser Asp Cys Glu Ala Ser Cys Pro Pro Ala Pro Glu Leu Phe Ser
    50                  55                  60
```

```
Pro Pro Val Pro Glu Ile Ala Glu Thr Val Thr Gln Thr Gln Pro Val
65                  70                  75                  80

Arg Leu Leu Ser Ser Glu Ser Glu Asp Glu Glu Glu Phe Ile Pro Leu
                85                  90                  95

Ala Gln Arg Leu Thr Cys Lys Phe Leu Thr His Lys Gln Leu Ser Pro
            100                 105                 110

Glu Asp Ser Ser Ser Pro Val Lys Ser Val Leu Asp His Gln Asn Asn
        115                 120                 125

Glu Gly Ala Ser Cys Asp Trp Lys Lys Pro Phe Pro Lys Ile Pro Glu
    130                 135                 140

Val Pro Leu His Asp Thr Pro Glu Arg Ser Ala Ala Asp Asn Lys Asp
145                 150                 155                 160

Leu Ile Leu Asp Pro Cys Cys Gln Leu Pro Ala Tyr Leu Ser Thr Cys
                165                 170                 175

Pro Gly Gln Ser Ser Ser Leu Ala Val Thr Lys Thr Asn Ser Asp Ile
            180                 185                 190

Leu Pro Pro Gln Lys Lys Thr Lys Pro Ser Gln Lys Val Gln Gly Arg
        195                 200                 205

Gly Ser His Gly Cys Arg Gln Gln Arg Gln Ala Arg Gln Lys Glu Ser
    210                 215                 220

Thr Leu Arg Arg Gln Glu Arg Lys Asn Ala Ala Leu Val Thr Arg Met
225                 230                 235                 240

Lys Ala Gln Arg Pro Glu Glu Cys Leu Lys His Ile Ile Val Val Leu
                245                 250                 255

Asp Pro Val Leu Leu Gln Met Glu Gly Gly Gly Gln Leu Leu Gly Ala
            260                 265                 270

Leu Gln Thr Met Glu Cys Arg Cys Val Ile Glu Ala Gln Ala Val Pro
        275                 280                 285

Cys Ser Val Thr Trp Arg Arg Arg Ala Gly Pro Ser Glu Asp Arg Glu
    290                 295                 300

Asp Trp Val Glu Glu Pro Thr Val Leu Val Leu Leu Arg Ala Glu Ala
305                 310                 315                 320

Phe Val Ser Met Ile Asp Asn Gly Lys Gln Gly Ser Leu Asp Ser Thr
                325                 330                 335

Met Lys Gly Lys Glu Thr Leu Gln Gly Phe Val Thr Asp Ile Thr Ala
            340                 345                 350

Lys Thr Ala Gly Lys Ala Leu Ser Leu Val Ile Val Asp Gln Glu Lys
        355                 360                 365

Cys Phe Ser Ala Gln Asn Pro Pro Arg Arg Gly Lys Gln Gly Ala Asn
    370                 375                 380

Lys Gln Thr Lys Lys Gln Gln Gln Arg Gln Pro Glu Ala Ser Ile Gly
385                 390                 395                 400

Ser Met Val Ser Arg Val Asp Ala Glu Glu Ala Leu Val Asp Leu Gln
                405                 410                 415

Leu His Thr Glu Ala Gln Ala Gln Ile Val Gln Ser Trp Lys Glu Leu
            420                 425                 430

Ala Asp Phe Thr Cys Ala Phe Thr Lys Ala Val Ala Glu Ala Pro Phe
        435                 440                 445

Lys Lys Leu Arg Asp Glu Thr Thr Phe Ser Phe Cys Leu Glu Ser Asp
    450                 455                 460

Trp Ala Gly Gly Val Lys Val Asp Leu Ala Gly Arg Gly Leu Ala Leu
465                 470                 475                 480
```

```
Val Trp Arg Arg Gln Ile Gln Gln Leu Asn Arg Val Ser Leu Glu Met
                485                 490                 495

Ala Ser Ala Val Val Asn Ala Tyr Pro Ser Pro Gln Leu Leu Val Gln
            500                 505                 510

Ala Tyr Gln Gln Cys Phe Ser Asp Lys Glu Arg Gln Asn Leu Leu Ala
        515                 520                 525

Asp Ile Gln Val Arg Arg Gly Glu Gly Val Thr Ser Thr Ser Arg Arg
    530                 535                 540

Ile Gly Pro Glu Leu Ser Arg Arg Ile Tyr Leu Gln Met Thr Thr Leu
545                 550                 555                 560

Gln Pro His Leu Ser Leu Asp Ser Ala Asp
                565                 570


<210> SEQ ID NO 43
<211> LENGTH: 1826
<212> TYPE: DNA
<213> ORGANISM: Homo sapiens
<220> FEATURE:
<221> NAME/KEY: CDS
<222> LOCATION: (94)..(1284)
<223> OTHER INFORMATION: SPO11

<400> SEQUENCE: 43

ccgctcagaa agcgcgggaa aggcacgcag ccacgcccca agggcgcagc ctaggacagg      60

ggcttctgga gcttctggca gccgtctgcc ctc atg gcc ttt gca cct atg ggg      114
                                     Met Ala Phe Ala Pro Met Gly
                                     1               5

ccc gag gcc tcg ttc ttc gac gtt ttg gac cga cac agg gag tcc ctg      162
Pro Glu Ala Ser Phe Phe Asp Val Leu Asp Arg His Arg Glu Ser Leu
        10                  15                  20

ctg gct gcc ctg agg aga ggt ggc agg gag ccc cca act ggg gga agc      210
Leu Ala Ala Leu Arg Arg Gly Gly Arg Glu Pro Pro Thr Gly Gly Ser
    25                  30                  35

cgc ctg gcc tcc agt tct gag gtt ctt gca tct ata gaa aat att atc      258
Arg Leu Ala Ser Ser Ser Glu Val Leu Ala Ser Ile Glu Asn Ile Ile
40                  45                  50                  55

caa gac ata atc aca agc ttg gca aga aat gaa gca cct gca ttc acg      306
Gln Asp Ile Ile Thr Ser Leu Ala Arg Asn Glu Ala Pro Ala Phe Thr
                60                  65                  70

ata gac aac aga tca agc tgg gaa aac ata aag ttt gaa gat tct gtg      354
Ile Asp Asn Arg Ser Ser Trp Glu Asn Ile Lys Phe Glu Asp Ser Val
            75                  80                  85

ggt ctt cag atg gta tcc cat tgc acc acc aga aag atc aaa agt gat      402
Gly Leu Gln Met Val Ser His Cys Thr Thr Arg Lys Ile Lys Ser Asp
        90                  95                  100

tca cca aaa tca gct caa aaa ttt tct cta atc ctt aaa ata ttg tcc      450
Ser Pro Lys Ser Ala Gln Lys Phe Ser Leu Ile Leu Lys Ile Leu Ser
    105                 110                 115

atg att tat aaa tta gta cag agc aac act tat gca acc aaa agg gac      498
Met Ile Tyr Lys Leu Val Gln Ser Asn Thr Tyr Ala Thr Lys Arg Asp
120                 125                 130                 135

ata tat tac act gac agt caa ctc ttt ggt aac cag act gtc gtc gac      546
Ile Tyr Tyr Thr Asp Ser Gln Leu Phe Gly Asn Gln Thr Val Val Asp
                140                 145                 150

aat att atc aat gac att tct tgc atg tta aaa gtg tca agg agg agt      594
Asn Ile Ile Asn Asp Ile Ser Cys Met Leu Lys Val Ser Arg Arg Ser
            155                 160                 165

cta cat ata tta tct aca tca aaa ggt tta att gct ggc aac tta aga      642
Leu His Ile Leu Ser Thr Ser Lys Gly Leu Ile Ala Gly Asn Leu Arg
        170                 175                 180
```

```
tac atc gag gaa gat ggc acc aaa gtg aat tgt acc tgt ggt gca acg      690
Tyr Ile Glu Glu Asp Gly Thr Lys Val Asn Cys Thr Cys Gly Ala Thr
    185                 190                 195

gct gtt gct gtg cca tcg aat att caa gga att cgg aat tta gtt aca      738
Ala Val Ala Val Pro Ser Asn Ile Gln Gly Ile Arg Asn Leu Val Thr
200                 205                 210                 215

gat gca aag ttt gta tta att gta gaa aaa gat gca aca ttt cag cgg      786
Asp Ala Lys Phe Val Leu Ile Val Glu Lys Asp Ala Thr Phe Gln Arg
                220                 225                 230

ctc cta gat gac aac ttt tgc aac aaa ttg tct cct tgc atc atg att      834
Leu Leu Asp Asp Asn Phe Cys Asn Lys Leu Ser Pro Cys Ile Met Ile
            235                 240                 245

acg gga aag gga gtt cct gat cta aac aca aga ctt tta gtc aag aaa      882
Thr Gly Lys Gly Val Pro Asp Leu Asn Thr Arg Leu Leu Val Lys Lys
        250                 255                 260

ctg tgg gat aca ttt cat gtt cct gtt ttc act ctt gta gat gct gat      930
Leu Trp Asp Thr Phe His Val Pro Val Phe Thr Leu Val Asp Ala Asp
    265                 270                 275

cca cat ggc ata gaa ata atg tgc atc tat aag tat gga tct atg tct      978
Pro His Gly Ile Glu Ile Met Cys Ile Tyr Lys Tyr Gly Ser Met Ser
280                 285                 290                 295

atg tct ttt gaa gct cat cat ctc aca gtt cca gct att aga tgg ctt     1026
Met Ser Phe Glu Ala His His Leu Thr Val Pro Ala Ile Arg Trp Leu
                300                 305                 310

ggt ctt ctc cct tct gat ctt aaa aga tta aat gta cct aaa gat agt     1074
Gly Leu Leu Pro Ser Asp Leu Lys Arg Leu Asn Val Pro Lys Asp Ser
            315                 320                 325

ttg att cca ctg aca aaa agg gac caa atg aaa ctt gac agt atc ctg     1122
Leu Ile Pro Leu Thr Lys Arg Asp Gln Met Lys Leu Asp Ser Ile Leu
        330                 335                 340

agg aga cct tat gtt acc tgc caa cca ttt tgg aga aaa gaa atg gaa     1170
Arg Arg Pro Tyr Val Thr Cys Gln Pro Phe Trp Arg Lys Glu Met Glu
    345                 350                 355

ata atg gca gac tct aaa atg aag gca gaa att caa gct ttg act ttc     1218
Ile Met Ala Asp Ser Lys Met Lys Ala Glu Ile Gln Ala Leu Thr Phe
360                 365                 370                 375

cta tca tca gat tat ctt tcc aga gtg tac tta cct aac aaa tta aaa     1266
Leu Ser Ser Asp Tyr Leu Ser Arg Val Tyr Leu Pro Asn Lys Leu Lys
                380                 385                 390

ttt gga gga tgg ata taa aaataaatca gaagaacttc tgattgccag            1314
Phe Gly Gly Trp Ile
            395

aggcttttca ttagttttgt tttgattggc aaatactatt gtggaaagaa catatattat   1374

attcttaatt ctgtaaaagt gaaataaaat aactttccgt taattatata tttttgtcaa   1434

aacaaatgct gtactccaat tttctttgca aggccttatt cttgcctcta tagagacaga   1494

tttctgtcct atcttctaaa gcaaattata aaagaatatg ttattttgac ctttaaatta   1554

tttttgaaaa aataatattt tatacatgtc atcaaagtct acaaaatatt taccttctac   1614

gatacaacta atgttaacgc ataaagtatc ttactggtaa caaaaatcat aatgatctga   1674

atttgagatg ttgcaaatga attgtggtgt ccggtagttt cttcttacat tttcctttgc   1734

ctttatactt taggggtctt actccattaa ttcatttgtt acattagtaa aattcagtat   1794

gaataaatat ttggattgat gtaaaaaaaa aa                                 1826

<210> SEQ ID NO 44
<211> LENGTH: 396
<212> TYPE: PRT
```

<213> ORGANISM: Homo sapiens

<400> SEQUENCE: 44

```
Met Ala Phe Ala Pro Met Gly Pro Glu Ala Ser Phe Phe Asp Val Leu
1               5                   10                  15

Asp Arg His Arg Glu Ser Leu Leu Ala Ala Leu Arg Arg Gly Gly Arg
            20                  25                  30

Glu Pro Pro Thr Gly Gly Ser Arg Leu Ala Ser Ser Ser Glu Val Leu
        35                  40                  45

Ala Ser Ile Glu Asn Ile Ile Gln Asp Ile Ile Thr Ser Leu Ala Arg
    50                  55                  60

Asn Glu Ala Pro Ala Phe Thr Ile Asp Asn Arg Ser Ser Trp Glu Asn
65                  70                  75                  80

Ile Lys Phe Glu Asp Ser Val Gly Leu Gln Met Val Ser His Cys Thr
                85                  90                  95

Thr Arg Lys Ile Lys Ser Asp Ser Pro Lys Ser Ala Gln Lys Phe Ser
            100                 105                 110

Leu Ile Leu Lys Ile Leu Ser Met Ile Tyr Lys Leu Val Gln Ser Asn
        115                 120                 125

Thr Tyr Ala Thr Lys Arg Asp Ile Tyr Tyr Thr Asp Ser Gln Leu Phe
    130                 135                 140

Gly Asn Gln Thr Val Val Asp Asn Ile Ile Asn Asp Ile Ser Cys Met
145                 150                 155                 160

Leu Lys Val Ser Arg Arg Ser Leu His Ile Leu Ser Thr Ser Lys Gly
                165                 170                 175

Leu Ile Ala Gly Asn Leu Arg Tyr Ile Glu Glu Asp Gly Thr Lys Val
            180                 185                 190

Asn Cys Thr Cys Gly Ala Thr Ala Val Ala Val Pro Ser Asn Ile Gln
        195                 200                 205

Gly Ile Arg Asn Leu Val Thr Asp Ala Lys Phe Val Leu Ile Val Glu
    210                 215                 220

Lys Asp Ala Thr Phe Gln Arg Leu Leu Asp Asp Asn Phe Cys Asn Lys
225                 230                 235                 240

Leu Ser Pro Cys Ile Met Ile Thr Gly Lys Gly Val Pro Asp Leu Asn
                245                 250                 255

Thr Arg Leu Leu Val Lys Lys Leu Trp Asp Thr Phe His Val Pro Val
            260                 265                 270

Phe Thr Leu Val Asp Ala Asp Pro His Gly Ile Glu Ile Met Cys Ile
        275                 280                 285

Tyr Lys Tyr Gly Ser Met Ser Met Ser Phe Glu Ala His His Leu Thr
    290                 295                 300

Val Pro Ala Ile Arg Trp Leu Gly Leu Leu Pro Ser Asp Leu Lys Arg
305                 310                 315                 320

Leu Asn Val Pro Lys Asp Ser Leu Ile Pro Leu Thr Lys Arg Asp Gln
                325                 330                 335

Met Lys Leu Asp Ser Ile Leu Arg Arg Pro Tyr Val Thr Cys Gln Pro
            340                 345                 350

Phe Trp Arg Lys Glu Met Glu Ile Met Ala Asp Ser Lys Met Lys Ala
        355                 360                 365

Glu Ile Gln Ala Leu Thr Phe Leu Ser Ser Asp Tyr Leu Ser Arg Val
    370                 375                 380

Tyr Leu Pro Asn Lys Leu Lys Phe Gly Gly Trp Ile
385                 390                 395
```

```
<210> SEQ ID NO 45
<211> LENGTH: 4555
<212> TYPE: DNA
<213> ORGANISM: Homo sapiens
<220> FEATURE:
<221> NAME/KEY: CDS
<222> LOCATION: (119)..(4372)
<223> OTHER INFORMATION: BLM

<400> SEQUENCE: 45

aatcggaata ggcaagcttc cggcgggaag tgagccaggg cttggcgcgg cggccgtggt      60

tgcggcgcgg gaagtttgga tcctggttcc gtccgctagg agtctgcgtg cgaggatt      118

atg gct gct gtt cct caa aat aat cta cag gag caa cta gaa cgt cac      166
Met Ala Ala Val Pro Gln Asn Asn Leu Gln Glu Gln Leu Glu Arg His
1               5                   10                  15

tca gcc aga aca ctt aat aat aaa tta agt ctt tca aaa cca aaa ttt      214
Ser Ala Arg Thr Leu Asn Asn Lys Leu Ser Leu Ser Lys Pro Lys Phe
            20                  25                  30

tca ggt ttc act ttt aaa aag aaa aca tct tca gat aac aat gta tct      262
Ser Gly Phe Thr Phe Lys Lys Lys Thr Ser Ser Asp Asn Asn Val Ser
        35                  40                  45

gta act aat gtg tca gta gca aaa aca cct gta tta aga aat aaa gat      310
Val Thr Asn Val Ser Val Ala Lys Thr Pro Val Leu Arg Asn Lys Asp
    50                  55                  60

gtt aat gtt acc gaa gac ttt tcc ttc agt gaa cct cta ccc aac acc      358
Val Asn Val Thr Glu Asp Phe Ser Phe Ser Glu Pro Leu Pro Asn Thr
65                  70                  75                  80

aca aat cag caa agg gtc aag gac ttc ttt aaa aat gct cca gca gga      406
Thr Asn Gln Gln Arg Val Lys Asp Phe Phe Lys Asn Ala Pro Ala Gly
                85                  90                  95

cag gaa aca cag aga ggt gga tca aaa tca tta ttg cca gat ttc ttg      454
Gln Glu Thr Gln Arg Gly Gly Ser Lys Ser Leu Leu Pro Asp Phe Leu
            100                 105                 110

cag act ccg aag gaa gtt gta tgc act acc caa aac aca cca act gta      502
Gln Thr Pro Lys Glu Val Val Cys Thr Thr Gln Asn Thr Pro Thr Val
        115                 120                 125

aag aaa tcc cgg gat act gct ctc aag aaa tta gaa ttt agt tct tca      550
Lys Lys Ser Arg Asp Thr Ala Leu Lys Lys Leu Glu Phe Ser Ser Ser
    130                 135                 140

cca gat tct tta agt acc atc aat gat tgg gat gat atg gat gac ttt      598
Pro Asp Ser Leu Ser Thr Ile Asn Asp Trp Asp Asp Met Asp Asp Phe
145                 150                 155                 160

gat act tct gag act tca aaa tca ttt gtt aca cca ccc caa agt cac      646
Asp Thr Ser Glu Thr Ser Lys Ser Phe Val Thr Pro Pro Gln Ser His
                165                 170                 175

ttt gta aga gta agc act gct cag aaa tca aaa aag ggt aag aga aac      694
Phe Val Arg Val Ser Thr Ala Gln Lys Ser Lys Lys Gly Lys Arg Asn
            180                 185                 190

ttt ttt aaa gca cag ctt tat aca aca aac aca gta aag act gat ttg      742
Phe Phe Lys Ala Gln Leu Tyr Thr Thr Asn Thr Val Lys Thr Asp Leu
        195                 200                 205

cct cca ccc tcc tct gaa agc gag caa ata gat ttg act gag gaa cag      790
Pro Pro Pro Ser Ser Glu Ser Glu Gln Ile Asp Leu Thr Glu Glu Gln
    210                 215                 220

aag gat gac tca gaa tgg tta agc agc gat gtg att tgc atc gat gat      838
Lys Asp Asp Ser Glu Trp Leu Ser Ser Asp Val Ile Cys Ile Asp Asp
225                 230                 235                 240

ggc ccc att gct gaa gtg cat ata aat gaa gat gct cag gaa agt gac      886
Gly Pro Ile Ala Glu Val His Ile Asn Glu Asp Ala Gln Glu Ser Asp
                245                 250                 255
```

```
tct ctg aaa act cat ttg gaa gat gaa aga gat aat agc gaa aag aag      934
Ser Leu Lys Thr His Leu Glu Asp Glu Arg Asp Asn Ser Glu Lys Lys
            260                 265                 270

aag aat ttg gaa gaa gct gaa tta cat tca act gag aaa gtt cca tgt      982
Lys Asn Leu Glu Glu Ala Glu Leu His Ser Thr Glu Lys Val Pro Cys
        275                 280                 285

att gaa ttt gat gat gat gat tat gat acg gat ttt gtt cca cct tct     1030
Ile Glu Phe Asp Asp Asp Asp Tyr Asp Thr Asp Phe Val Pro Pro Ser
    290                 295                 300

cca gaa gaa att att tct gct tct tct tcc tct tca aaa tgc ctt agt     1078
Pro Glu Glu Ile Ile Ser Ala Ser Ser Ser Ser Ser Lys Cys Leu Ser
305                 310                 315                 320

acg tta aag gac ctt gac acc tct gac aga aaa gag gat gtt ctt agc     1126
Thr Leu Lys Asp Leu Asp Thr Ser Asp Arg Lys Glu Asp Val Leu Ser
                325                 330                 335

aca tca aaa gat ctt ttg tca aaa cct gag aaa atg agt atg cag gag     1174
Thr Ser Lys Asp Leu Leu Ser Lys Pro Glu Lys Met Ser Met Gln Glu
            340                 345                 350

ctg aat cca gaa acc agc aca gac tgt gac gct aga cag ata agt tta     1222
Leu Asn Pro Glu Thr Ser Thr Asp Cys Asp Ala Arg Gln Ile Ser Leu
        355                 360                 365

cag cag cag ctt att cat gtg atg gag cac atc tgt aaa tta att gat     1270
Gln Gln Gln Leu Ile His Val Met Glu His Ile Cys Lys Leu Ile Asp
    370                 375                 380

act att cct gat gat aaa ctg aaa ctt ttg gat tgt ggg aac gaa ctg     1318
Thr Ile Pro Asp Asp Lys Leu Lys Leu Leu Asp Cys Gly Asn Glu Leu
385                 390                 395                 400

ctt cag cag cgg aac ata aga agg aaa ctt cta acg gaa gta gat ttt     1366
Leu Gln Gln Arg Asn Ile Arg Arg Lys Leu Leu Thr Glu Val Asp Phe
                405                 410                 415

aat aaa agt gat gcc agt ctt ctt ggc tca ttg tgg aga tac agg cct     1414
Asn Lys Ser Asp Ala Ser Leu Leu Gly Ser Leu Trp Arg Tyr Arg Pro
            420                 425                 430

gat tca ctt gat ggc cct atg gag ggt gat tcc tgc cct aca ggg aat     1462
Asp Ser Leu Asp Gly Pro Met Glu Gly Asp Ser Cys Pro Thr Gly Asn
        435                 440                 445

tct atg aag gag tta aat ttt tca cac ctt ccc tca aat tct gtt tct     1510
Ser Met Lys Glu Leu Asn Phe Ser His Leu Pro Ser Asn Ser Val Ser
    450                 455                 460

cct ggg gac tgt tta ctg act acc acc cta gga aag aca gga ttc tct     1558
Pro Gly Asp Cys Leu Leu Thr Thr Thr Leu Gly Lys Thr Gly Phe Ser
465                 470                 475                 480

gcc acc agg aag aat ctt ttt gaa agg cct tta ttc aat acc cat tta     1606
Ala Thr Arg Lys Asn Leu Phe Glu Arg Pro Leu Phe Asn Thr His Leu
                485                 490                 495

cag aag tcc ttt gta agt agc aac tgg gct gaa aca cca aga cta gga     1654
Gln Lys Ser Phe Val Ser Ser Asn Trp Ala Glu Thr Pro Arg Leu Gly
            500                 505                 510

aaa aaa aat gaa agc tct tat ttc cca gga aat gtt ctc aca agc act     1702
Lys Lys Asn Glu Ser Ser Tyr Phe Pro Gly Asn Val Leu Thr Ser Thr
        515                 520                 525

gct gtg aaa gat cag aat aaa cat act gct tca ata aat gac tta gaa     1750
Ala Val Lys Asp Gln Asn Lys His Thr Ala Ser Ile Asn Asp Leu Glu
    530                 535                 540

aga gaa acc caa cct tcc tat gat att gat aat ttt gac ata gat gac     1798
Arg Glu Thr Gln Pro Ser Tyr Asp Ile Asp Asn Phe Asp Ile Asp Asp
545                 550                 555                 560

ttt gat gat gat gat gac tgg gaa gac ata atg cat aat tta gca gcc     1846
Phe Asp Asp Asp Asp Asp Trp Glu Asp Ile Met His Asn Leu Ala Ala
```

```
                565                 570                 575

agc aaa tct tcc aca gct gcc tat caa ccc atc aag gaa ggt cgg cca      1894
Ser Lys Ser Ser Thr Ala Ala Tyr Gln Pro Ile Lys Glu Gly Arg Pro
            580                 585                 590

att aaa tca gta tca gaa aga ctt tcc tca gcc aag aca gac tgt ctt      1942
Ile Lys Ser Val Ser Glu Arg Leu Ser Ser Ala Lys Thr Asp Cys Leu
        595                 600                 605

cca gtg tca tct act gct caa aat ata aac ttc tca gag tca att cag      1990
Pro Val Ser Ser Thr Ala Gln Asn Ile Asn Phe Ser Glu Ser Ile Gln
    610                 615                 620

aat tat act gac aag tca gca caa aat tta gca tcc aga aat ctg aaa      2038
Asn Tyr Thr Asp Lys Ser Ala Gln Asn Leu Ala Ser Arg Asn Leu Lys
625                 630                 635                 640

cat gag cgt ttc caa agt ctt agt ttt cct cat aca aag gaa atg atg      2086
His Glu Arg Phe Gln Ser Leu Ser Phe Pro His Thr Lys Glu Met Met
                645                 650                 655

aag att ttt cat aaa aaa ttt ggc ctg cat aat ttt aga act aat cag      2134
Lys Ile Phe His Lys Lys Phe Gly Leu His Asn Phe Arg Thr Asn Gln
            660                 665                 670

cta gag gcg atc aat gct gca ctg ctt ggt gaa gac tgt ttt atc ctg      2182
Leu Glu Ala Ile Asn Ala Ala Leu Leu Gly Glu Asp Cys Phe Ile Leu
        675                 680                 685

atg ccg act gga ggt ggt aag agt ttg tgt tac cag ctc cct gcc tgt      2230
Met Pro Thr Gly Gly Gly Lys Ser Leu Cys Tyr Gln Leu Pro Ala Cys
    690                 695                 700

gtt tct cct ggg gtc act gtt gtc att tct ccc ttg aga tca ctt atc      2278
Val Ser Pro Gly Val Thr Val Val Ile Ser Pro Leu Arg Ser Leu Ile
705                 710                 715                 720

gta gat caa gtc caa aag ctg act tcc ttg gat att cca gct aca tat      2326
Val Asp Gln Val Gln Lys Leu Thr Ser Leu Asp Ile Pro Ala Thr Tyr
                725                 730                 735

ctg aca ggt gat aag act gac tca gaa gct aca aat att tac ctc cag      2374
Leu Thr Gly Asp Lys Thr Asp Ser Glu Ala Thr Asn Ile Tyr Leu Gln
            740                 745                 750

tta tca aaa aaa gac cca atc ata aaa ctt cta tat gtc act cca gaa      2422
Leu Ser Lys Lys Asp Pro Ile Ile Lys Leu Leu Tyr Val Thr Pro Glu
        755                 760                 765

aag atc tgt gca agt aac aga ctc att tct act ctg gag aat ctc tat      2470
Lys Ile Cys Ala Ser Asn Arg Leu Ile Ser Thr Leu Glu Asn Leu Tyr
    770                 775                 780

gag agg aag ctc ttg gca cgt ttt gtt att gat gaa gca cat tgt gtc      2518
Glu Arg Lys Leu Leu Ala Arg Phe Val Ile Asp Glu Ala His Cys Val
785                 790                 795                 800

agt cag tgg gga cat gat ttt cgt caa gat tac aaa aga atg aat atg      2566
Ser Gln Trp Gly His Asp Phe Arg Gln Asp Tyr Lys Arg Met Asn Met
                805                 810                 815

ctt cgc cag aag ttt cct tct gtt ccg gtg atg gct ctt acg gcc aca      2614
Leu Arg Gln Lys Phe Pro Ser Val Pro Val Met Ala Leu Thr Ala Thr
            820                 825                 830

gct aat ccc agg gta cag aag gac atc ctg act cag ctg aag att ctc      2662
Ala Asn Pro Arg Val Gln Lys Asp Ile Leu Thr Gln Leu Lys Ile Leu
        835                 840                 845

aga cct cag gtg ttt agc atg agc ttt aac aga cat aat ctg aaa tac      2710
Arg Pro Gln Val Phe Ser Met Ser Phe Asn Arg His Asn Leu Lys Tyr
    850                 855                 860

tat gta tta ccg aaa aag cct aaa aag gtg gca ttt gat tgc cta gaa      2758
Tyr Val Leu Pro Lys Lys Pro Lys Lys Val Ala Phe Asp Cys Leu Glu
865                 870                 875                 880

tgg atc aga aag cac cac cca tat gat tca ggg ata att tac tgc ctc      2806
```

```
Trp Ile Arg Lys His His Pro Tyr Asp Ser Gly Ile Ile Tyr Cys Leu
                885                 890                 895

tcc agg cga gaa tgt gac acc atg gct gac acg tta cag aga gat ggg     2854
Ser Arg Arg Glu Cys Asp Thr Met Ala Asp Thr Leu Gln Arg Asp Gly
            900                 905                 910

ctc gct gct ctt gct tac cat gct ggc ctc agt gat tct gcc aga gat     2902
Leu Ala Ala Leu Ala Tyr His Ala Gly Leu Ser Asp Ser Ala Arg Asp
        915                 920                 925

gaa gtg cag cag aag tgg att aat cag gat ggc tgt cag gtt atc tgt     2950
Glu Val Gln Gln Lys Trp Ile Asn Gln Asp Gly Cys Gln Val Ile Cys
    930                 935                 940

gct aca att gca ttt gga atg ggg att gac aaa ccg gac gtg cga ttt     2998
Ala Thr Ile Ala Phe Gly Met Gly Ile Asp Lys Pro Asp Val Arg Phe
945                 950                 955                 960

gtg att cat gca tct ctc cct aaa tct gtg gag ggt tac tac caa gaa     3046
Val Ile His Ala Ser Leu Pro Lys Ser Val Glu Gly Tyr Tyr Gln Glu
                965                 970                 975

tct ggc aga gct gga aga gat ggg gaa ata tct cac tgc ctg ctt ttc     3094
Ser Gly Arg Ala Gly Arg Asp Gly Glu Ile Ser His Cys Leu Leu Phe
            980                 985                 990

tat acc tat cat gat gtg acc aga  ctg aaa aga ctt ata  atg atg gaa   3142
Tyr Thr Tyr His Asp Val Thr Arg  Leu Lys Arg Leu Ile  Met Met Glu
        995                 1000                 1005

aaa gat  gga aac cat cat aca  aga gaa act cac ttc  aat aat ttg      3187
Lys Asp  Gly Asn His His Thr  Arg Glu Thr His Phe  Asn Asn Leu
    1010                 1015                 1020

tat agc  atg gta cat tac tgt  gaa aat ata acg gaa  tgc agg aga      3232
Tyr Ser  Met Val His Tyr Cys  Glu Asn Ile Thr Glu  Cys Arg Arg
    1025                 1030                 1035

ata cag  ctt ttg gcc tac ttt  ggt gaa aat gga ttt  aat cct gat      3277
Ile Gln  Leu Leu Ala Tyr Phe  Gly Glu Asn Gly Phe  Asn Pro Asp
    1040                 1045                 1050

ttt tgt  aag aaa cac cca gat  gtt tct tgt gat aat  tgc tgt aaa      3322
Phe Cys  Lys Lys His Pro Asp  Val Ser Cys Asp Asn  Cys Cys Lys
    1055                 1060                 1065

aca aag  gat tat aaa aca aga  gat gtg act gac gat  gtg aaa agt      3367
Thr Lys  Asp Tyr Lys Thr Arg  Asp Val Thr Asp Asp  Val Lys Ser
    1070                 1075                 1080

att gta  aga ttt gtt caa gaa  cat agt tca tca caa  gga atg aga      3412
Ile Val  Arg Phe Val Gln Glu  His Ser Ser Ser Gln  Gly Met Arg
    1085                 1090                 1095

aat ata  aaa cat gta ggt cct  tct gga aga ttt act  atg aat atg      3457
Asn Ile  Lys His Val Gly Pro  Ser Gly Arg Phe Thr  Met Asn Met
    1100                 1105                 1110

ctg gtc  gac att ttc ttg ggg  agt aag agt gca aaa  atc cag tca      3502
Leu Val  Asp Ile Phe Leu Gly  Ser Lys Ser Ala Lys  Ile Gln Ser
    1115                 1120                 1125

ggt ata  ttt gga aaa gga tct  gct tat tca cga cac  aat gcc gaa      3547
Gly Ile  Phe Gly Lys Gly Ser  Ala Tyr Ser Arg His  Asn Ala Glu
    1130                 1135                 1140

aga ctt  ttt aaa aag ctg ata  ctt gac aag att ttg  gat gaa gac      3592
Arg Leu  Phe Lys Lys Leu Ile  Leu Asp Lys Ile Leu  Asp Glu Asp
    1145                 1150                 1155

tta tat  atc aat gcc aat gac  cag gcg atc gct tat  gtg atg ctc      3637
Leu Tyr  Ile Asn Ala Asn Asp  Gln Ala Ile Ala Tyr  Val Met Leu
    1160                 1165                 1170

gga aat  aaa gcc caa act gta  cta aat ggc aat tta  aag gta gac      3682
Gly Asn  Lys Ala Gln Thr Val  Leu Asn Gly Asn Leu  Lys Val Asp
    1175                 1180                 1185
```

```
ttt atg  gaa aca gaa aat tcc  agc agt gtg aaa aaa  caa aaa gcg      3727
Phe Met  Glu Thr Glu Asn Ser  Ser Ser Val Lys Lys  Gln Lys Ala
    1190                 1195                 1200

tta gta  gca aaa gtg tct cag  agg gaa gag atg gtt  aaa aaa tgt      3772
Leu Val  Ala Lys Val Ser Gln  Arg Glu Glu Met Val  Lys Lys Cys
    1205                 1210                 1215

ctt gga  gaa ctt aca gaa gtc  tgc aaa tct ctg ggg  aaa gtt ttt      3817
Leu Gly  Glu Leu Thr Glu Val  Cys Lys Ser Leu Gly  Lys Val Phe
    1220                 1225                 1230

ggt gtc  cat tac ttc aat att  ttt aat acc gtc act  ctc aag aag      3862
Gly Val  His Tyr Phe Asn Ile  Phe Asn Thr Val Thr  Leu Lys Lys
    1235                 1240                 1245

ctt gca  gaa tct tta tct tct  gat cct gag gtt ttg  ctt caa att      3907
Leu Ala  Glu Ser Leu Ser Ser  Asp Pro Glu Val Leu  Leu Gln Ile
    1250                 1255                 1260

gat ggt  gtt act gaa gac aaa  ctg gaa aaa tat ggt  gcg gaa gtg      3952
Asp Gly  Val Thr Glu Asp Lys  Leu Glu Lys Tyr Gly  Ala Glu Val
    1265                 1270                 1275

att tca  gta tta cag aaa tac  tct gaa tgg aca tcg  cca gct gaa      3997
Ile Ser  Val Leu Gln Lys Tyr  Ser Glu Trp Thr Ser  Pro Ala Glu
    1280                 1285                 1290

gac agt  tcc cca ggg ata agc  ctg tcc agc agc aga  ggc ccc gga      4042
Asp Ser  Ser Pro Gly Ile Ser  Leu Ser Ser Ser Arg  Gly Pro Gly
    1295                 1300                 1305

aga agt  gcc gct gag gag ctc  gac gag gaa ata ccc  gta tct tcc      4087
Arg Ser  Ala Ala Glu Glu Leu  Asp Glu Glu Ile Pro  Val Ser Ser
    1310                 1315                 1320

cac tac  ttt gca agt aaa acc  aga aat gaa agg aag  agg aaa aag      4132
His Tyr  Phe Ala Ser Lys Thr  Arg Asn Glu Arg Lys  Arg Lys Lys
    1325                 1330                 1335

atg cca  gcc tcc caa agg tct  aag agg aga aaa act  gct tcc agt      4177
Met Pro  Ala Ser Gln Arg Ser  Lys Arg Arg Lys Thr  Ala Ser Ser
    1340                 1345                 1350

ggt tcc  aag gca aag ggg ggg  tct gcc aca tgt aga  aag ata tct      4222
Gly Ser  Lys Ala Lys Gly Gly  Ser Ala Thr Cys Arg  Lys Ile Ser
    1355                 1360                 1365

tcc aaa  acg aaa tcc tcc agc  atc att gga tcc agt  tca gcc tca      4267
Ser Lys  Thr Lys Ser Ser Ser  Ile Ile Gly Ser Ser  Ser Ala Ser
    1370                 1375                 1380

cat act  tct caa gcg aca tca  gga gcc aat agc aaa  ttg ggg att      4312
His Thr  Ser Gln Ala Thr Ser  Gly Ala Asn Ser Lys  Leu Gly Ile
    1385                 1390                 1395

atg gct  cca ccg aag cct ata  aat aga ccg ttt ctt  aag cct tca      4357
Met Ala  Pro Pro Lys Pro Ile  Asn Arg Pro Phe Leu  Lys Pro Ser
    1400                 1405                 1410

tat gca  ttc tca taa caaccgaatc tcaatgtaca tagaccctct ttcttgtttg    4412
Tyr Ala  Phe Ser
    1415

tcagcatctg accatctgtg actataaagc tgttattctt gttataccat ttgaagtttt   4472

tactcgtctc tattaatatt taaataaatg ctggggggtg atagttcttc tttttaaaat   4532

aaacattttc ttttgaataa gca                                           4555
```

<210> SEQ ID NO 46
<211> LENGTH: 1417
<212> TYPE: PRT
<213> ORGANISM: Homo sapiens

<400> SEQUENCE: 46

```
Met Ala Ala Val Pro Gln Asn Asn Leu Gln Glu Gln Leu Glu Arg His
```

```
1               5                   10                  15

Ser Ala Arg Thr Leu Asn Asn Lys Leu Ser Leu Ser Lys Pro Lys Phe
            20                  25                  30

Ser Gly Phe Thr Phe Lys Lys Lys Thr Ser Ser Asp Asn Asn Val Ser
        35                  40                  45

Val Thr Asn Val Ser Val Ala Lys Thr Pro Val Leu Arg Asn Lys Asp
    50                  55                  60

Val Asn Val Thr Glu Asp Phe Ser Phe Ser Glu Pro Leu Pro Asn Thr
65                  70                  75                  80

Thr Asn Gln Gln Arg Val Lys Asp Phe Phe Lys Asn Ala Pro Ala Gly
                85                  90                  95

Gln Glu Thr Gln Arg Gly Gly Ser Lys Ser Leu Leu Pro Asp Phe Leu
            100                 105                 110

Gln Thr Pro Lys Glu Val Val Cys Thr Thr Gln Asn Thr Pro Thr Val
        115                 120                 125

Lys Lys Ser Arg Asp Thr Ala Leu Lys Lys Leu Glu Phe Ser Ser Ser
    130                 135                 140

Pro Asp Ser Leu Ser Thr Ile Asn Asp Trp Asp Asp Met Asp Asp Phe
145                 150                 155                 160

Asp Thr Ser Glu Thr Ser Lys Ser Phe Val Thr Pro Pro Gln Ser His
                165                 170                 175

Phe Val Arg Val Ser Thr Ala Gln Lys Ser Lys Lys Gly Lys Arg Asn
            180                 185                 190

Phe Phe Lys Ala Gln Leu Tyr Thr Thr Asn Thr Val Lys Thr Asp Leu
        195                 200                 205

Pro Pro Pro Ser Ser Glu Ser Glu Gln Ile Asp Leu Thr Glu Glu Gln
    210                 215                 220

Lys Asp Asp Ser Glu Trp Leu Ser Ser Asp Val Ile Cys Ile Asp Asp
225                 230                 235                 240

Gly Pro Ile Ala Glu Val His Ile Asn Glu Asp Ala Gln Glu Ser Asp
                245                 250                 255

Ser Leu Lys Thr His Leu Glu Asp Glu Arg Asp Asn Ser Glu Lys Lys
            260                 265                 270

Lys Asn Leu Glu Glu Ala Glu Leu His Ser Thr Glu Lys Val Pro Cys
        275                 280                 285

Ile Glu Phe Asp Asp Asp Asp Tyr Asp Thr Asp Phe Val Pro Pro Ser
    290                 295                 300

Pro Glu Glu Ile Ile Ser Ala Ser Ser Ser Ser Ser Lys Cys Leu Ser
305                 310                 315                 320

Thr Leu Lys Asp Leu Asp Thr Ser Asp Arg Lys Glu Asp Val Leu Ser
                325                 330                 335

Thr Ser Lys Asp Leu Leu Ser Lys Pro Glu Lys Met Ser Met Gln Glu
            340                 345                 350

Leu Asn Pro Glu Thr Ser Thr Asp Cys Asp Ala Arg Gln Ile Ser Leu
        355                 360                 365

Gln Gln Gln Leu Ile His Val Met Glu His Ile Cys Lys Leu Ile Asp
    370                 375                 380

Thr Ile Pro Asp Asp Lys Leu Lys Leu Leu Asp Cys Gly Asn Glu Leu
385                 390                 395                 400

Leu Gln Gln Arg Asn Ile Arg Arg Lys Leu Leu Thr Glu Val Asp Phe
                405                 410                 415

Asn Lys Ser Asp Ala Ser Leu Leu Gly Ser Leu Trp Arg Tyr Arg Pro
            420                 425                 430
```

```
Asp Ser Leu Asp Gly Pro Met Glu Gly Asp Ser Cys Pro Thr Gly Asn
        435                 440                 445

Ser Met Lys Glu Leu Asn Phe Ser His Leu Pro Ser Asn Ser Val Ser
    450                 455                 460

Pro Gly Asp Cys Leu Leu Thr Thr Thr Leu Gly Lys Thr Gly Phe Ser
465                 470                 475                 480

Ala Thr Arg Lys Asn Leu Phe Glu Arg Pro Leu Phe Asn Thr His Leu
                485                 490                 495

Gln Lys Ser Phe Val Ser Ser Asn Trp Ala Glu Thr Pro Arg Leu Gly
            500                 505                 510

Lys Lys Asn Glu Ser Ser Tyr Phe Pro Gly Asn Val Leu Thr Ser Thr
        515                 520                 525

Ala Val Lys Asp Gln Asn Lys His Thr Ala Ser Ile Asn Asp Leu Glu
    530                 535                 540

Arg Glu Thr Gln Pro Ser Tyr Asp Ile Asp Asn Phe Asp Ile Asp Asp
545                 550                 555                 560

Phe Asp Asp Asp Asp Asp Trp Glu Asp Ile Met His Asn Leu Ala Ala
                565                 570                 575

Ser Lys Ser Ser Thr Ala Ala Tyr Gln Pro Ile Lys Glu Gly Arg Pro
            580                 585                 590

Ile Lys Ser Val Ser Glu Arg Leu Ser Ser Ala Lys Thr Asp Cys Leu
        595                 600                 605

Pro Val Ser Ser Thr Ala Gln Asn Ile Asn Phe Ser Glu Ser Ile Gln
    610                 615                 620

Asn Tyr Thr Asp Lys Ser Ala Gln Asn Leu Ala Ser Arg Asn Leu Lys
625                 630                 635                 640

His Glu Arg Phe Gln Ser Leu Ser Phe Pro His Thr Lys Glu Met Met
                645                 650                 655

Lys Ile Phe His Lys Lys Phe Gly Leu His Asn Phe Arg Thr Asn Gln
            660                 665                 670

Leu Glu Ala Ile Asn Ala Ala Leu Leu Gly Glu Asp Cys Phe Ile Leu
        675                 680                 685

Met Pro Thr Gly Gly Gly Lys Ser Leu Cys Tyr Gln Leu Pro Ala Cys
    690                 695                 700

Val Ser Pro Gly Val Thr Val Val Ile Ser Pro Leu Arg Ser Leu Ile
705                 710                 715                 720

Val Asp Gln Val Gln Lys Leu Thr Ser Leu Asp Ile Pro Ala Thr Tyr
                725                 730                 735

Leu Thr Gly Asp Lys Thr Asp Ser Glu Ala Thr Asn Ile Tyr Leu Gln
            740                 745                 750

Leu Ser Lys Lys Asp Pro Ile Ile Lys Leu Leu Tyr Val Thr Pro Glu
        755                 760                 765

Lys Ile Cys Ala Ser Asn Arg Leu Ile Ser Thr Leu Glu Asn Leu Tyr
    770                 775                 780

Glu Arg Lys Leu Leu Ala Arg Phe Val Ile Asp Glu Ala His Cys Val
785                 790                 795                 800

Ser Gln Trp Gly His Asp Phe Arg Gln Asp Tyr Lys Arg Met Asn Met
                805                 810                 815

Leu Arg Gln Lys Phe Pro Ser Val Pro Val Met Ala Leu Thr Ala Thr
            820                 825                 830

Ala Asn Pro Arg Val Gln Lys Asp Ile Leu Thr Gln Leu Lys Ile Leu
        835                 840                 845
```

```
Arg Pro Gln Val Phe Ser Met Ser Phe Asn Arg His Asn Leu Lys Tyr
    850                 855                 860

Tyr Val Leu Pro Lys Lys Pro Lys Lys Val Ala Phe Asp Cys Leu Glu
865                 870                 875                 880

Trp Ile Arg Lys His His Pro Tyr Asp Ser Gly Ile Ile Tyr Cys Leu
                885                 890                 895

Ser Arg Arg Glu Cys Asp Thr Met Ala Asp Thr Leu Gln Arg Asp Gly
            900                 905                 910

Leu Ala Ala Leu Ala Tyr His Ala Gly Leu Ser Asp Ser Ala Arg Asp
        915                 920                 925

Glu Val Gln Gln Lys Trp Ile Asn Gln Asp Gly Cys Gln Val Ile Cys
    930                 935                 940

Ala Thr Ile Ala Phe Gly Met Gly Ile Asp Lys Pro Asp Val Arg Phe
945                 950                 955                 960

Val Ile His Ala Ser Leu Pro Lys Ser Val Glu Gly Tyr Tyr Gln Glu
                965                 970                 975

Ser Gly Arg Ala Gly Arg Asp Gly Glu Ile Ser His Cys Leu Leu Phe
            980                 985                 990

Tyr Thr Tyr His Asp Val Thr Arg  Leu Lys Arg Leu Ile  Met Met Glu
        995                 1000                1005

Lys Asp  Gly Asn His His Thr  Arg Glu Thr His Phe  Asn Asn Leu
    1010                 1015                1020

Tyr Ser  Met Val His Tyr Cys  Glu Asn Ile Thr Glu  Cys Arg Arg
    1025                 1030                1035

Ile Gln  Leu Leu Ala Tyr Phe  Gly Glu Asn Gly Phe  Asn Pro Asp
    1040                 1045                1050

Phe Cys  Lys Lys His Pro Asp  Val Ser Cys Asp Asn  Cys Cys Lys
    1055                 1060                1065

Thr Lys  Asp Tyr Lys Thr Arg  Asp Val Thr Asp Asp  Val Lys Ser
    1070                 1075                1080

Ile Val  Arg Phe Val Gln Glu  His Ser Ser Ser Gln  Gly Met Arg
    1085                 1090                1095

Asn Ile  Lys His Val Gly Pro  Ser Gly Arg Phe Thr  Met Asn Met
    1100                 1105                1110

Leu Val  Asp Ile Phe Leu Gly  Ser Lys Ser Ala Lys  Ile Gln Ser
    1115                 1120                1125

Gly Ile  Phe Gly Lys Gly Ser  Ala Tyr Ser Arg His  Asn Ala Glu
    1130                 1135                1140

Arg Leu  Phe Lys Lys Leu Ile  Leu Asp Lys Ile Leu  Asp Glu Asp
    1145                 1150                1155

Leu Tyr  Ile Asn Ala Asn Asp  Gln Ala Ile Ala Tyr  Val Met Leu
    1160                 1165                1170

Gly Asn  Lys Ala Gln Thr Val  Leu Asn Gly Asn Leu  Lys Val Asp
    1175                 1180                1185

Phe Met  Glu Thr Glu Asn Ser  Ser Ser Val Lys Lys  Gln Lys Ala
    1190                 1195                1200

Leu Val  Ala Lys Val Ser Gln  Arg Glu Glu Met Val  Lys Lys Cys
    1205                 1210                1215

Leu Gly  Glu Leu Thr Glu Val  Cys Lys Ser Leu Gly  Lys Val Phe
    1220                 1225                1230

Gly Val  His Tyr Phe Asn Ile  Phe Asn Thr Val Thr  Leu Lys Lys
    1235                 1240                1245

Leu Ala  Glu Ser Leu Ser Ser  Asp Pro Glu Val Leu  Leu Gln Ile
```

```
    1250                1255                1260

Asp Gly  Val Thr Glu Asp Lys  Leu Glu Lys Tyr Gly  Ala Glu Val
    1265                1270                1275

Ile Ser  Val Leu Gln Lys Tyr  Ser Glu Trp Thr Ser  Pro Ala Glu
    1280                1285                1290

Asp Ser  Ser Pro Gly Ile Ser  Leu Ser Ser Ser Arg  Gly Pro Gly
    1295                1300                1305

Arg Ser  Ala Ala Glu Glu Leu  Asp Glu Glu Ile Pro  Val Ser Ser
    1310                1315                1320

His Tyr  Phe Ala Ser Lys Thr  Arg Asn Glu Arg Lys  Arg Lys Lys
    1325                1330                1335

Met Pro  Ala Ser Gln Arg Ser  Lys Arg Arg Lys Thr  Ala Ser Ser
    1340                1345                1350

Gly Ser  Lys Ala Lys Gly Gly  Ser Ala Thr Cys Arg  Lys Ile Ser
    1355                1360                1365

Ser Lys  Thr Lys Ser Ser Ser  Ile Ile Gly Ser Ser  Ser Ala Ser
    1370                1375                1380

His Thr  Ser Gln Ala Thr Ser  Gly Ala Asn Ser Lys  Leu Gly Ile
    1385                1390                1395

Met Ala  Pro Pro Lys Pro Ile  Asn Arg Pro Phe Leu  Lys Pro Ser
    1400                1405                1410

Tyr Ala  Phe Ser
    1415
```

<210> SEQ ID NO 47
<211> LENGTH: 10636
<212> TYPE: DNA
<213> ORGANISM: Homo sapiens
<220> FEATURE:
<221> NAME/KEY: CDS
<222> LOCATION: (972)..(3419)
<223> OTHER INFORMATION: ATXN1

<400> SEQUENCE: 47

```
gaggagagag cagagtatac cgcagacatc atttctacta cagtggcgga gccgtacagg      60

acctgtttca ctgcaggggg atccaaaaca agccccgtgg agcagcagcc agagcaacag     120

cagccgcaag acattgtttc tctccctctg ccccccttc  cccacgcaac cccagatcca     180

tttacacttt acagttttac ctcacaaaaa ctactacaag caccaagctc cctgatggaa     240

aggagcatcg tgcatcaagt caccagggtg gtccattcaa gctgcagatt tgtttgtcat     300

ccttgtacag caatctcctc ctccactgcc actacaggga agtgcatcac atgtcagcat     360

actggagcat agtgaaagag tctattttga agcttcaaac ttagtgctgc tgcagaccag     420

gaacaagaga gaaagagtgg atttcagcct gcacggatgg tcttgaaaca caaatggttt     480

ttggtctagg cgttttacac tgagattctc cactgccacc ctttctactc aagcaaaatc     540

ttcgtgaaaa gatctgctgc aaggaactga tagcttatgg ttctccattg tgatgaaagc     600

acatggtaca gttttccaaa gaaattagac cattttcttc gtgagaaaga aatcgacgtg     660

ctgttttcat agggtatttc tcacttctct gtgaaaggaa gaaagaacac gcctgagccc     720

aagagccctc aggagccctc cagagcctgt gggaagtctc catggtgaag tataggctga     780

ggctacctgt gaacagtacg cagtgaatgt tcatccagag ctgctgttgg cggattgtac     840

ccacggggag atgattcctc atgaagagcc tggatcccct acagaaatca aatgtgactt     900

tccgtttatc agactaaaat cagagccatc cagacagtga aacagtcacc gtggaggggg     960
```

```
gacggcgaaa a atg aaa tcc aac caa gag cgg agc aac gaa tgc ctg cct      1010
             Met Lys Ser Asn Gln Glu Arg Ser Asn Glu Cys Leu Pro
             1               5                   10

ccc aag aag cgc gag atc ccc gcc acc agc cgg tcc tcc gag gag aag       1058
Pro Lys Lys Arg Glu Ile Pro Ala Thr Ser Arg Ser Ser Glu Glu Lys
    15                  20                  25

gcc cct acc ctg ccc agc gac aac cac cgg gtg gag ggc aca gca tgg       1106
Ala Pro Thr Leu Pro Ser Asp Asn His Arg Val Glu Gly Thr Ala Trp
30                  35                  40                  45

ctc ccg ggc aac cct ggt ggc cgg ggc cac ggg ggc ggg agg cat ggg       1154
Leu Pro Gly Asn Pro Gly Gly Arg Gly His Gly Gly Gly Arg His Gly
                50                  55                  60

ccg gca ggg acc tcg gtg gag ctt ggt tta caa cag gga ata ggt tta       1202
Pro Ala Gly Thr Ser Val Glu Leu Gly Leu Gln Gln Gly Ile Gly Leu
            65                  70                  75

cac aaa gca ttg tcc aca ggg ctg gac tac tcc ccg ccc agc gct ccc       1250
His Lys Ala Leu Ser Thr Gly Leu Asp Tyr Ser Pro Pro Ser Ala Pro
        80                  85                  90

agg tct gtc ccc gtg gcc acc acg ctg cct gcc gcg tac gcc acc ccg       1298
Arg Ser Val Pro Val Ala Thr Thr Leu Pro Ala Ala Tyr Ala Thr Pro
    95                  100                 105

cag cca ggg acc ccg gtg tcc ccc gtg cag tac gct cac ctg ccg cac       1346
Gln Pro Gly Thr Pro Val Ser Pro Val Gln Tyr Ala His Leu Pro His
110                 115                 120                 125

acc ttc cag ttc att ggg tcc tcc caa tac agt gga acc tat gcc agc       1394
Thr Phe Gln Phe Ile Gly Ser Ser Gln Tyr Ser Gly Thr Tyr Ala Ser
                130                 135                 140

ttc atc cca tca cag ctg atc ccc cca acc gcc aac ccc gtc acc agt       1442
Phe Ile Pro Ser Gln Leu Ile Pro Pro Thr Ala Asn Pro Val Thr Ser
            145                 150                 155

gca gtg gcc tcg gcc gca ggg gcc acc act cca tcc cag cgc tcc cag       1490
Ala Val Ala Ser Ala Ala Gly Ala Thr Thr Pro Ser Gln Arg Ser Gln
        160                 165                 170

ctg gag gcc tat tcc act ctg ctg gcc aac atg ggc agt ctg agc cag       1538
Leu Glu Ala Tyr Ser Thr Leu Leu Ala Asn Met Gly Ser Leu Ser Gln
    175                 180                 185

acg ccg gga cac aag gct gag cag cag cag cag cag cag cag cag cag       1586
Thr Pro Gly His Lys Ala Glu Gln Gln Gln Gln Gln Gln Gln Gln Gln
190                 195                 200                 205

cag cag cag cat cag cat cag cag cag cag cag cag cag cag cag cag       1634
Gln Gln Gln His Gln His Gln Gln Gln Gln Gln Gln Gln Gln Gln Gln
                210                 215                 220

cag cag cag cag cac ctc agc agg gct ccg ggg ctc atc acc ccg ggg       1682
Gln Gln Gln Gln His Leu Ser Arg Ala Pro Gly Leu Ile Thr Pro Gly
            225                 230                 235

tcc ccc cca cca gcc cag cag aac cag tac gtc cac att tcc agt tct       1730
Ser Pro Pro Pro Ala Gln Gln Asn Gln Tyr Val His Ile Ser Ser Ser
        240                 245                 250

ccg cag aac acc ggc cgc acc gcc tct cct ccg gcc atc ccc gtc cac       1778
Pro Gln Asn Thr Gly Arg Thr Ala Ser Pro Pro Ala Ile Pro Val His
    255                 260                 265

ctc cac ccc cac cag acg atg atc cca cac acg ctc acc ctg ggg ccc       1826
Leu His Pro His Gln Thr Met Ile Pro His Thr Leu Thr Leu Gly Pro
270                 275                 280                 285

ccc tcc cag gtc gtc atg caa tac gcc gac tcc ggc agc cac ttt gtc       1874
Pro Ser Gln Val Val Met Gln Tyr Ala Asp Ser Gly Ser His Phe Val
                290                 295                 300

cct cgg gag gcc acc aag aaa gct gag agc agc cgg ctg cag cag gcc       1922
Pro Arg Glu Ala Thr Lys Lys Ala Glu Ser Ser Arg Leu Gln Gln Ala
            305                 310                 315
```

```
atc cag gcc aag gag gtc ctg aac ggt gag atg gag aag agc cgg cgg      1970
Ile Gln Ala Lys Glu Val Leu Asn Gly Glu Met Glu Lys Ser Arg Arg
        320                 325                 330

tac ggg gcc ccg tcc tca gcc gac ctg ggc ctg ggc aag gca ggc ggc      2018
Tyr Gly Ala Pro Ser Ser Ala Asp Leu Gly Leu Gly Lys Ala Gly Gly
    335                 340                 345

aag tcg gtt cct cac ccg tac gag tcc agg cac gtg gtg gtc cac ccg      2066
Lys Ser Val Pro His Pro Tyr Glu Ser Arg His Val Val Val His Pro
350                 355                 360                 365

agc ccc tca gac tac agc agt cgt gat cct tcg ggg gtc cgg gcc tct      2114
Ser Pro Ser Asp Tyr Ser Ser Arg Asp Pro Ser Gly Val Arg Ala Ser
                370                 375                 380

gtg atg gtc ctg ccc aac agc aac acg ccc gca gct gac ctg gag gtg      2162
Val Met Val Leu Pro Asn Ser Asn Thr Pro Ala Ala Asp Leu Glu Val
            385                 390                 395

caa cag gcc act cat cgt gaa gcc tcc cct tct acc ctc aac gac aaa      2210
Gln Gln Ala Thr His Arg Glu Ala Ser Pro Ser Thr Leu Asn Asp Lys
        400                 405                 410

agt ggc ctg cat tta ggg aag cct ggc cac cgg tcc tac gcg ctc tca      2258
Ser Gly Leu His Leu Gly Lys Pro Gly His Arg Ser Tyr Ala Leu Ser
    415                 420                 425

ccc cac acg gtc att cag acc aca cac agt gct tca gag cca ctc ccg      2306
Pro His Thr Val Ile Gln Thr Thr His Ser Ala Ser Glu Pro Leu Pro
430                 435                 440                 445

gtg gga ctg cca gcc acg gcc ttc tac gca ggg act caa ccc cct gtc      2354
Val Gly Leu Pro Ala Thr Ala Phe Tyr Ala Gly Thr Gln Pro Pro Val
                450                 455                 460

atc ggc tac ctg agc ggc cag cag caa gca atc acc tac gcc ggc agc      2402
Ile Gly Tyr Leu Ser Gly Gln Gln Gln Ala Ile Thr Tyr Ala Gly Ser
            465                 470                 475

ctg ccc cag cac ctg gtg atc ccc ggc aca cag ccc ctg ctc atc ccg      2450
Leu Pro Gln His Leu Val Ile Pro Gly Thr Gln Pro Leu Leu Ile Pro
        480                 485                 490

gtc ggc agc act gac atg gaa gcg tcg ggg gca gcc ccg gcc ata gtc      2498
Val Gly Ser Thr Asp Met Glu Ala Ser Gly Ala Ala Pro Ala Ile Val
    495                 500                 505

acg tca tcc ccc cag ttt gct gca gtg cct cac acg ttc gtc acc acc      2546
Thr Ser Ser Pro Gln Phe Ala Ala Val Pro His Thr Phe Val Thr Thr
510                 515                 520                 525

gcc ctt ccc aag agc gag aac ttc aac cct gag gcc ctg gtc acc cag      2594
Ala Leu Pro Lys Ser Glu Asn Phe Asn Pro Glu Ala Leu Val Thr Gln
                530                 535                 540

gcc gcc tac cca gcc atg gtg cag gcc cag atc cac ctg cct gtg gtg      2642
Ala Ala Tyr Pro Ala Met Val Gln Ala Gln Ile His Leu Pro Val Val
            545                 550                 555

cag tcc gtg gcc tcc ccg gcg gcg gct ccc cct acg ctg cct ccc tac      2690
Gln Ser Val Ala Ser Pro Ala Ala Ala Pro Pro Thr Leu Pro Pro Tyr
        560                 565                 570

ttc atg aaa ggc tcc atc atc cag ttg gcc aac ggg gag cta aag aag      2738
Phe Met Lys Gly Ser Ile Ile Gln Leu Ala Asn Gly Glu Leu Lys Lys
    575                 580                 585

gtg gaa gac tta aaa aca gaa gat ttc atc cag agt gca gag ata agc      2786
Val Glu Asp Leu Lys Thr Glu Asp Phe Ile Gln Ser Ala Glu Ile Ser
590                 595                 600                 605

aac gac ctg aag atc gac tcc agc acc gta gag agg att gaa gac agc      2834
Asn Asp Leu Lys Ile Asp Ser Ser Thr Val Glu Arg Ile Glu Asp Ser
                610                 615                 620

cat agc ccg ggc gtg gcc gtg ata cag ttc gcc gtc ggg gag cac cga      2882
His Ser Pro Gly Val Ala Val Ile Gln Phe Ala Val Gly Glu His Arg
```

```
            625                 630                 635

gcc cag gtc agc gtt gaa gtt ttg gta gag tat cct ttt ttt gtg ttt     2930
Ala Gln Val Ser Val Glu Val Leu Val Glu Tyr Pro Phe Phe Val Phe
        640                 645                 650

gga cag ggc tgg tca tcc tgc tgt ccg gag aga acc agc cag ctc ttt     2978
Gly Gln Gly Trp Ser Ser Cys Cys Pro Glu Arg Thr Ser Gln Leu Phe
    655                 660                 665

gat ttg ccg tgt tcc aaa ctc tca gtt ggg gat gtc tgc atc tcg ctt     3026
Asp Leu Pro Cys Ser Lys Leu Ser Val Gly Asp Val Cys Ile Ser Leu
670                 675                 680                 685

acc ctc aag aac ctg aag aac ggc tct gtt aaa aag ggc cag ccc gtg     3074
Thr Leu Lys Asn Leu Lys Asn Gly Ser Val Lys Lys Gly Gln Pro Val
                690                 695                 700

gat ccc gcc agc gtc ctg ctg aag cac tca aag gcc gac ggc ctg gcg     3122
Asp Pro Ala Ser Val Leu Leu Lys His Ser Lys Ala Asp Gly Leu Ala
            705                 710                 715

ggc agc aga cac agg tat gcc gag cag gaa aac gga atc aac cag ggg     3170
Gly Ser Arg His Arg Tyr Ala Glu Gln Glu Asn Gly Ile Asn Gln Gly
        720                 725                 730

agt gcc cag atg ctc tct gag aat ggc gaa ctg aag ttt cca gag aaa     3218
Ser Ala Gln Met Leu Ser Glu Asn Gly Glu Leu Lys Phe Pro Glu Lys
    735                 740                 745

atg gga ttg cct gca gcg ccc ttc ctc acc aaa ata gaa ccc agc aag     3266
Met Gly Leu Pro Ala Ala Pro Phe Leu Thr Lys Ile Glu Pro Ser Lys
750                 755                 760                 765

ccc gcg gca acg agg aag agg agg tgg tcg gcg cca gag agc cgc aaa     3314
Pro Ala Ala Thr Arg Lys Arg Arg Trp Ser Ala Pro Glu Ser Arg Lys
                770                 775                 780

ctg gag aag tca gaa gac gaa cca cct ttg act ctt cct aag cct tct     3362
Leu Glu Lys Ser Glu Asp Glu Pro Pro Leu Thr Leu Pro Lys Pro Ser
            785                 790                 795

cta att cct cag gag gtt aag att tgc att gaa ggc cgg tct aat gta     3410
Leu Ile Pro Gln Glu Val Lys Ile Cys Ile Glu Gly Arg Ser Asn Val
        800                 805                 810

ggc aag tag aggcagcgtg ggggaaagga aacgtggctc tcccttatca             3459
Gly Lys
    815

tttgtatcca gattactgta ctgtaggcta aaataacaca gtatttacat gttatcttct   3519

taattttagg tttctgttct aaccttgtca ttagagttac agcaggtgtg tcgcaggaga   3579

ctggtgcata tgctttttcc acgagtgtct gtcagtgagc gggcgggagg aagggcacag   3639

caggagcggt cagggctcca ggcatccccg gggaagaaag gaacggggct tcacagtgcc   3699

tgccttctct agcggcacag aagcagccgg gggcgctgac tcccgctagt gtcaggagaa   3759

aagtcccgtg ggaagggtcc tgcaggggtg cagggttgca cgcatgtggg ggtgcacagg   3819

cgctgtggcg gcgagtgagg gtctcttttt ctctgcctcc ctctgcctca ctctcttgct   3879

atcggcatgg gccggggggg ttcagagcag tgtcctcctg gggttcccac gtgcaaaatc   3939

aacatcagga acccagcttc agggcatcgc ggagacgcgt cagatggcag atttggaaag   3999

ttaaccattt aaaagaacat ttttctctcc aacatatttt acaataaaag caacttttaa   4059

ttgtatagat atatatttcc ccctatgggg cctgactgca ctgatatata ttttttttaa   4119

agagcaactg ccacatgcgg gatttcattt ctgcttttta ctagtgcagc gatgtcacca   4179

gggtgttgtg gtggacaggg aagcccctgc tgtcatggcc ccacatgggg taaggggggt   4239

tgggggtggg ggagagggag agagcgaaca cccacgctgg tttctgtgca gtgttaggaa   4299

aaccaatcag gttattgcat tgacttcact cccaagaggt agatgcaaac tgcccttcag   4359
```

```
tgagagcaac agaagctctt cacgttgagt ttgcgaaatc tttttgtctt tgaactctag   4419
tactgtttat agttcatgac tatggacaac tcgggtgcca cttttttttt ttttcagatt   4479
ccagtgtgac atgaggaatt agattttgaa gatgagcata tattactatc tttaagcatt   4539
taaaaatact gttcacactt tattaccaag catcttggtc tctcattcaa caagtactgt   4599
atctcacttt aaactctttg gggaaaaaac aaaaacaaaa aaaactaagt tgctttcttt   4659
ttttcaacac tgtaactaca tttcagctct gcagaattgc tgaagagcaa gatattgaaa   4719
gtttcaatgt ggtttaaagg gatgaatgtg aattatgaac tagtatgtga caataaatga   4779
ccaccaagta ctacctgacg ggaggcactt ttcactttga tgtctgagaa tcagttcaag   4839
gcatatgcag agttggcaga gaaactgaga gaaaagggat ggagaagaga atactcattt   4899
ttgtccagtg tttttctttt taagatgaac ttttaaagaa ccttgcgatt tgcacatatt   4959
gagtttataa cttgtgtgat attcctgcag tttttatcca ataacattgt gggaaaggtt   5019
tgggggactg aacgagcata aataaatgta gcaaaatttc tttctaacct gcctaaactc   5079
taggccattt tataaggtta tgttcctttg aaaattcatt ttggtctttt taccacatct   5139
gtcacaaaaa gccaggtctt agcgggctct tagaaactct gagaattttc ttcagattca   5199
ttgagagagt tttccataaa gacatttata tatgtgagca agattttttt taaacaatta   5259
ctttattatt gttgttatta atgttatttt cagaatggct tttttttttc tattcaaaat   5319
caaatcgaga tttaatgttt ggtacaaacc cagaaagggt atttcatagt ttttaaacct   5379
ttcattccca gagatccgaa atatcatttg tgggttttga atgcatcttt aaagtgcttt   5439
aaaaaaaagt tttataagta gggagaaatt tttaaatatt cttacttgga tggctgcaac   5499
taaactgaac aaatacctga cttttctttt accccattga aaatagtact ttcttcgttt   5559
cacaaattaa aaaaaaaatc tggtatcaac ccacattttg gctgtctagt attcatttac   5619
atttagggtt caccaggact aatgattttt ataaaccgtt ttctggggtg taccaaaaac   5679
atttgaatag gtttagaata gctagaatag ttccttgact ttcctcgaat ttcattaccc   5739
tctcagcatg cttgcagaga gctgggtggg ctcattcttg cagtcatact gcttatttag   5799
tgctgtattt tttaaacgtt tctgttcaga gaacttgctt aatcttccat atattctgct   5859
cagggcactt gcaattatta ggttttgttt ttctttttgt tttttagcct ttgatggtaa   5919
gaggaatacg ggctgccaca tagactttgt tctcattaat atcactattt acaactcatg   5979
tggactcaga aaaacacaca ccaccttttg gcttacttcg agtattgaat tgactggatc   6039
cactaaacca acactaagat gggaaaacac acatggtttg gagcaatagg aacatcatca   6099
taatttttgt ggttctattt caggtatagg aattataaaa taattggttc tttctaaaca   6159
cttgtcccat ttcattctct tgcttttttta gcatgtgcaa tactttctgt gccaatagag   6219
tctgaccagt gtgctatata gttaaagctc attccctttt ggctttttcc ttgtttggtt   6279
gatcttcccc attctggcca gagcagggct ggagggaagg agccaggagg gagagagcct   6339
cccacctttc ccctgctgcg gatgctgagt gctggggcgg ggagccttca ggagccccgt   6399
gcgtctgccg ccacgttgca gaaagagcca gccaaggaga cccgggggag gaaccgcagt   6459
gtcccctgtc accacacgga atagtgaatg tggagtgtgg agaggaagga ggcagattca   6519
tttctaagac gcactctgga gccatgtagc ctggagtcaa cccattttcc acggtctttt   6579
ctgcaagtgg gcaggcccct cctcggggtc tgtgtccttg agacttggag ccctgcctct   6639
gagcctggac gggaagtgtg gcctgttgtg tgtgtgcgtt ctgagcgtgt tggccagtgg   6699
```

-continued

```
ctgtggaggg gaccacctgc cacccacggt caccactccc ttgtggcagc tttctcttca   6759

aataggaaga acgcacagag ggcaggagcc tcctgtttgc agacgttggc gggccccgag   6819

gctcccagag cagcctctgt caccgcttct gtgtagcaaa cattaacgat gacaggggta   6879

gaaattcttc ggtgccgttc agcttacaag gatcagccat gtgcctctgt actatgtcca   6939

ctttgcaata tttaccgaca gccgtctttt gttctttctt tcctgttttc catttttaaa   6999

ctagtaacag caggcctttt gcgtttacaa tggaacacaa tcaccaagaa attagtcagg   7059

gcgaaaagaa aaaaataata ctattaataa gaaaccaaca aacaagaacc tctctttcta   7119

gggatttcta aatatataaa atgactgttc cttagaatgt ttaacttaag aattatttca   7179

gtttgtctgg gccacactgg ggcagagggg ggagggaggg atacagagat ggatgccact   7239

tacctcagat cttttaaagt ggaaatccaa attgaatttt catttggact ttcaggataa   7299

ttttctatgt tggtcaactt ttcgttttcc ctaactcacc cagtttagtt tgggatgatt   7359

tgatttctgt tgttgttgat cccatttcta acttggaatt gtgagcctct atgttttctg   7419

ttaggtgagt gtgttgggtt ttttcccccc accaggaagt ggcagcatcc ctccttctcc   7479

cctaaaggga ctctgcggaa cctttcacac ctctttctca gggacggggc aggtgtgtgt   7539

gtggtacact gacgtgtcca gaagcagcac tttgactgct ctggagtagg gttgtacaat   7599

ttcaaggaat gtttggattt cctgcatctt gtggattact ccttagatac cgcatagatt   7659

gcaatataat gctgcatgtt caagatgaac agtagctcct agtaatcata aaatccactc   7719

tttgcacagt ttgatcttta ctgaaatatg ttgccaaaat ttatttttgt tgttgtagct   7779

ctggatttg ttttgttttg ttttttaagg aaacgattga caataccctt taacatctgt   7839

gactactaag gaaacctatt tctttcatag agagaaaaat ctccaatgct tttgaagaca   7899

ctaataccgt gctatttcag atatgggtga ggaagcagag ctctcggtac cgaaggccgg   7959

gcttcttgag ctgtgttggt tgtcatggct actgtttcat gaaccacaag cagctcaaca   8019

gactggtctg ttgccttctg aaaccctttg cacttcaatt tgcaccaggt gaaaacaggg   8079

ccagcagact ccatggccca attcggtttc ttcggtggtg atgtgaaagg agagaattac   8139

actttttttt tttttaagtg gcgtggaggc ctttgcttcc acatttgttt ttaacccaga   8199

atttctgaaa tagagaattt aagaacacat caagtaataa atatacagag aatatacttt   8259

tttataaagc acatgcatct gctattgtgt tgggttggtt tcctctcttt tccacggaca   8319

gtgttgtgtt tctggcatag ggaaactcca aacaacttgc acacctctac tccggagctg   8379

agatttcttt tacatagatg acctcgcttc aaatacgtta ccttactgat gataggatct   8439

tttcttgtag cactatacct tgtgggaatt ttttttaaa tgtacacctg atttgagaag   8499

ctgaagaaaa caaaattttg aagcactcac tttgaggagt acaggtaatg ttttaaaaaa   8559

ttgcacaaaa gaaaaatgaa tgtcgaaatg attcattcag tgtttgaaag atatggctct   8619

gttgaaacaa tgagtttcat actttgtttg taaaaaaaaa aaagcagaga agggttgaaa   8679

gttacatgtt tttttgtata tagaaatttg tcatgtctaa atgatcagat ttgtatggtt   8739

atggcctgga agaattacta cgtaaaaggc tcttaaacta tacctatgct tattgttatt   8799

tttgttacat atagccctcg tctgagggag gggaactcgg tattctgcga tttgagaata   8859

ctgttcattc ctatgctgaa agtacttctc tgagctccct tcttagtcta aactcttaag   8919

ccattgcaac ttctttttct tcagagatga tgtttgacat tttcagcact tcctgttcct   8979

ataaacccaa agaatataat cttgaacacg aagtgtttgt aacaagggat ccaggctacc   9039

aatcaaacag gactcattat ggggacaaaa aaaaaaatta tttcaccttc tttcccccca   9099
```

```
cacctcattt aaatgggggg agtaaaaaca tgatttcaat gtaaatgcct cattttattt   9159

tagttttatt ttgattttta tttaatataa agaggccaga ataaatacgg agcatcttct   9219

cagaatagta ttcctgtcca aaaatcaagc cggacagtgg aaactggaca gctgtgggga   9279

tattaagcac ccccacttac aattcttaaa ttcagaatct cgtcccctcc cttctcgttg   9339

aaggcaactg ttctggtagc taactttctc ctgtgtaatg gcgggaggga acaccggctt   9399

cagtttttca tgtccccatg acttgcatac aaatggttca actgtattaa aattaagtgc   9459

atttggccaa taggtagtat ctatacaata acaacaatct ctaagaattt ccataacttt   9519

tcttatctga aaggactcaa gtcttccact gcagatacat tggaggcttc acccacgttt   9579

tctttccctt tagtttgttt gctgtctgga tggccaatga gcctgtctcc ttttctgtgg   9639

ccaatctgaa ggccttcgtt ggaagtgttg tttacagtaa tccttaccaa gataacatac   9699

tgtcctccag aataccaagt attaggtgac actagctcaa gctgttgtct tcagagcagt   9759

taccaagaag ctcggtgcac aggttttctc tggttcttac aggaaccacc tactctttca   9819

gttttctggc ccaggagtgg ggtaaatcct ttagttagtg catttgaact tgatacctgt   9879

gcattcagtt ctgtgaatac tgcccttttt ggcggggttt cctcatctcc ccagcctgaa   9939

ctgctcaact ctaaacccaa attagtgtca gccgaaagga ggtttcaaga tagtcctgtc   9999

agtatttgtg gtgaccttca gattagacag tcttcatttc cagccagtgg agtcctggct  10059

ccagagccat ctctgagact cgtactactg gatgttttaa tatcagatca ttacccacca  10119

tatgcctccc acaggccaag ggaaaacaga caccagaact tgggttgagg gcactaccag  10179

actgacatgg ccagtacaga ggagaactag ggaaggaatg atgttttgca ccttattgaa  10239

aagaaaattt taagtgcata cataatagtt aagagctttt attgtgacag gagaactttt  10299

ttccatatgc gtgcatactc tctgtaattc cagtgtaaaa tattgtactt gcactagctt  10359

ttttaaacaa atattaaaaa atggaagaat tcatattcta ttttctaatc gtggtgtgtc  10419

tatttgtagg atacactcga gtctgtttat tgaattttat ggtccctttc tttgatggtg  10479

cttgcaggtt ttctaggtag aaattatttc attattataa taaaacaatg tttgattcaa  10539

aatttgaaca aaattgtttt aaataaattg tctgtatacc agtacaagtt tattgtttca  10599

gtatactcgt actaataaaa taacagtgcc aattgca                           10636
```

<210> SEQ ID NO 48
<211> LENGTH: 815
<212> TYPE: PRT
<213> ORGANISM: Homo sapiens

<400> SEQUENCE: 48

```
Met Lys Ser Asn Gln Glu Arg Ser Asn Glu Cys Leu Pro Pro Lys Lys
1               5                   10                  15

Arg Glu Ile Pro Ala Thr Ser Arg Ser Ser Glu Glu Lys Ala Pro Thr
            20                  25                  30

Leu Pro Ser Asp Asn His Arg Val Glu Gly Thr Ala Trp Leu Pro Gly
        35                  40                  45

Asn Pro Gly Gly Arg Gly His Gly Gly Gly Arg His Gly Pro Ala Gly
    50                  55                  60

Thr Ser Val Glu Leu Gly Leu Gln Gln Gly Ile Gly Leu His Lys Ala
65                  70                  75                  80

Leu Ser Thr Gly Leu Asp Tyr Ser Pro Pro Ser Ala Pro Arg Ser Val
                85                  90                  95
```

```
Pro Val Ala Thr Thr Leu Pro Ala Ala Tyr Ala Thr Pro Gln Pro Gly
            100                 105                 110

Thr Pro Val Ser Pro Val Gln Tyr Ala His Leu Pro His Thr Phe Gln
        115                 120                 125

Phe Ile Gly Ser Ser Gln Tyr Ser Gly Thr Tyr Ala Ser Phe Ile Pro
    130                 135                 140

Ser Gln Leu Ile Pro Pro Thr Ala Asn Pro Val Thr Ser Ala Val Ala
145                 150                 155                 160

Ser Ala Ala Gly Ala Thr Thr Pro Ser Gln Arg Ser Gln Leu Glu Ala
                165                 170                 175

Tyr Ser Thr Leu Leu Ala Asn Met Gly Ser Leu Ser Gln Thr Pro Gly
            180                 185                 190

His Lys Ala Glu Gln Gln Gln Gln Gln Gln Gln Gln Gln Gln Gln Gln
        195                 200                 205

His Gln His Gln Gln Gln Gln Gln Gln Gln Gln Gln Gln Gln Gln Gln
    210                 215                 220

Gln His Leu Ser Arg Ala Pro Gly Leu Ile Thr Pro Gly Ser Pro Pro
225                 230                 235                 240

Pro Ala Gln Gln Asn Gln Tyr Val His Ile Ser Ser Ser Pro Gln Asn
                245                 250                 255

Thr Gly Arg Thr Ala Ser Pro Pro Ala Ile Pro Val His Leu His Pro
            260                 265                 270

His Gln Thr Met Ile Pro His Thr Leu Thr Leu Gly Pro Pro Ser Gln
        275                 280                 285

Val Val Met Gln Tyr Ala Asp Ser Gly Ser His Phe Val Pro Arg Glu
    290                 295                 300

Ala Thr Lys Lys Ala Glu Ser Ser Arg Leu Gln Gln Ala Ile Gln Ala
305                 310                 315                 320

Lys Glu Val Leu Asn Gly Glu Met Glu Lys Ser Arg Arg Tyr Gly Ala
                325                 330                 335

Pro Ser Ser Ala Asp Leu Gly Leu Gly Lys Ala Gly Gly Lys Ser Val
            340                 345                 350

Pro His Pro Tyr Glu Ser Arg His Val Val Val His Pro Ser Pro Ser
        355                 360                 365

Asp Tyr Ser Ser Arg Asp Pro Ser Gly Val Arg Ala Ser Val Met Val
    370                 375                 380

Leu Pro Asn Ser Asn Thr Pro Ala Ala Asp Leu Glu Val Gln Gln Ala
385                 390                 395                 400

Thr His Arg Glu Ala Ser Pro Ser Thr Leu Asn Asp Lys Ser Gly Leu
                405                 410                 415

His Leu Gly Lys Pro Gly His Arg Ser Tyr Ala Leu Ser Pro His Thr
            420                 425                 430

Val Ile Gln Thr Thr His Ser Ala Ser Glu Pro Leu Pro Val Gly Leu
        435                 440                 445

Pro Ala Thr Ala Phe Tyr Ala Gly Thr Gln Pro Pro Val Ile Gly Tyr
    450                 455                 460

Leu Ser Gly Gln Gln Gln Ala Ile Thr Tyr Ala Gly Ser Leu Pro Gln
465                 470                 475                 480

His Leu Val Ile Pro Gly Thr Gln Pro Leu Leu Ile Pro Val Gly Ser
                485                 490                 495

Thr Asp Met Glu Ala Ser Gly Ala Ala Pro Ala Ile Val Thr Ser Ser
            500                 505                 510
```

-continued

```
Pro Gln Phe Ala Ala Val Pro His Thr Phe Val Thr Thr Ala Leu Pro
        515                 520                 525

Lys Ser Glu Asn Phe Asn Pro Glu Ala Leu Val Thr Gln Ala Ala Tyr
    530                 535                 540

Pro Ala Met Val Gln Ala Gln Ile His Leu Pro Val Val Gln Ser Val
545                 550                 555                 560

Ala Ser Pro Ala Ala Ala Pro Pro Thr Leu Pro Pro Tyr Phe Met Lys
                565                 570                 575

Gly Ser Ile Ile Gln Leu Ala Asn Gly Glu Leu Lys Lys Val Glu Asp
            580                 585                 590

Leu Lys Thr Glu Asp Phe Ile Gln Ser Ala Glu Ile Ser Asn Asp Leu
        595                 600                 605

Lys Ile Asp Ser Ser Thr Val Glu Arg Ile Glu Asp Ser His Ser Pro
    610                 615                 620

Gly Val Ala Val Ile Gln Phe Ala Val Gly Glu His Arg Ala Gln Val
625                 630                 635                 640

Ser Val Glu Val Leu Val Glu Tyr Pro Phe Phe Val Phe Gly Gln Gly
                645                 650                 655

Trp Ser Ser Cys Cys Pro Glu Arg Thr Ser Gln Leu Phe Asp Leu Pro
            660                 665                 670

Cys Ser Lys Leu Ser Val Gly Asp Val Cys Ile Ser Leu Thr Leu Lys
        675                 680                 685

Asn Leu Lys Asn Gly Ser Val Lys Lys Gly Gln Pro Val Asp Pro Ala
    690                 695                 700

Ser Val Leu Leu Lys His Ser Lys Ala Asp Gly Leu Ala Gly Ser Arg
705                 710                 715                 720

His Arg Tyr Ala Glu Gln Glu Asn Gly Ile Asn Gln Gly Ser Ala Gln
                725                 730                 735

Met Leu Ser Glu Asn Gly Glu Leu Lys Phe Pro Glu Lys Met Gly Leu
            740                 745                 750

Pro Ala Ala Pro Phe Leu Thr Lys Ile Glu Pro Ser Lys Pro Ala Ala
        755                 760                 765

Thr Arg Lys Arg Arg Trp Ser Ala Pro Glu Ser Arg Lys Leu Glu Lys
    770                 775                 780

Ser Glu Asp Glu Pro Pro Leu Thr Leu Pro Lys Pro Ser Leu Ile Pro
785                 790                 795                 800

Gln Glu Val Lys Ile Cys Ile Glu Gly Arg Ser Asn Val Gly Lys
                805                 810                 815
```